United States Patent
Li et al.

(10) Patent No.: US 9,818,959 B2
(45) Date of Patent: *Nov. 14, 2017

(54) METAL-ASSISTED DELAYED FLUORESCENT EMITTERS CONTAINING TRIDENTATE LIGANDS

(71) Applicant: Arizona Board of Regents on behalf of Arizona State University, Scottsdale, AZ (US)

(72) Inventors: Jian Li, Tempe, AZ (US); Guijie Li, Tempe, AZ (US)

(73) Assignee: Arizona Board of Regents on behlaf of Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/809,981

(22) Filed: Jul. 27, 2015

(65) Prior Publication Data

US 2016/0043331 A1 Feb. 11, 2016

Related U.S. Application Data

(60) Provisional application No. 62/030,235, filed on Jul. 29, 2014.

(51) Int. Cl.
*C07F 15/00* (2006.01)
*H01L 51/50* (2006.01)
(Continued)

(52) U.S. Cl.
CPC ............ *H01L 51/0087* (2013.01); *C07F 1/12* (2013.01); *C07F 9/65683* (2013.01);
(Continued)

(58) Field of Classification Search
CPC ...................................................... C07F 15/00
(Continued)

(56) References Cited

U.S. PATENT DOCUMENTS

| | | | |
|---|---|---|---|
| 4,769,292 | A | 9/1988 | Tang et al. |
| 5,707,745 | A | 1/1998 | Forrest et al. |
| 5,844,363 | A | 12/1998 | Gu et al. |
| 6,200,695 | B1 | 3/2001 | Arai et al. |

(Continued)

FOREIGN PATENT DOCUMENTS

| CN | 1777663 | 5/2006 |
|---|---|---|
| CN | 1894269 | 1/2007 |

(Continued)

OTHER PUBLICATIONS

V. Thamilarasan et al., "Green-emitting phosphorescent iridium(III) complex: Structural, photophysical and electrochemical properties," Inorganica Chimica Acta, vol. 408, 2013, pp. 240-245.

(Continued)

*Primary Examiner* — Charanjit Aulakh
(74) *Attorney, Agent, or Firm* — Fish & Richardson P.C.

(57) ABSTRACT

Tridentate platinum, palladium, and gold complexes of Formulas A-I and A-II and tridentate iridium and rhodium compounds of Formulas B-I, B-II, and B-III suitable for delayed fluorescent and phosphorescent or phosphorescent emitters in display and lighting applications.

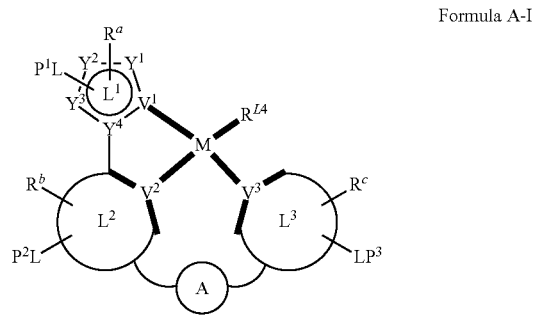

Formula A-I

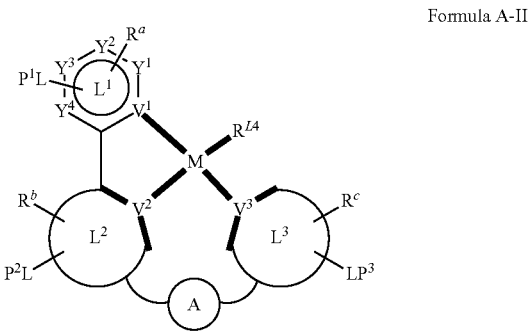

Formula A-II

Formula B-I (Continued)

-continued

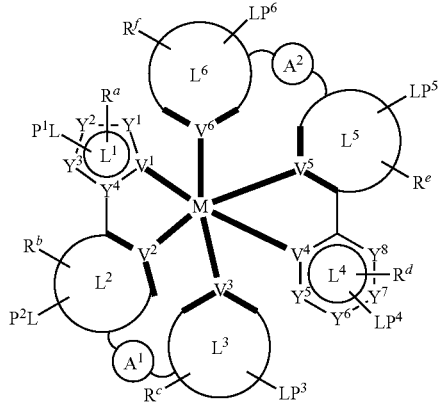

Formula B-II

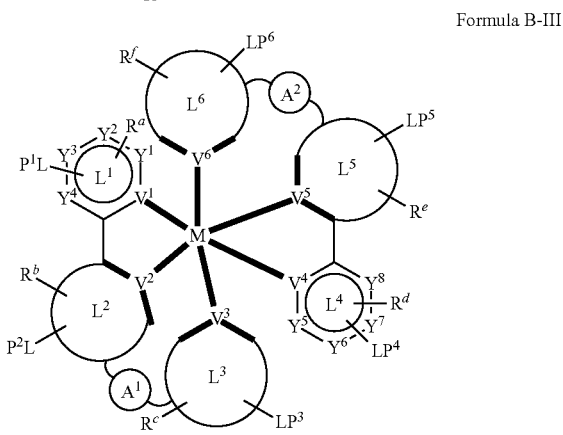

Formula B-III

20 Claims, 3 Drawing Sheets

(51) Int. Cl.
| | |
|---|---|
| *C07F 1/12* | (2006.01) |
| *H01L 51/00* | (2006.01) |
| *C09K 11/06* | (2006.01) |
| *C07F 9/6568* | (2006.01) |
| *H05B 33/14* | (2006.01) |

(52) U.S. Cl.
CPC ........ *C07F 9/65685* (2013.01); *C07F 15/006* (2013.01); *C07F 15/0033* (2013.01); *C07F 15/0073* (2013.01); *C07F 15/0086* (2013.01); *C09K 11/06* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1044* (2013.01); *C09K 2211/1048* (2013.01); *C09K 2211/1059* (2013.01); *C09K 2211/1088* (2013.01); *C09K 2211/1092* (2013.01); *C09K 2211/1096* (2013.01); *C09K 2211/185* (2013.01); *H01L 51/5012* (2013.01); *H01L 51/5016* (2013.01)

(58) Field of Classification Search
USPC .............................................. 546/2; 313/504
See application file for complete search history.

(56) References Cited

U.S. PATENT DOCUMENTS

| | | | |
|---|---|---|---|
| 6,303,238 B1 | 10/2001 | Thompson et al. | |
| 6,780,528 B2 | 8/2004 | Tsuboyama et al. | |
| 7,002,013 B1 | 2/2006 | Chi et al. | |
| 7,037,599 B2 | 5/2006 | Culligan et al. | |
| 7,064,228 B1 | 6/2006 | Yu et al. | |
| 7,279,704 B2 | 10/2007 | Walters et al. | |
| 7,332,232 B2 | 2/2008 | Ma et al. | |
| 7,442,797 B2 | 10/2008 | Itoh et al. | |
| 7,501,190 B2 | 3/2009 | Ise | |
| 7,655,322 B2 | 2/2010 | Forrest et al. | |
| 7,947,383 B2 | 5/2011 | Ise et al. | |
| 8,389,725 B2 * | 3/2013 | Li ...................... | C07F 15/0086 313/504 |
| 8,617,723 B2 | 12/2013 | Stoessel | |
| 8,816,080 B2 | 8/2014 | Li et al. | |
| 8,871,361 B2 | 10/2014 | Xia et al. | |
| 8,927,713 B2 | 1/2015 | Li et al. | |
| 8,946,417 B2 | 2/2015 | Jian et al. | |
| 9,059,412 B2 | 6/2015 | Zeng et al. | |
| 9,221,857 B2 | 12/2015 | Li et al. | |
| 9,224,963 B2 | 12/2015 | Li et al. | |
| 9,238,668 B2 | 1/2016 | Li et al. | |
| 9,312,505 B2 | 4/2016 | Brooks et al. | |
| 9,324,957 B2 | 4/2016 | Li et al. | |
| 9,382,273 B2 | 7/2016 | Li et al. | |
| 9,385,329 B2 | 7/2016 | Li et al. | |
| 9,425,415 B2 | 8/2016 | Li et al. | |
| 9,461,254 B2 | 10/2016 | Tsai et al. | |
| 9,550,801 B2 | 1/2017 | Li et al. | |
| 9,617,291 B2 | 4/2017 | Li et al. | |
| 2001/0019782 A1 | 9/2001 | Igarashi et al. | |
| 2002/0068190 A1 | 6/2002 | Tsuboyama et al. | |
| 2003/0062519 A1 | 4/2003 | Yamazaki et al. | |
| 2003/0186077 A1 | 10/2003 | Chen | |
| 2004/0230061 A1 | 11/2004 | Seo et al. | |
| 2005/0170207 A1 | 8/2005 | Ma et al. | |
| 2005/0260446 A1 | 11/2005 | Mackenzie et al. | |
| 2006/0024522 A1 | 2/2006 | Thompson et al. | |
| 2006/0073359 A1 | 4/2006 | Ise et al. | |
| 2006/0094875 A1 | 5/2006 | Itoh et al. | |
| 2006/0127696 A1 | 6/2006 | Stossel | |
| 2006/0182992 A1 | 8/2006 | Nii | |
| 2006/0202197 A1 | 9/2006 | Nakayama et al. | |
| 2006/0210831 A1 | 9/2006 | Sano et al. | |
| 2006/0255721 A1 | 11/2006 | Igarashi | |
| 2006/0263635 A1 | 11/2006 | Ise | |
| 2006/0286406 A1 | 12/2006 | Igarashi et al. | |
| 2007/0057630 A1 | 3/2007 | Nishita et al. | |
| 2007/0059551 A1 | 3/2007 | Yamazaki | |
| 2007/0082284 A1 | 4/2007 | Stoessel et al. | |
| 2007/0103060 A1 | 5/2007 | Itoh et al. | |
| 2008/0001530 A1 | 1/2008 | Ise et al. | |
| 2008/0036373 A1 | 2/2008 | Itoh et al. | |
| 2008/0054799 A1 | 3/2008 | Satou | |
| 2008/0079358 A1 | 4/2008 | Satou | |
| 2008/0241518 A1 | 10/2008 | Satou et al. | |
| 2008/0241589 A1 | 10/2008 | Fukunaga et al. | |
| 2009/0026936 A1 | 1/2009 | Satou et al. | |
| 2009/0026939 A1 | 1/2009 | Kinoshita et al. | |
| 2009/0032989 A1 | 2/2009 | Karim et al. | |
| 2009/0039768 A1 | 2/2009 | Igarashi et al. | |
| 2009/0079340 A1 | 3/2009 | Kinoshita et al. | |
| 2009/0128008 A1 | 5/2009 | Ise et al. | |
| 2009/0218561 A1 | 9/2009 | Kitamura et al. | |
| 2009/0261721 A1 | 10/2009 | Murakami et al. | |
| 2009/0267500 A1 | 10/2009 | Kinoshita et al. | |
| 2010/0000606 A1 | 1/2010 | Thompson et al. | |
| 2010/0013386 A1 | 1/2010 | Thompson et al. | |
| 2010/0141127 A1 | 6/2010 | Xia et al. | |
| 2010/0171111 A1 | 7/2010 | Takada et al. | |
| 2012/0095232 A1 | 4/2012 | Li et al. | |
| 2012/0181528 A1 | 7/2012 | Takada et al. | |
| 2012/0215001 A1 | 8/2012 | Li et al. | |
| 2012/0223634 A1 | 9/2012 | Xia et al. | |
| 2012/0264938 A1 | 10/2012 | Li | |

(56) References Cited

U.S. PATENT DOCUMENTS

| | | |
|---|---|---|
| 2012/0302753 A1 | 11/2012 | Li |
| 2013/0048963 A1 | 2/2013 | Beers et al. |
| 2013/0168656 A1 | 7/2013 | Tsai et al. |
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0203248 A1 | 7/2014 | Zhou et al. |
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0228914 A1 | 8/2015 | Li et al. |
| 2015/0287938 A1 | 10/2015 | Li et al. |
| 2015/0318500 A1 | 11/2015 | Li |
| 2015/0349279 A1 | 12/2015 | Li et al. |
| 2015/0380666 A1 | 12/2015 | Szigethy et al. |
| 2016/0028028 A1 | 1/2016 | Li et al. |
| 2016/0043331 A1 | 2/2016 | Li et al. |
| 2016/0072082 A1 | 3/2016 | Brooks et al. |
| 2016/0133861 A1 | 5/2016 | Li et al. |
| 2016/0133862 A1 | 5/2016 | Li et al. |
| 2016/0194344 A1 | 7/2016 | Li et al. |
| 2016/0197291 A1 | 7/2016 | Li et al. |
| 2016/0285015 A1 | 9/2016 | Li et al. |
| 2016/0359120 A1 | 12/2016 | Li |
| 2016/0359125 A1 | 12/2016 | Li et al. |
| 2017/0005278 A1 | 1/2017 | Li et al. |
| 2017/0012224 A1 | 1/2017 | Li et al. |
| 2017/0047533 A1 | 2/2017 | Li et al. |
| 2017/0066792 A1 | 3/2017 | Li et al. |
| 2017/0069855 A1 | 3/2017 | Li |

FOREIGN PATENT DOCUMENTS

| | | |
|---|---|---|
| CN | 101142223 | 3/2008 |
| CN | 101667626 | 3/2010 |
| CN | 102449108 A | 5/2012 |
| CN | 102892860 | 1/2013 |
| CN | 102971396 | 3/2013 |
| CN | 104232076 | 12/2014 |
| CN | 104693243 | 6/2015 |
| CN | 105367605 A1 | 3/2016 |
| CN | 105418591 A1 | 3/2016 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 | 9/2009 |
| EP | 2417217 | 2/2012 |
| EP | 2112213 | 7/2012 |
| EP | 2711999 | 3/2014 |
| JP | 2002105055 | 4/2002 |
| JP | 2003342284 | 12/2003 |
| JP | 2005267557 | 9/2005 |
| JP | 2005310733 | 11/2005 |
| JP | 2006047240 | 2/2006 |
| JP | 2006232784 | 9/2006 |
| JP | 2006242080 | 9/2006 |
| JP | 2006242081 | 9/2006 |
| JP | 2006256999 | 9/2006 |
| JP | 2006257238 | 9/2006 |
| JP | 2006261623 | 9/2006 |
| JP | 2006290988 | 10/2006 |
| JP | 2006313796 | 11/2006 |
| JP | 2006332622 | 12/2006 |
| JP | 2006351638 | 12/2006 |
| JP | 2007019462 | 1/2007 |
| JP | 2007031678 | 2/2007 |
| JP | 2007042875 | 2/2007 |
| JP | 2007053132 | 3/2007 |
| JP | 2007066581 | 3/2007 |
| JP | 2007073620 | 3/2007 |
| JP | 2007073845 | 3/2007 |
| JP | 2007073900 | 3/2007 |
| JP | 2007080593 | 3/2007 |
| JP | 2007080677 | 3/2007 |
| JP | 2007088105 | 4/2007 |
| JP | 2007088164 | 4/2007 |
| JP | 2007096259 | 4/2007 |
| JP | 2007110067 | 4/2007 |
| JP | 2007110102 | 4/2007 |
| JP | 2007258550 | 10/2007 |
| JP | 2007324309 | 12/2007 |
| JP | 2008010353 | 1/2008 |
| JP | 2008091860 | 4/2008 |
| JP | 2008103535 | 5/2008 |
| JP | 2008108617 | 5/2008 |
| JP | 2008109085 | 5/2008 |
| JP | 2008109103 | 5/2008 |
| JP | 2008160087 | 7/2008 |
| JP | 2008198801 | 8/2008 |
| JP | 2008270729 | 11/2008 |
| JP | 2008270736 | 11/2008 |
| JP | 2009016184 | 1/2009 |
| JP | 2009016579 | 1/2009 |
| JP | 2009032977 | 2/2009 |
| JP | 2009032988 | 2/2009 |
| JP | 2009076509 | 4/2009 |
| JP | 2009266943 | 11/2009 |
| JP | 2009267171 | 11/2009 |
| JP | 2009267244 | 11/2009 |
| JP | 2009272339 | 11/2009 |
| JP | 2009283891 | 12/2009 |
| JP | 2010135689 | 6/2010 |
| JP | 2012222255 | 11/2012 |
| JP | 2013525436 | 6/2013 |
| JP | 5604505 | 10/2014 |
| JP | 2014221807 | 11/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201249851 | 12/2012 |
| TW | 201307365 | 2/2013 |
| WO | WO0070655 | 11/2000 |
| WO | WO2004003108 A1 | 1/2004 |
| WO | WO2004085450 | 10/2004 |
| WO | WO2004108857 | 12/2004 |
| WO | WO2005042444 | 5/2005 |
| WO | WO2005042550 | 5/2005 |
| WO | WO2005113704 | 12/2005 |
| WO | WO2006033440 | 3/2006 |
| WO | WO2006067074 | 6/2006 |
| WO | WO2006098505 | 9/2006 |
| WO | WO2006115299 | 11/2006 |
| WO | WO2006115301 | 11/2006 |
| WO | WO2007034985 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 | 10/2008 |
| WO | WO2009017211 | 2/2009 |
| WO | WO2010007098 | 1/2010 |
| WO | WO2010056669 | 5/2010 |
| WO | WO2010093176 | 8/2010 |
| WO | WO2010118026 | 10/2010 |
| WO | WO2011137429 | 11/2011 |
| WO | WO2011137431 | 11/2011 |
| WO | WO2012112853 | 8/2012 |
| WO | WO2012142387 | 10/2012 |
| WO | WO2012162488 | 11/2012 |

(56) References Cited

FOREIGN PATENT DOCUMENTS

| WO | WO2012163471 | 12/2012 |
|---|---|---|
| WO | WO2013130483 | 9/2013 |
| WO | WO2014016611 A1 | 1/2014 |
| WO | WO2014031977 | 2/2014 |
| WO | WO2014047616 | 3/2014 |
| WO | WO2014109814 | 7/2014 |
| WO | WO2015027060 | 2/2015 |
| WO | WO2015131158 | 9/2015 |
| WO | WO2016025921 | 2/2016 |
| WO | WO2016029186 | 2/2016 |

OTHER PUBLICATIONS

Rui Zhu et al., "Color tuning based on a six-membered chelated iridium (III) complex with aza-aromatic ligand," Chemistry Letters, vol. 34, No. 12, 2005, pp. 1668-1669.
Wong; Challenges in organometallic research—Great opportunity for solar cells and OLEDs, Journal of Organometallic Chemistry, 2009, 694, 2644-2647.
JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.
Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Barry O'Brien et al.: White organic light emitting diodes using Pt-based red, green and blue phosphorescent dopants. Proc. SPIE, vol. 8829, pp. 1-6, Aug. 25, 2013.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)$_3$ and its derivatives", J. Phys. Chem. C, vol. 117, pp. 5314-5327 (2013).
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate O^N^C^N Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate O^N^C^N ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-043597-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Murakami; JP 2007258550, English machine translation from EPO, Oct. 4, 2007. 80 pages.
Murakami; JP 2007324309, English machine translation from EPO, Dec. 13, 2007, 89 pages.
Dorwald; "Side Reactions in Organic Synthesis: A Guide to Successful Synthesis Design," Chapter 1, 2005 Wiley-VCH Verlag GmbH & Co. KGaA, Wienheim, 32 pages.
Marc Lepeltier et al., "Efficient blue green organic light-emitting devices based on a monofluorinated heteroleptic iridium(III) complex," Synthetic Metals, vol. 199, 2015, pp. 139-146.

(56) References Cited

OTHER PUBLICATIONS

Stefan Bernhard, "The First Six Years: A Report," Department of Chemistry, Princeton University, May 2008, 11 pages.

* cited by examiner

METAL-ASSISTED DELAYED FLUORESCENT EMITTERS CONTAINING TRIDENTATE LIGANDS

CROSS-REFERENCE TO RELATED APPLICATION

This application claims priority to U.S. Ser. No. 62/030,235 entitled "METAL-ASSISTED DELAYED FLUORESCENT EMITTERS CONTAINING TRIDENTATED LIGANDS" and filed on Jul. 29, 2014, which is incorporated by reference herein in its entirety.

TECHNICAL FIELD

The present disclosure relates to tridentate platinum, palladium, gold, iridium, and rhodium complexes for phosphorescent or delayed fluorescent and phosphorescent or emitters in display and lighting applications, and specifically to phosphorescent or delayed fluorescent and phosphorescent tridentate metal complexes having modified emission spectra.

BACKGROUND

Compounds capable of absorbing and/or emitting light can be suited for use in a wide variety of optical and electroluminescent devices, including, for example, photo-absorbing devices such as solar- and photo-sensitive devices, organic light emitting diodes (OLEDs), photo-emitting devices, or devices capable of both photo-absorption and emission and as markers for bio-applications. Much research has been devoted to the discovery and optimization of organic and organometallic materials for using in optical and electroluminescent devices. Generally, research in this area aims to accomplish a number of goals, including improvements in absorption and emission efficiency and improvements in the stability of devices, as well as improvements in processing ability.

Despite significant advances in research devoted to optical and electro-optical materials (e.g., red and green phosphorescent organometallic materials are commercially available and have been used as phosphors in organic light emitting diodes (OLEDs), lighting, and advanced displays), many currently available materials exhibit a number of disadvantages, including poor processing ability, inefficient emission or absorption, and less than ideal stability, among others.

Good blue emitters are particularly scarce, with one challenge being the stability of the blue devices. The choice of the host materials has an impact on the stability and the efficiency of the devices. The lowest triplet excited state energy of the blue phosphors is very high compared with that of the red and green phosphors, which means that the lowest triplet excited state energy of host materials for the blue devices should be even higher. Thus, one of the problems is that there are limited host materials to be used for the blue devices. Accordingly, a need exists for new materials which exhibit improved performance in optical emitting and absorbing applications.

SUMMARY

The present disclosure relates to platinum, palladium, gold, iridium, and rhodium compounds suitable for emitters in organic light emitting diodes (OLEDs) and display and lighting applications.

Disclosed herein are metal-assisted delayed fluorescent and phosphorescent emitters, metal-assisted delayed fluorescent emitters, and phosphorescent emitters of Formula A-I and Formula A-II:

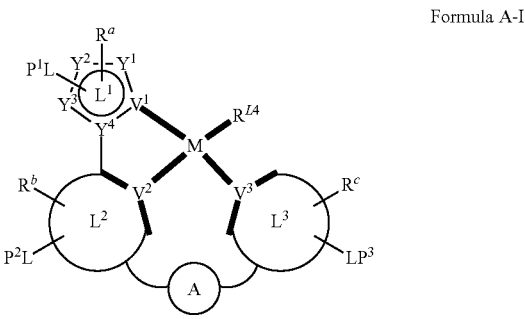

Formula A-I

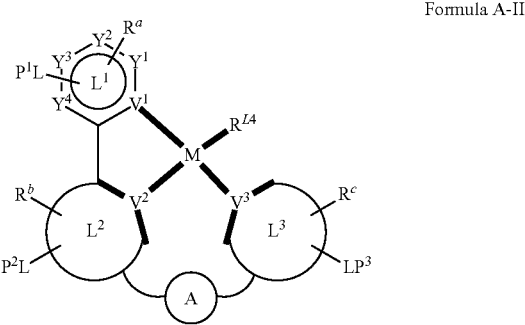

Formula A-II wherein:

M is Pt, Pd, or Au, $L^1$ is a five-membered heterocyclyl, five-membered heteroaryl, five-membered carbene, five-membered N-heterocyclic carbene, a six-membered aryl, or six-membered heteroaryl, each of $L^2$ and $L^3$ is independently substituted or unsubstituted aryl, cycloalkyl, cycloalkenyl, heteroaryl, heterocyclyl, carbene, or N-heterocyclic carbene, $R^{L4}$ is an inorganic anion or organic anion as described herein, each of $LP^1$, $LP^2$, and $LP^3$ is independently a fluorescent luminophore, each of $LP^1$, $LP^2$, and $LP^3$ is independently present or absent, and at least one of $LP^1$, $LP^2$, or $LP^3$ is present, A is $CH_2$, $CR^1R^2$, $C=O$, $CH_2$, $SiR^1R^2$, $GeH_2$, $GeR^1R^2$, NH, $NR^3$, PH, $PR^3$, $R^3P=O$, $AsR^3$, $R^3As=O$, O, S, $S=O$, $SO_2$, Se, $Se=O$, $SeO_2$, BH, $BR^3$, $R^3Bi=O$, BiH, or $BiR^3$, and optionally forms more than one bond with $L^2$, $L^3$, or both, thereby forming a ring system with $L^2$, a ring system with $L^3$, or both, each of $V^1$, $V^2$, and $V^3$ is independently N, C, P, B, or Si, each of $Y^1$, $Y^2$, $Y^3$, and $Y^4$ is independently C, N, O, S, $S=O$, $SO_2$, Se, $Se=O$, $SeO_2$, $PR^3$, $R^3P=O$, $AsR^3$, $R^3As=O$, or $BR^3$, each of $R^a$, $R^b$, and $R^c$ is independently present or absent, and if present each of $R^a$, $R^b$, and $R^c$ independently represents a mono-, di-, or tri-substitution, and each $R^a$, $R^b$, and $R^c$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of $R^1$, $R^2$, and $R^3$ is independently hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, monoalkylamino, dialkylamino, monoarylamino, diarylamino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, mercapto, sulfo, carboxyl, hydrazino, substituted silyl, or polymeric; or any conjugate or combination thereof.

In one aspect, each of $LP^1$, $LP^2$ and $LP^3$ is independently an aromatic hydrocarbon, an aromatic hydrocarbon derivative, a polyphenyl hydrocarbon, a hydrocarbon with condensed aromatic nuclei, naphthalene, anthracene, phenanthrene, chrysene, pyrene, triphenylene, perylene, acenaphthene, tetracene, pentacene, tetraphene, coronene, fluorene, biphenyl, p-terphenyl, o-diphenylbenzene, m-diphenylbenzene, p-quaterphenyl, benzo[a]tetracene, benzo[k]tetraphene, indeno[1,2,3-cd]fluoranthene, tetrabenzo[de,hi,op,st]pentacene, arylethylene, arylacetylene, an arylacetylene derivative, a diarylethylene, a diarylpolyene, a diaryl-substituted vinylbenzene, a distyrylbenzene, a trivinylbenzene, an arylacetylene, a functional substitution product of stilbene, a five-, six- or seven-membered heterocyclic compound derivative, a furan derivative, a thiophene derivative, a pyrrole derivative, an aryl-substituted oxazole, a 1,3,4-oxadiazole, a 1,3,4-thiadiazole, an aryl-substituted 2-pyrazoline, an aryl-substituted pyrazole, a benzazole, 2H-benzotriazole, a substitution product of 2H-benzotriazole, a heterocycle with one, two or three nitrogen atoms, an oxygen-containing heterocycle, a coumarin, a coumarin derivative, a dye, an acridine dye, a xanthene dye, an oxazine, or a thiazine.

In another aspect, two or more of $R^a$ are optionally linked together, two or more of $R^b$ are optionally linked together, two or more of $R^c$ are optionally linked together, or any combination thereof.

Disclosed herein are metal-assisted delayed fluorescent and phosphorescent emitters, metal-assisted delayed fluorescent emitters or phosphorescent emitters of Formula B-I, Formula B-II and Formula B-III:

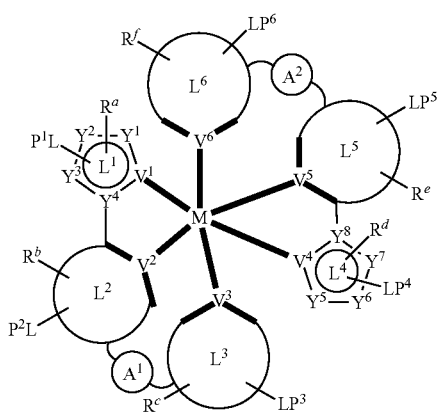

Formula B-I

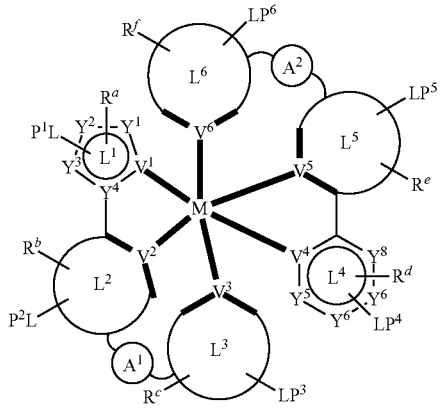

Formula B-II

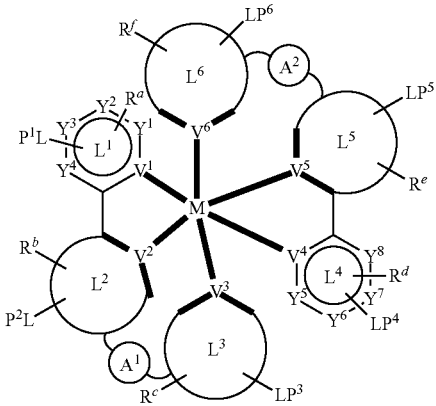

Formula B-III wherein:

M is Ir or Rh, each of $L^1$ and $L^4$ is independently a five-membered heterocyclyl, five-membered heteroaryl, five-membered carbene, five-membered N-heterocyclic carbene, six-membered aryl, or six-membered heteroaryl, each of $L^2$, $L^3$, $L^5$, and $L^6$ is independently substituted or unsubstituted aryl, cycloalkyl, cycloalkenyl, heteroaryl, heterocyclyl, carbene, or N-heterocyclic carbene, each of $LP^1$, $LP^2$, $LP^3$, $LP^4$, $LP^5$, and $LP^6$ is independently a fluorescent luminophore, each of $LP^1$, $LP^2$, $LP^3$, $LP^4$, $LP^5$, and $LP^6$ is independently present or absent, and at least one of $LP^1$, $LP^2$, $LP^3$, $LP^4$, $LP^5$, and $LP^6$ is present, each of $A^1$ and $A^2$ is independently $CH_2$, $CR^1R^2$, C=O, $CH_2$, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$, and $A^1$ optionally forms more than one bond with $L^2$, $L^3$, or both, thereby forming a ring system with $L^2$, a ring system with $L^3$, or both, and $A^2$ optionally forms more than one bond with $L^5$, $L^6$, or both, thereby forming a ring system with $L^5$, a ring system with $L^6$, or both, each of $V^1$, $V^2$, $V^3$, $V^4$, $V^5$, and $V^6$ is independently N, C, P, B, or Si, each of $Y^1$, $Y^2$, $Y^3$, $Y^4$, $Y^5$, $Y^6$, $Y^7$, and $Y^8$ is independently C, N, O, S, S=O, $SO_2$, Se, Se=O, $SeO_2$, $PR^3$, $R^3P$=O, $AsR^3$, $R^3As$=O, or $BR^3$, each of $R^a$, $R^b$, $R^c$, $R^d$, $R^e$, and $R^f$ is independently present or absent, and if present each of $R^a$, $R^b$, $R^c$, $R^d$, $R^e$, and $R^f$ is independently a mono-, di-, or tri-substitution, and each $R^a$, $R^b$, $R^c$, $R^d$, $R^e$, and $R^f$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, each of $LP^1$, $LP^2$, $LP^3$, $LP^4$, $LP^5$ and $LP^6$ is independently an aromatic hydrocarbon, an aromatic hydrocarbon derivative, a polyphenyl hydrocarbon, a hydrocarbon with condensed aromatic nuclei, naphthalene, anthracene, phenanthrene, chrysene, pyrene, triphenylene, perylene, acenaphthene, tetracene, pentacene, tetraphene, coronene, fluorene, biphenyl, p-terphenyl, o-diphenylbenzene, m-diphenylbenzene, p-quaterphenyl, benzo[a]tetracene, benzo[k]tetraphene, indeno[1,2,3-cd]fluoranthene, tetrabenzo[de,hi,op,st]pentacene, an arylethylene derivative, an arylacetylene derivative, a diarylethylene, a diarylpolyene, a diaryl-substituted vinylbenzene, a distyrylbenzene, a trivinylbenzene, an arylacetylene, a functional substitution product of stilbene, a five-, six- or seven-membered heterocyclic compound derivative, a furan derivative, a thiophene derivative, a pyrrole derivative, an aryl-substituted oxazole, an 1,3,4-oxadiazole, an 1,3,4-thiadiazole, an aryl-substituted 2-pyrazoline, an aryl-substituted pyrazole, a benzazole, 2H-benzotriazole, a substitution product of 2H-benzotriazole, a heterocycle with one, two, or three nitrogen atoms, an oxygen-containing heterocycle, a coumarin, a coumarin derivative, a dye, an acridine dye, a xanthene dye, an oxazine, or a thiazine.

In another aspect, two or more of $R^a$ are optionally linked together, two or more of $R^b$ are optionally linked together, two or more of $R^c$ are optionally linked together, two or more of $R^d$ are optionally linked together, two or more of $R^e$ are optionally linked together, two or more of $R^f$ are optionally linked together, or any combination thereof.

In some cases, the structures of Formulas B-I and B-III are symmetrical, and certain of the variables described herein are not independently selected. In one example, Formula B-I is symmetrical, and $A^1=A^2$, $L^1=L^4$, $L^2=L^5$, $L^3=L^6$, $LP^1=LP^4$, $LP^2=LP^5$, $LP^3=LP^6$, $R^a=R^d$, $R^b=R^e$, $R^c=R^e$, $V^1=V^4$, $V^2=V^5$, $V^3=V^6$, $Y^1=Y^5$, $Y^2=Y^6$, $Y^3=Y^7$, and $Y^4=Y^8$. In other cases, the structures of Formulas B-I and B-III are asymmetrical.

Also disclosed herein are compositions including one or more of the compounds disclosed herein, as well as devices, such as OLEDs, including one or more of the compounds or compositions disclosed herein.

Additional aspects will be set forth in the description which follows. Advantages will be realized and attained by means of the elements and combinations particularly pointed out in the claims. It is to be understood that both the foregoing general description and the following detailed description are exemplary and explanatory only and are not restrictive.

DETAILED DESCRIPTION

Figure 1:
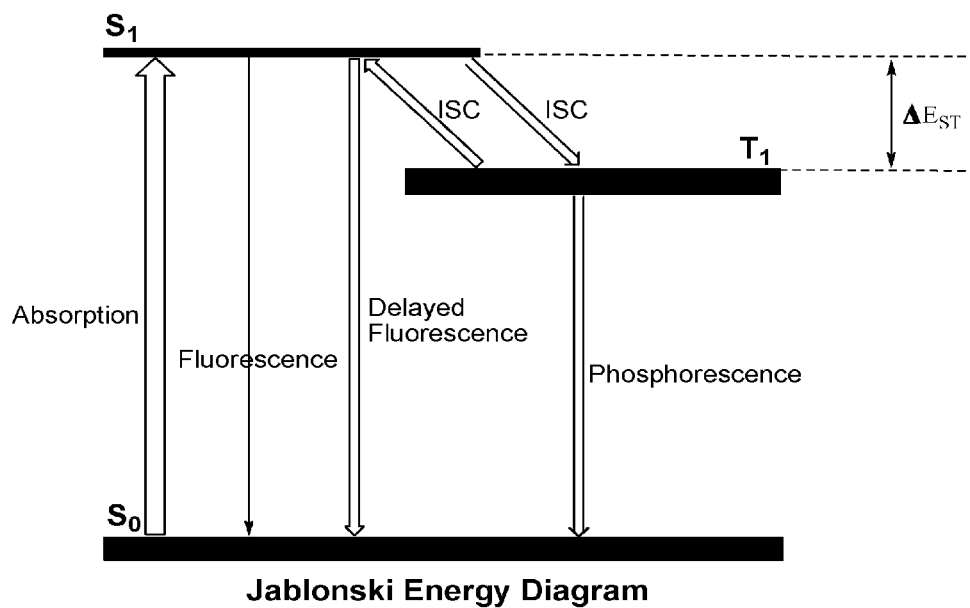
FIG. 1 is a Jablonski Energy Diagram depicting the emission pathways of fluorescence, phosphorescence, and delayed fluorescence.

This disclosure provides a materials design route to reduce the energy gap between the lowest triplet excited state and the lowest singlet excited state of the metal compounds to afford delayed fluorescent materials which can be an approach to solve the problems of the blue emitters. The present disclosure can be understood more readily by reference to the following detailed description and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the aspects of this disclosure, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" or "optionally" means that the subsequently described event or circumstance can or cannot occur, and that the description includes instances where said event or circumstance occurs and instances where it does not.

Disclosed are the components to be used to prepare the compositions disclosed herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

As referred to herein, a linking atom or group connects two atoms such as, for example, an N atom and a C atom. A linking atom or group is in one aspect disclosed as A, $A^1$, $A^2$, $A^3$, etc. herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties.

The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A," "$A^1$," and "$A^2$" or other designations are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C\!\!=\!\!C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "polymeric" includes polyalkylene, polyether, polyester, and other groups with repeating units, such as, but not limited to —(CH$_2$O)$_n$—CH$_3$, —(CH$_2$CH$_2$O)$_n$—CH$_3$, —[CH$_2$CH(CH$_3$)]$_n$—CH$_3$, —[CH$_2$CH(COOCH$_3$)]$_n$—CH$_3$, —[CH$_2$CH(COOCH$_2$CH$_3$)]$_n$—CH$_3$, and —[CH$_2$CH(COO$^t$Bu)]$_n$—CH$_3$, where n is an integer (e.g., n>1 or n>2).

The term "halide" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

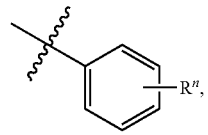

which is understood to be equivalent to a formula:

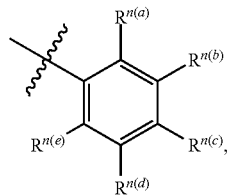

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to R, $R^1$, $R^2$, $R^3$, $R^4$, $R^5$, $R^6$, etc. are made in chemical structures and moieties disclosed and described herein. Any description of R, $R^1$, $R^2$, $R^3$, $R^4$, $R^5$, $R^6$, etc. in the specification is applicable to any structure or moiety reciting R, $R^1$, $R^2$, $R^3$, $R^4$, $R^5$, $R^6$, etc. respectively.

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Excitons decay from singlet excited states to the ground state to yield prompt luminescence, which is fluorescence. Excitons decay from triplet excited states to the ground state to generate luminescence, which is phosphorescence. Because the strong spin-orbit coupling of the heavy metal atom enhances intersystem crossing (ISC) very efficiently between singlet and triplet excited states, phosphorescent metal complexes, such as platinum, iridium and palladium complexes, have demonstrated their potential to harvest both the singlet and triplet excitons to achieve 100% internal quantum efficiency. Thus phosphorescent metal complexes are good candidates as dopants in the emissive layer of organic light emitting devices (OLEDs)

However, to date, blue electroluminescent devices remain the most challenging area of this technology, due at least in part to stability of the blue devices. It has been proved that the choice of host materials plays a role in the stability of the blue devices. But the lowest triplet excited state ($T_1$) energy of the blue phosphors is very high, which indicates that the lowest triplet excited state ($T_1$) energy of host materials for the blue devices should be even higher. As such, development of the host materials for the blue devices can be difficult.

This disclosure provides a materials design route by introducing fluorescent luminophore(s) to the ligand of the metal complexes. Thereby, chemical structures of the fluorescent luminophores and the ligands may be modified, and the metal can be changed to adjust the singlet state energy and the triplet state energy of the metal complexes, which all could affect the optical properties of the complexes and therefore properties such as emission and absorption spectra. The energy gap ($\Delta E_{ST}$) between the lowest triplet excited state ($T_1$) and the lowest singlet excited state ($S_1$) may also be adjusted. When $\Delta E_{ST}$ becomes small enough, intersystem crossing (ISC) from the lowest triplet excited state ($T_1$) to the lowest singlet excited state ($S_1$) occurs efficiently. Excitons can therefore undergo non-radiative relaxation via ISC from $T_1$ to $S_1$, then relax from $S_1$ to $S_0$, leading to delayed fluorescence (see FIG. 1). Through this pathway, higher energy excitons can be obtained from a lower excited state (from $T_1 \rightarrow S_1$), which means more host materials can be available for the dopants.

The metal complexes described herein can be tailored or tuned to a particular emission or absorption characteristic for a specific application. The optical properties of the metal complexes in this disclosure can be tuned by varying the structure of the ligand surrounding the metal center or varying the structure of fluorescent luminophore(s) on the ligands. For example, the metal complexes having a ligand with electron donating substituents or electron withdrawing substituents can be generally exhibit different optical properties, including emission and absorption spectra. The color of the metal complexes can be tuned by modifying the conjugated groups on the fluorescent luminophores and ligands.

The emission of complexes described herein can be tuned, for example, from the ultraviolet to near-infrared, by, for example, modifying the ligand or fluorescent luminophore structure. A fluorescent luminophore is a group of atoms in an organic molecule that can absorb energy to generate singlet excited state(s). The singlet exciton(s) produce(s) decay rapidly to yield prompt luminescence. In one aspect, the complexes provide emission over a majority of the visible spectrum. In one example, the complexes described herein emit light over a range of from about 400 nm to about 700 nm. In another aspect, the complexes described herein have improved stability and efficiency over traditional emission complexes. In yet another aspect, the complexes are useful as luminescent labels in, for example, bio-applications, anti-cancer agents, emitters in organic light emitting diodes (OLEDs), or a combination thereof. In another aspect, the complexes described herein suitable for light emitting devices, such as, for example, compact fluorescent lamps (CFL), light emitting diodes (LED), incandescent lamps, and the like.

Disclosed herein are compounds, compound complexes, or complexes including platinum, palladium, gold, iridium, and rhodium. The terms "compound," "complex," and "compound complex" are used interchangeably herein. In one aspect, the compounds disclosed herein have a neutral charge.

The compounds disclosed herein exhibit desirable properties and have emission and/or absorption spectra that can be tuned via the selection of appropriate ligands. The compounds disclosed herein include delayed fluorescent emitters, phosphorescent emitters, or a combination thereof. In one aspect, the compounds disclosed herein are delayed fluorescent emitters. In another aspect, the compounds disclosed herein are phosphorescent emitters. In yet another aspect, a compound disclosed herein is both a delayed fluorescent emitter and a phosphorescent emitter. In another aspect, any one or more of the compounds, structures, or portions thereof, specifically recited herein, can be excluded.

The compounds disclosed herein are suited for use in a wide variety of optical and electro-optical devices, including, but not limited to, photo-absorbing devices such as solar- and photo-sensitive devices, organic light emitting diodes (OLEDs), photo-emitting devices, luminescent devices and displays, full color displays, and devices capable of both photo-absorption and emission and as markers for bio-applications. In another aspect, the compounds provide improved efficiency and/or operational lifetimes in lighting devices, such as, for example, organic light emitting devices, as compared to conventional materials.

The compounds described herein can be made using a variety of methods, including, but not limited to those recited in the Examples.

Metal-assisted delayed fluorescent and phosphorescent emitters, metal-assisted delayed fluorescent emitters, and phosphorescent emitters include compounds of Formula A-I and Formula A-II:

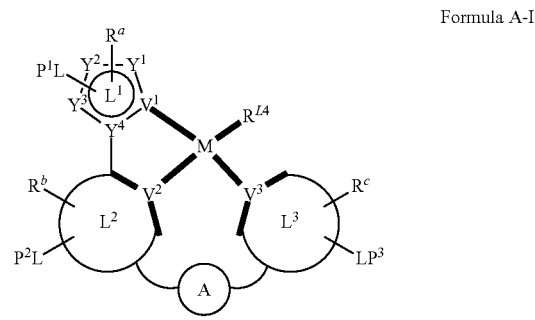

Formula A-I

Formula A-II

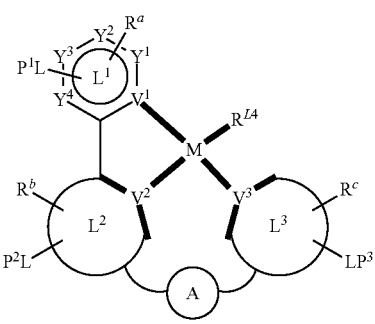

wherein:

M is Pt, Pd, or Au,

L$^1$ is a five-membered heterocyclyl, five-membered heteroaryl, five-membered carbene, five-membered N-heterocyclic carbene, a six-membered aryl, or six-membered heteroaryl, each of L$^2$ and L$^3$ is independently substituted or unsubstituted aryl, cycloalkyl, cycloalkenyl, heteroaryl, heterocyclyl, carbene, or N-heterocyclic carbene, R$^{L4}$ is an inorganic anion or organic anion as defined herein, each of LP$^1$, LP$^2$, and LP$^3$ is independently a fluorescent luminophore, each of LP$^1$, LP$^2$, and LP$^3$ is independently present or absent, and at least one of LP$^1$, LP$^2$, or LP$^3$ is present, A is CH$_2$, CR$^1$R$^2$, C=O, CH$_2$, SiR$^1$R$^2$, GeH$_2$, GeR$^1$R$^2$, NH, NR$^3$, PH, PR$^3$, R$^3$P=O, AsR$^3$, R$^3$As=O, O, S, S=O, SO$_2$, Se, Se=O, SeO$_2$, BH, BR$^3$, R$^3$Bi=O, BiH, or BiR$^3$, and optionally forms more than one bond with L$^2$, L$^3$, or both, thereby forming a ring system with L$^2$, a ring system with L$^3$, or both, each of V$^1$, V$^2$, and V$^3$ is independently N, C, P, B, or Si, each of Y$^1$, Y$^2$, Y$^3$, and Y$^4$ is independently C, N, O, S, S=O, SO$_2$, Se, Se=O, SeO$_2$, PR$^3$, R$^3$P=O, AsR$^3$, R$^3$As=O, or BR$^3$, each of R$^a$, R$^b$, and R$^c$ is independently present or absent, and if present each of R$^a$, R$^b$, and R$^c$ independently represents mono-, di-, or tri-substitutions, and each of R$^a$, R$^b$, and R$^c$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of R$^1$, R$^2$, and R$^3$ is independently hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, monoalkylamino, dialkylamino, monoarylamino, diarylamino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, mercapto, sulfo, carboxyl, hydrazino, substituted silyl, or polymeric; or any conjugate or combination thereof.

In one aspect, each of LP$^1$, LP$^2$ and LP$^3$ is independently an aromatic hydrocarbon, an aromatic hydrocarbon derivative, a polyphenyl hydrocarbon, a hydrocarbon with condensed aromatic nuclei, naphthalene, anthracene, phenanthrene, chrysene, pyrene, triphenylene, perylene, acenaphthene, tetracene, pentacene, tetraphene, coronene, fluorene, biphenyl, p-terphenyl, o-diphenylbenzene, m-diphenylbenzene, p-quaterphenyl, benzo[a]tetracene, benzo[k]tetraphene, indeno[1,2,3-cd]fluoranthene, tetrabenzo[de,hi,op,st]pentacene, arylethylene, arylacetylene, an arylacetylene derivative, a diarylethylene, a diarylpolyene, a diaryl-substituted vinylbenzene, a distyrylbenzene, a trivinylbenzene, an arylacetylene, a functional substitution product of stilbene, a five-, six- or seven-membered heterocyclic compound derivative, a furan derivative, a thiophene derivative, a pyrrole derivative, an aryl-substituted oxazole, a 1,3,4-oxadiazole, a 1,3,4-thiadiazole, an aryl-substituted 2-pyrazoline, an aryl-substituted pyrazole, a benzazole, 2H-benzotriazole, a substitution product of 2H-benzotriazole, a heterocycle with one, two or three nitrogen atoms, an oxygen-containing heterocycle, a coumarin, a coumarin derivative, a dye, an acridine dye, a xanthene dye, an oxazine, or a thiazine.

In some cases, two or more of R$^a$ are optionally linked together, two or more of R$^b$ are optionally linked together, two or more of R$^c$ are optionally linked together, or any combination thereof.

In another aspect, metal-assisted delayed fluorescent and phosphorescent emitters, metal-assisted delayed fluorescent emitters or phosphorescent emitters have the structure of one of Formulas A-1-A-10:

A-1

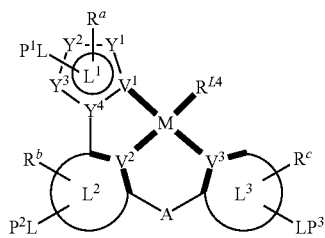

A-2

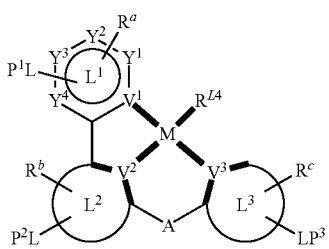

A-3

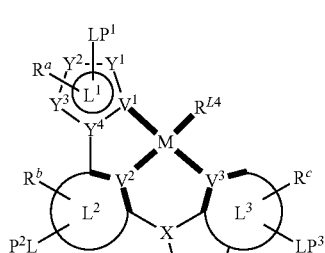

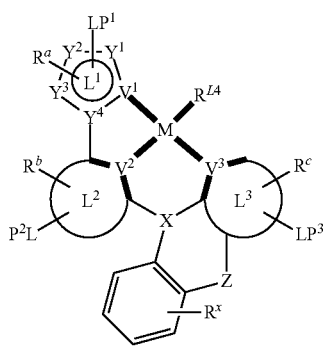

A-4

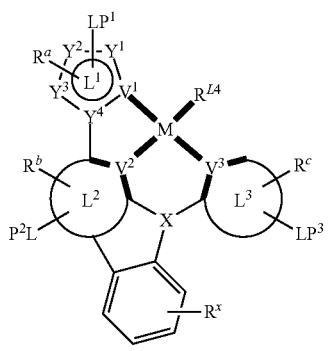

A-5

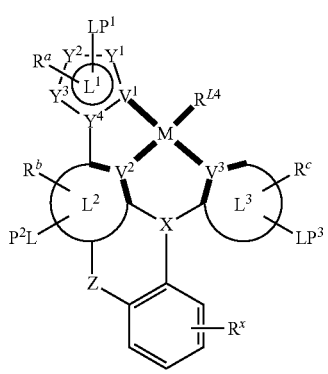

A-6

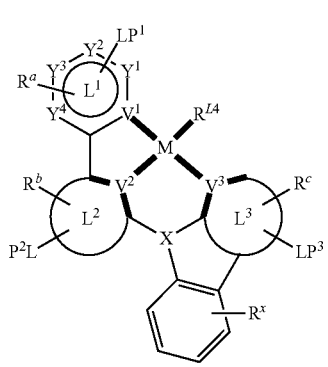

A-7

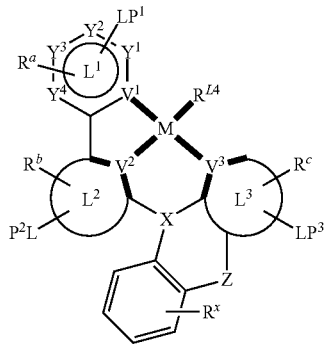

A-8

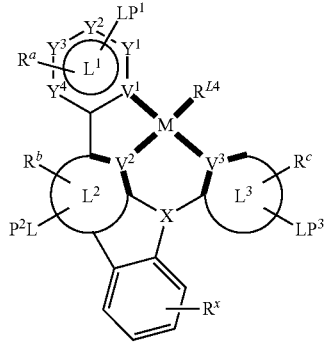

A-9

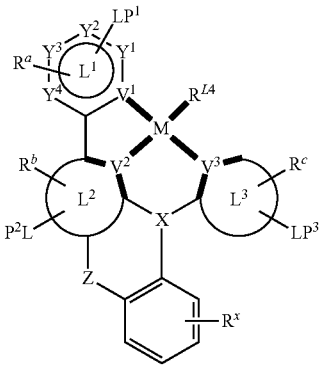

A-10

M is Pt, Pd, or Au, $L^1$ is a five-membered heterocyclyl, five-membered heteroaryl, five-membered carbene, five-membered N-heterocyclic carbene, a six-membered aryl, or six-membered heteroaryl, each of $L^2$ and $L^3$ is independently substituted or unsubstituted aryl, cycloalkyl, cycloalkenyl, heteroaryl, heterocyclyl, carbene, or N-heterocyclic carbene, $R^{L4}$ is an inorganic anion or organic anion, each of $LP^1$, $LP^2$, and $LP^3$ is independently a fluorescent luminophore, each of $LP^1$, $LP^2$, and $LP^3$ is independently present or absent, and at least one of $LP^1$, $LP^2$, or $LP^3$ is present, A is $CH_2$, $CR^1R^2$, $C=O$, $CH_2$, $SiR^1R^2$, $GeH_2$, $GeR^1R^2$, NH, $NR^3$, PH, $PR^3$, $R^3P=O$, $AsR^3$, $R^3As=O$, O, S, $S=O$, $SO_2$, Se, $Se=O$, $SeO_2$, BH, $BR^3$, $R^3Bi=O$, BiH, or $BiR^3$, each of $V^1$, $V^2$, and $V^3$ is independently N, C, P, B, or Si, each of $Y^1$, $Y^2$, $Y^3$, and $Y^4$ is independently C, N, O, S, $S=O$, $SO_2$, Se, $Se=O$, $SeO_2$, $PR^3$, $R^3P=O$, $AsR^3$, $R^3As=O$, or $BR^3$, each of $R^a$, $R^b$, and $R^c$ is independently present or absent, and if present each of $R^a$, $R^b$ and $R^c$ is independently a mono-, di-, tri-, or tetra-substitution, valency permitting, and each $R^a$, $R^b$, and $R^c$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, $R^x$ is present or absent, and if present $R^x$ is a mono-, di-, tri-, tetra-, or penta-substitution, and each $R^x$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, X is N, P, P=O, As, As=O, $CR^1$, CH, $SiR^1$, SiH, $GeR^1$, GeH, B, Bi, or Bi=O, and Z is a linking atom or a linking group, and each of $R^1$, $R^2$, and $R^3$ is independently hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, monoalkylamino, dialkylamino, monoarylamino, diarylamino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, mercapto, sulfo, carboxyl, hydrazino, substituted ilyl, or polymeric; or any conjugate or combination thereof. In one aspect, each of $LP^1$, $LP^2$ and $LP^3$ is independently an aromatic hydrocarbon, an aromatic hydrocarbon derivative, a polyphenyl hydrocarbon, a hydrocarbon with condensed aromatic nuclei, naphthalene, anthracene, phenanthrene, chrysene, pyrene, triphenylene, perylene, acenaphthene, tetracene, pentacene, tetraphene, coronene, fluorene, biphenyl, p-terphenyl, o-diphenylbenzene, m-diphenylbenzene, p-quaterphenyl, benzo[a]tetracene, benzo[k]tetraphene, indeno[1,2,3-cd]fluoranthene, tetrabenzo[de,hi,op,st]pentacene, arylethylene, arylacetylene, an arylacetylene derivative, a diarylethylene, a diarylpolyene, a diaryl-substituted vinylbenzene, a distyrylbenzene, a trivinylbenzene, an arylacetylene, a functional substitution product of stilbene, a five-, six- or seven-membered heterocyclic compound derivative, a furan derivative, a thiophene derivative, a pyrrole derivative, an aryl-substituted oxazole, a 1,3,4-oxadiazole, a 1,3,4-thiadiazole, an aryl-substituted 2-pyrazoline, an aryl-substituted pyrazole, a benzazole, 2H-benzotriazole, a substitution product of 2H-benzotriazole, a heterocycle with one, two or three nitrogen atoms, an oxygen-containing heterocycle, a coumarin, a coumarin derivative, a dye, an acridine dye, a xanthene dye, an oxazine, or a thiazine.

In another aspect, two or more of $R^a$ are optionally linked together, two or more of $R^b$ are optionally linked together, two or more of $R^c$ are optionally linked together, or any combination thereof.

Disclosed herein are metal-assisted delayed fluorescent and phosphorescent emitters, metal-assisted delayed fluorescent emitters or phosphorescent emitters of Formula B-I, Formula B-II, and Formula B-III:

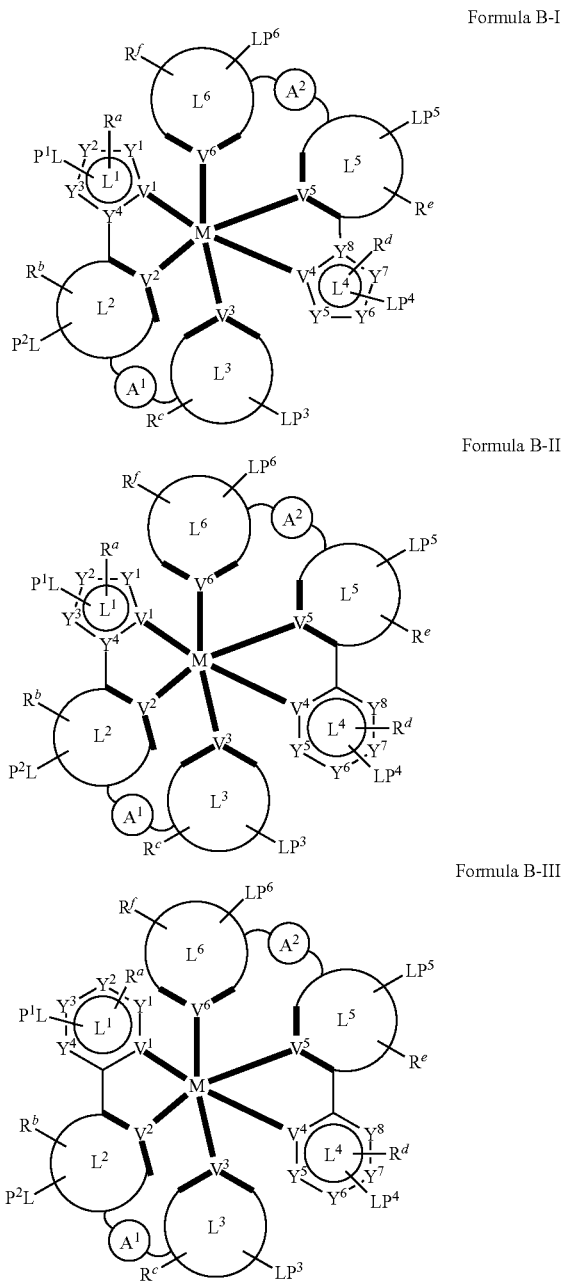

wherein:
M is Ir or Rh,
each of $L^1$ and $L^4$ is independently a five-membered heterocyclyl, five-membered heteroaryl, five-membered carbene, five-membered N-heterocyclic carbene, six-membered aryl, or six-membered heteroaryl,
each of $L^2$, $L^3$, $L^5$, and $L^6$ is independently substituted or unsubstituted aryl, cycloalkyl, cycloalkenyl, heteroaryl, heterocyclyl, carbene, or N-heterocyclic carbene,
each of $LP^1$, $LP^2$, $LP^3$, $LP^4$, $LP^5$, and $LP^6$ is independently a fluorescent luminophore, each of $LP^1$, $LP^2$, $LP^3$, $LP^4$, $LP^5$, and $LP^6$ is independently present or absent, and at least one of $LP^1$, $LP^2$, $LP^3$, $LP^4$, $LP^5$, and $LP^6$ is present, each of $A^1$ and $A^2$ is independently $CH_2$, $CR^1R^2$, $C=O$, $CH_2$, $SiR^1R^2$, $GeH_2$, $GeR^1R^2$, NH, $NR^3$, PH, $PR^3$, $R^3P=O$, $AsR^3$, $R^3As=O$, O, S, $S=O$, $SO_2$, Se, $Se=O$, $SeO_2$, BH, $BR^3$, $R^3Bi=O$, BiH, or $BiR^3$, and $A^1$ optionally forms more than one bond with $L^2$, $L^3$, or both, thereby forming a ring system with $L^2$, a ring system with $L^3$, or both, and $A^2$ optionally forms more than one bond with $L^5$, $L^6$, or both, thereby forming a ring system with $L^5$, a ring system with $L^6$, or both, each of $V^1$, $V^2$, $V^3$, $V^4$, $V^5$, and $V^6$ is independently N, C, P, B, or Si, each of $Y^1$, $Y^2$, $Y^3$, $Y^4$, $Y^5$, $Y^6$, $Y^7$, and $Y^8$ is independently C, N, O, S, $S=O$, $SO_2$, Se, $Se=O$, $SeO_2$, $PR^3$, $R^3P=O$, $AsR^3$, $R^3As=O$, or $BR^3$, each of $R^a$, $R^b$, $R^c$, $R^d$, $R^e$, and $R^f$ is independently present or absent, and if present each of $R^a$, $R^b$, $R^c$, $R^d$, $R^e$, and $R^f$ is independently a mono-, di-, or tri-substitution, and each $R^a$, $R^b$, $R^c$, $R^d$, $R^e$, and $R^f$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In some cases, the structures of Formulas B-I and B-III are symmetrical, and certain of the variables described herein are not independently selected. In one example, Formula B-I is symmetrical, and $A^1=A^2$, $L^1=L^4$, $L^2=L^5$, $L^3=L^6$, $LP^1=LP^4$, $LP^2=LP^5$, $LP^3=LP^6$, $R^a=R^d$, $R^b=R^e$, $R^c=R^e$, $V^1=V^4$, $V^2=V^5$, $V^3=V^6$, $Y^1=Y^5$, $Y^2=Y^6$, $Y^3=Y^7$, and $Y^4=Y^8$. In other cases, the structures of Formulas B-I and B-III are asymmetrical.

In one aspect, each of $LP^1$, $LP^2$, $LP^3$, $LP^4$, $LP^5$, and $LP^6$ is independently an aromatic hydrocarbon, an aromatic hydrocarbon derivative, a polyphenyl hydrocarbon, a hydrocarbon with condensed aromatic nuclei, naphthalene, anthracene, phenanthrene, chrysene, pyrene, triphenylene, perylene, acenaphthene, tetracene, pentacene, tetraphene, coronene, fluorene, biphenyl, p-terphenyl, o-diphenylbenzene, m-diphenylbenzene, p-quaterphenyl, benzo[a]tetracene, benzo[k]tetraphene, indeno[1,2,3-cd]fluoranthene, tetrabenzo[de,hi,op,st]pentacene, an arylethylene derivative, an arylacetylene derivative, a diarylethylene, a diarylpolyene, a diaryl-substituted vinylbenzene, a distyrylbenzene, a trivinylbenzene, an arylacetylene, a functional substitution product of stilbene, a five-, six- or seven-membered heterocyclic compound derivative, a furan derivative, a thiophene derivative, a pyrrole derivative, an aryl-substituted oxazole, an 1,3,4-oxadiazole, an 1,3,4-thiadiazole, an aryl-substituted 2-pyrazoline, an aryl-substituted pyrazole, a benzazole, 2H-benzotriazole, a substitution product of 2H-benzotriazole, a heterocycle with one, two, or three nitrogen atoms, an oxygen-containing heterocycle, a coumarin, a coumarin derivative, a dye, an acridine dye, a xanthene dye, an oxazine, or a thiazine.

In another aspect, two or more of $R^a$ are optionally linked together, two or more of $R^b$ are optionally linked together, two or more of $R^c$ are optionally linked together, two or more of $R^d$ are optionally linked together, two or more of $R^e$ are optionally linked together, two or more of $R^f$ are optionally linked together, or any combination thereof.

The metal-assisted delayed fluorescent and phosphorescent emitters, metal-assisted delayed fluorescent emitters or phosphorescent emitters of Formula B-I, Formula B-II, and Formula B-III may have the structure of any of symmetrical formulas B-1-B-10 or asymmetrical formulas B-11-B-65:

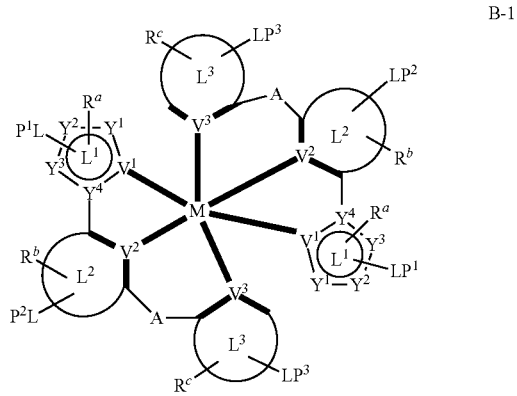

B-1

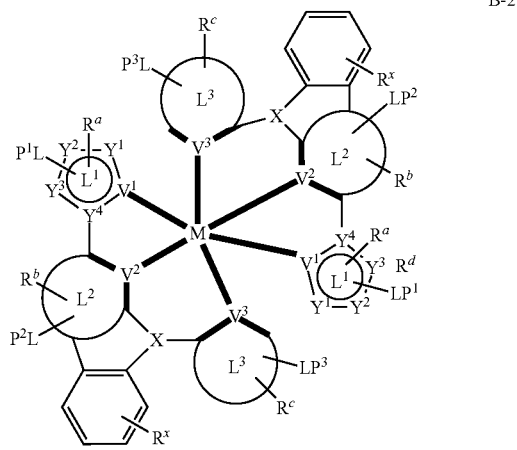

B-2

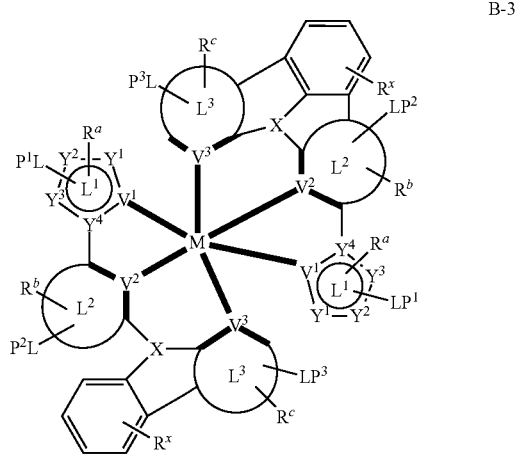

B-3

B-4
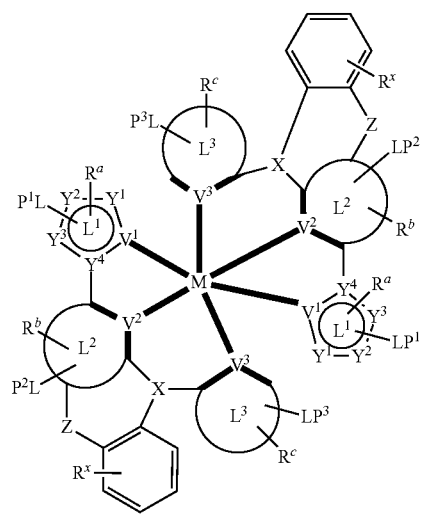
B-7
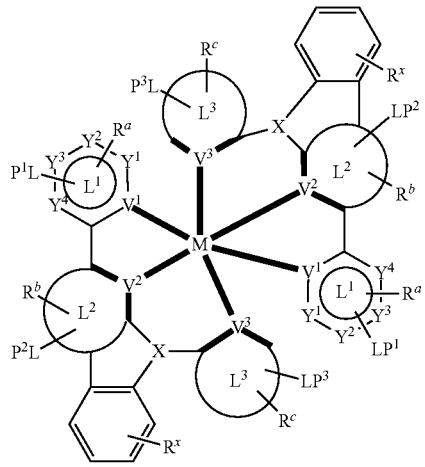
B-5
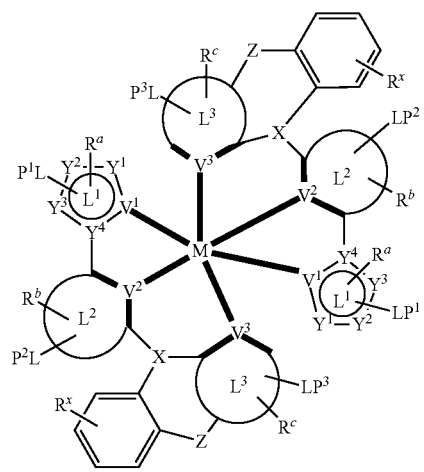
B-8
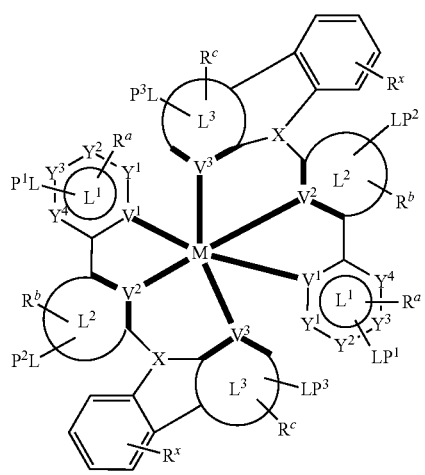
B-6
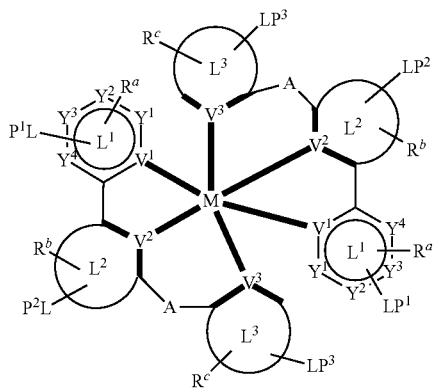
B-9
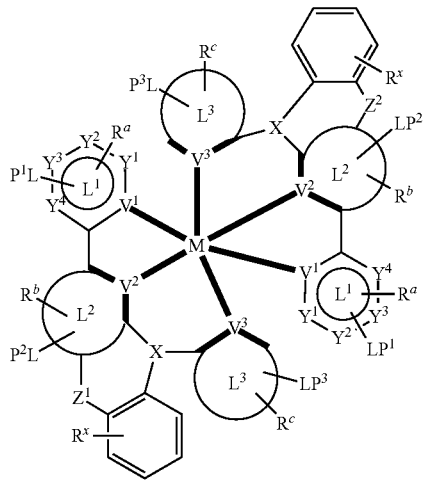

B-10
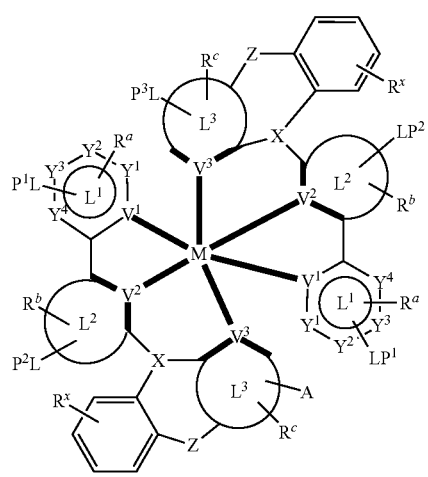
B-13
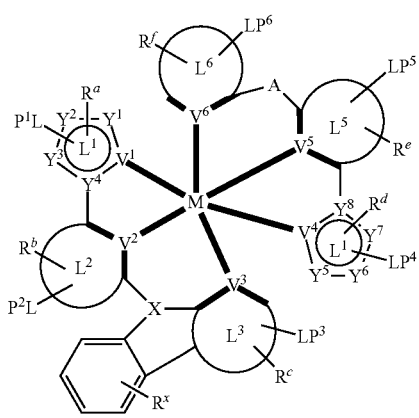
B-11
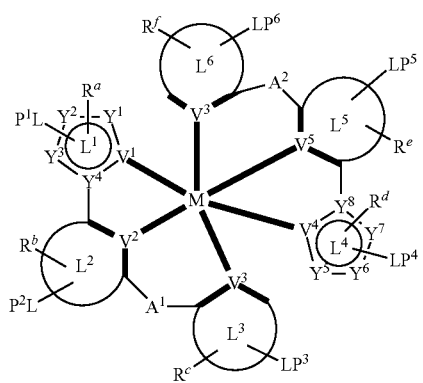
B-14
B-12
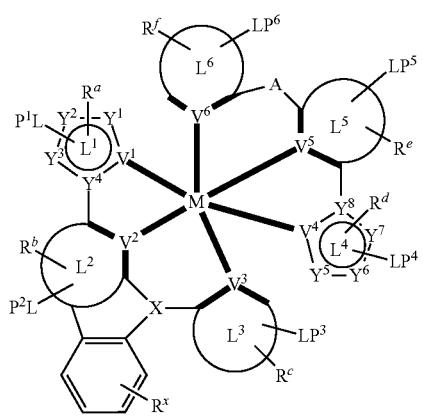
B-15
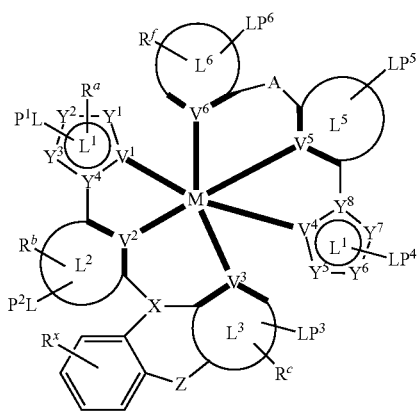

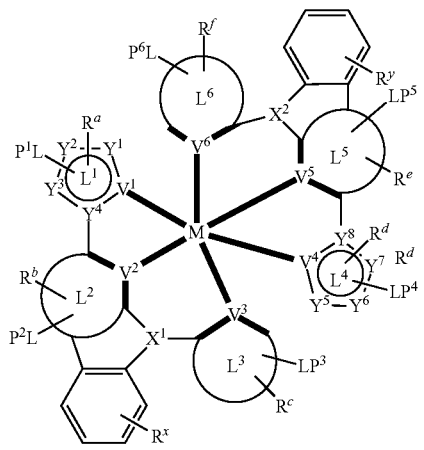
B-16
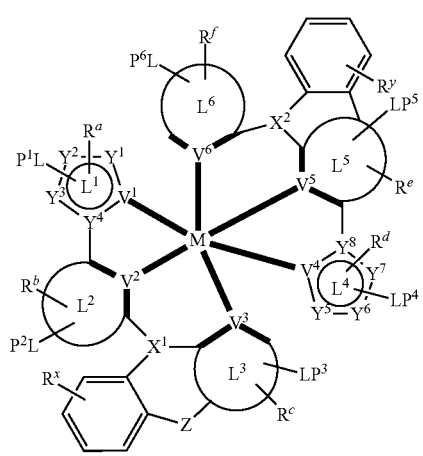
B-19
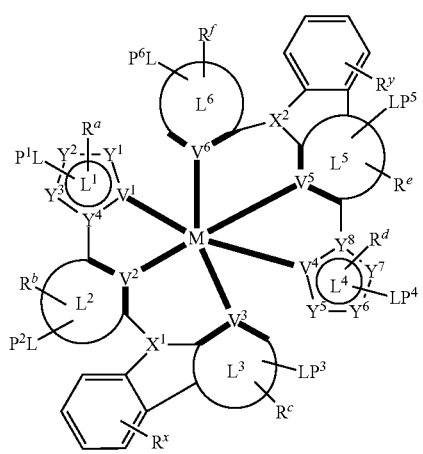
B-17
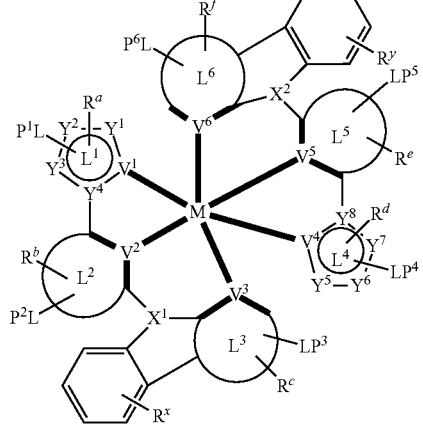
B-20
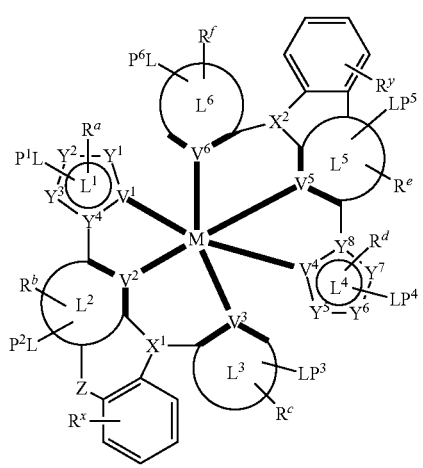
B-18
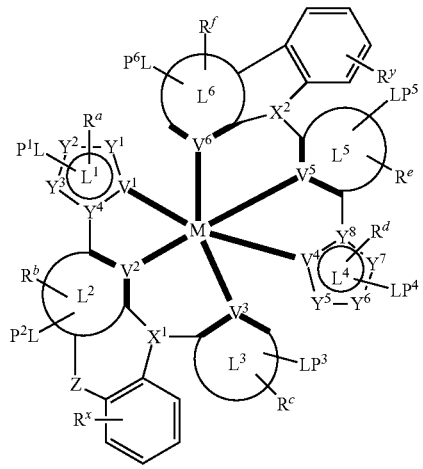
B-21

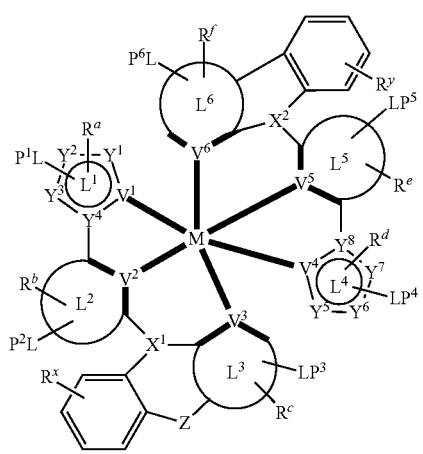
B-22
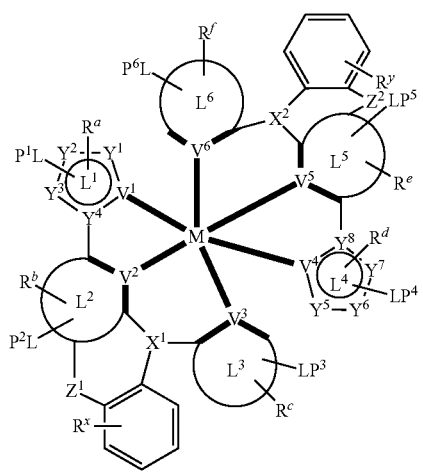
B-23
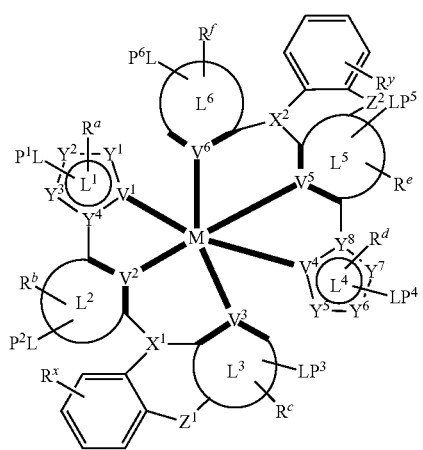
B-24
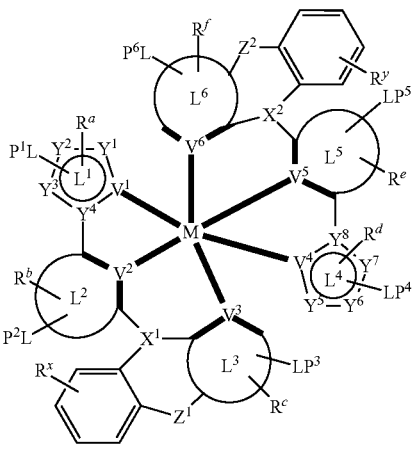
B-25
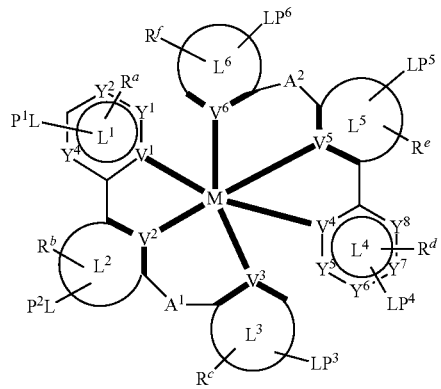
B-26
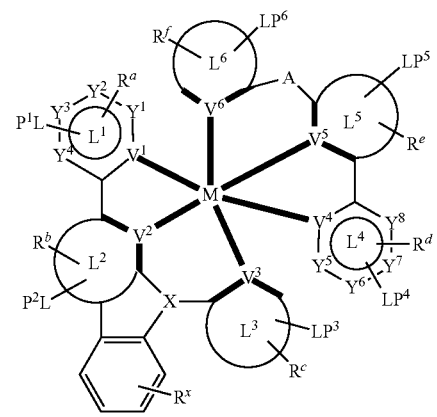
B-27

B-28
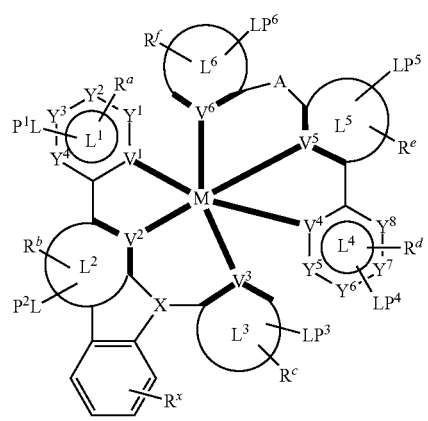
B-29
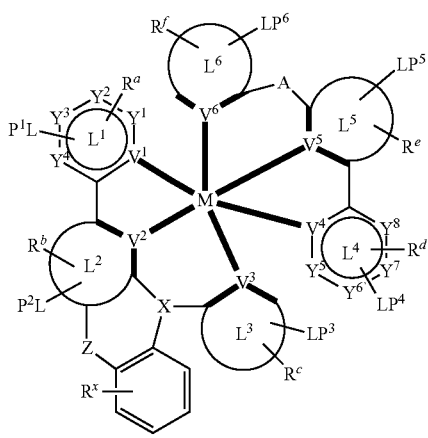
B-30
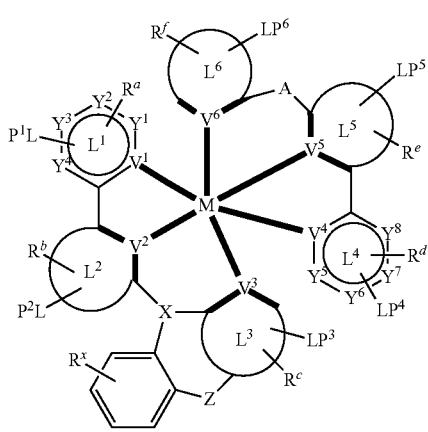
B-31
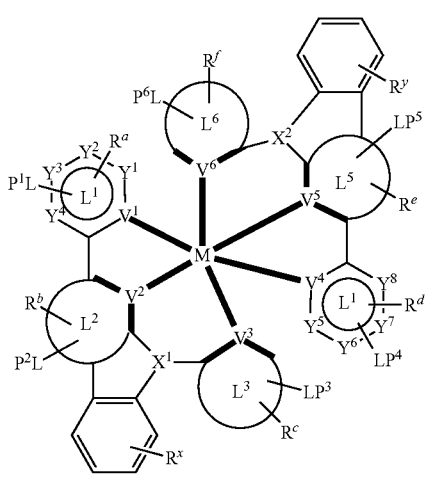
B-32
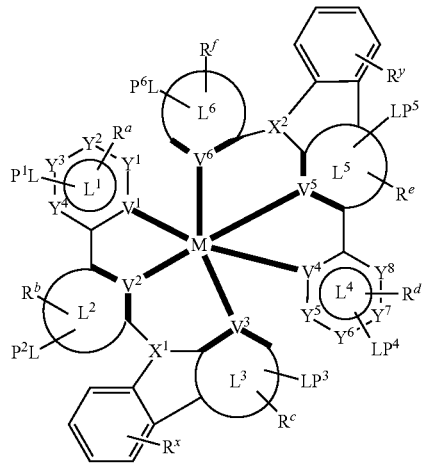
B-33
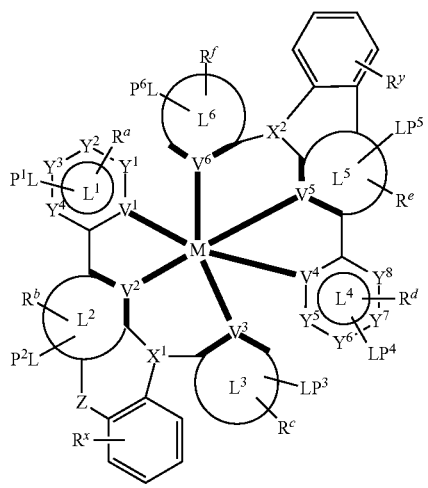

B-34
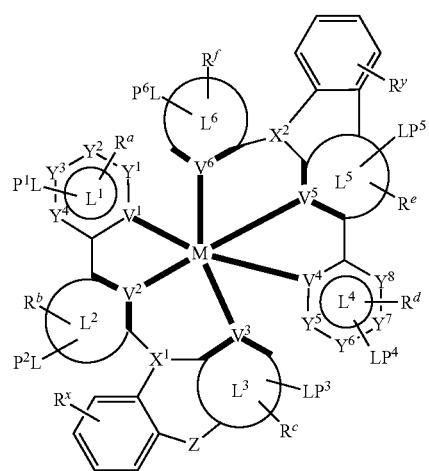
B-35
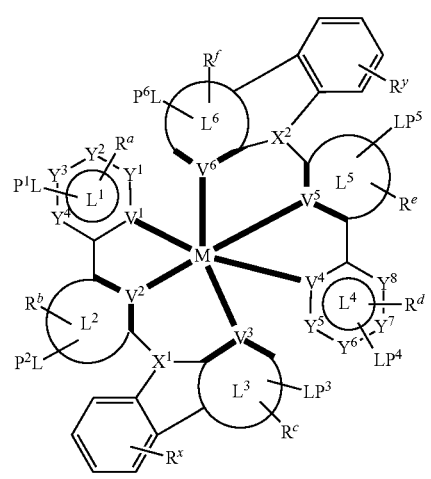
B-36
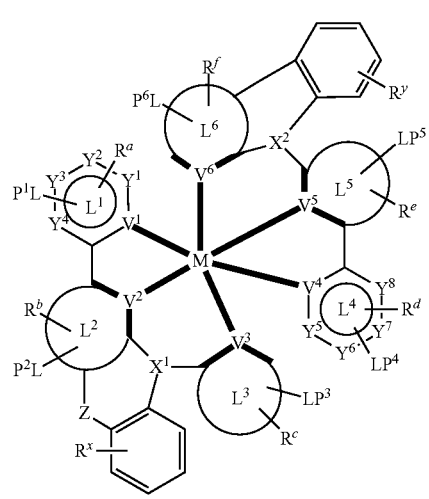
B-37
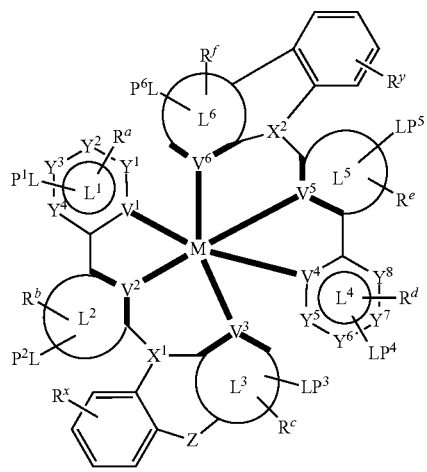
B-39
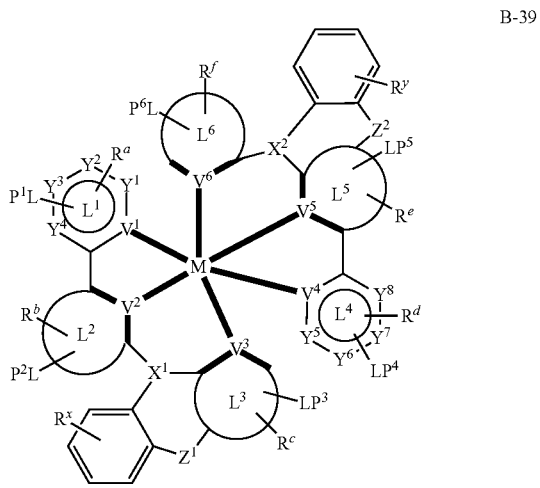
B-40
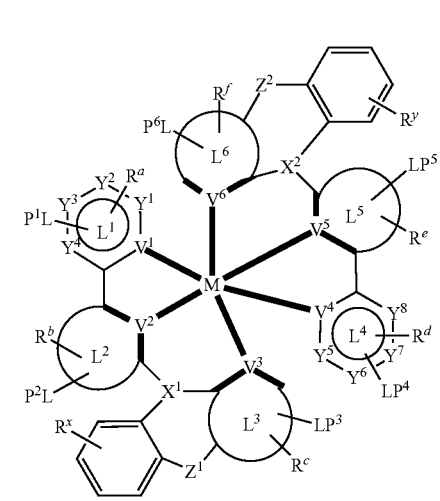

B-41
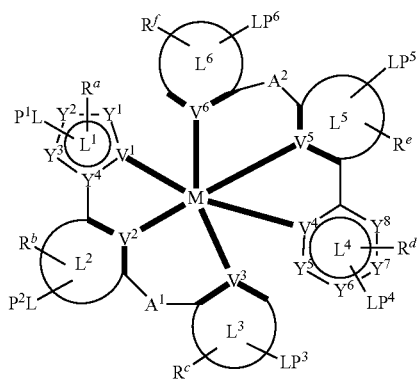
B-42
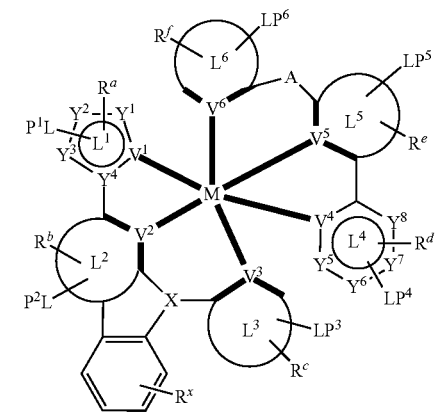
B-43

B-44
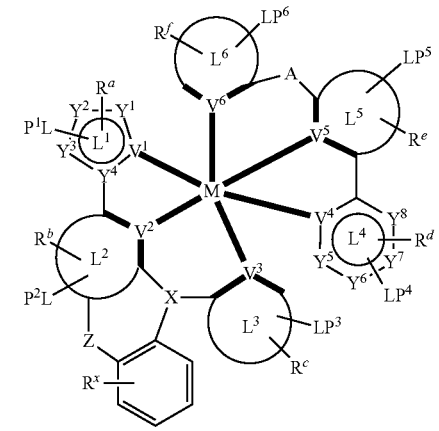
B-45
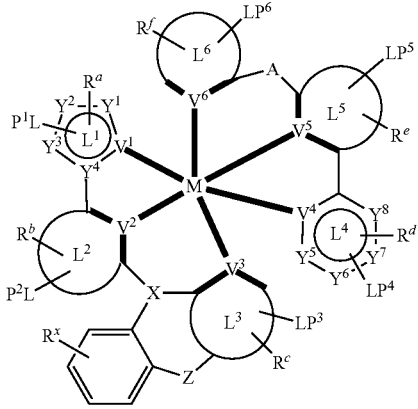
B-46
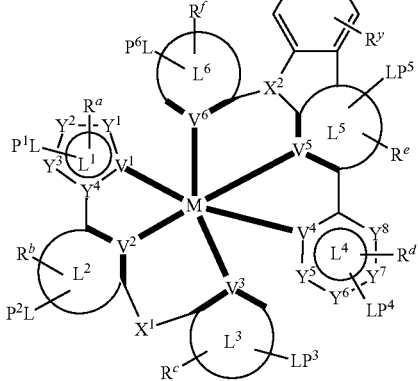
B-47
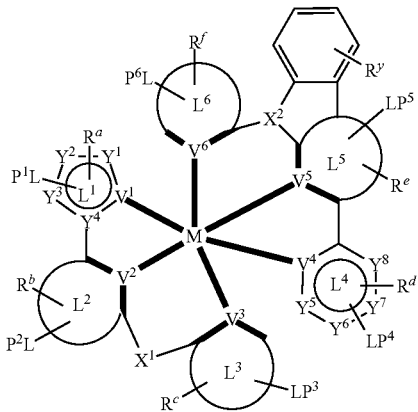

B-48
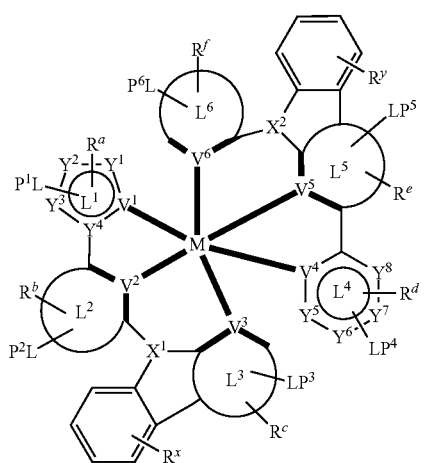
B-49
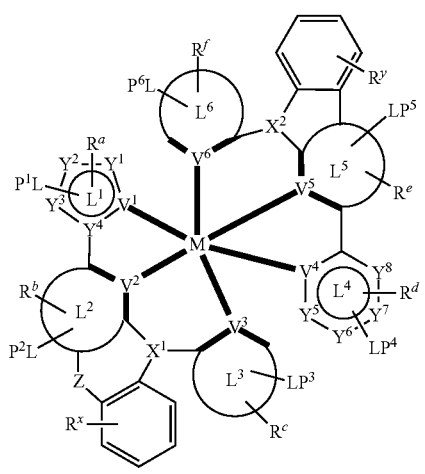
B-50
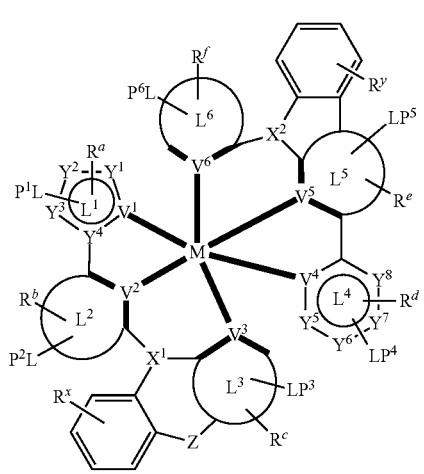
B-51
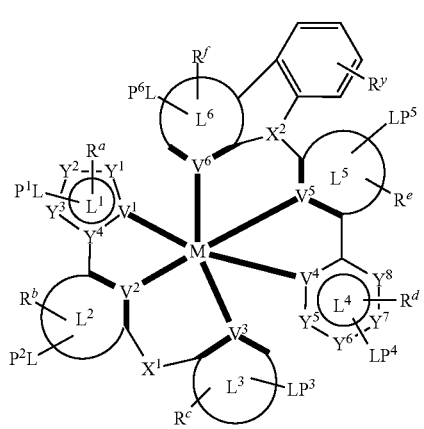
B-52
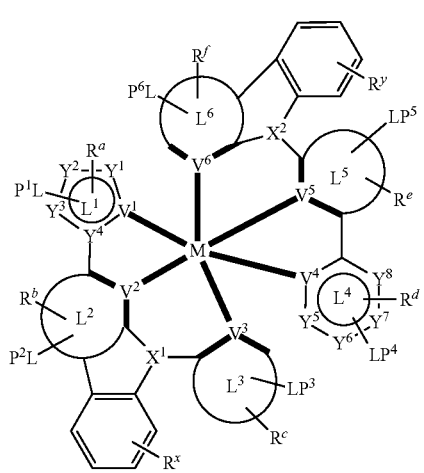
B-53
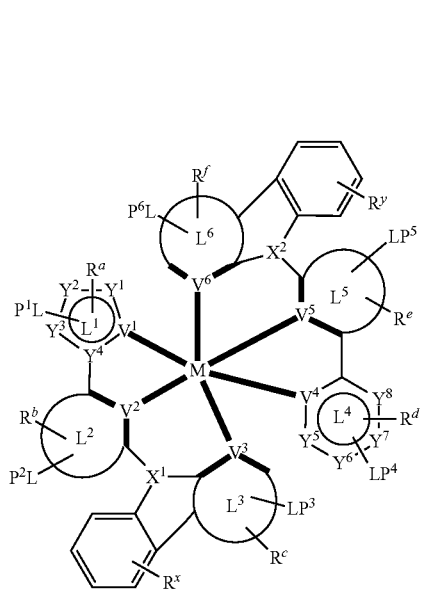

B-54
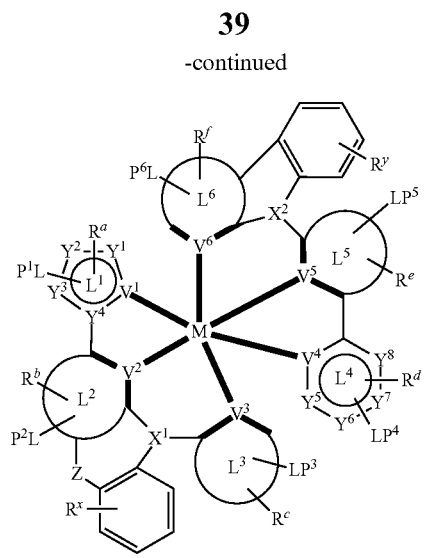
B-57
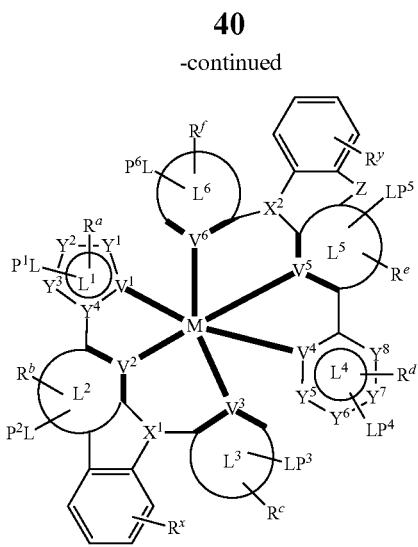
B-55
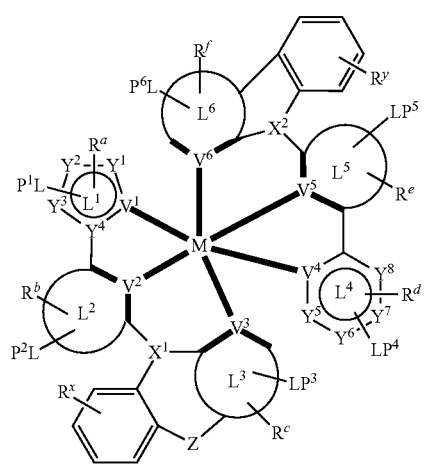
B-58
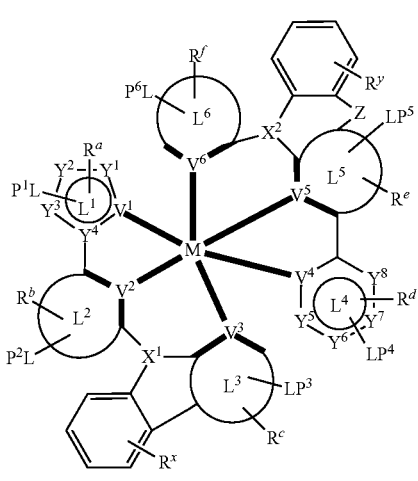
B-56
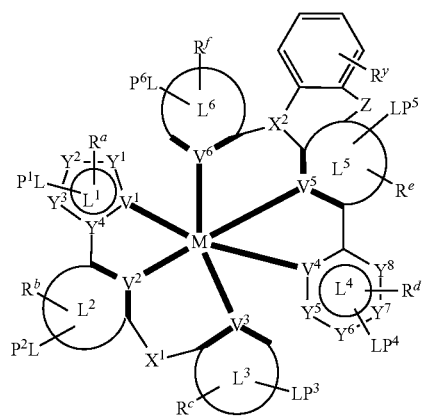
B-59
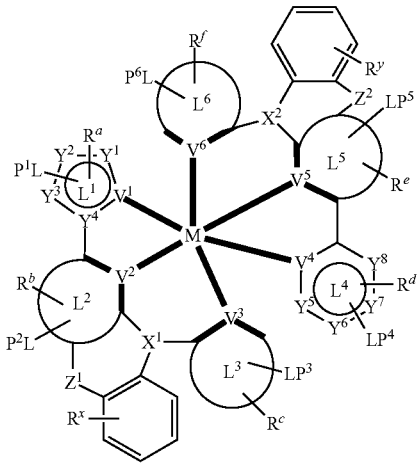

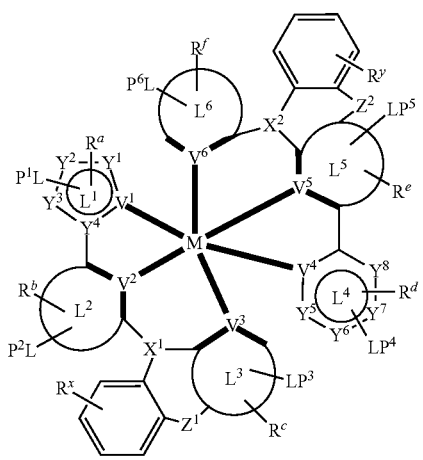

B-60

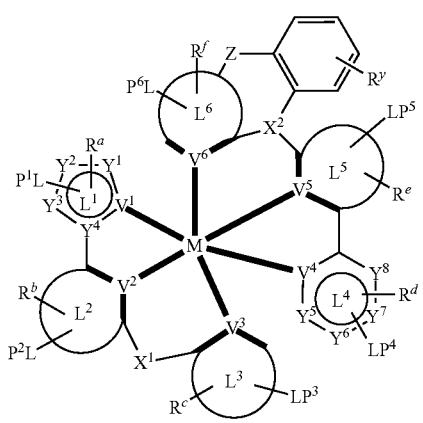

B-61

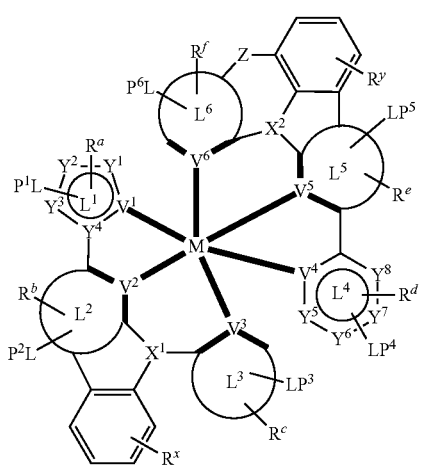

B-62

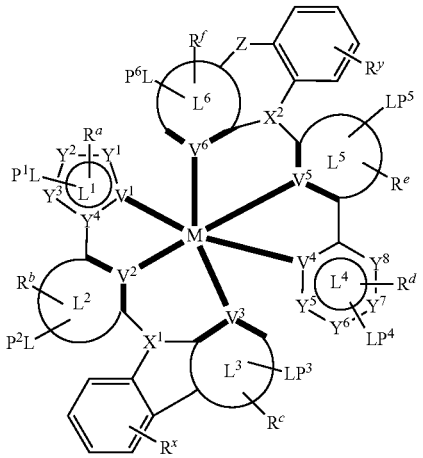

B-63

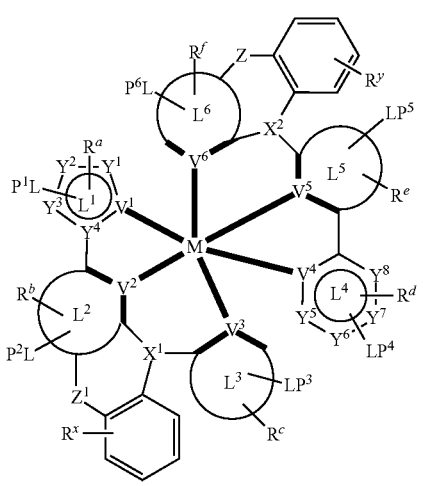

B-64

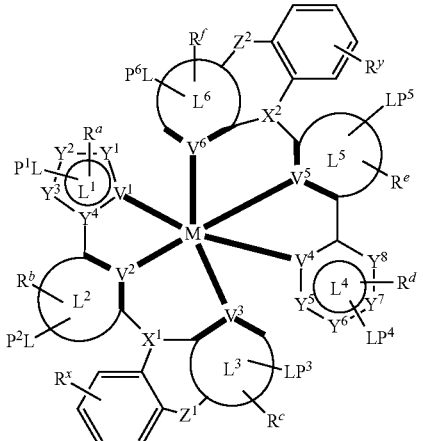

B-65 wherein Formulas B-1 through B-10 are symmetrical, and for Formulas B-1 through B10:

M is Ir or Rh, $L^1$ and $L^4$ are five-membered heterocyclyl, five-membered heteroaryl, five-membered carbene, five-membered N-heterocyclic carbene, six-membered aryl, or six-membered heteroaryl, each of $L^2$ and $L^3$ is independently substituted or unsubstituted aryl, cycloalkyl, cycloalkenyl, heteroaryl, heterocyclyl, carbene, or N-heterocyclic carbene, each of LP$^1$, LP$^2$, and LP$^3$ is independently a fluorescent luminophore, each of LP$^1$, LP$^2$, and LP$^3$ is independently present or absent, and at least one of LP$^1$, LP$^2$, and LP$^3$ is present, A is CH$_2$, CR$^1$R$^2$, C=O, CH$_2$, SiR$^1$R$^2$, GeH$_2$, GeR$^1$R$^2$, NH, NR$^3$, PH, PR$^3$, R$^3$P=O, AsR$^3$, R$^3$As=O, O, S, S=O, SO$_2$, Se, Se=O, SeO$_2$, BH, BR$^3$, R$^3$Bi=O, BiH, or BiR$^3$, each of V$^1$, V$^2$, and V$^3$ is independently N, C, P, B, or Si, each of Y$^1$, Y$^2$, Y$^3$, and Y$^4$ is independently C, N, O, S, S=O, SO$_2$, Se, Se=O, SeO$_2$, PR$^3$, R$^3$P=O, AsR$^3$, R$^3$As=O, or BR$^3$, each of R$^a$, R$^b$, and R$^c$ is independently present or absent, and if present each of R$^a$, R$^b$, and R$^c$ is independently a mono-, di-, or tri-substitution, and each R$^a$, R$^b$, and R$^c$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, each of R$^1$, R$^2$, and R$^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, X is N, P, P=O, As, As=O, CR$^1$, CH, SiR$^1$, SiH, GeR$^1$, GeH, B, Bi, or Bi=O, each of Z is a linking atom or linking group, and R$^x$ is present or absent, and if present each R$^x$ is a mono-, di-, tri-, or tetra-substitution, and each R$^x$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof;

wherein Formulas B-11 through B-65 are asymmetrical, and for Formulas B-11 through B-65:

M is Ir or Rh, each of L$^1$ and L$^4$ is independently a five-membered heterocyclyl, five-membered heteroaryl, five-membered carbene, five-membered N-heterocyclic carbene, six-membered aryl, or six-membered heteroaryl, each of L$^2$, L$^3$, L$^5$, and L$^6$ is independently substituted or unsubstituted aryl, cycloalkyl, cycloalkenyl, heteroaryl, heterocyclyl, carbene, or N-heterocyclic carbene, each of LP$^1$, LP$^2$, LP$^3$, LP$^4$, LP$^5$, and LP$^6$ is independently a fluorescent luminophore, each of LP$^1$, LP$^2$, LP$^3$, LP$^4$, LP$^5$, and LP$^6$ is independently present or absent, and at least one of LP$^1$, LP$^2$, LP$^3$, LP$^4$, LP$^5$, and LP$^6$ is present, each of A, A$^1$, and A$^2$ is independently CH$_2$, CR$^1$R$^2$, C=O, CH$_2$, SiR$^1$R$^2$, GeH$_2$, GeR$^1$R$^2$, NH, NR$^3$, PH, PR$^3$, R$^3$P=O, AsR$^3$, R$^3$As=O, O, S, S=O, SO$_2$, Se, Se=O, SeO$_2$, BH, BR$^3$, R$^3$Bi=O, BiH, or BiR$^3$, each of V$^1$, V$^2$, V$^3$, V$^4$, V$^5$, and V$^6$ is independently N, C, P, B, or Si, each of Y$^1$, Y$^2$, Y$^3$, Y$^4$, Y$^5$, Y$^6$, Y$^7$, and Y$^8$ is independently C, N, O, S, S=O, SO$_2$, Se, Se=O, SeO$_2$, PR$^3$, R$^3$P=O, AsR$^3$, R$^3$As=O, or BR$^3$, each of R$^a$, R$^b$, R$^c$, R$^d$, R$^e$, and R$^f$ is independently present or absent, and if present each of R$^a$, R$^b$, R$^c$, R$^d$, R$^e$, and R$^f$ is independently a mono-, di-, tri-, or tetra-substitution, and each R$^a$, R$^b$, R$^c$, R$^d$, R$^e$, and R$^f$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, each of R$^1$, R$^2$, and R$^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, each of X, X$^1$, and X$^2$ is independently N, P, P=O, As, As=O, CR$^1$, CH, SiR$^1$, SiH, GeR$^1$, GeH, B, Bi, or Bi=O, each of Z, Z$^1$, and Z$^2$ is a linking atom or linking group, and each of R$^x$ and R$^y$ is independently present or absent, and if present each of R$^x$ and R$^y$ is a mono-, di-, tri-, or tetra-substitution, and each R$^x$ and R$^y$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, each of LP$^1$, LP$^2$, LP$^3$, LP$^4$, LP$^5$ and LP$^6$ is independently an aromatic hydrocarbon, an aromatic hydrocarbon derivative, a polyphenyl hydrocarbon, a hydrocarbon with condensed aromatic nuclei, naphthalene, anthracene, phenanthrene, chrysene, pyrene, triphenylene, perylene, acenaphthene, tetracene, pentacene, tetraphene, coronene, fluorene, biphenyl, p-terphenyl, o-diphenylbenzene, m-diphenylbenzene, p-quaterphenyl, benzo[a]tetracene, benzo[k]tetraphene, indeno[1,2,3-cd]fluoranthene, tetrabenzo[de,hi,op,st]pentacene, an arylethylene derivative, an arylacetylene derivative, a diarylethylene, a diarylpolyene, a diaryl-substituted vinylbenzene, a distyrylbenzene, a trivinylbenzene, an arylacetylene, a functional substitution product of stilbene, a five-, six- or seven-membered heterocyclic compound derivative, a furan derivative, a thiophene derivative, a pyrrole derivative, an aryl-substituted oxazole, an 1,3,4-oxadiazole, an 1,3,4-thiadiazole, an aryl-substituted 2-pyrazoline, an aryl-substituted pyrazole, a benzazole, 2H-benzotriazole, a substitution product of 2H-benzotriazole, a heterocycle with one, two, or three nitrogen atoms, an oxygen-containing heterocycle, a coumarin, a coumarin derivative, a dye, an acridine dye, a xanthene dye, an oxazine, or a thiazine.

In another aspect, two or more of $R^a$ are optionally linked together, two or more of $R^b$ are optionally linked together, two or more of $R^c$ are optionally linked together, two or more of $R^d$ are optionally linked together, two or more of $R^e$ are optionally linked together, two or more of $R^f$ are optionally linked together, or any combination thereof.

In one aspect, for any of the formulas depicted in this disclosure, M-$R^{L4}$ represents one or more of the following structures, where $R^{L4}$ is an organic or inorganic anion:

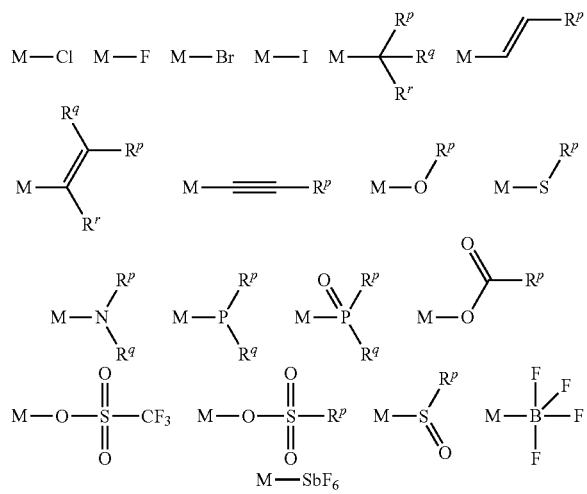

wherein each of $R^p$, $R^q$, and $R^r$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In some cases, two or more of $R^p$ are optionally linked together, two or more of $R^q$ are optionally linked together, two or more of $R^r$ are optionally linked together, or any combination thereof.

In one aspect, for any of the formulas depicted in this disclosure, each of

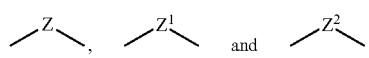

(also denoted as Z, $Z^1$, and $Z^2$ herein) is independently one or more of the following structures:

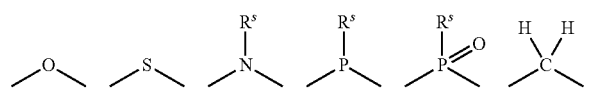

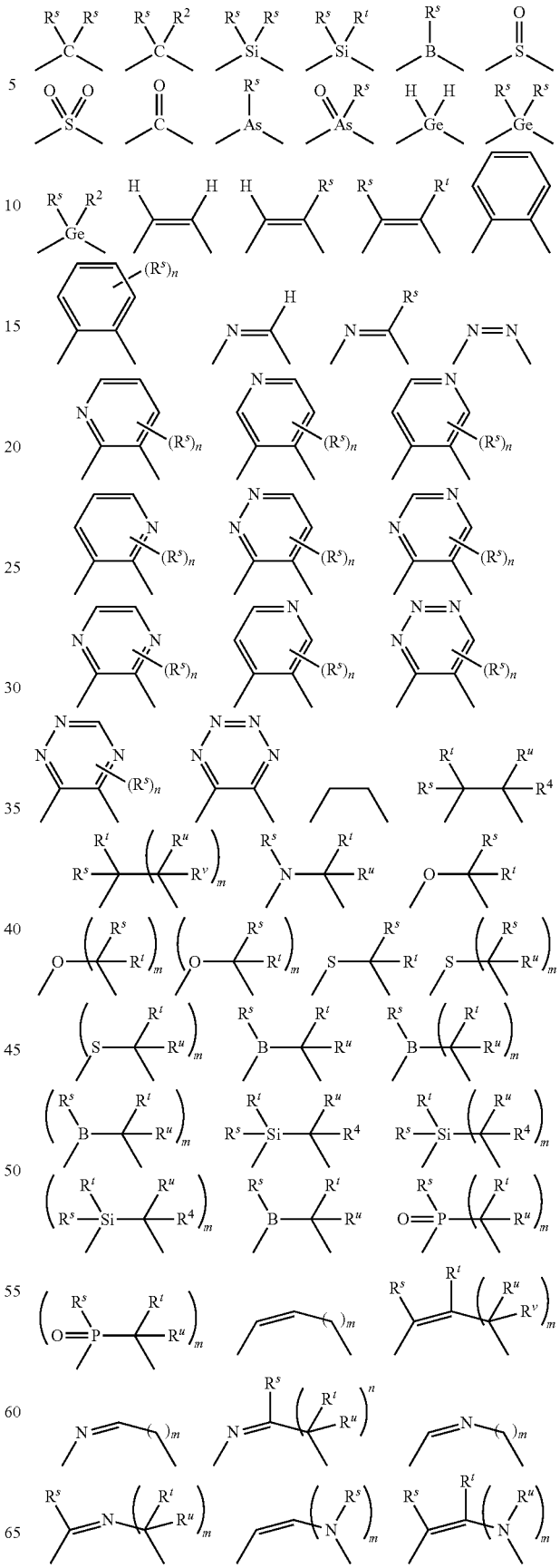

-continued

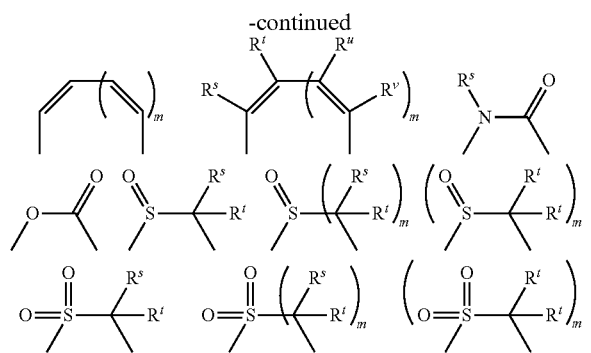

wherein:

n is an integer from 0 to 4, m is an integer from 1 to 3, each of $R^s$, $R^t$, $R^u$, and $R^v$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, for any of the formulas depicted in this disclosure, each five-membered heterocyclyl

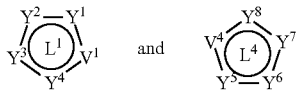

independently represents one of the following structures:

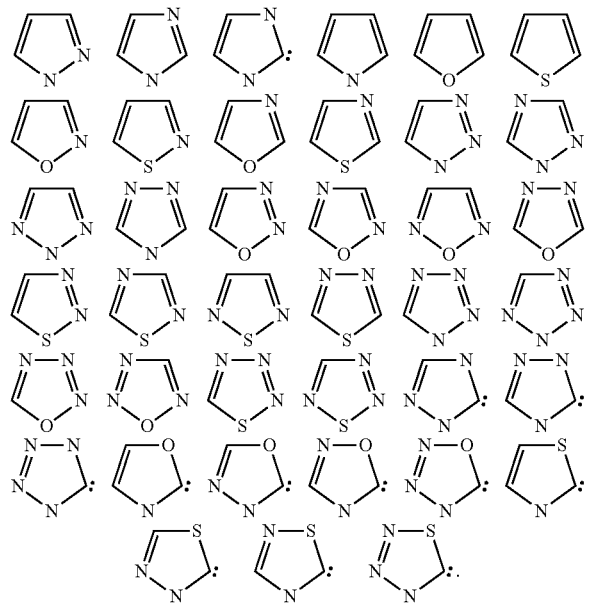

One or more of each of $R^a$ and $R^d$ may be independently bonded to

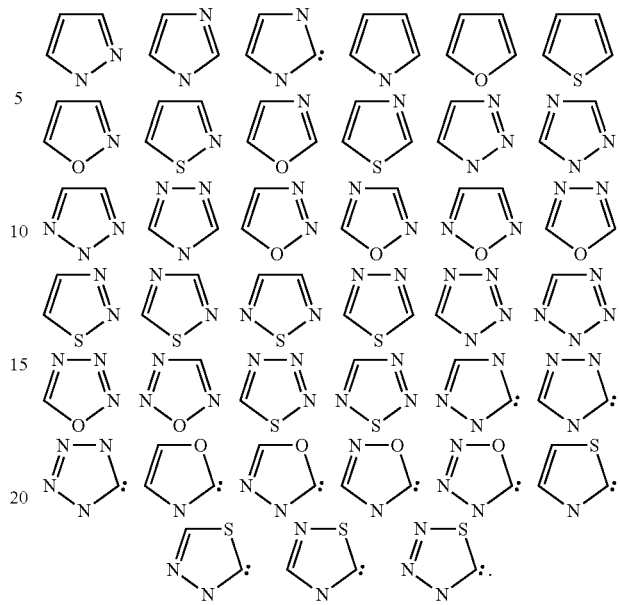

In another aspect, for any of the formulas depicted in this disclosure, each six-membered heterocyclyl

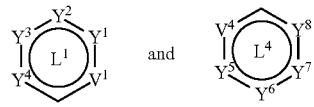

independently represents one of the following structures:

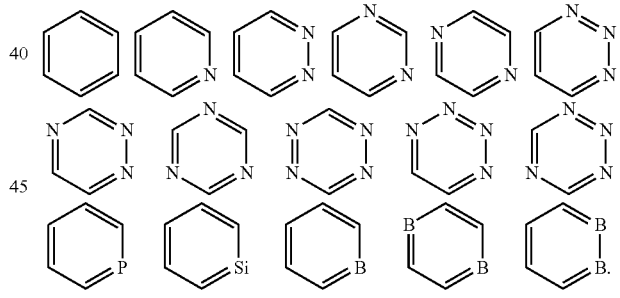

One or more of each of $R^a$ and $R^d$ may be independently bonded to

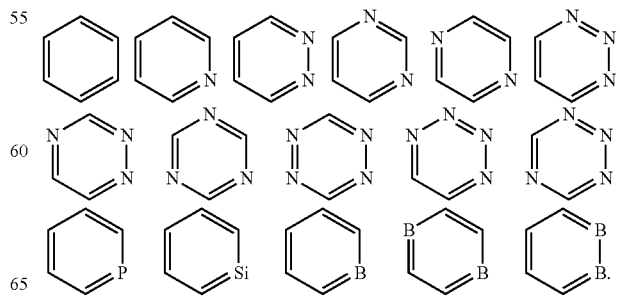

In one aspect, for any of the formulas depicted in this disclosure, each of
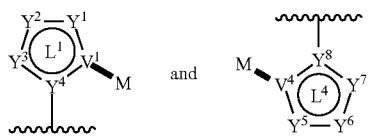 and
independently represents one of the following structures:
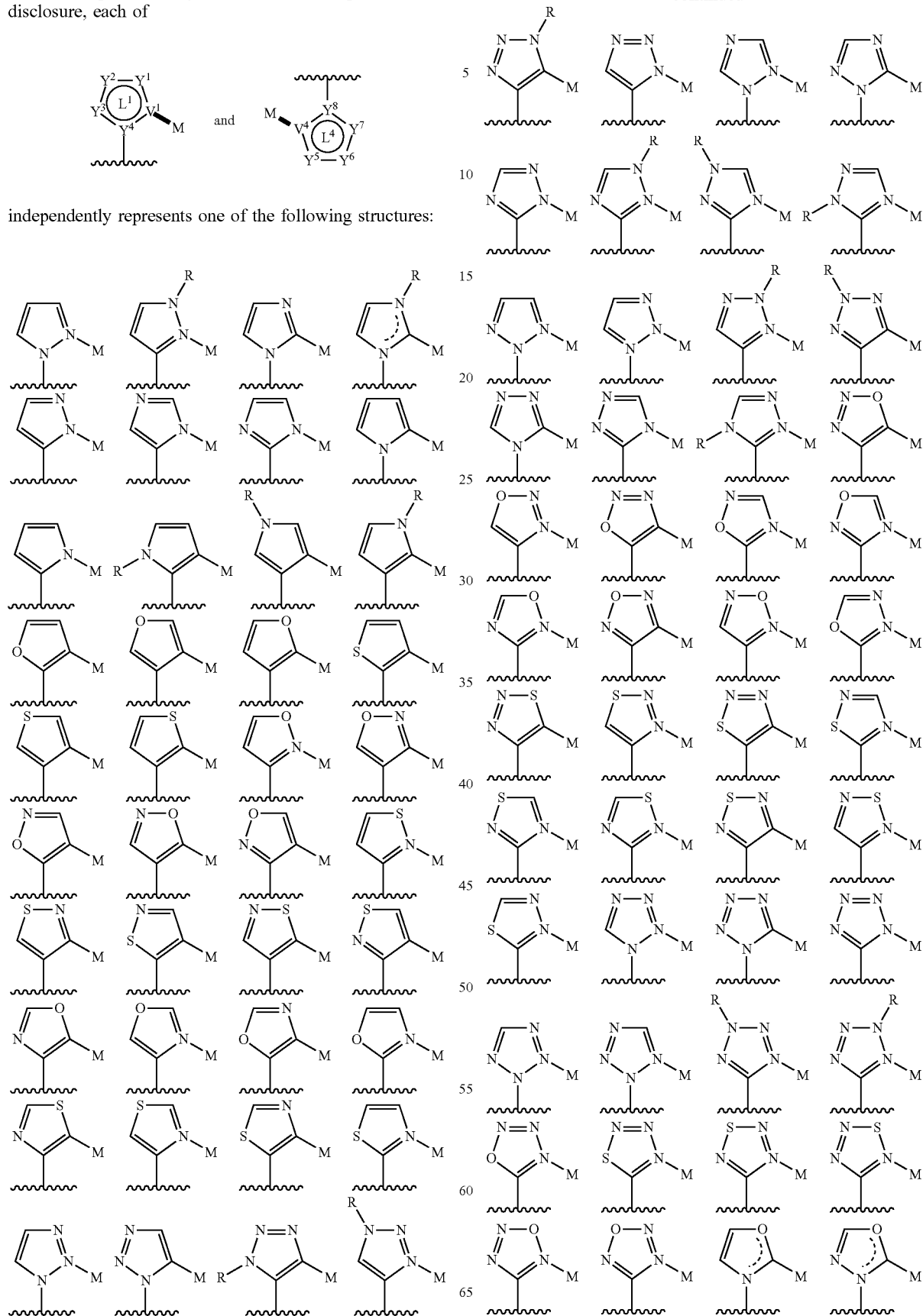

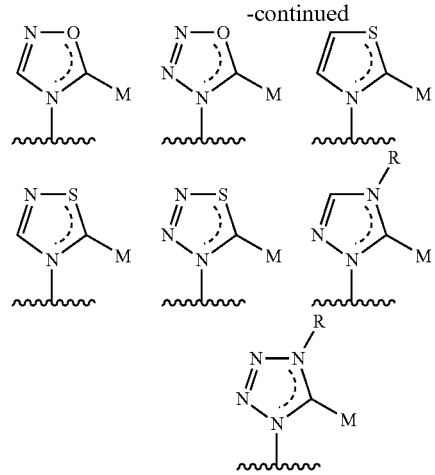

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, for any of the formulas depicted in this disclosure, each of

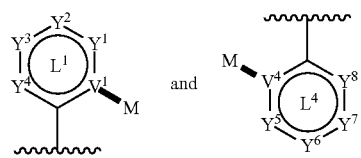

independently represents:

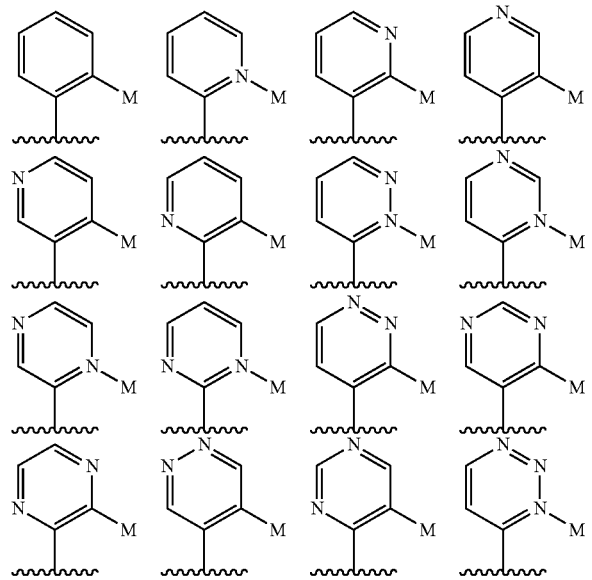

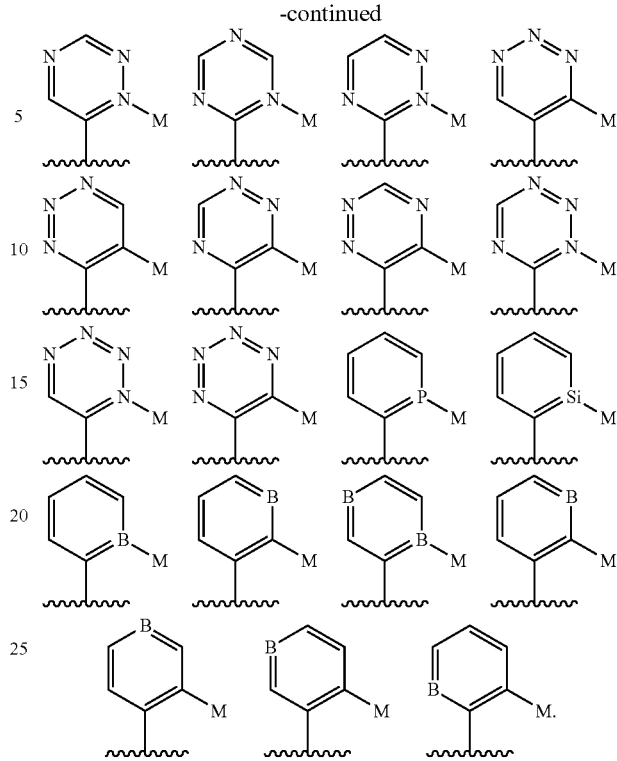

In one aspect, for any of the formulas depicted in this disclosure, each of

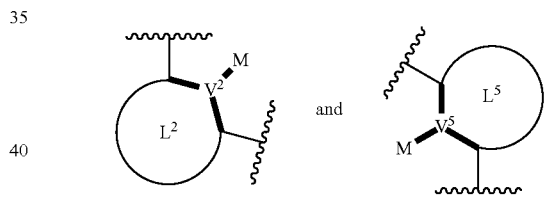

independently represents:

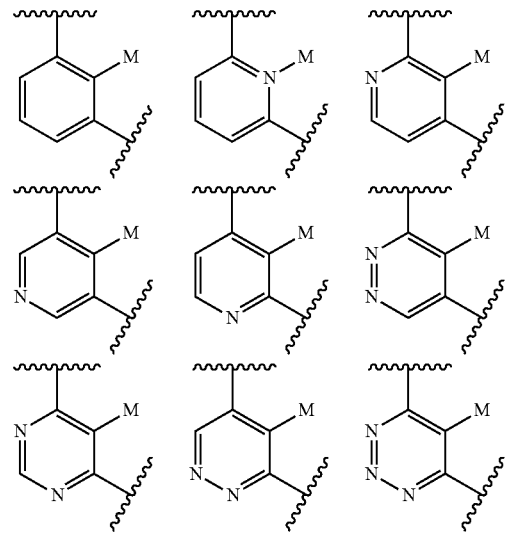

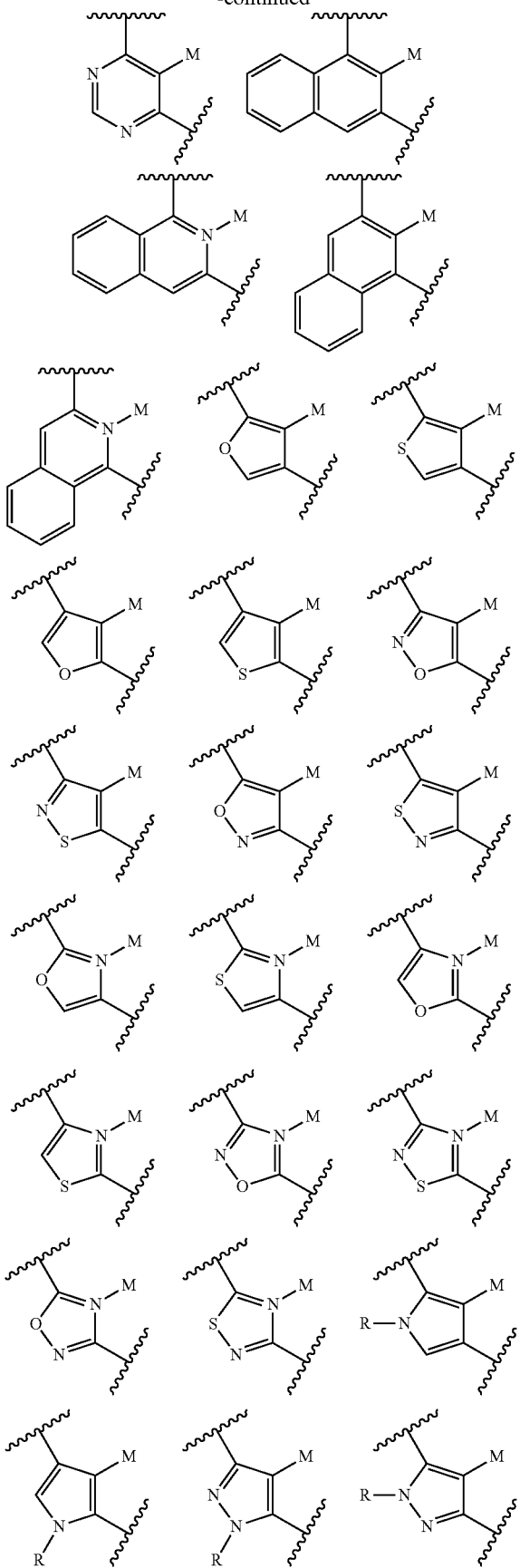
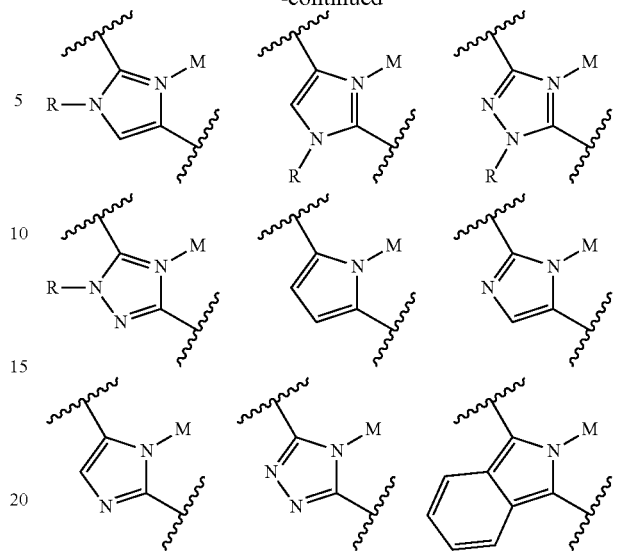

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, for any of the formulas depicted in this disclosure, each of

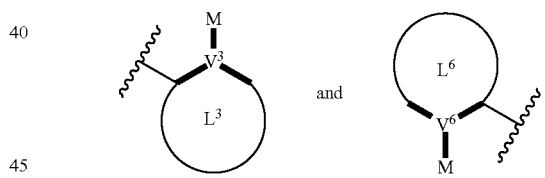

independently represents:

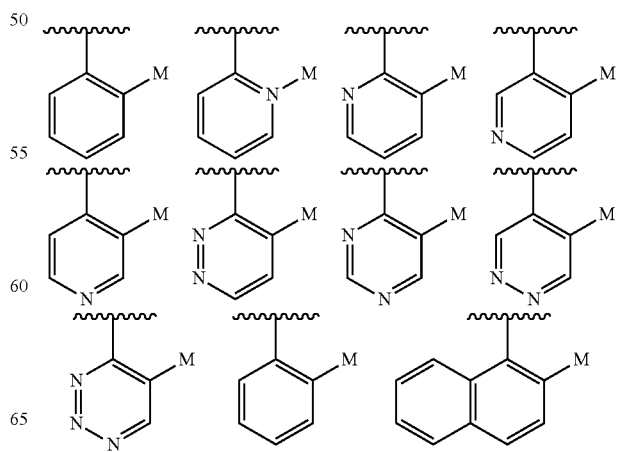

55
-continued
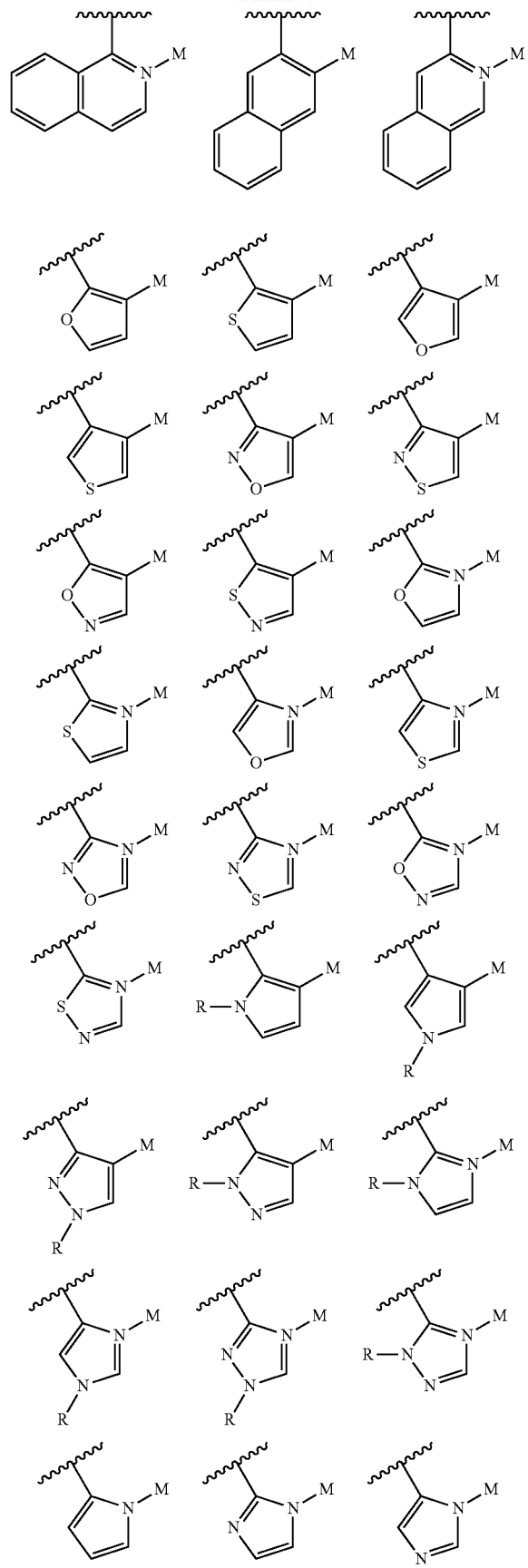
56
-continued
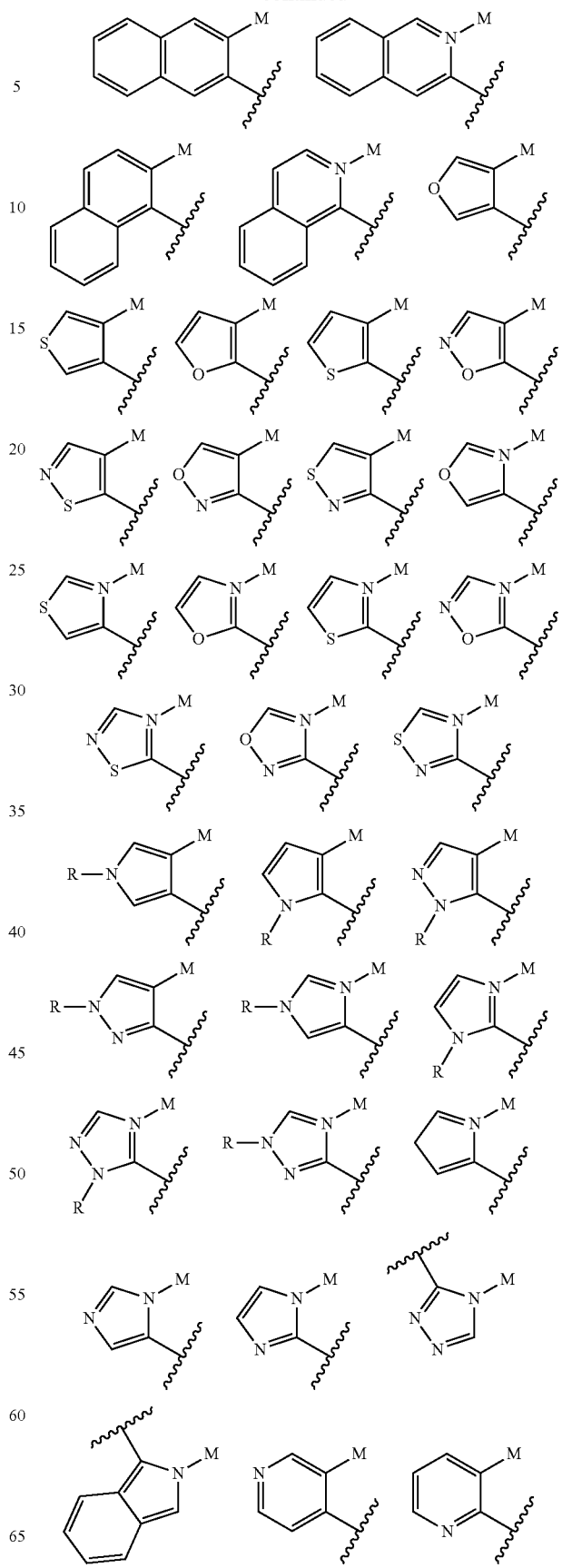

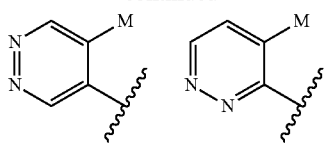

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, for any of the formulas depicted in this disclosure, each fluorescent luminophore $LP^1$, $LP^2$, $LP^3$, $LP^4$, $LP^5$, and $LP^6$ independently represents:

1. Aromatic Hydrocarbons and their Derivatives

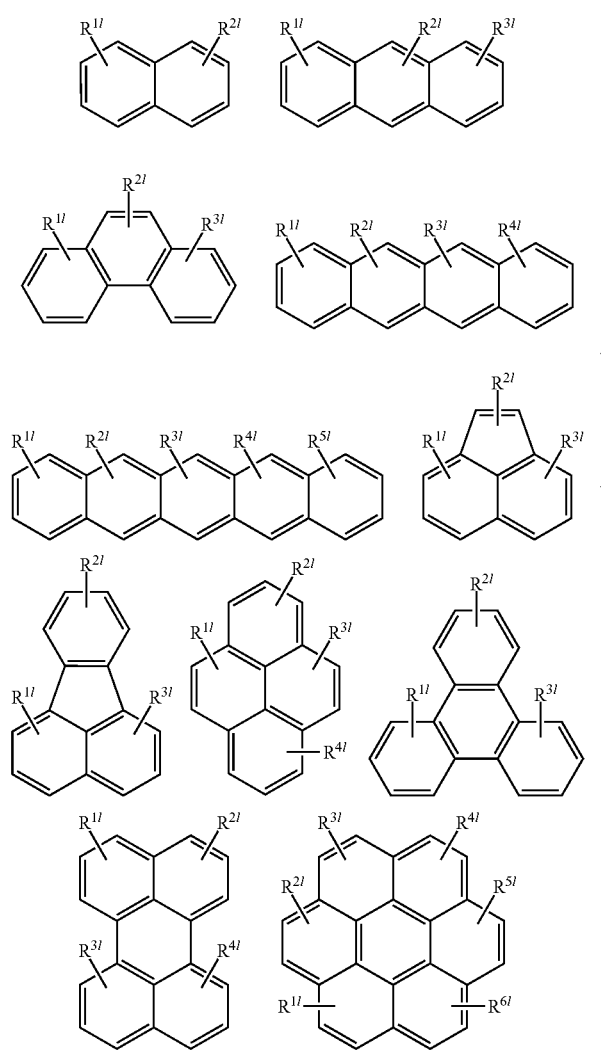

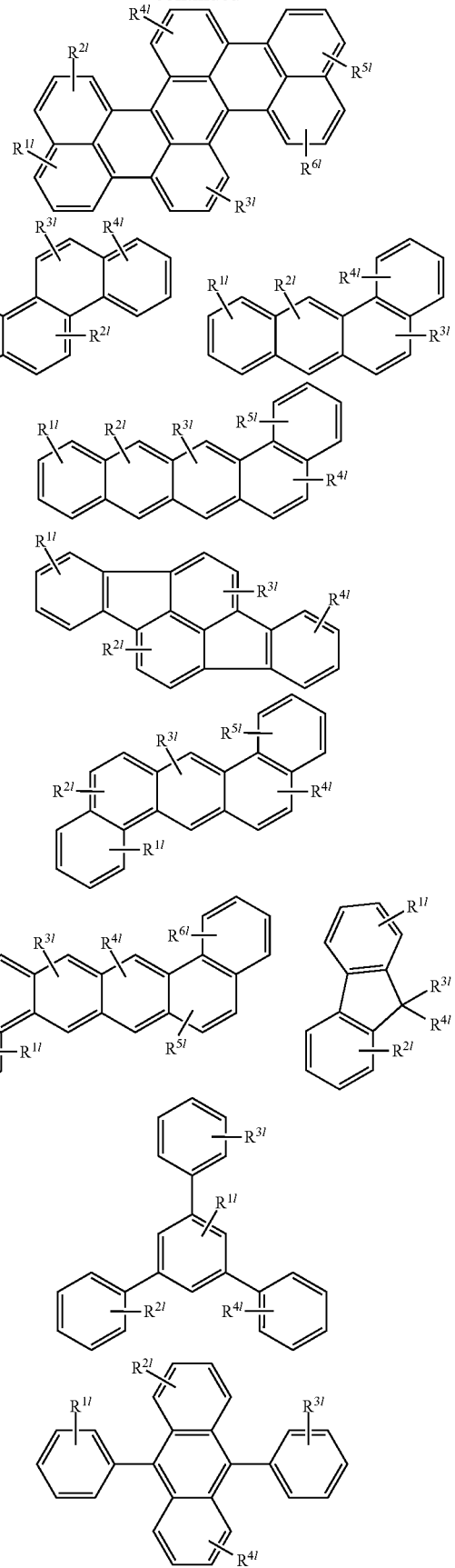

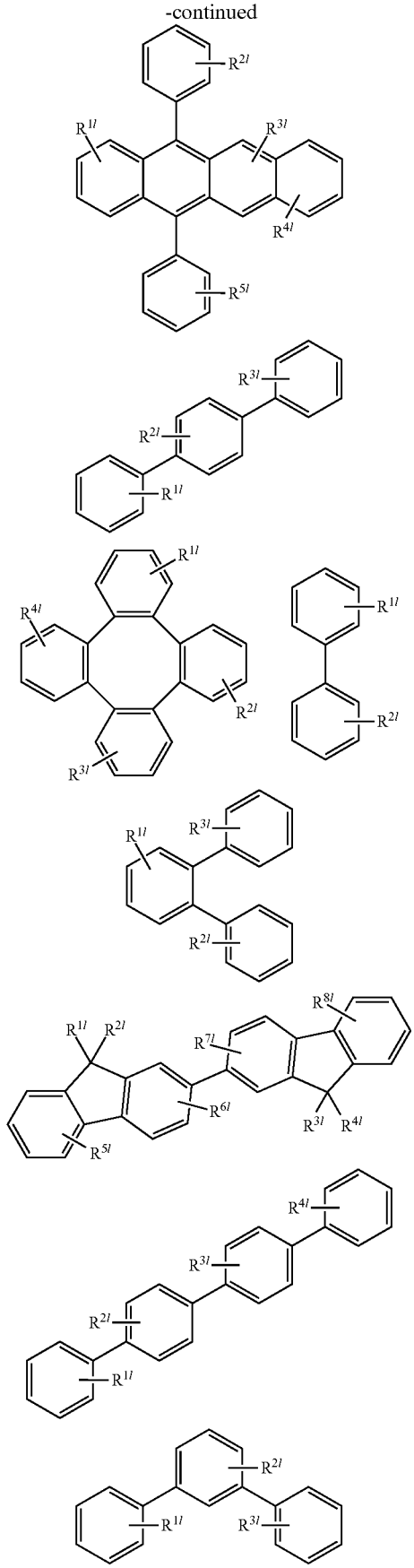
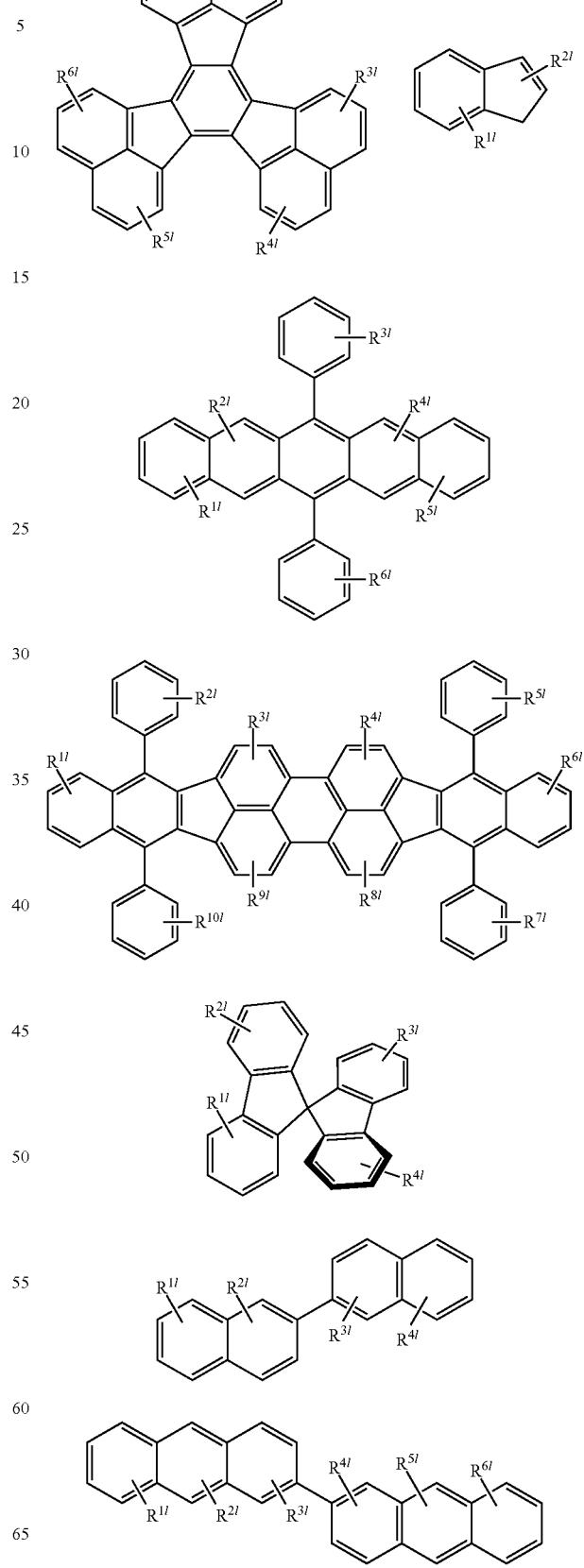

-continued
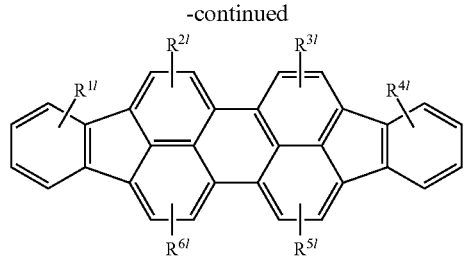
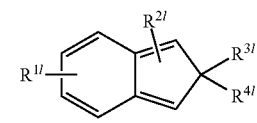
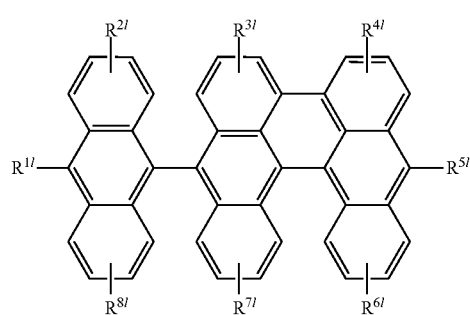
2. Arylethylene, Arylacetylene and their Derivatives
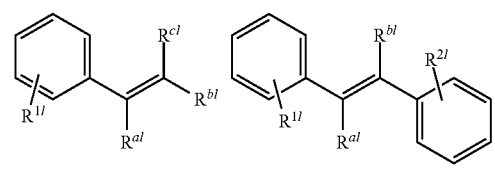
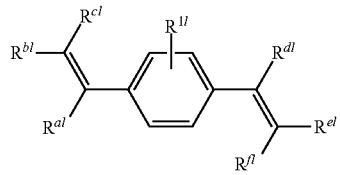
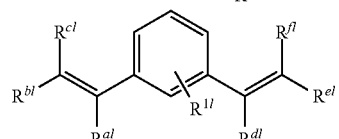
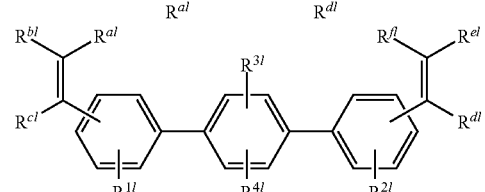
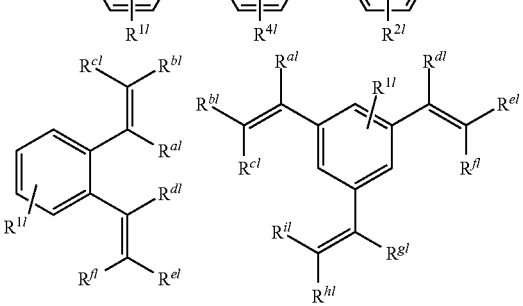
-continued
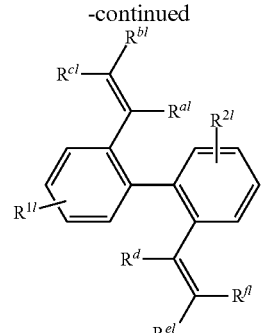
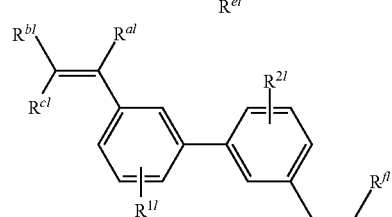
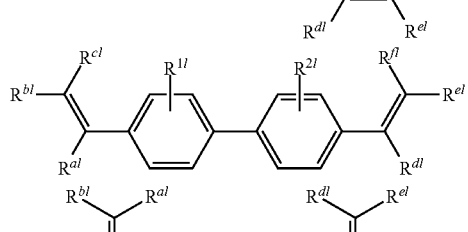
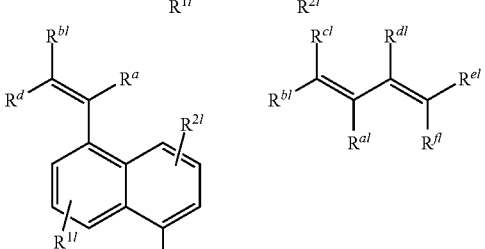
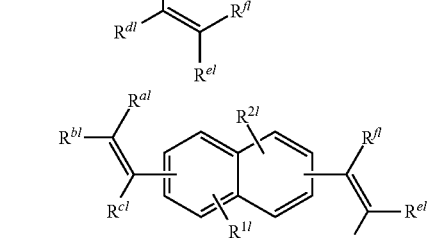
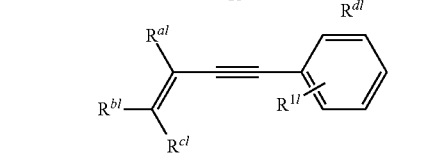
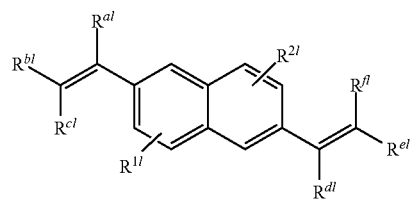

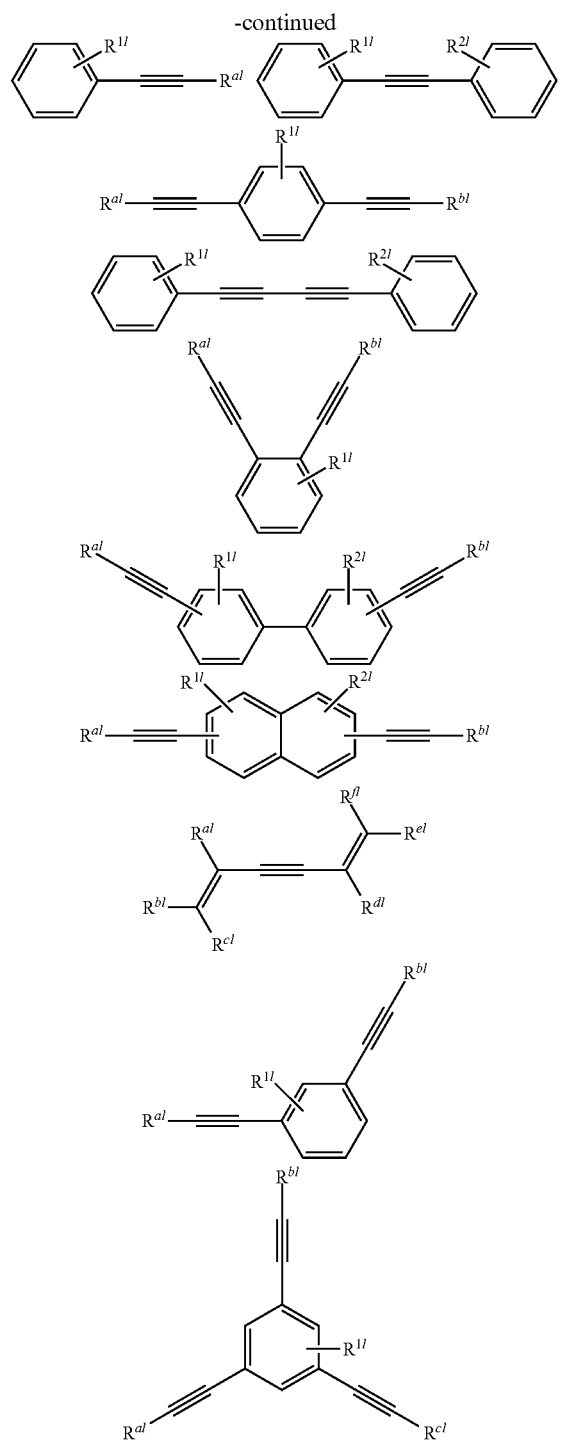
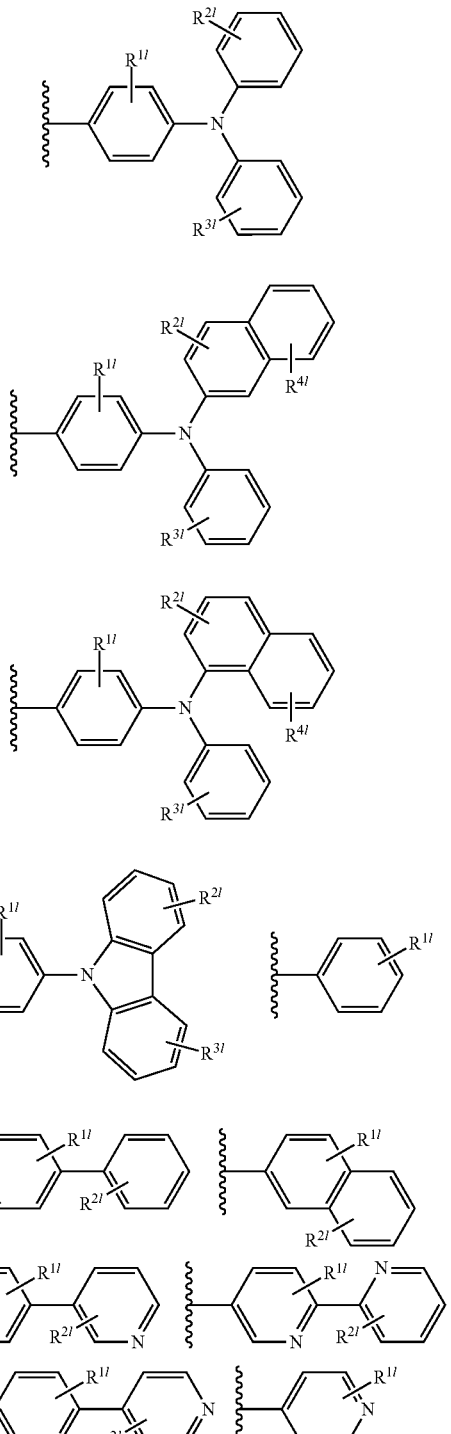
wherein $R^{al}$, $R^{bl}$, $R^{cl}$, $R^{dl}$, $R^{el}$, $R^{fl}$, $R^{gl}$, $R^{hl}$ and $R^{il}$ can be one of the following structure:
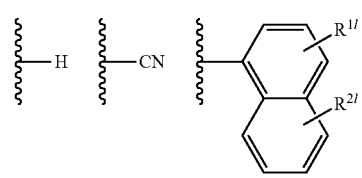

3. Heterocyclic Compounds and their Derivatives

-continued
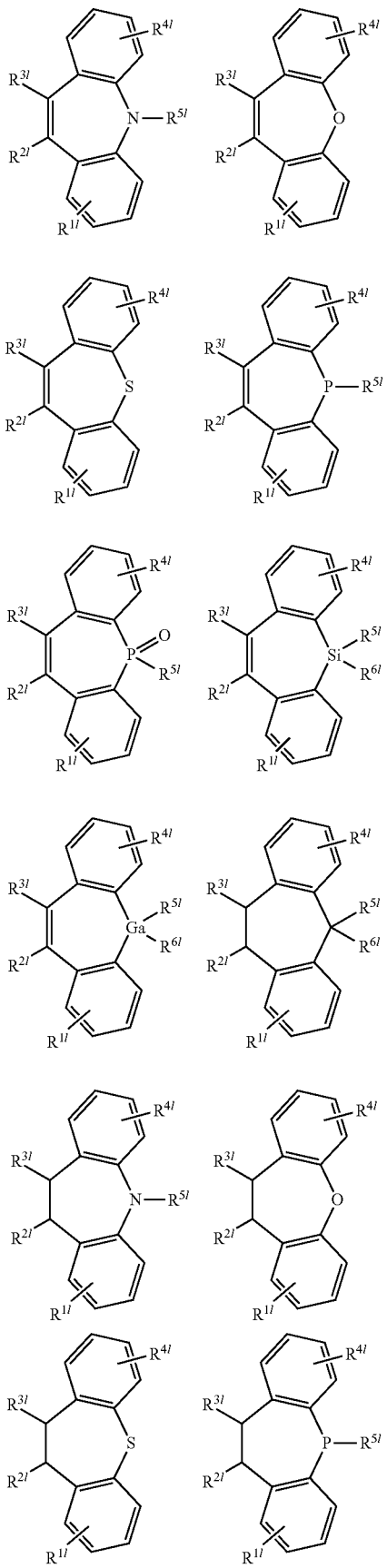
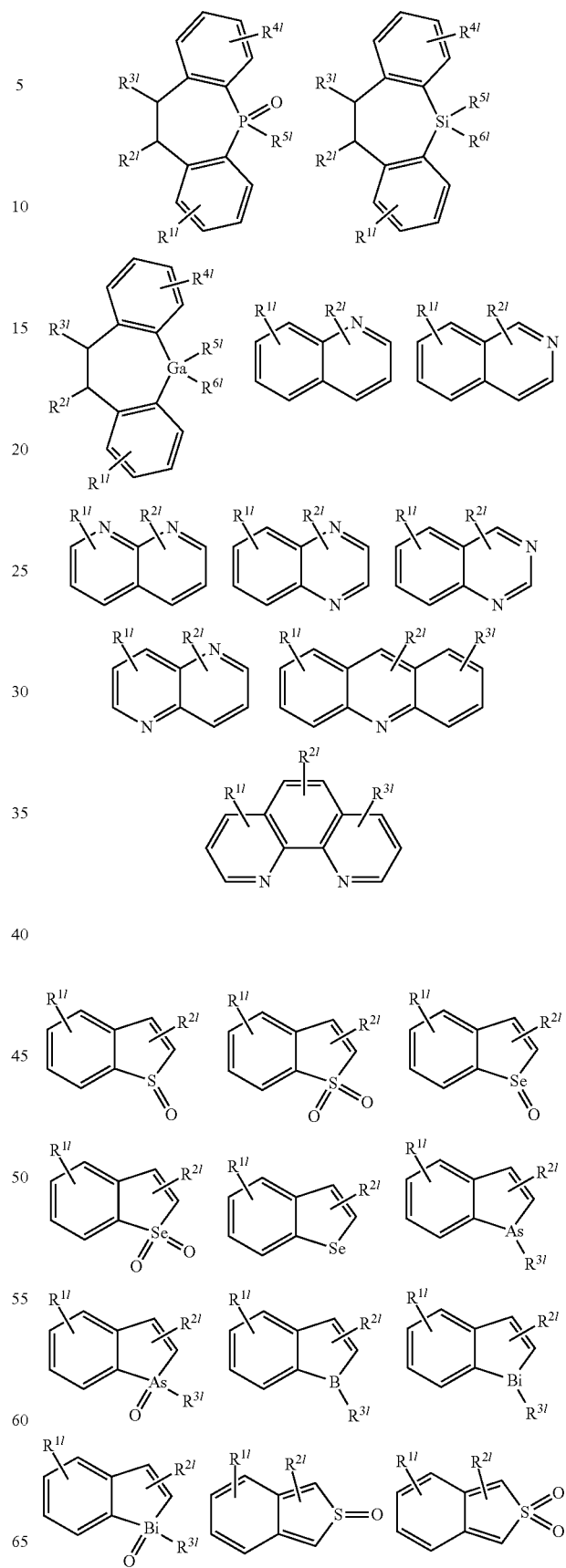

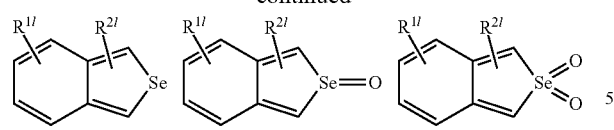
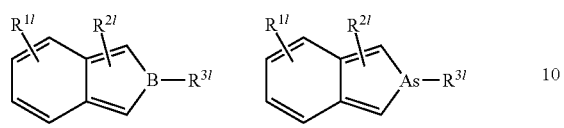
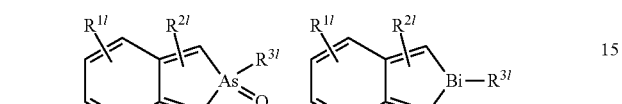
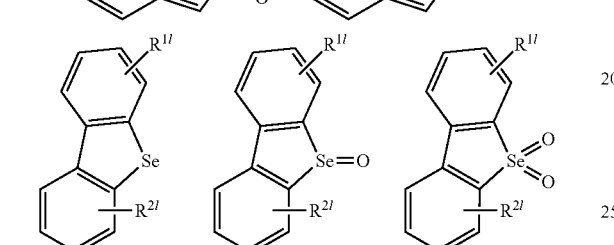
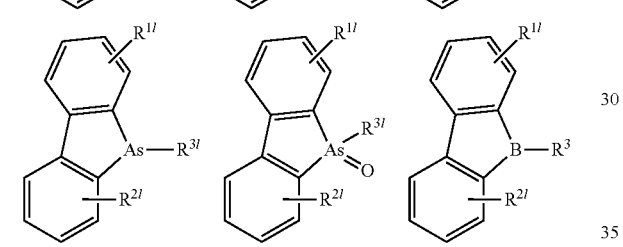
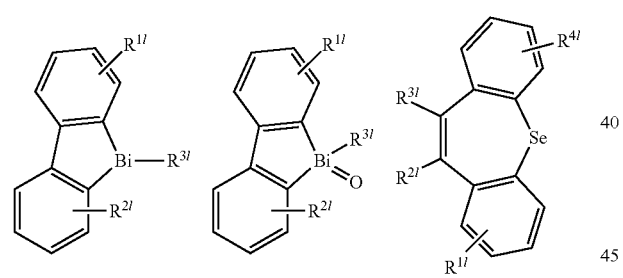

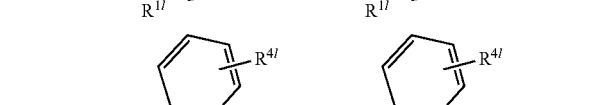
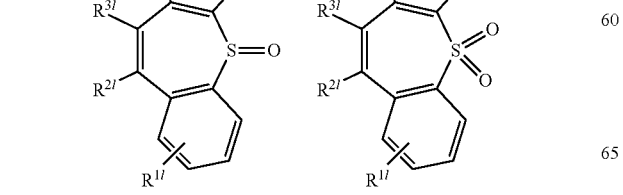
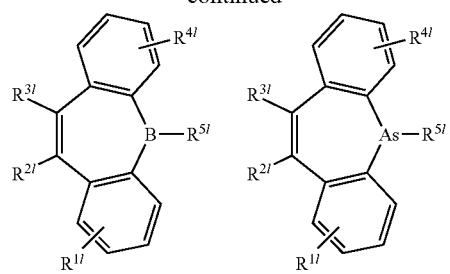
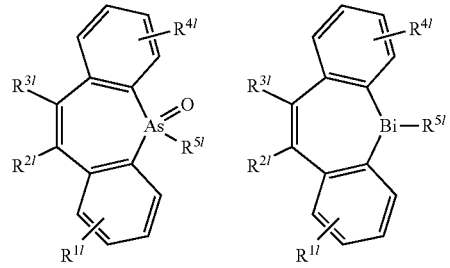
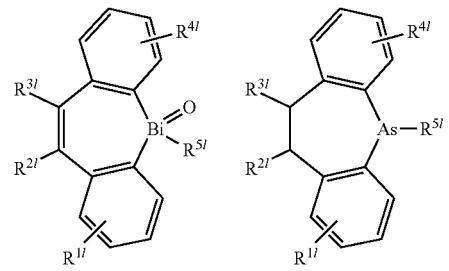
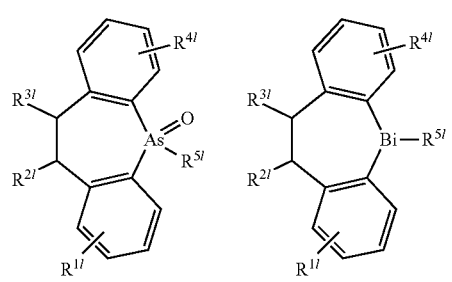
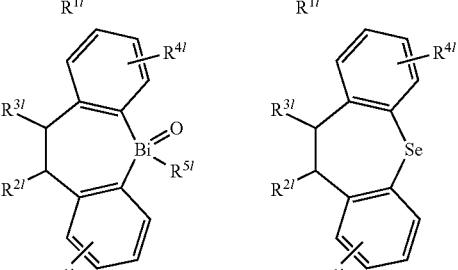
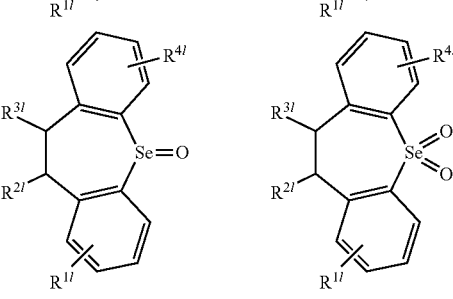

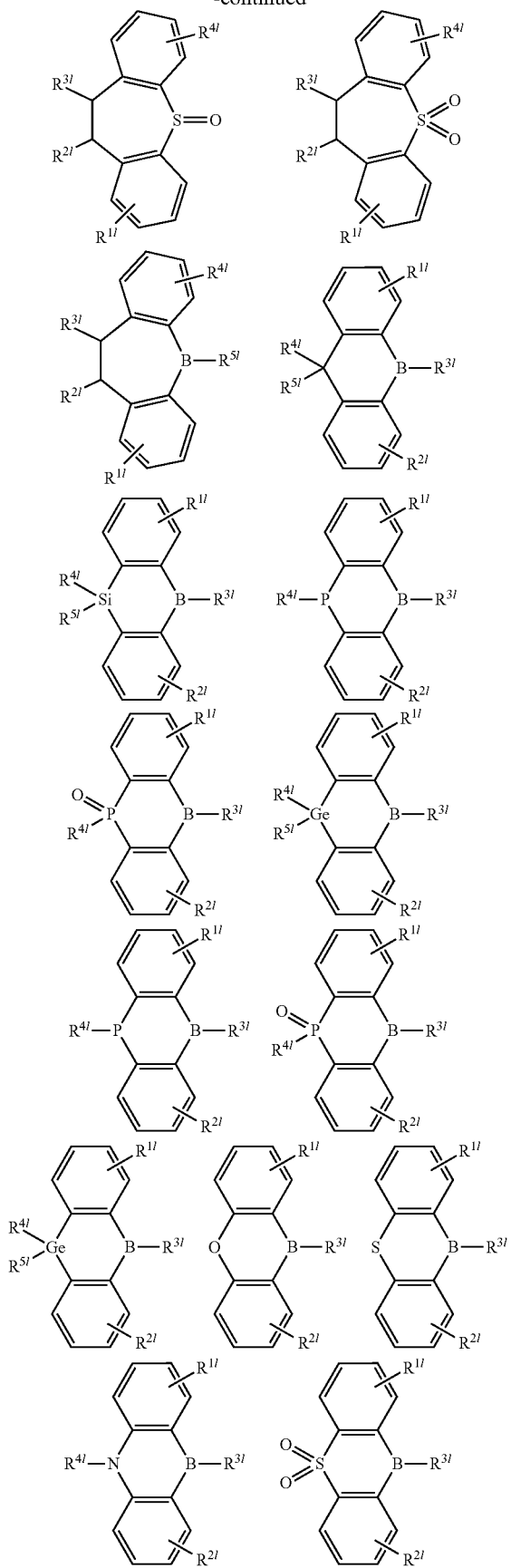
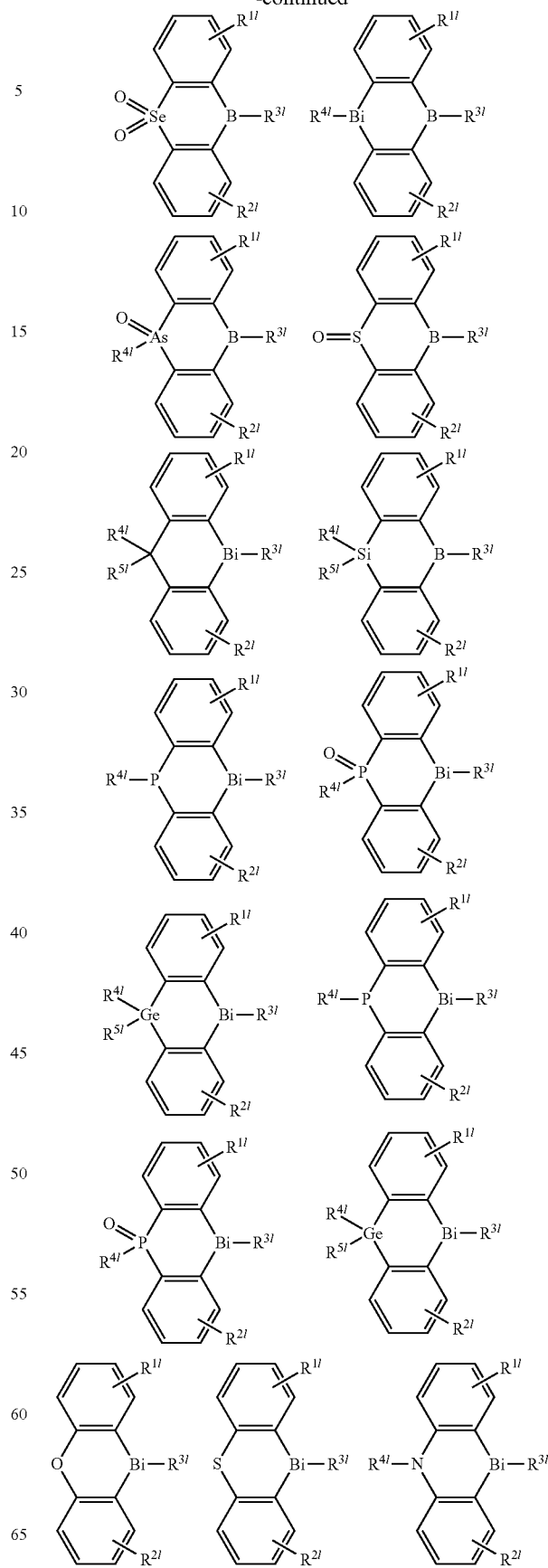

-continued
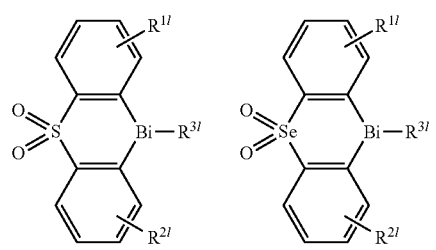
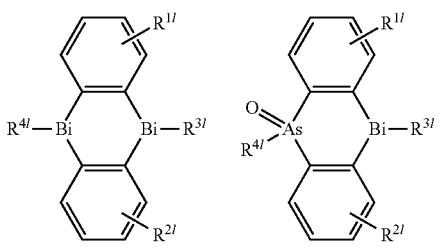
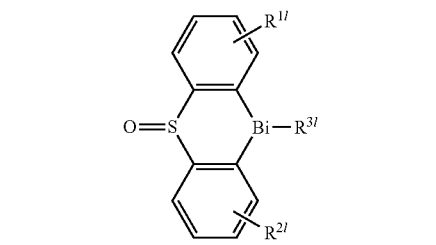
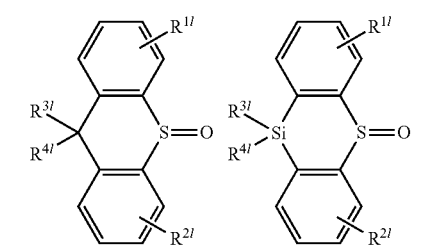
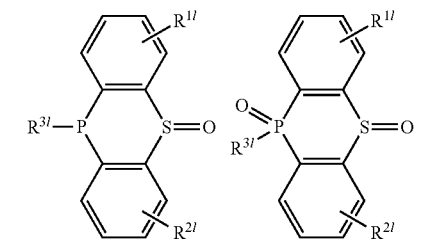
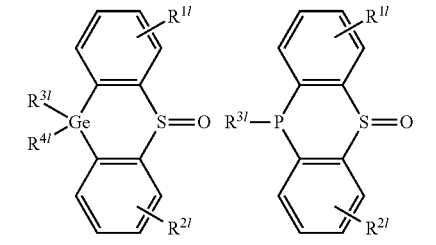
-continued
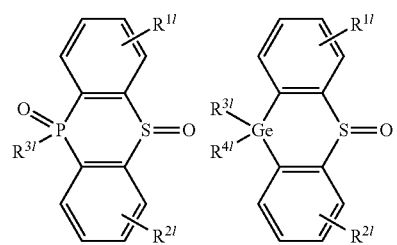
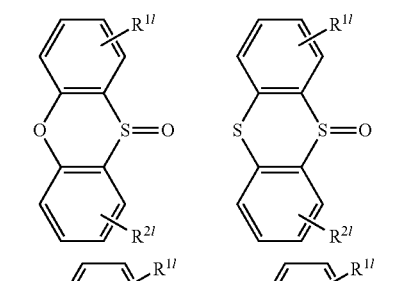
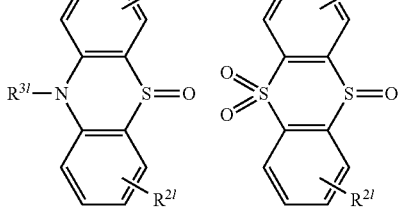
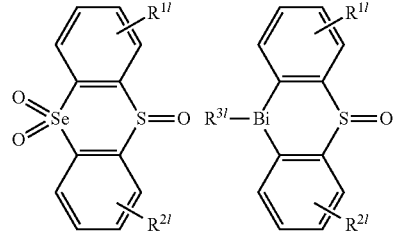
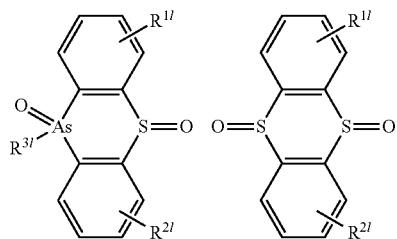
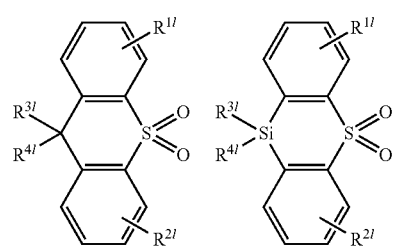
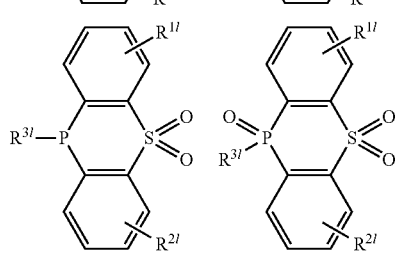

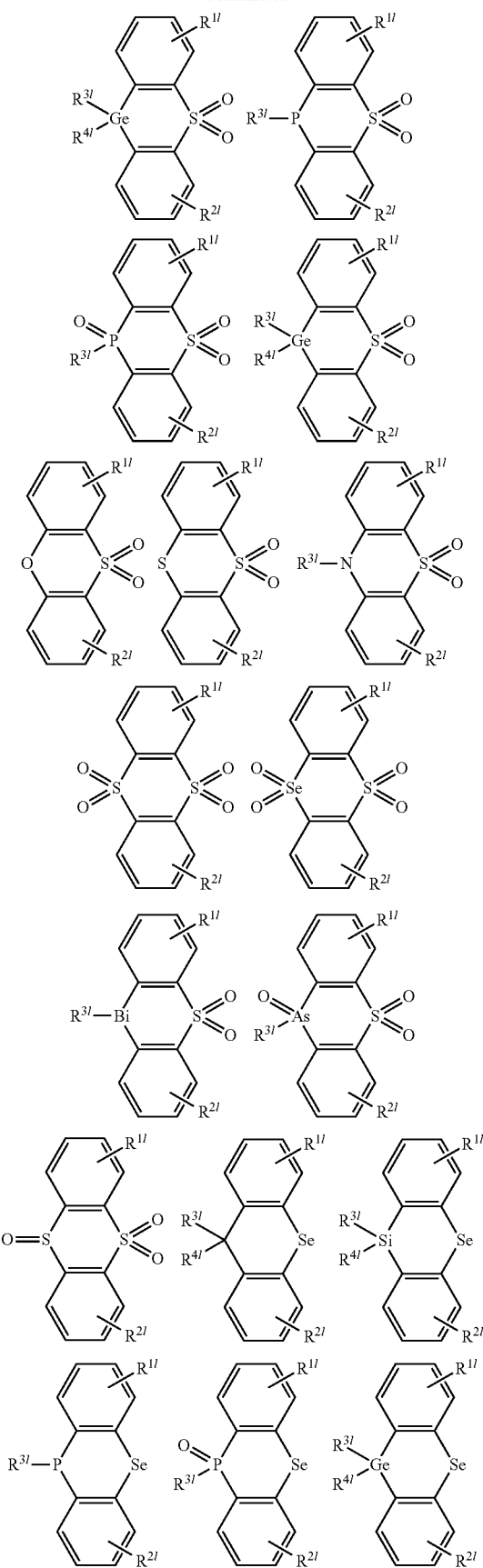
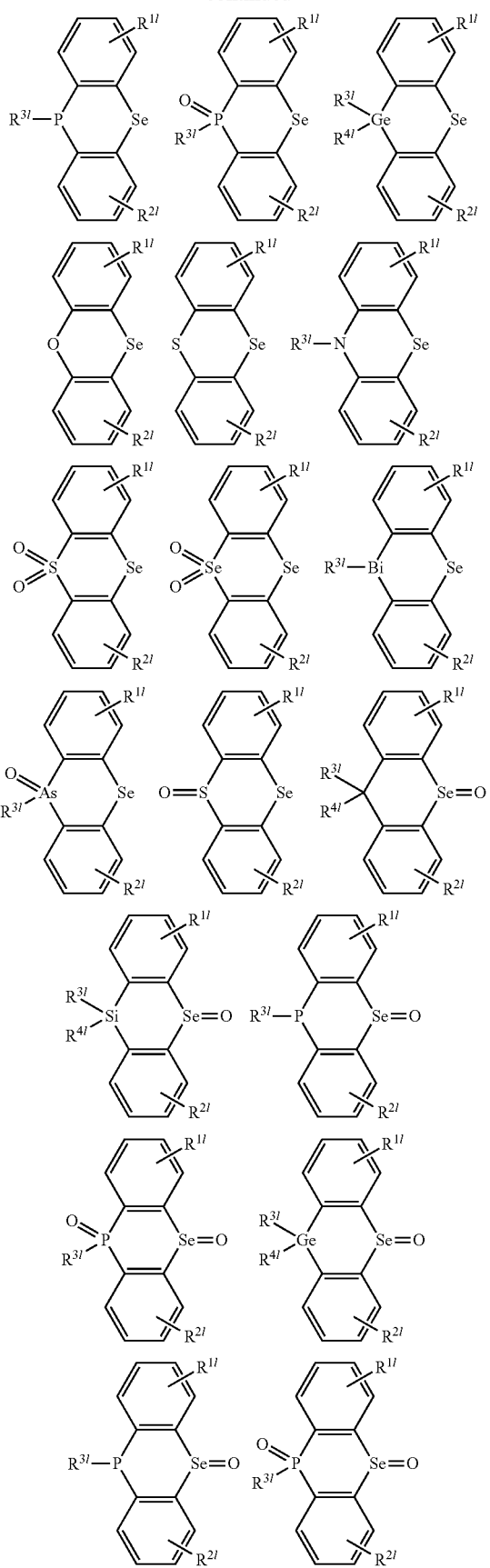

-continued
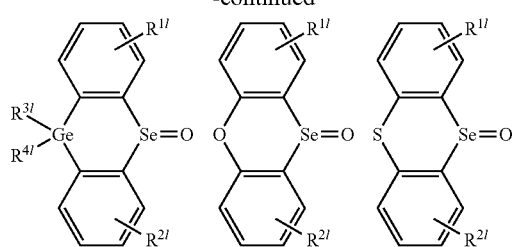
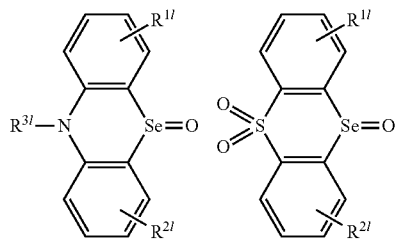
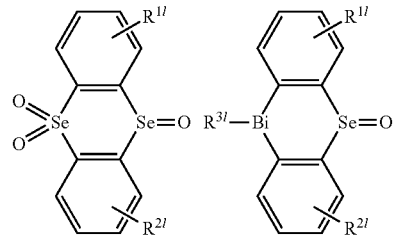
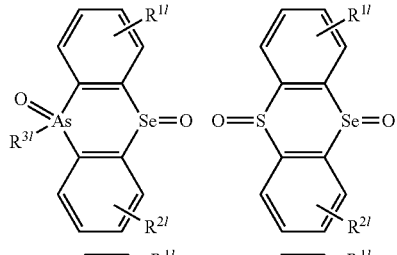
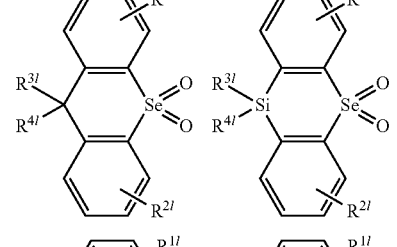
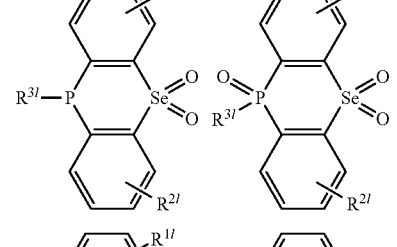
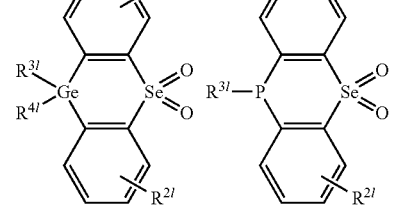
-continued
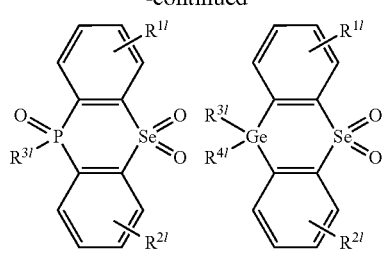
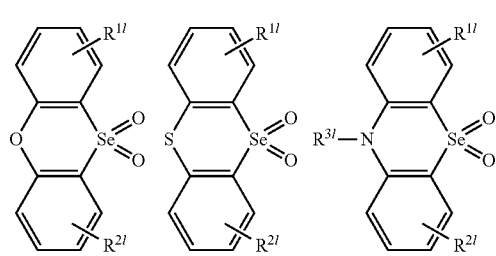
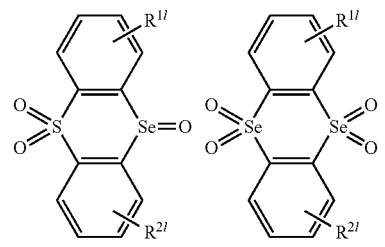
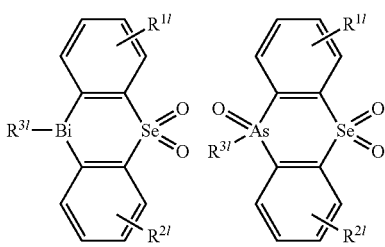
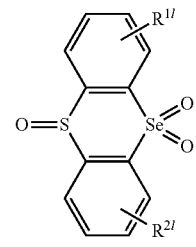
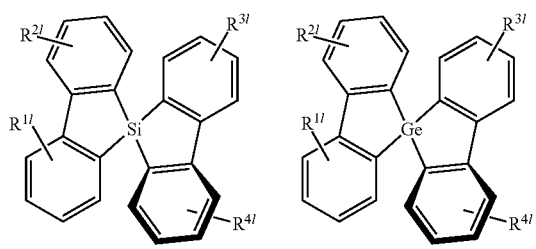

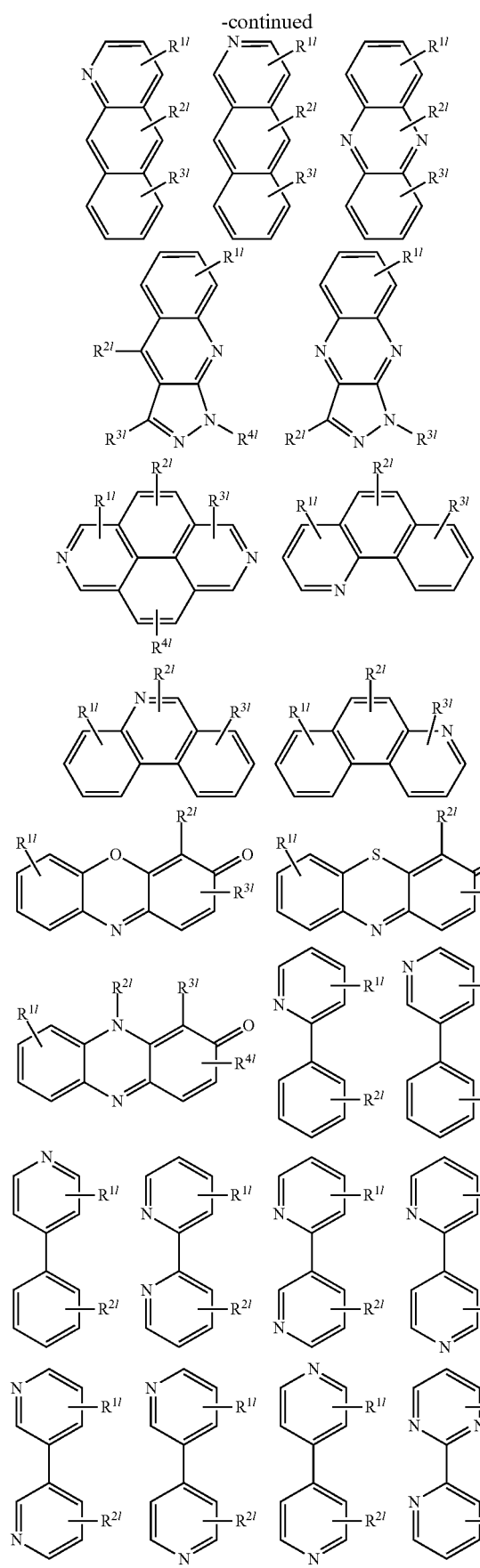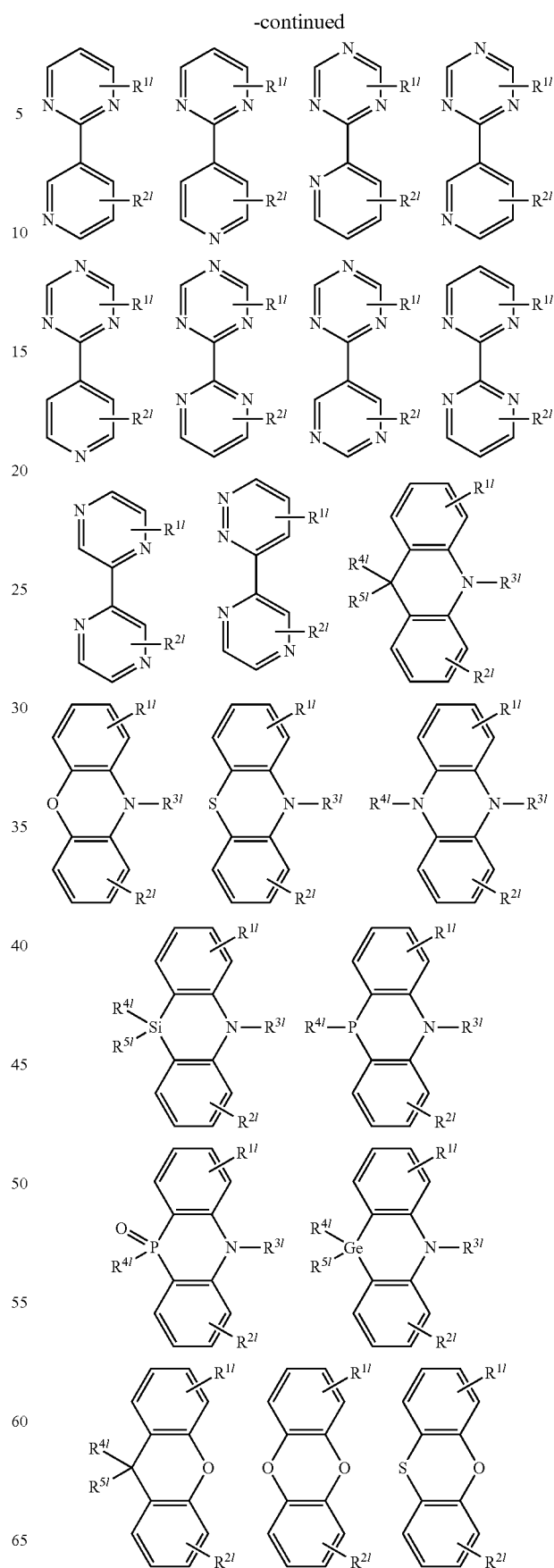

-continued
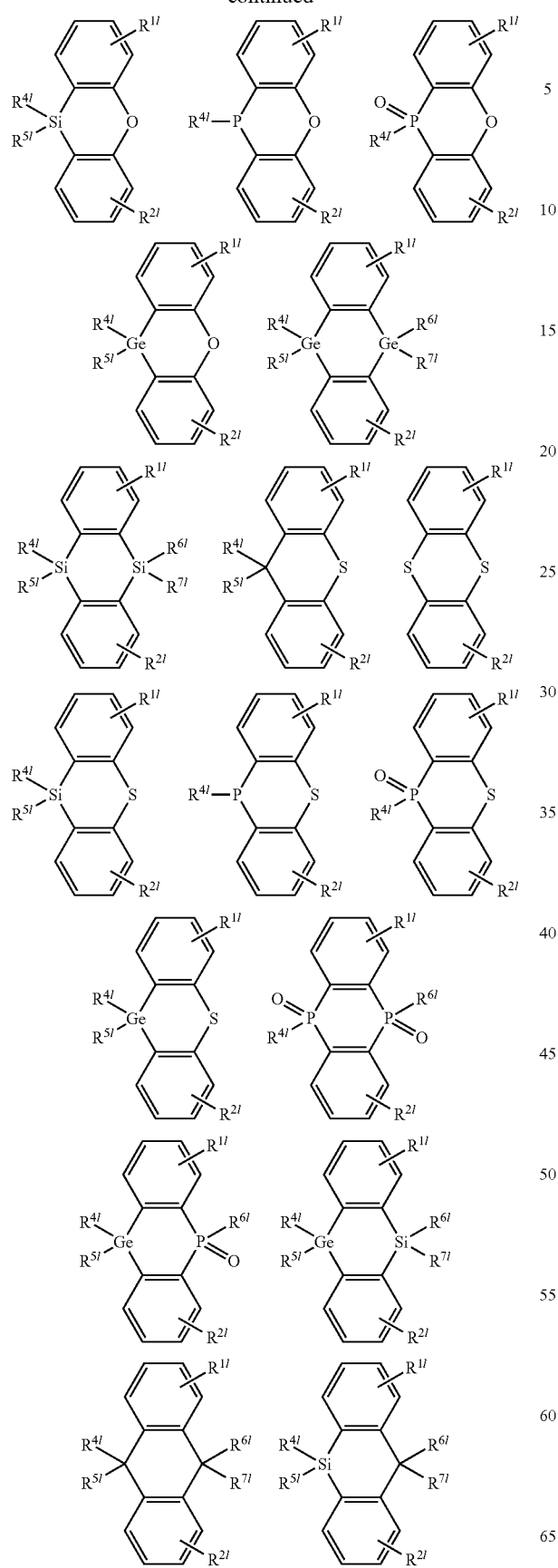
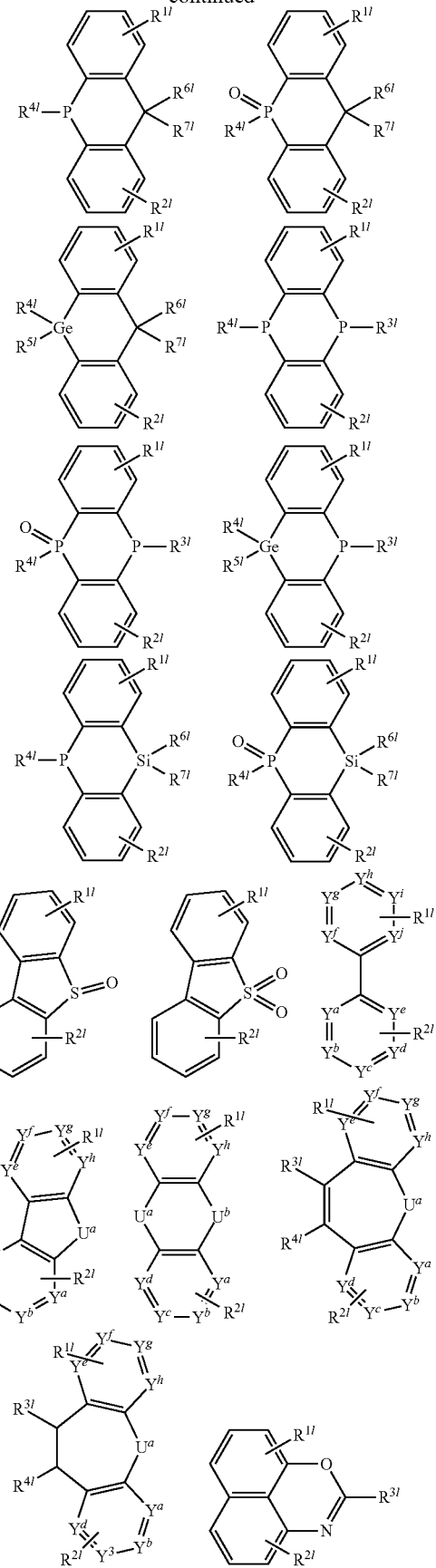

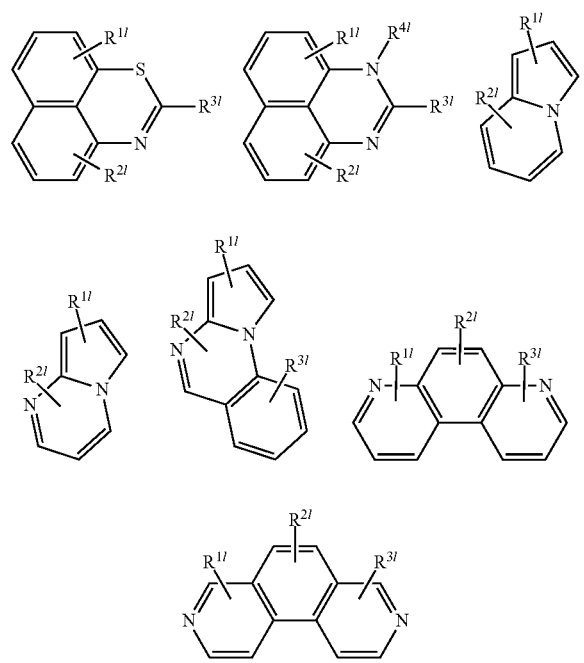
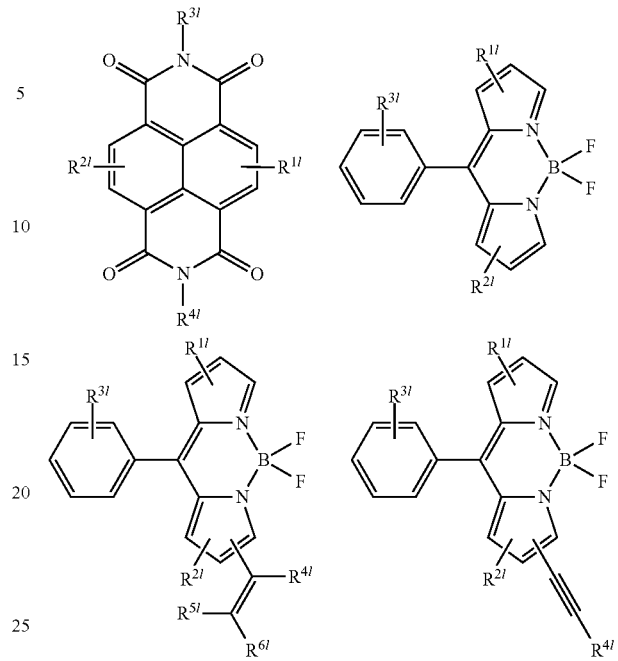
4. Other Fluorescent Luminophores
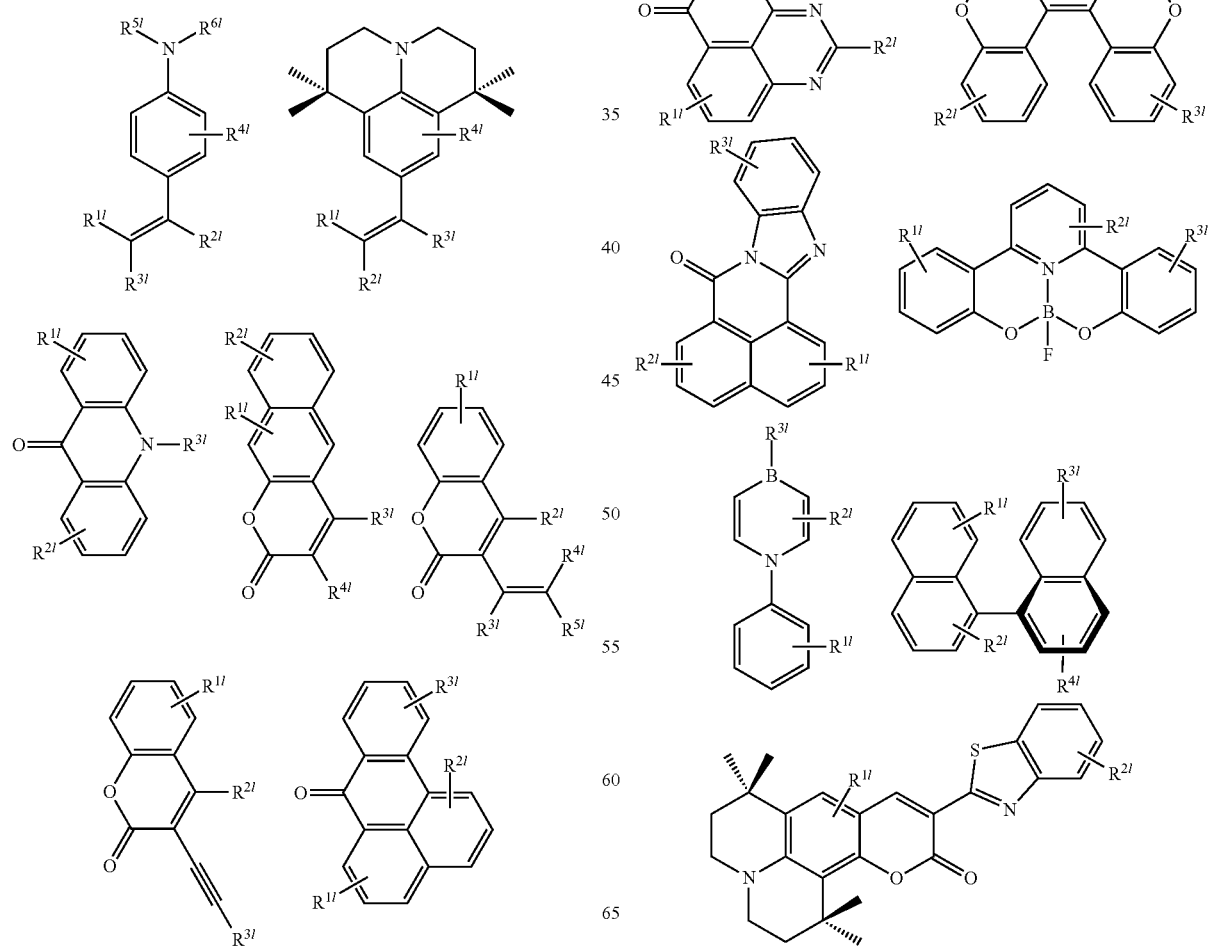

-continued

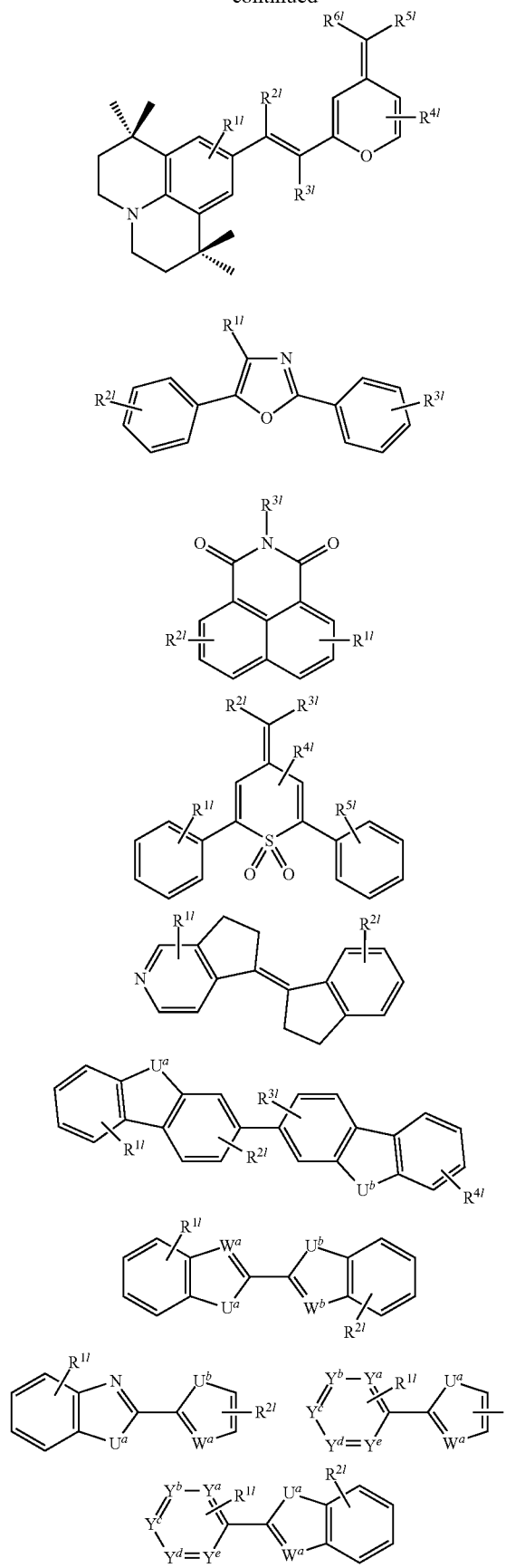
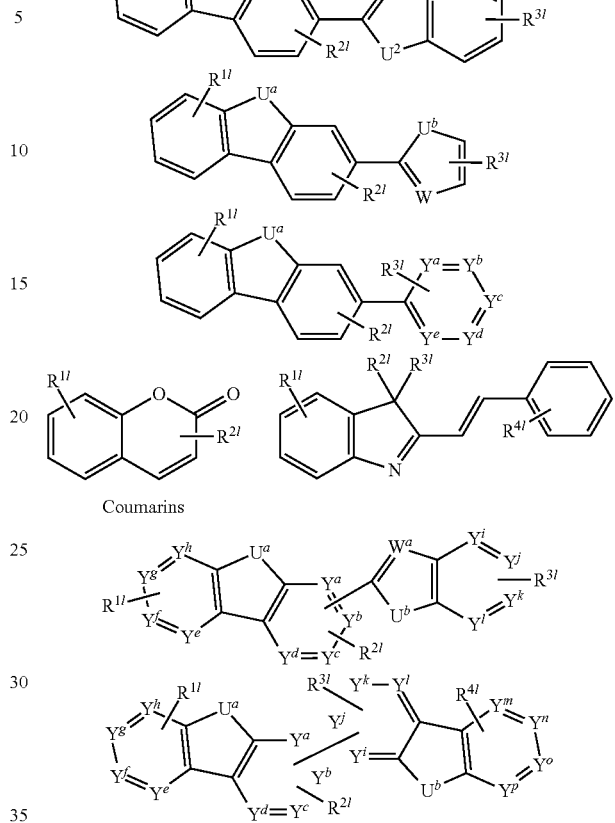

wherein:
each of $R^{1l}$, $R^{2l}$, $R^{3l}$, $R^{4l}$, $R^{5l}$, $R^{6l}$, $R^{7l}$, and $R^{8l}$ is a mono-, di-, tri-, or tetra-substitution and each is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, each of $Y^a$, $Y^b$, $Y^c$, $Y^d$, $Y^e$, $Y^f$, $Y^g$, $Y^h$, $Y^i$, $Y^j$, $Y^k$, $Y^l$, $Y^m$, $Y^n$, $Y^o$, and $Y^p$ is independently C, N or B, each of $U^a$, $U^b$, and $U^c$ is independently $CH_2$, $CR^1R^2$, C=O, $CH_2$, $SiR^1R^2$, $GeH_2$, $GeR^1R^2$, NH, $NR^3$, PH, $PR^3$, $R^3P=O$, $AsR^3$, $R^3As=O$, O, S, S=O, $SO_2$, Se, Se=O, $SeO_2$, BH, $BR^3$, $R^3Bi=O$, BiH, or $BiR^3$, and each of $W^a$, $W^b$, and $W^c$ is independently CH, $CR^1$, $SiR^1$, GeH, $GeR^1$, N, P, B, Bi, or Bi=O, where $R^1$, $R^2$, and $R^3$ are as defined herein.

In one aspect, fluorescent luminophore $LP^1$ is covalently bonded to $L^1$ directly, $LP^2$ is covalently bonded to $L^2$ directly, $LP^3$ is covalently bonded to $L^3$ directly, $LP^4$ is covalently bonded to $L^4$ directly, fluorescent luminophore $LP^5$ is covalently bonded to $L^5$ directly, fluorescent luminophore $LP^6$ is covalently bonded to $L^6$ directly, or any combination thereof. In another aspect, fluorescent luminophore $LP^1$ is covalently bonded to $L^1$ by a linking atom or linking group, LP² is covalently bonded to L² by a linking atom or linking group, LP³ is covalently bonded to L³ by a linking atom or linking group, LP⁴ is covalently bonded to L⁴ by a linking atom or linking group, fluorescent luminophore LP⁵ is covalently bonded to L⁵ by a linking atom or linking group, fluorescent luminophore LP⁶ is covalently bonded to L⁶ by a linking atom or linking group, or any combination thereof. In some aspects, each linking atom or linking group is independently one of the following structures.

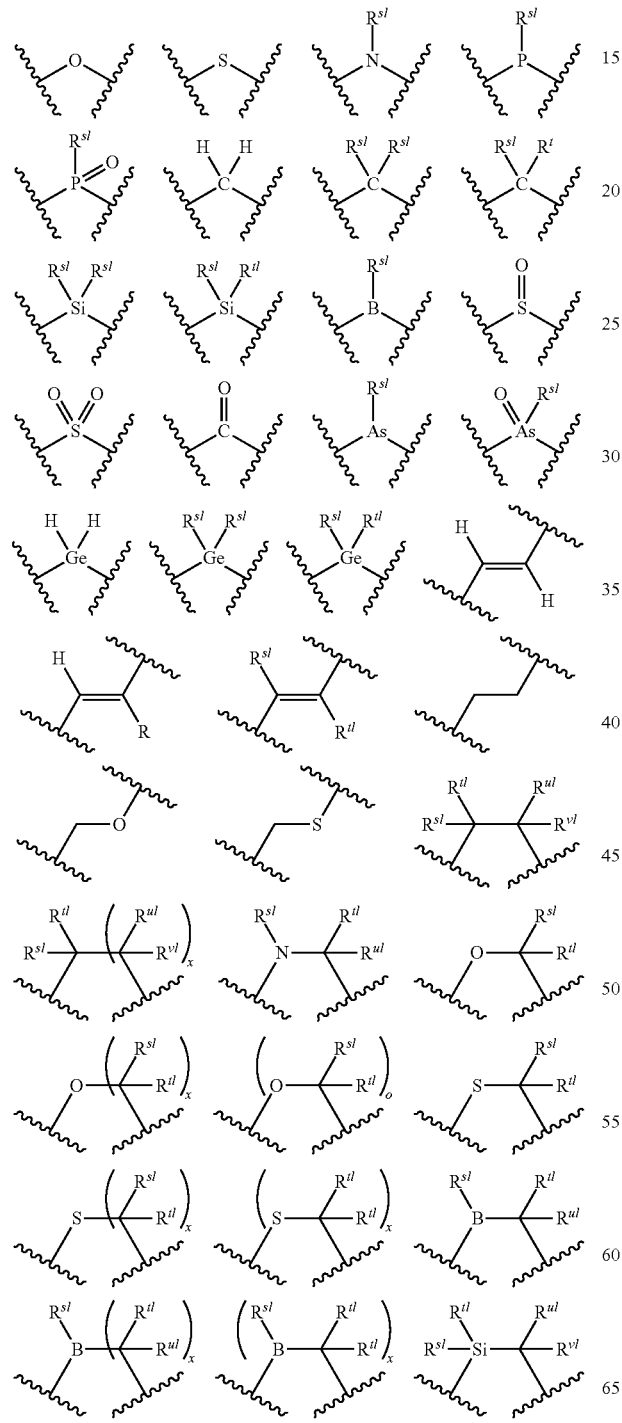
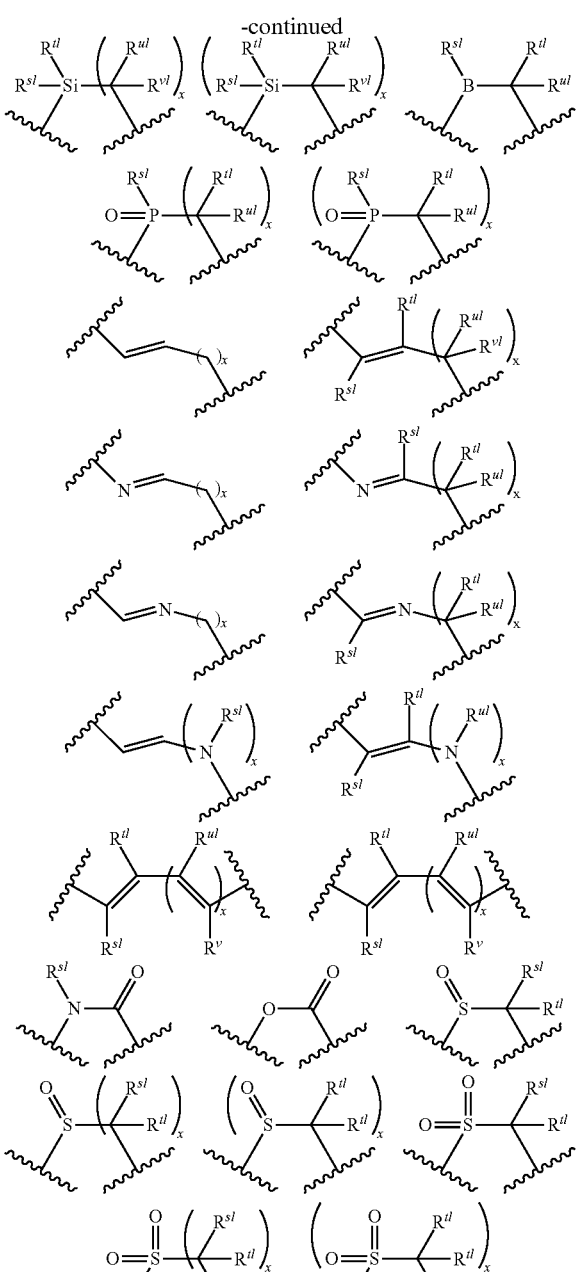

wherein:
x is an integer from 1 to 10,
each of $R^{sl}$, $R^{tl}$, $R^{ul}$, and $R^{vl}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, the linking atom and linking group recited above is covalently bonded to any atom of the fluorescent luminophore $LP^1$, $LP^2$, $LP^3$, $LP^4$, $LP^5$, and $LP^6$ if valency permits. For example, if $LP^1$ is

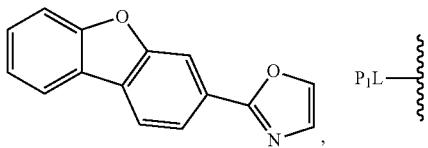

can be

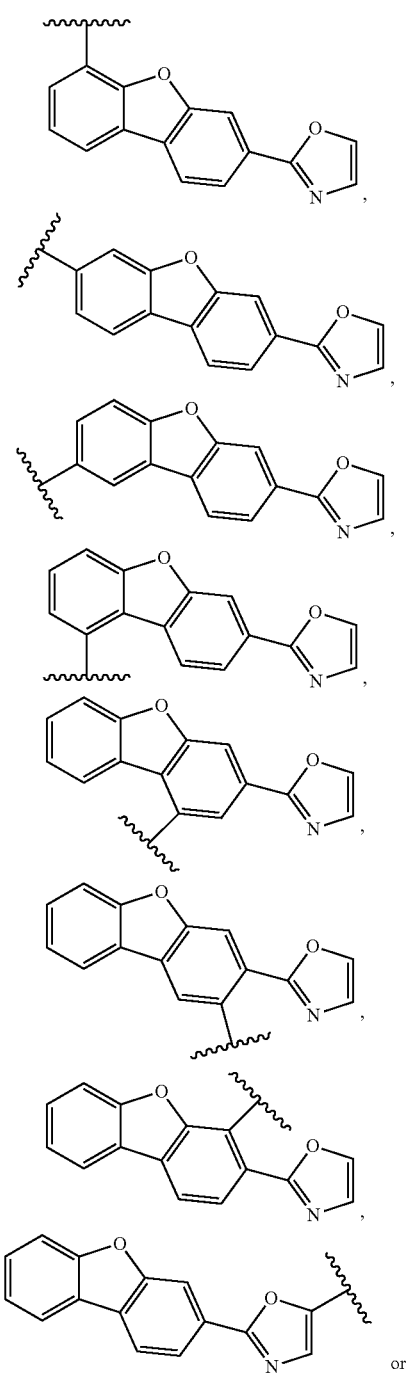

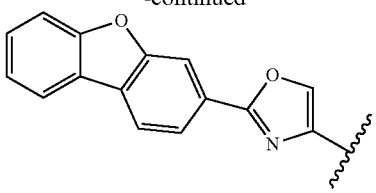

In one aspect, at least one $R^a$ is present. In another aspect, $R^a$ is absent. In one aspect, $R^a$ is a mono-substitution. In another aspect, $R^a$ is a di-substitution. In yet another aspect, $R^a$ is a tri-substitution.

In one aspect, $R^a$ is connected to at least $Y^1$. In another aspect, $R^a$ is connected to at least $Y^2$. In yet another aspect, $R^a$ is connected to at least $Y^3$. In one aspect, $R^a$ is connected to at least $Y^1$ and $Y^2$. In one aspect, $R^a$ is connected to at least $Y^1$ and $Y^3$. In one aspect, $R^a$ is connected to at least $Y^2$ and $Y^3$. In one aspect, $R^a$ is connected to $Y^1$, $Y^2$, and $Y^3$.

In one aspect, $R^a$ is a di-substitution and the $R^a$'s are linked together. When the $R^a$'s are linked together the resulting structure may be a cyclic structure that includes a portion of the five-membered cyclic structure as described herein. For example, a cyclic structure may be formed when the di-substitution is of $Y^1$ and $Y^2$ and the $R^a$'s are linked together. A cyclic structure may also be formed when the di-substitution is of $Y^2$ and $Y^3$ and the $R^a$'s are linked together. A cyclic structure can also be formed when the di-substitution is of $Y^3$ and $Y^4$ and the $R^a$'s are linked together.

In one aspect, each $R^a$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. Two or more of $R^a$ may be linked together.

In one aspect, at least one $R^b$ is present. In another aspect, $R^b$ is absent. In one aspect, $R^b$ is a mono-substitution. In another aspect, $R^b$ is a di-substitution. In yet another aspect, $R^b$ is a tri-substitution.

In one aspect, each $R^b$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. Two or more of $R^b$ may be linked together.

In one aspect, at least one $R^c$ is present. In another aspect, $R^c$ is absent. In one aspect, $R^c$ is a mono-substitution. In another aspect, $R^c$ is a di-substitution. In yet another aspect, $R^c$ is a tri-substitution.

In one aspect, each $R^c$ is deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. Two or more of $R^c$ may be linked together.

In one aspect, at least one $R^d$ is present. In another aspect, $R^d$ is absent. In one aspect, $R^d$ is a mono-substitution. In another aspect, $R^d$ is a di-substitution. In yet another aspect, $R^d$ is a tri-substitution.

In one aspect, $R^d$ is connected to at least $Y^5$. In another aspect, $R^d$ is connected to at least $Y^6$. In yet another aspect, $R^d$ is connected to at least $Y^7$. In one aspect, $R^d$ is connected to at least $Y^5$ and $Y^6$. In one aspect, $R^d$ is connected to at least $Y^5$ and $Y^7$. In one aspect, $R^d$ is connected to at least $Y^6$ and $Y^7$. In one aspect, $R^d$ is connected to $Y^5$, $Y^6$, and $Y^7$.

In one aspect, $R^d$ is a di-substitution and the $R^d$'s are linked together. When the $R^d$'s are linked together the resulting structure can be a cyclic structure which includes a portion of the five-membered cyclic structure as described herein. For example, a cyclic structure can be formed when the di-substitution is of $Y^5$ and $Y^6$ and the $R^d$'s are linked together. A cyclic structure can also be formed when the di-substitution is of $Y^6$ and $Y^7$ and the $R^d$'s are linked together. A cyclic structure can also be formed when the di-substitution is of $Y^7$ and $Y^8$ and the $R^d$'s are linked together. Two or more of may be linked together. Similarly, two or more of $R^e$ or $R^f$ may be linked together.

In one aspect, $R^1$ and $R^2$ are linked to form the cyclic structure

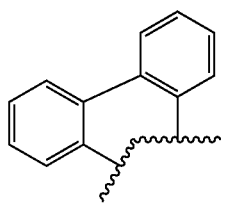

In one aspect, X is N, P, P=O, As, As=O, $CR^1$, CH, $SiR^1$, SiH, $GeR^1$, GeH, B, Bi, or Bi=O. In one example, X is N or P. In another example, X is P=O, As, As=O, $CR^1$, CH, $SiR^1$, SiH, $GeR^1$, GeH, B, Bi, or Bi=O. In another aspect, X is Z, $Z^1$, or $Z^2$ (e.g., a linking group such as $NR^1$, $PR^1$, P=$OR^1$, $AsR^1$, As=$OR^1$, $C(R^1)_2$, $CH(R^1)$, $Si(R^1)_2$, $SiH(R^1)$, $Ge(R^1)_2$, $GeH(R^1)$, $BR^1$, $BiR^1$, or Bi=$O(R^1)$) $R^1$ is as defined herein.

In one aspect, Y is N, P, P=O, As, As=O, $CR^1$, CH, $SiR^1$, SiH, $GeR^1$, GeH, B, Bi, or Bi=O. In one example, Y is N or P. In another example, Y is P=O, As, As=O, $CR^1$, CH, $SiR^1$, SiH, $GeR^1$, GeH, B, Bi, or Bi=O. In another aspect, Y is Z, $Z^1$, or $Z^2$ (e.g., a linking group such as $NR^1$, $PR^1$, P=$OR^1$, $AsR^1$, As=$OR^1$, $C(R^1)_2$, $CH(R^1)$, $Si(R^1)_2$, $SiH(R^1)$, $Ge(R^1)_2$, $GeH(R^1)$, $BR^1$, $BiR^1$, or Bi=$O(R^1)$) $R^1$ is as defined herein.

In one aspect, $L^2$ is aryl, cycloalkyl, cycloalkenyl, heteroaryl, heterocyclyl, carbene, or N-heterocyclic carbene. In one example, $L^2$ is aryl, cycloalkyl, cycloalkenyl, heteroaryl, or N-heterocyclyl. In another example, $L^2$ is aryl or heteroaryl. In yet another example, $L^2$ is aryl. In one aspect, $L^2$ is

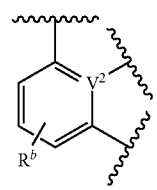

for example,

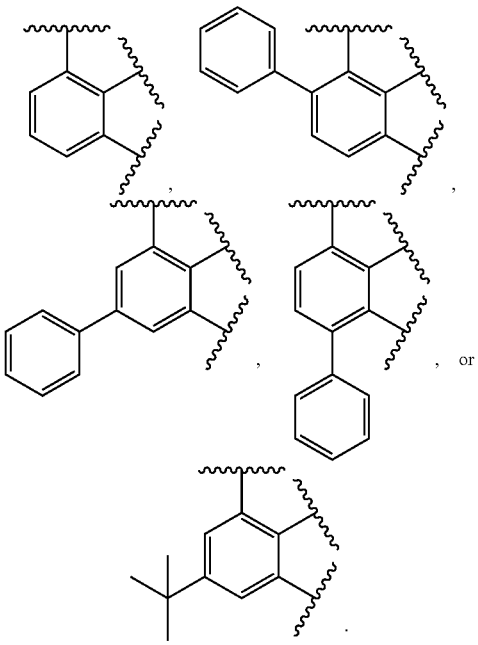

In another aspect, $L^2$ is

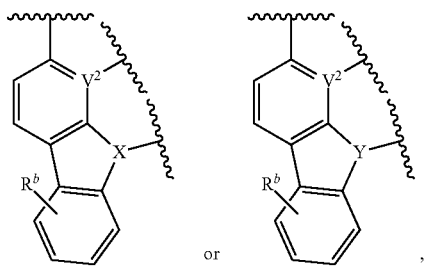

for example,

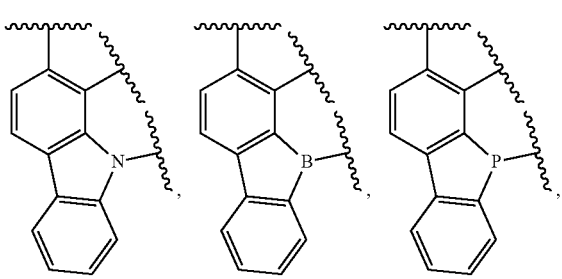

-continued
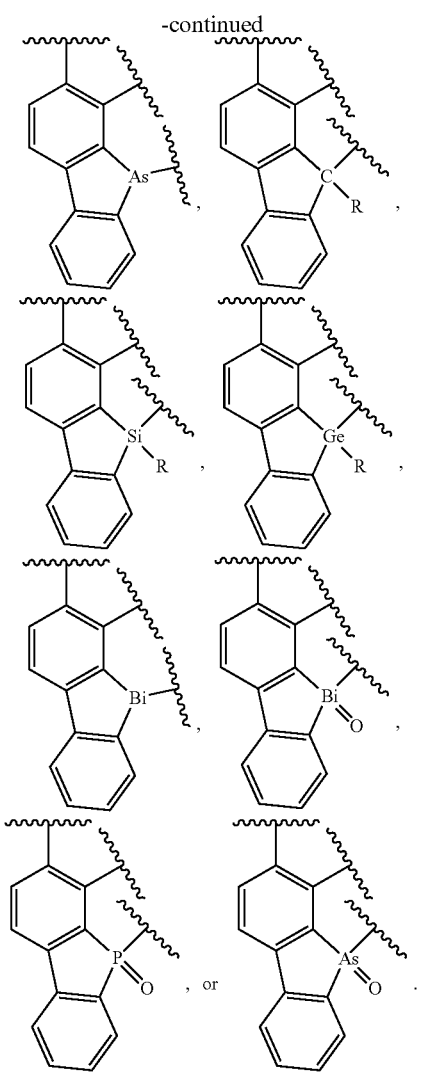
In another aspect, L² is
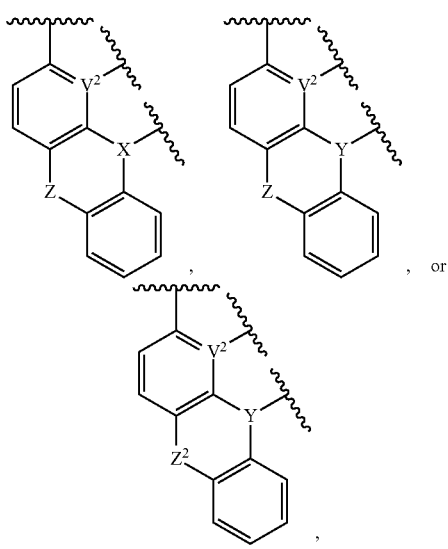
for example,
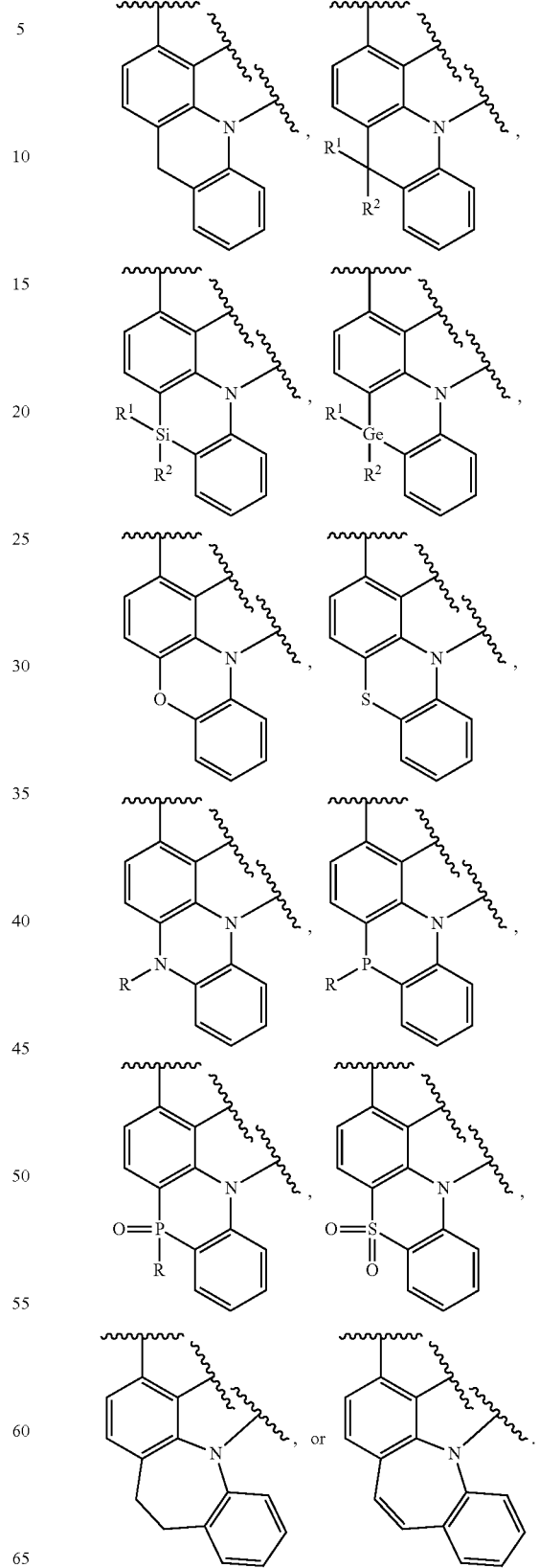

In another aspect, L² is

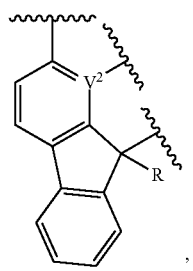

wherein each R, R¹, and R² is independently hydrogen, alkyl, alkenyl, alkynyl, aryl, cycloalkyl, cycloalkenyl, heteroaryl, heterocyclyl, halogen, hydroxyl, amino, or thiol. In one aspect, V² is N, C, P, B, or Si. In one example, V² is N or C. In another example, V² is C.

In one aspect, L³ is aryl, cycloalkyl, cycloalkenyl, heteroaryl, heterocyclyl, carbene, or N-heterocyclic carbene. In one example, L³ is aryl, cycloalkyl, cycloalkenyl, heteroaryl, or heterocyclyl. In another example, L³ is aryl or heteroaryl. In yet another example, L³ is aryl. In one aspect, L³ represents

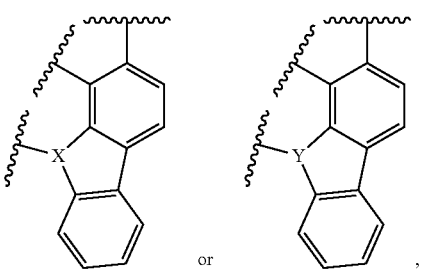

for example,

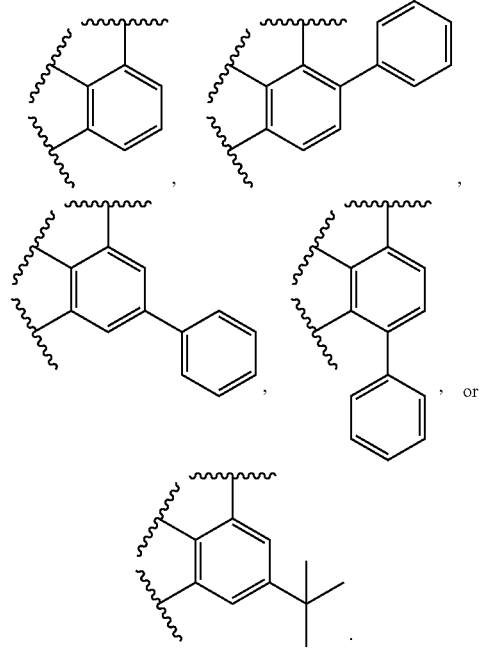

In another aspect, L³ is

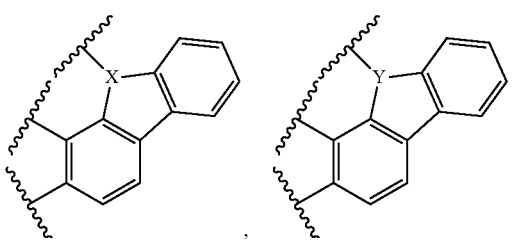

for example,

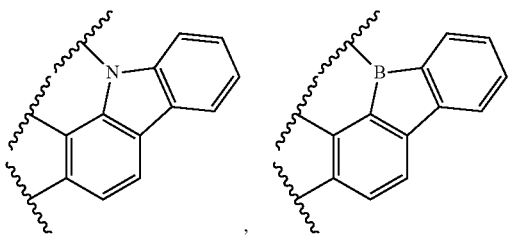

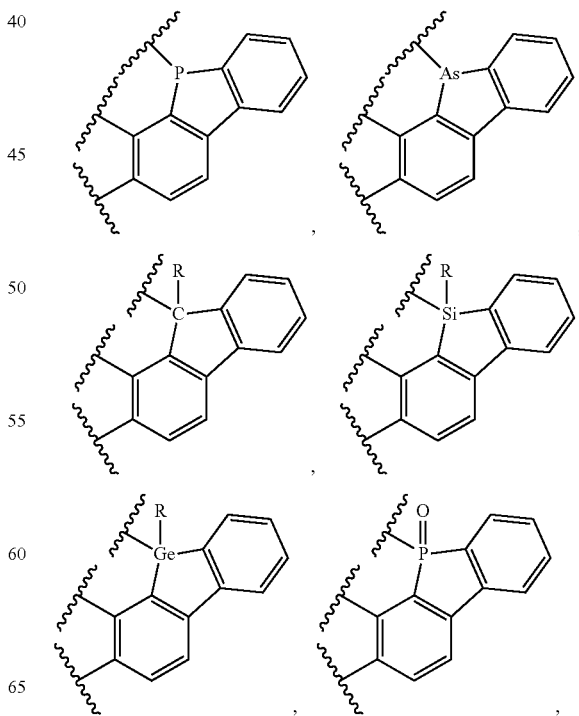

, or

-continued

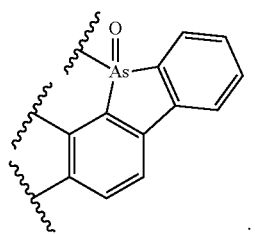

In another aspect, $L^3$ is

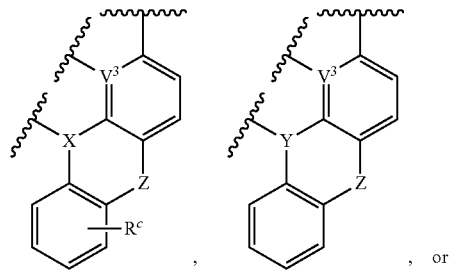

for example,

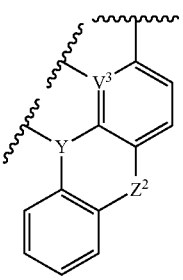

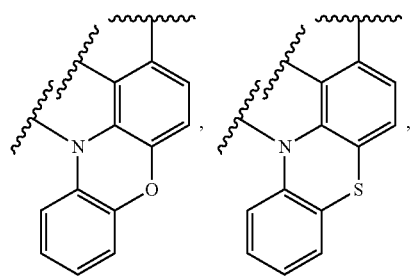

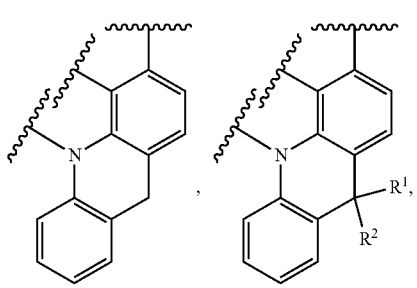

-continued

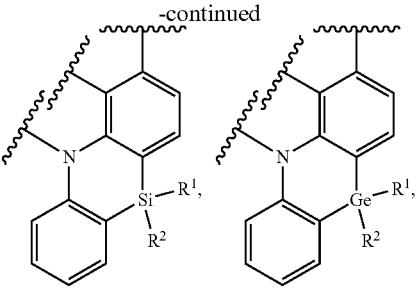

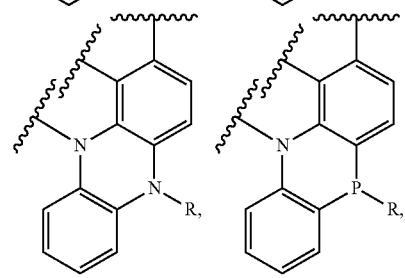

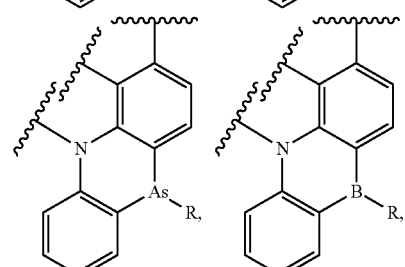

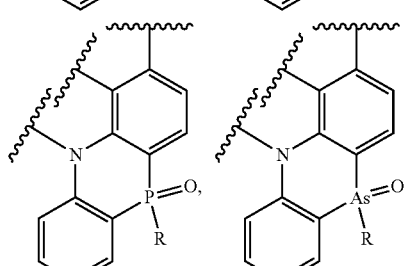

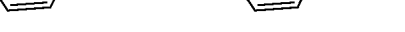

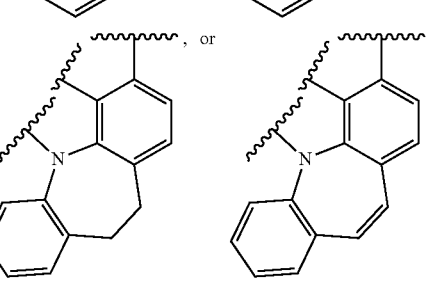

wherein each of R, $R^1$, and $R^2$ is independently hydrogen, alkyl, alkenyl, alkynyl, aryl, cycloalkyl, cycloalkenyl, heteroaryl, heterocyclyl, halogen, hydroxyl, amino, or thiol. In one aspect, $V^3$ is N, C, P, B, or Si. In one example, $V^3$ is N or C. In another example, $V^3$ is C.

In one aspect, $L^4$ is aryl, cycloalkyl, cycloalkenyl, heteroaryl, heterocyclyl, carbene, or N-heterocyclic carbene. For example, $L^4$ is aryl, cycloalkyl, cycloalkenyl, heteroaryl, or heterocyclyl. In another example, $L^4$ is aryl or heteroaryl. In yet another example, $L^4$ is heteroaryl. In yet another example, $L^4$ is heterocyclyl. It is understood that, $V^4$ can be a part of $L^4$ and is intended to include the description of $L^4$ above. In one aspect, $L^4$ is

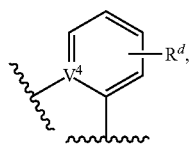

for example,

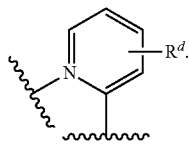

In yet another aspect, $L^4$ is

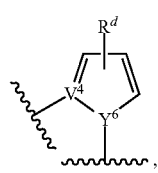

for example,

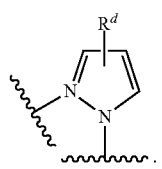

In yet another aspect, $L^4$ is

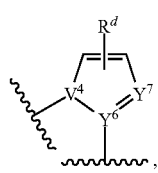

for example,

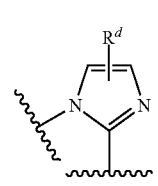

and

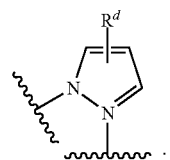

In yet another aspect, $L^4$ is

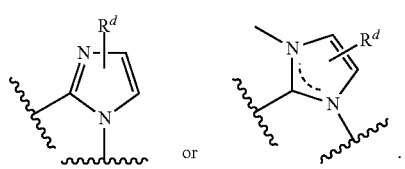

In yet another aspect, $L^4$ is

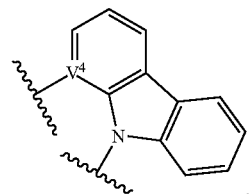

In one aspect, $V^4$ represents N, C, P, B, or Si. In one example, $V^4$ is N or C. In another example, $V^4$ is N.

In one aspect, the platinum, palladium, gold, iridium, or rhodium complexes depicted in this disclosure includes the following structures.

Structures Pt-1

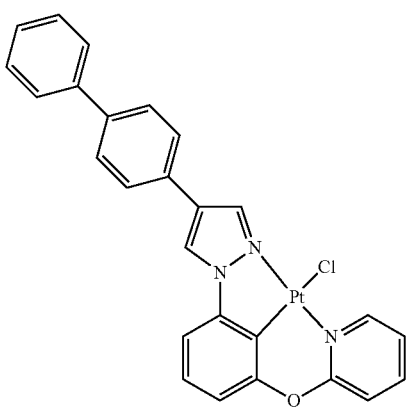

101
-continued
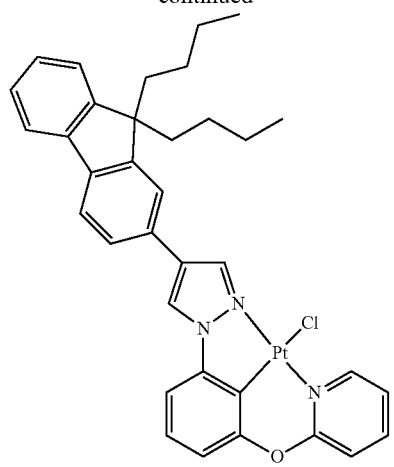
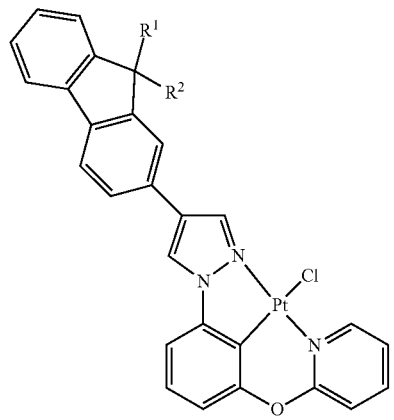
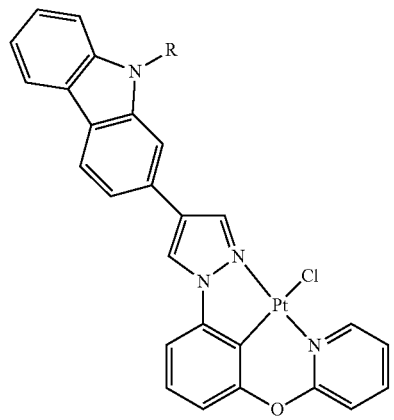
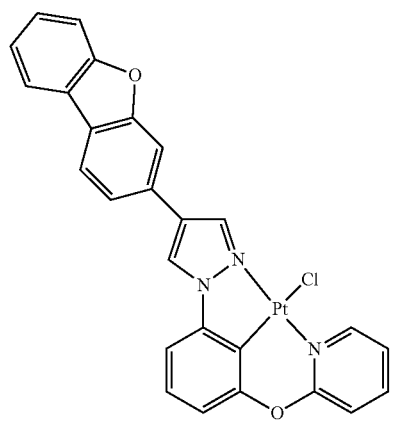
102
-continued
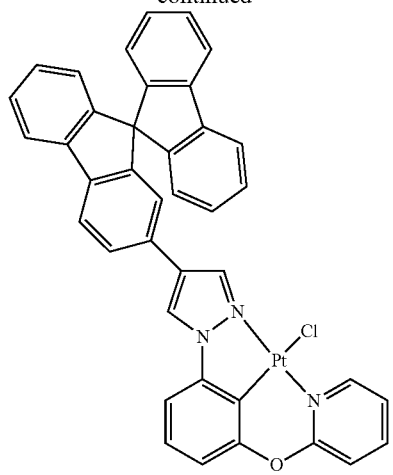
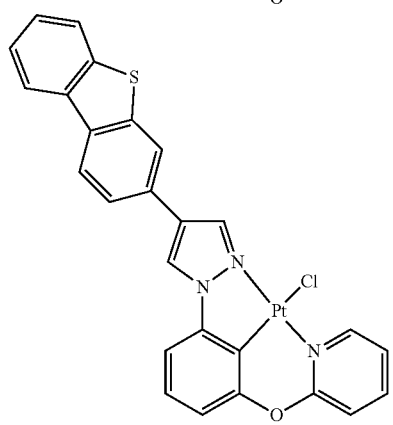
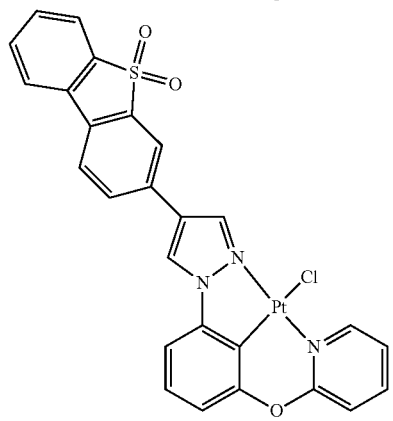
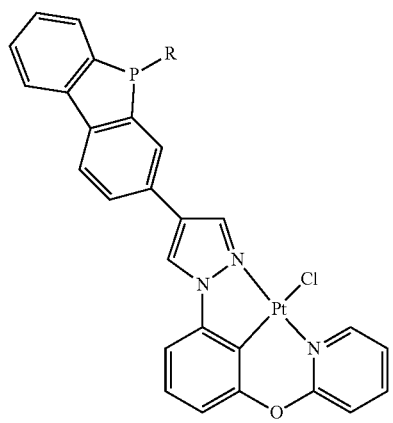

103
-continued
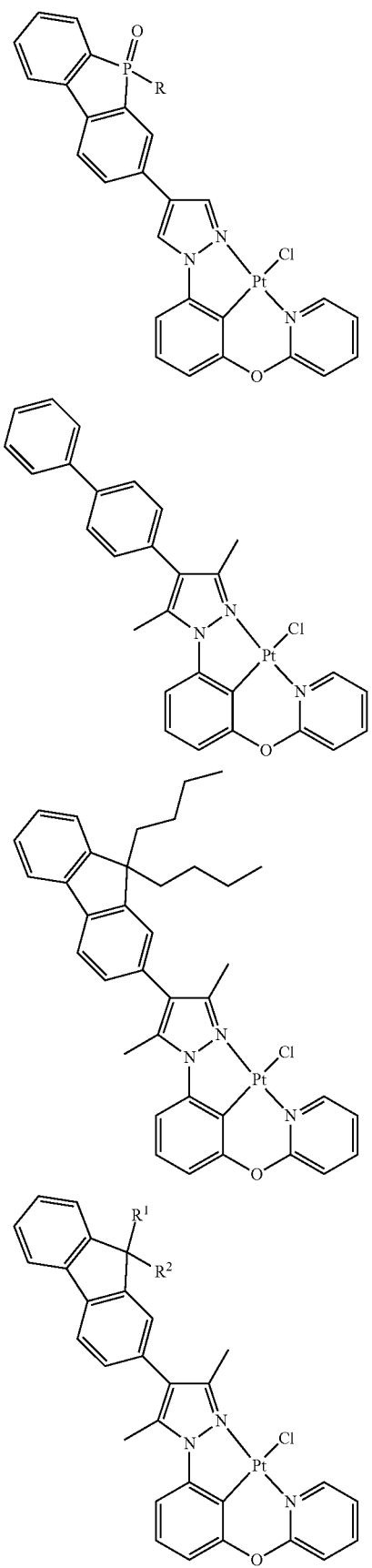
104
-continued
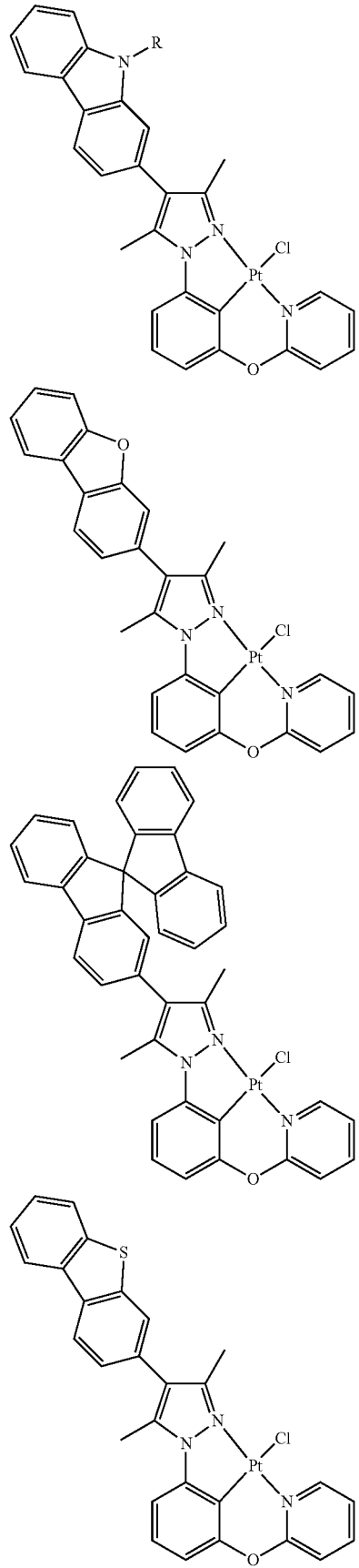

105
-continued
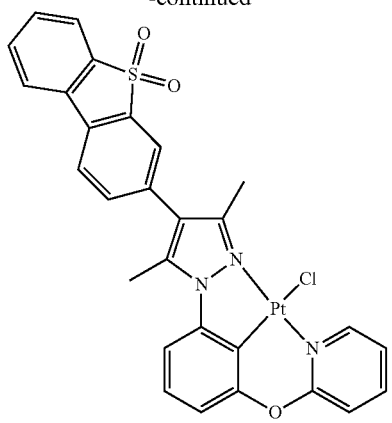
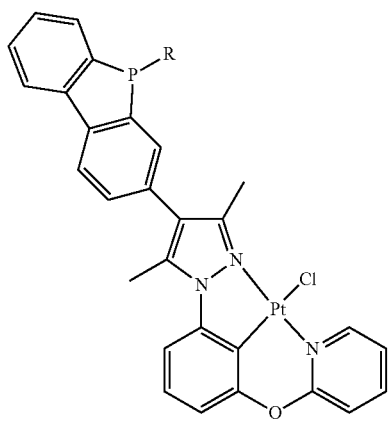
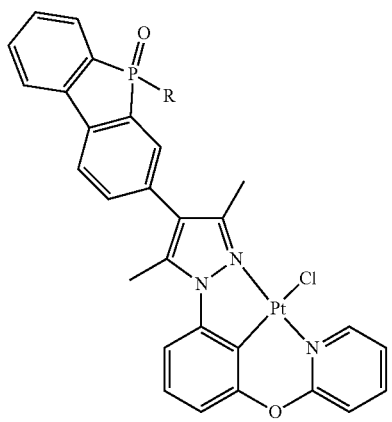
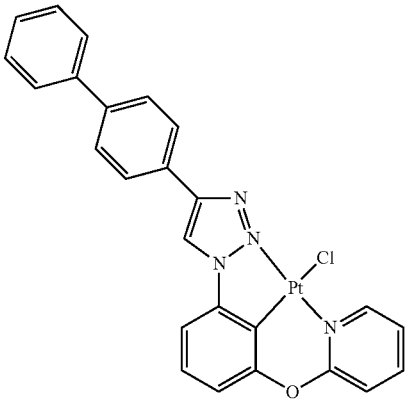
106
-continued
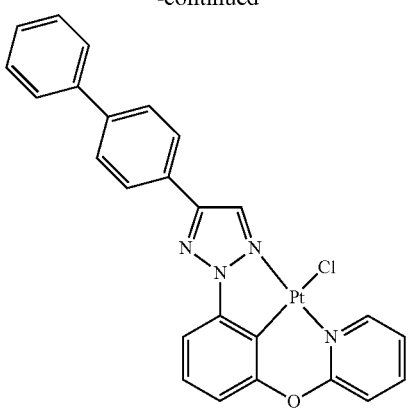
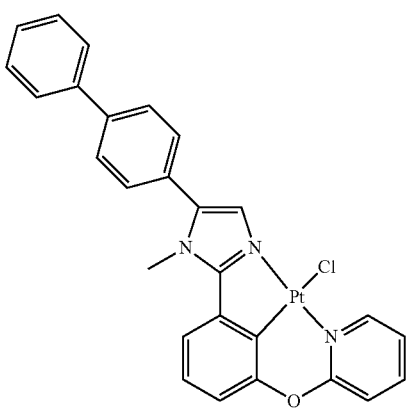
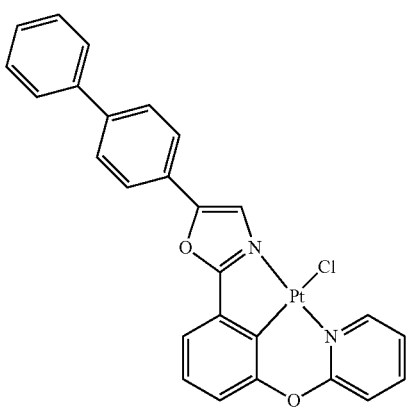
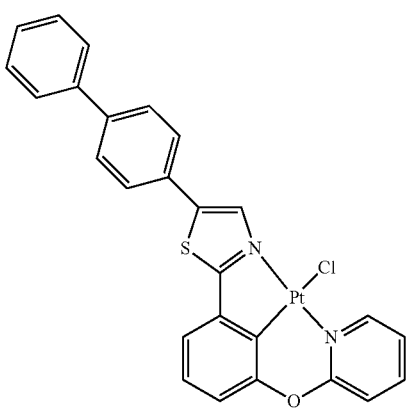

107
-continued
Structures Pt-2
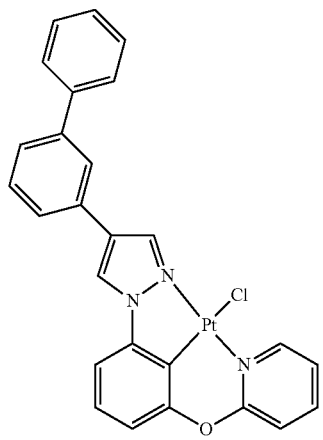
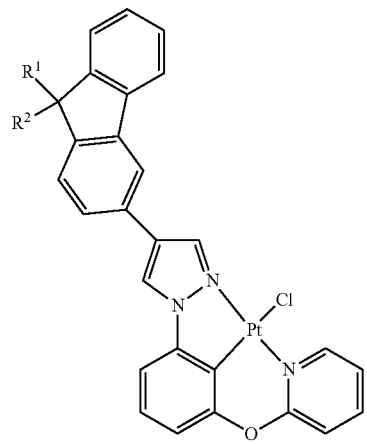
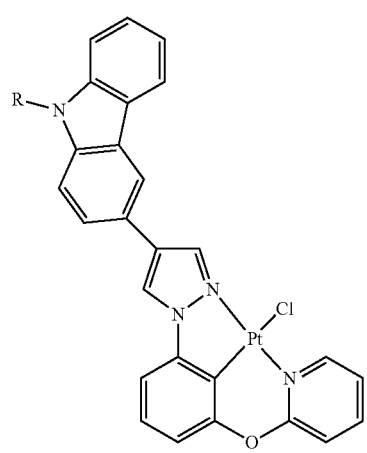
108
-continued
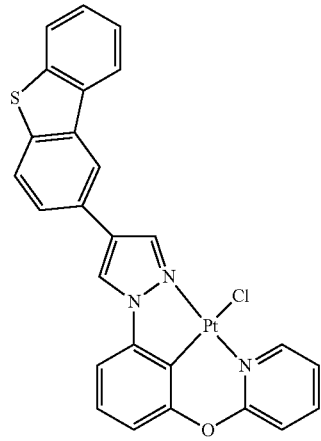
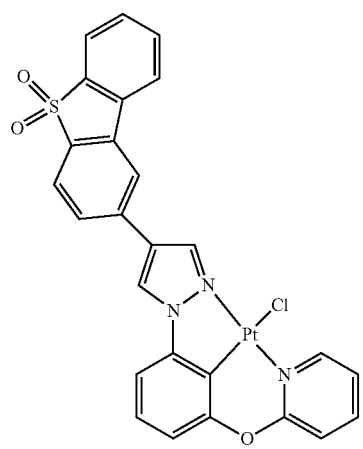
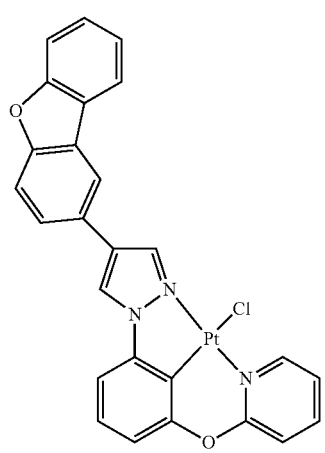

109
-continued
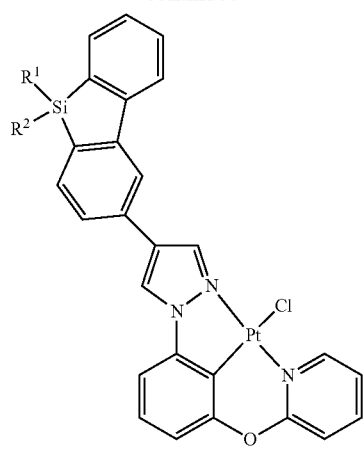
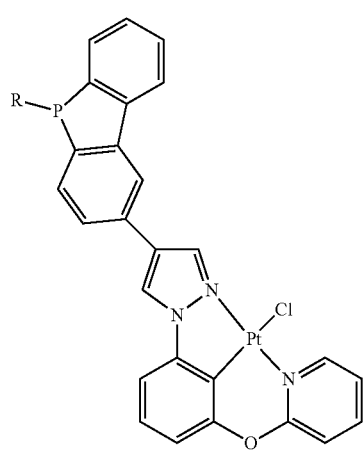
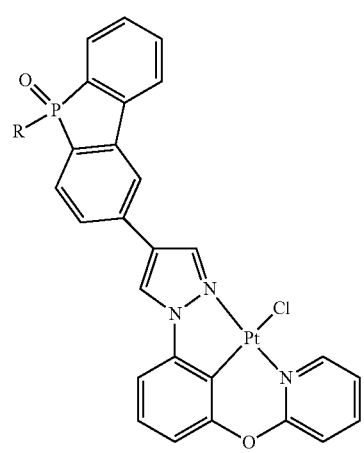
110
-continued
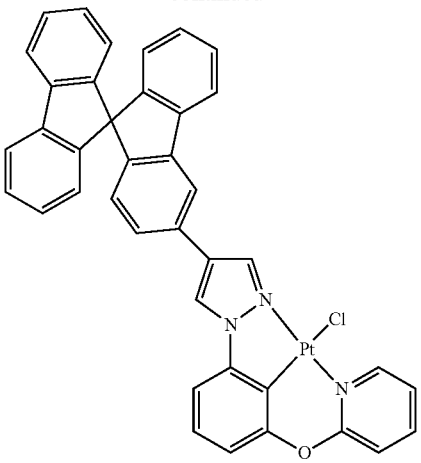
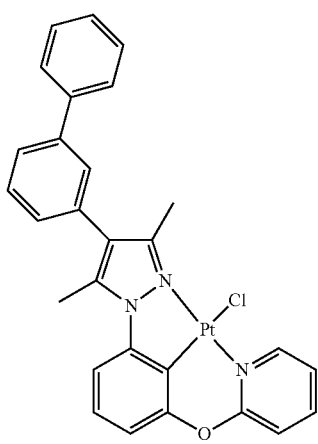
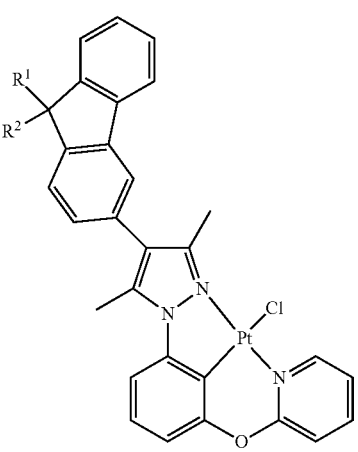

111
-continued
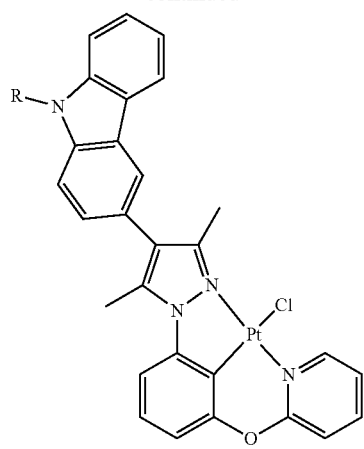
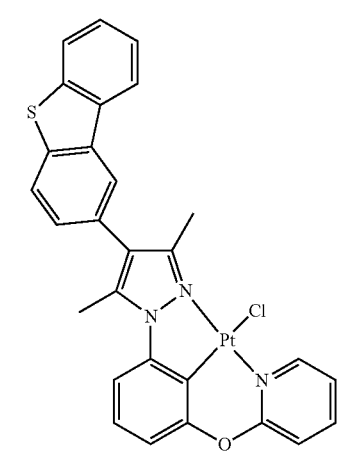
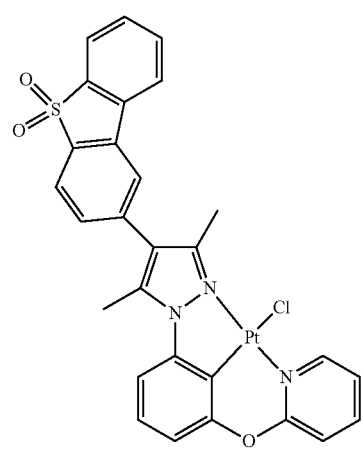
112
-continued
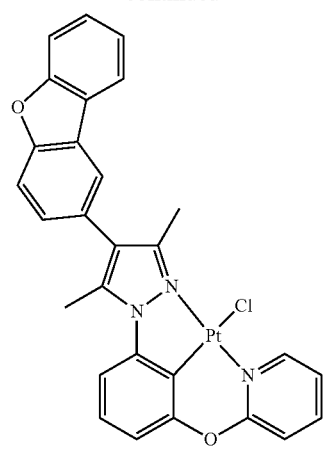
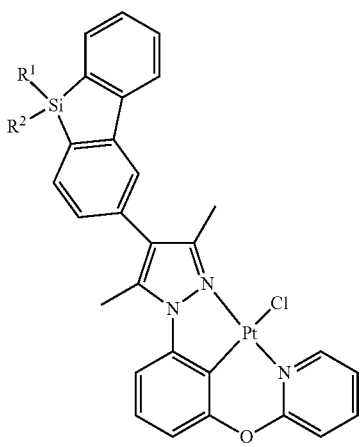
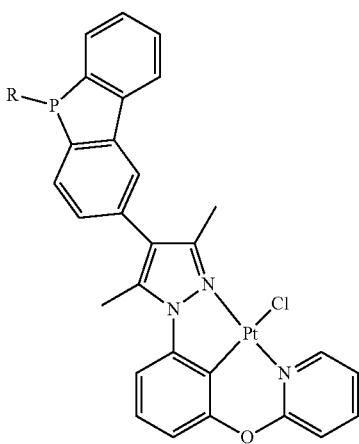

113
-continued
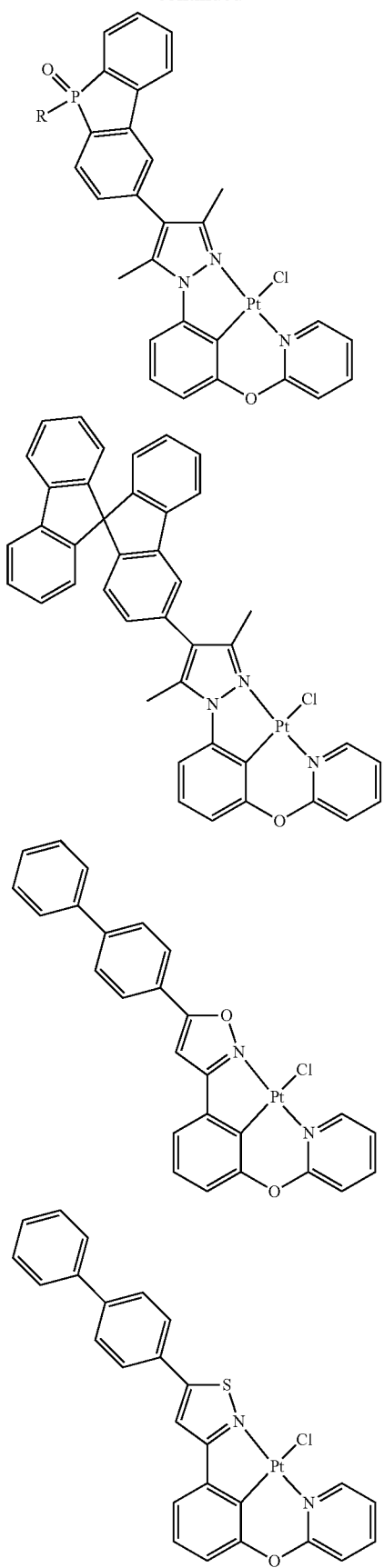
114
-continued
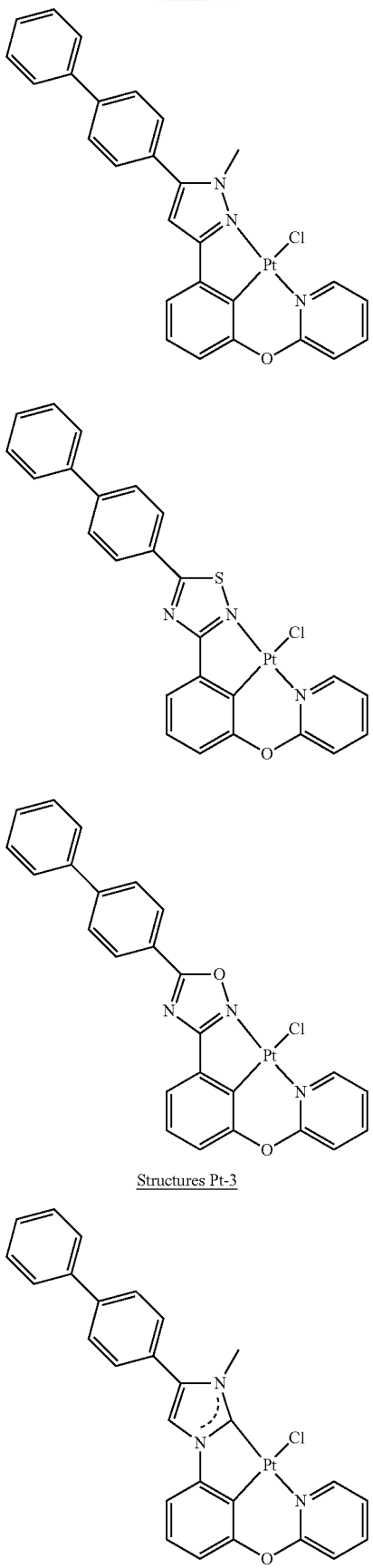
Structures Pt-3

115
-continued
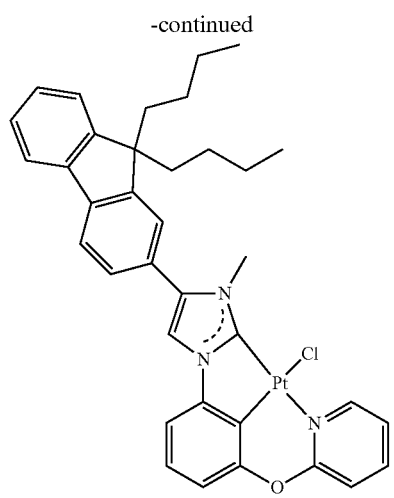
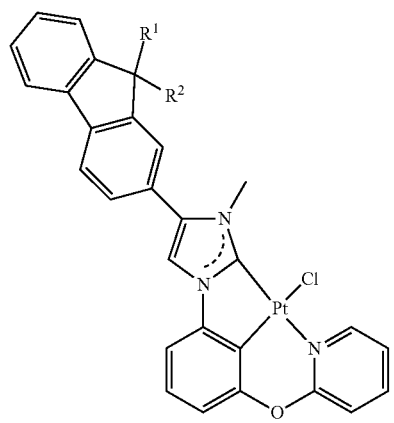
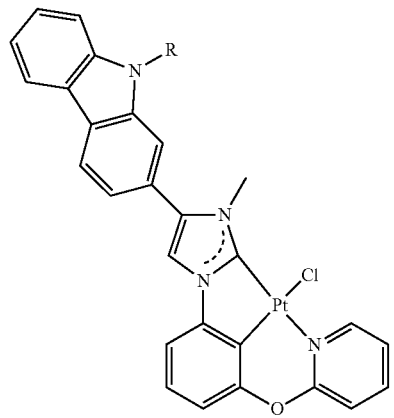
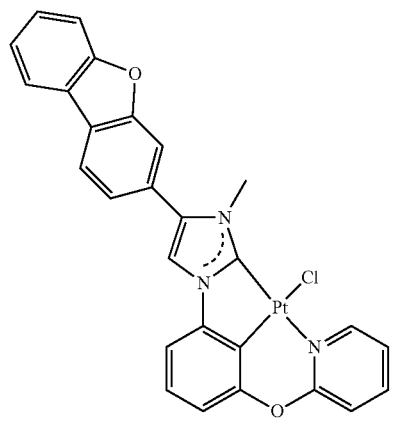
116
-continued
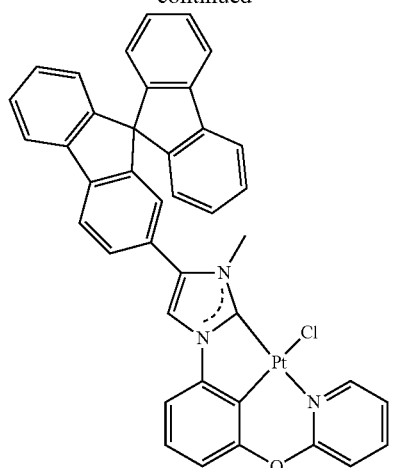
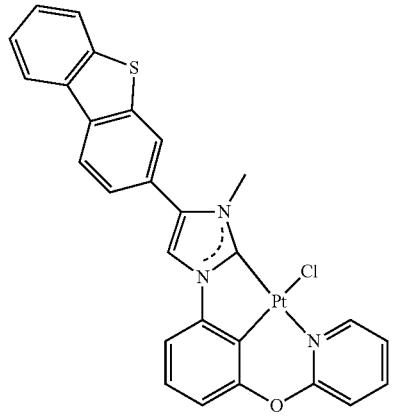
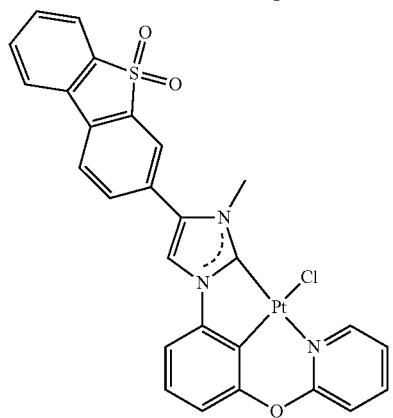
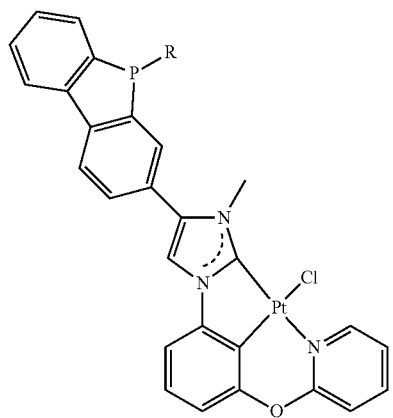

117
-continued
118
-continued
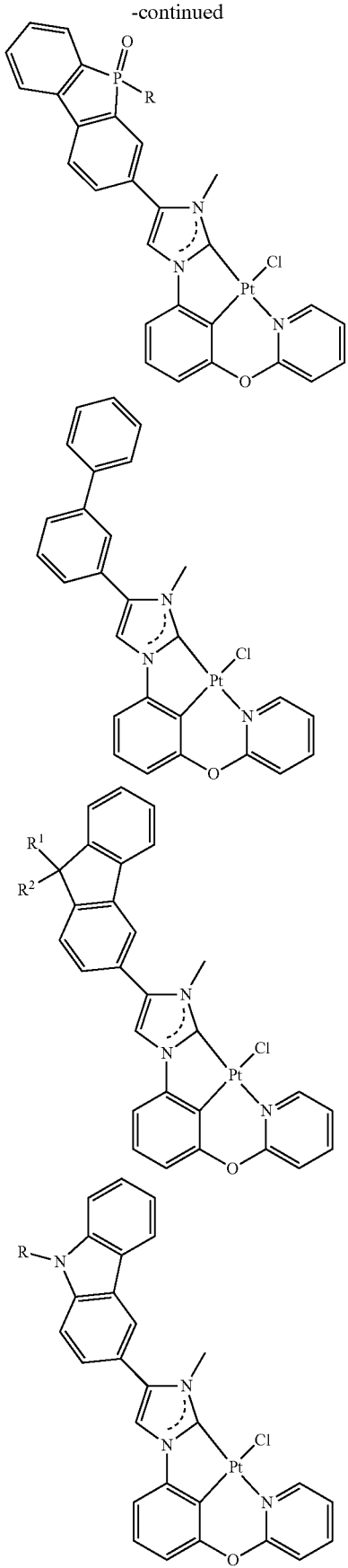
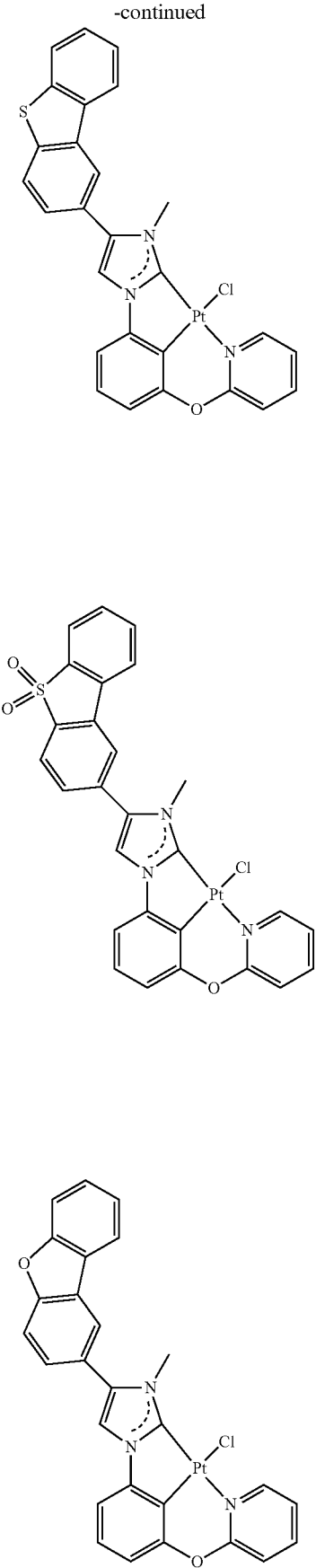

119
-continued
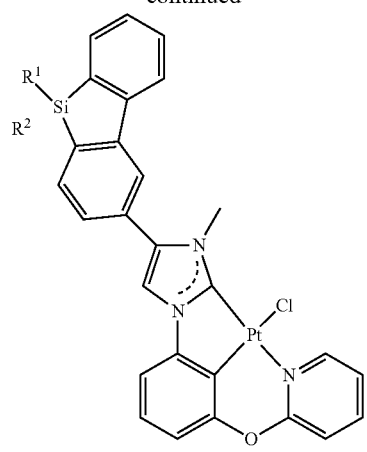
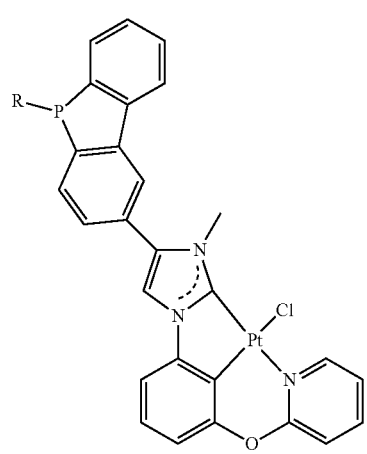
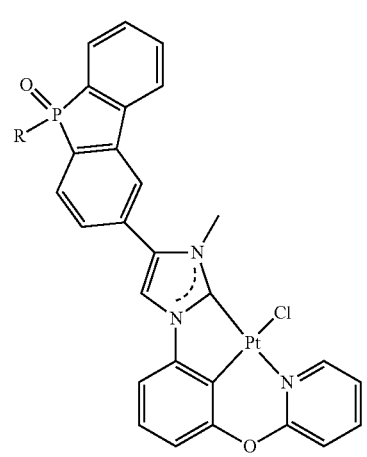
120
-continued
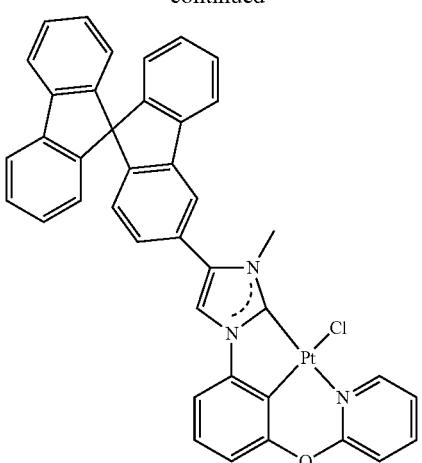
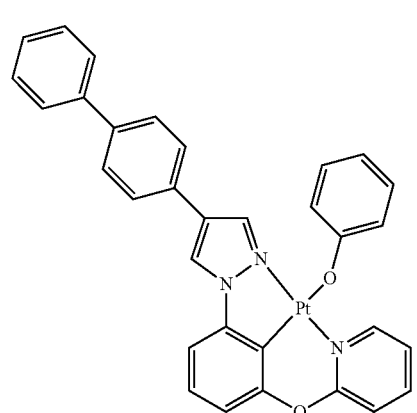
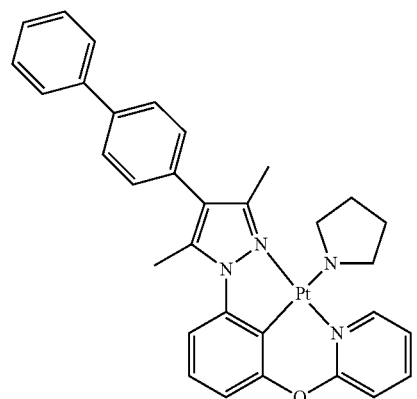
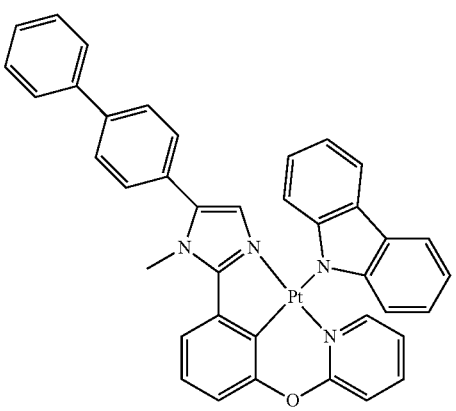

121
-continued
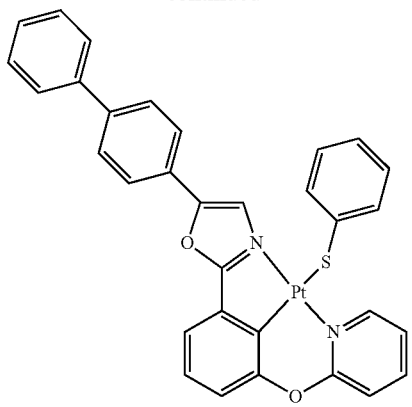
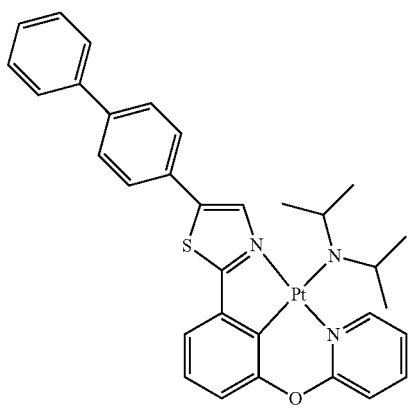
Structures Pt-4
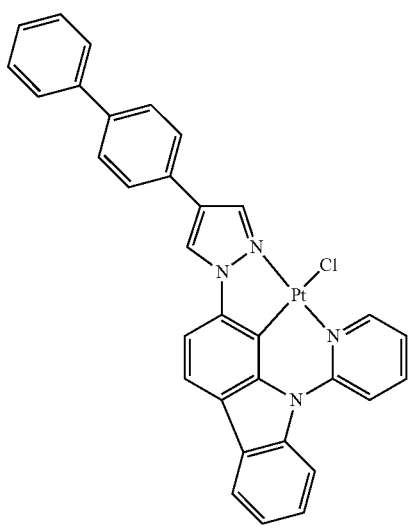
122
-continued
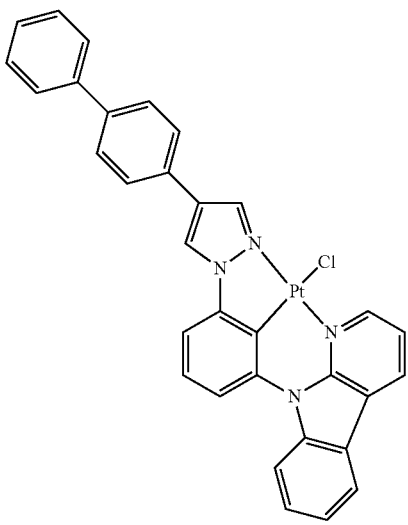
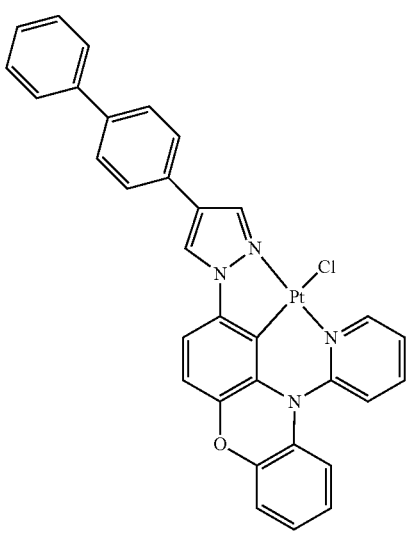
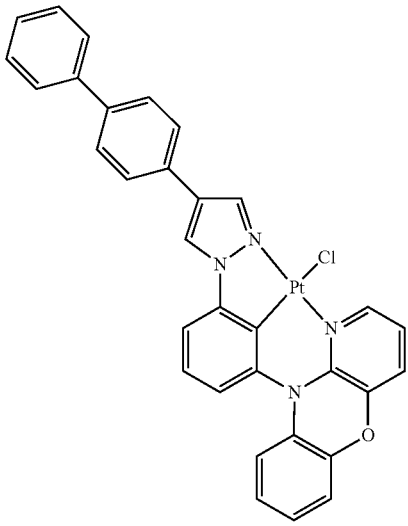

123
-continued
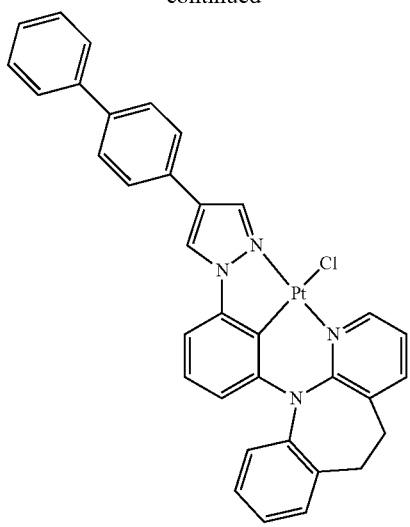
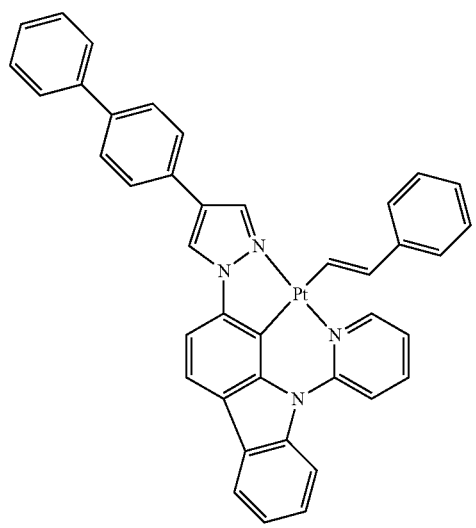
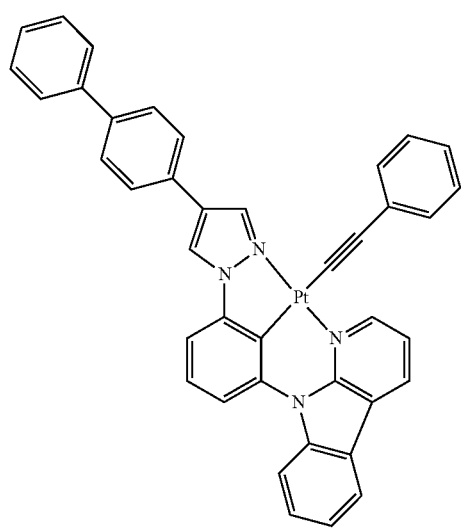
124
-continued
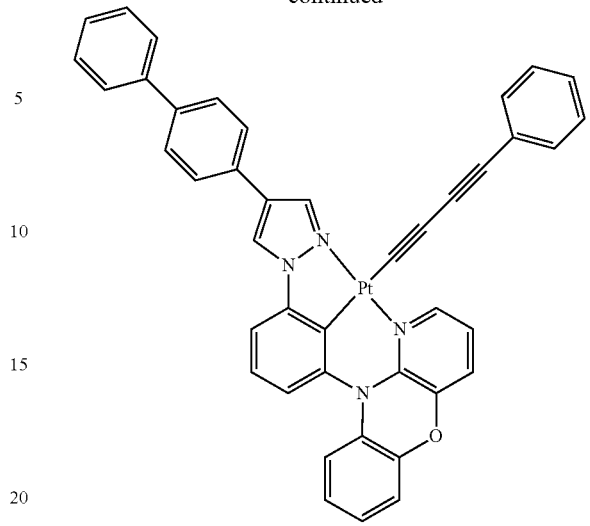
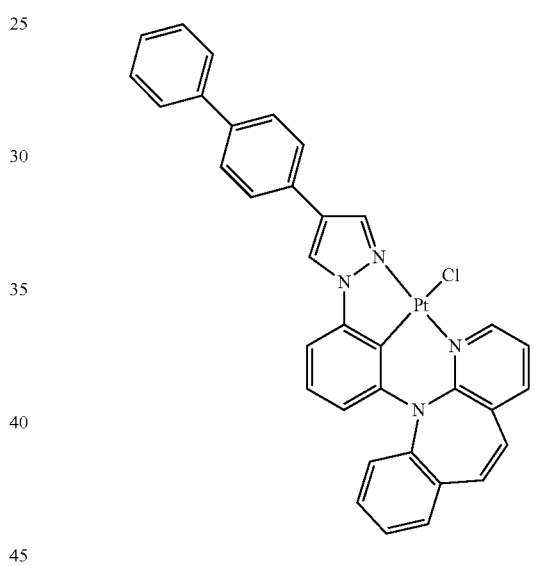
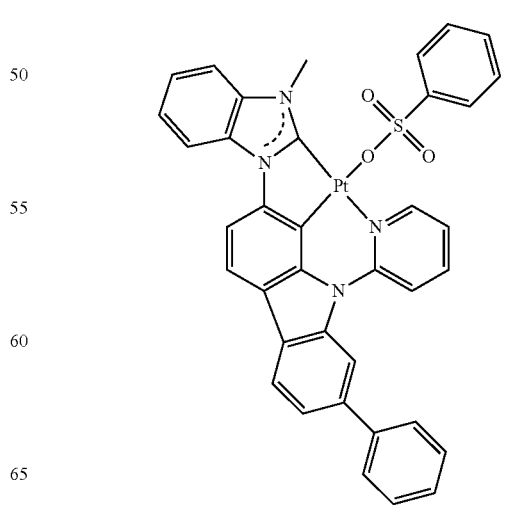

125
-continued

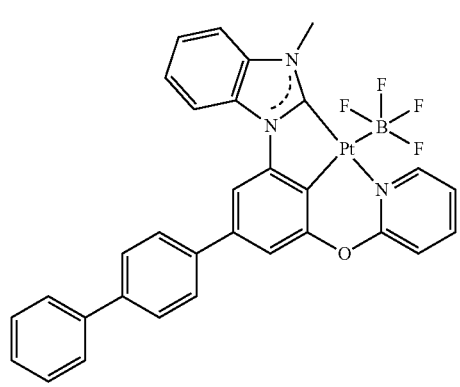
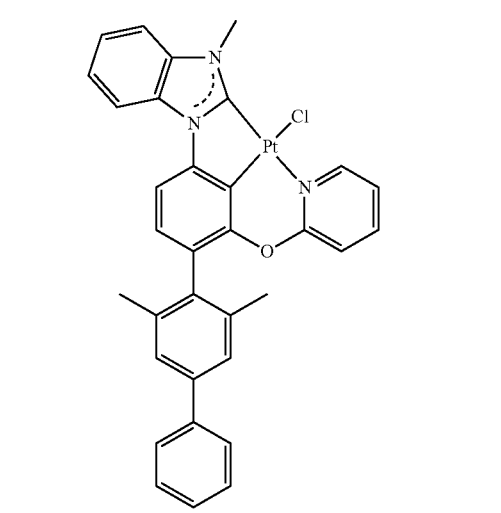
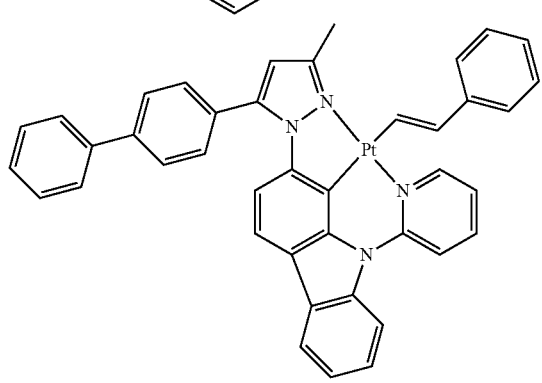
126
-continued
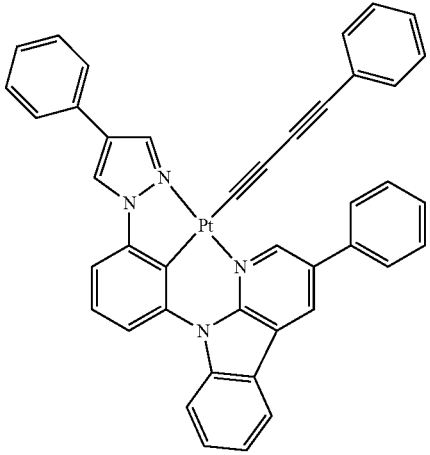
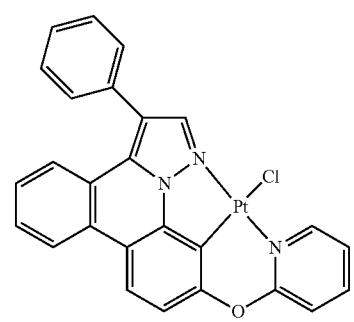
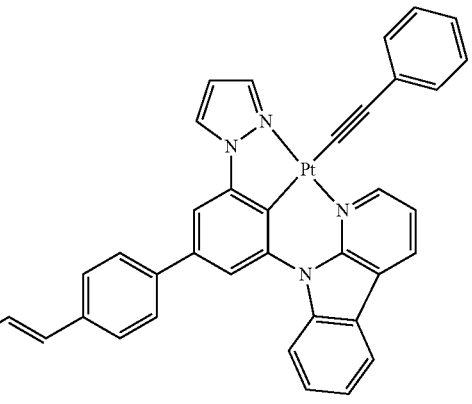
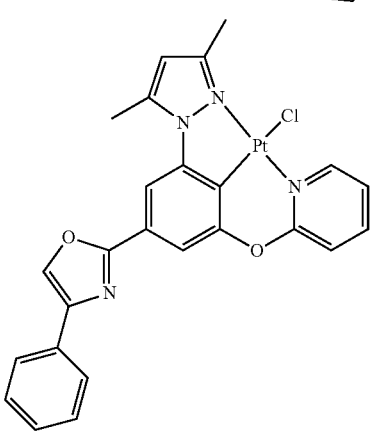

127
-continued
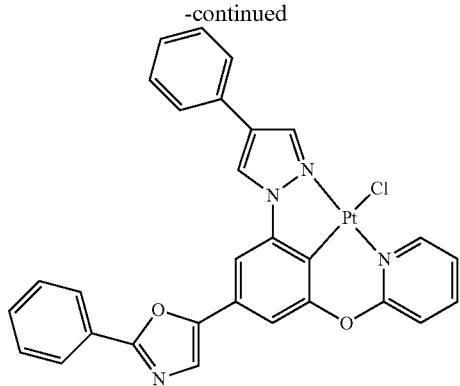
Structures Pt-5
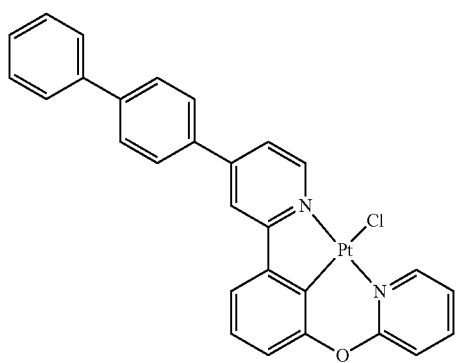
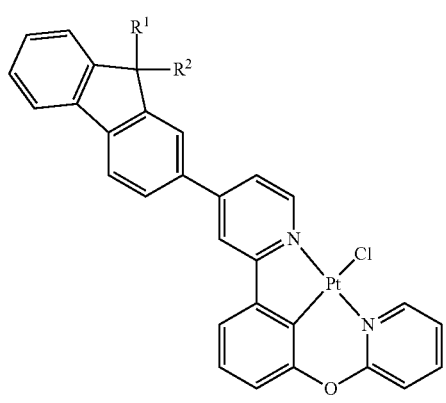
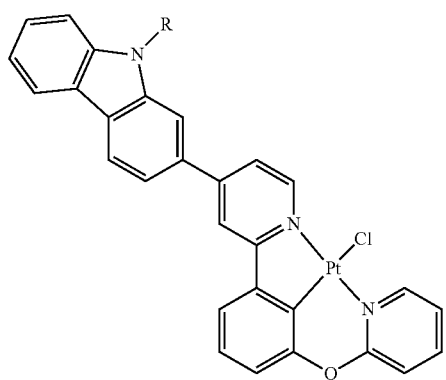
128
-continued
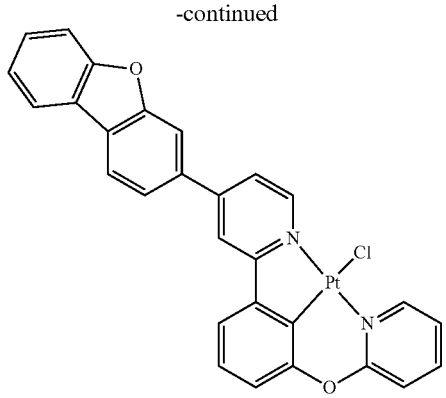
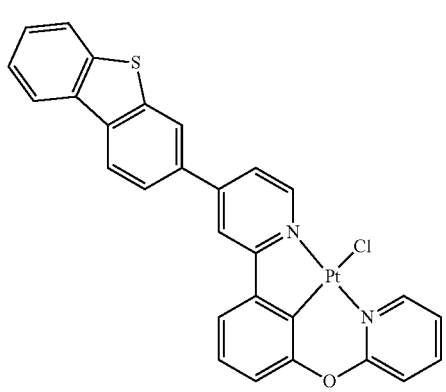
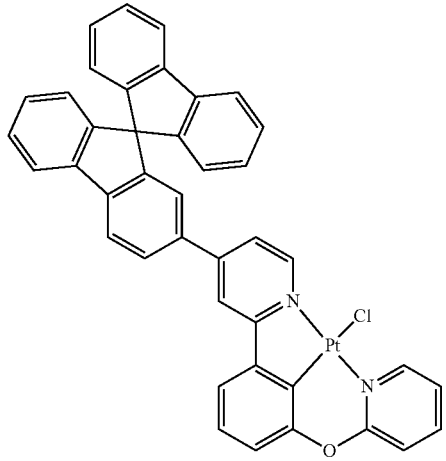
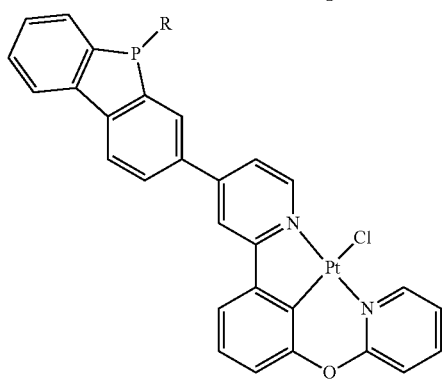

-continued
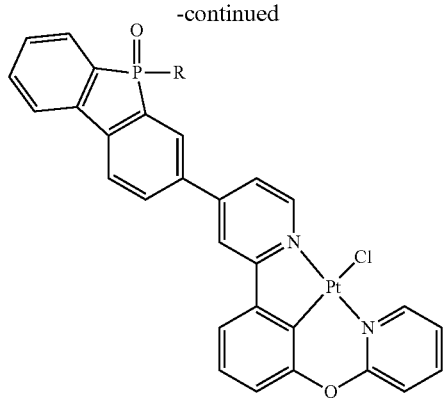
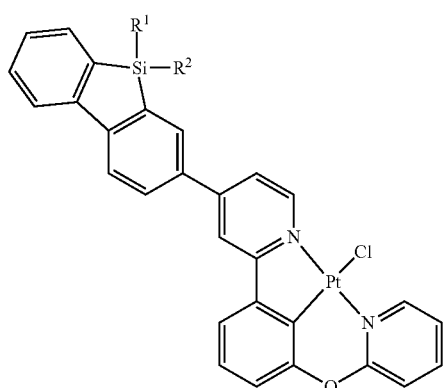
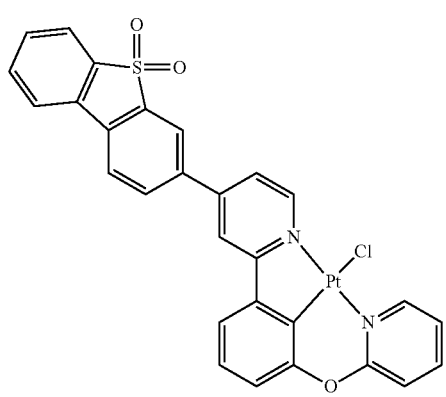
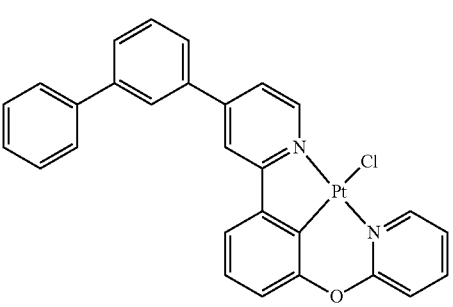
-continued
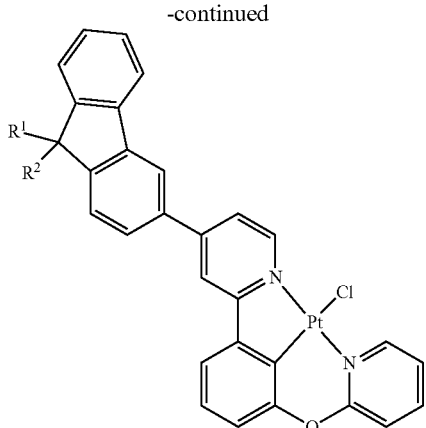
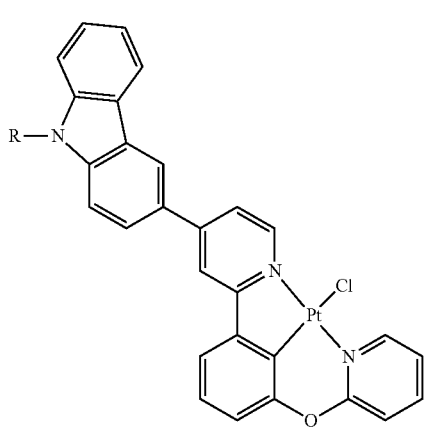
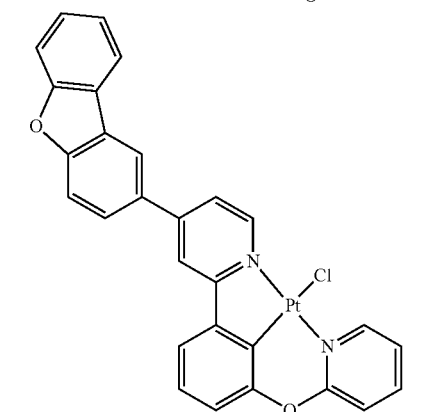
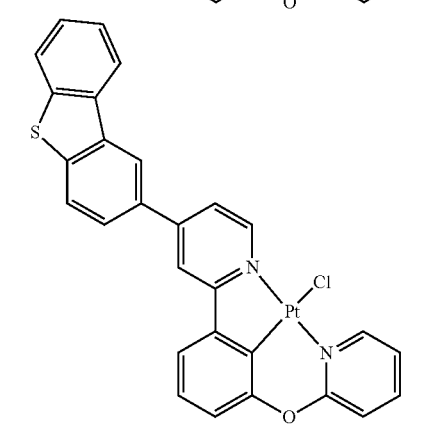

131
-continued
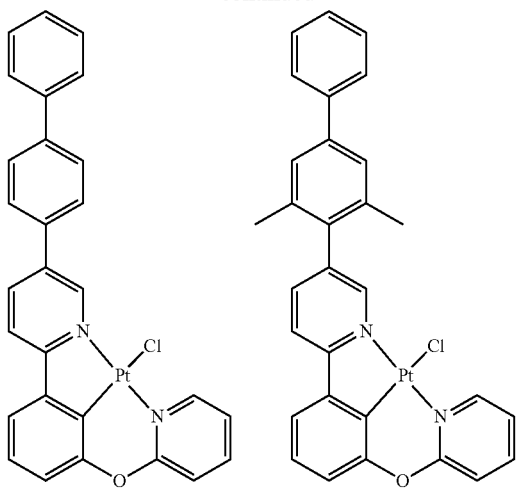
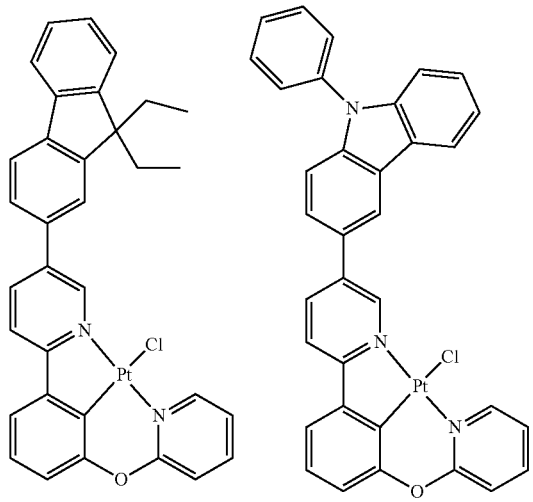
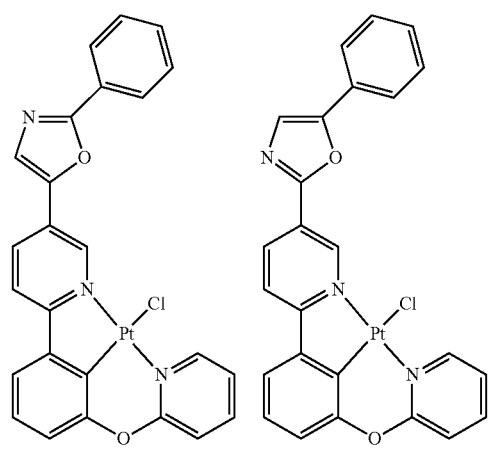
132
-continued
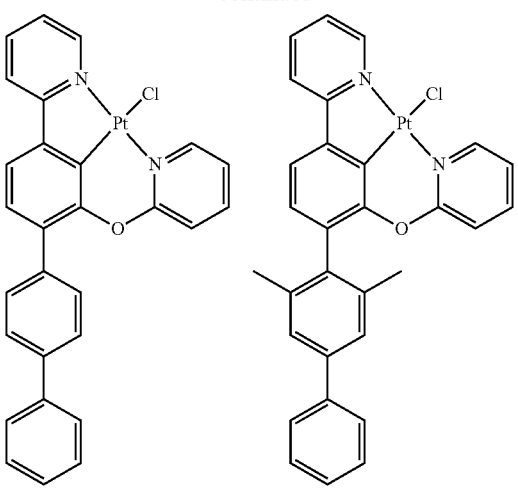
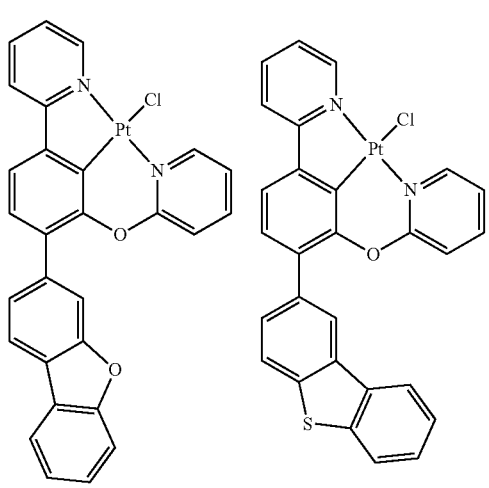
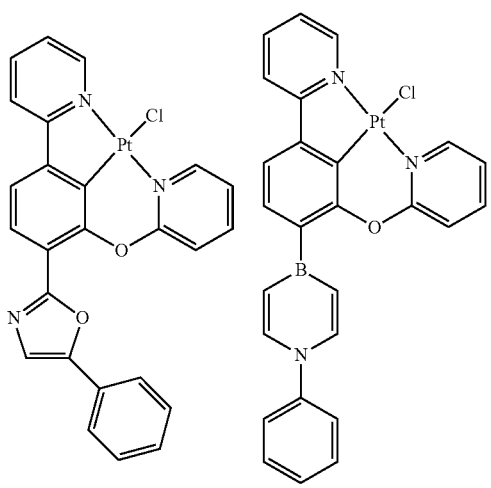

Structures Pt-6
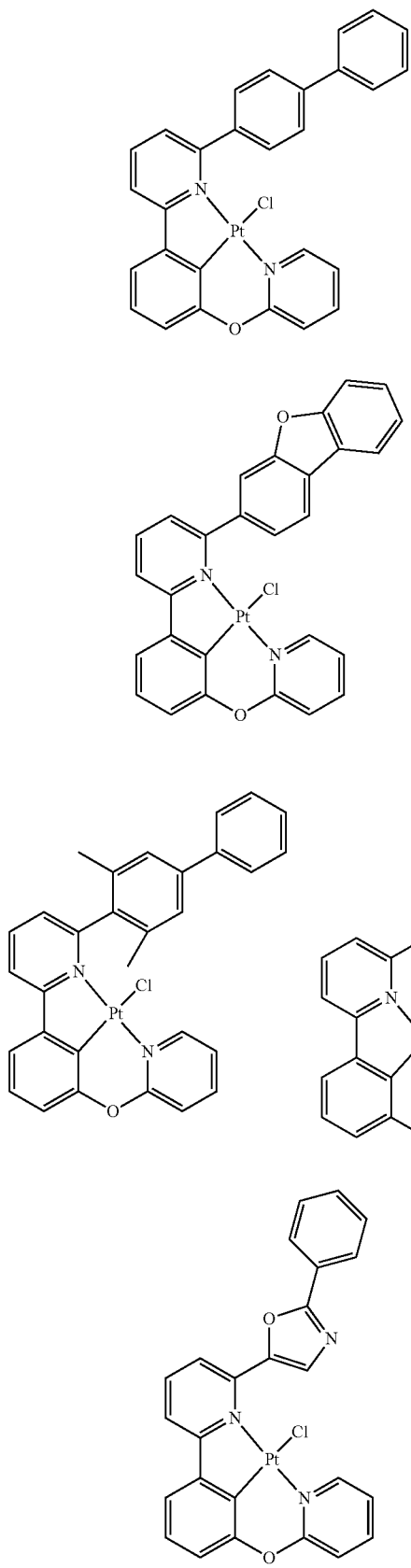
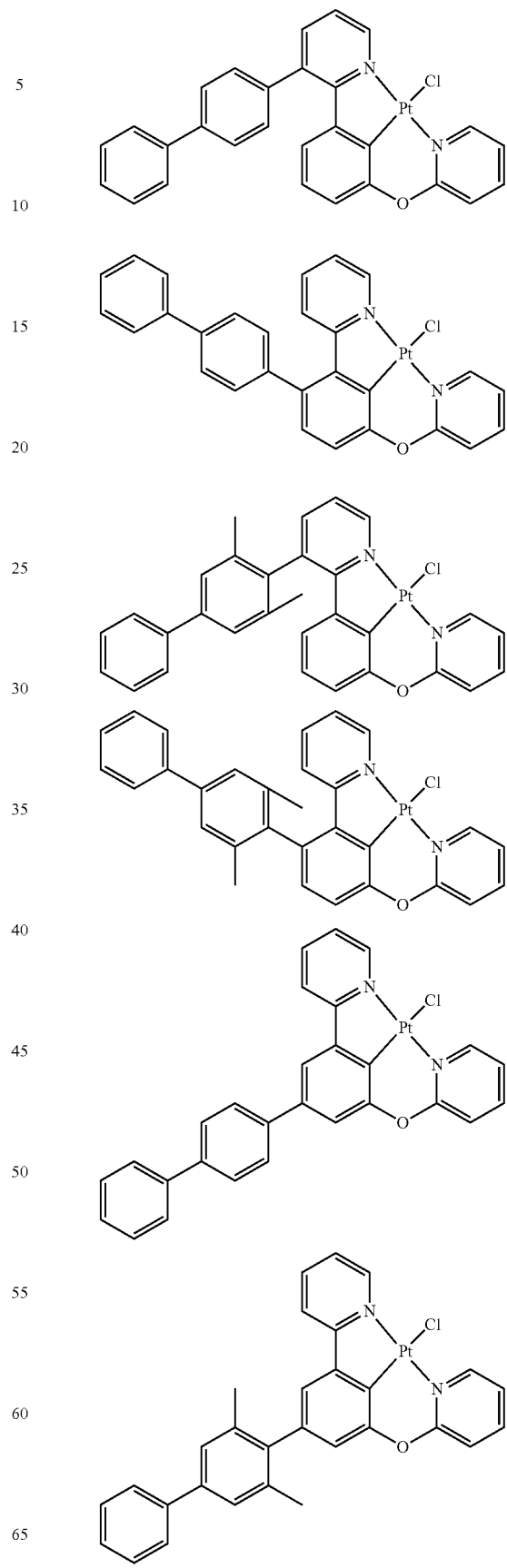

135
-continued
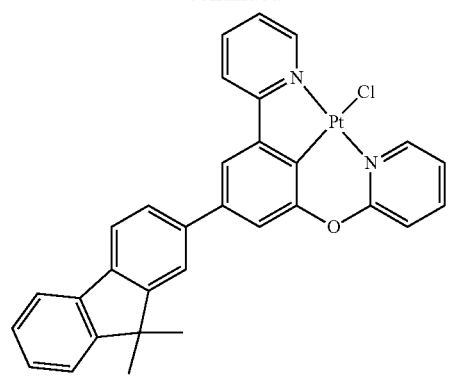
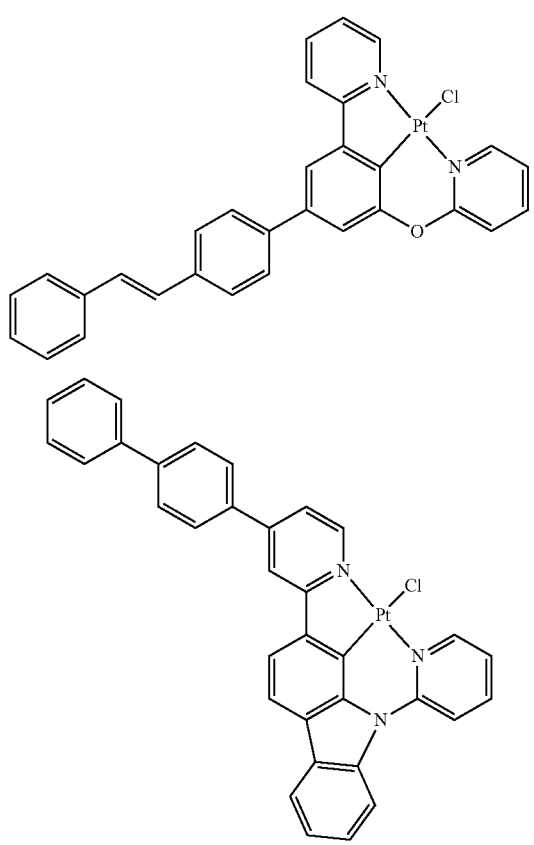
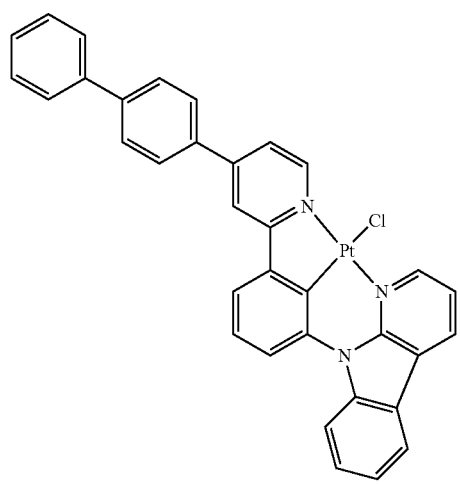
136
-continued
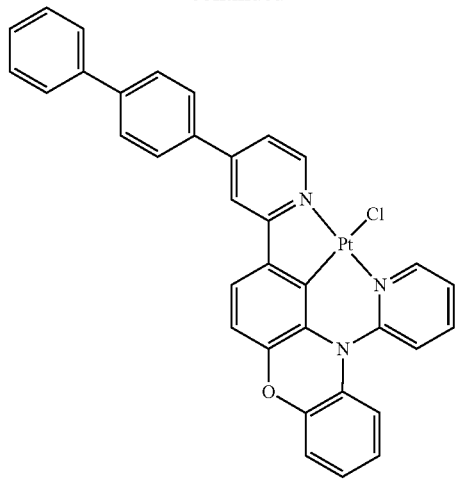
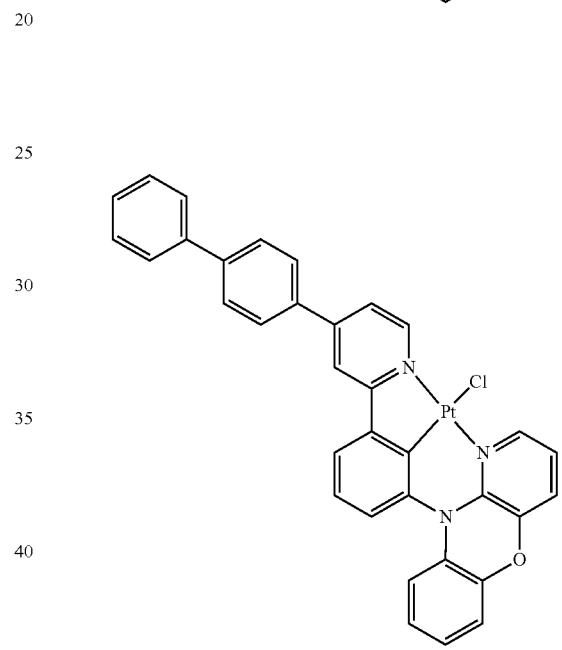
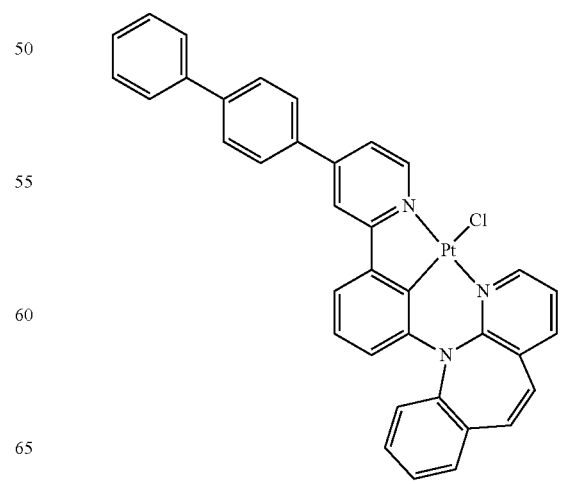

137
-continued
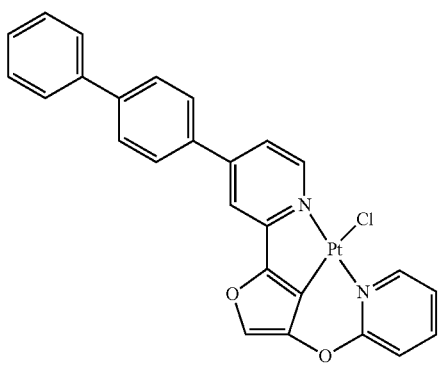
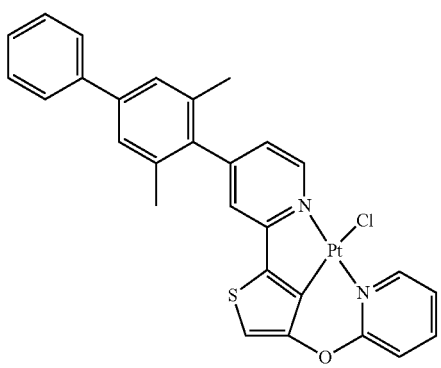
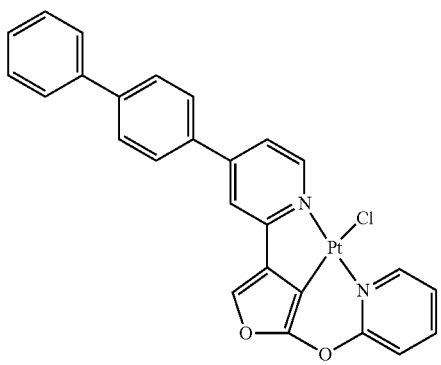
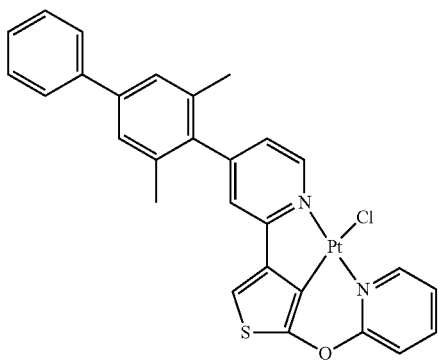
138
-continued
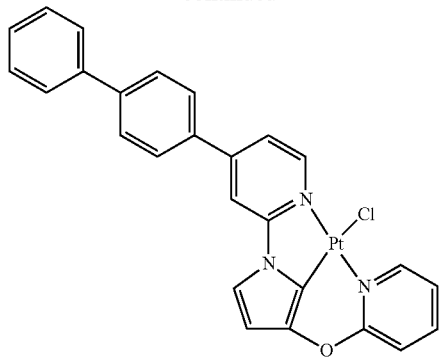
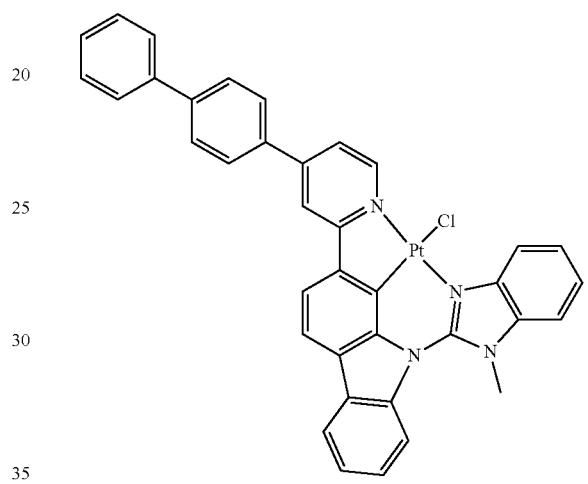
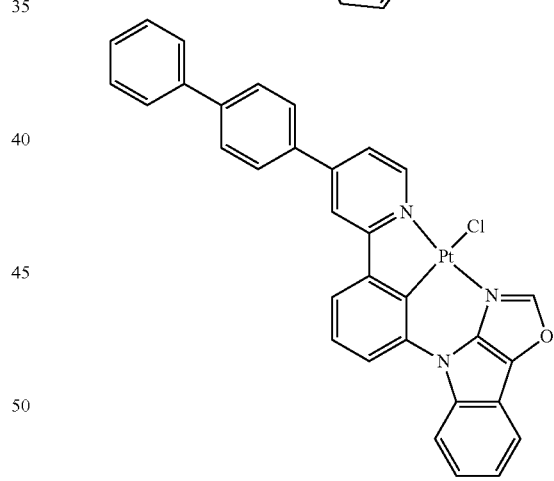
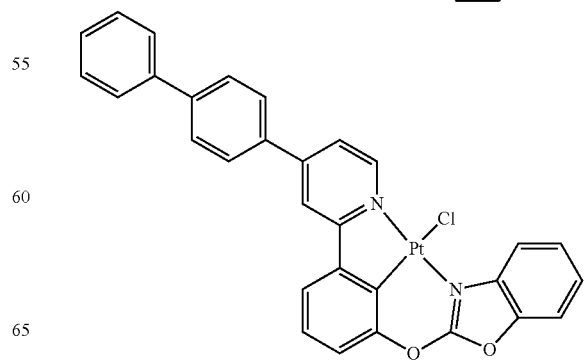

139
-continued
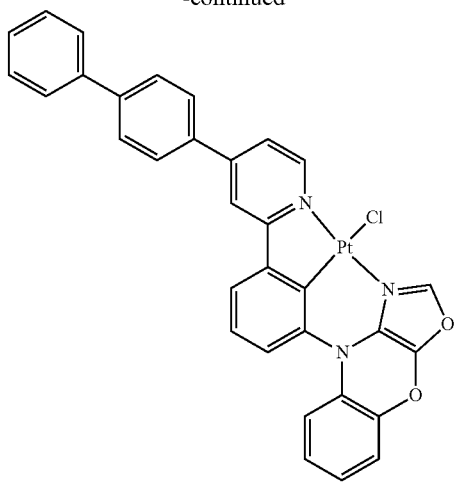
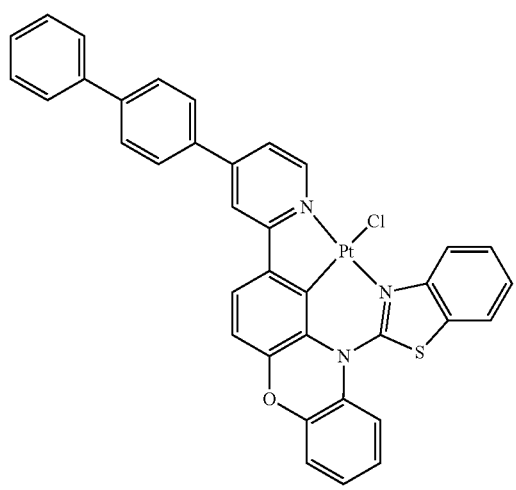
Structures Pt-7
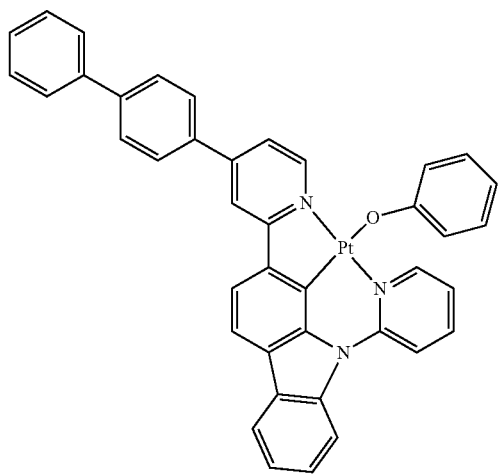
140
-continued
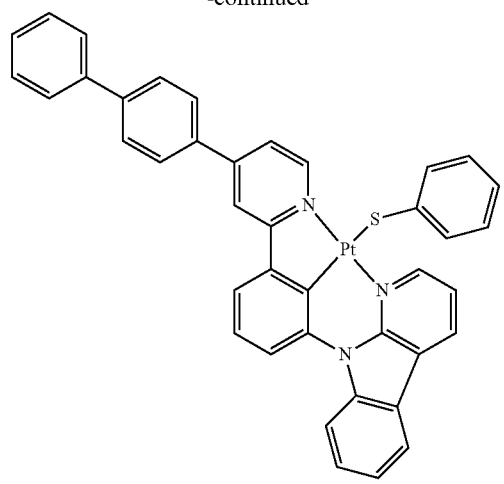
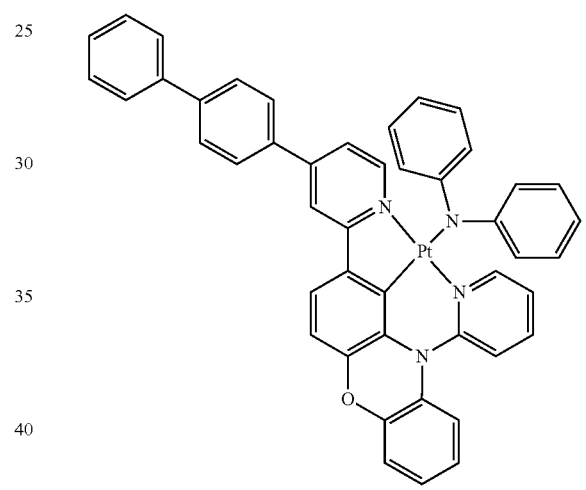
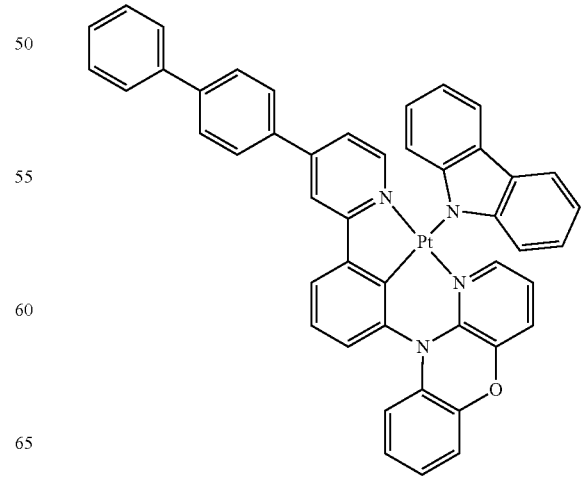

141
-continued
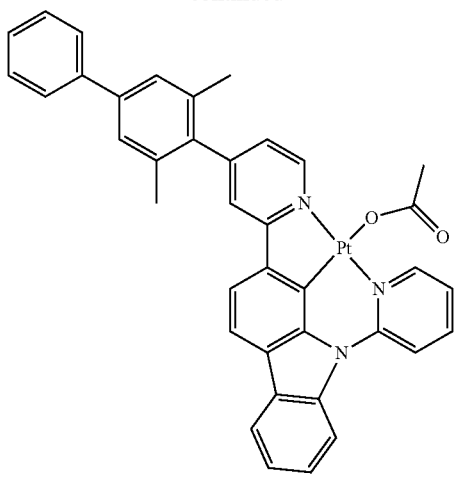
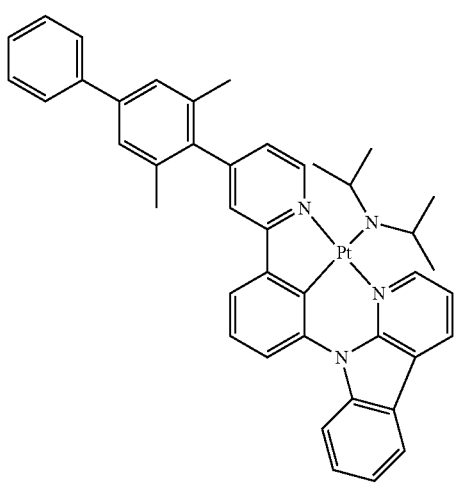
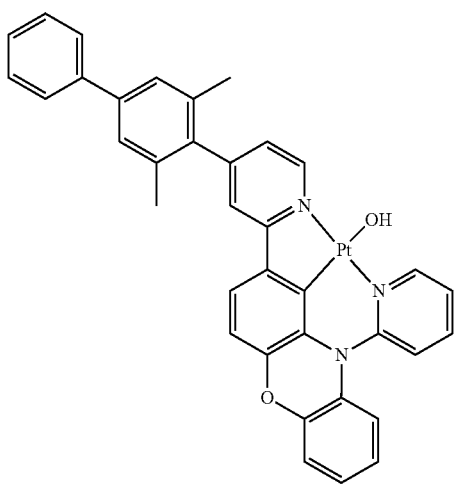
142
-continued
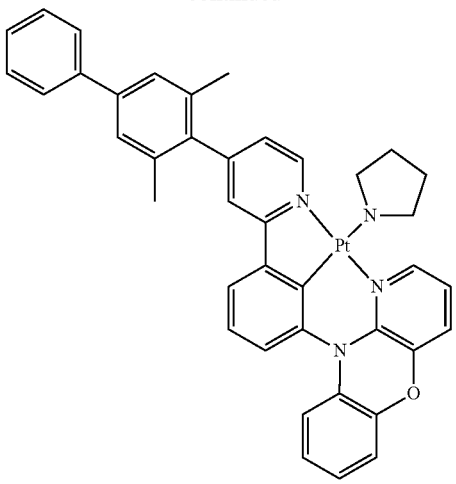
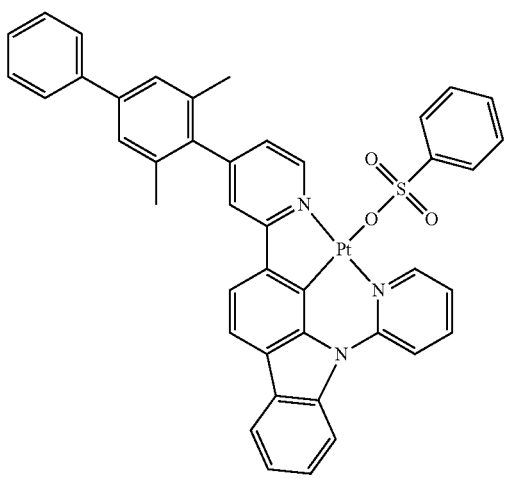
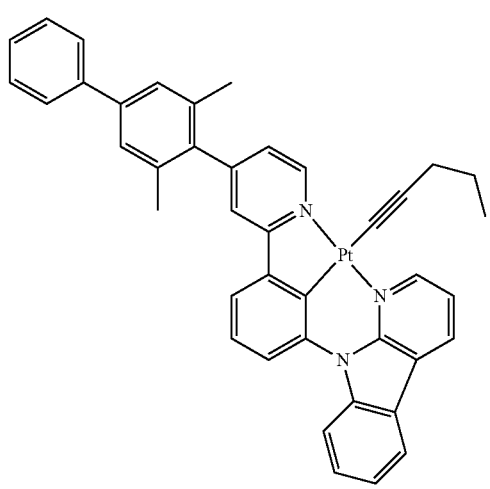

143
-continued
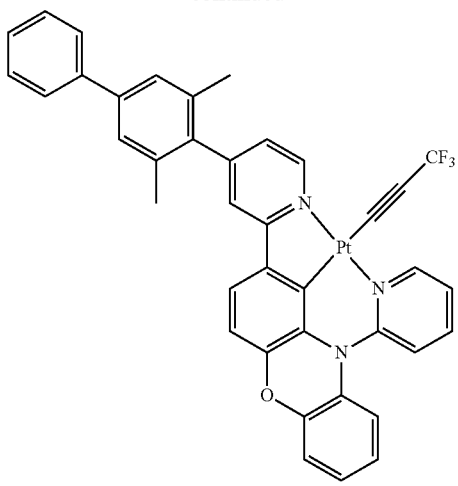
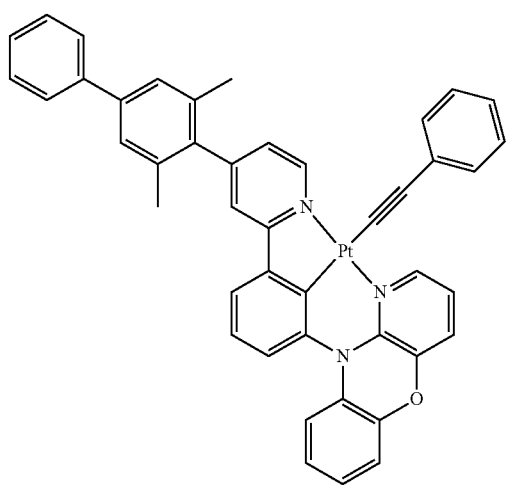
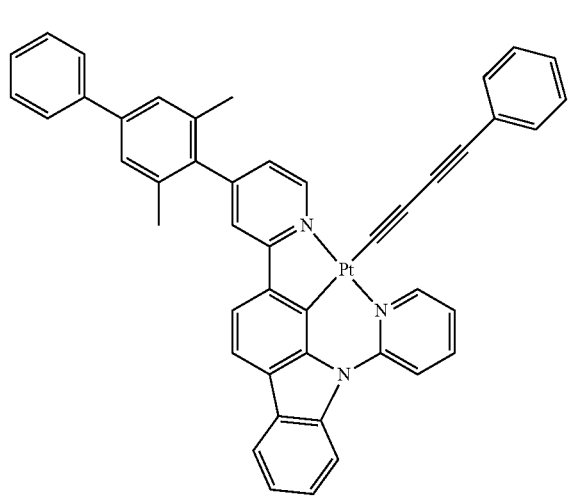
144
-continued
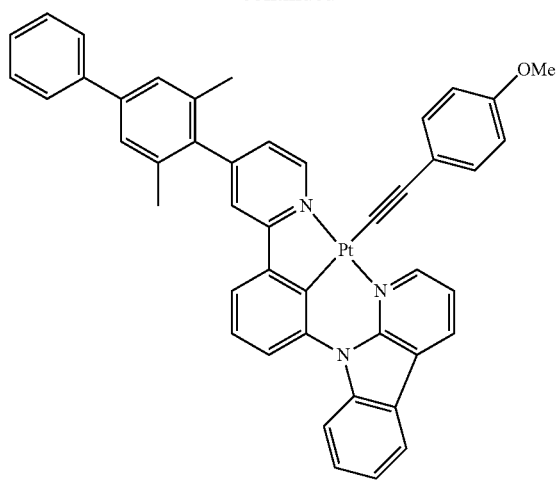
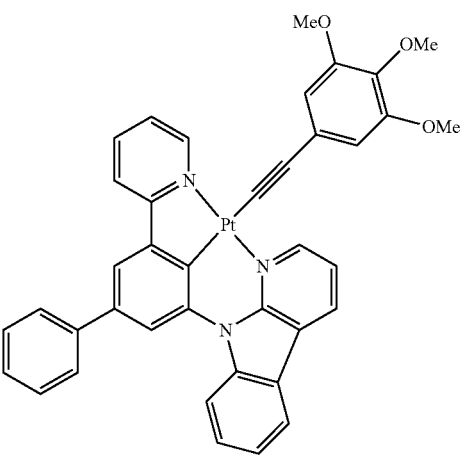
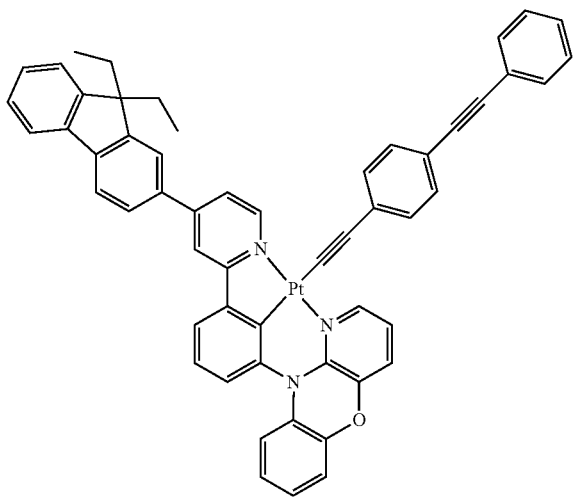

145
-continued
146
-continued
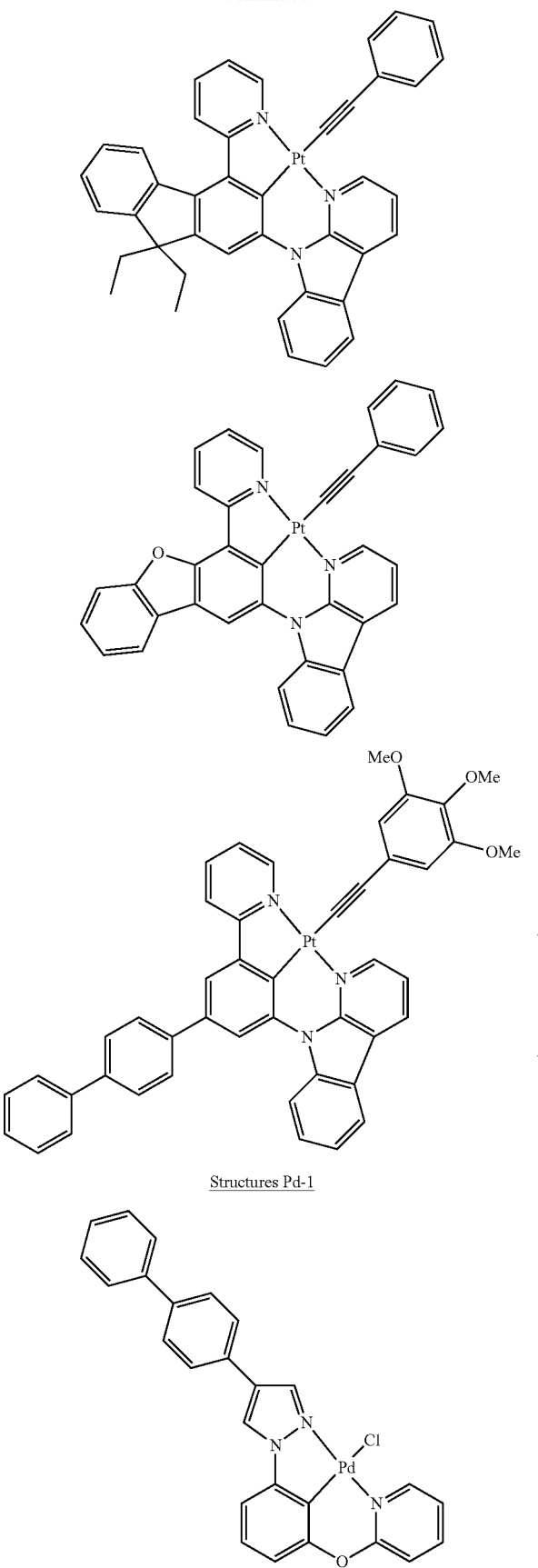
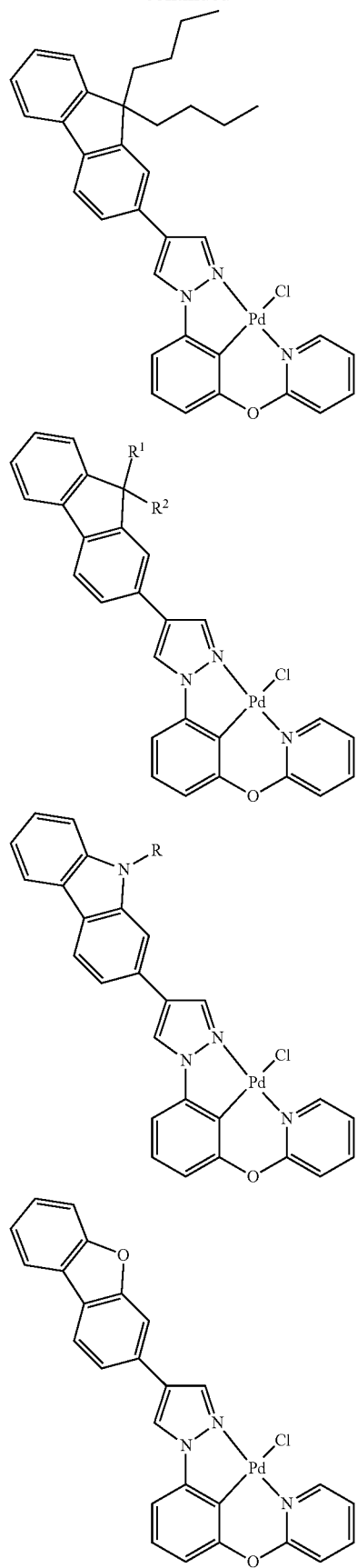
Structures Pd-1

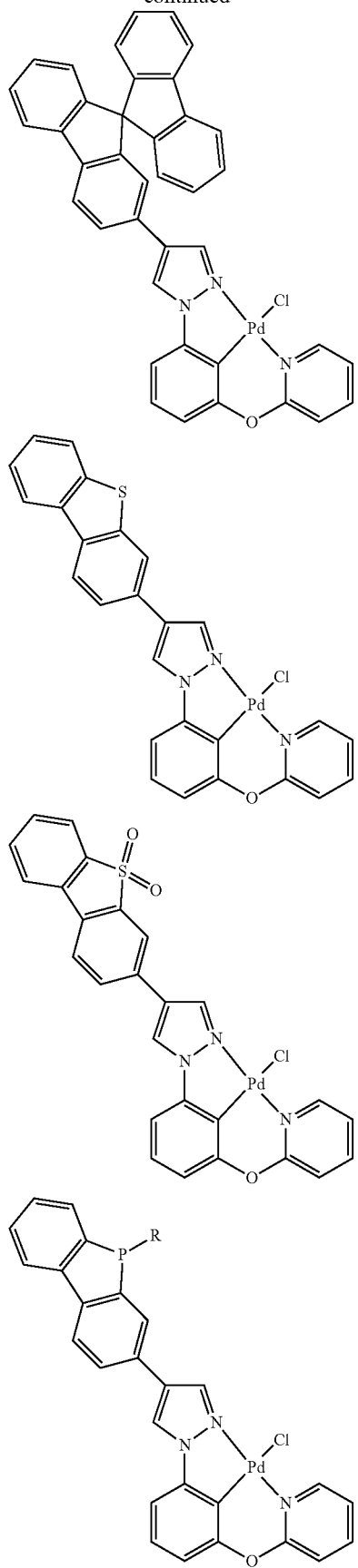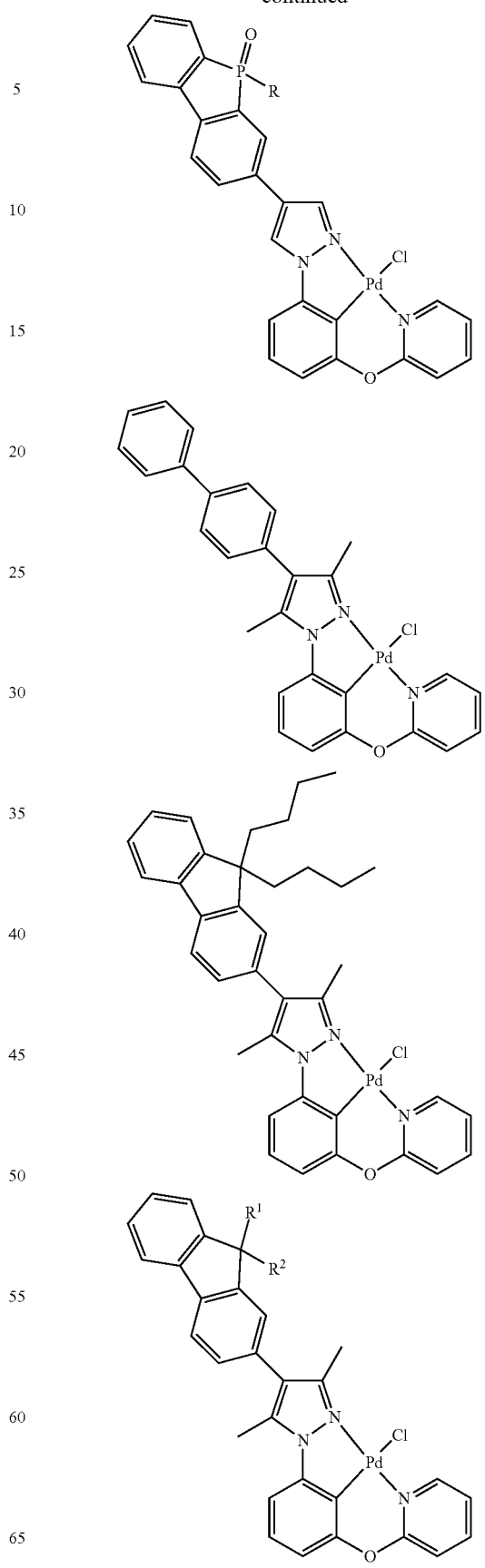

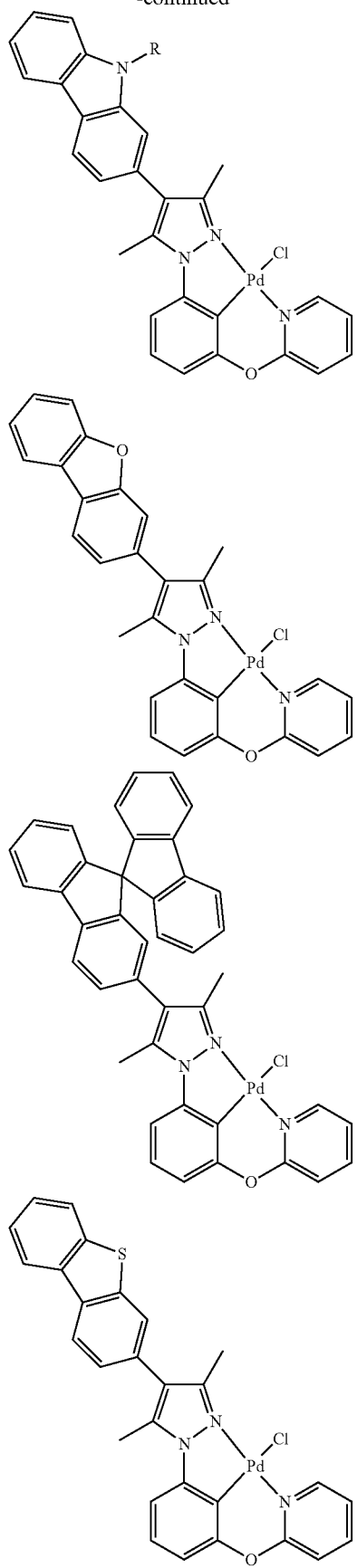
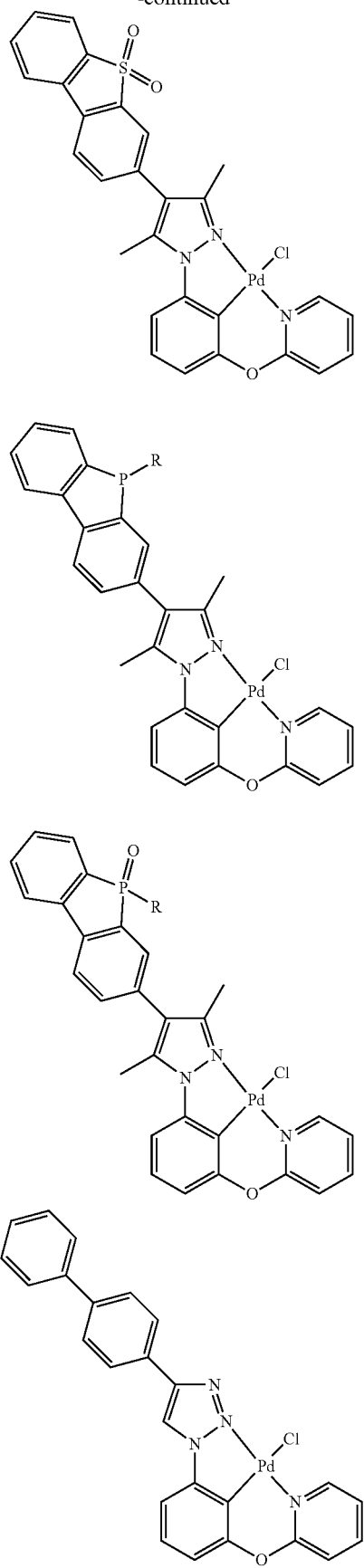

151
-continued

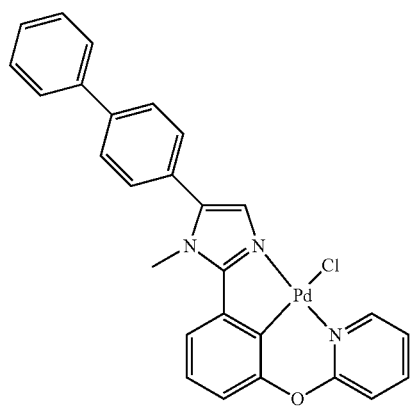
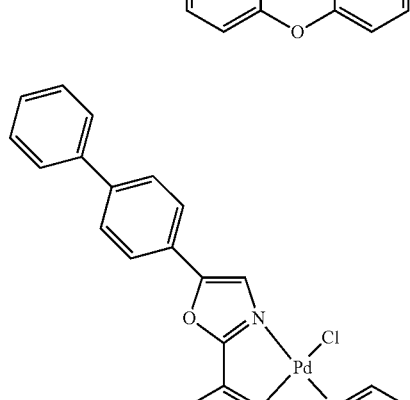
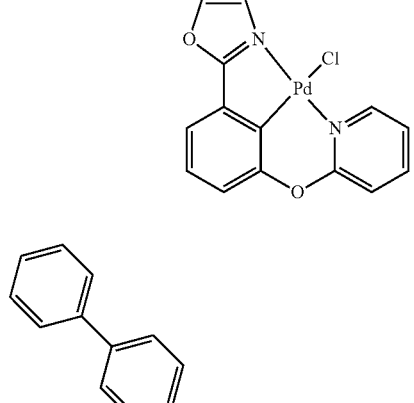
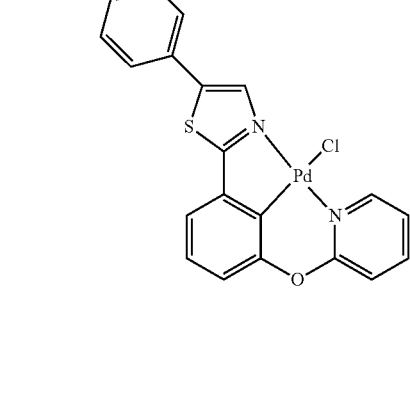
152
-continued
Structures Pd-2
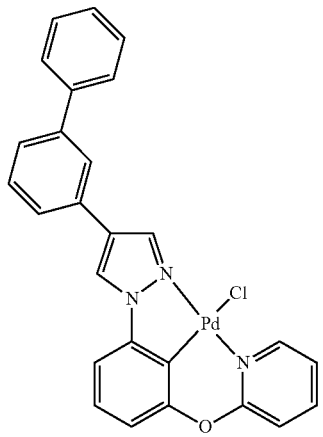
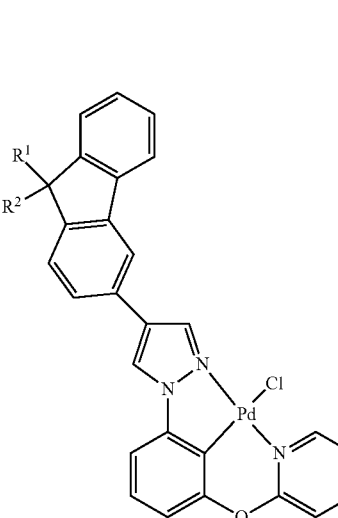
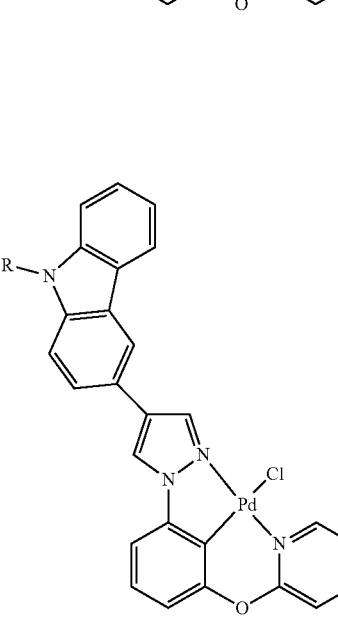

153
-continued
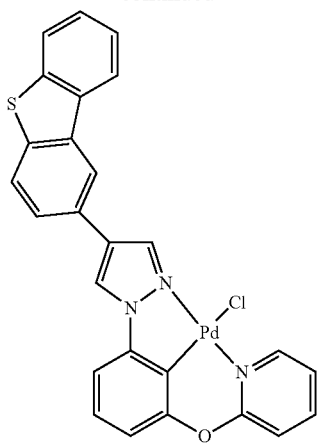
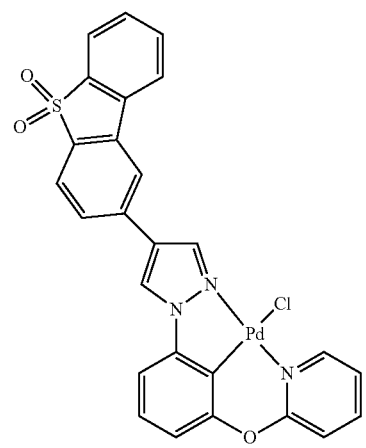
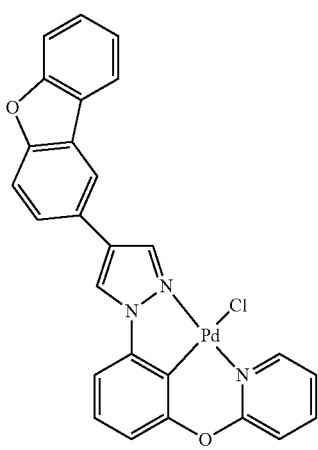
154
-continued
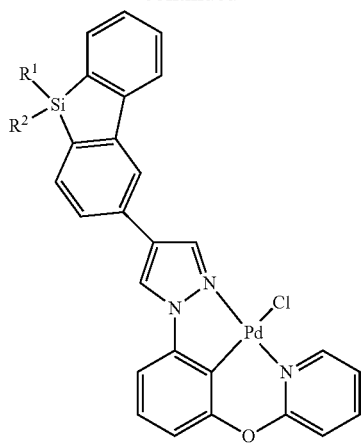
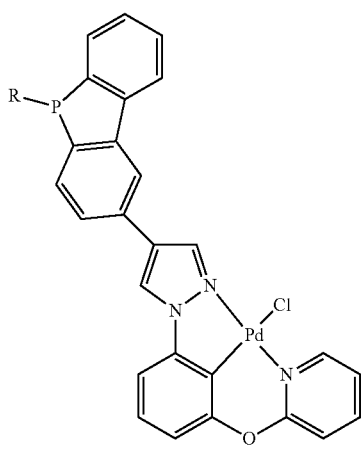
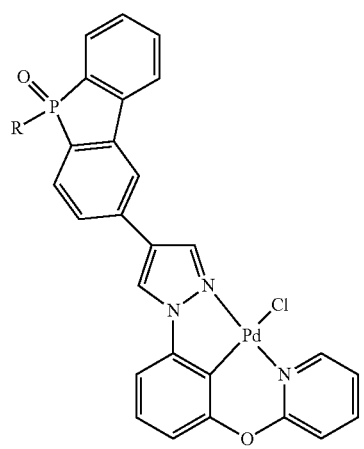

155
-continued
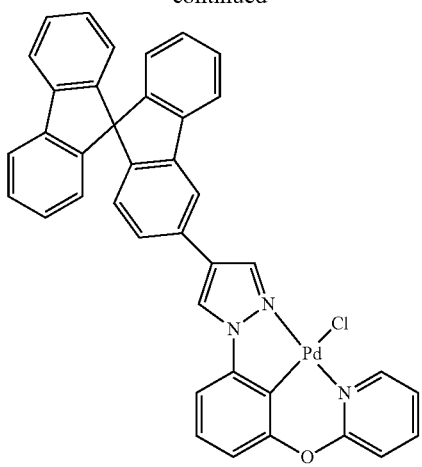
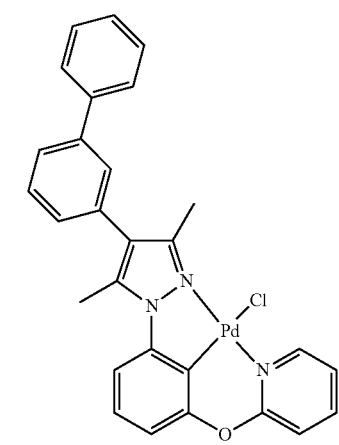
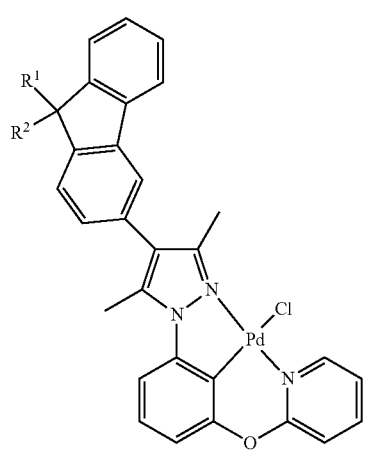
156
-continued
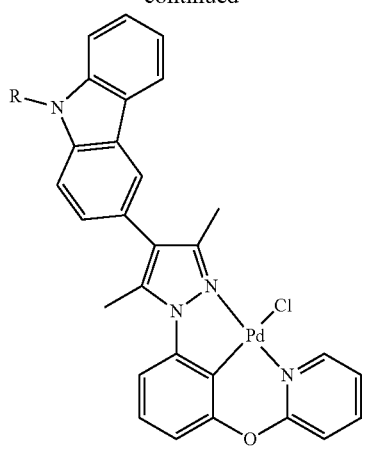
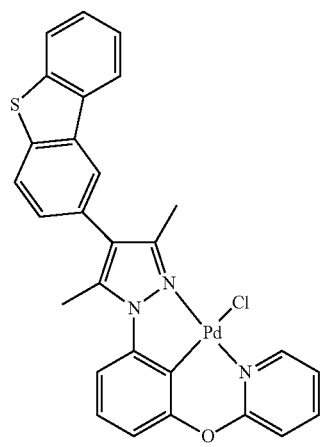
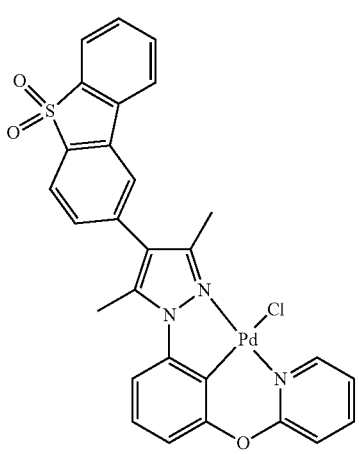

157
-continued
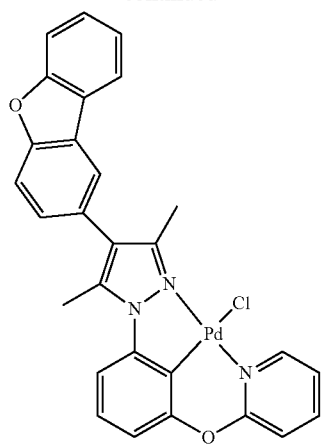
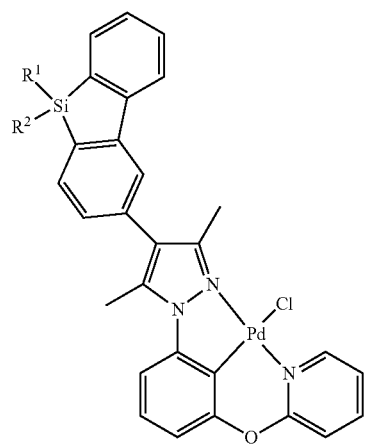
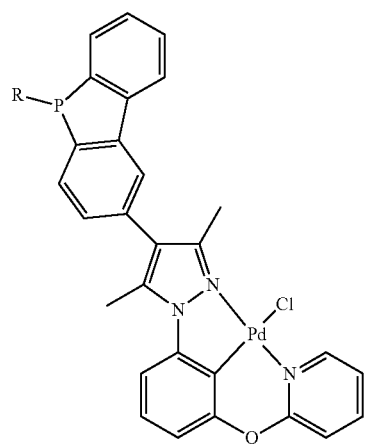
158
-continued
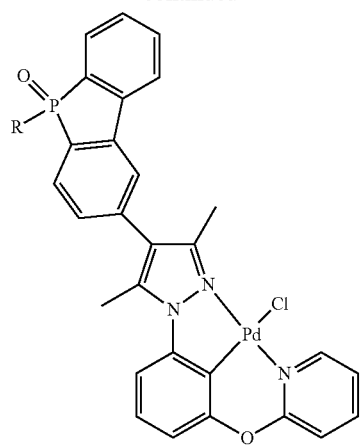
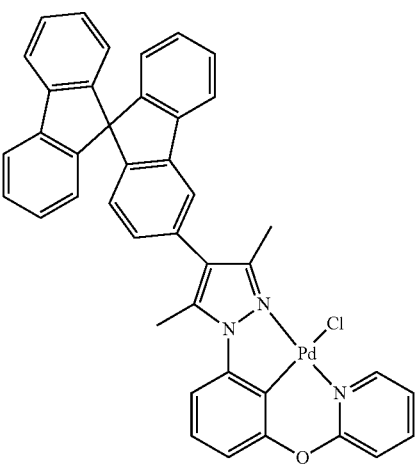

159
-continued
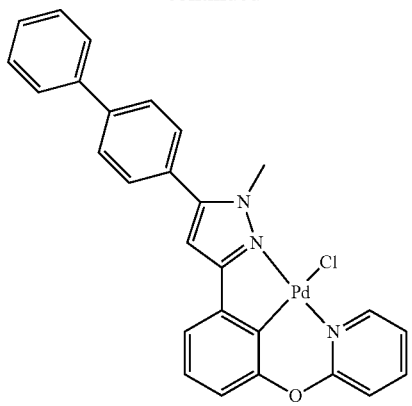
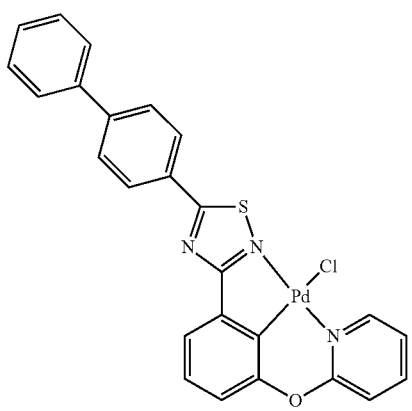
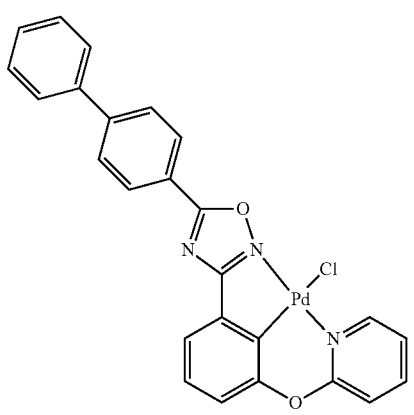
Structures Pd-3

160
-continued
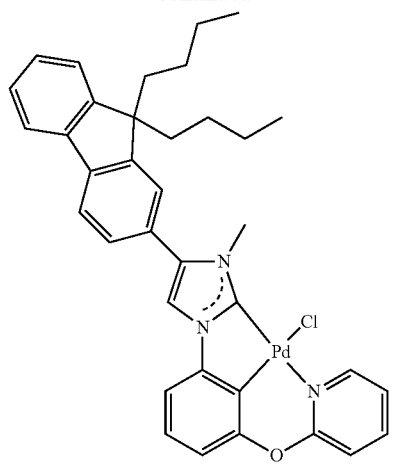
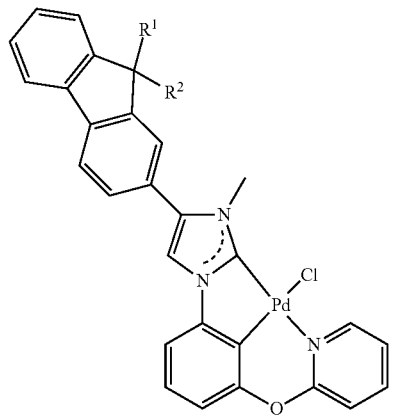
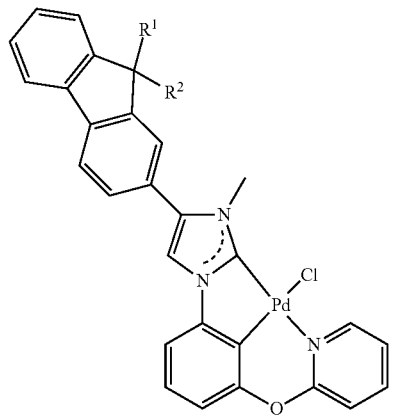
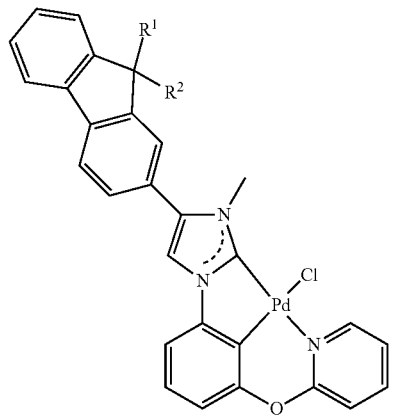

161
-continued
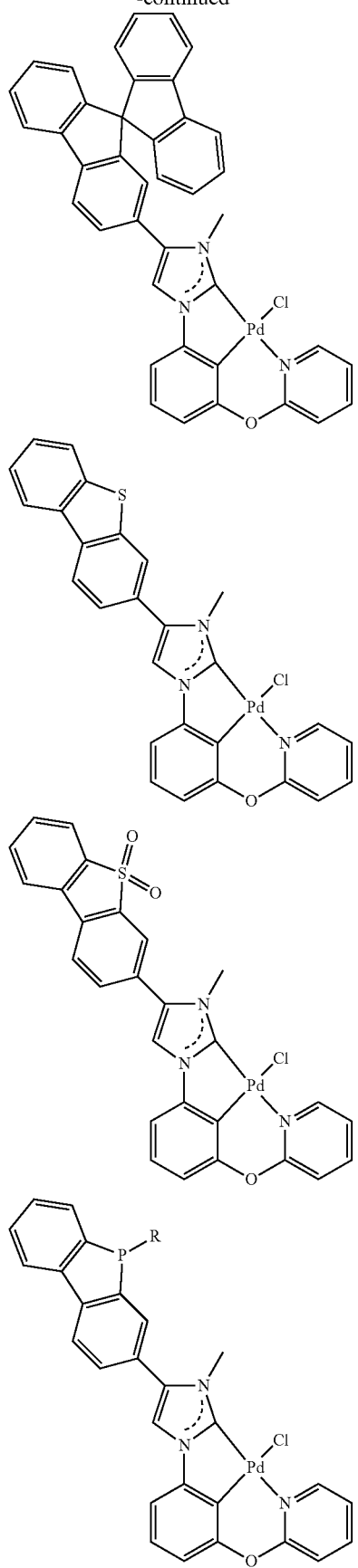
162
-continued
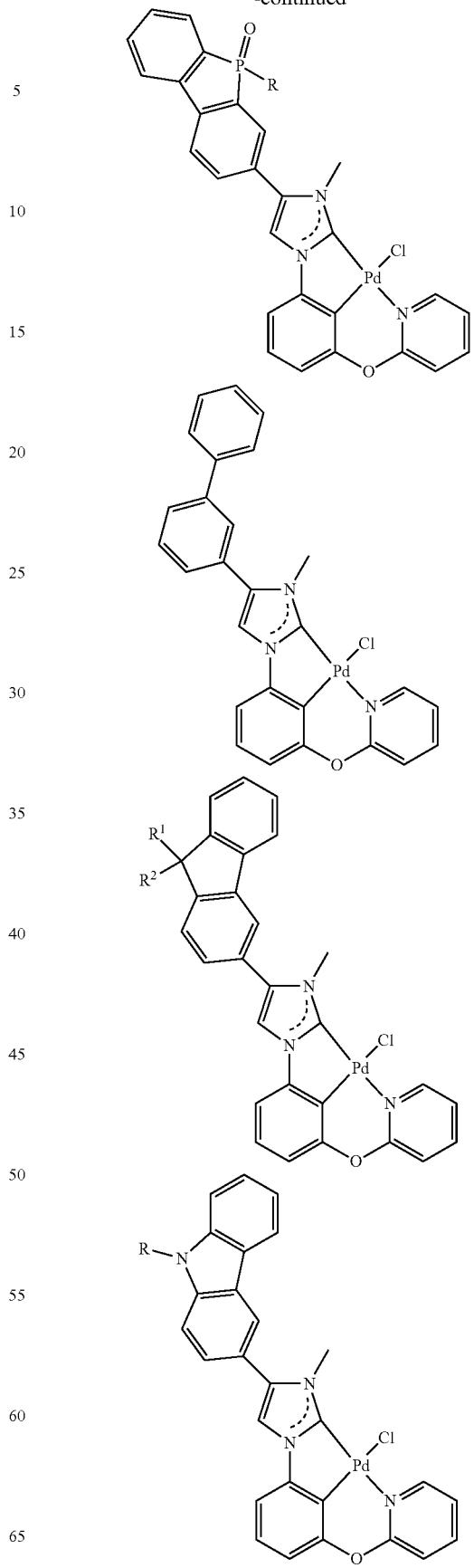

163
-continued
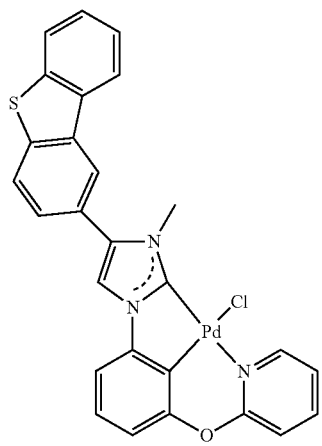
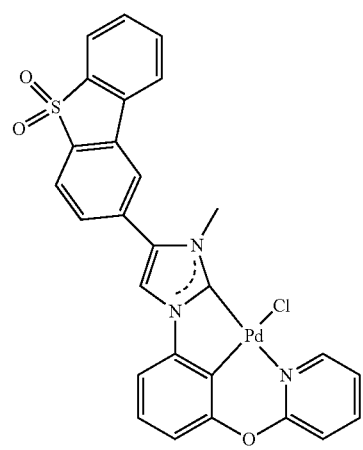
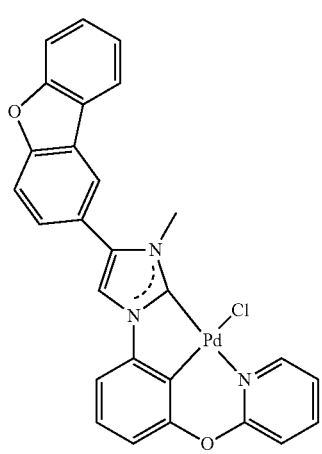
164
-continued
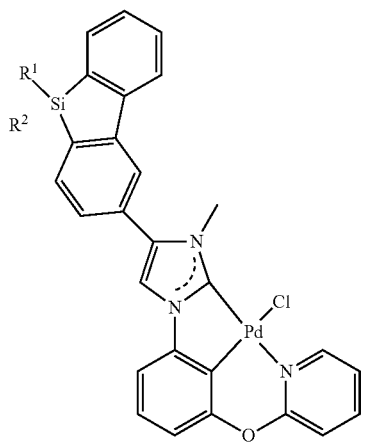
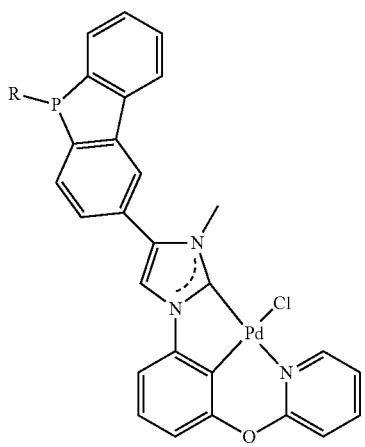
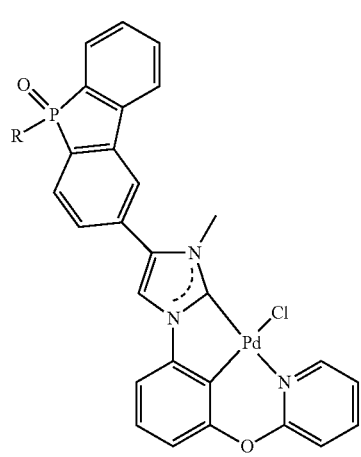

165
-continued
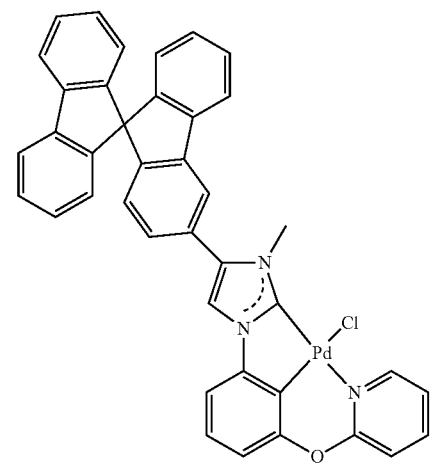
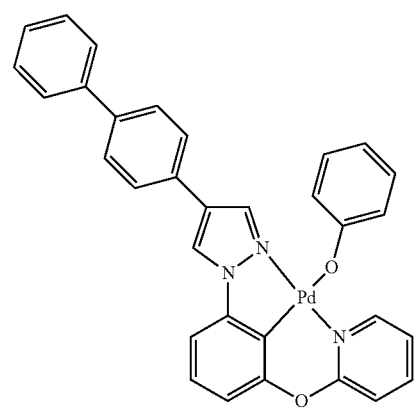
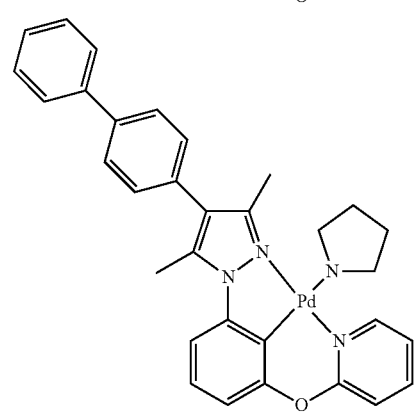
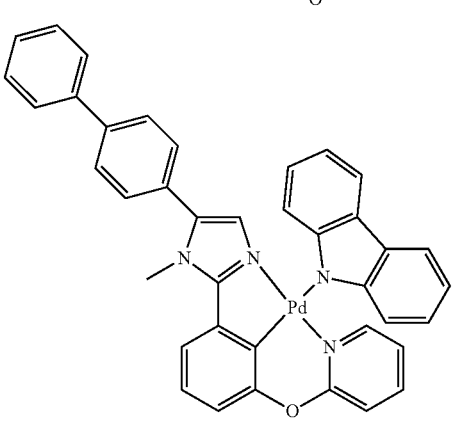
166
-continued
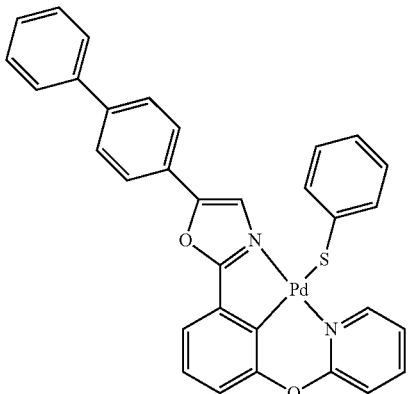
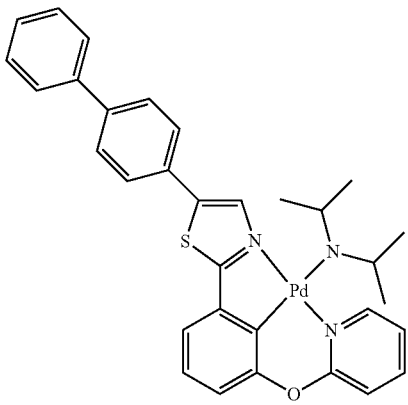
Structures Pd-4
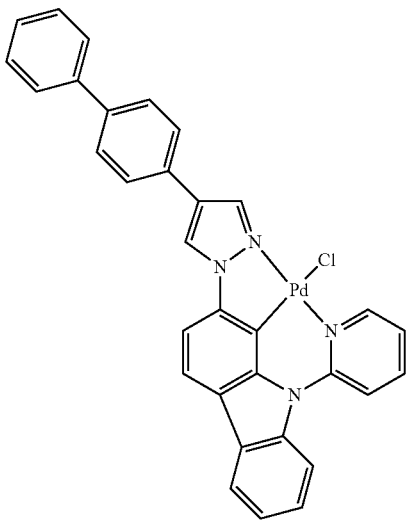

167
-continued
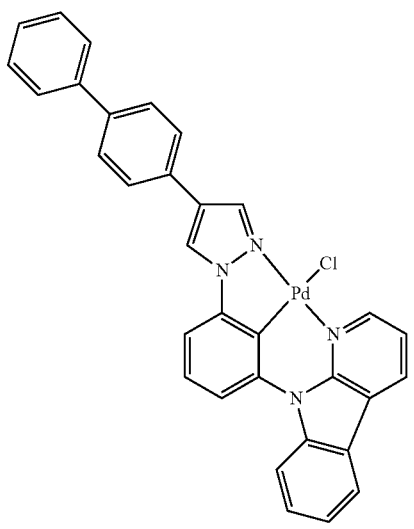
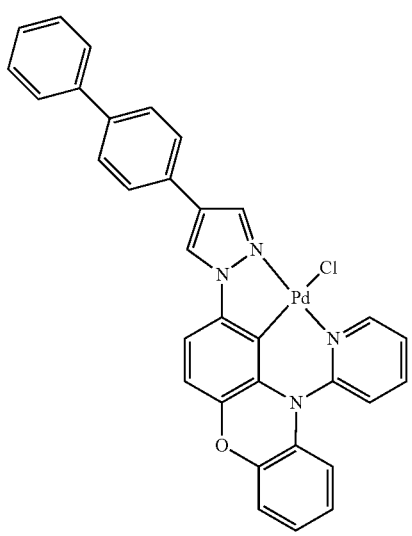
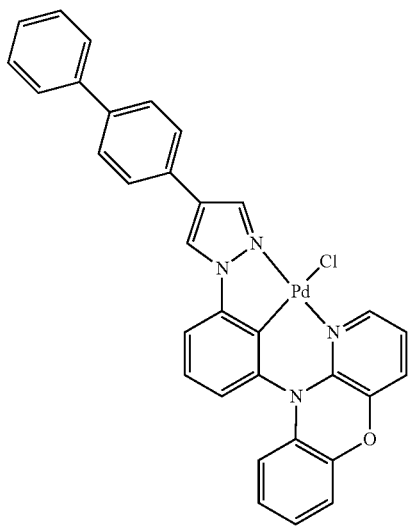
168
-continued
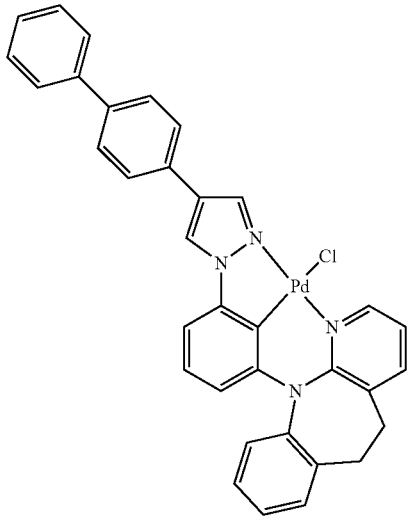
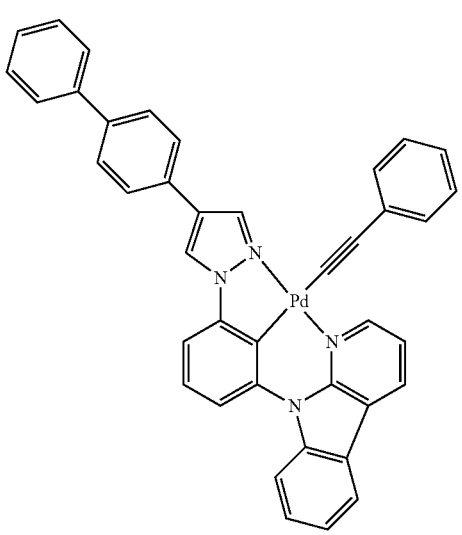

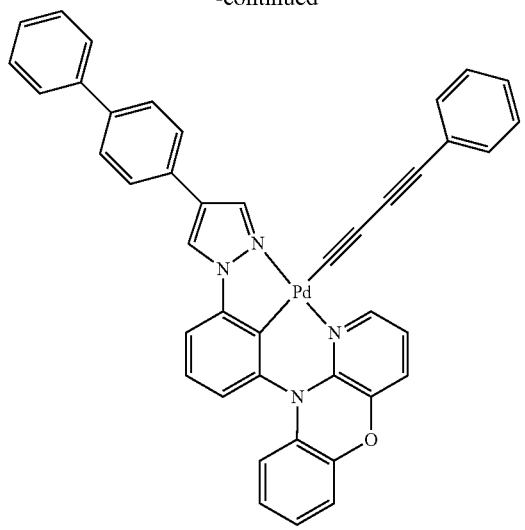
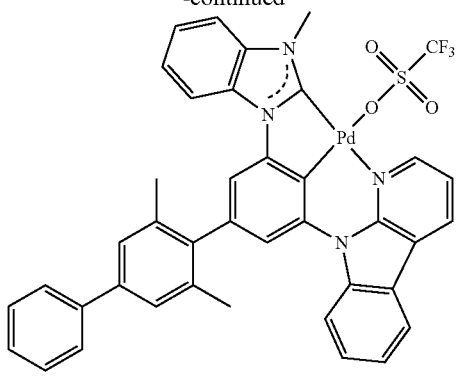
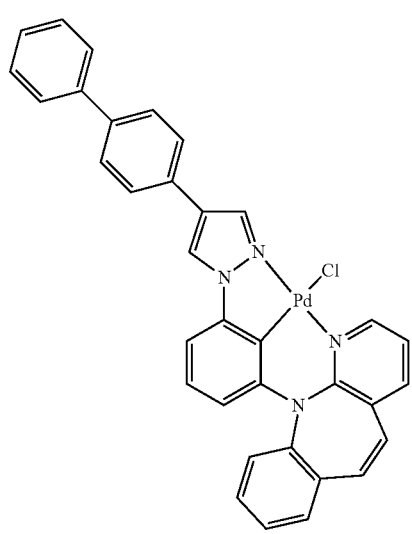
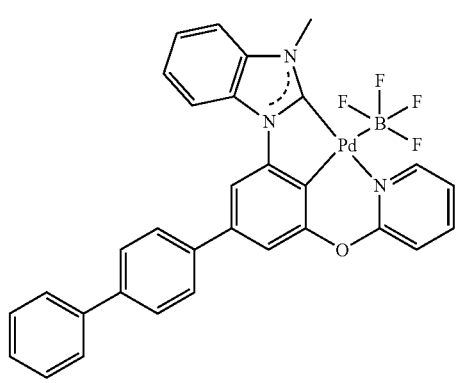
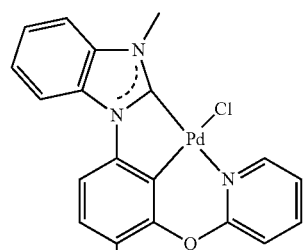
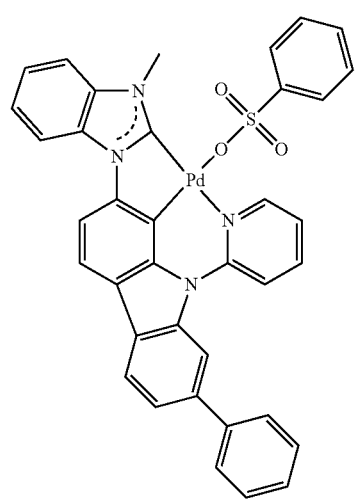
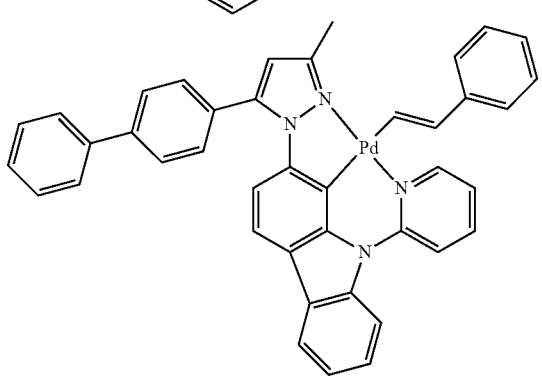

171
-continued
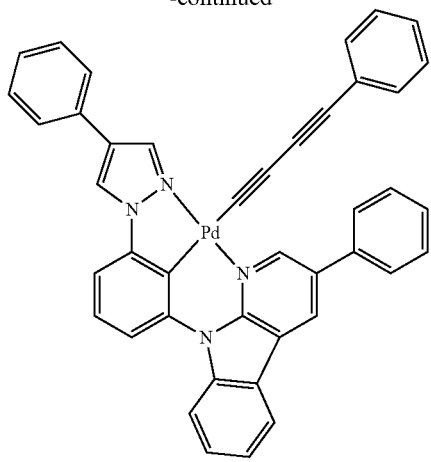
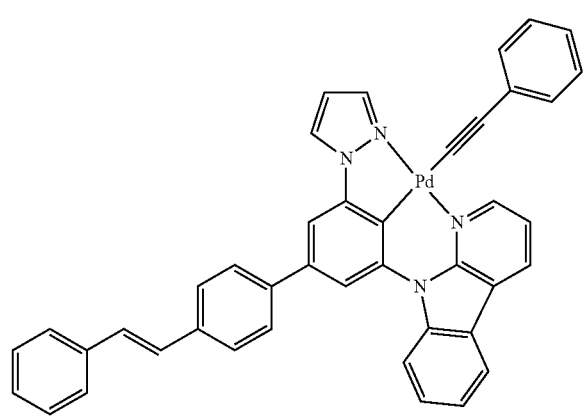
172
-continued
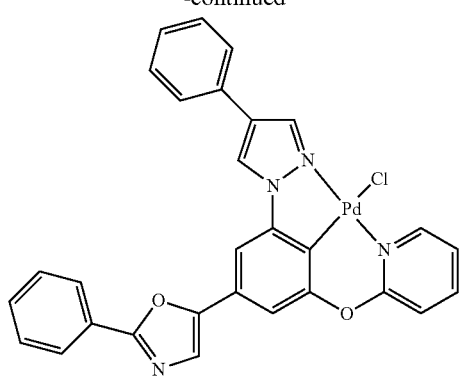
Structures Pd-5
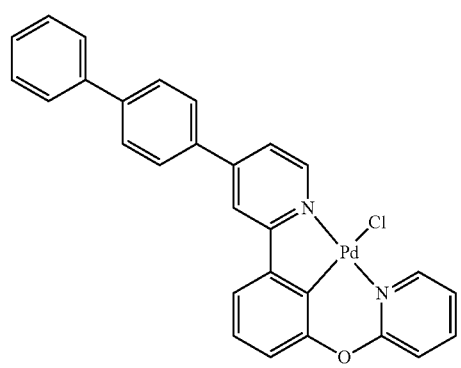
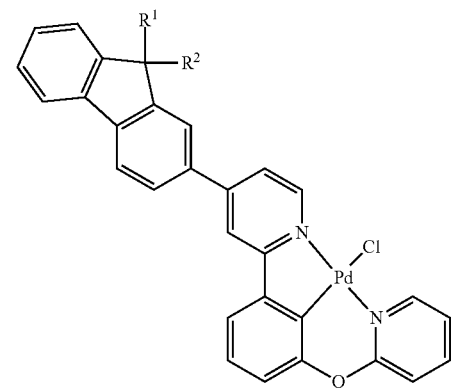
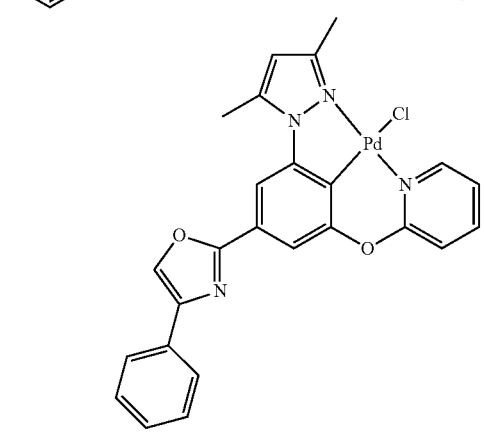

173
-continued
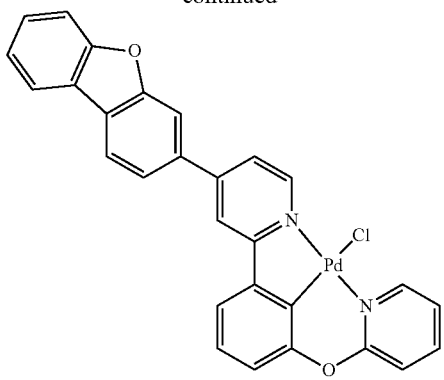
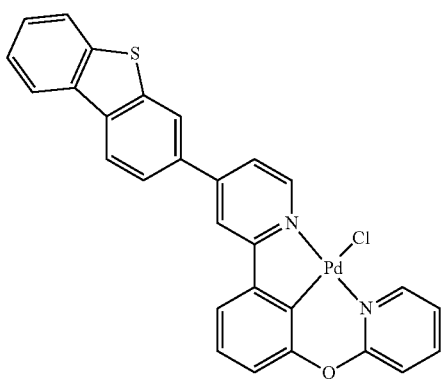
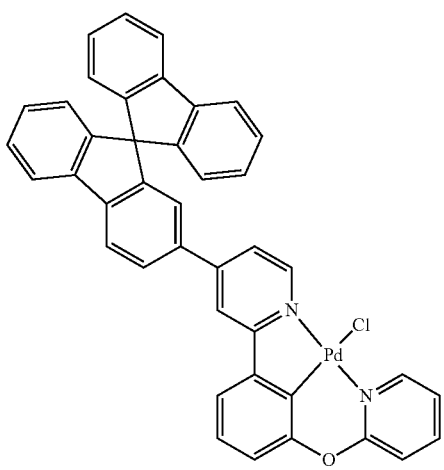
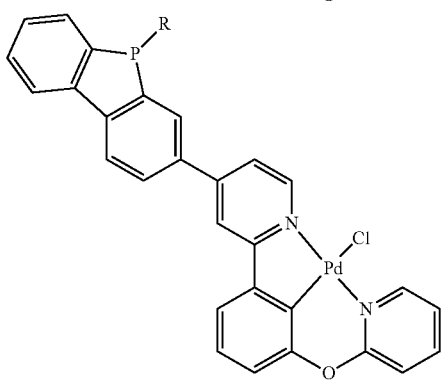
174
-continued
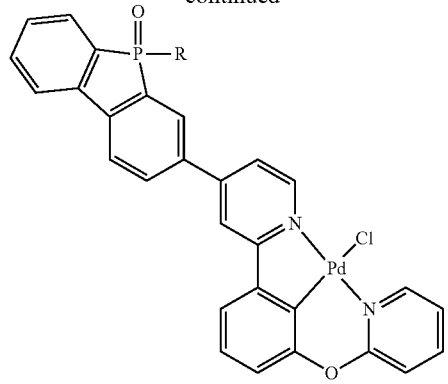
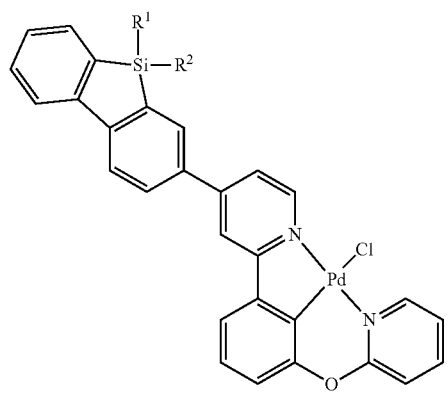
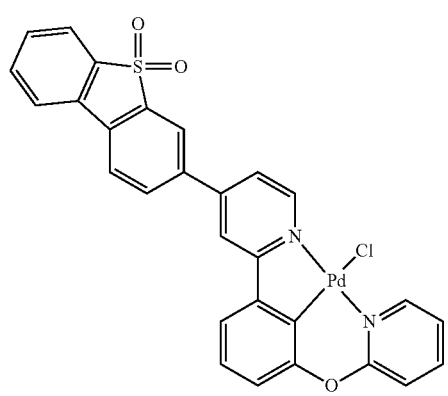
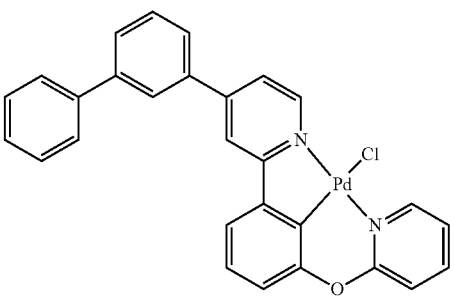

175
-continued
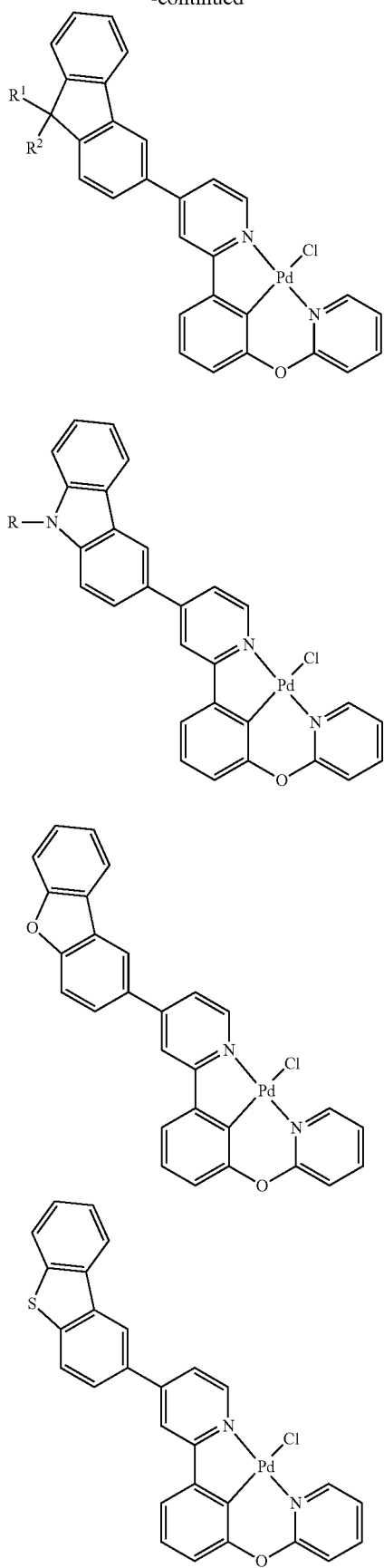
176
-continued
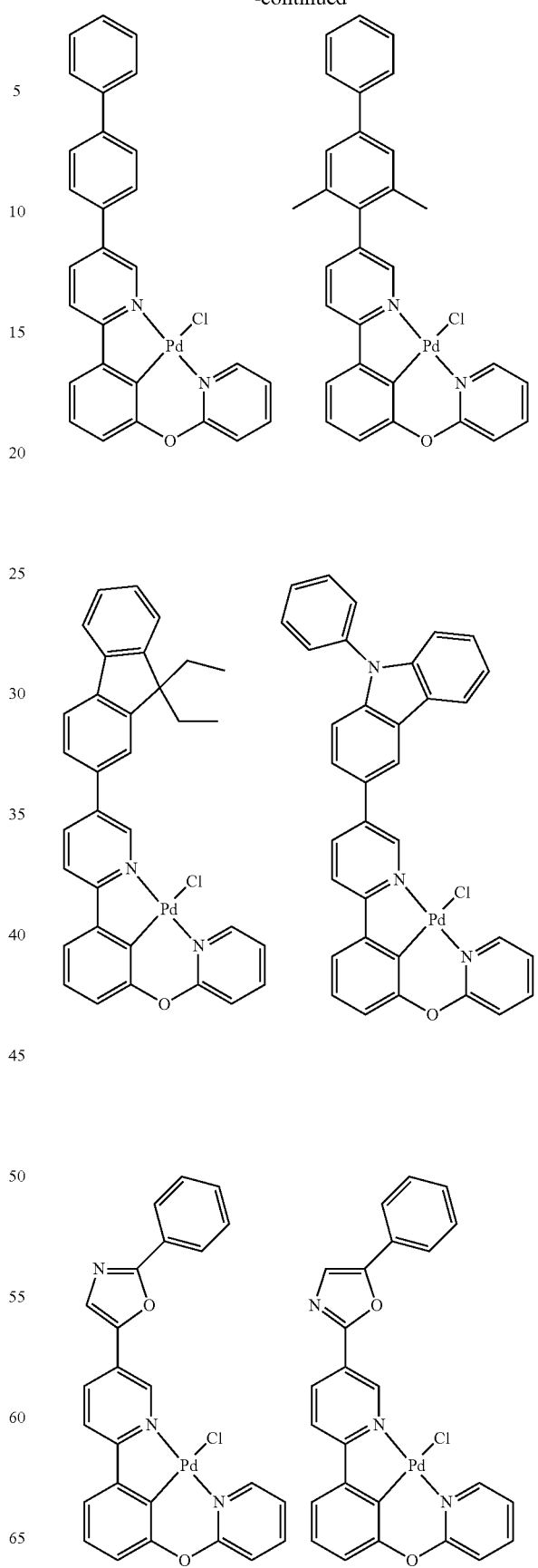

177
-continued
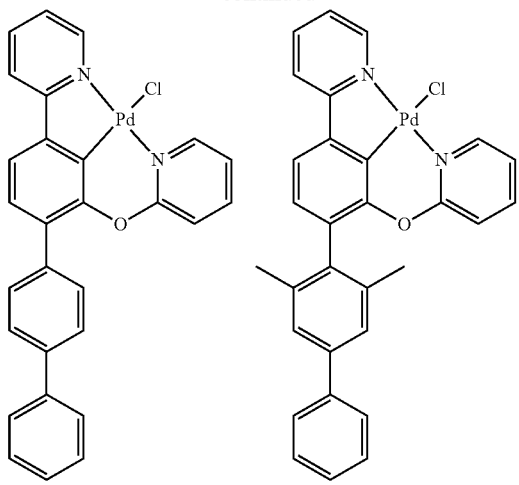
178
-continued
Structures Pd-6
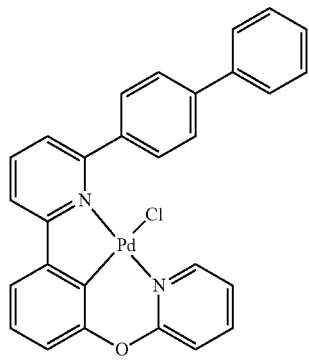
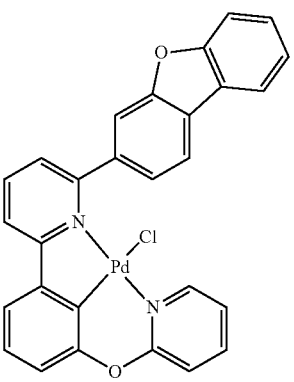
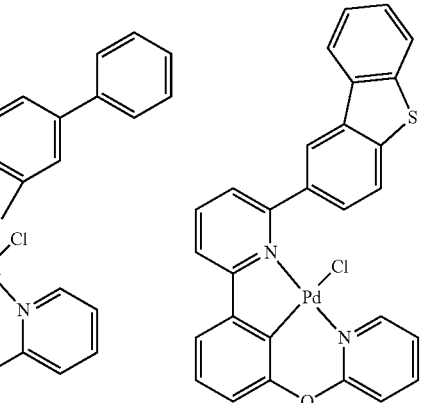
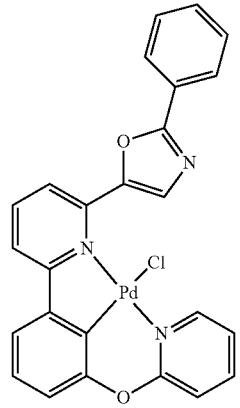

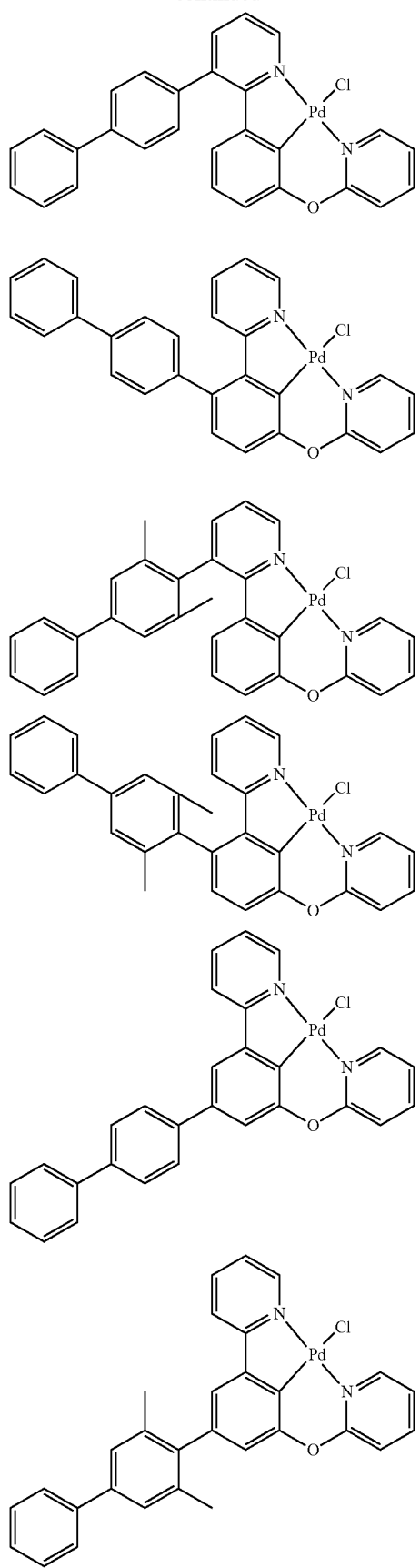
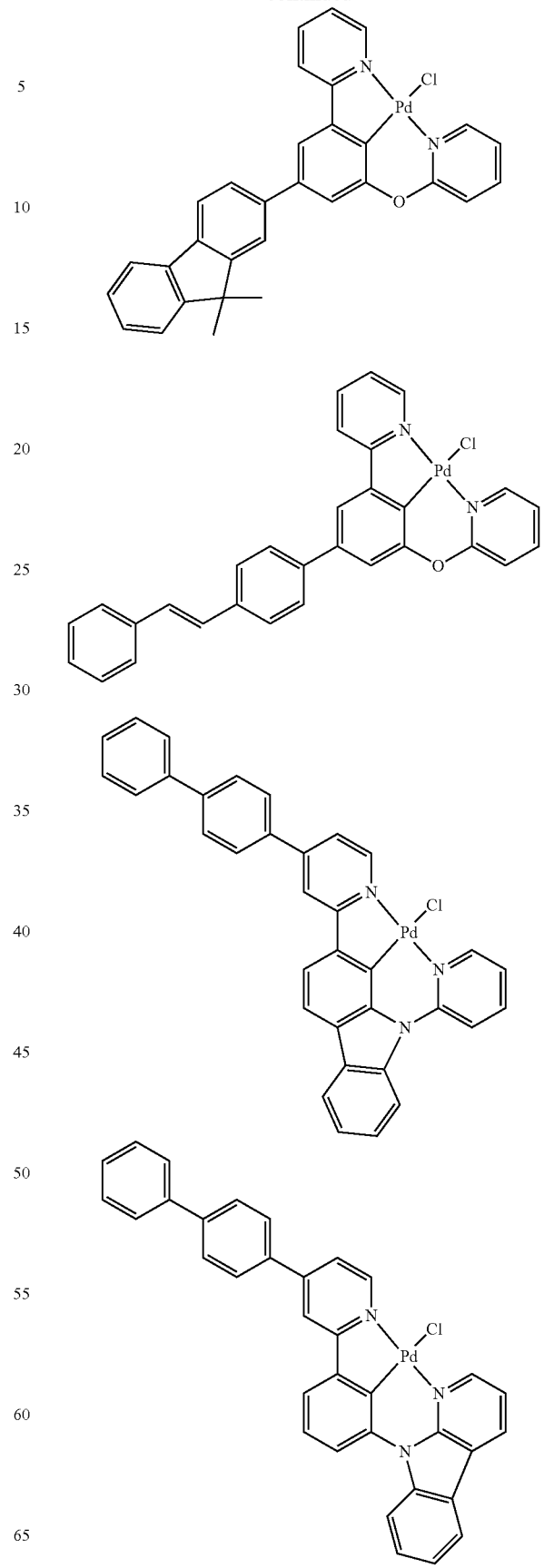

181
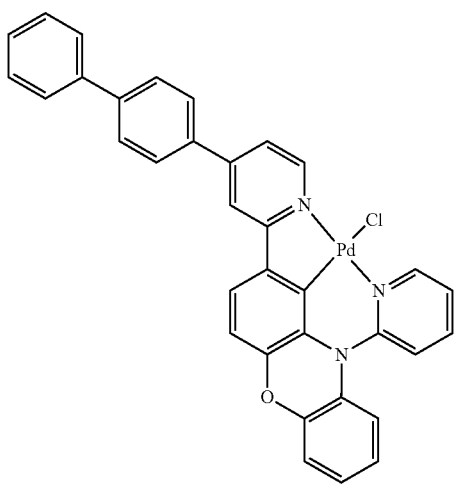
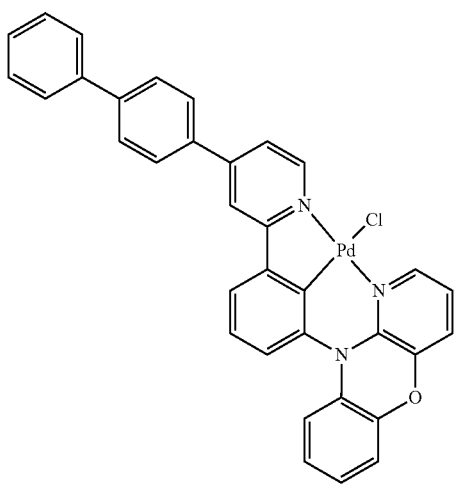
182
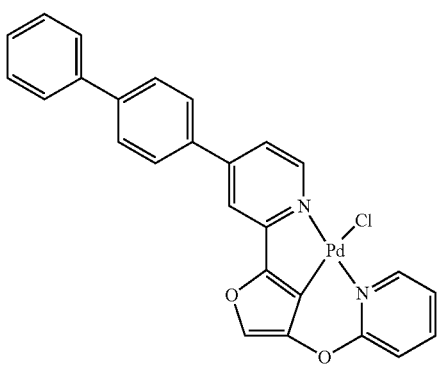
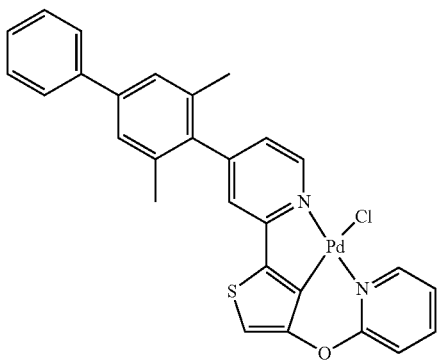
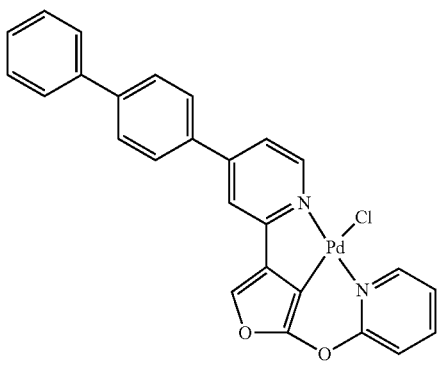
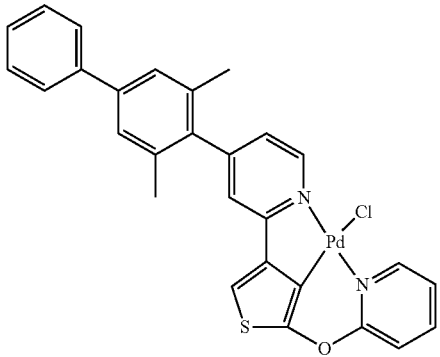

183
-continued
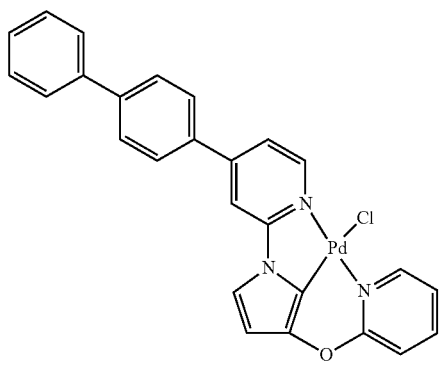
184
-continued
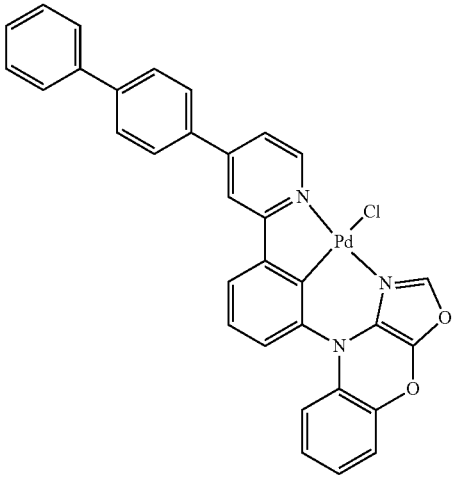
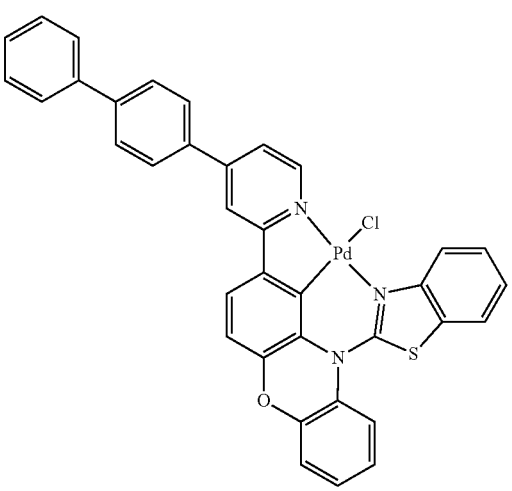
Structures Pd-7
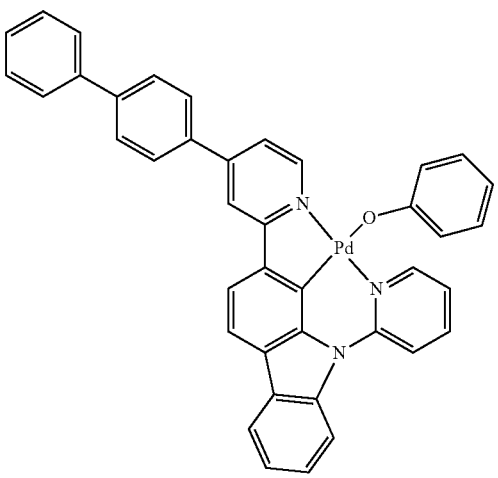

185
-continued
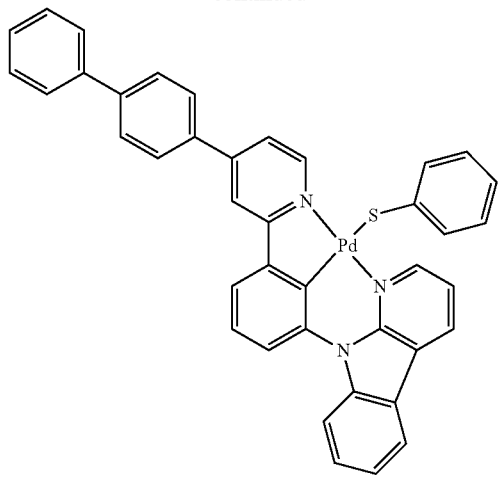
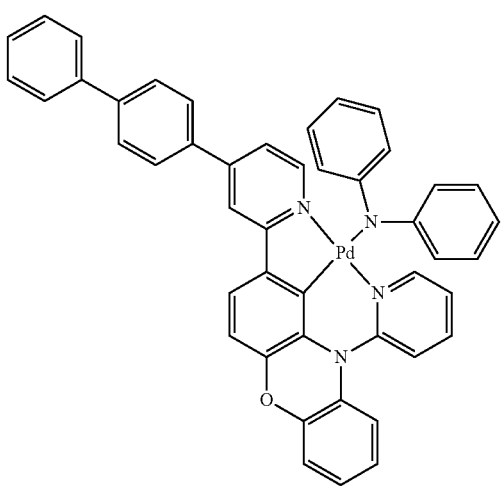
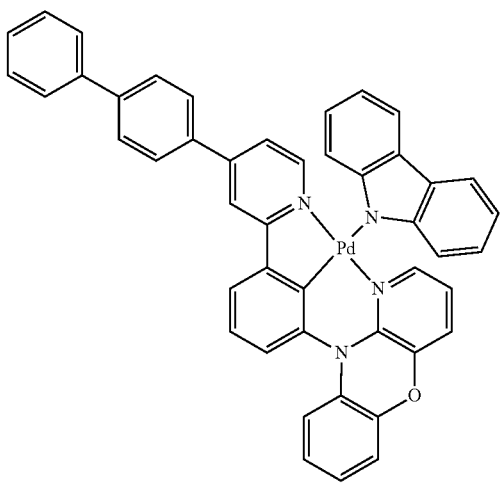
186
-continued
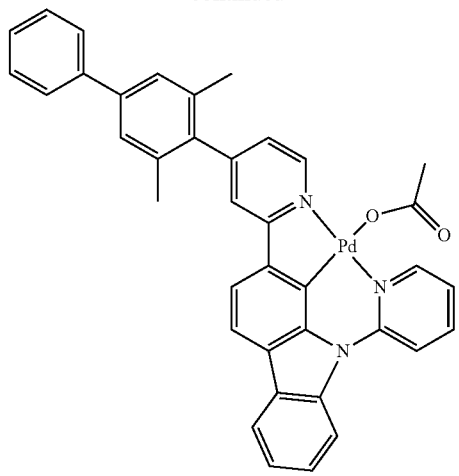
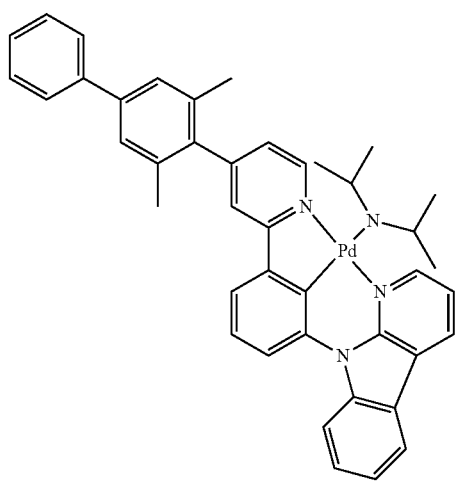
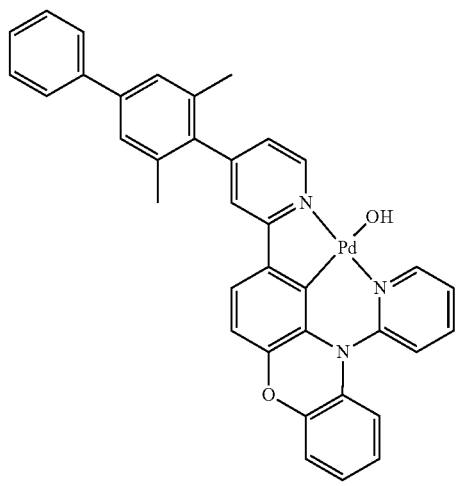

187
-continued
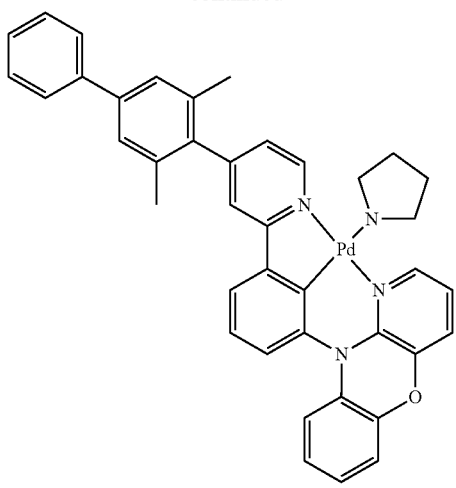
188
-continued
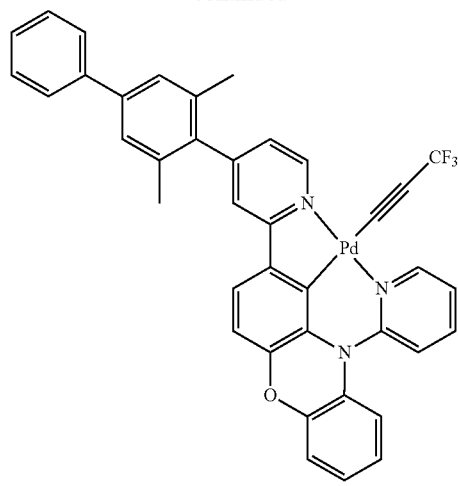
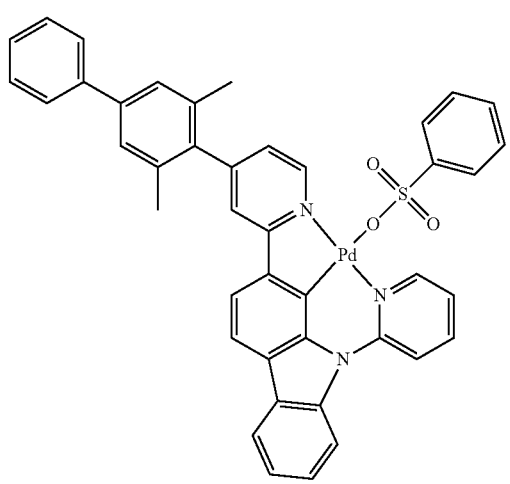
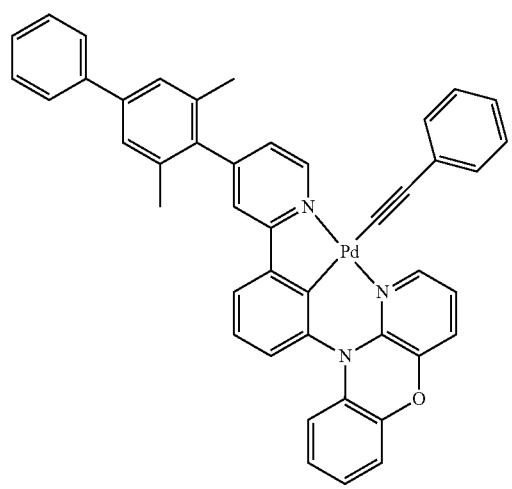
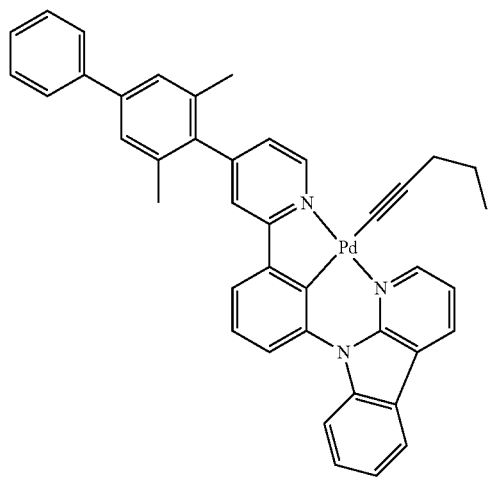
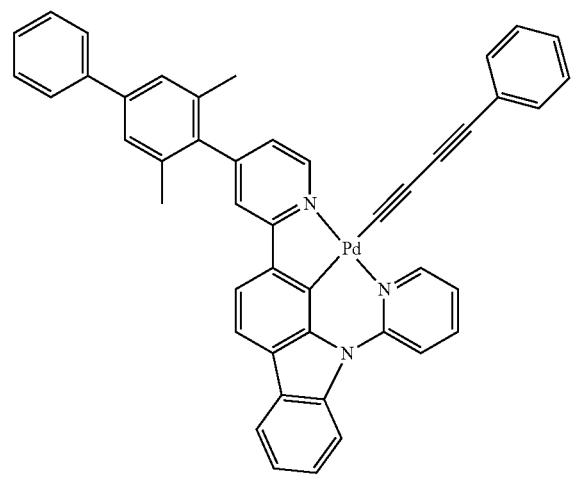

189
-continued
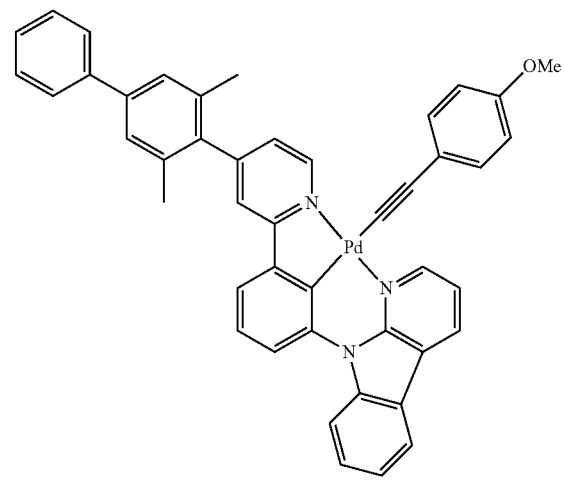
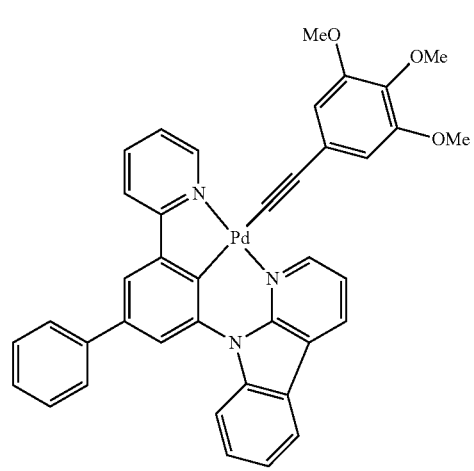
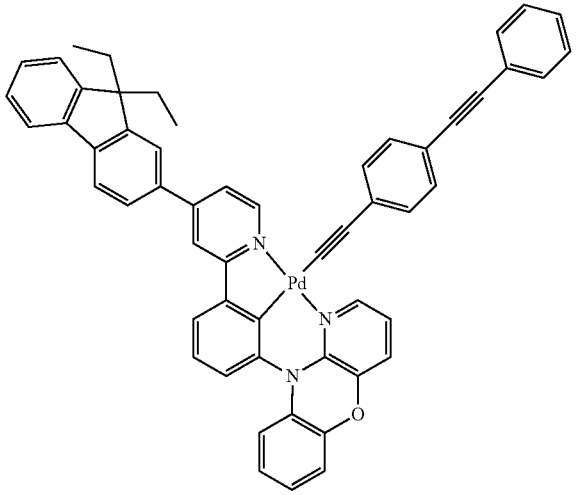
190
-continued
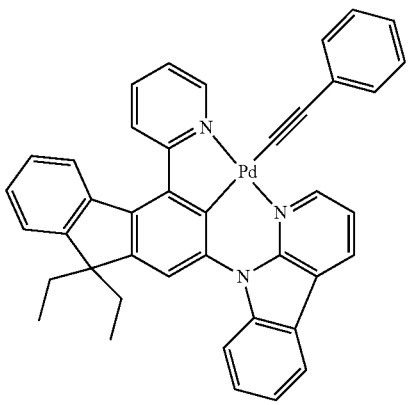
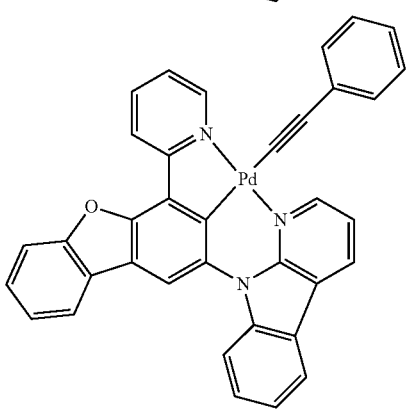
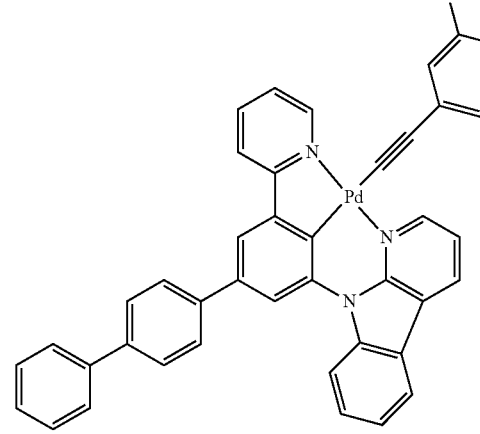
Structures Au-1
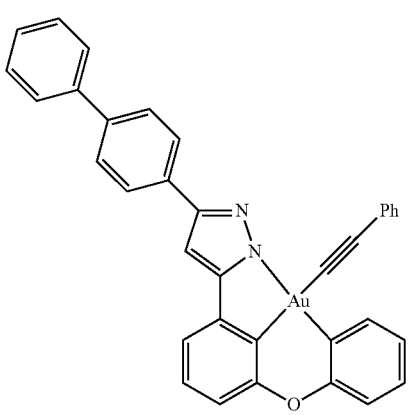

191
-continued
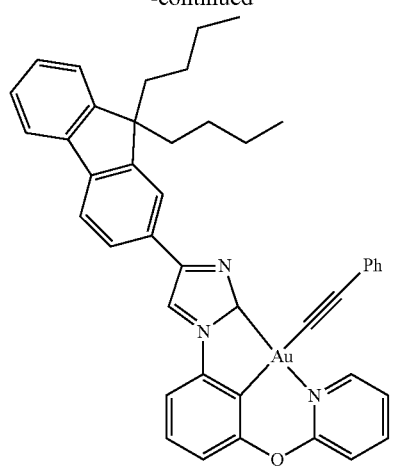
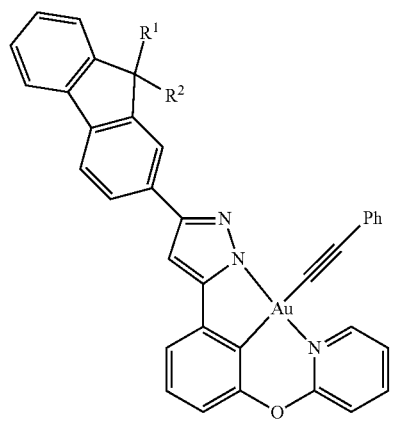
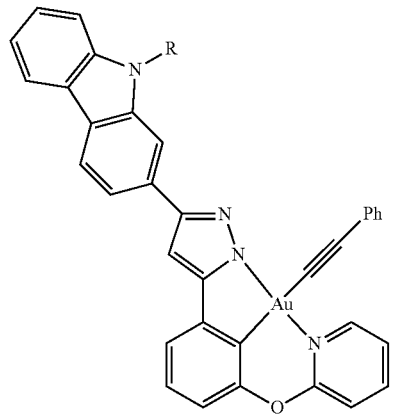
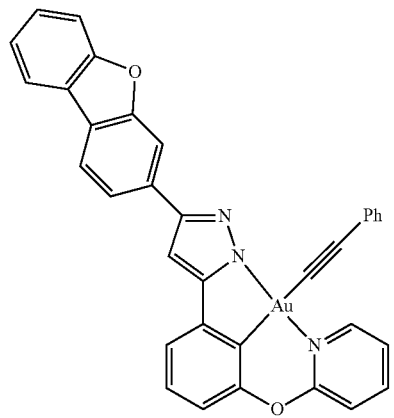
192
-continued
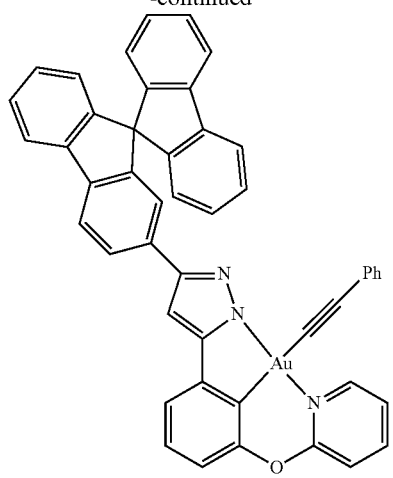
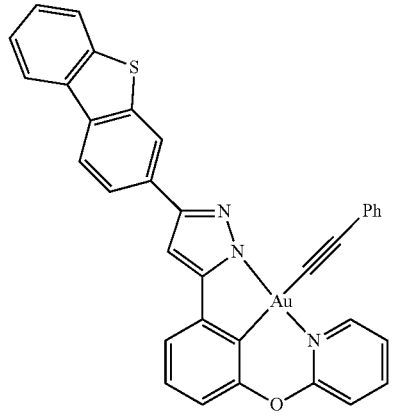
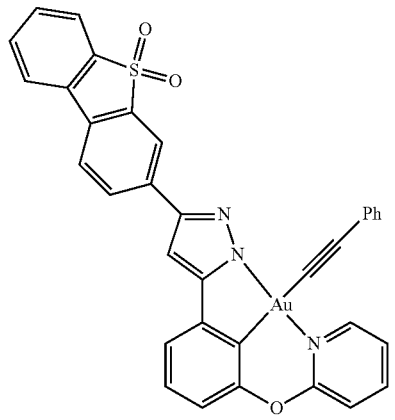
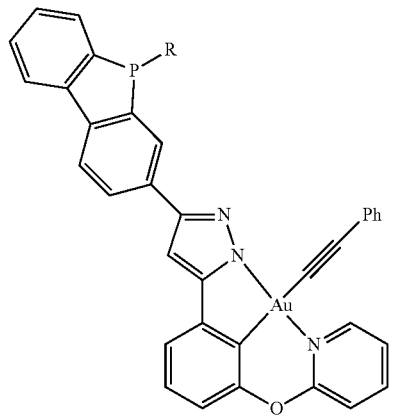

193
-continued
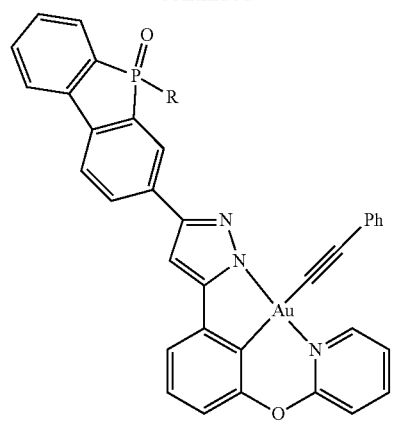
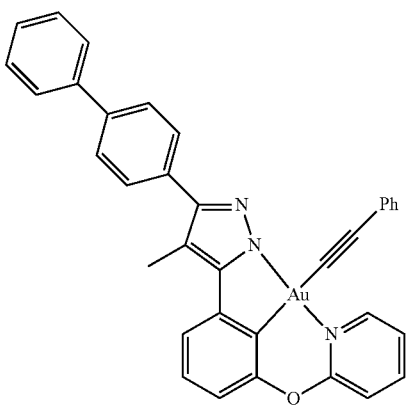
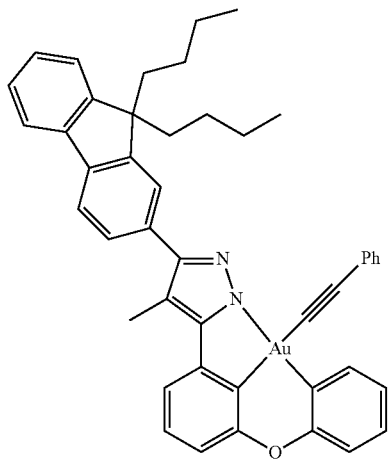
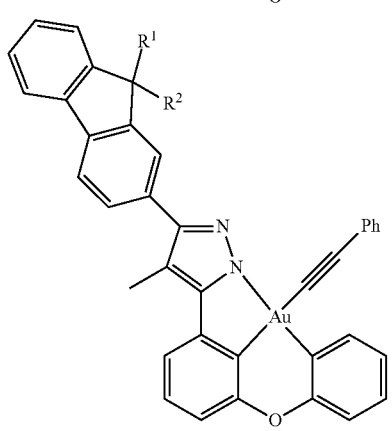
194
-continued
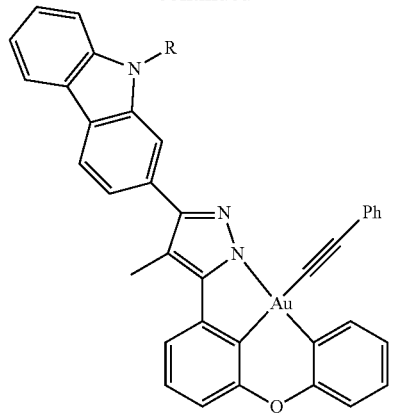
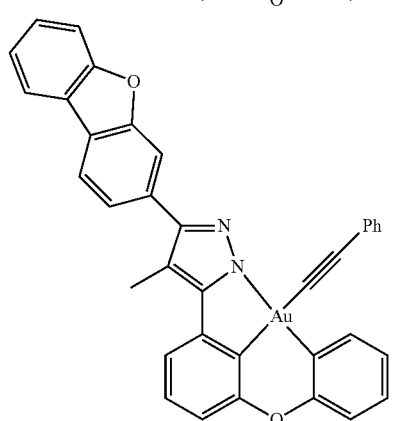
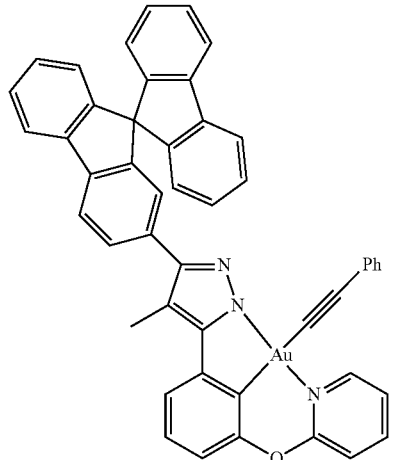
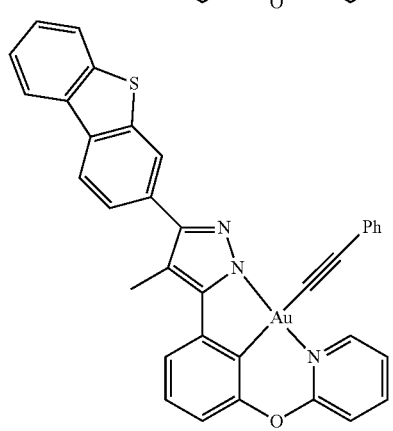

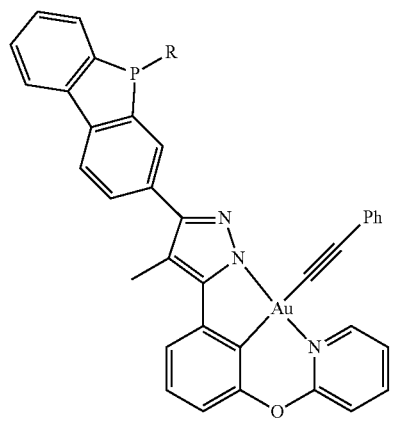
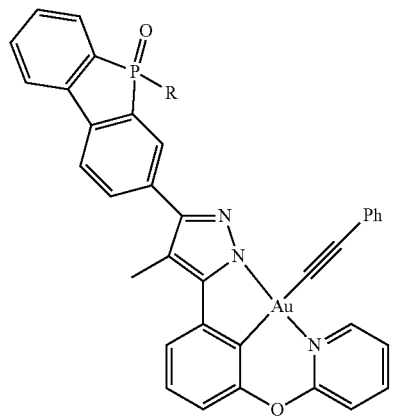
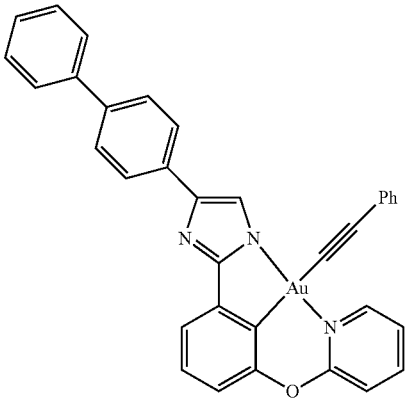
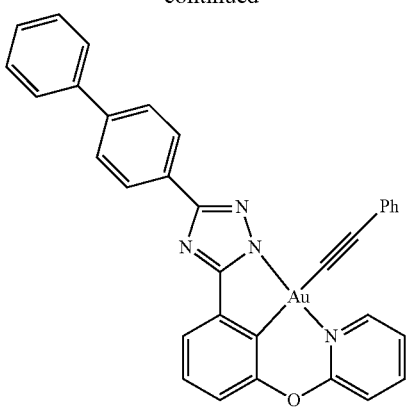
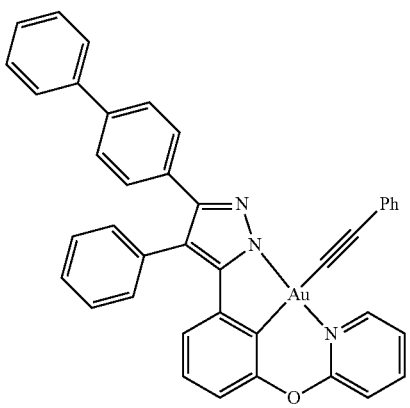
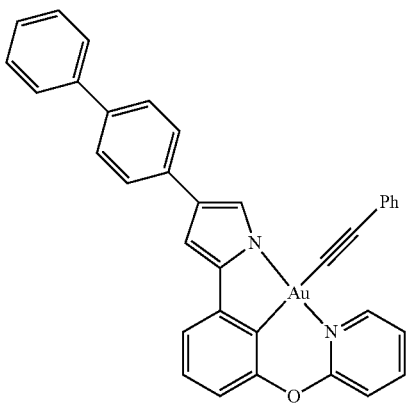
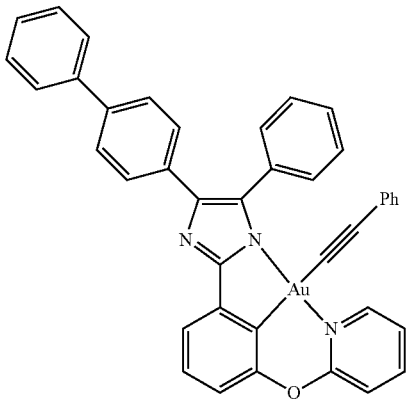

197
-continued
Structures Au-2
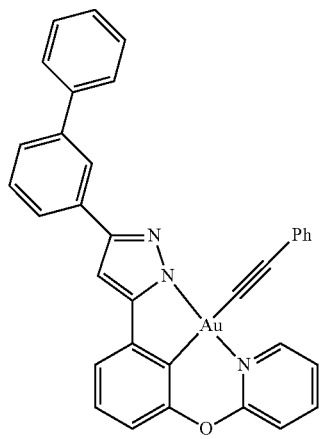
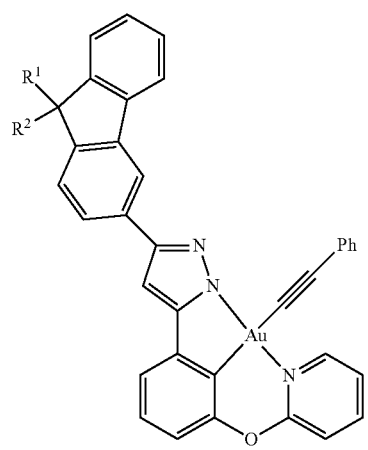
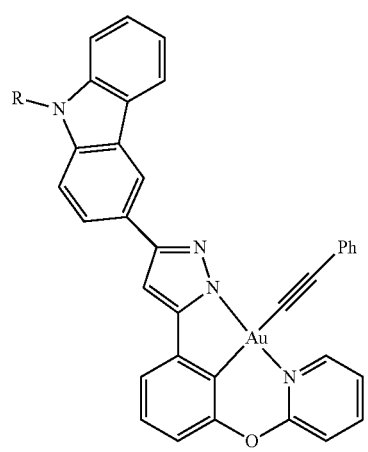
198
-continued
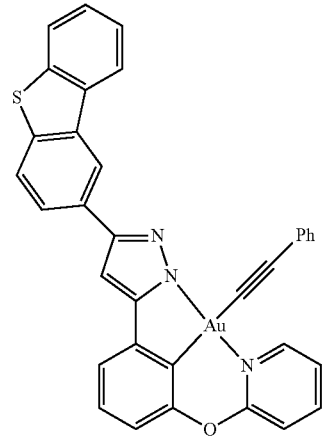
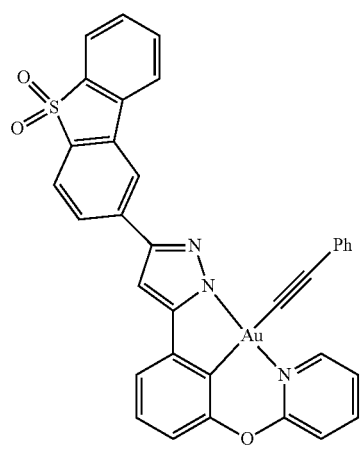
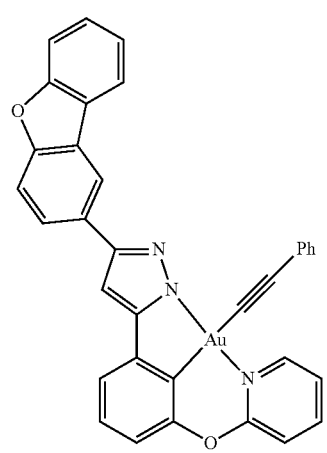

199
-continued
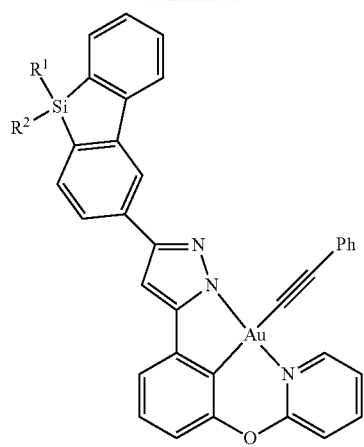
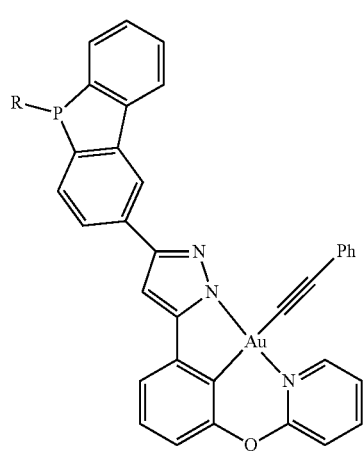
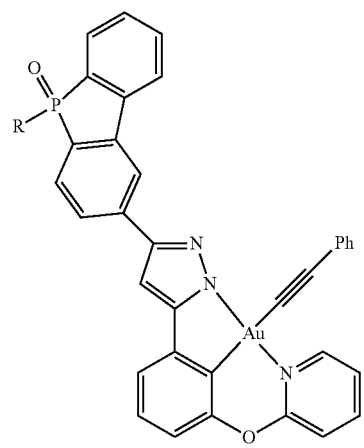
200
-continued
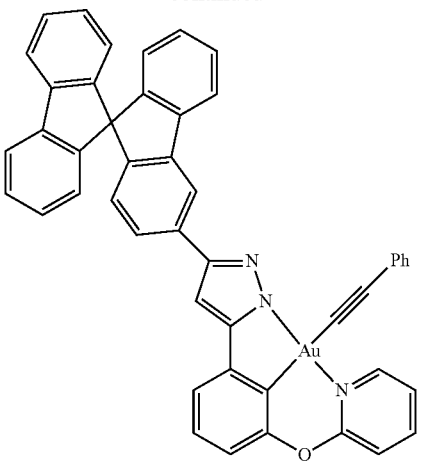
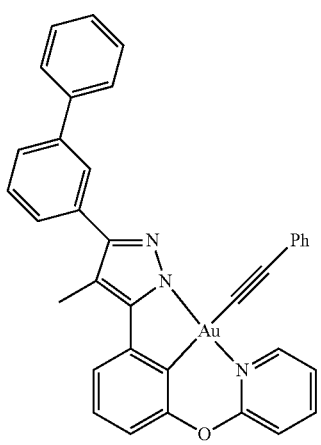
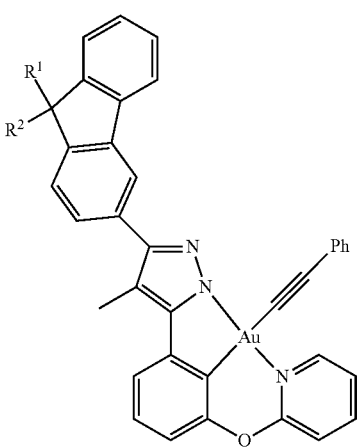

201
-continued
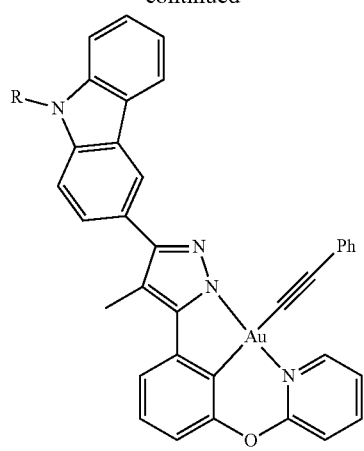
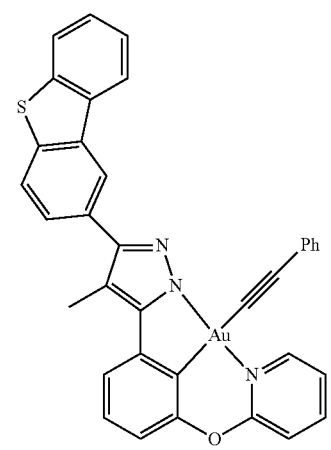
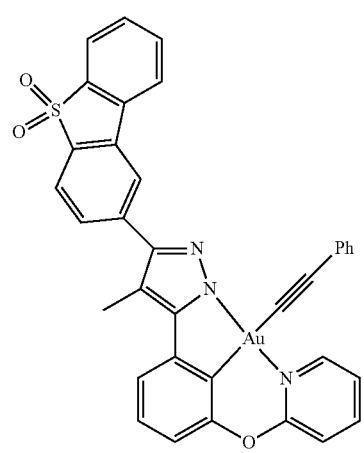
202
-continued
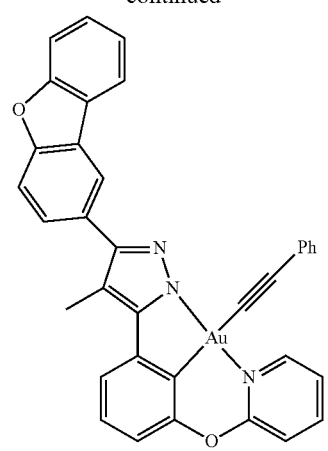
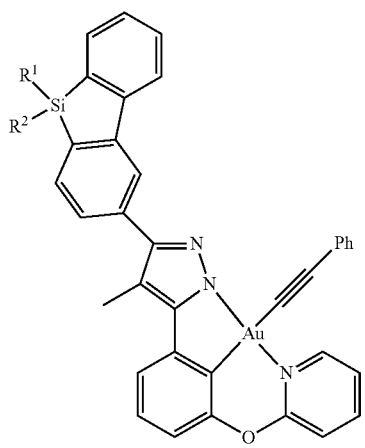
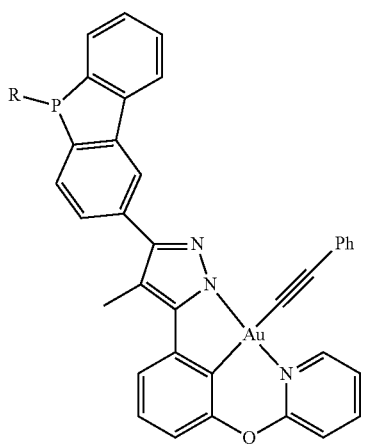

203
-continued
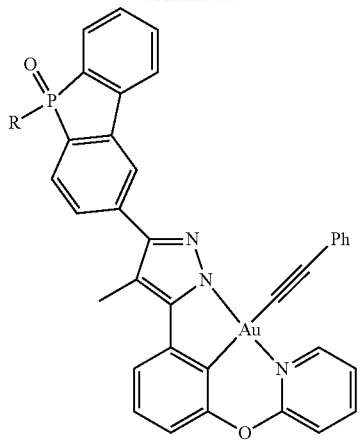
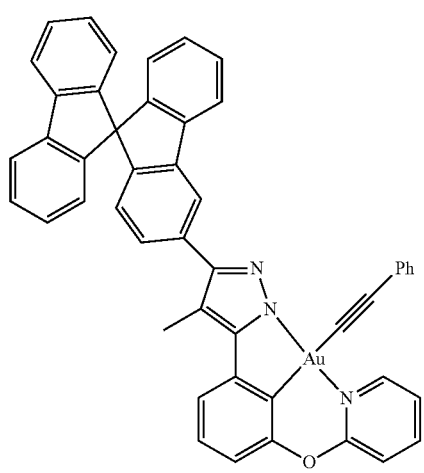
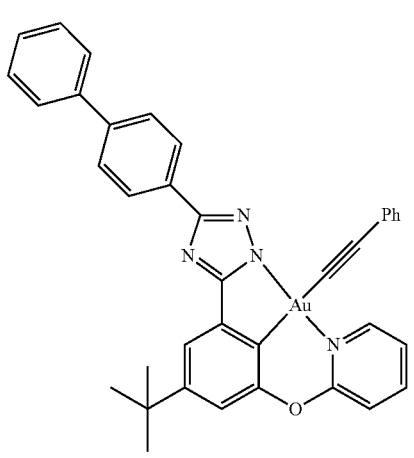
204
-continued
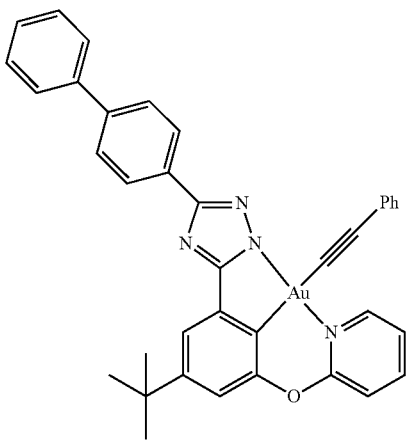
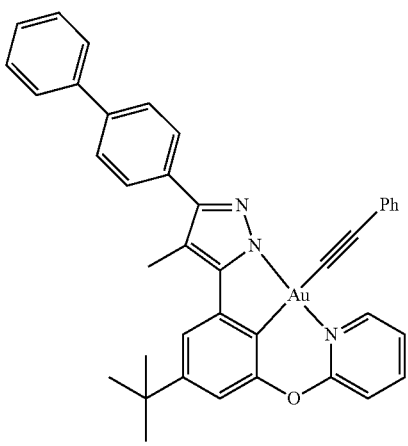
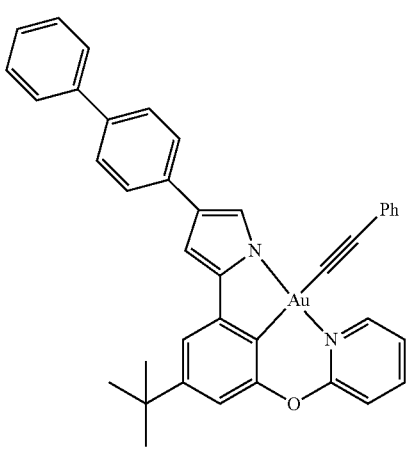

205
-continued
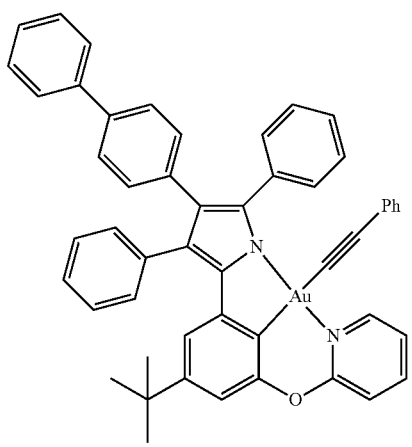
Structures Au-3
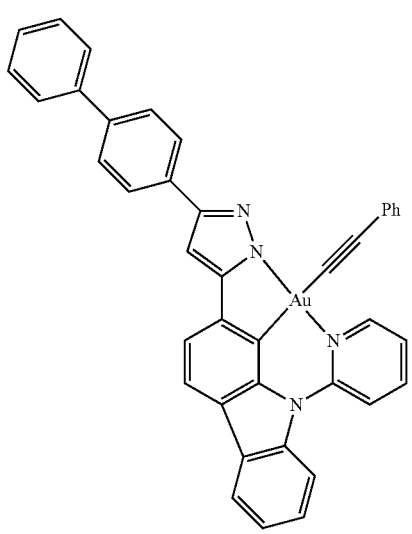
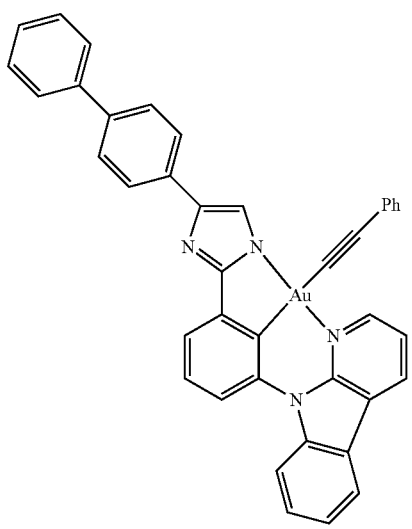
206
-continued
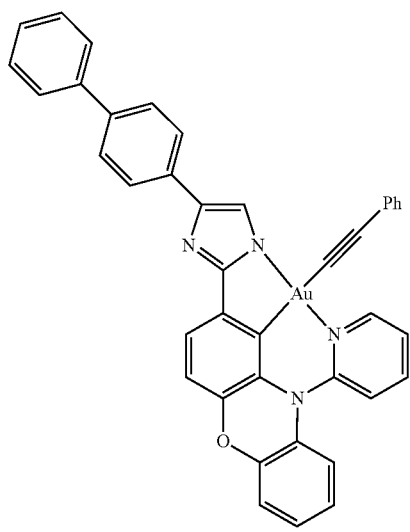
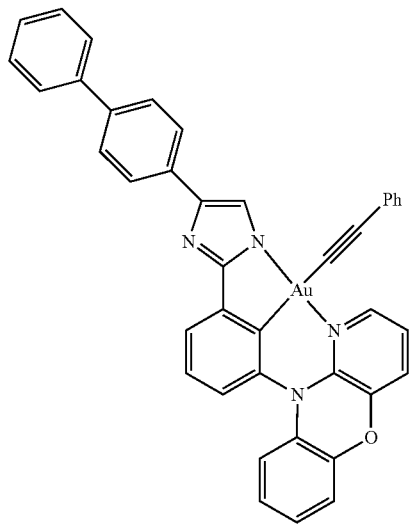
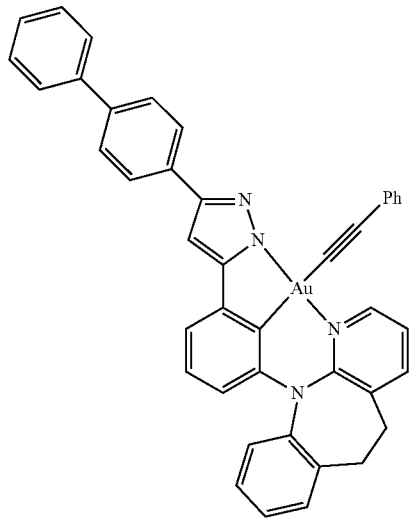

207
-continued
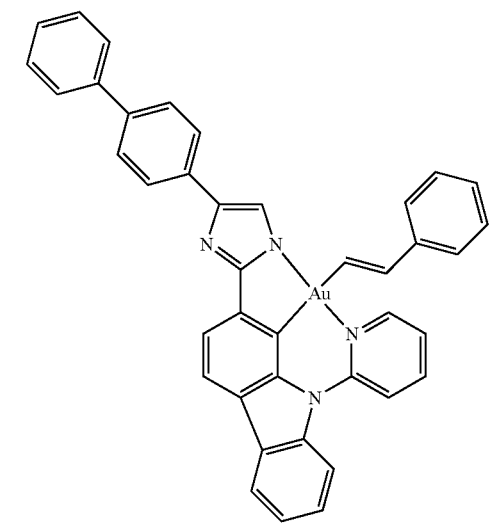
208
-continued
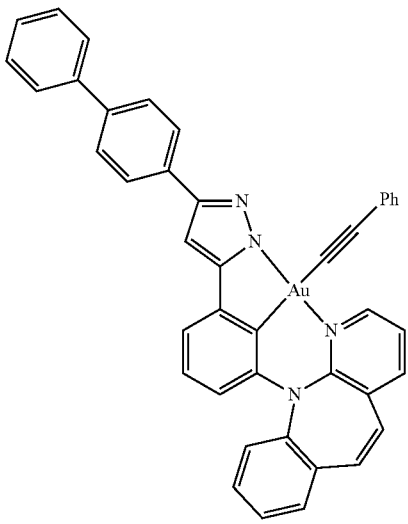
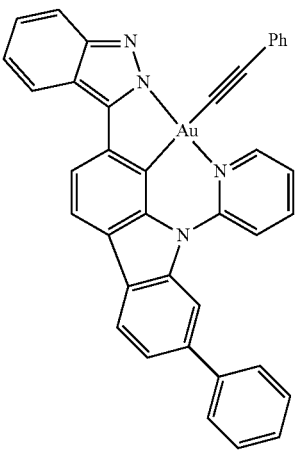
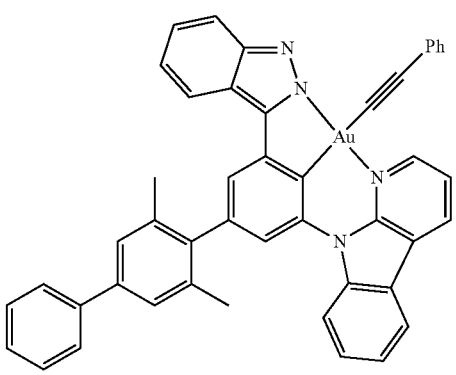
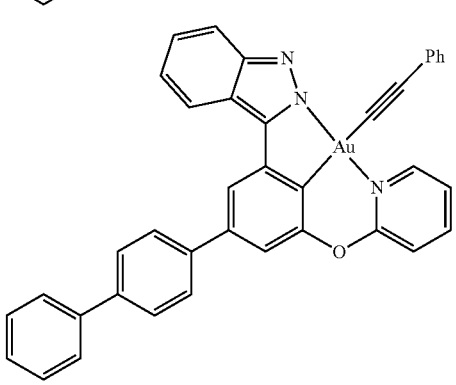

209
-continued
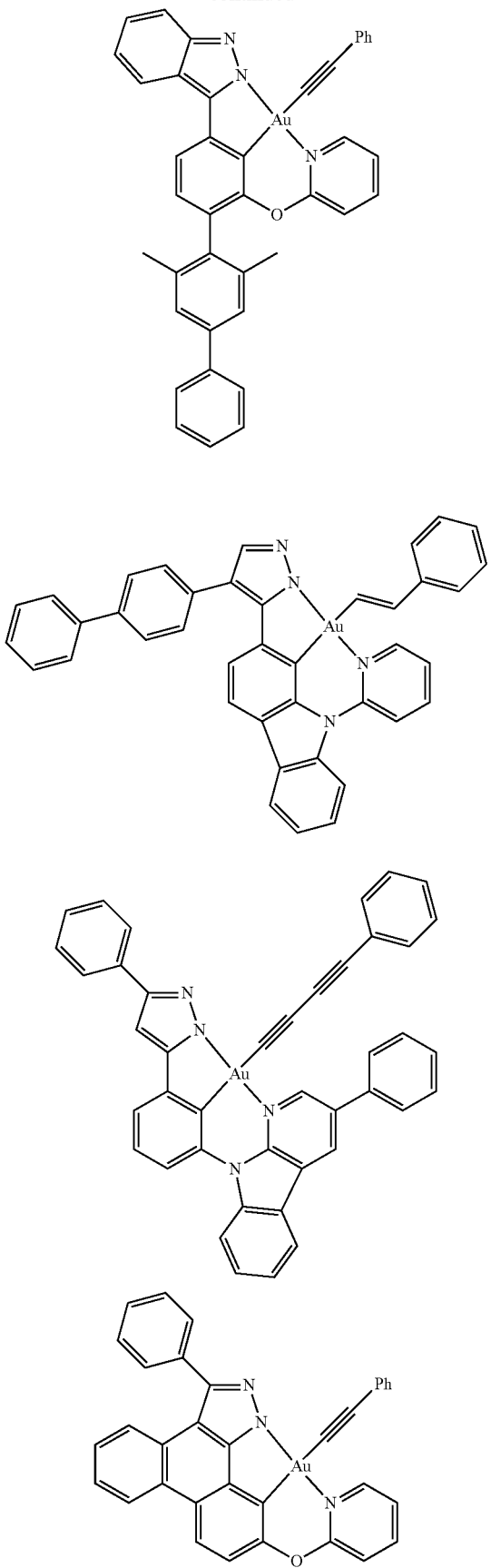
210
-continued
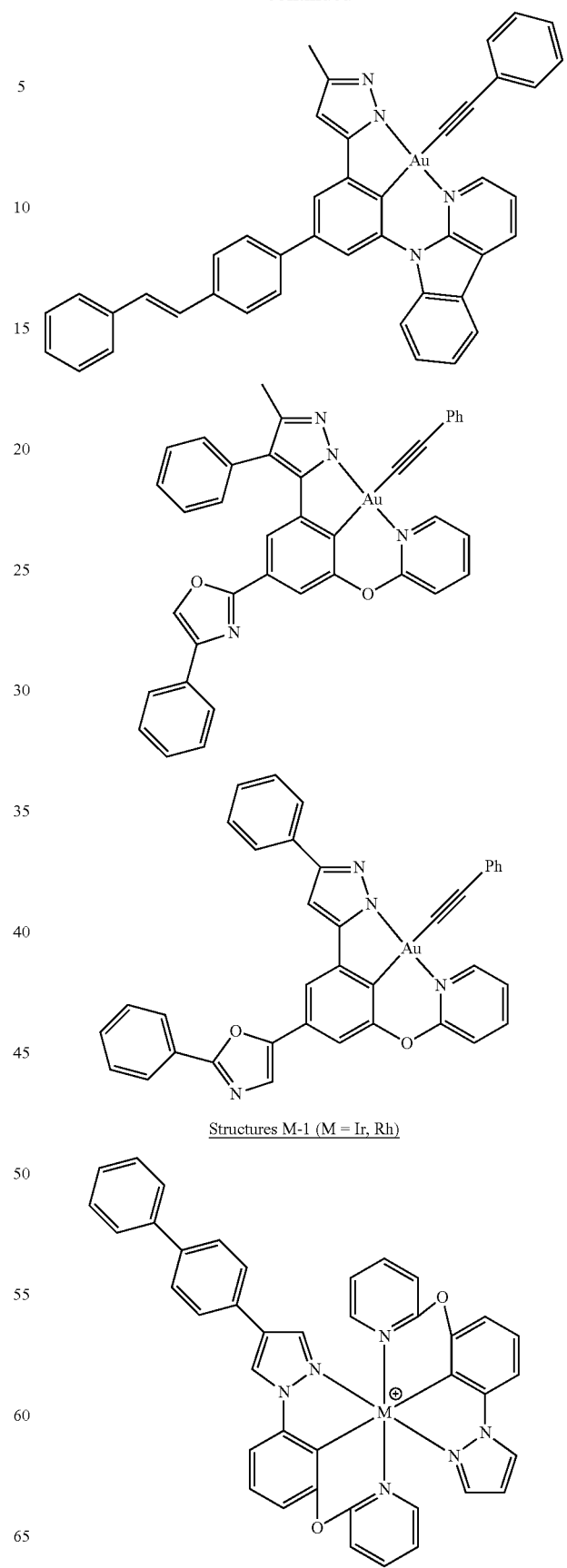
Structures M-1 (M = Ir, Rh)

211
-continued
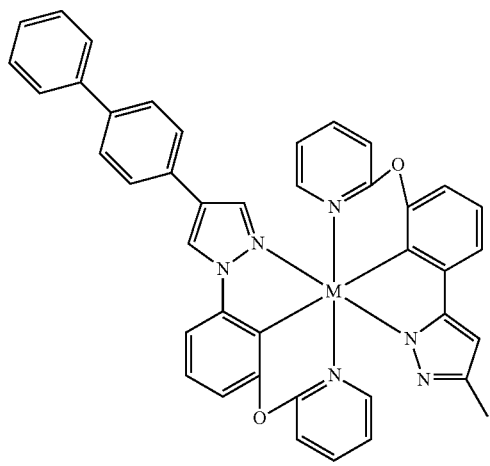
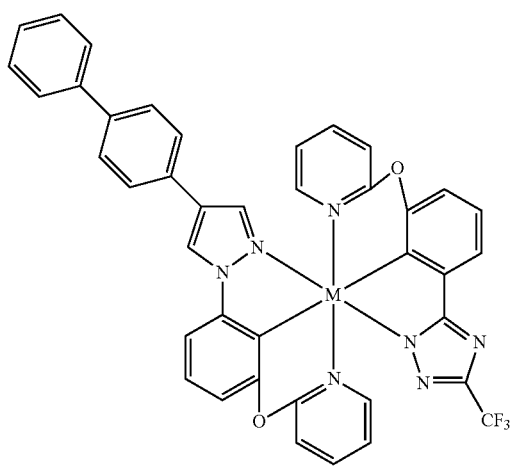
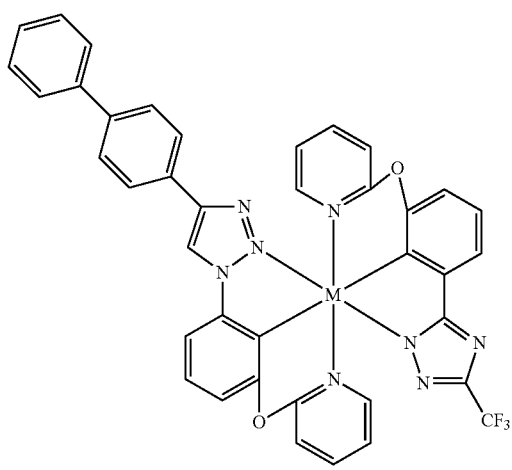
212
-continued
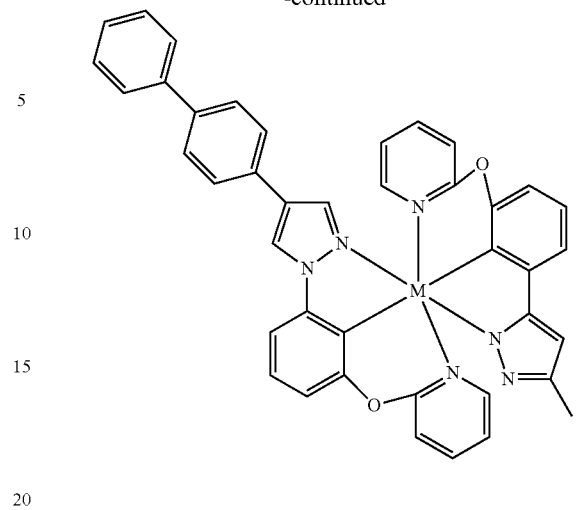
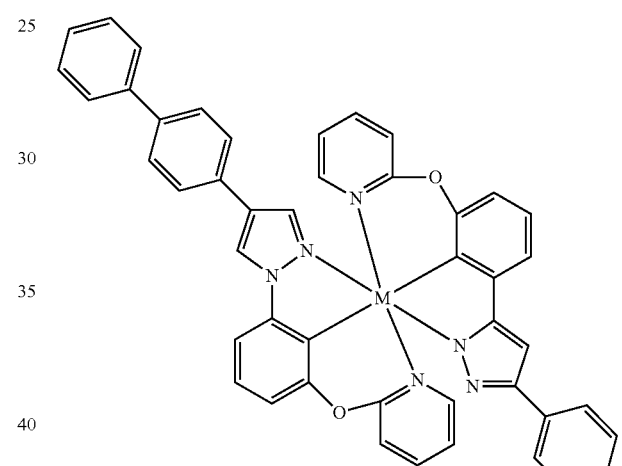
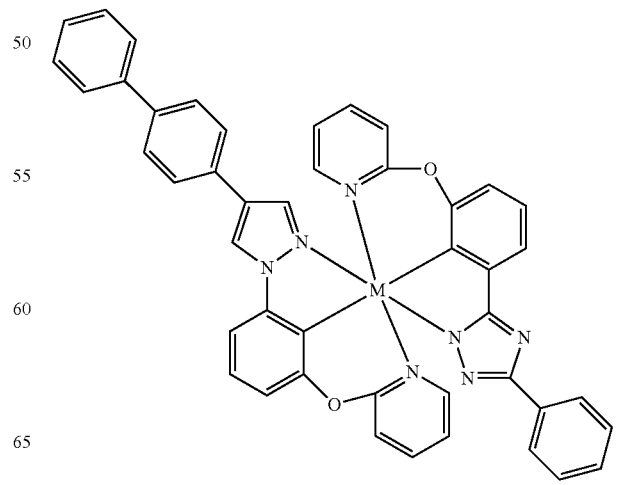

213
-continued
214
-continued
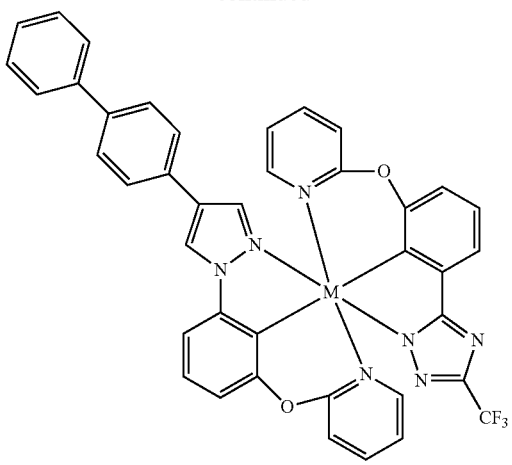
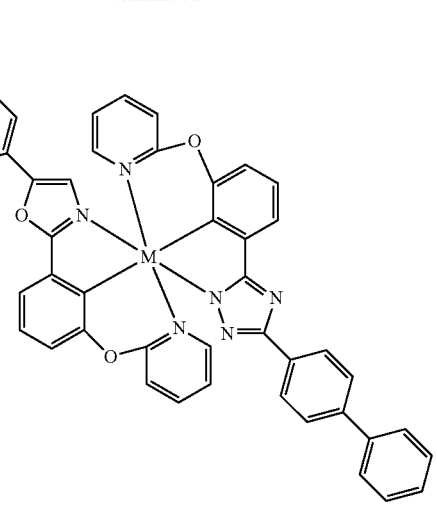
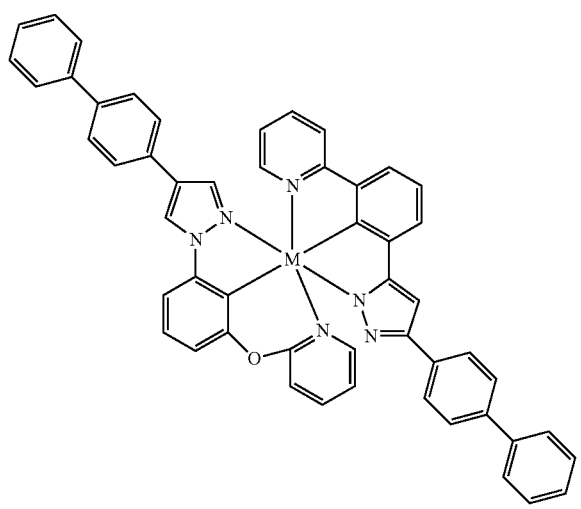
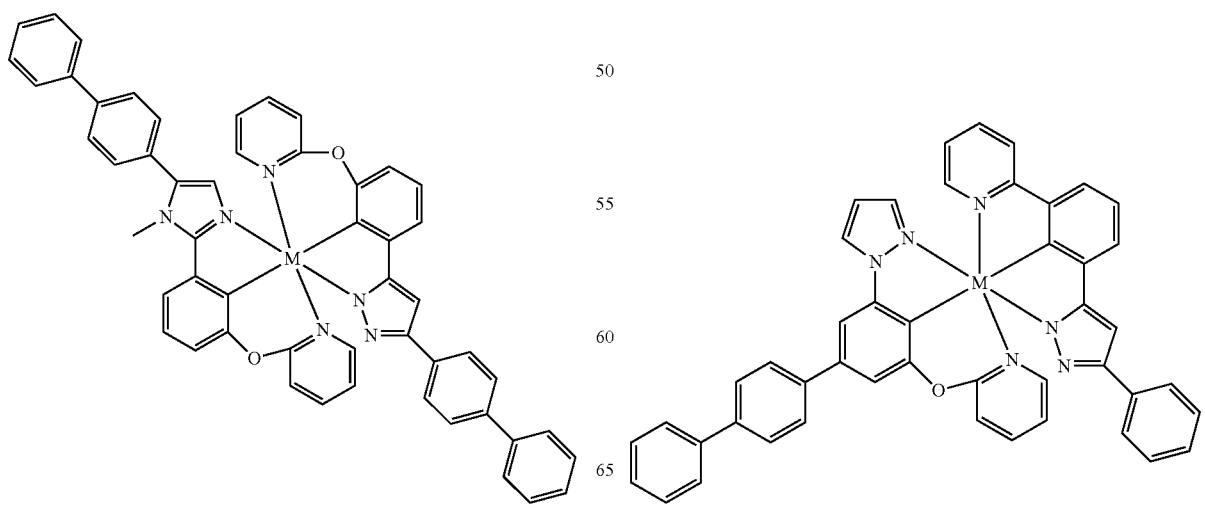

215
-continued
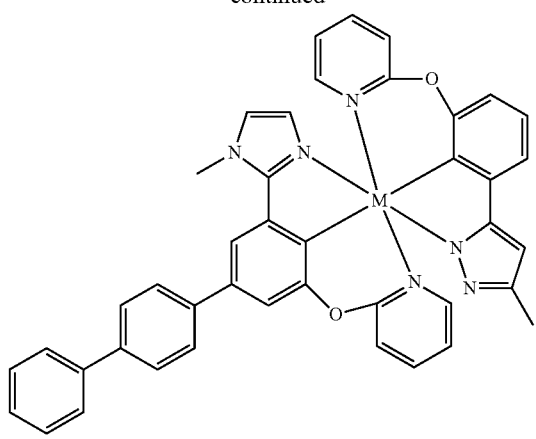
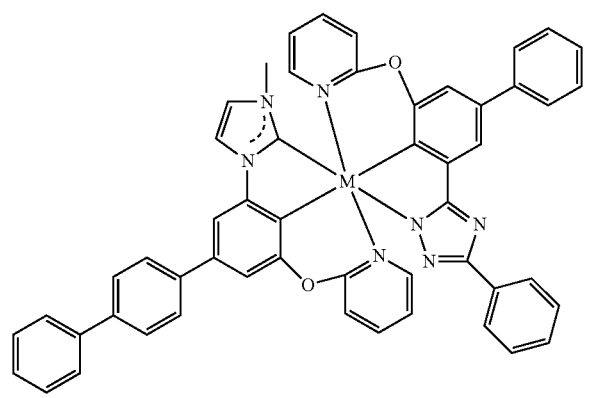
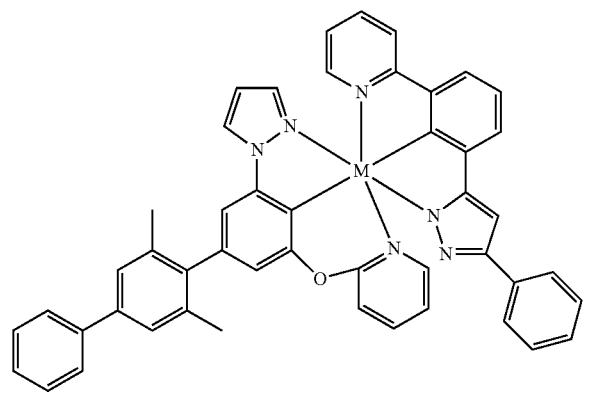
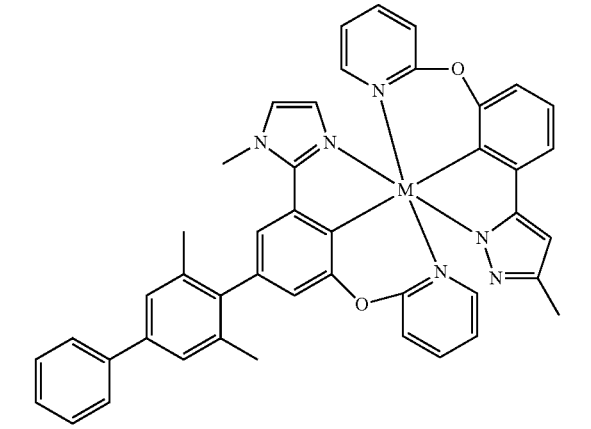
216
-continued
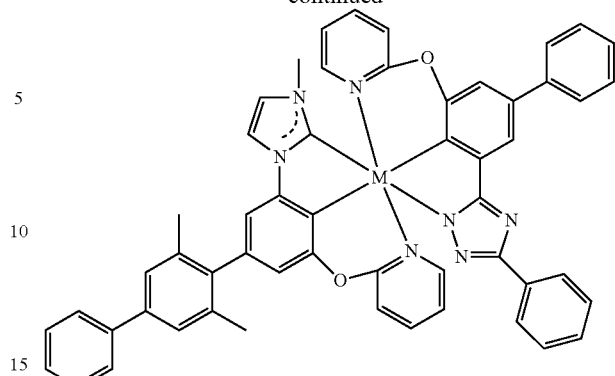
Structures M-2 (M = Ir, Rh)
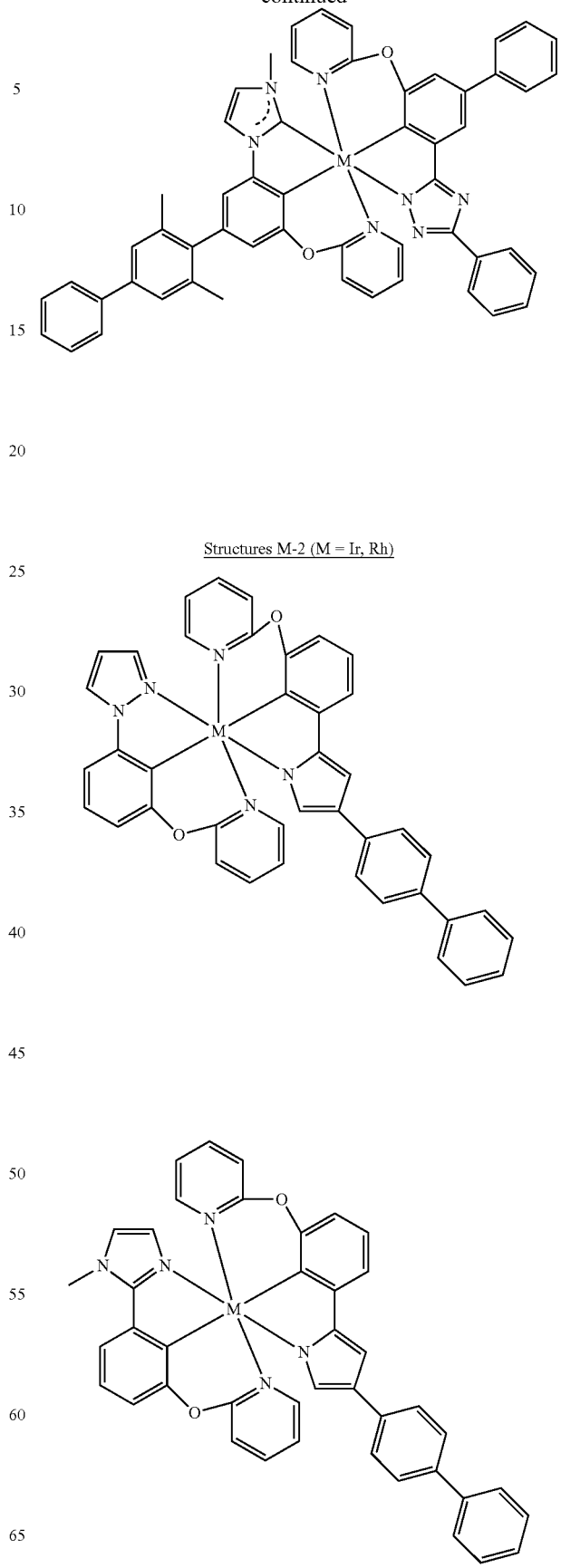

217
-continued
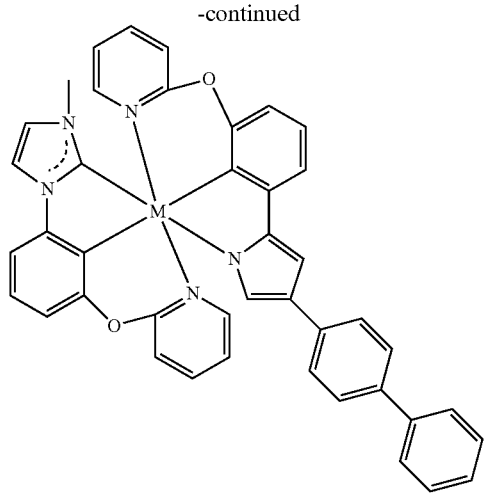
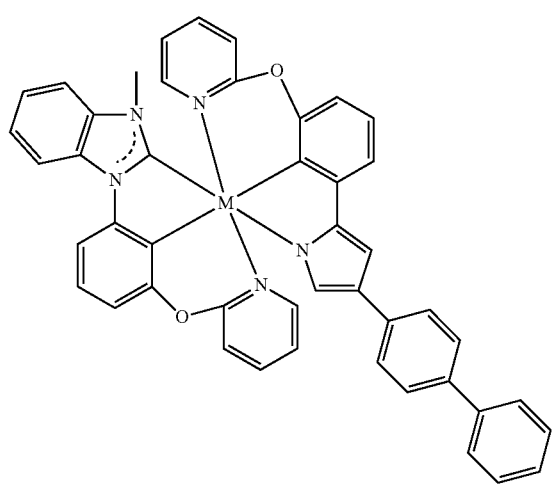
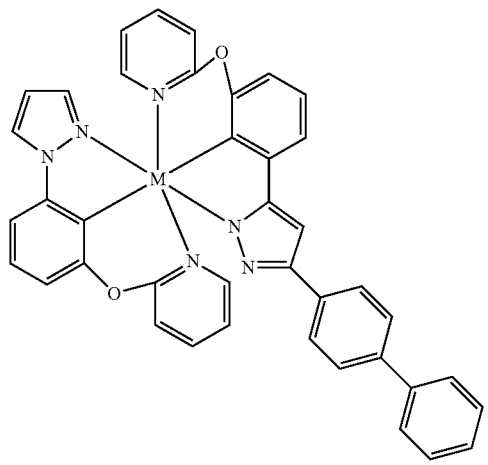
218
-continued
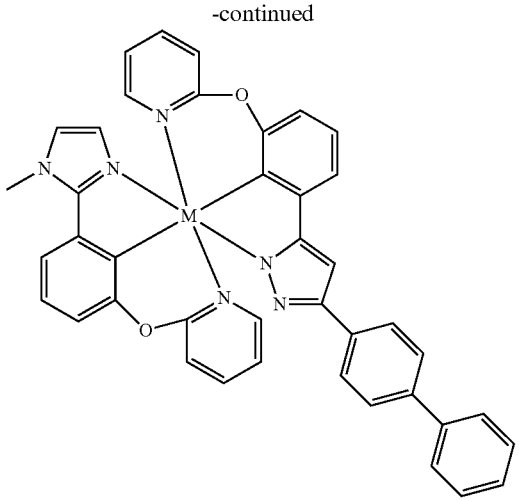
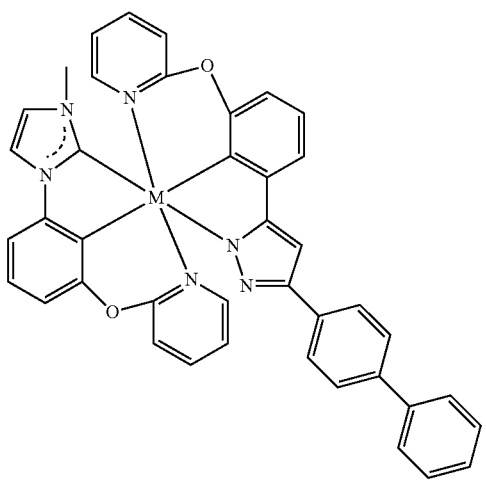
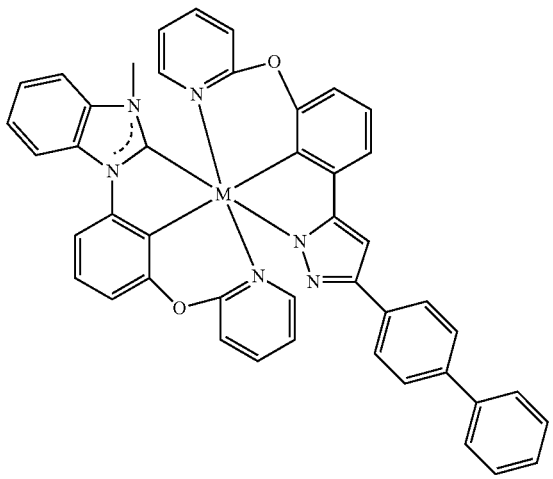

219
-continued
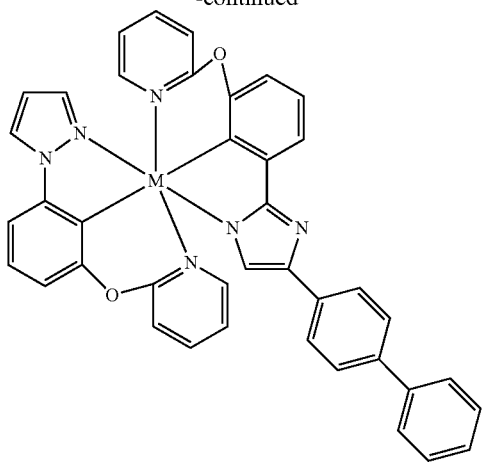
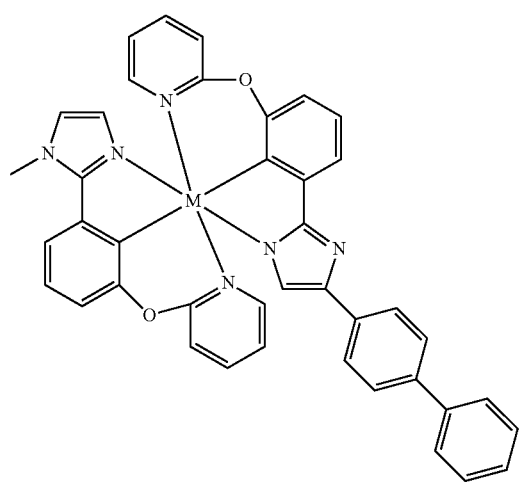
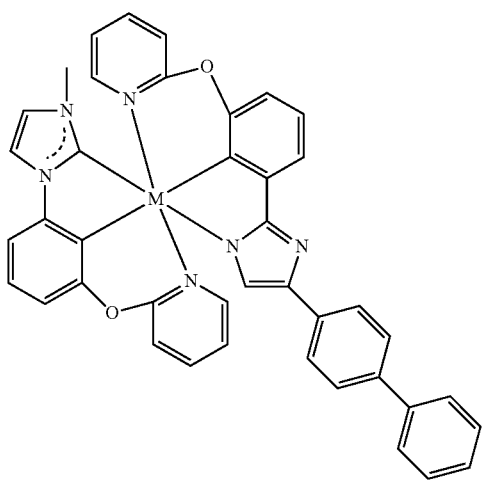
220
-continued
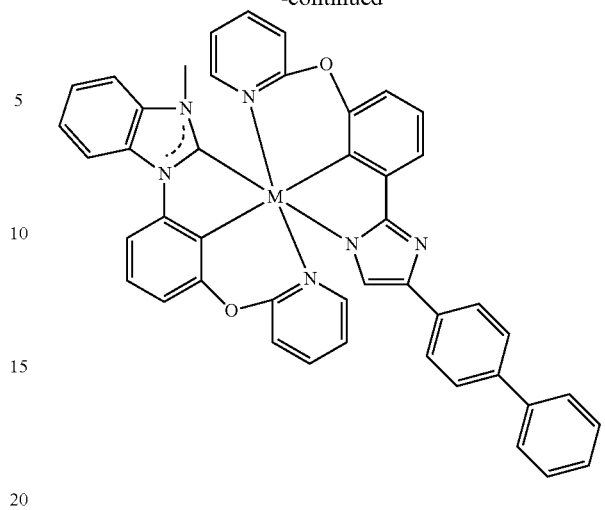
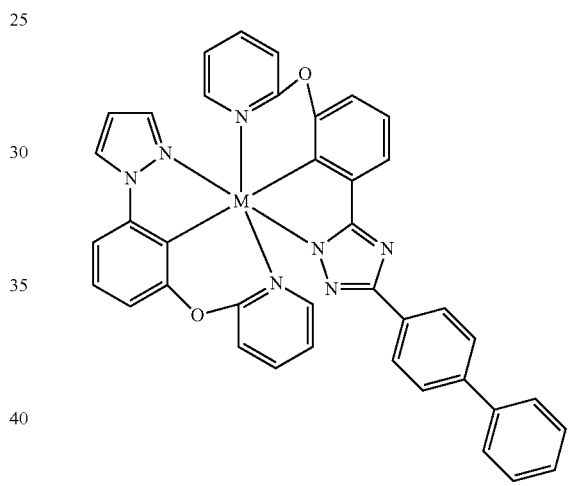
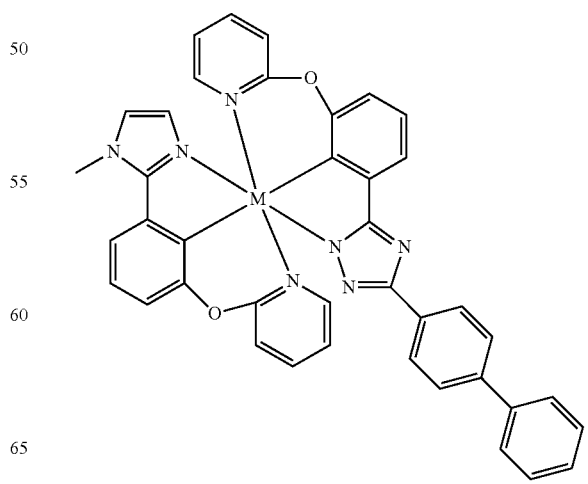

221
-continued
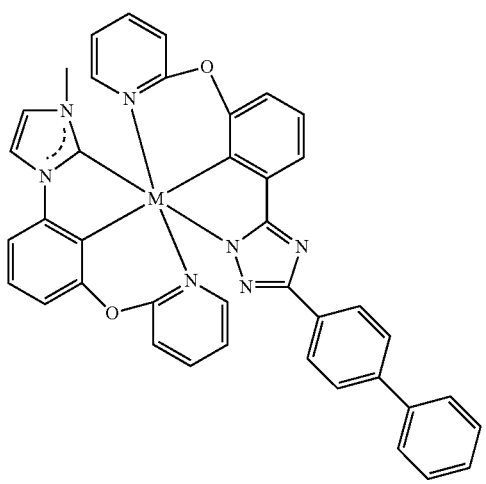
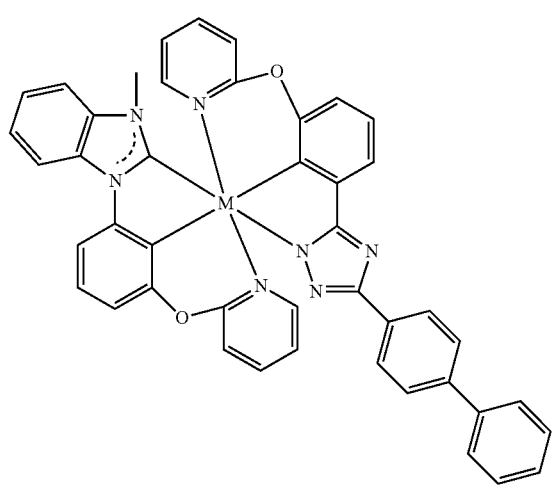
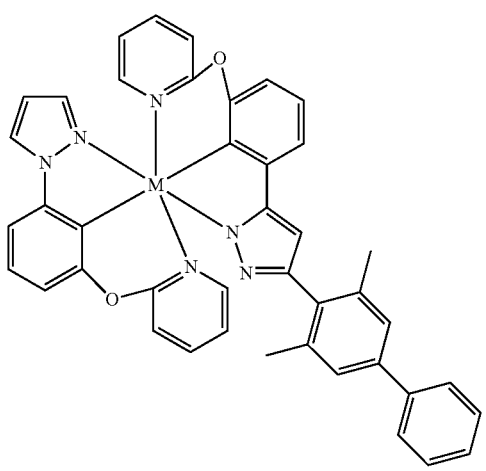
222
-continued
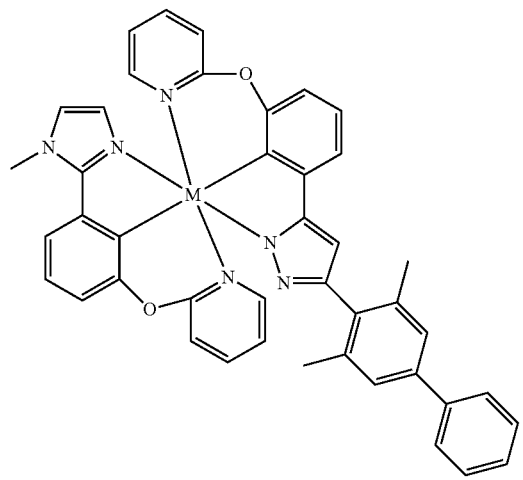
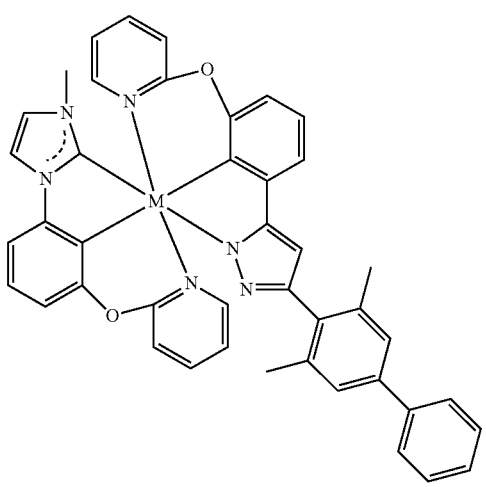
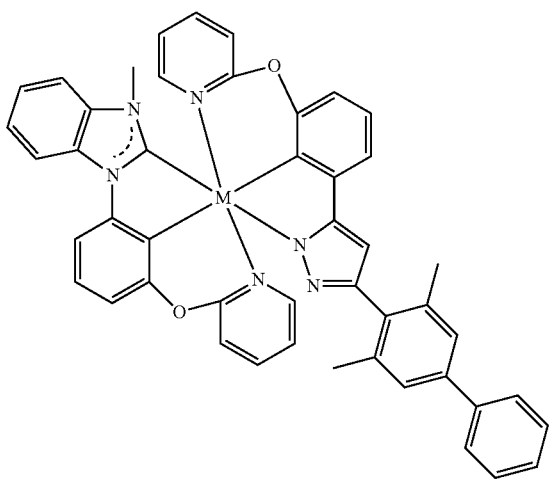

Structures M-3 (M = Ir, Rh)
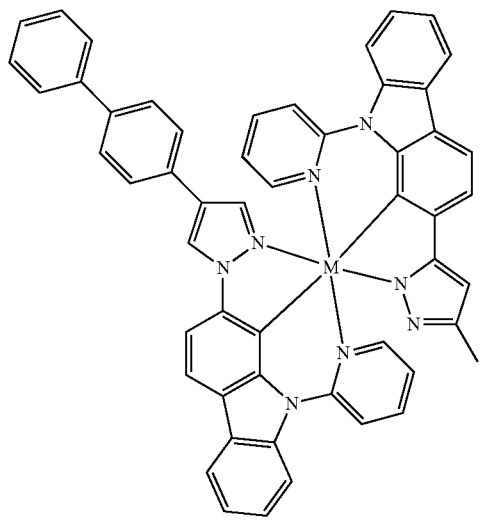
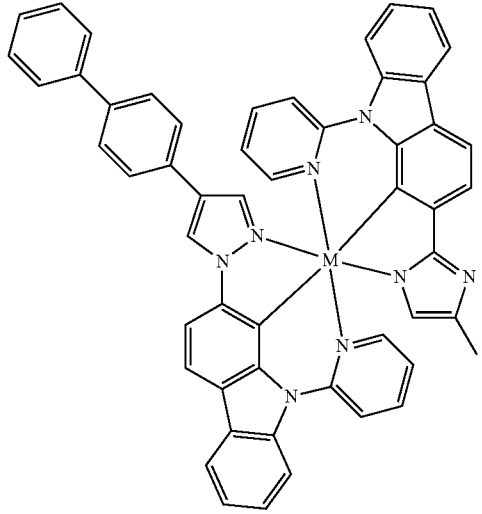
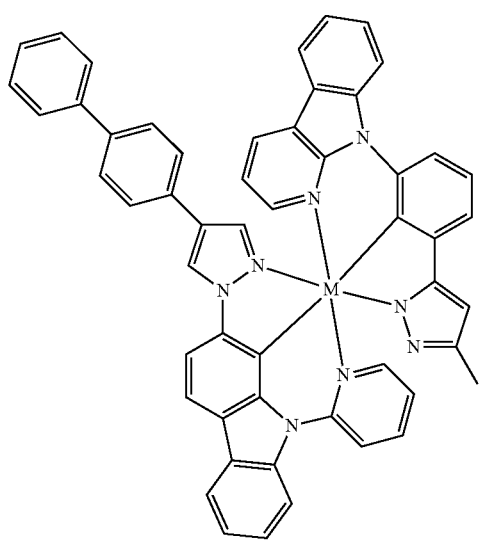
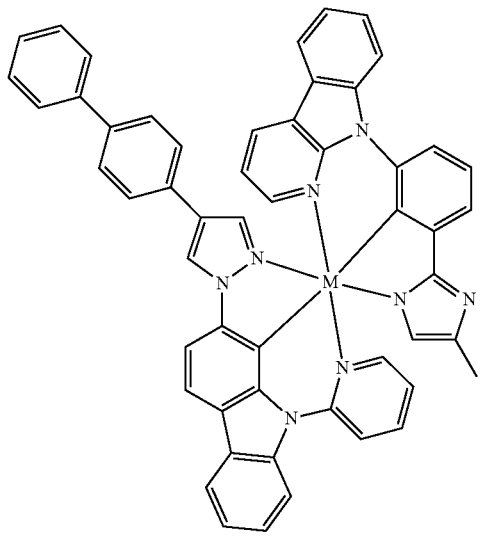
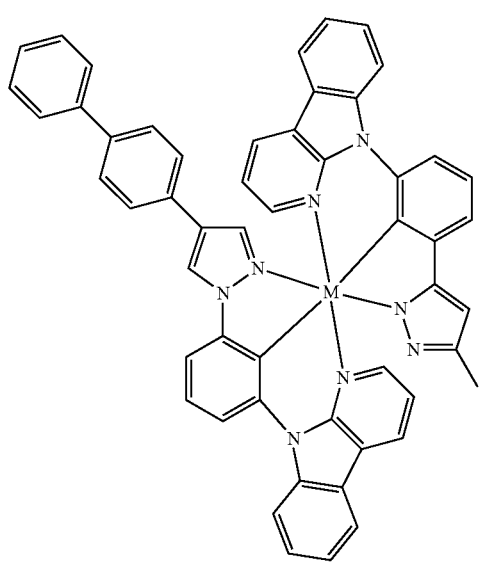
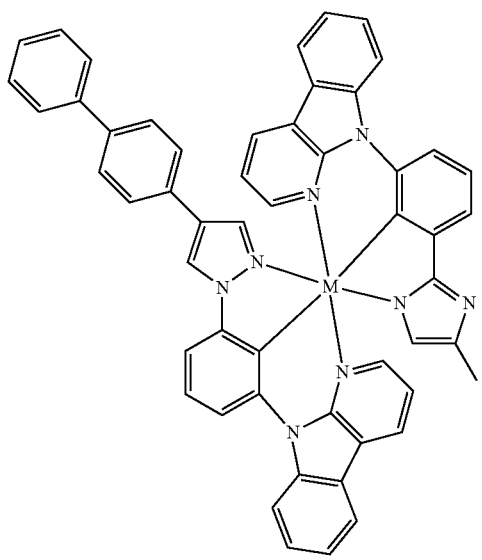

225
-continued
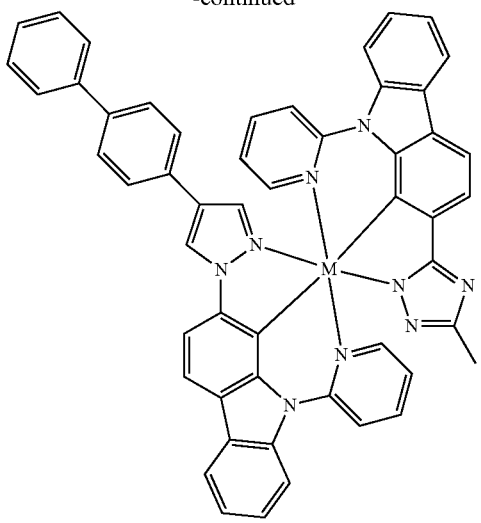
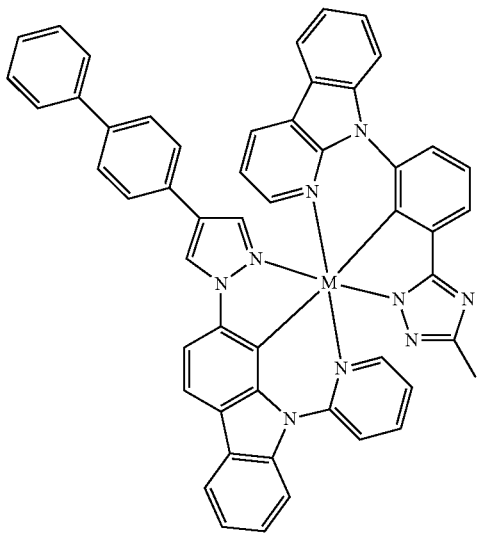
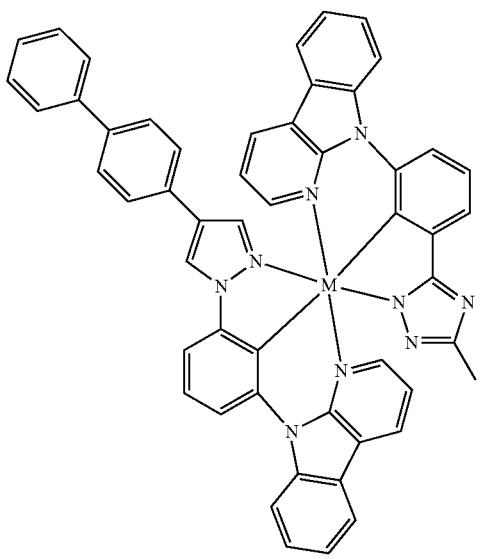
226
-continued
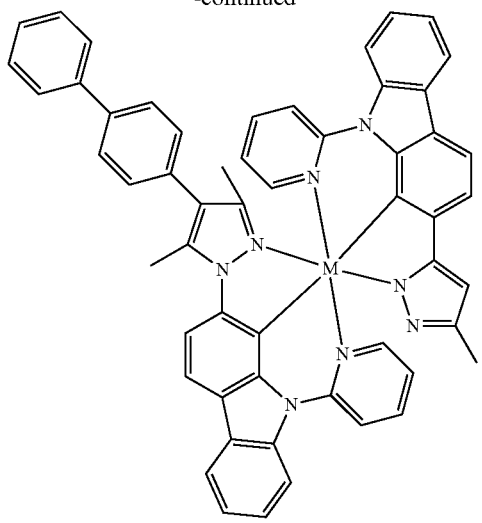
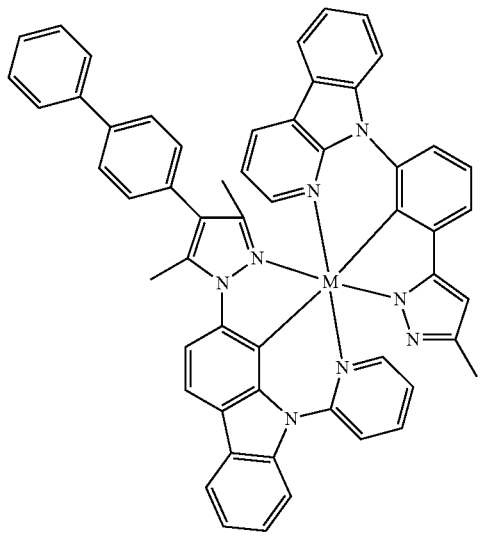
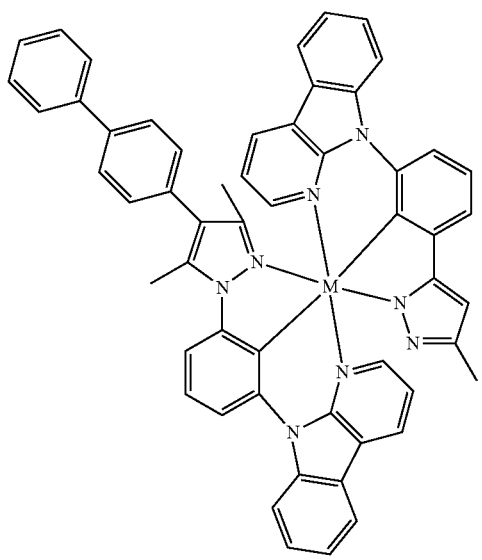

227
-continued
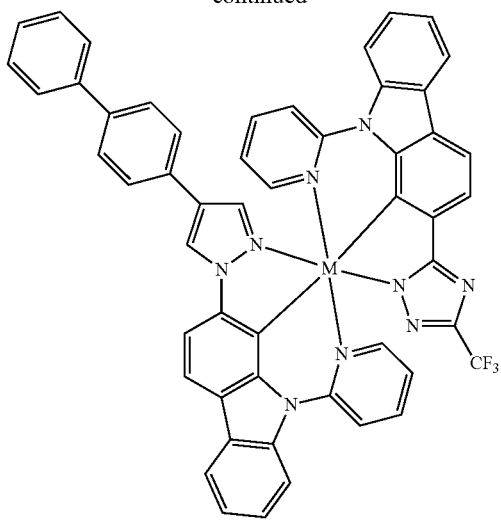
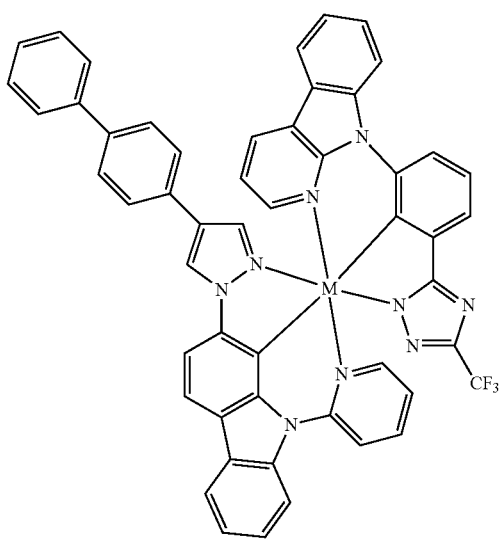
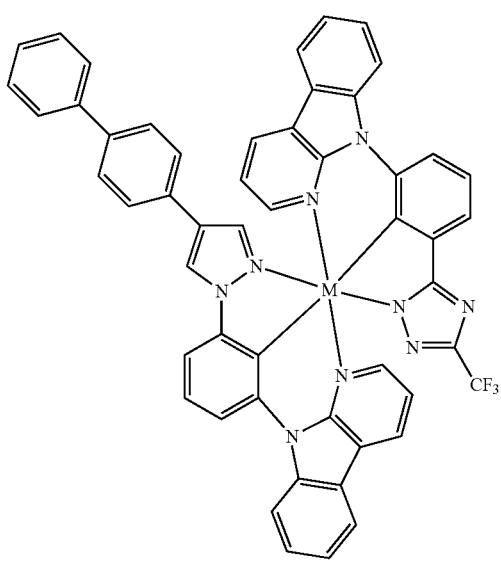
228
-continued
Structures M-4 (M = Ir, Rh)
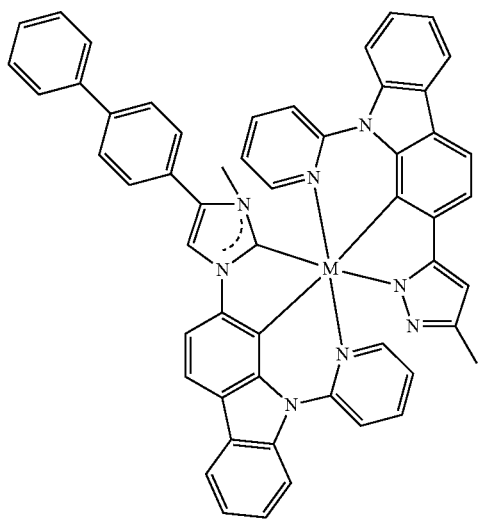
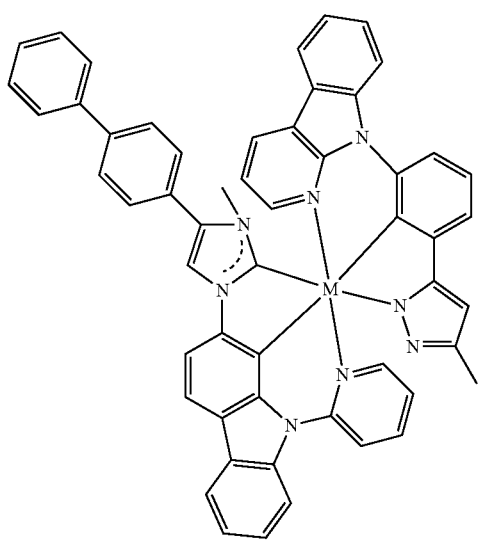
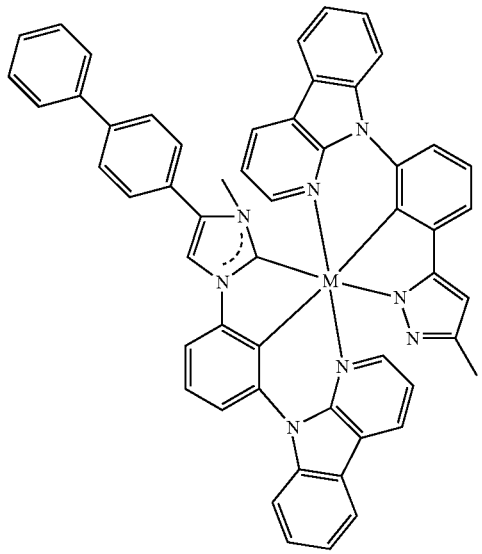

229
-continued
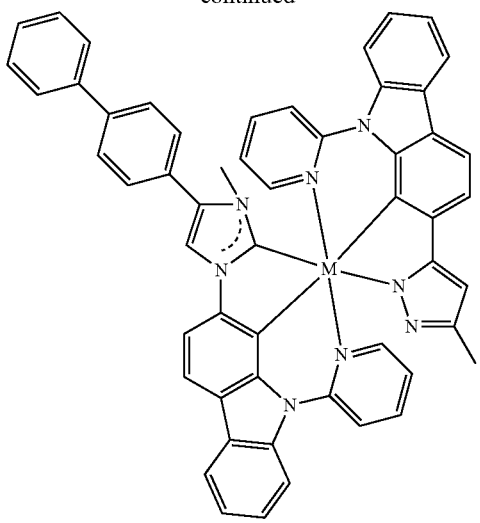
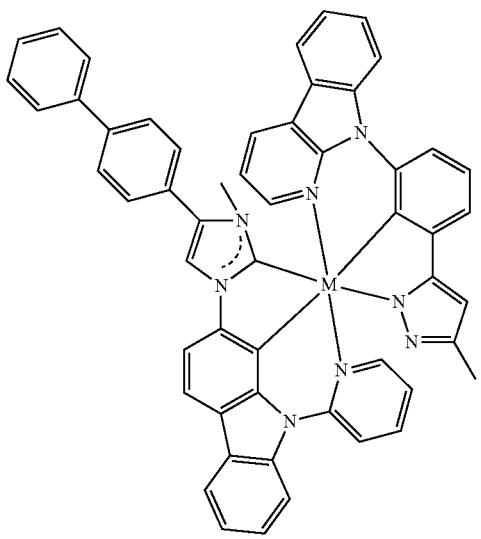
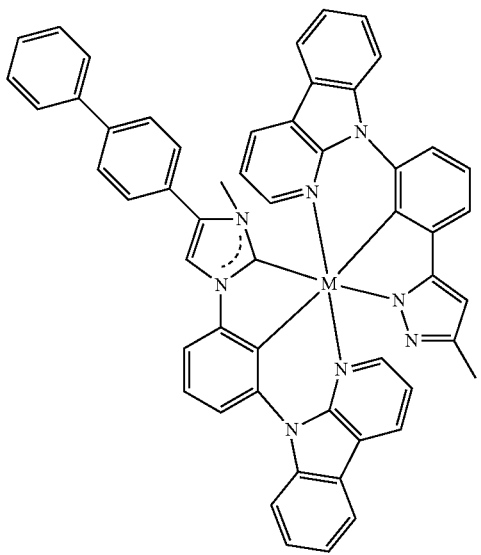
230
-continued
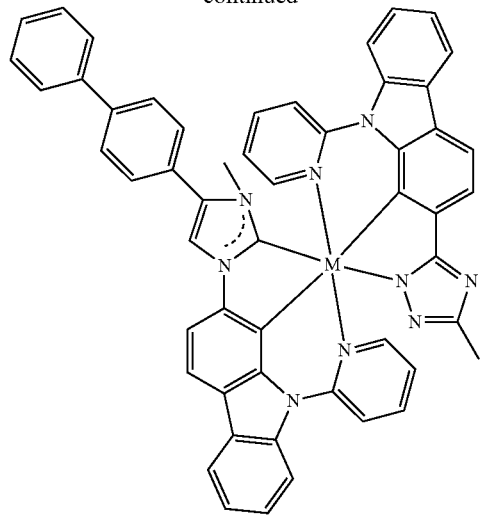
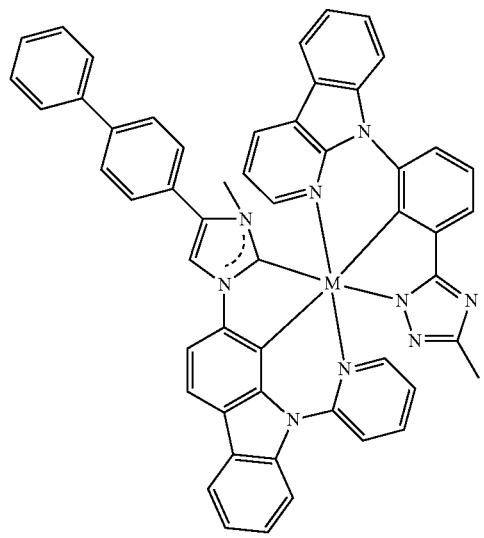
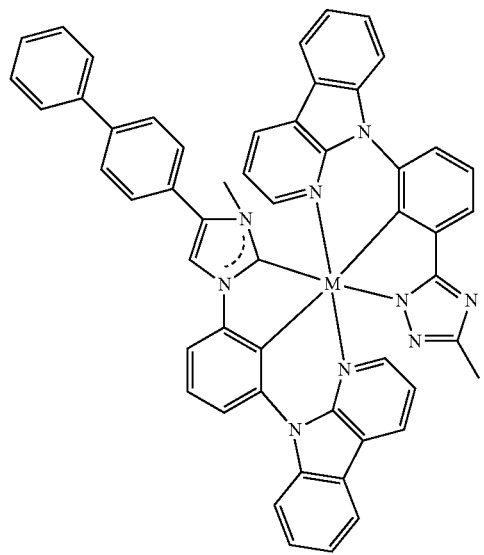

231
-continued
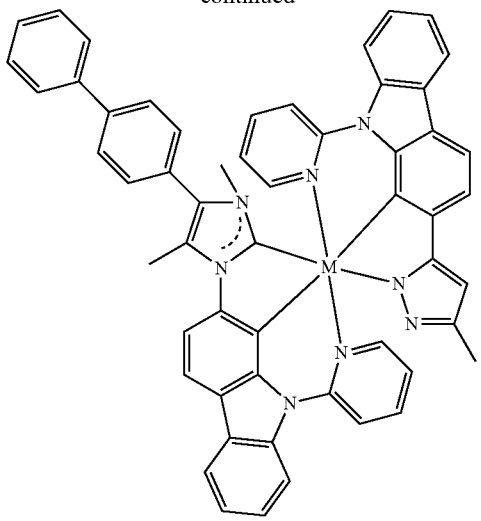
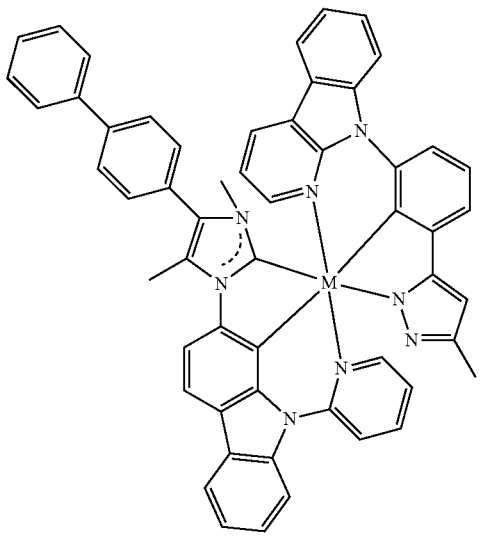
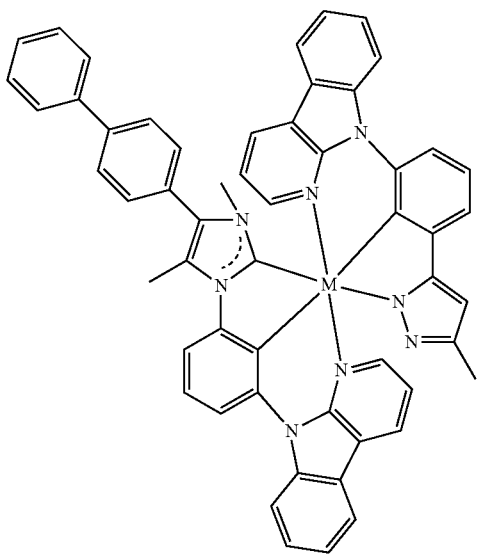
232
-continued
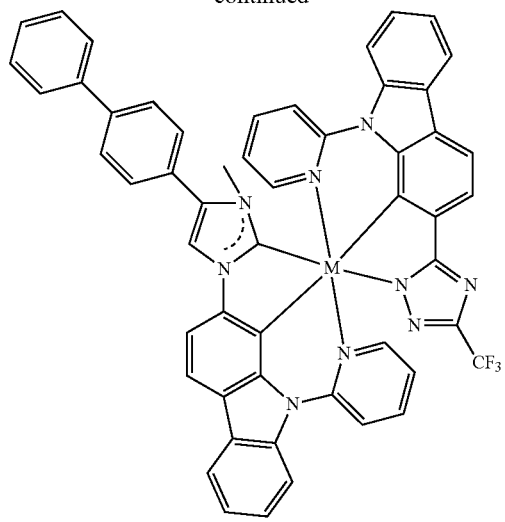
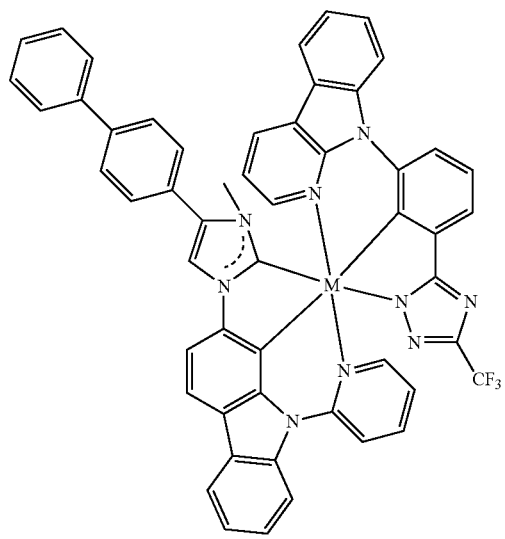
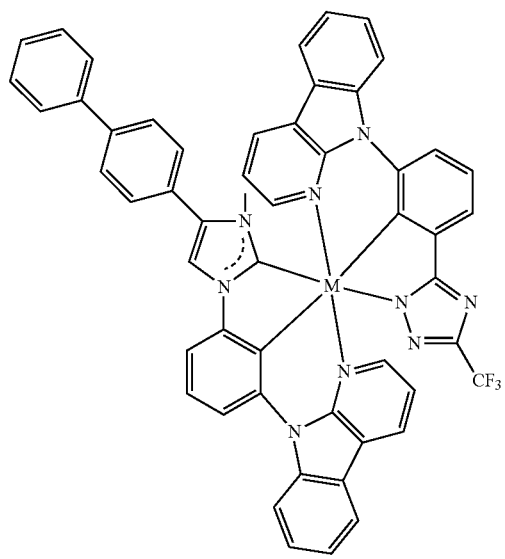

Structures M-5 (M = Ir, Rh)
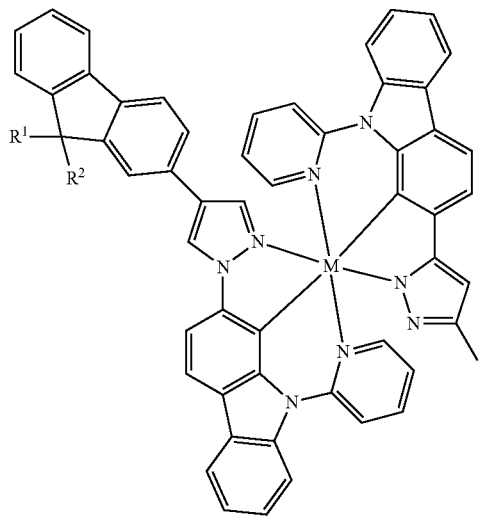
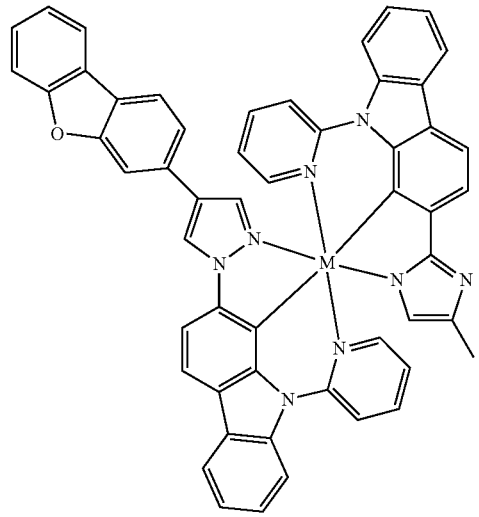
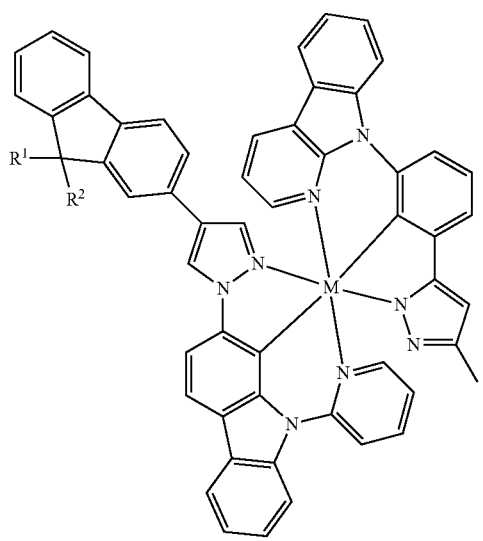
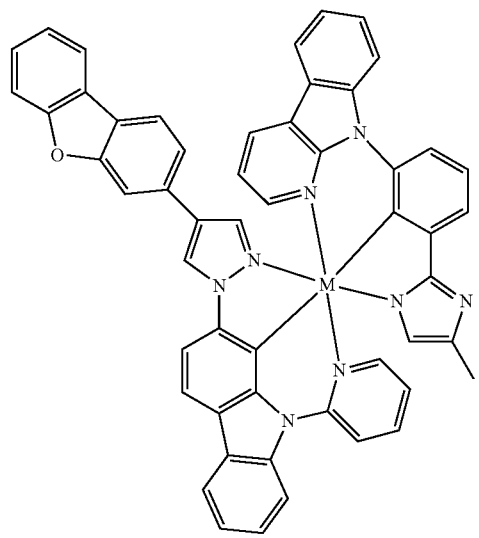
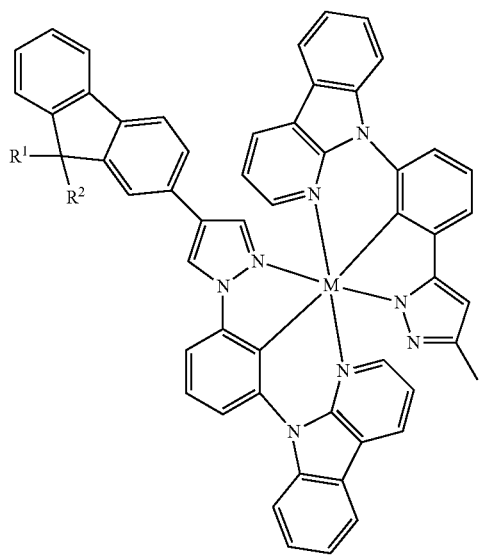
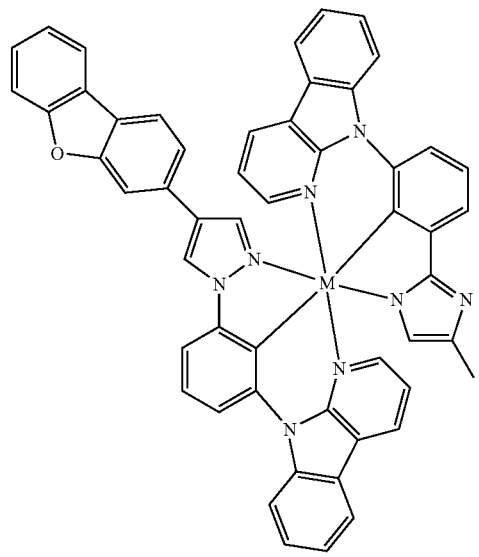

235
-continued
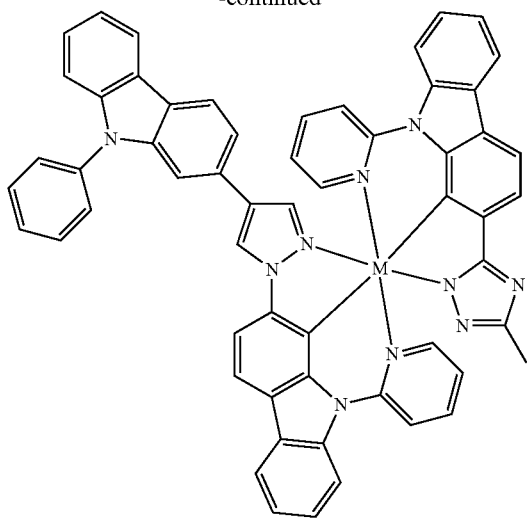
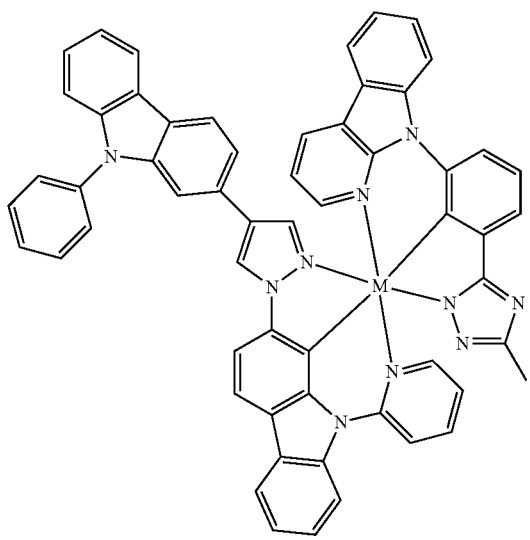
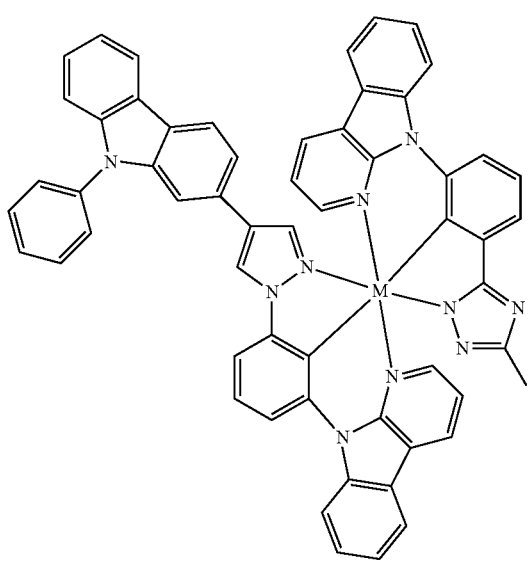
236
-continued
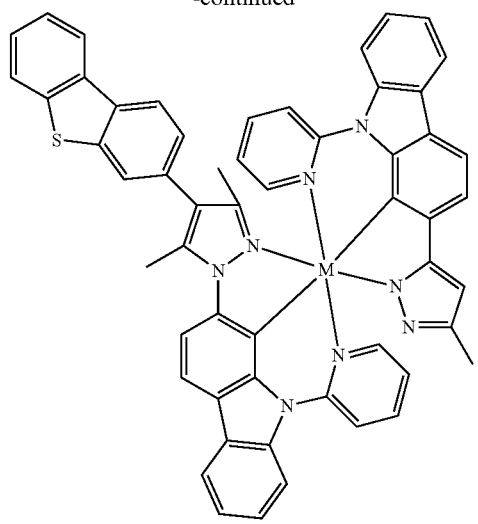
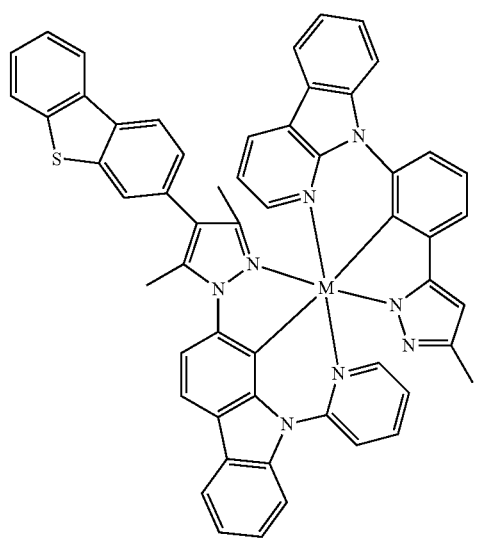
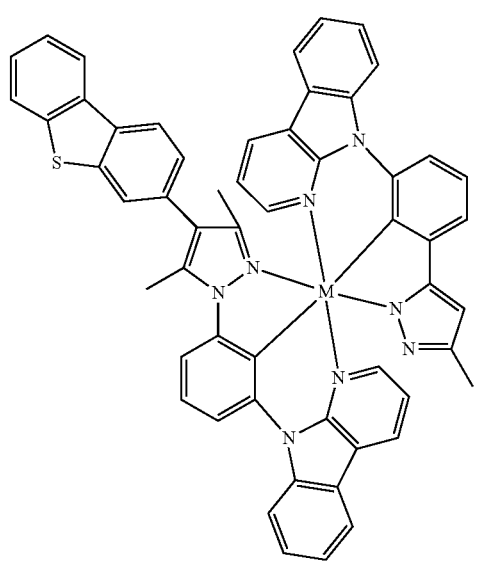

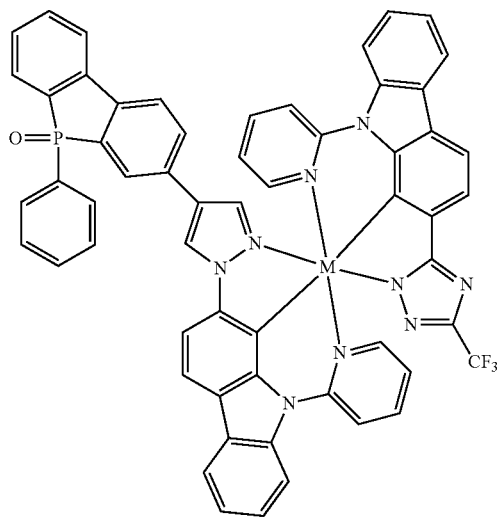
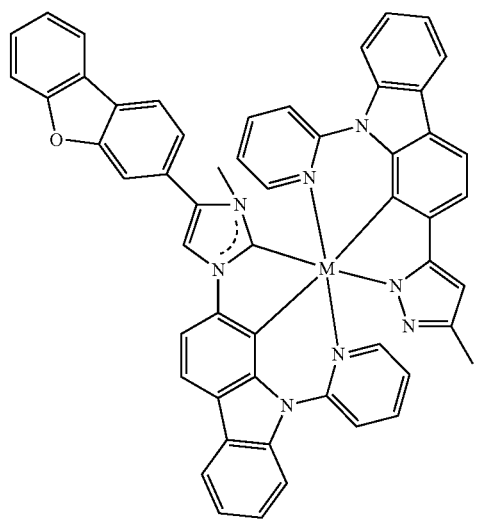
Structures M-6 (M = Ir, Rh)
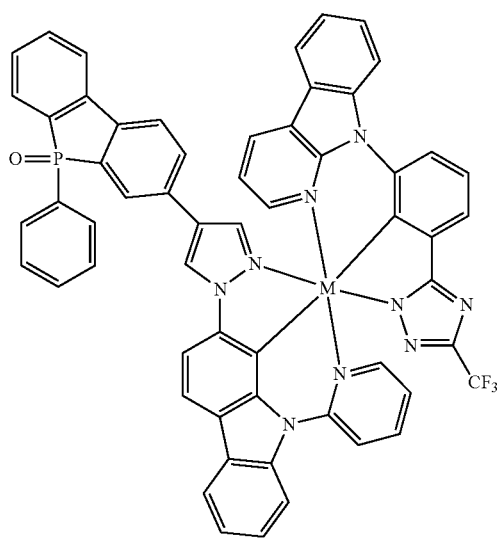
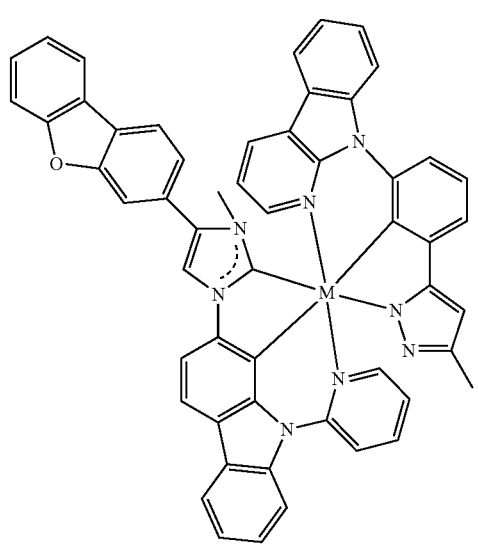
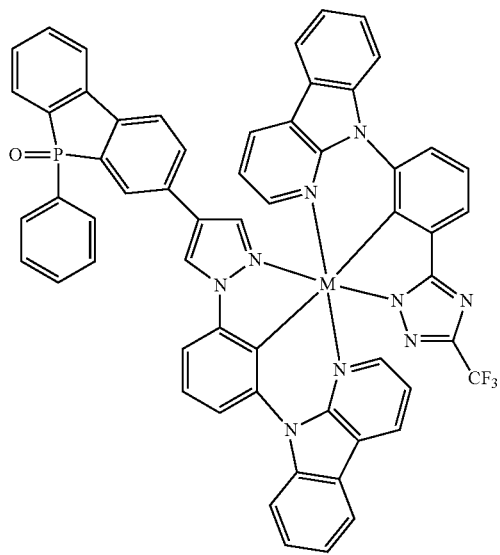
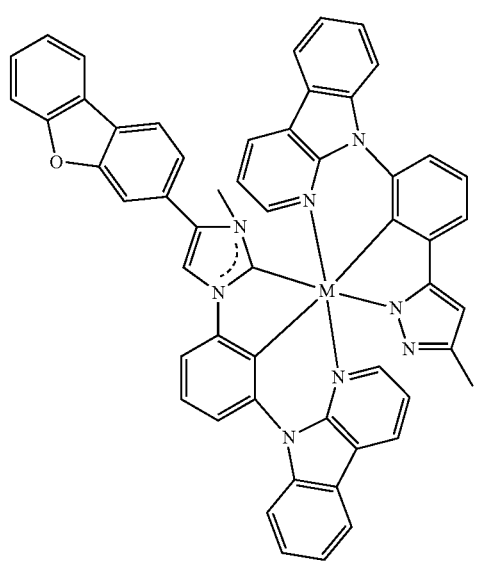

239
-continued
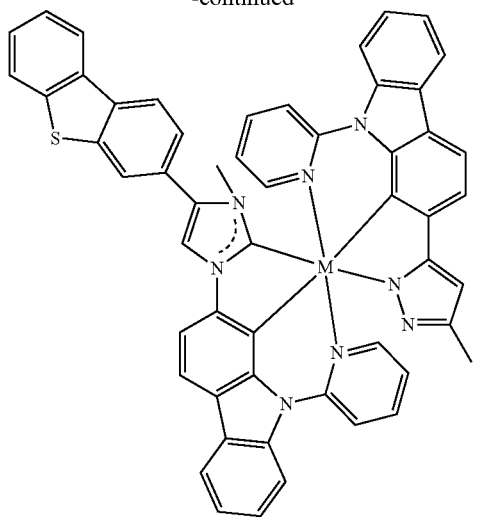
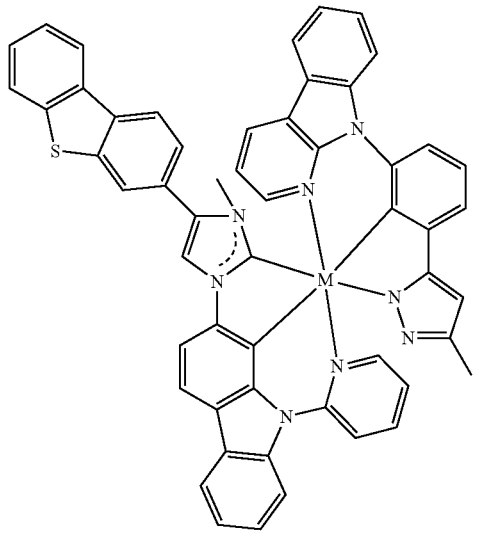
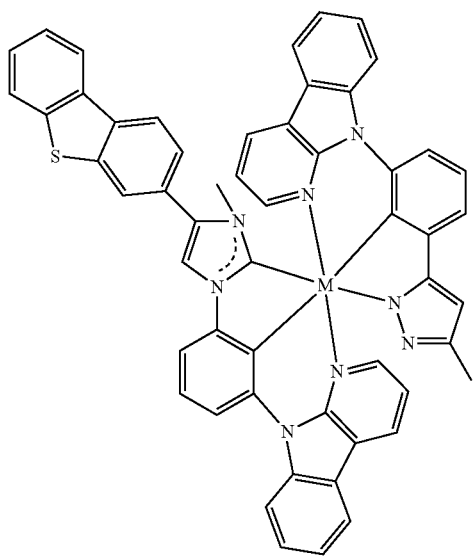
240
-continued
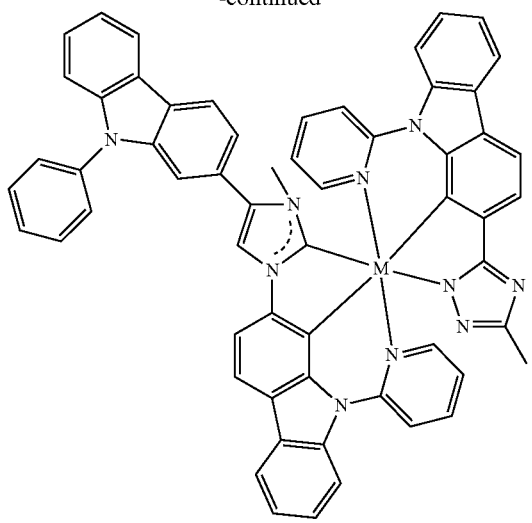

241
-continued
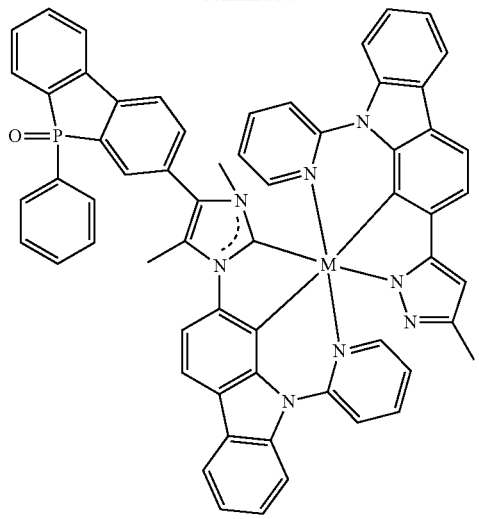
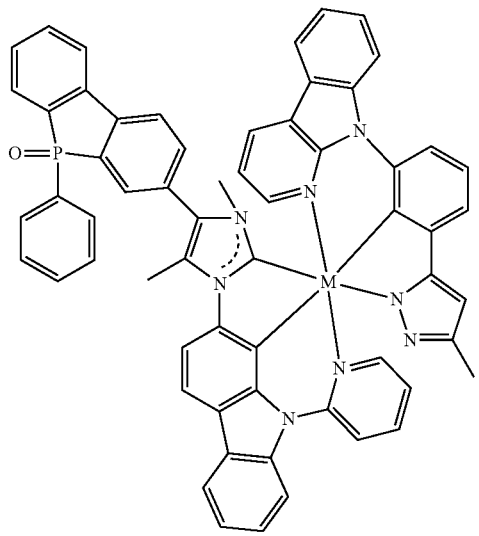
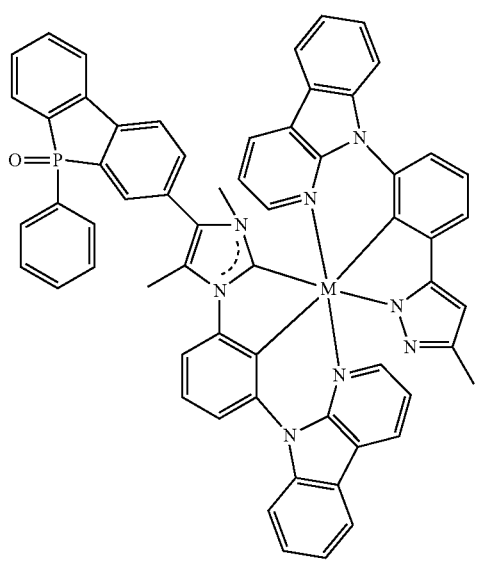
242
-continued
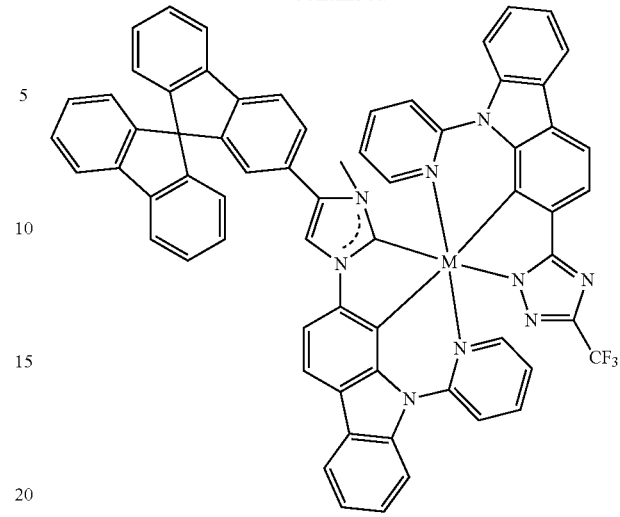
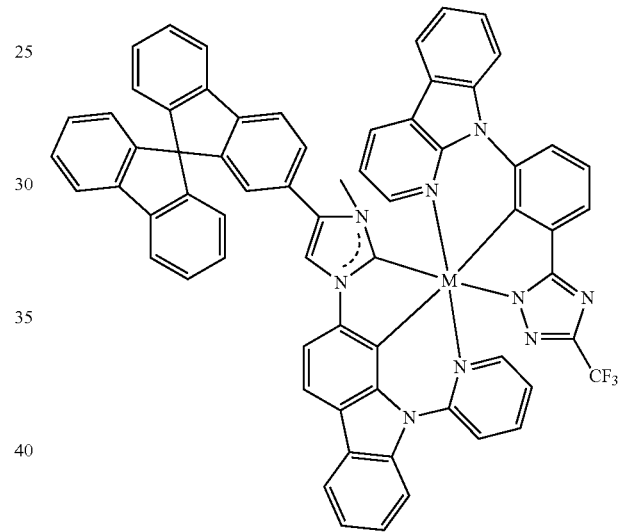

-continued
Structures M-7 (M = Ir, Rh)
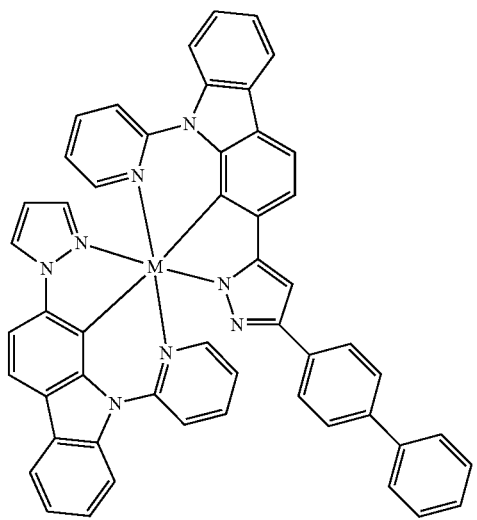
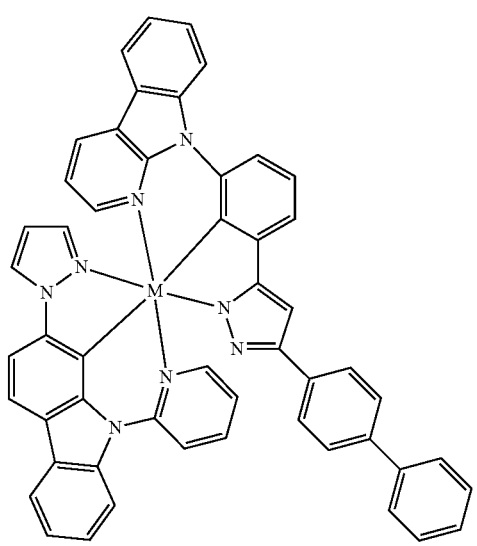
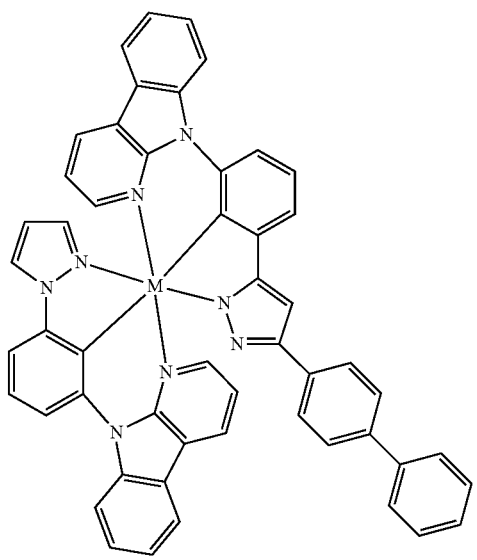
-continued
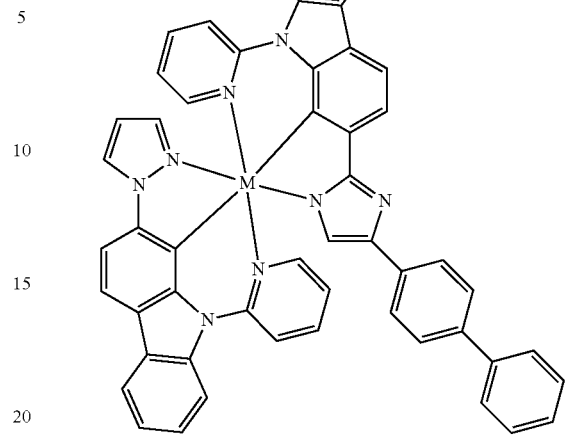
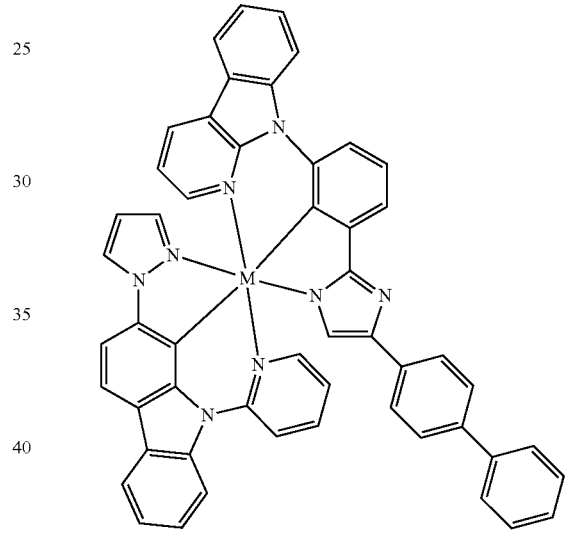
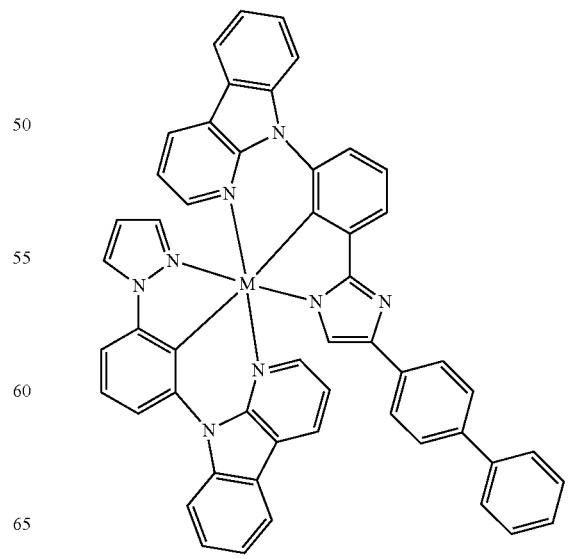

245 -continued
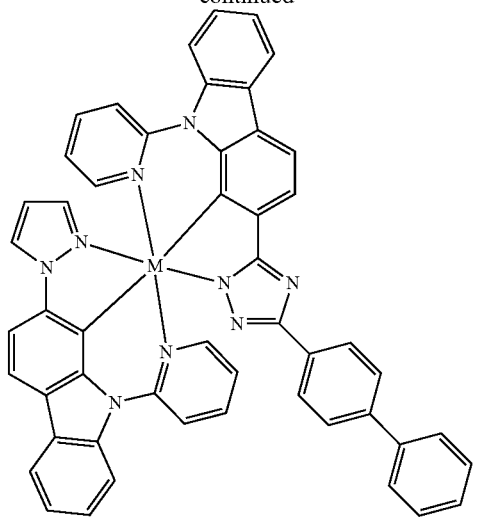
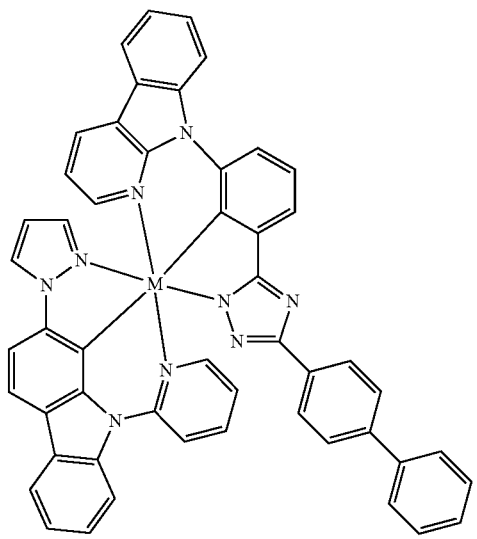
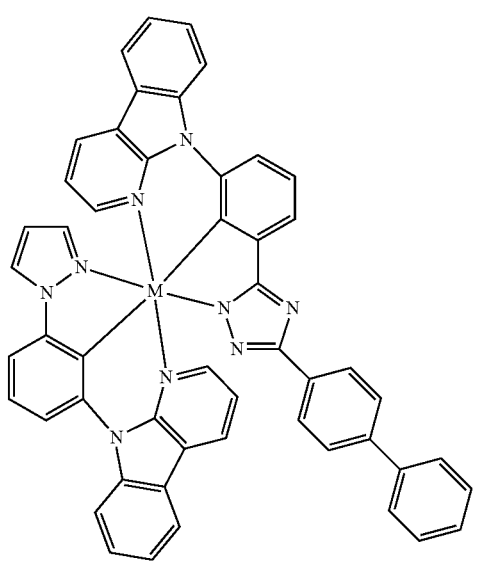
246 -continued
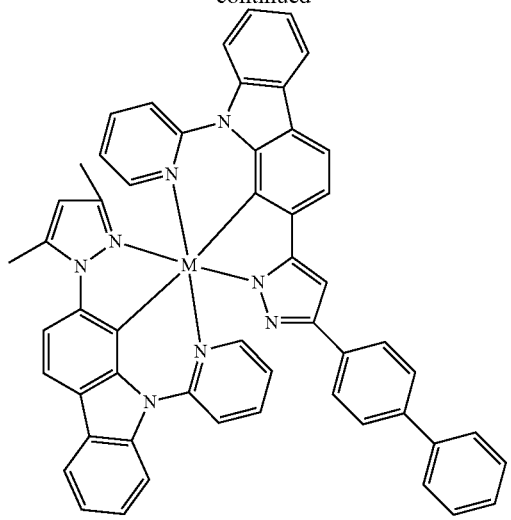
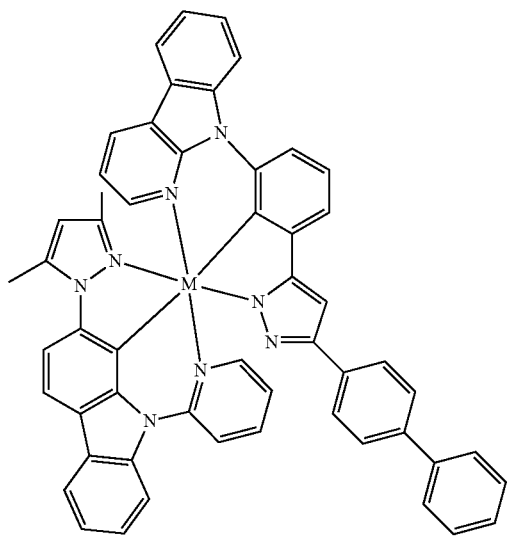
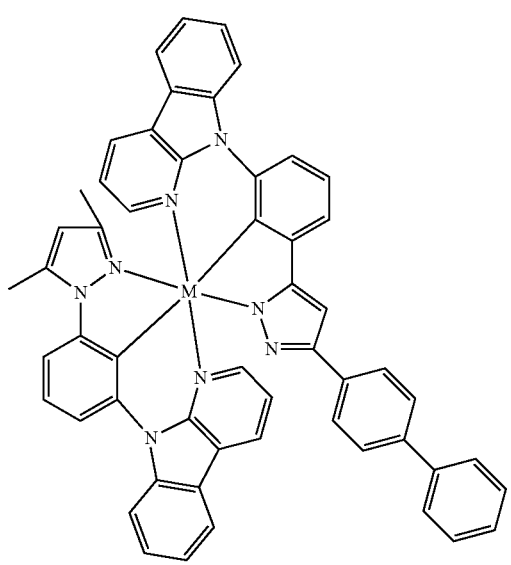

247
-continued
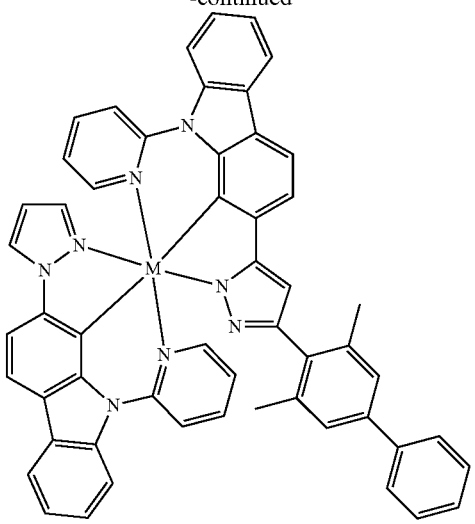
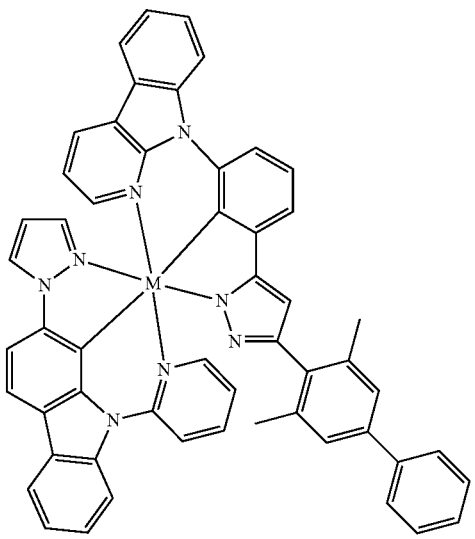
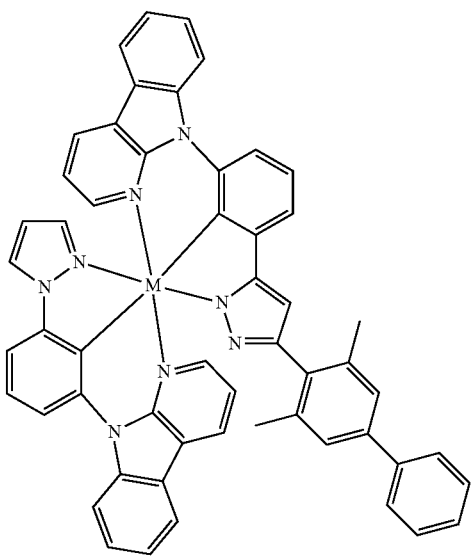
248
-continued
Structures M-8 (M = Ir, Rh)
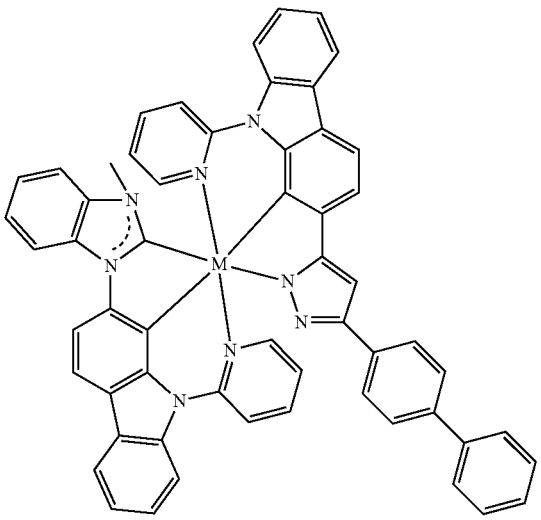
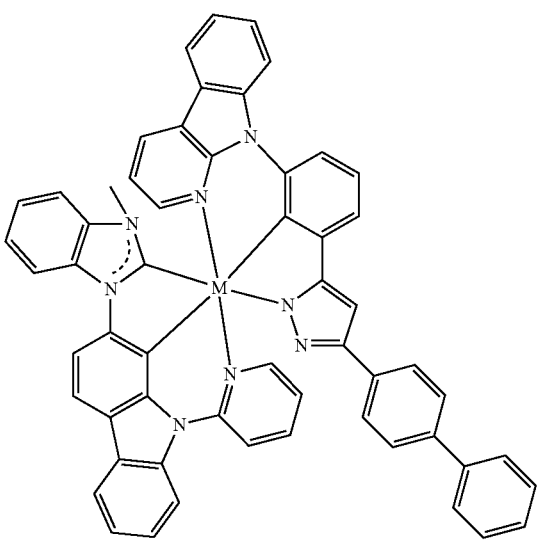
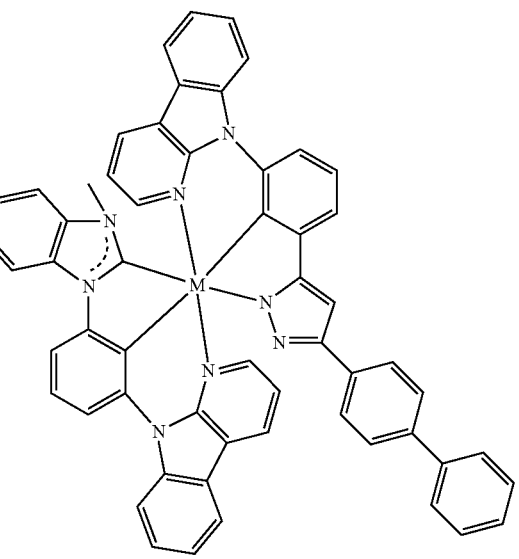

249
-continued
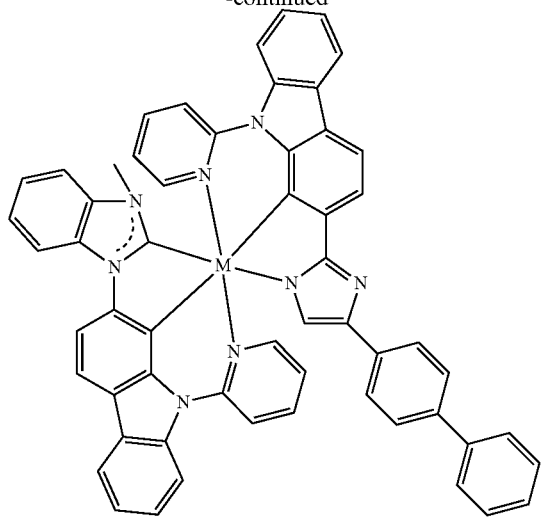
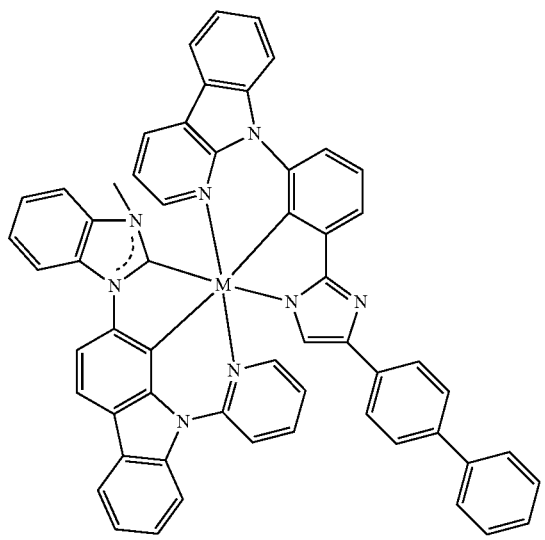
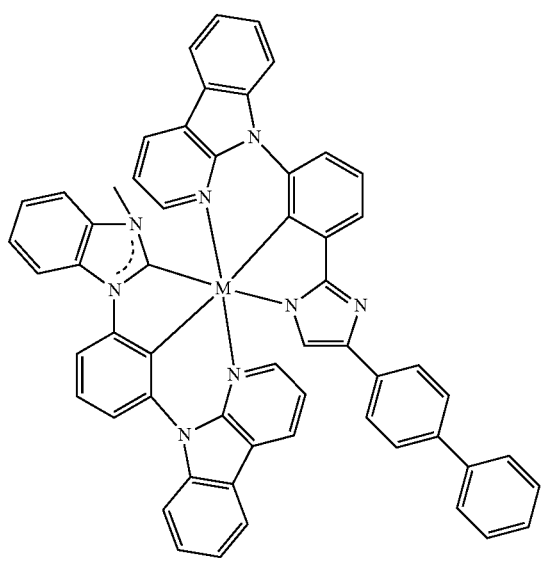
250
-continued
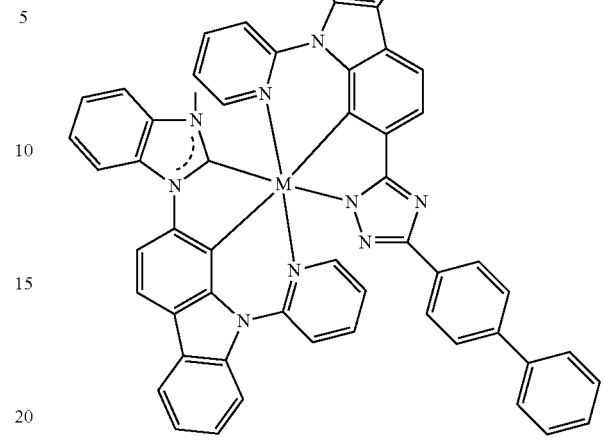
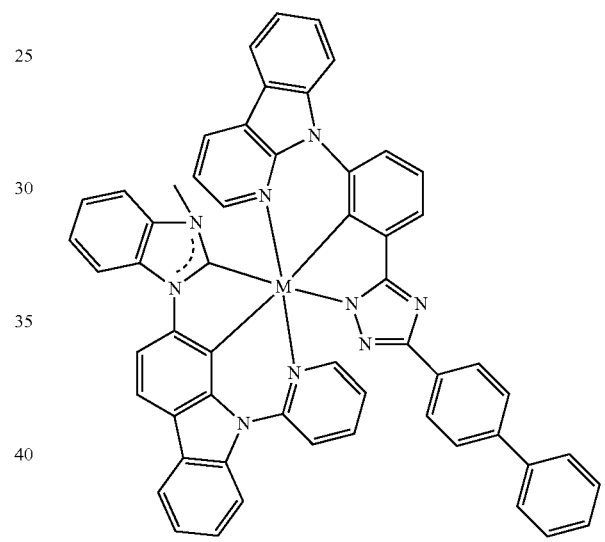
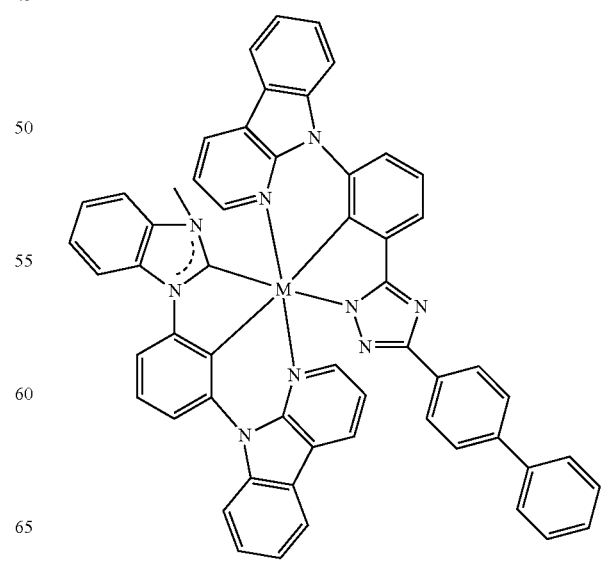

251
-continued
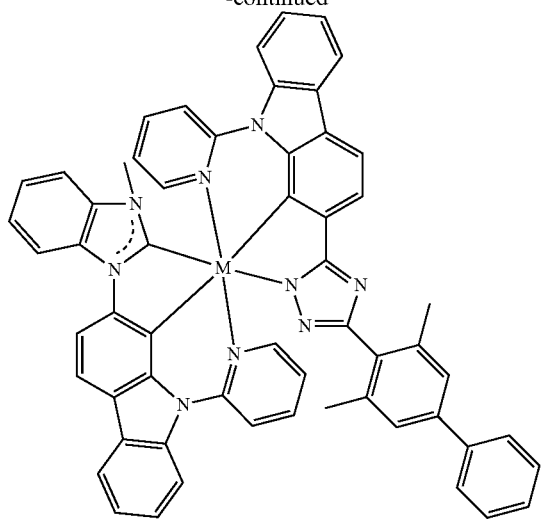
252
-continued
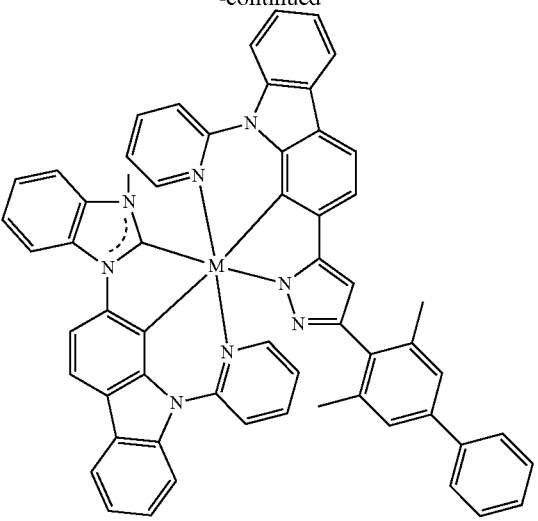
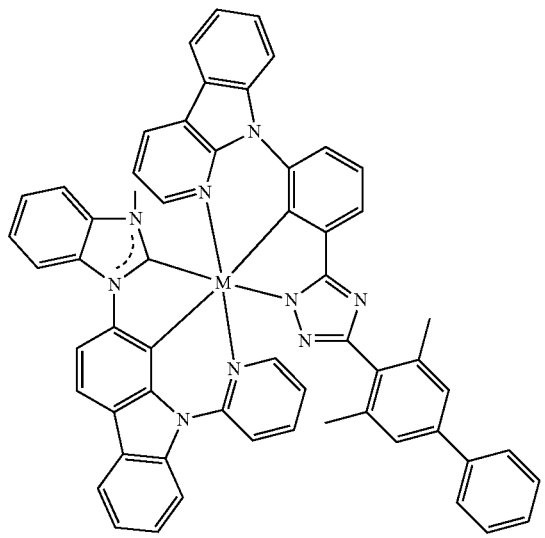
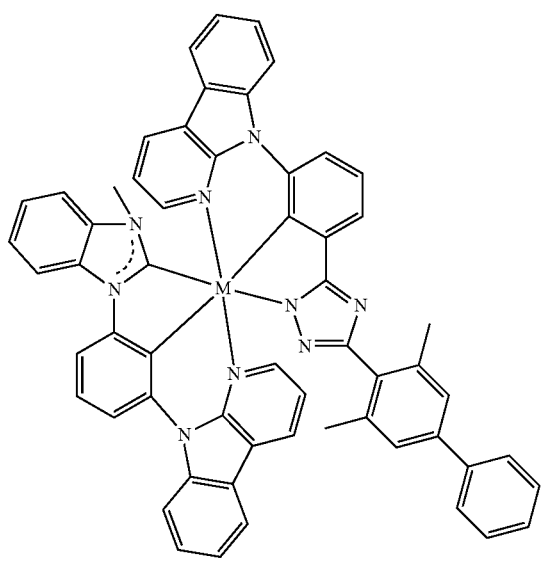
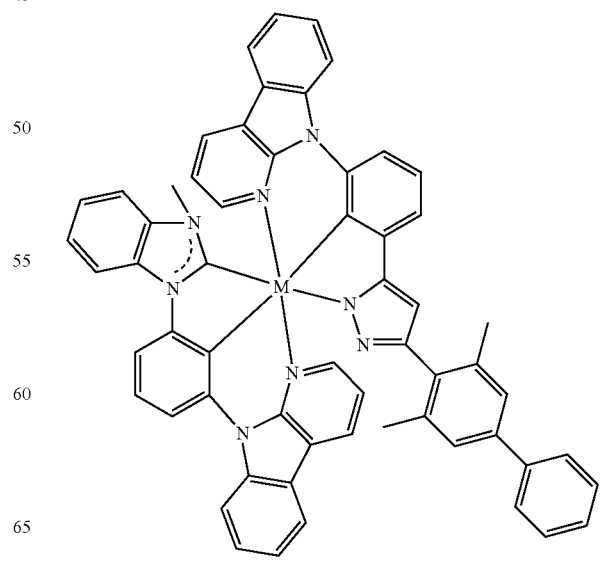

Structures M-9 (M = Ir, Rh)
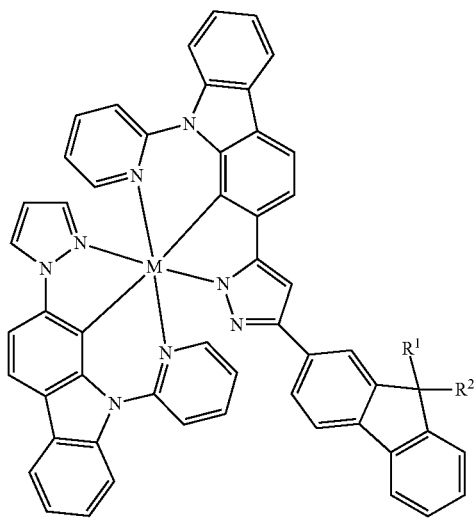
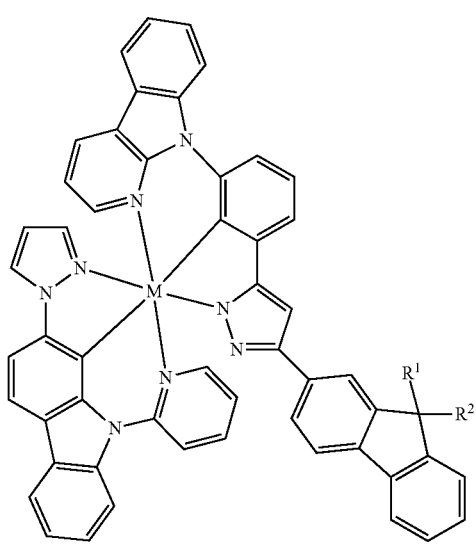
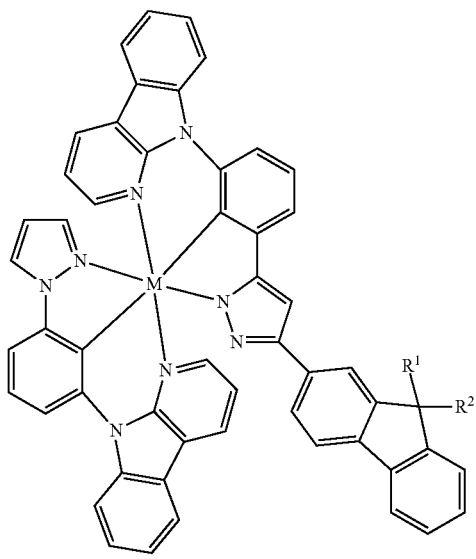
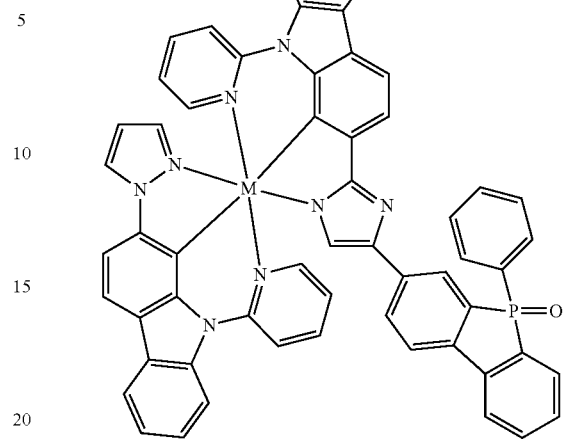
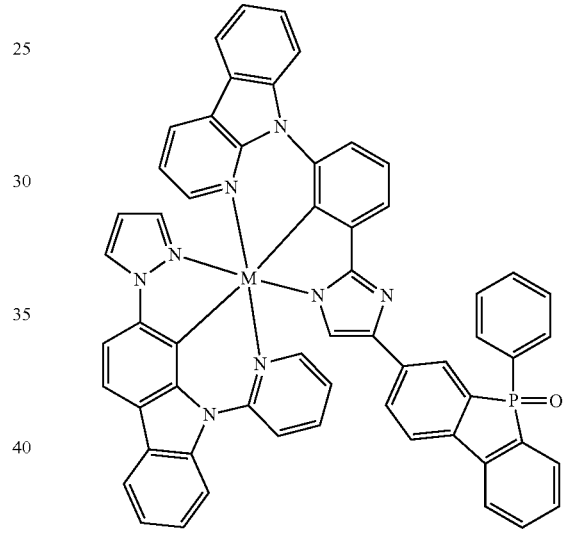
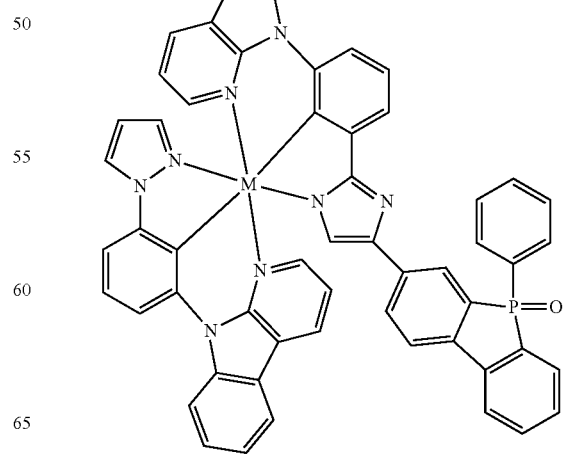

255
-continued
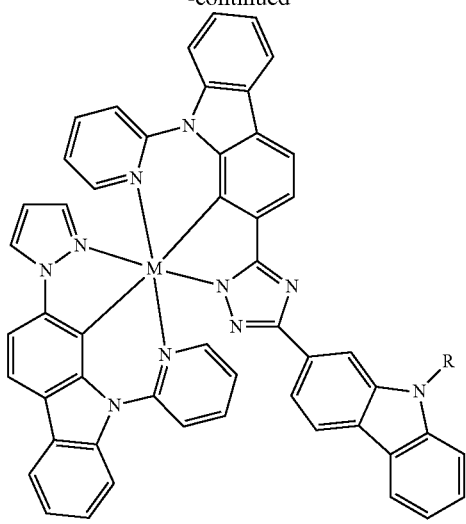
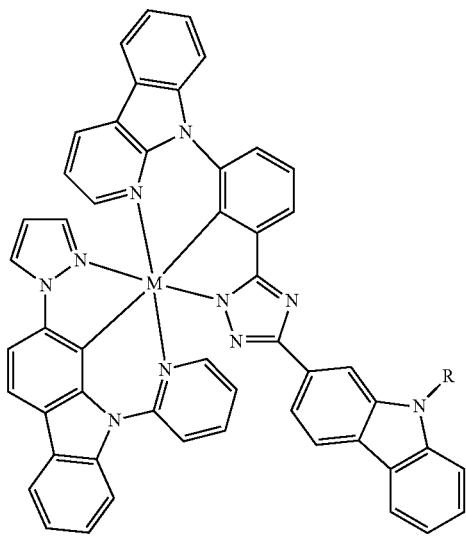
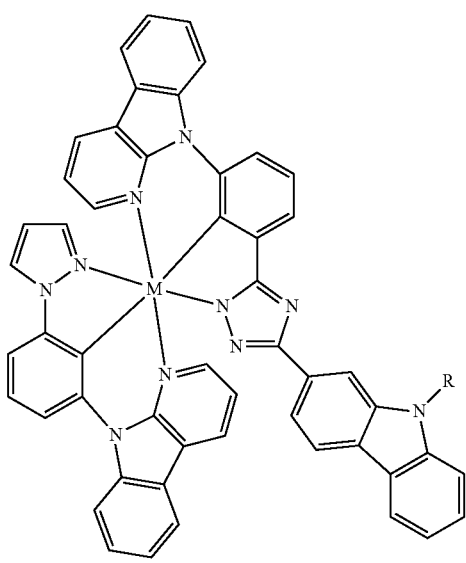
256
-continued
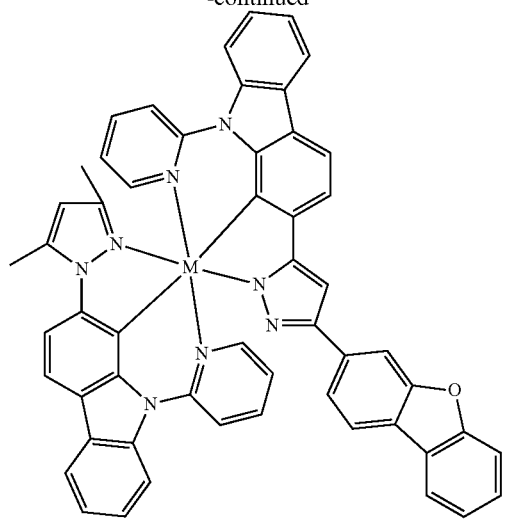
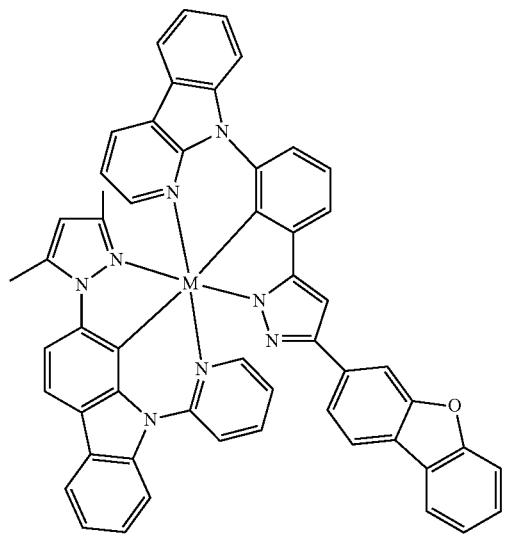
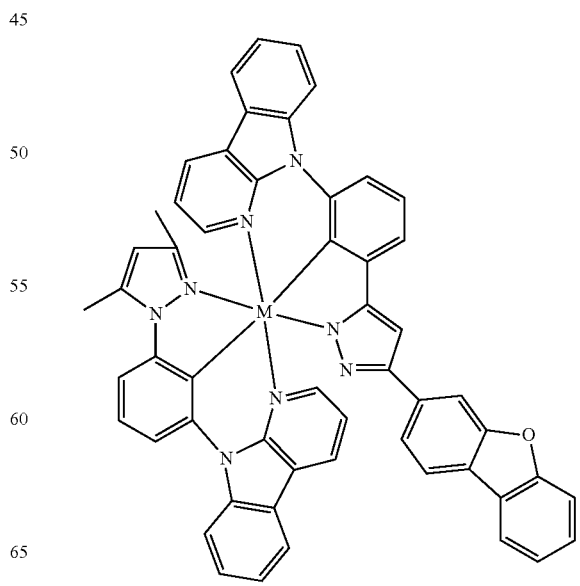

-continued
Structures M-10 (M = Ir, Rh)
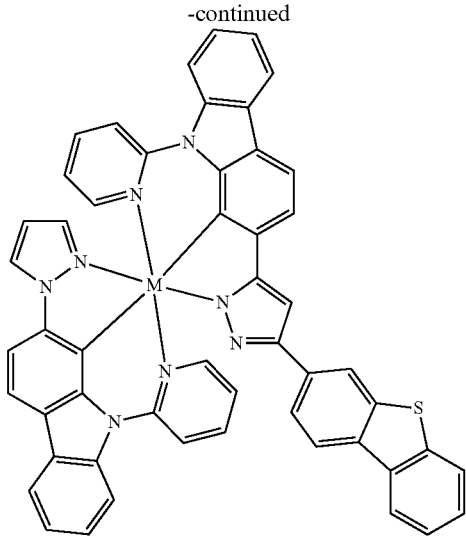
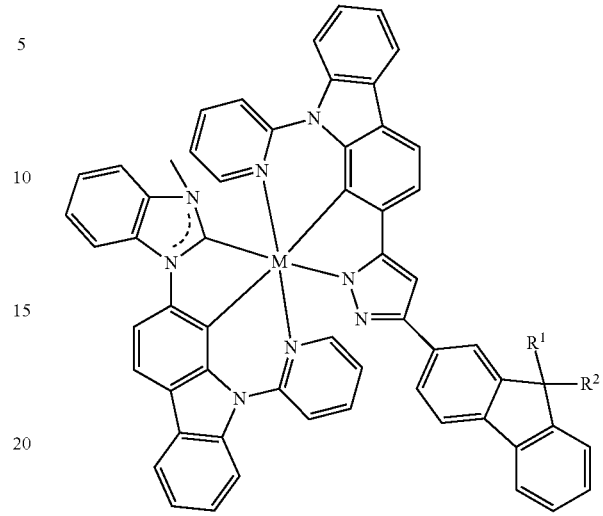
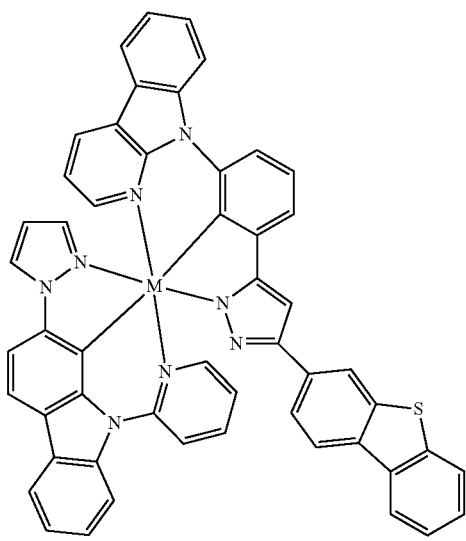
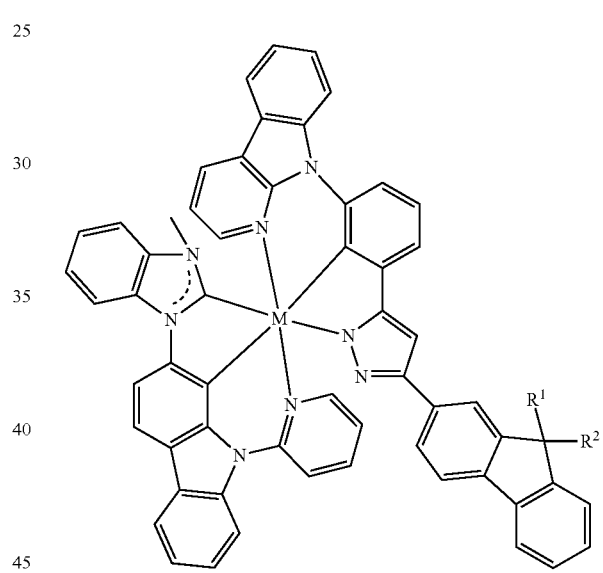
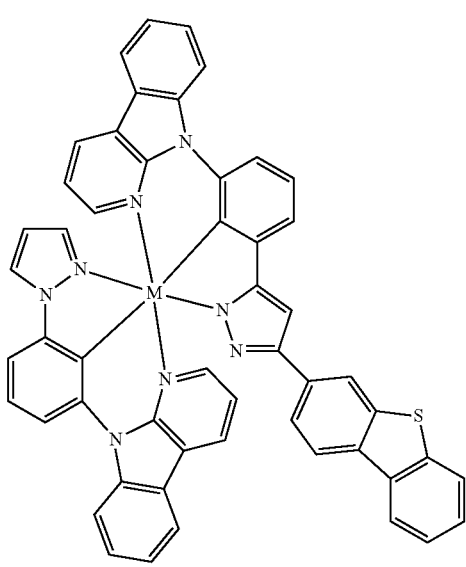
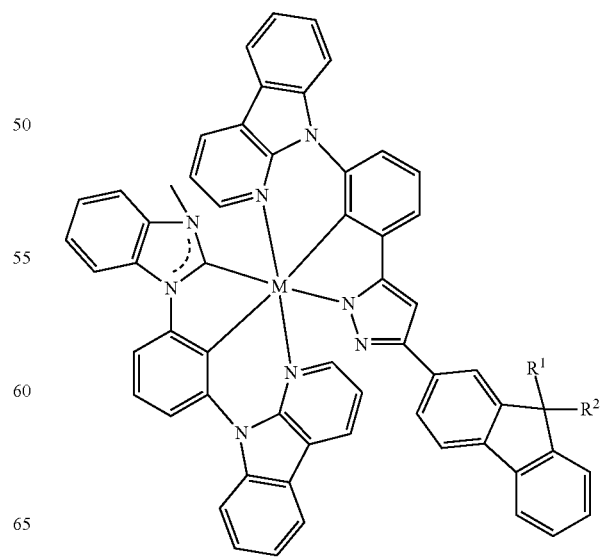

259
-continued
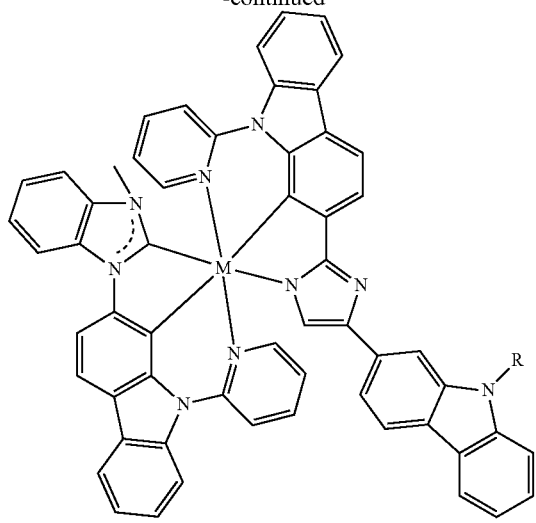
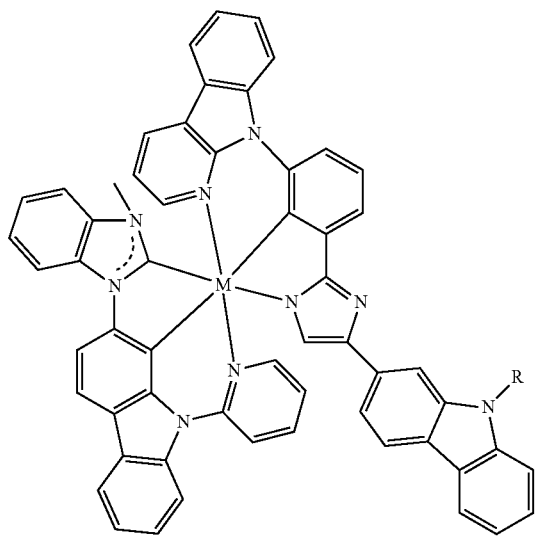
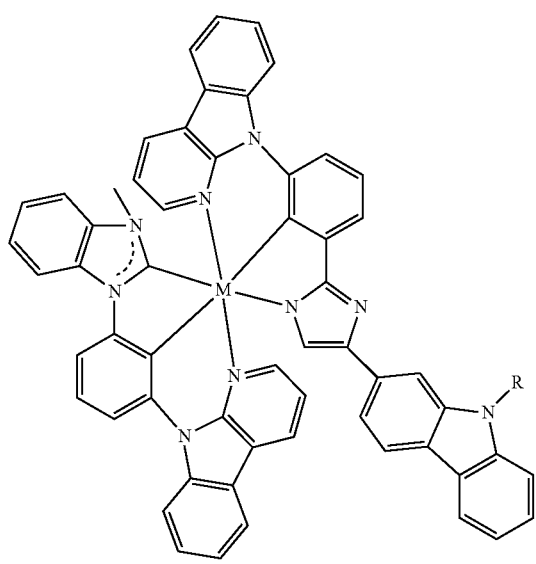
260
-continued
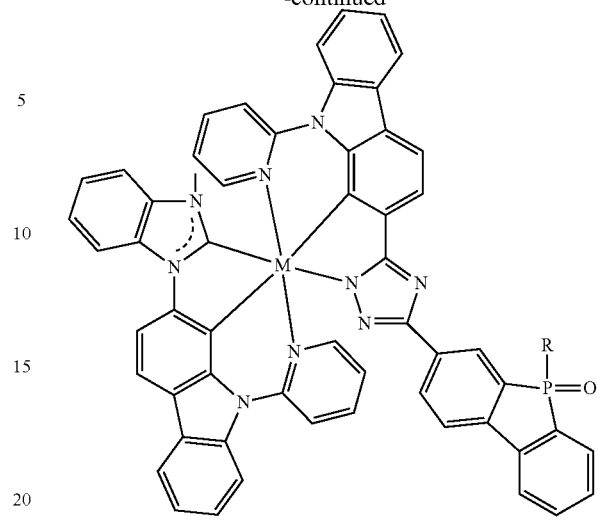
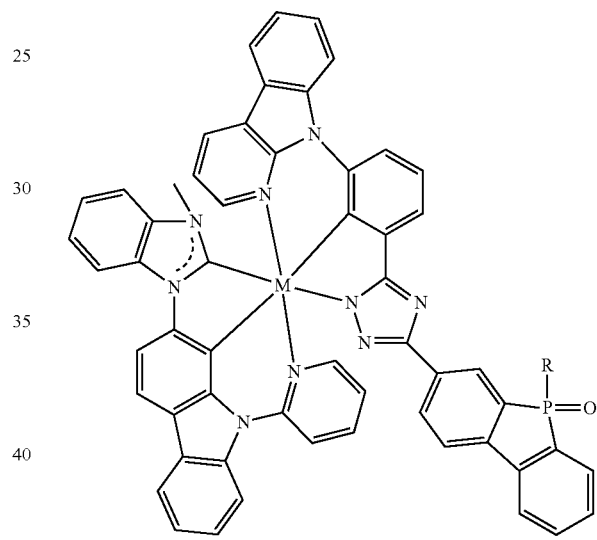
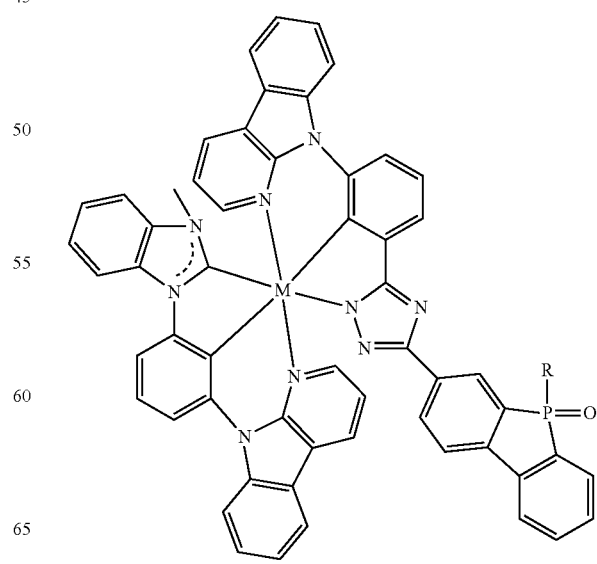

261
-continued
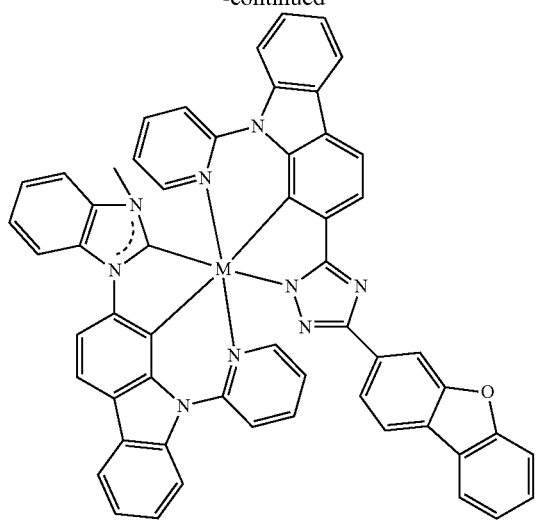
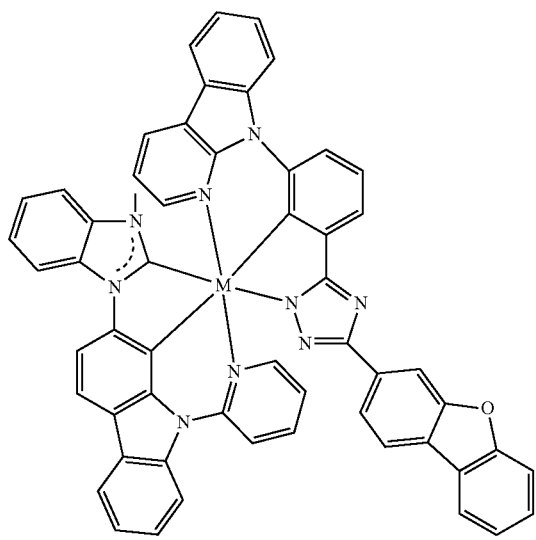
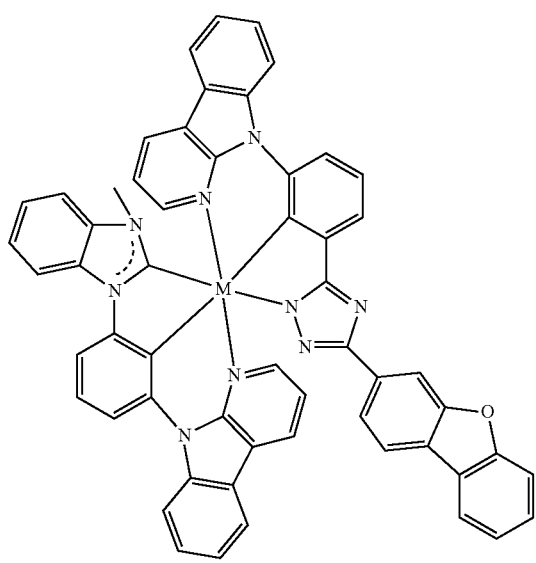
262
-continued
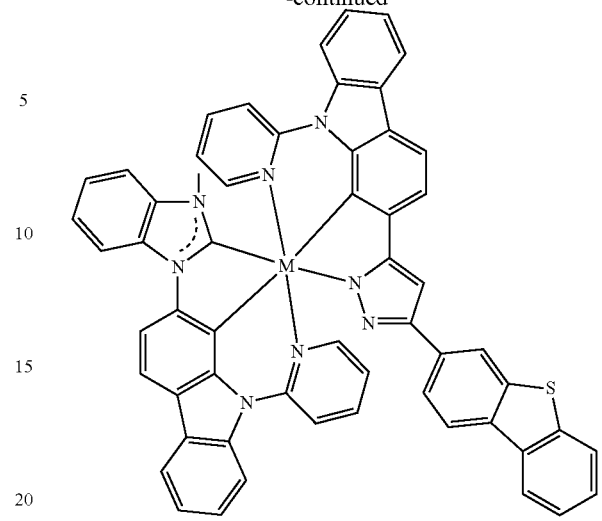
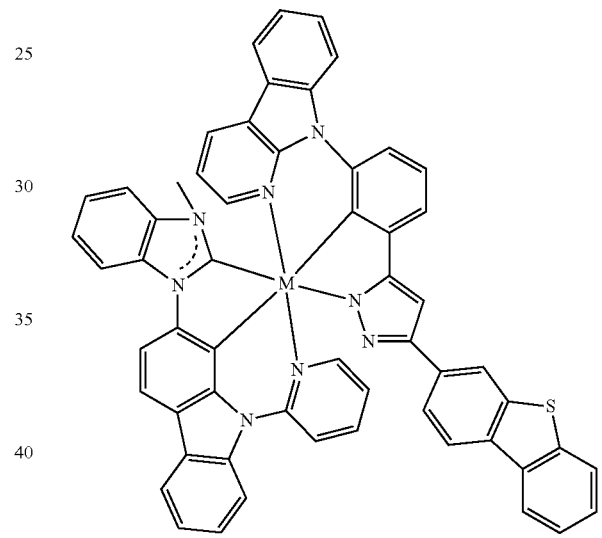
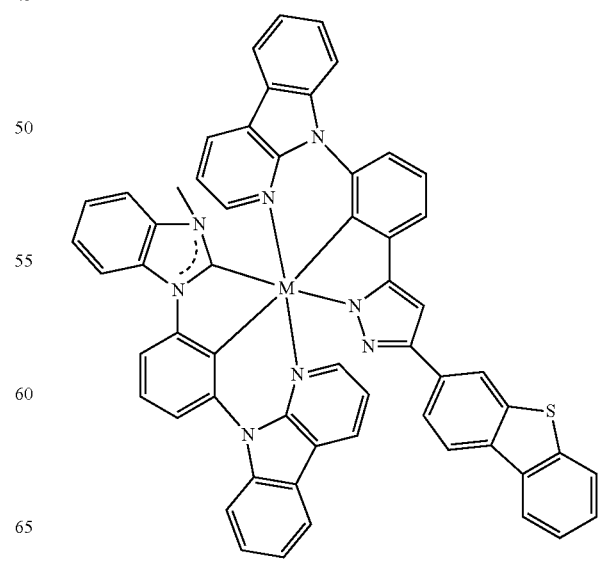

Structures M-11 (M = Ir, Rh)
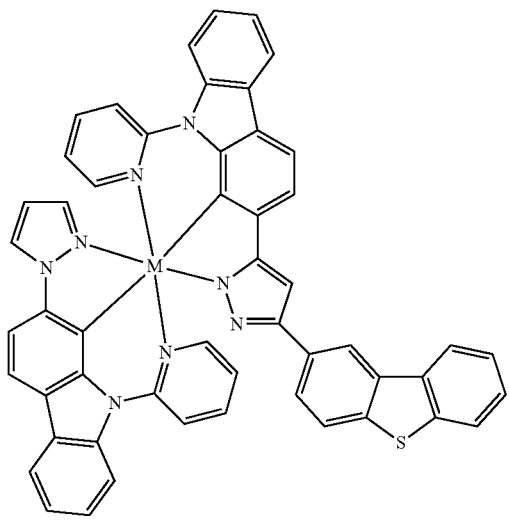
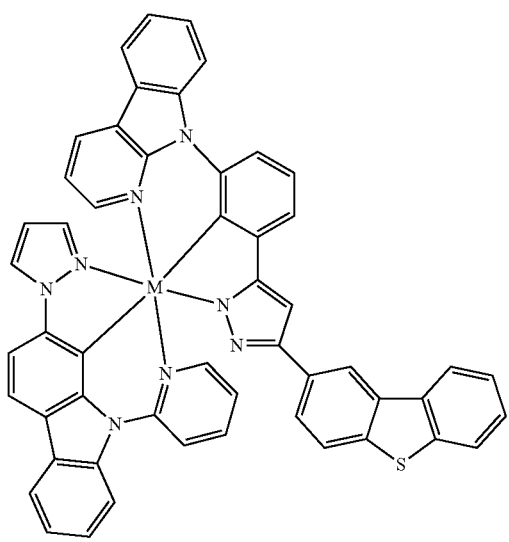
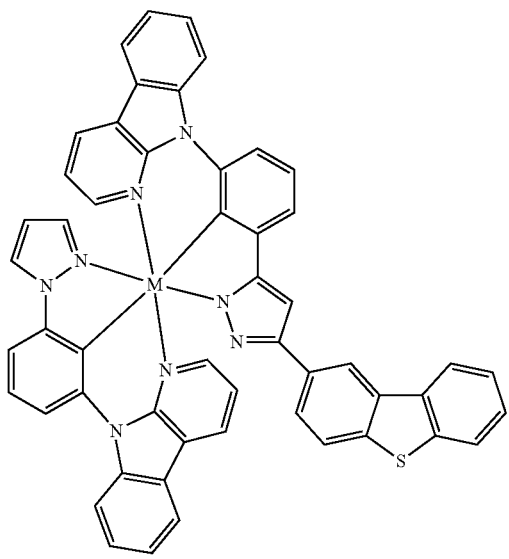
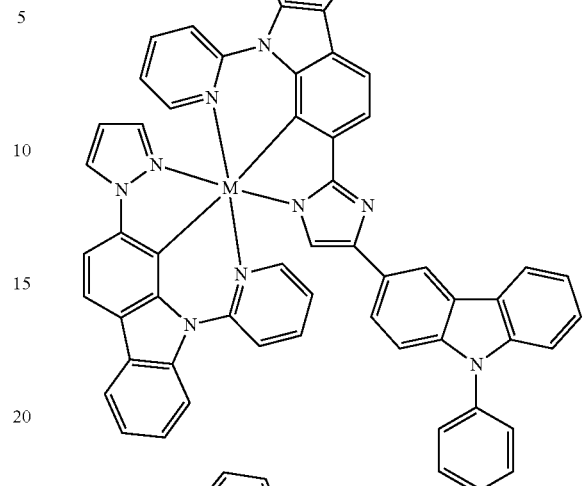
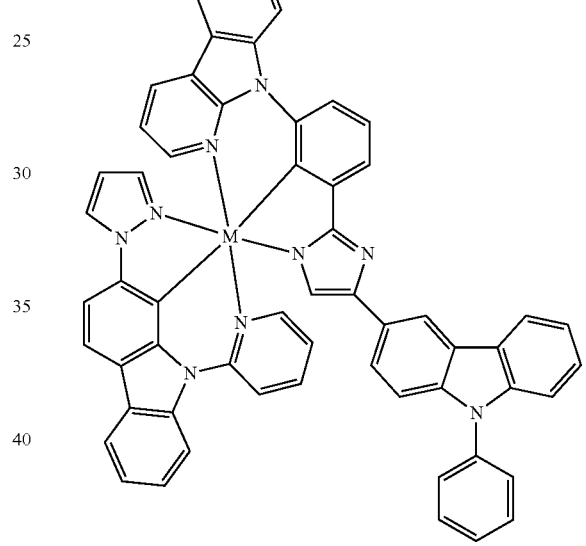
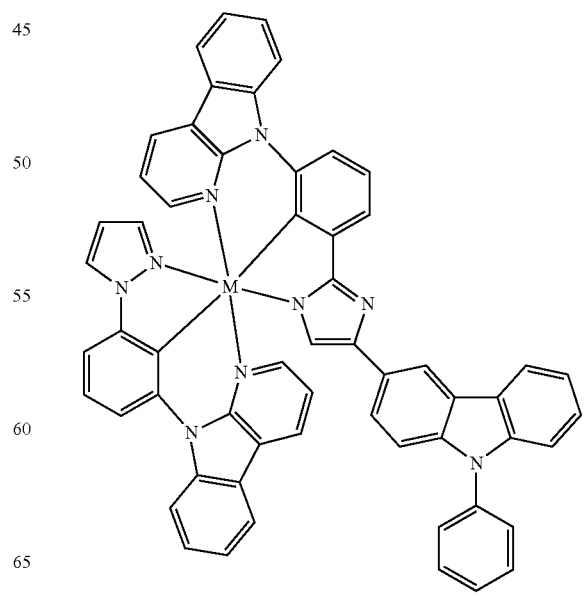

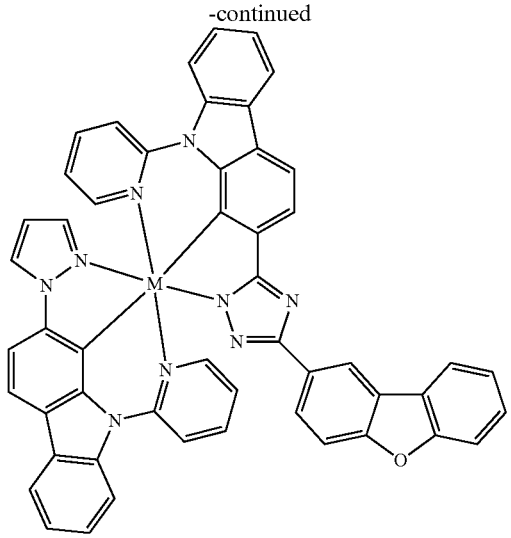
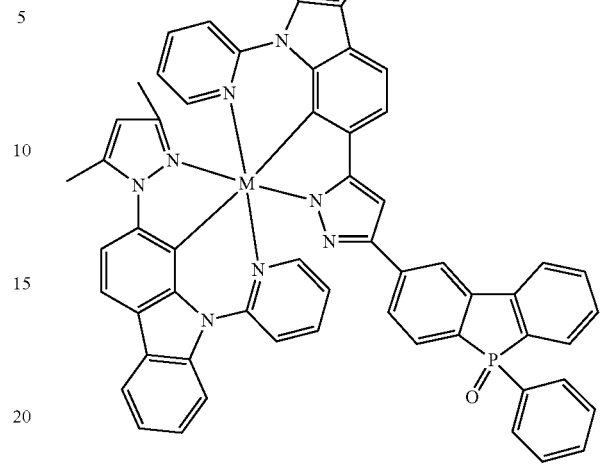
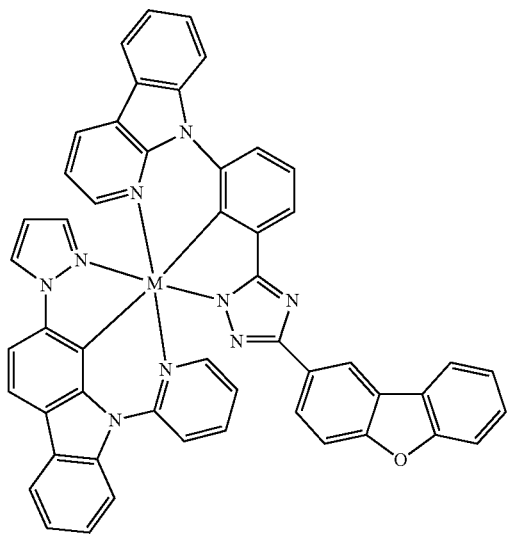
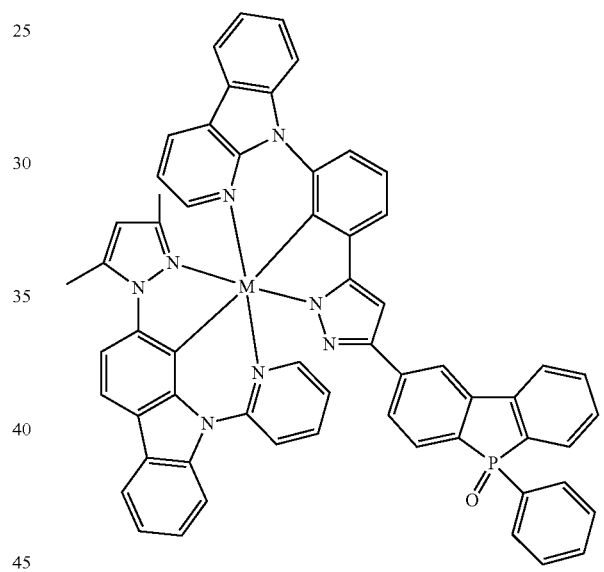
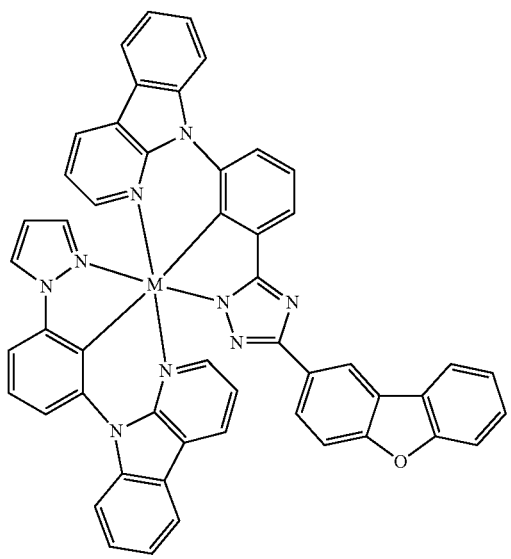
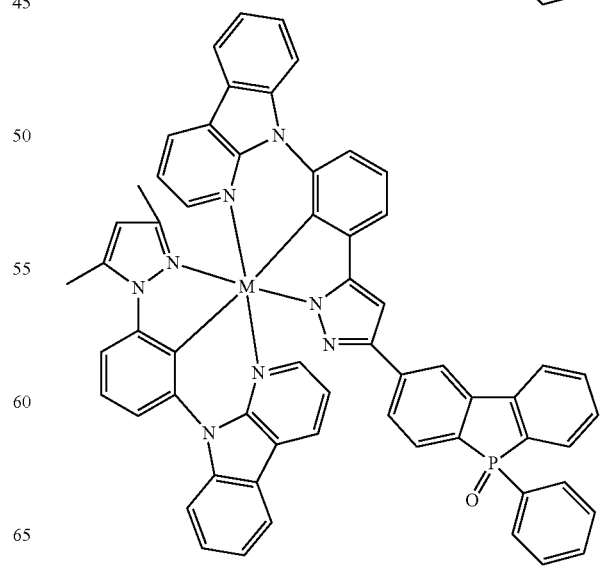

267
-continued
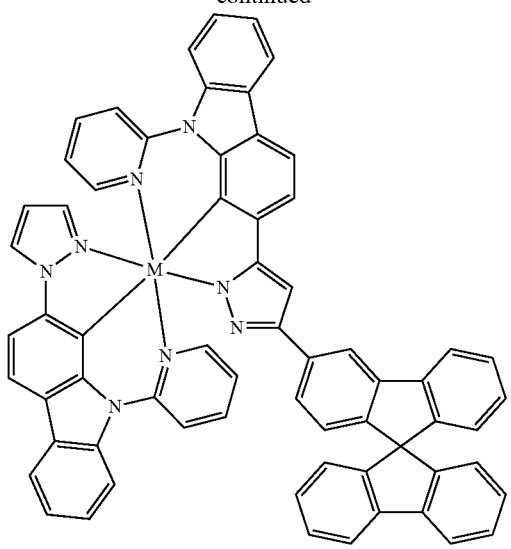
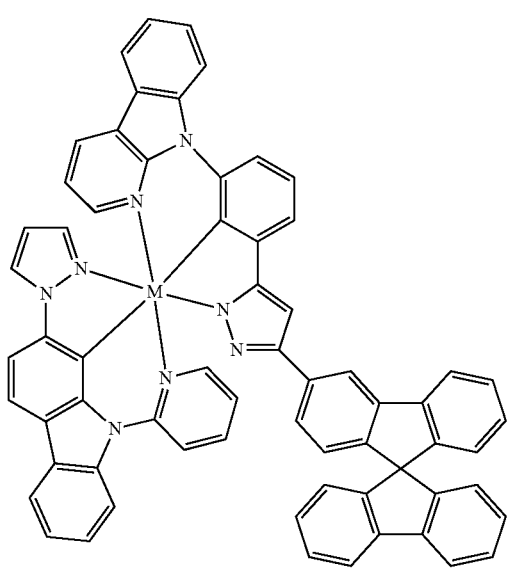
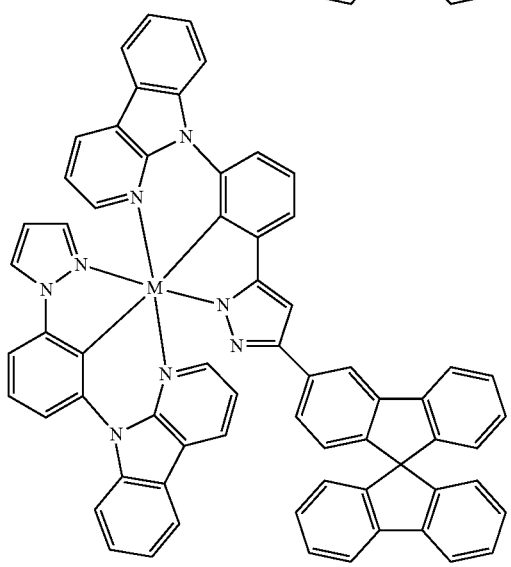
268
-continued
Structures M-12 (M = Ir, Rh)
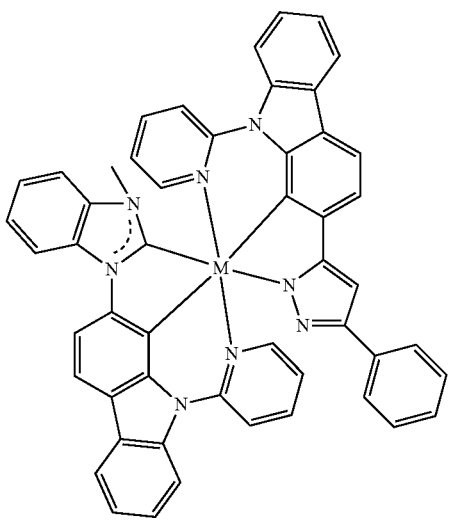
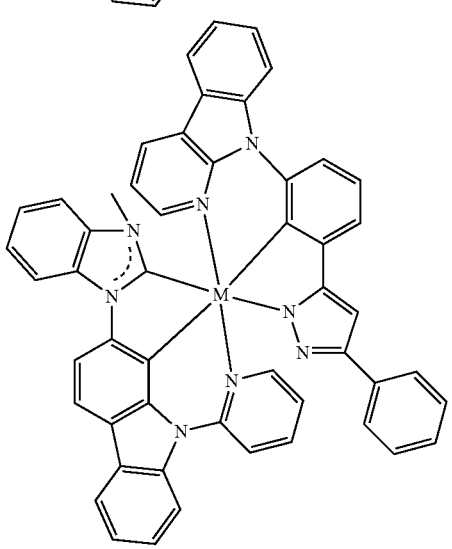
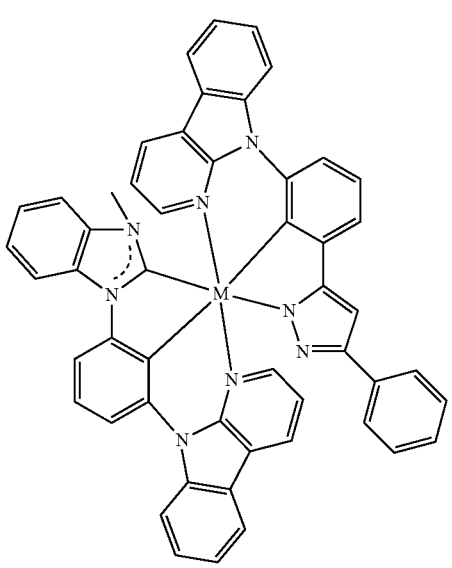

269
-continued
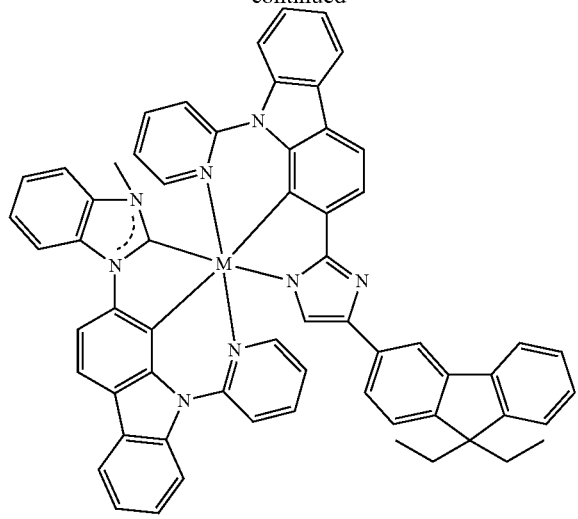
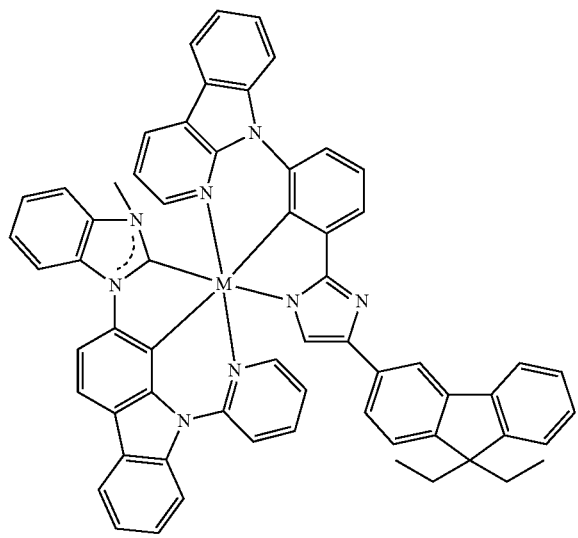
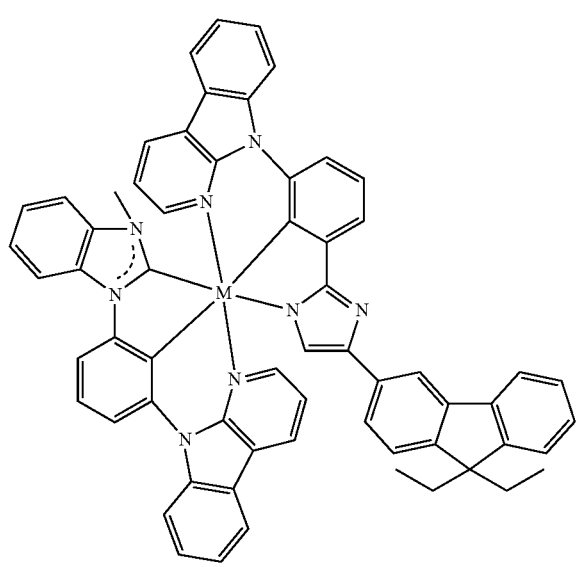
270
-continued
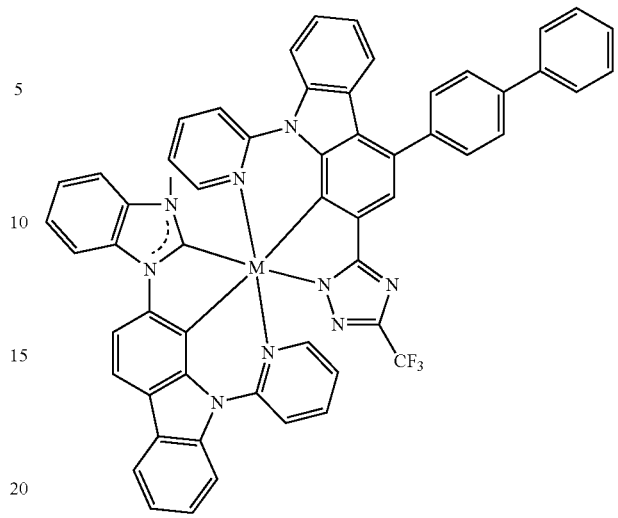
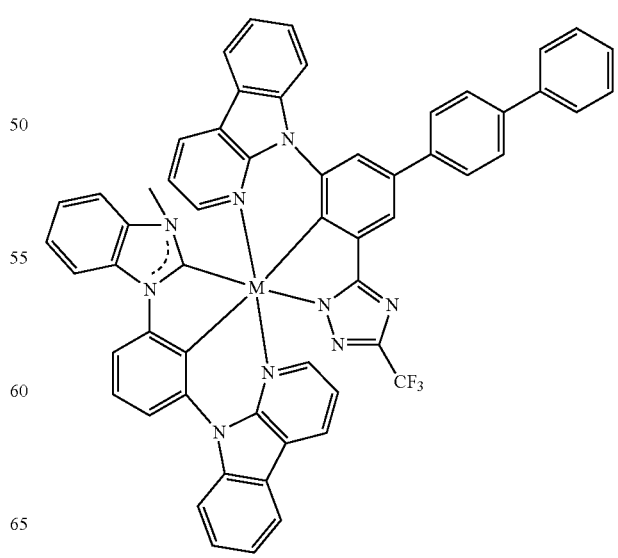

271
-continued
272
-continued
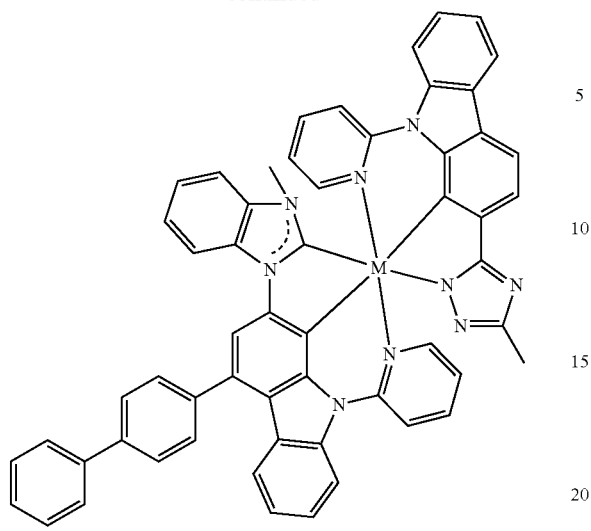
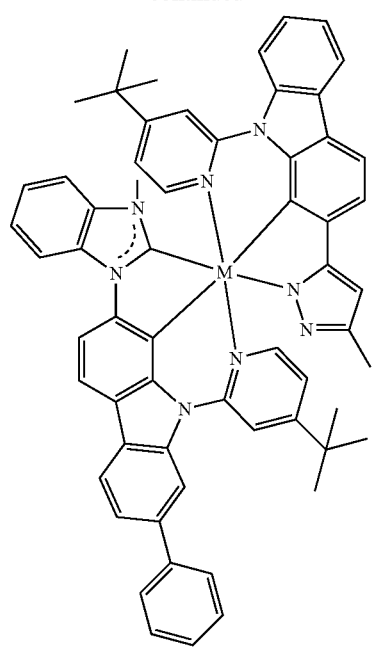
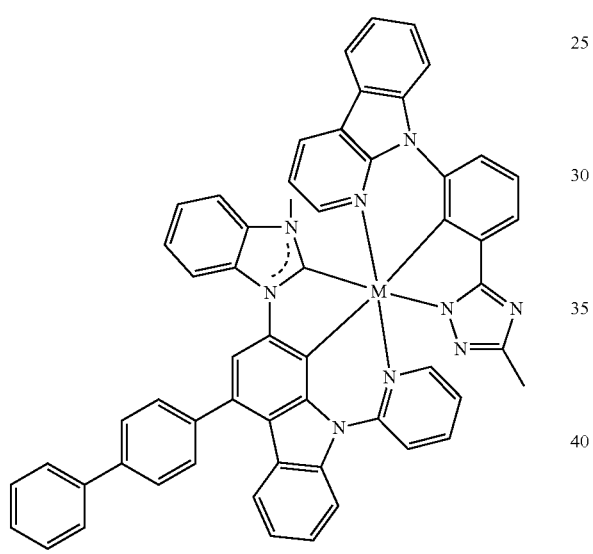
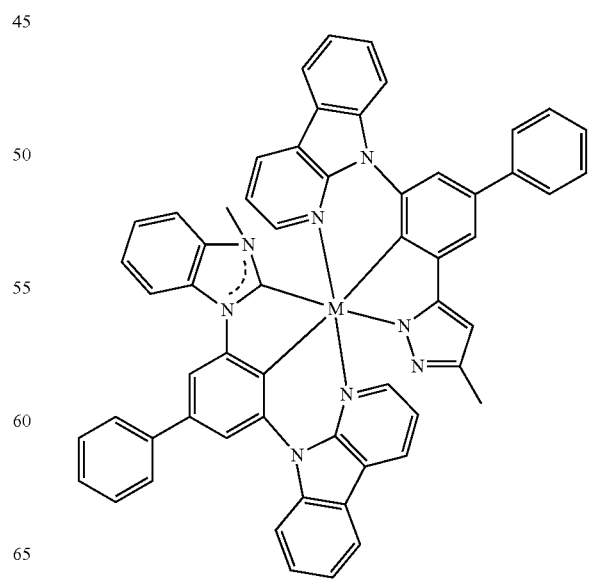

273
-continued
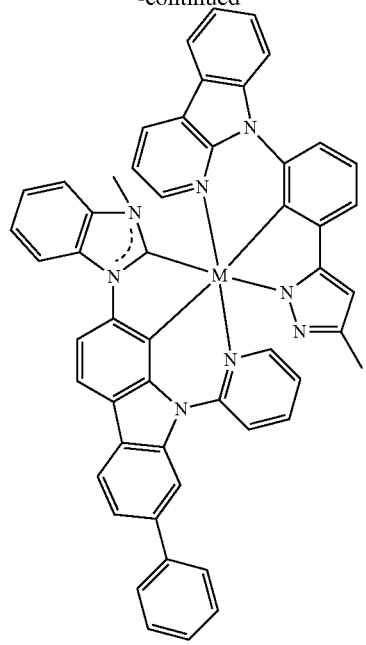
Structures M-13 (M = Ir, Rh)
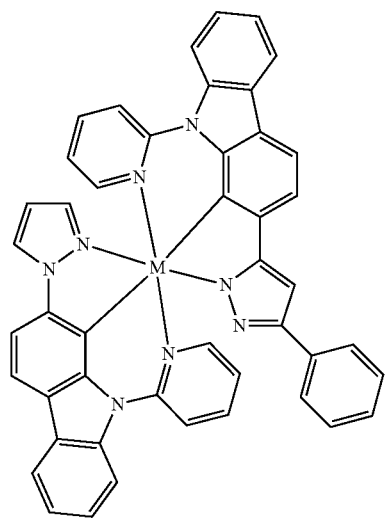
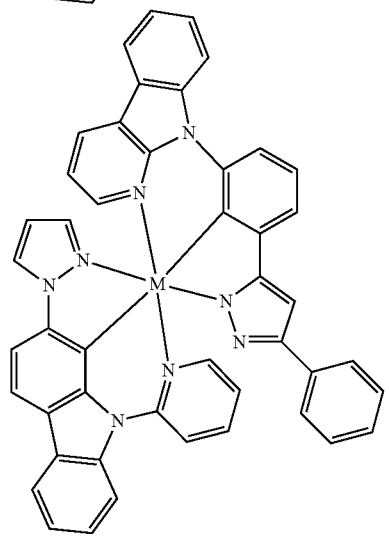
274
-continued
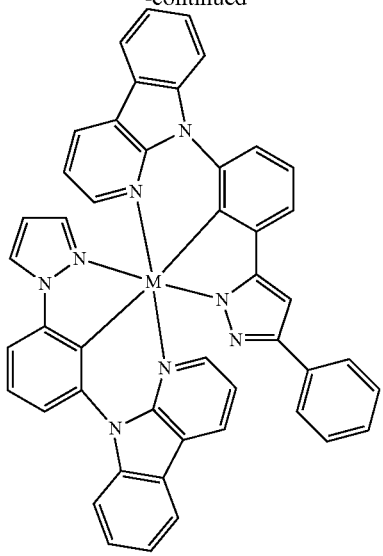
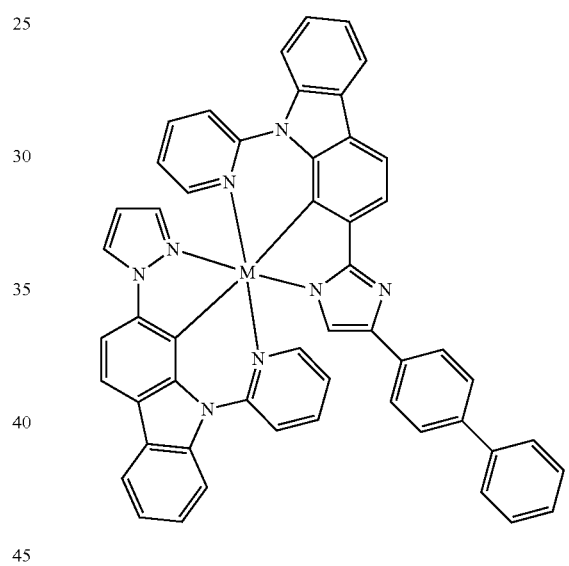
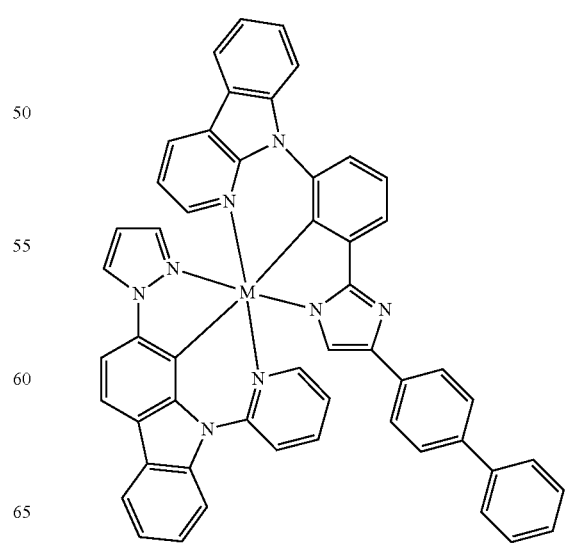

275
-continued
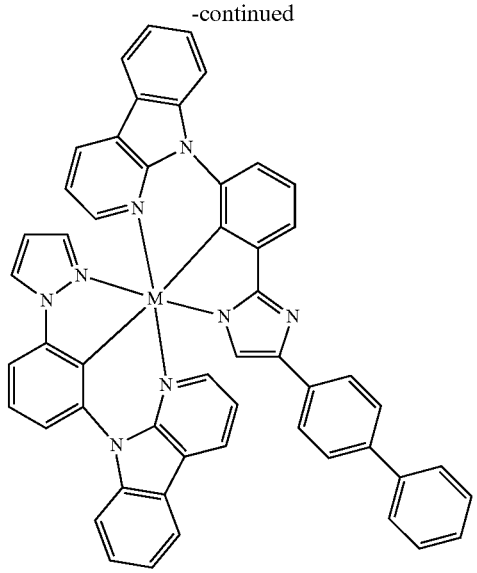
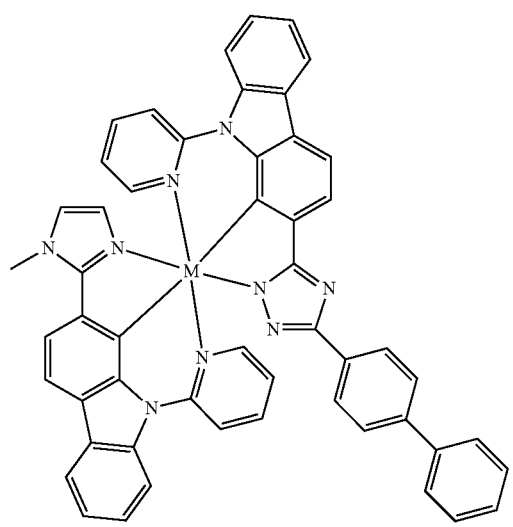
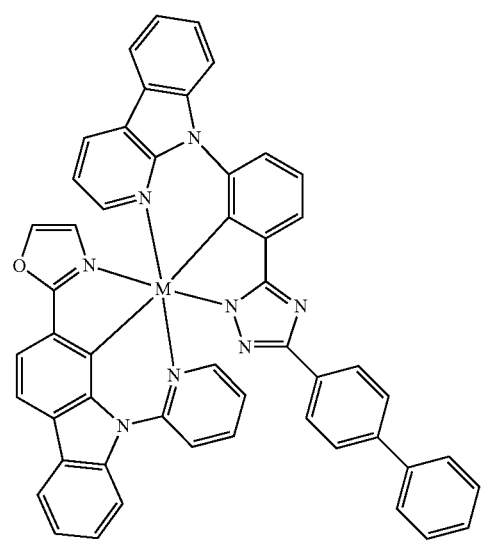
276
-continued
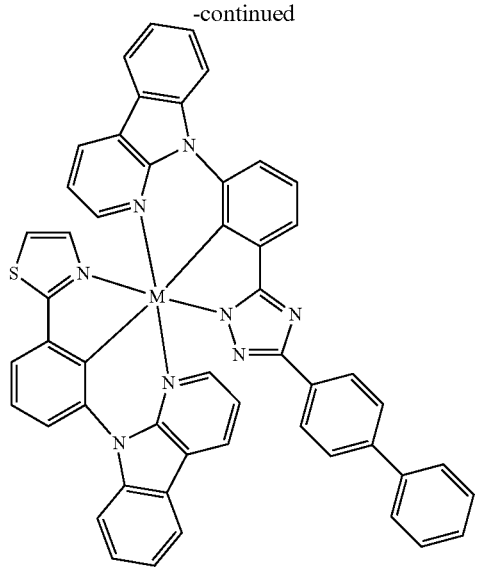
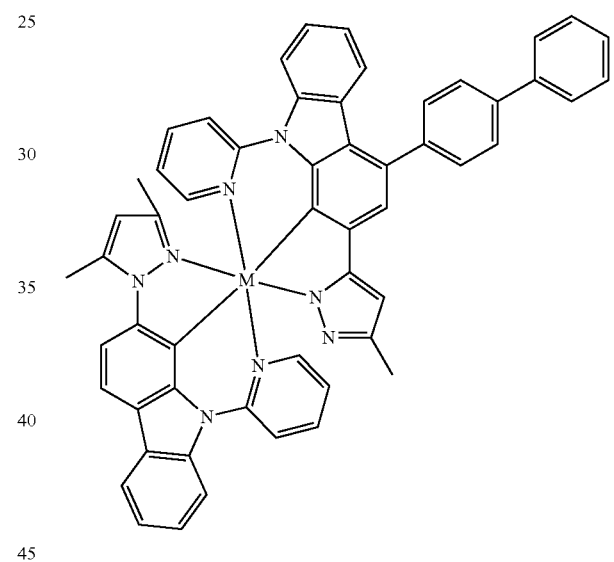
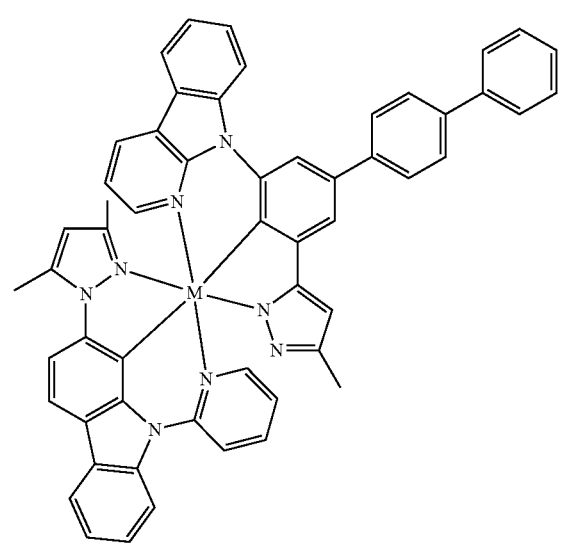

277
-continued
278
-continued
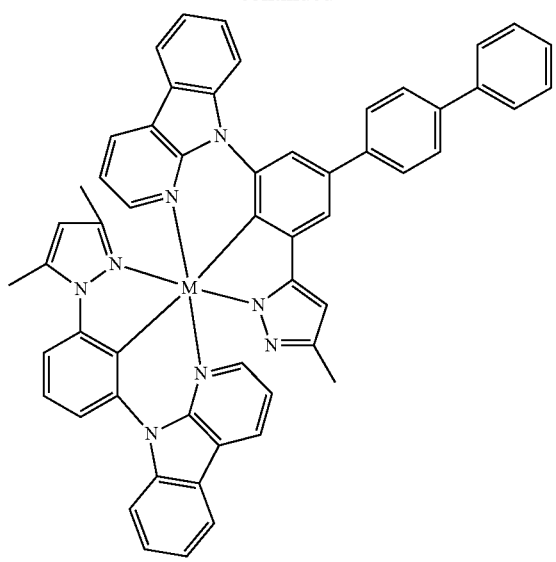
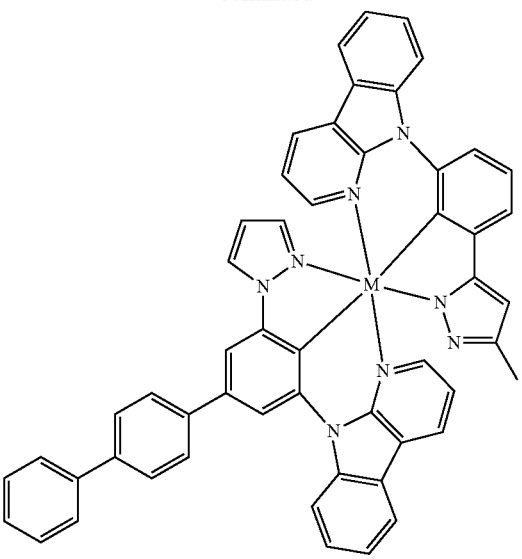
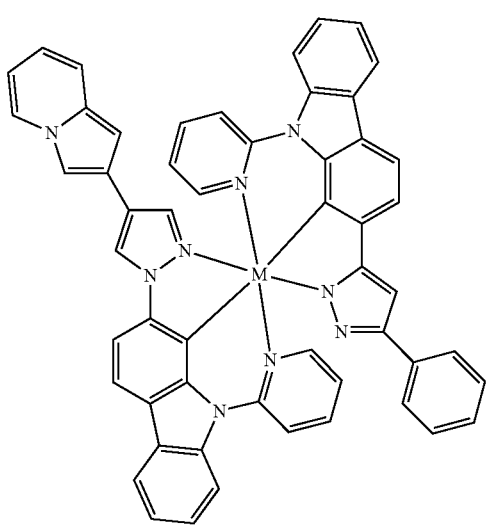
Structures M-14 (M = Ir, Rh)
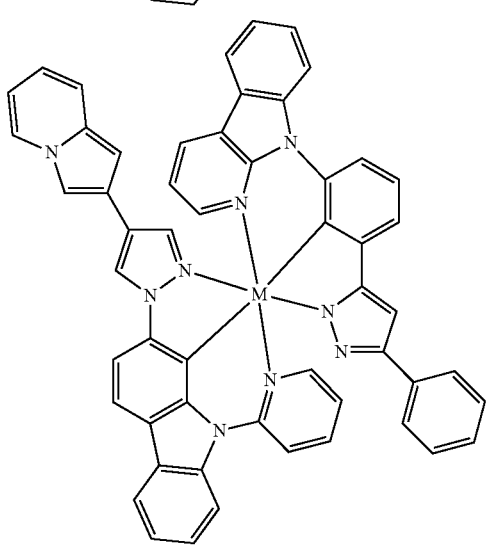

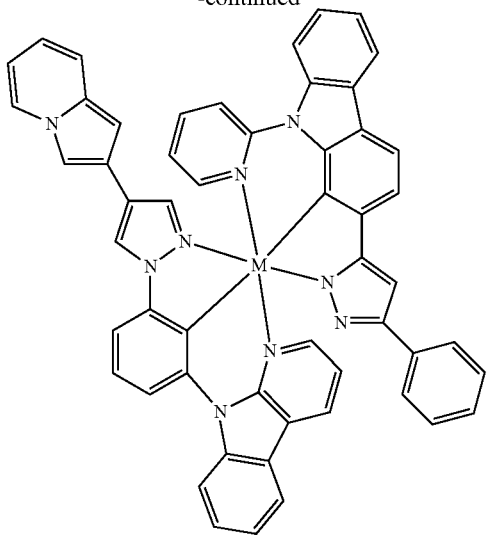
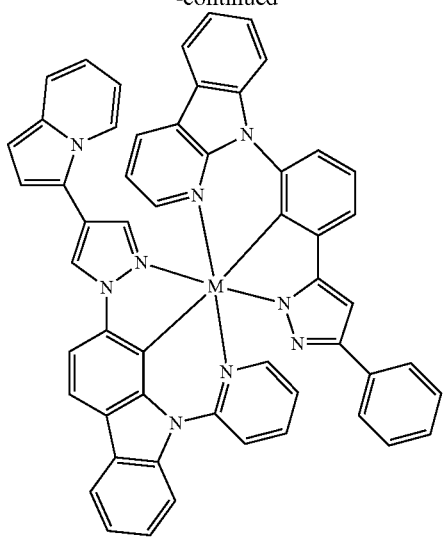
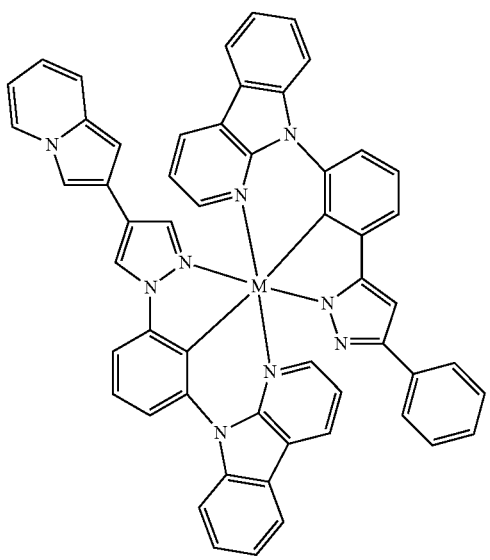
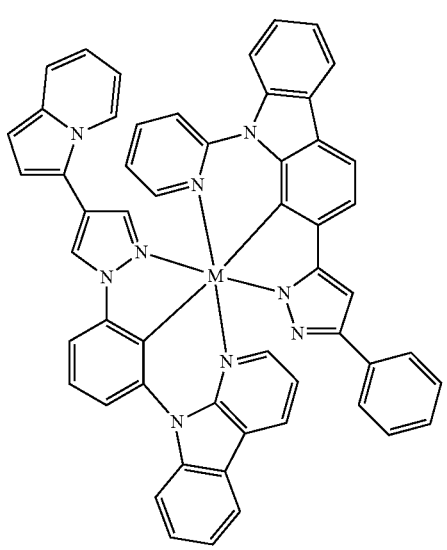
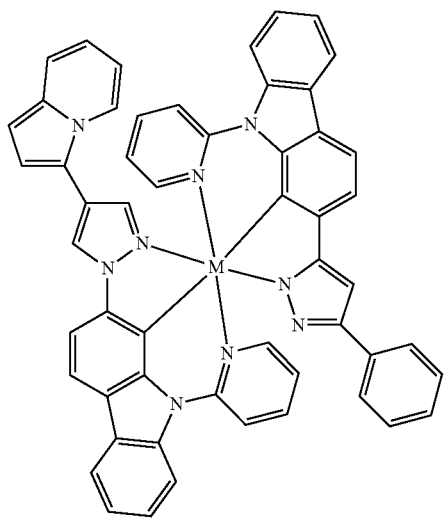

281
-continued
282
-continued
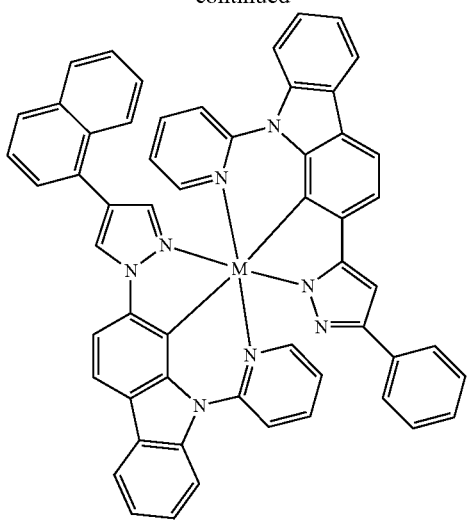
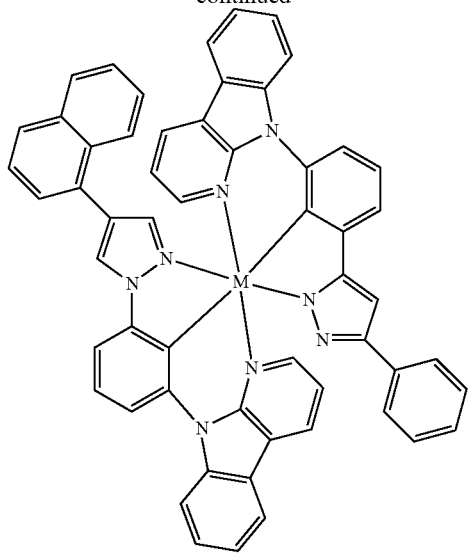
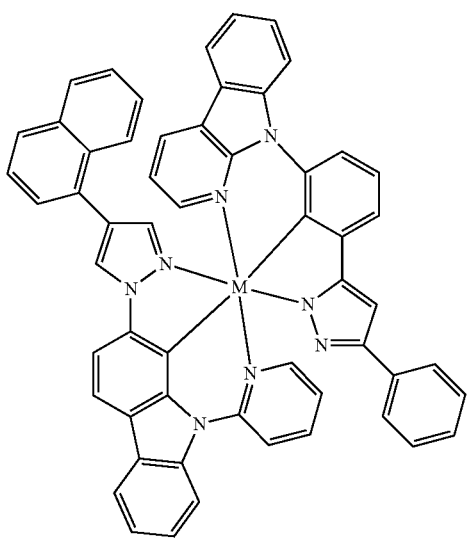
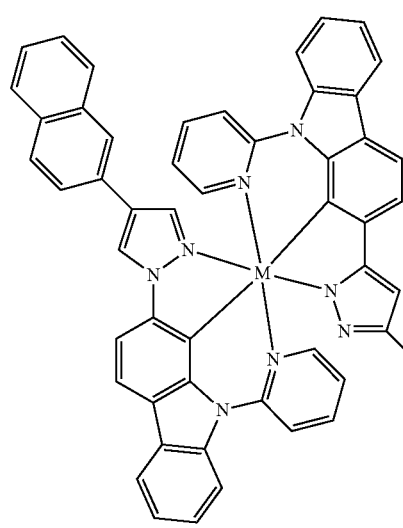
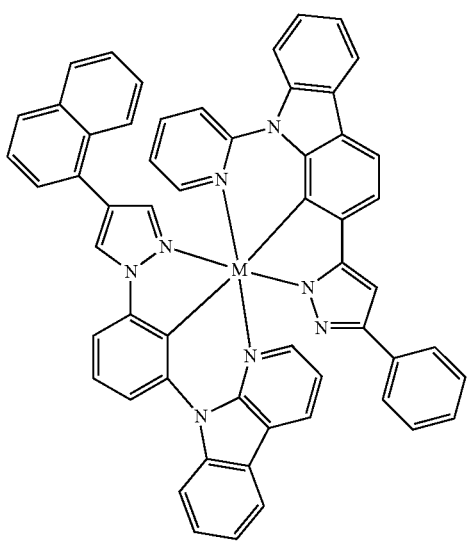
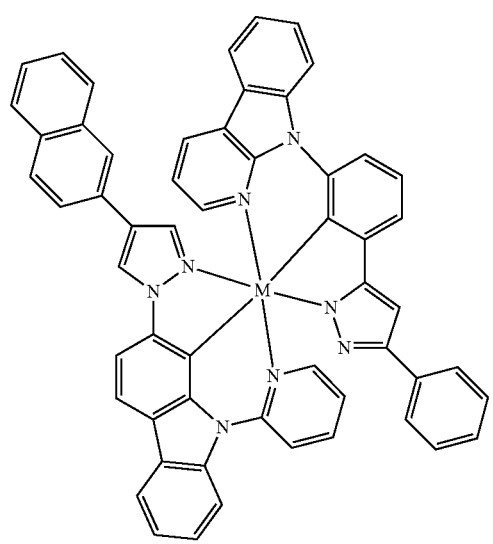

283
-continued
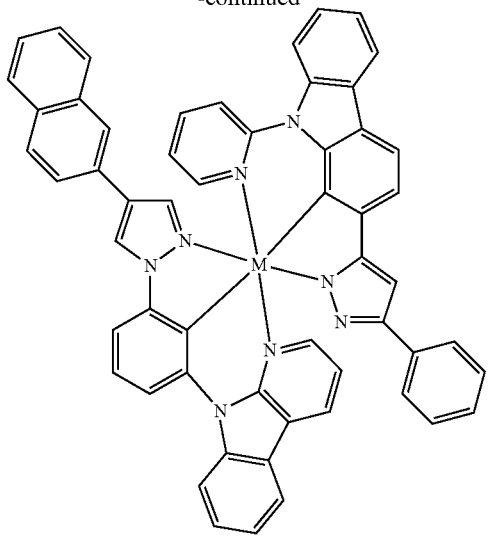
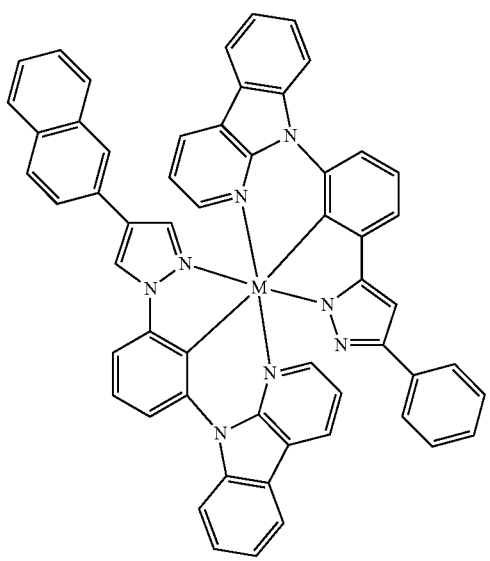
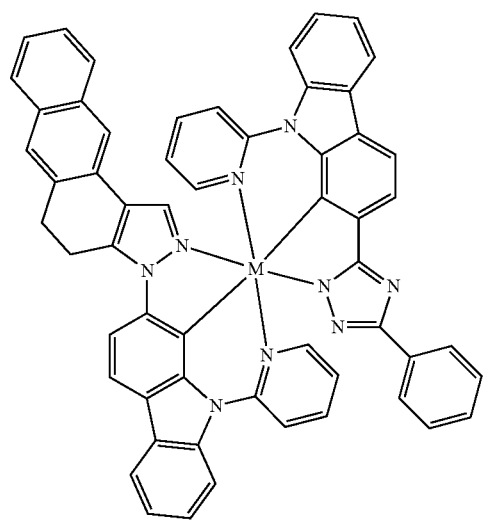
284
-continued
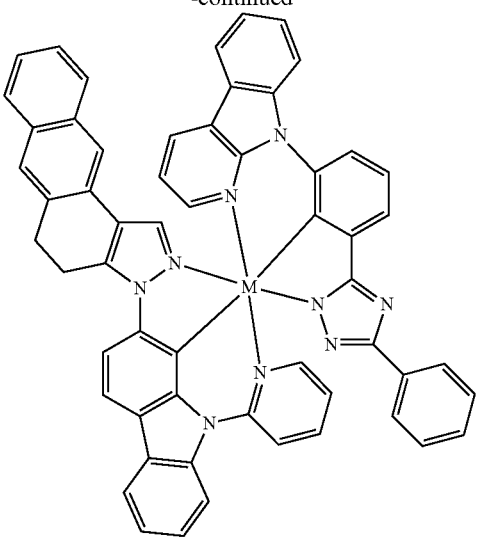
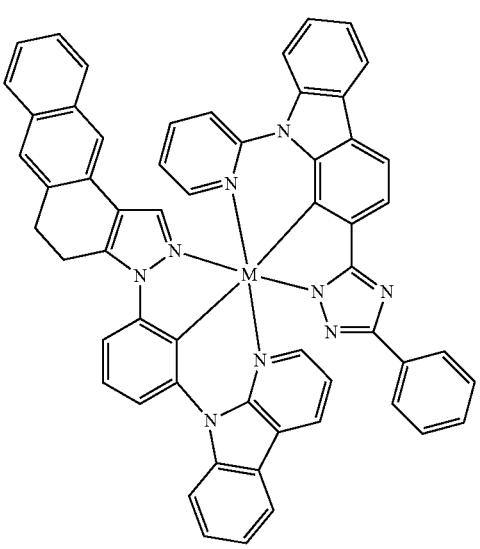
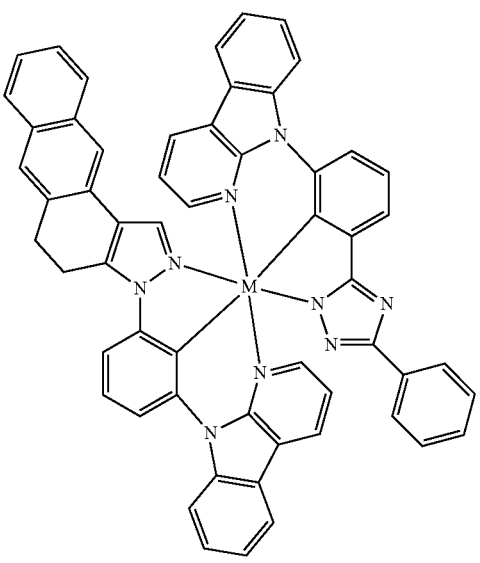

-continued
Structures M-15 (M = Ir, Rh)
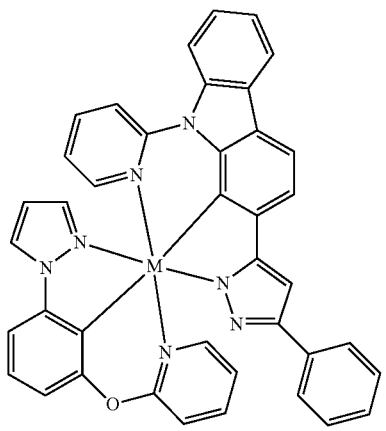
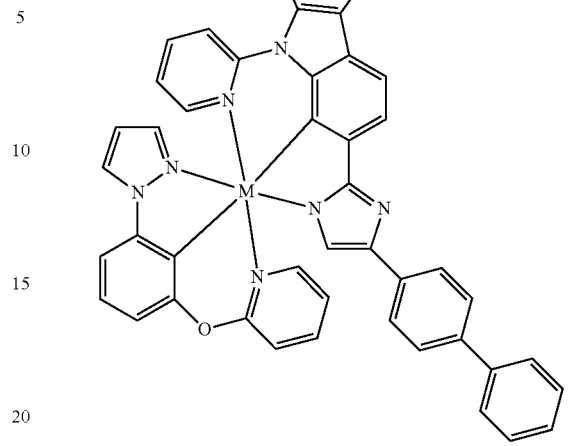
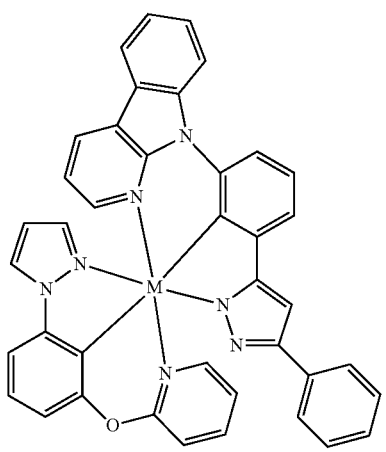
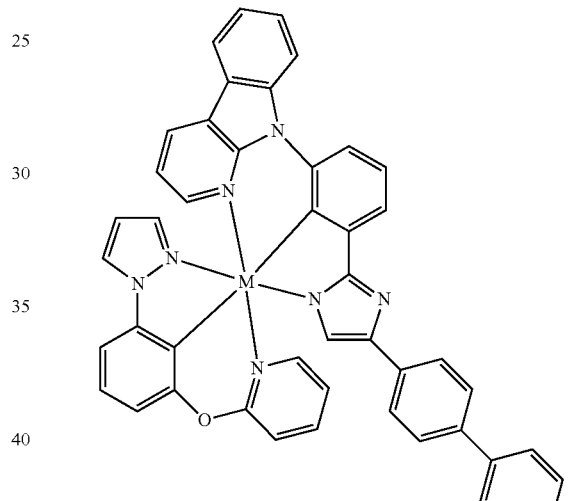
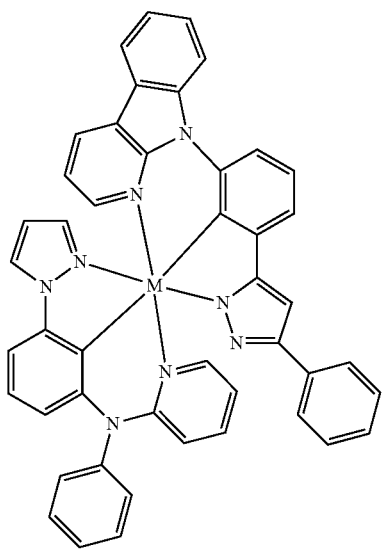
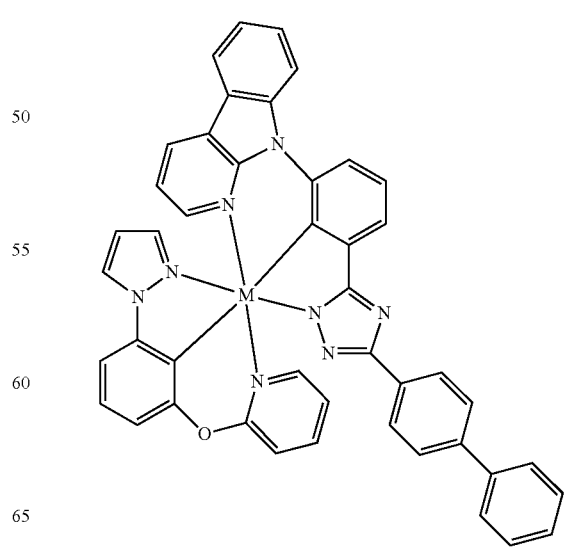

287
-continued
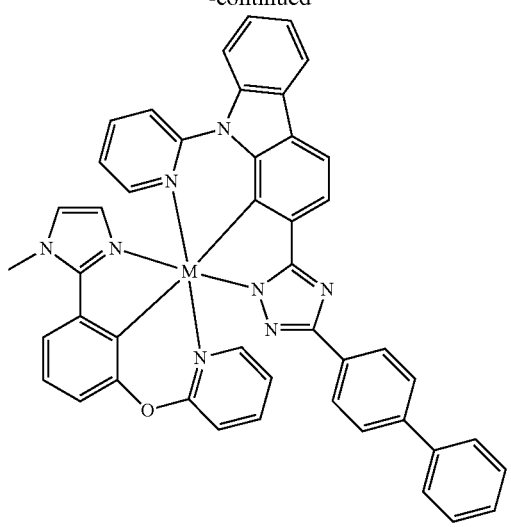
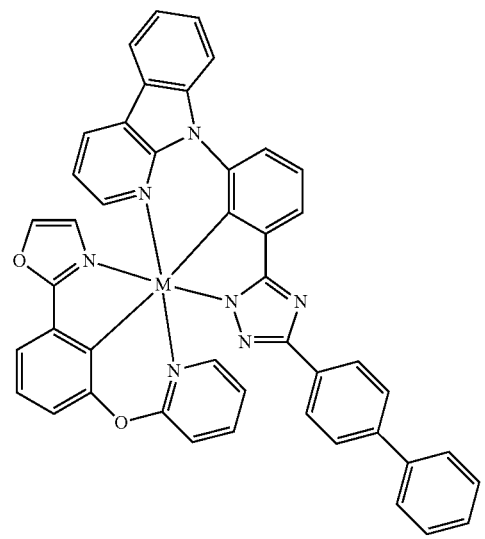
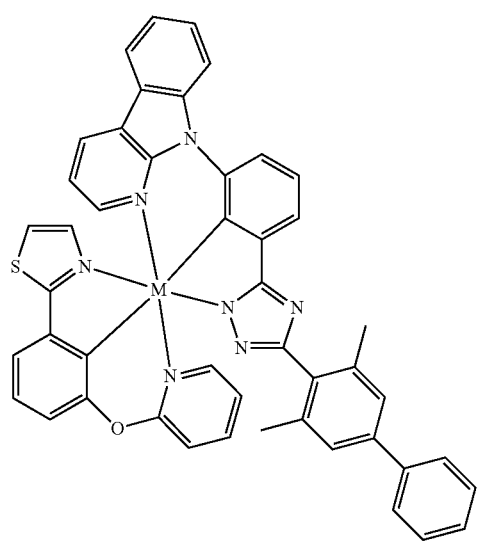
288
-continued
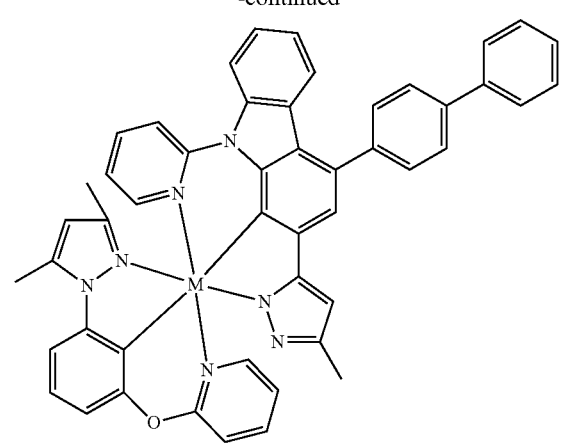
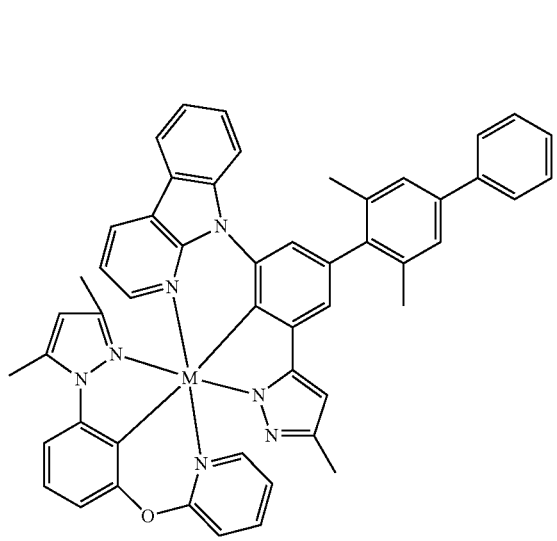

289
-continued
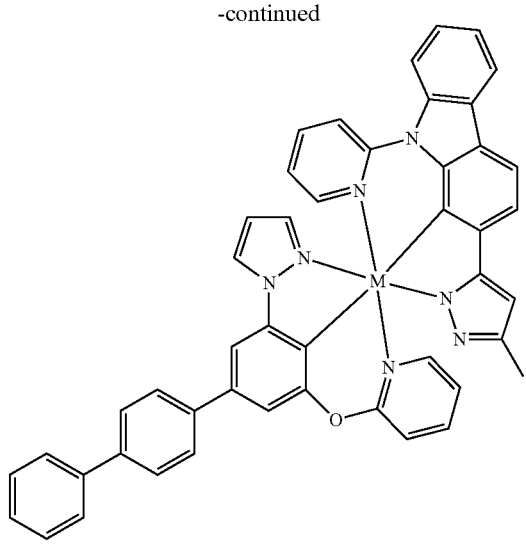
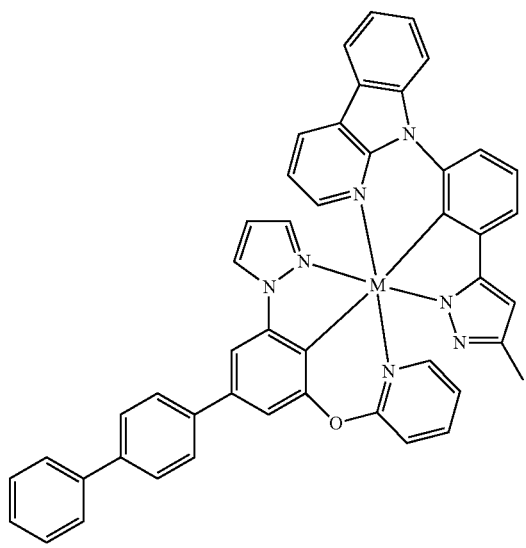
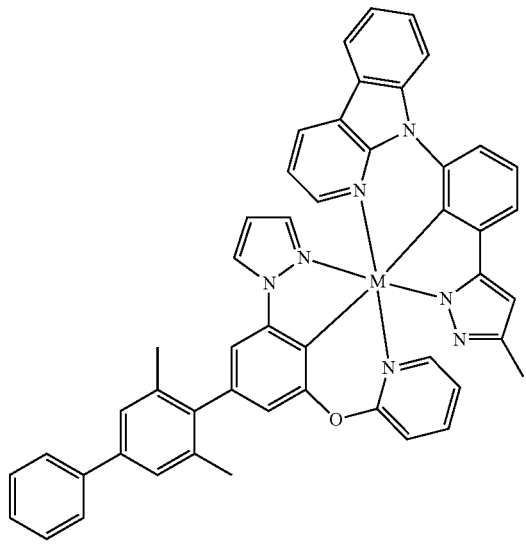
290
-continued
Structures M-16 (M = Ir, Rh)
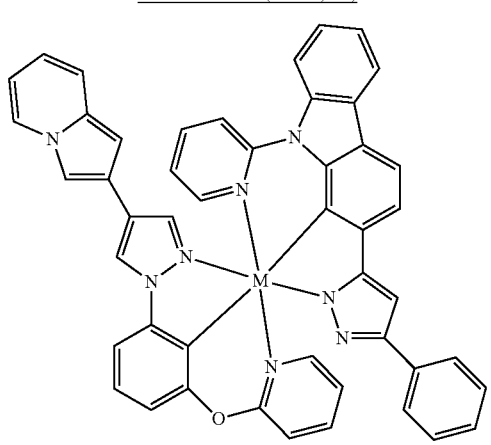
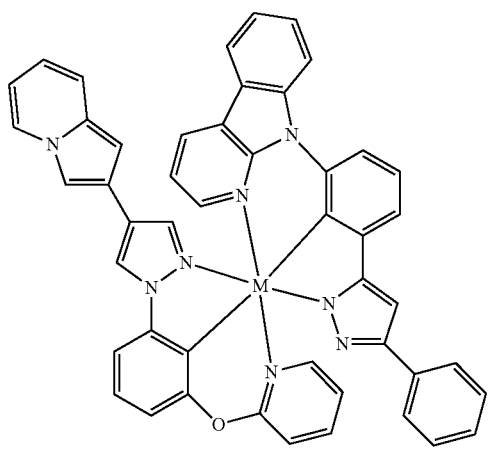
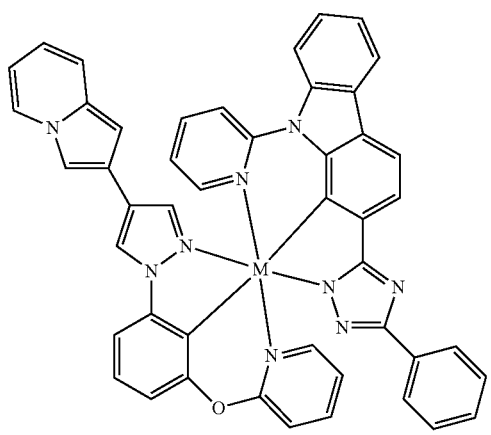

291
-continued
292
-continued
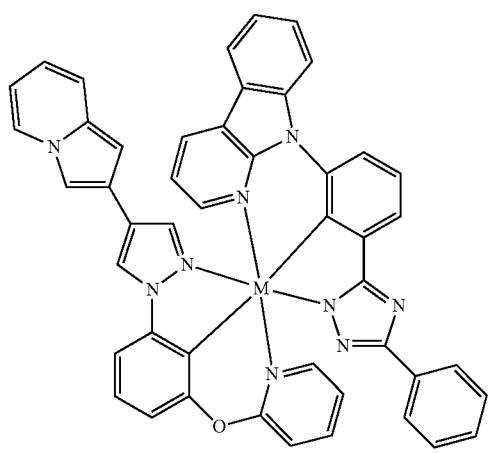
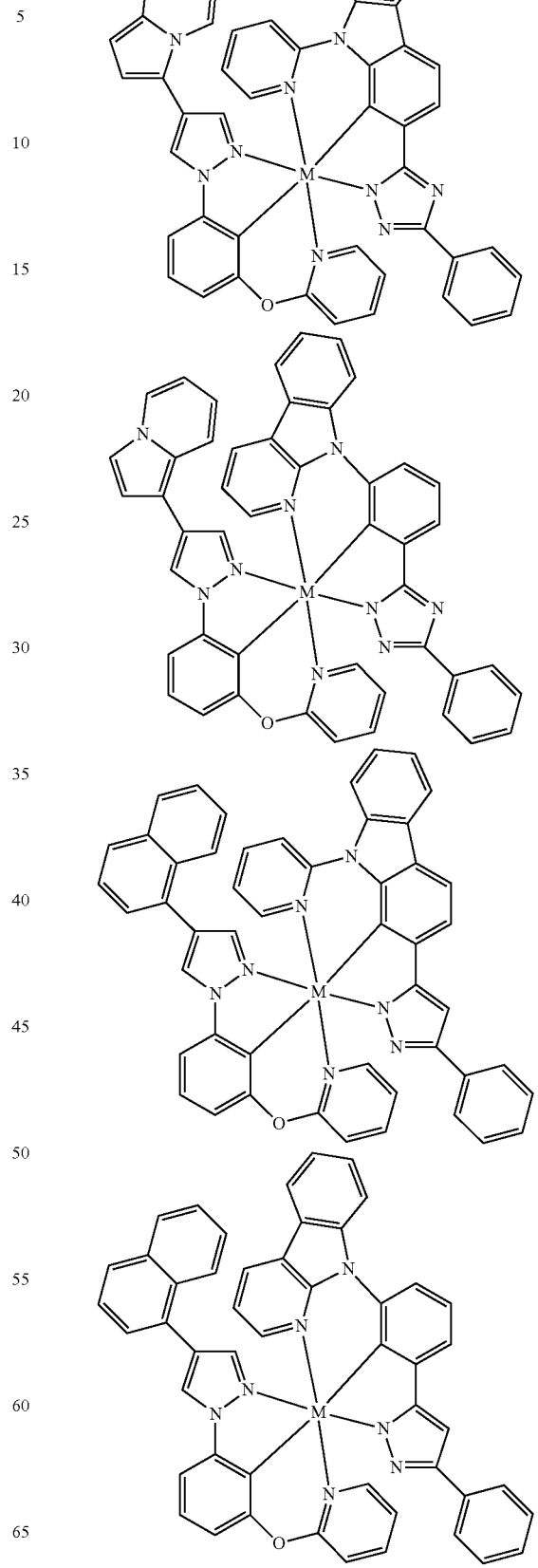

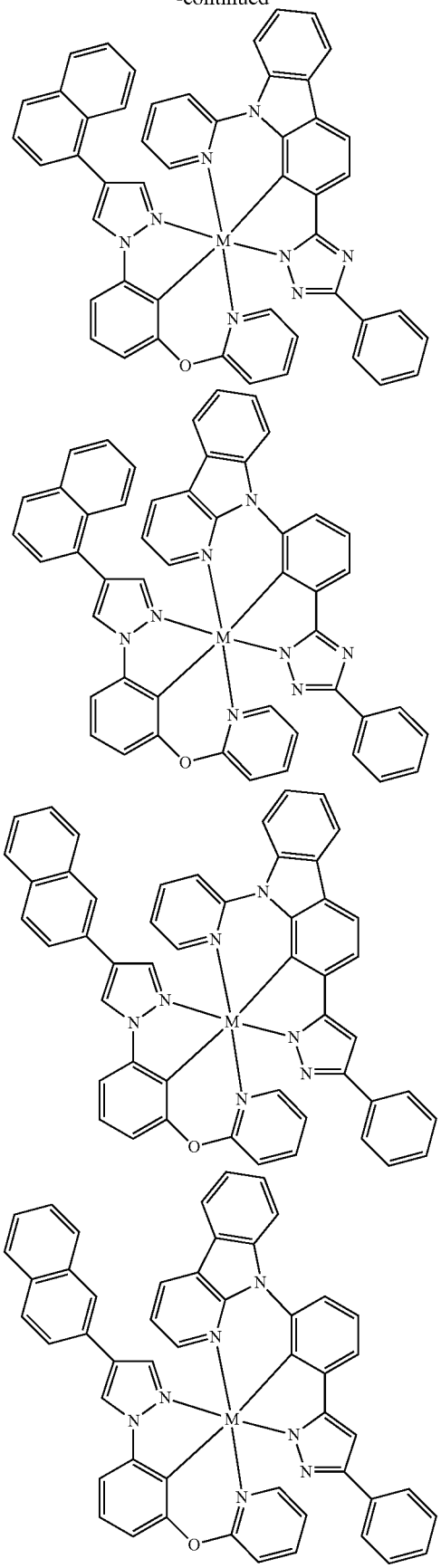
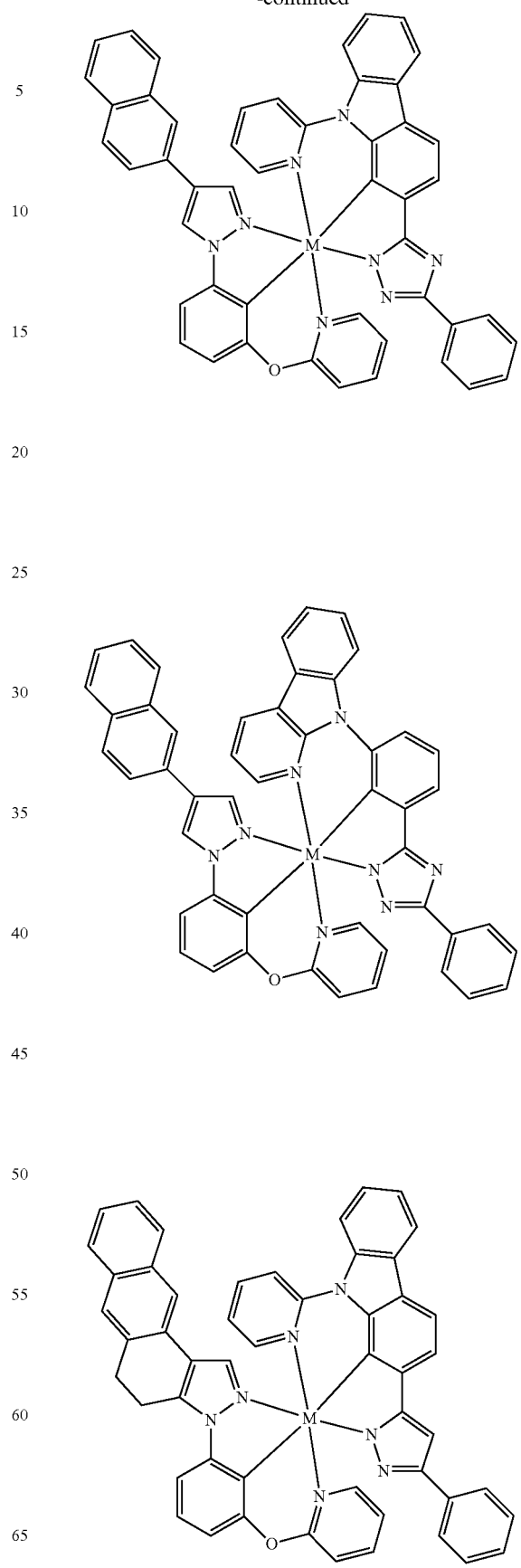

-continued
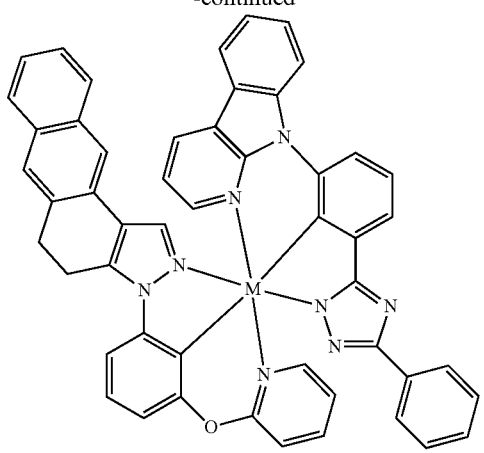
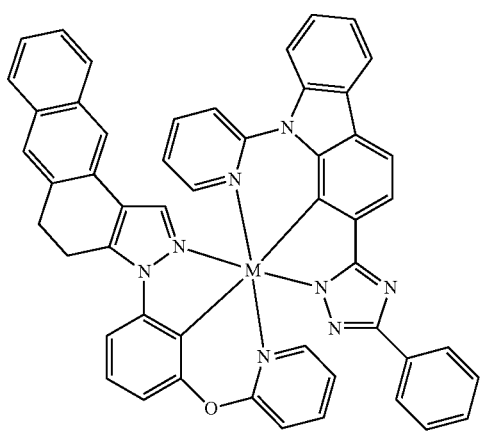
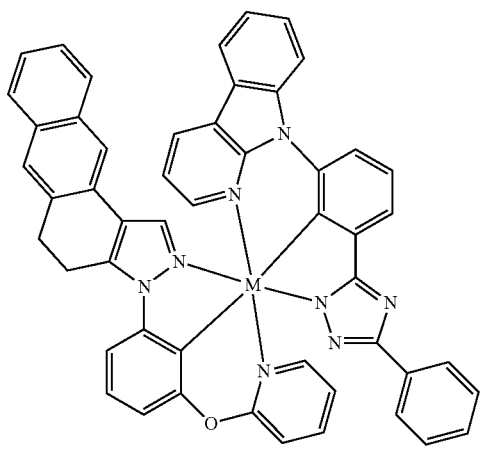
Structures M-17 (M = Ir, Rh)
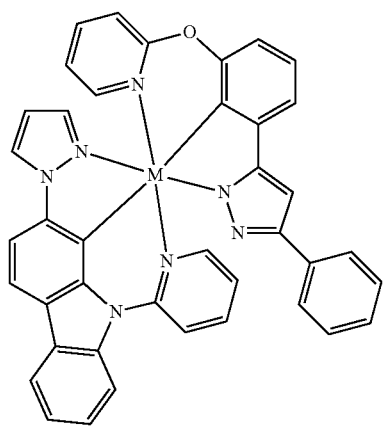
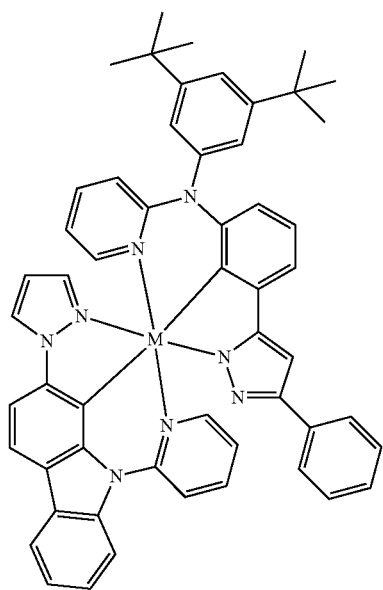
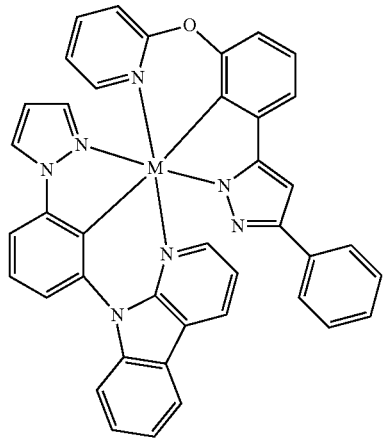

297
-continued
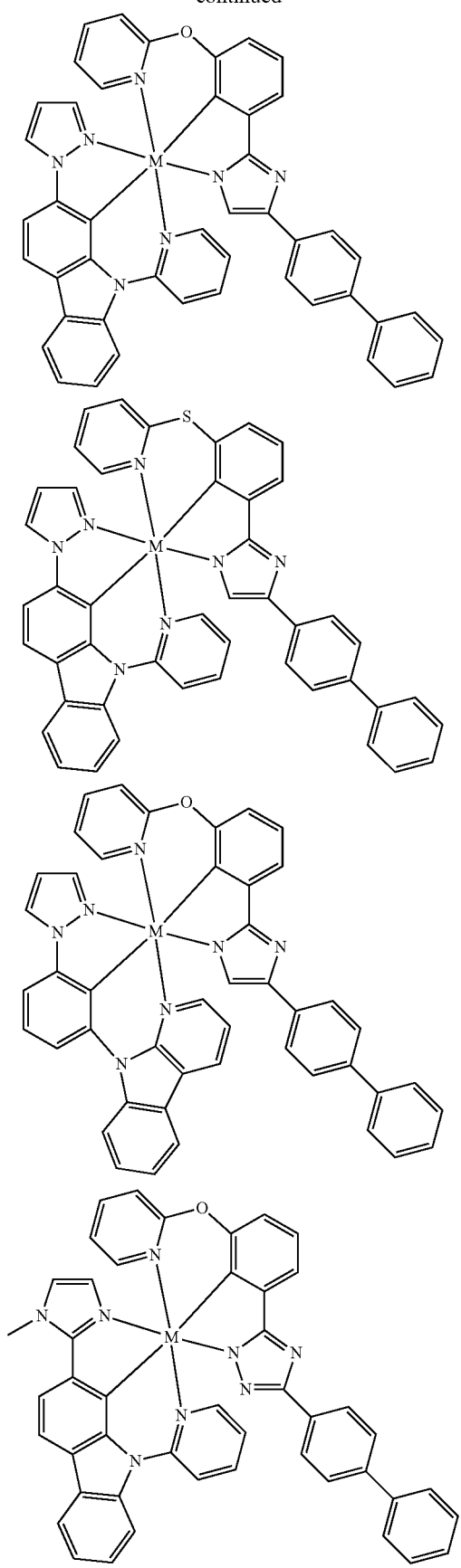
298
-continued
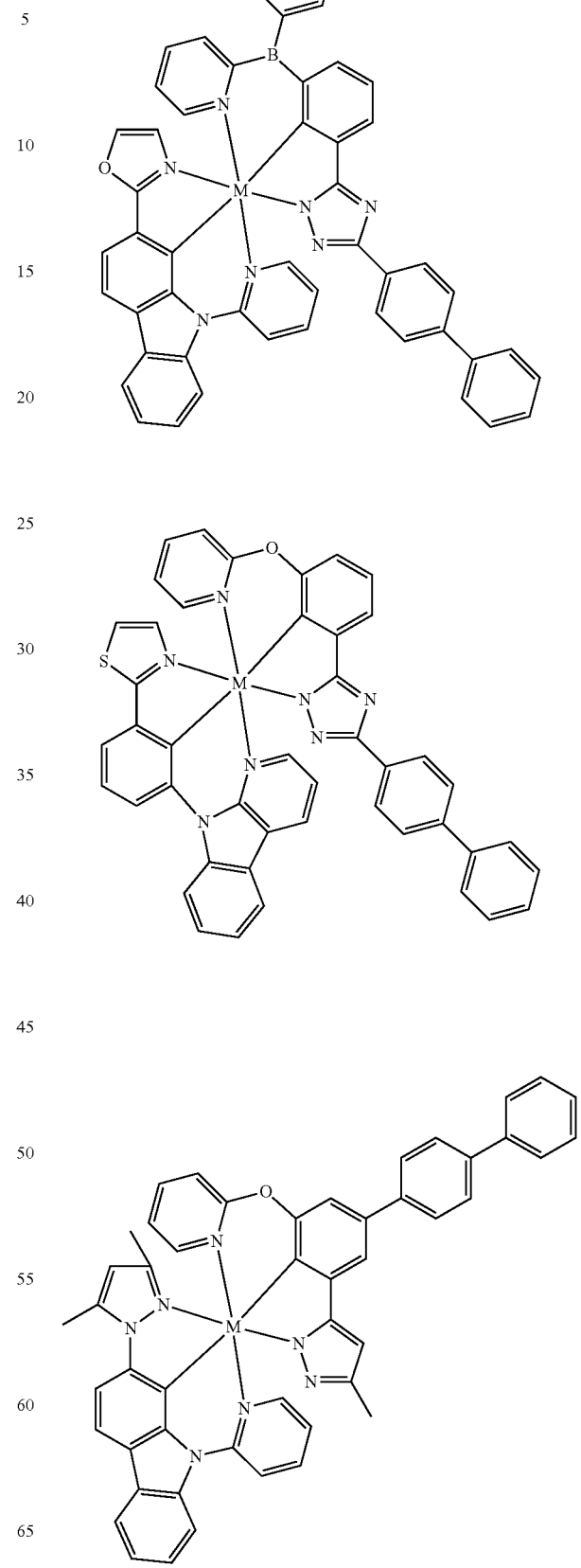

299
-continued
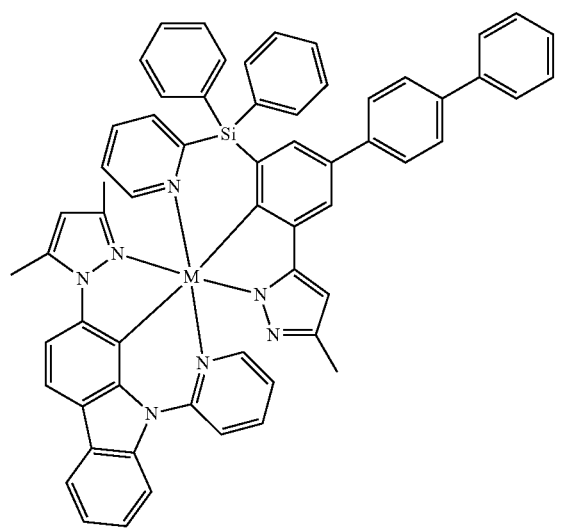
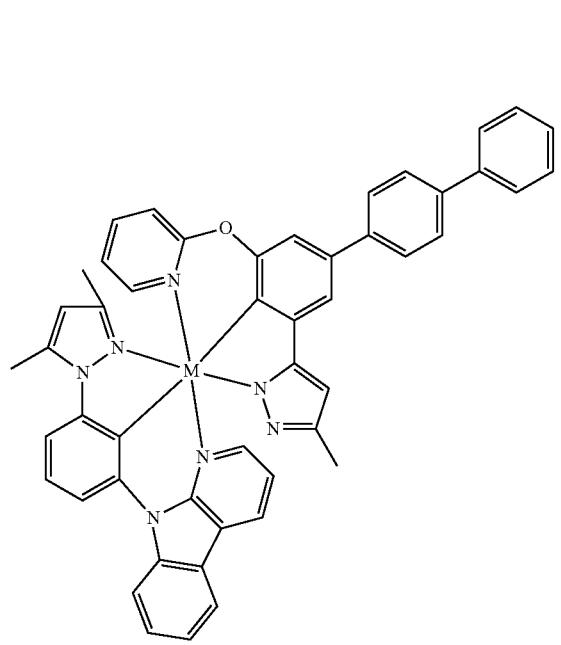
300
-continued
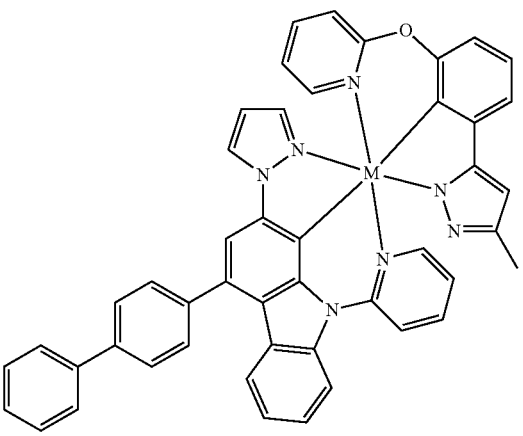
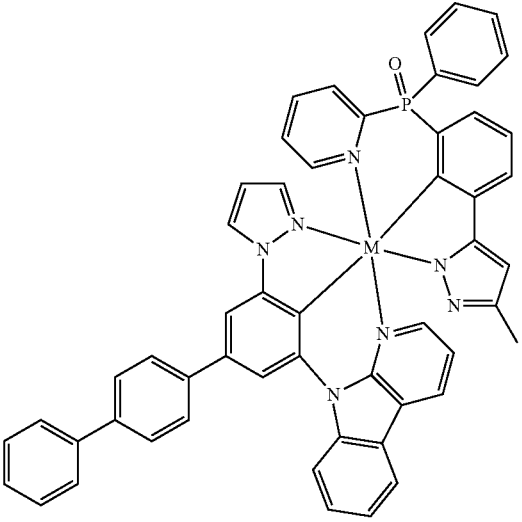
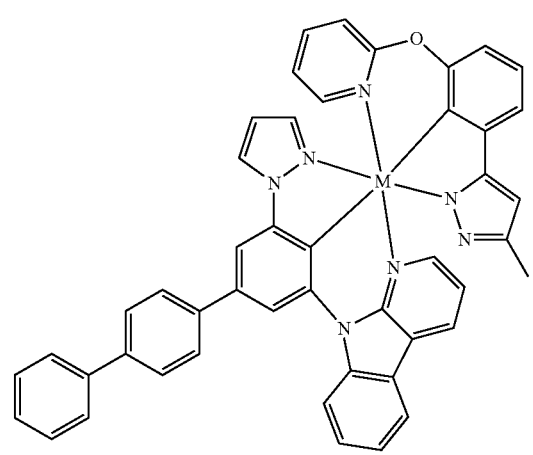
Structures M-18 (M = Ir, Rh)
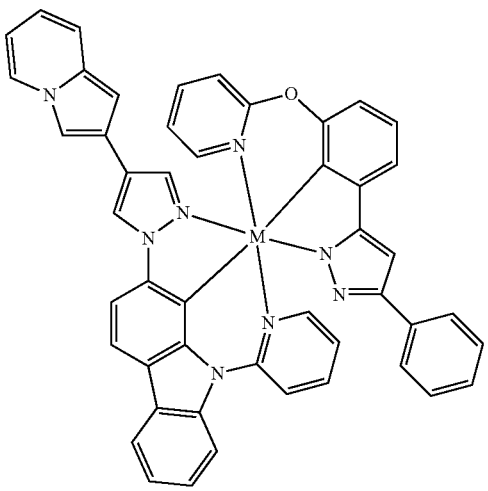

301
-continued
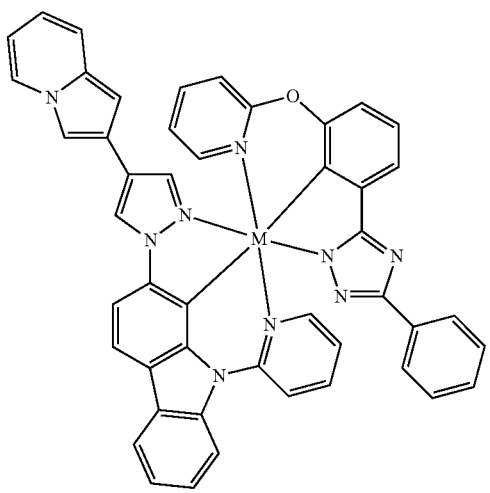
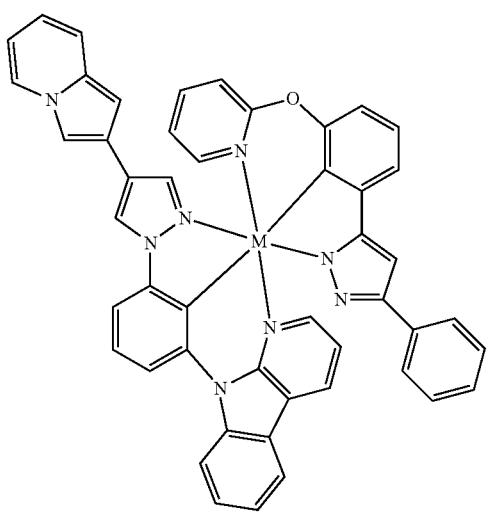
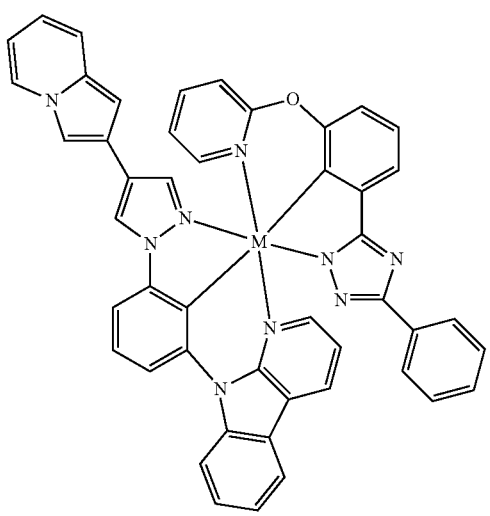
302
-continued
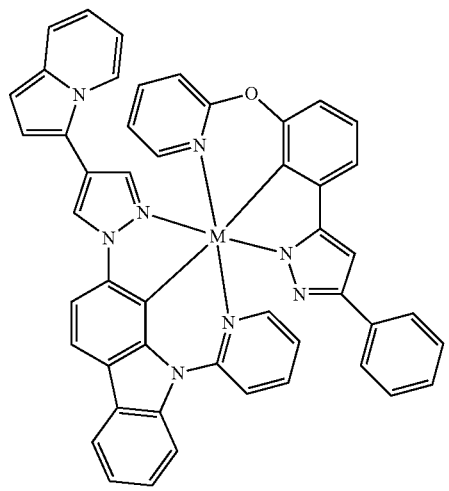
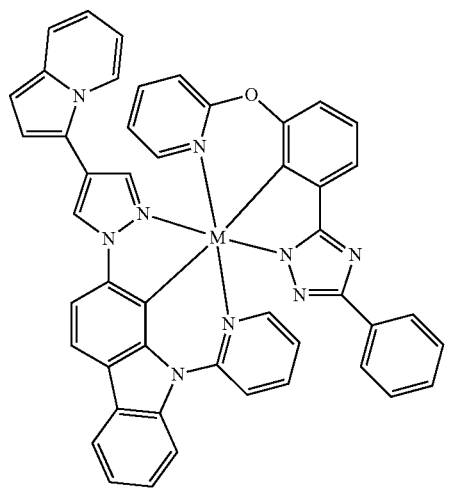
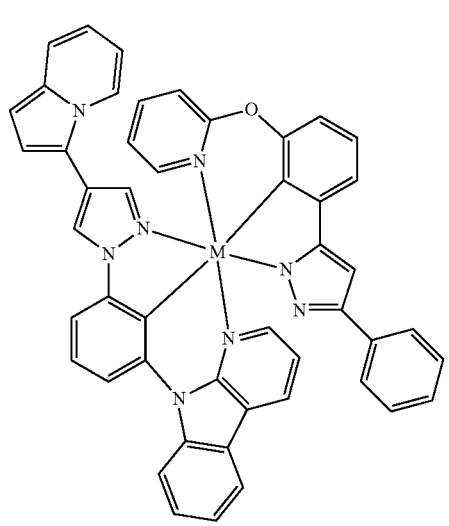

303
-continued
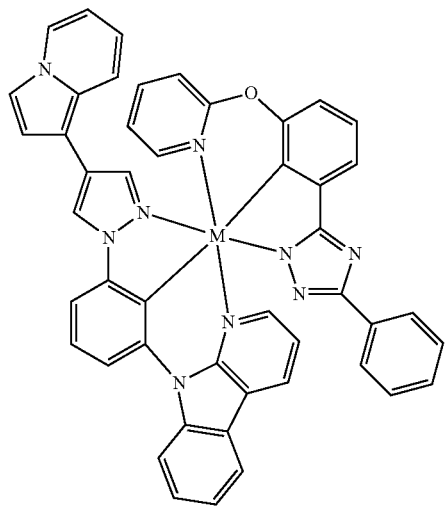
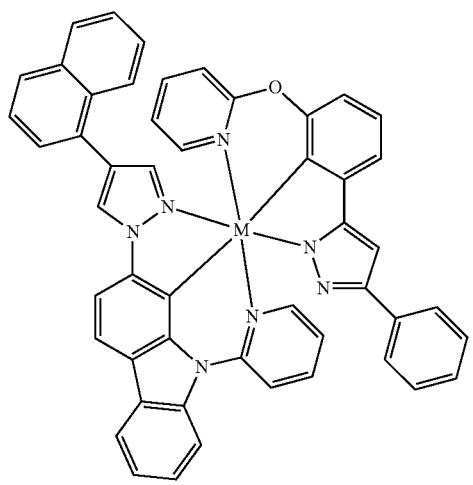
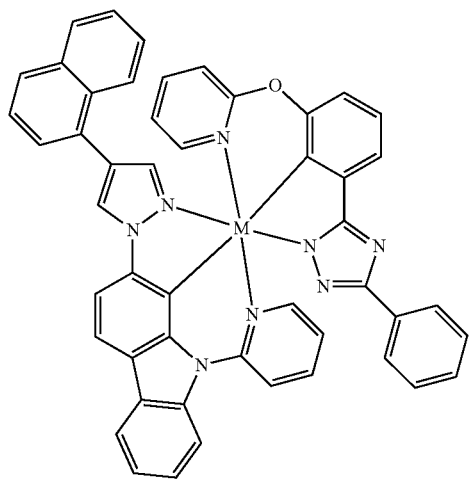
304
-continued
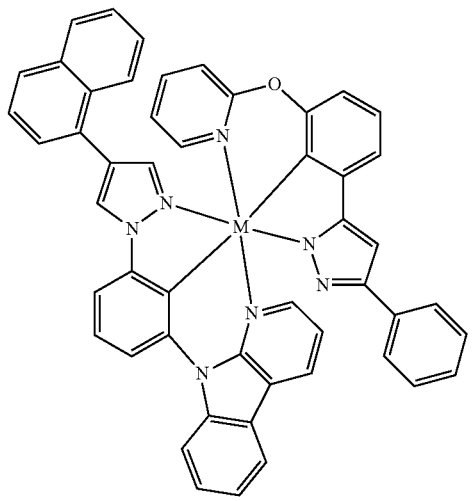
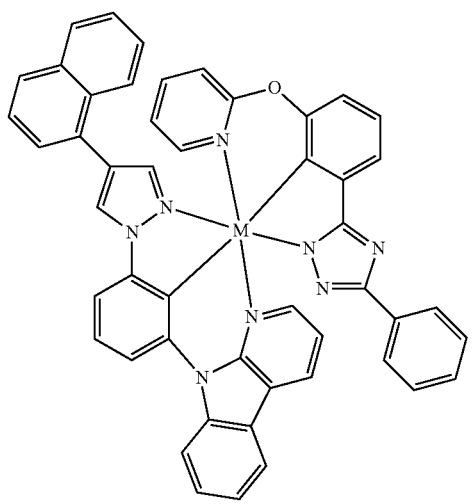
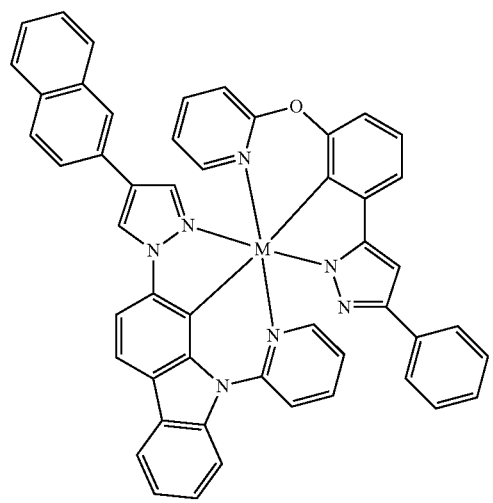

305
-continued
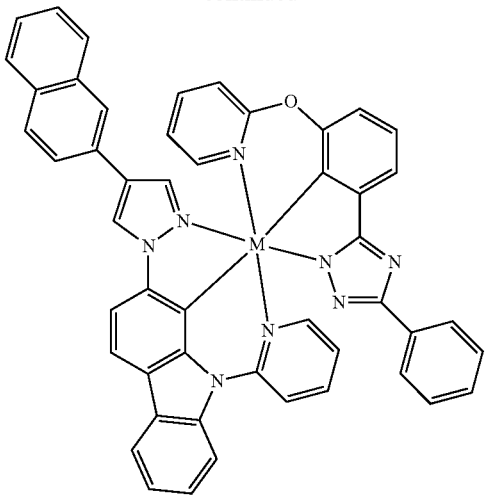
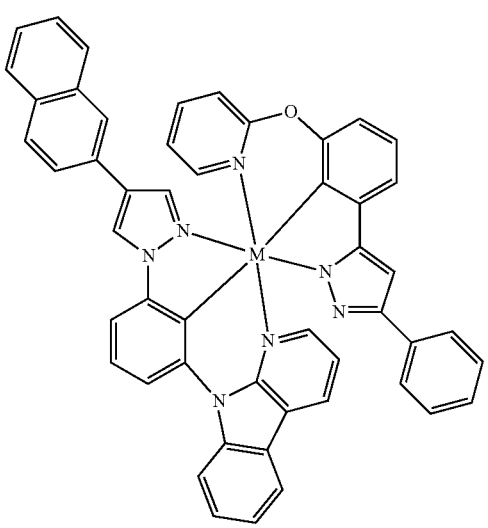
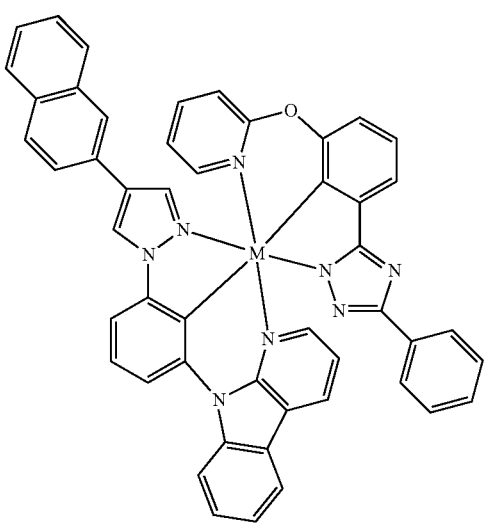
306
-continued
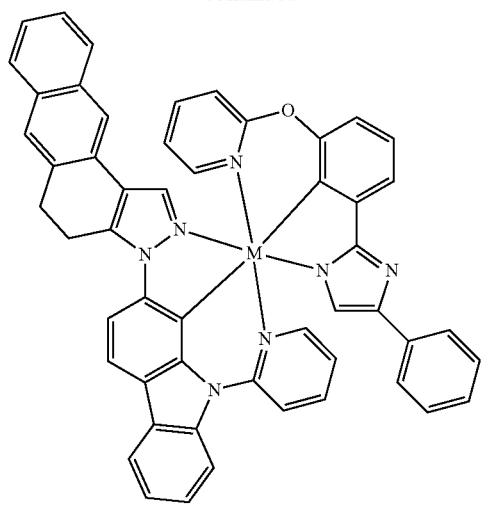
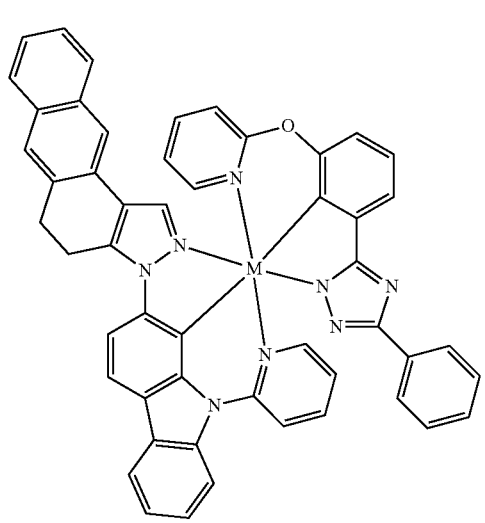
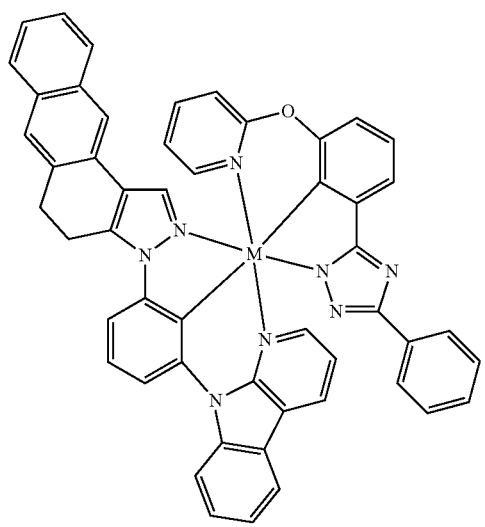

307
-continued
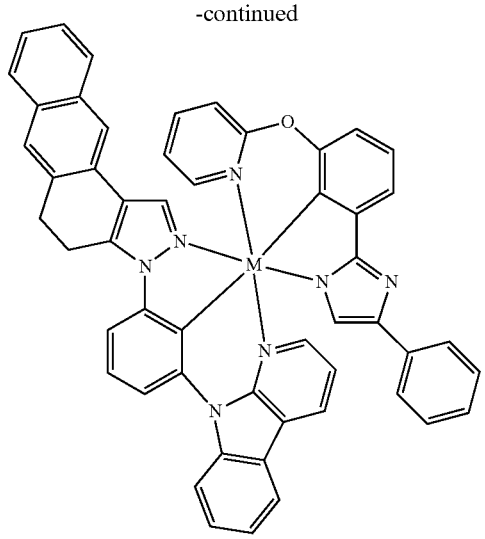
Structures M-19 (M = Ir, Rh)
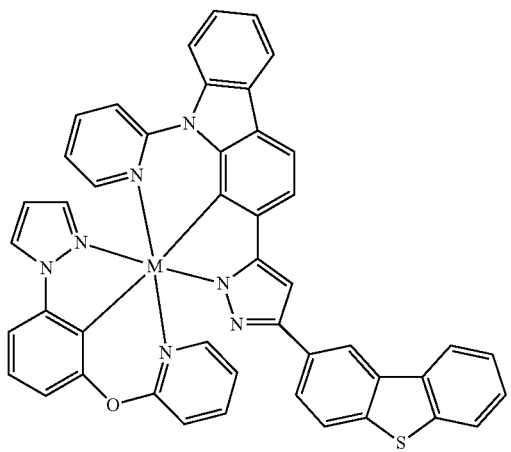
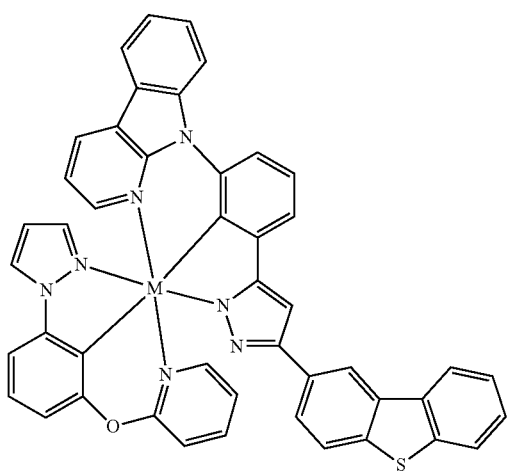
308
-continued
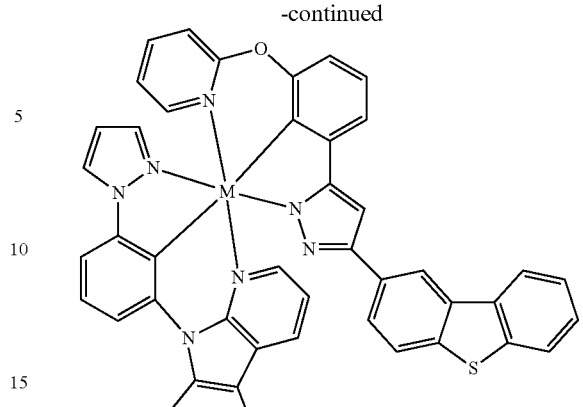
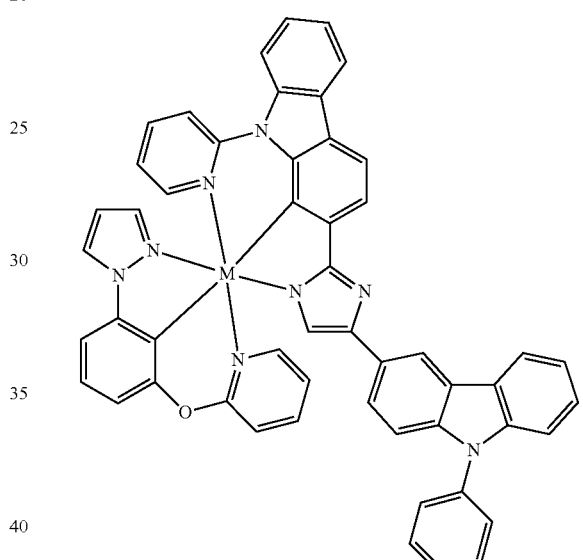
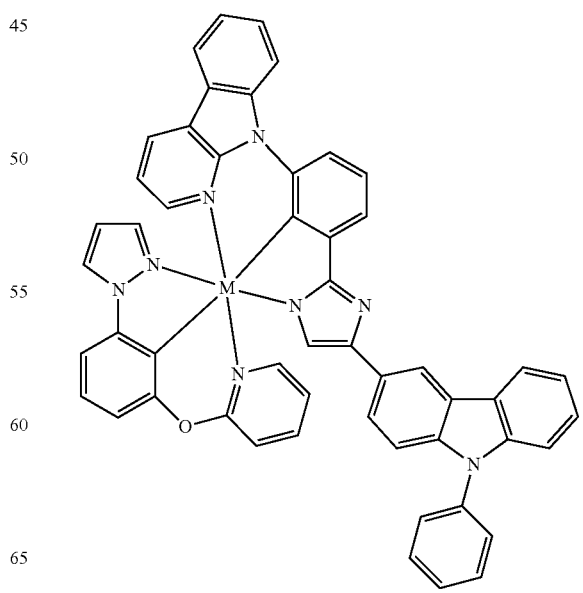

309
-continued
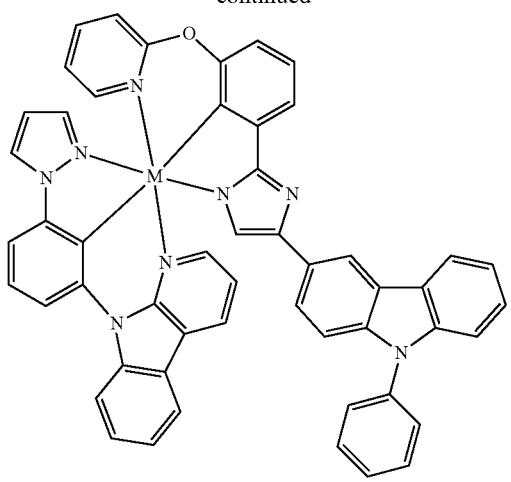
310
-continued
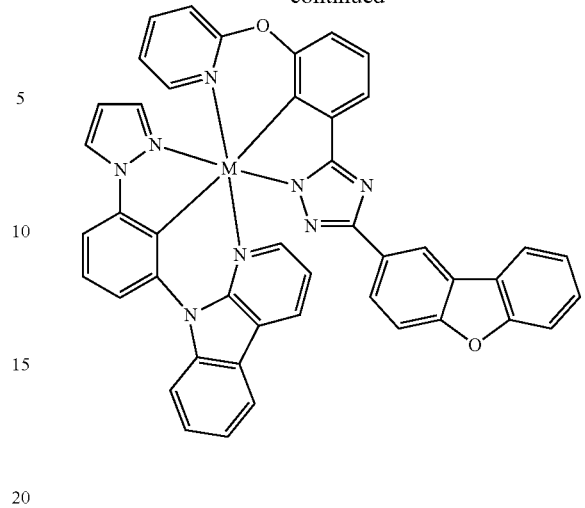
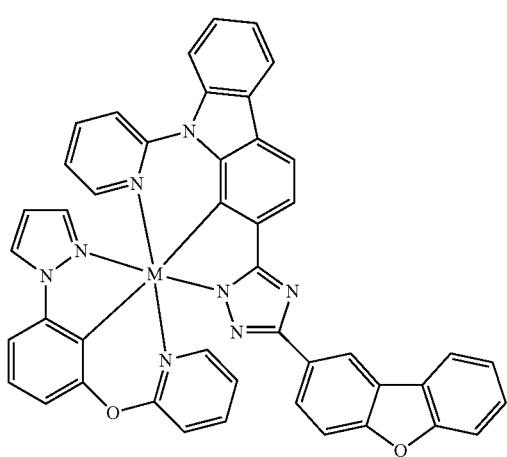
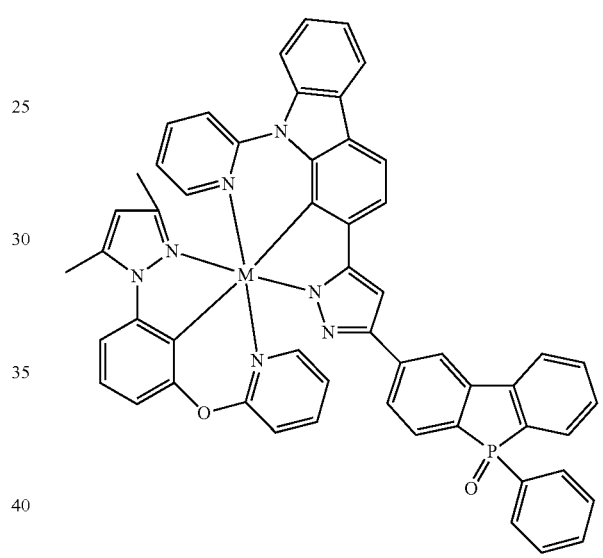
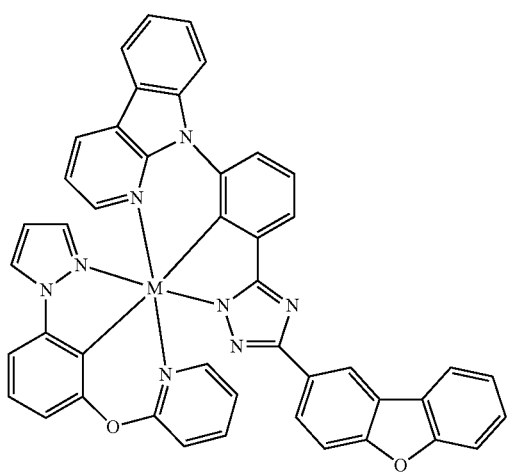
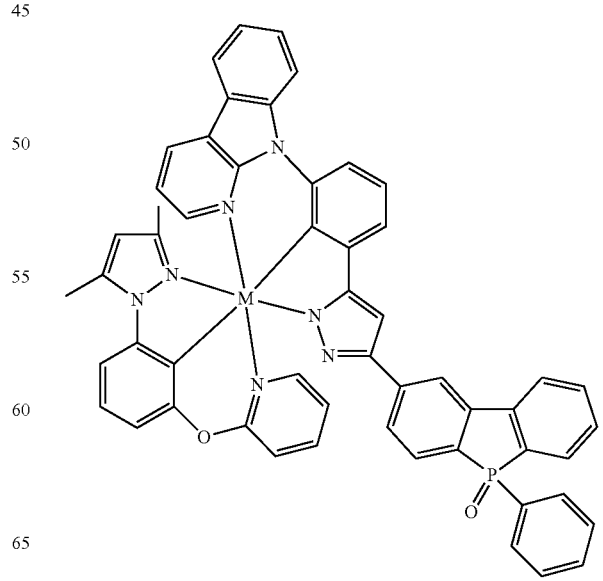

311
-continued
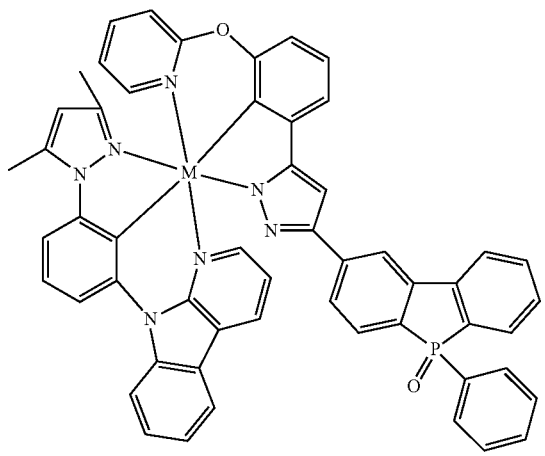
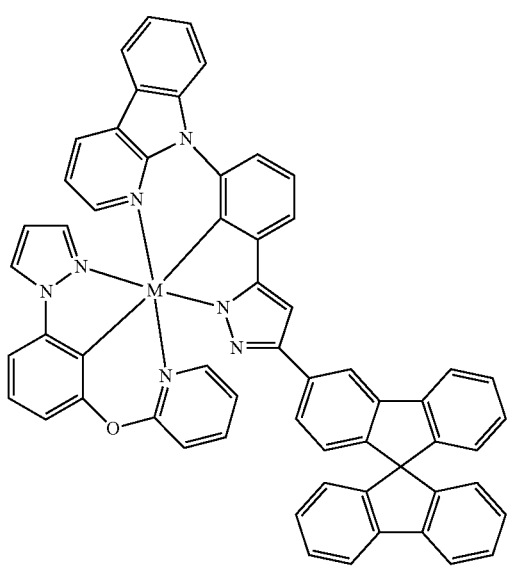
312
-continued
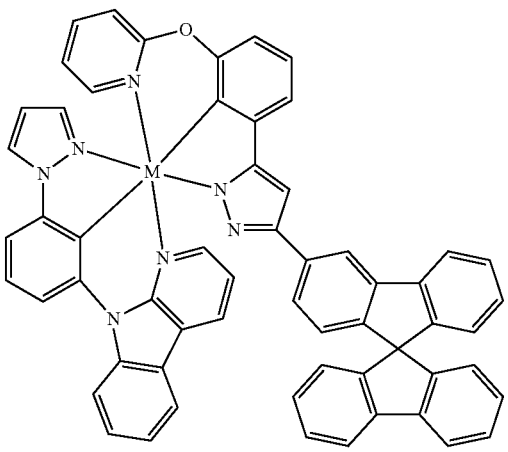
Structures M-20 (M = Ir, Rh)
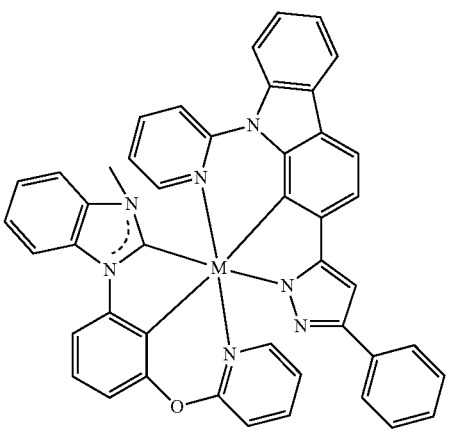

313
-continued
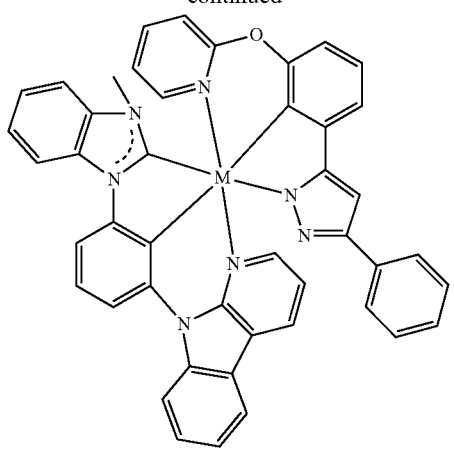
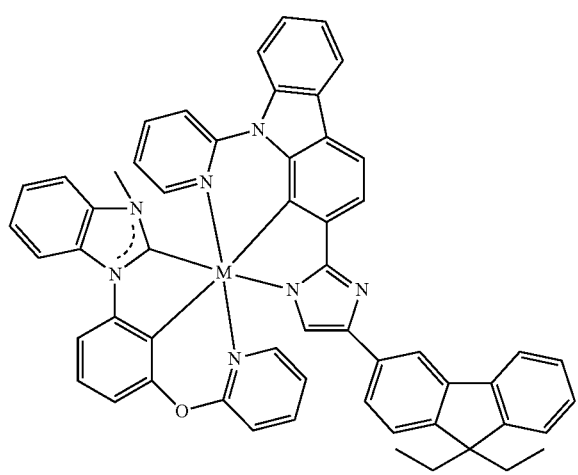
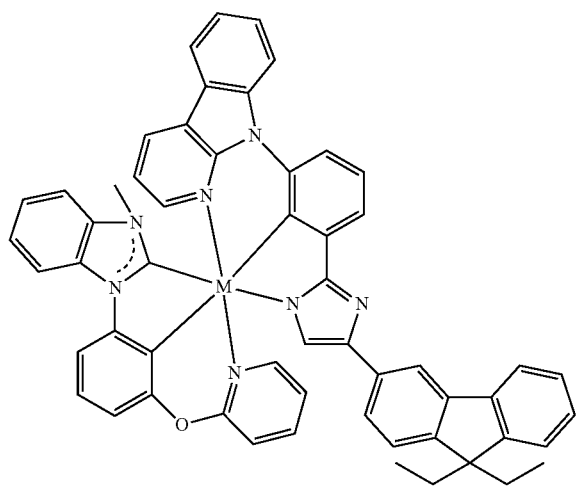
314
-continued
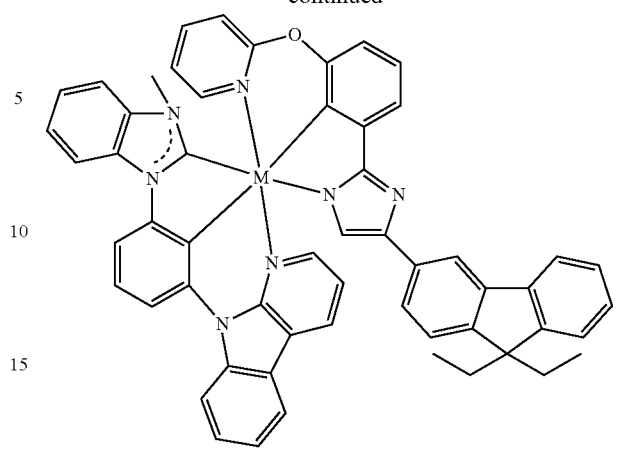
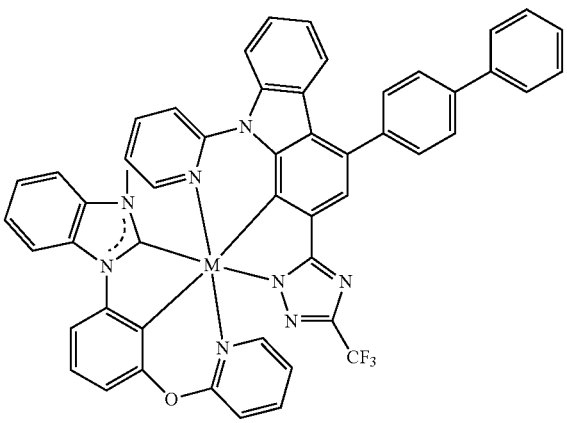

315
-continued
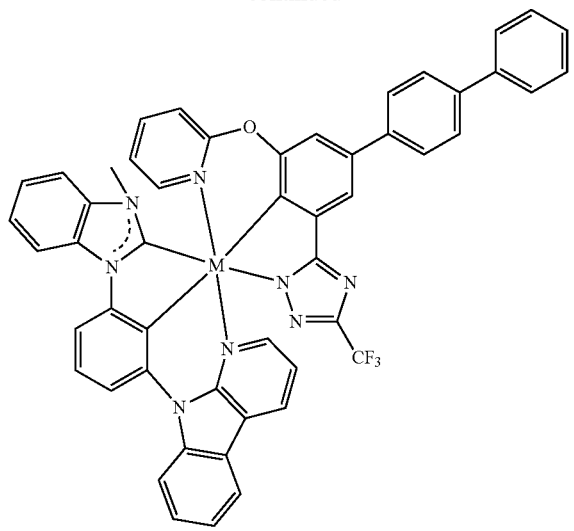
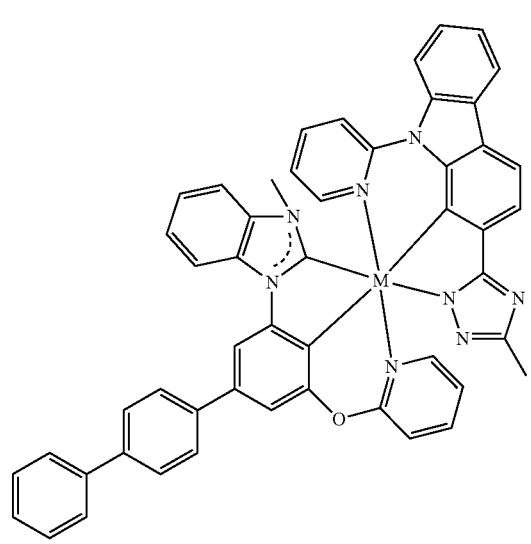
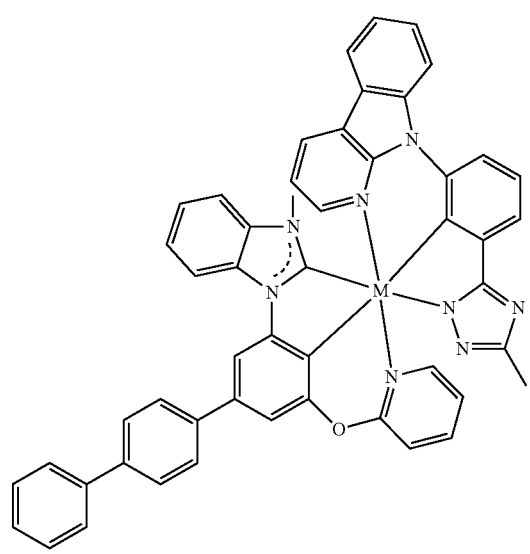
316
-continued
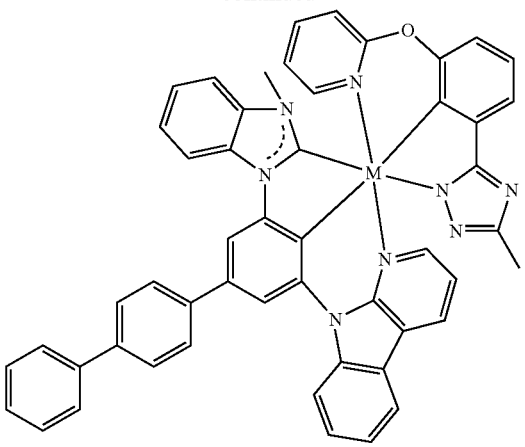
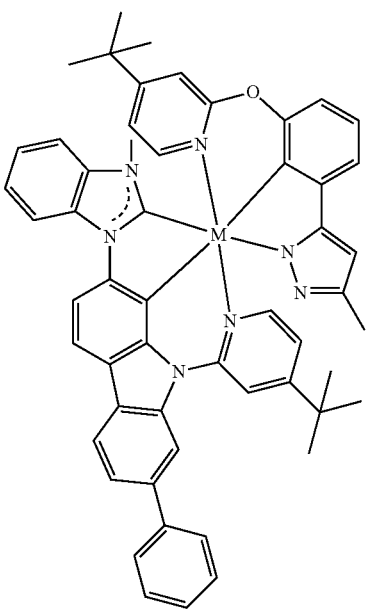
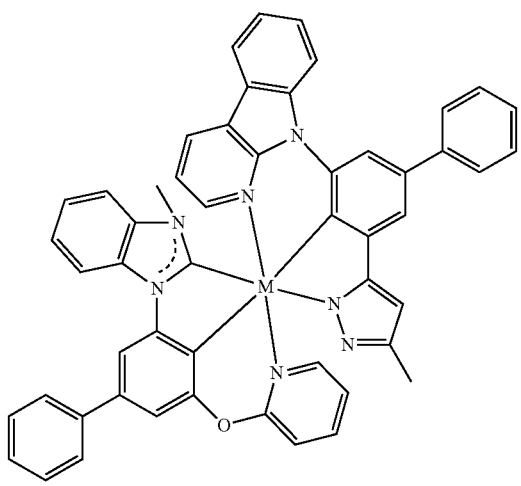

317
-continued
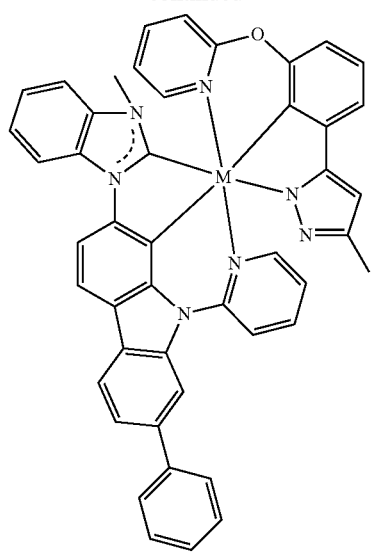
Structures M-21 (M = Ir, Rh)
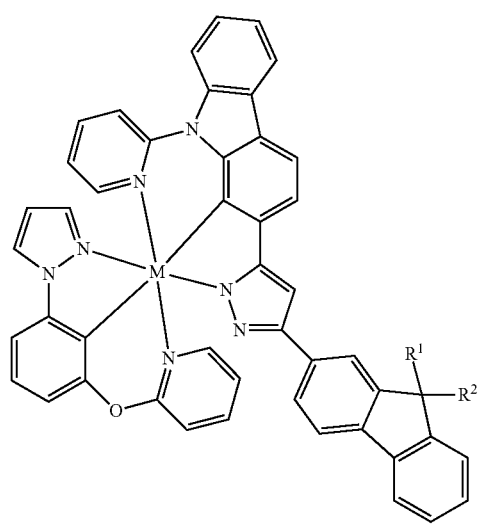
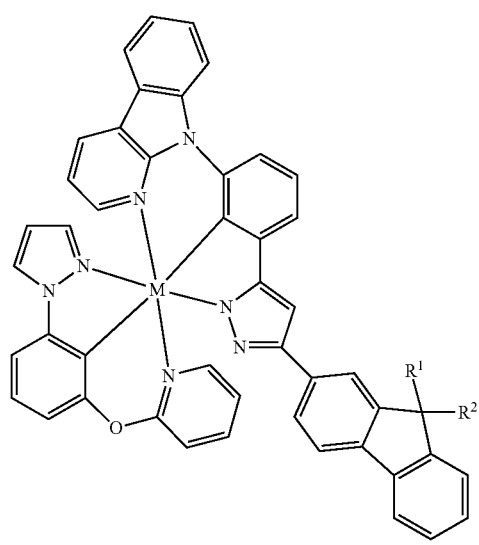
318
-continued
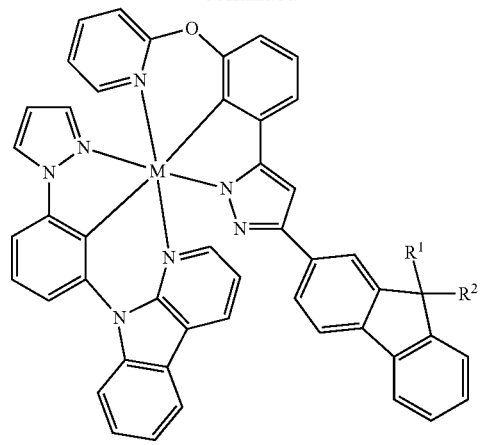
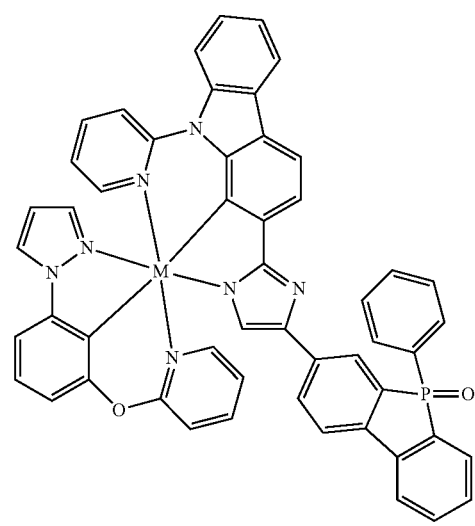
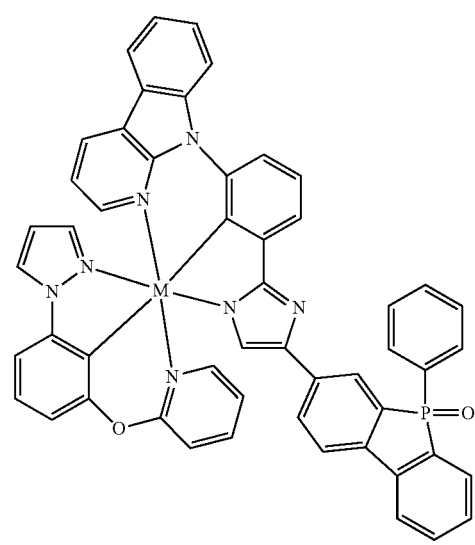

319
-continued
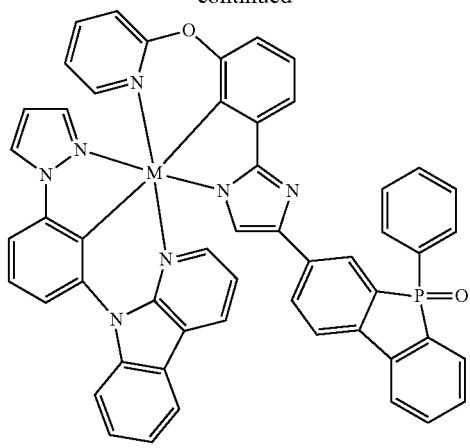
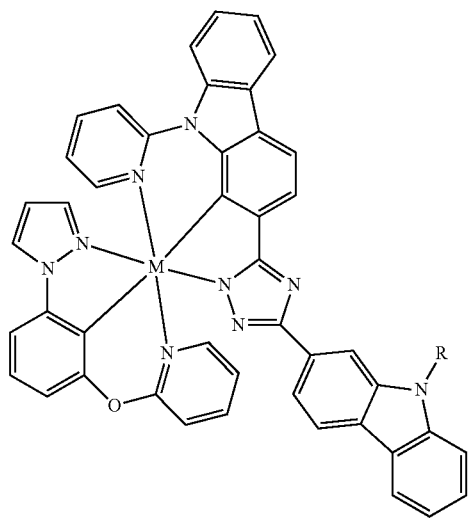
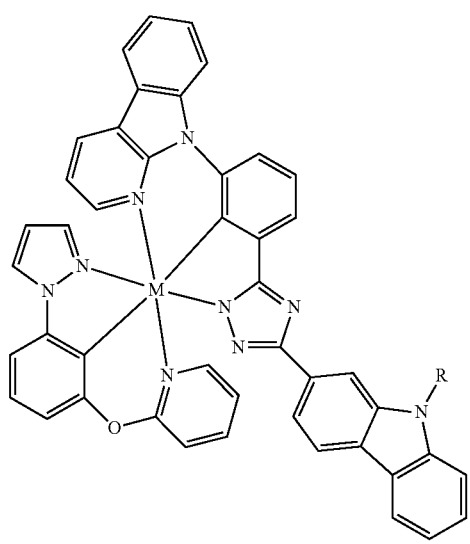
320
-continued
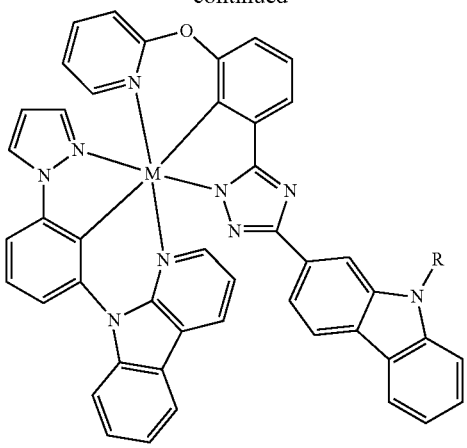
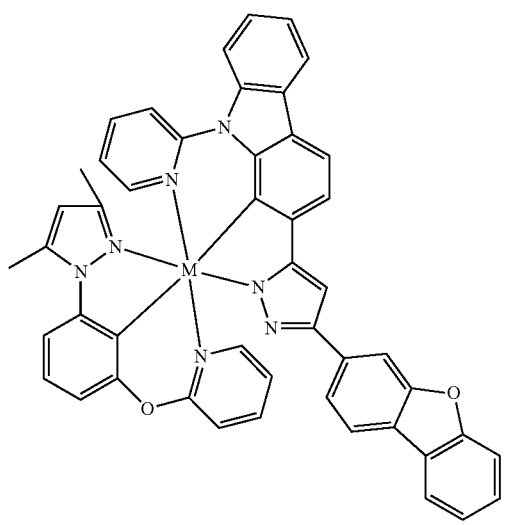
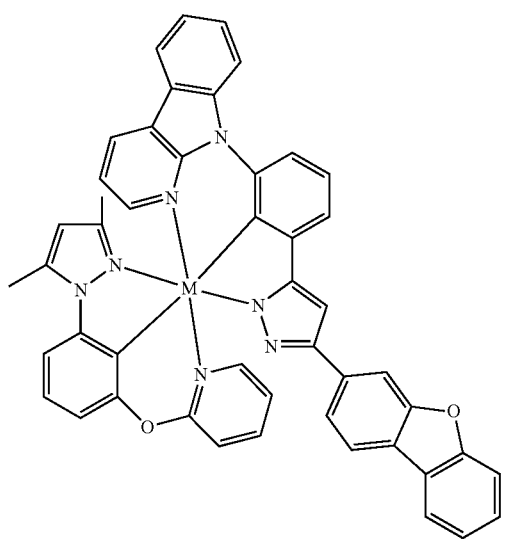

321
-continued
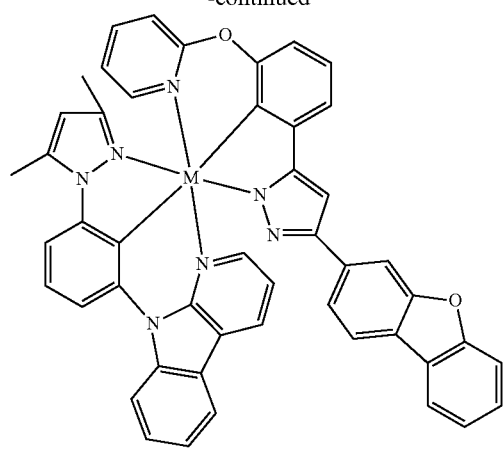
322
-continued
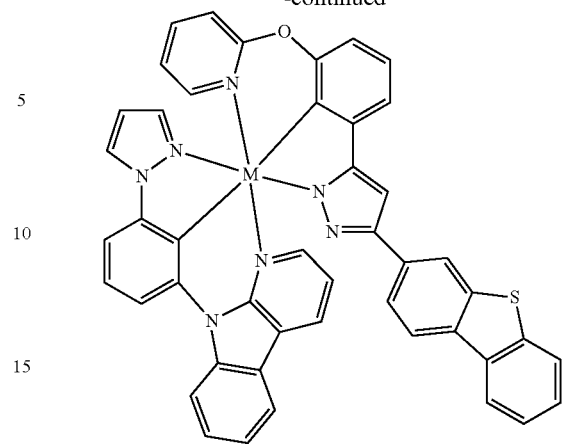
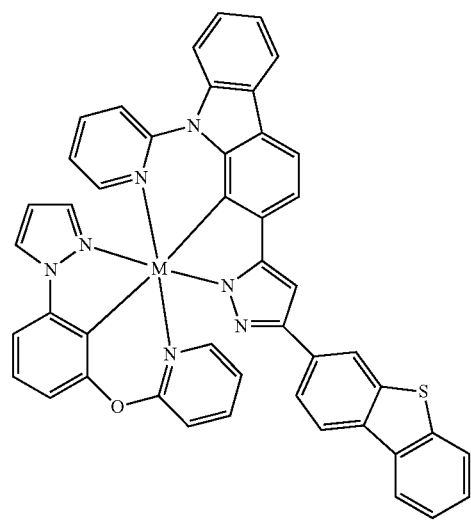
Structures M-22 (M = Ir, Rh)
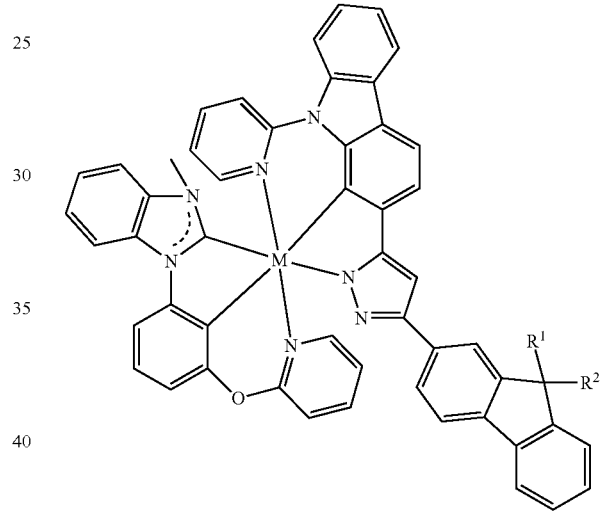
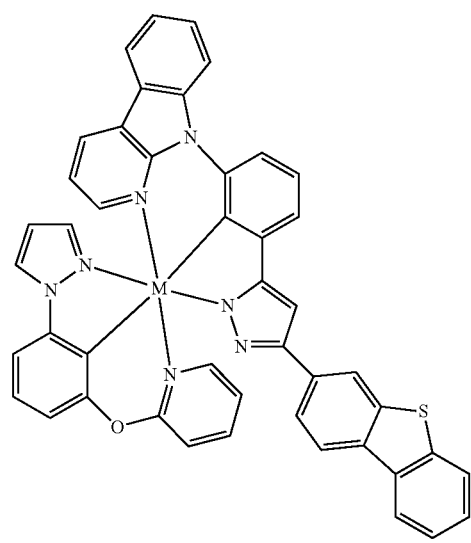
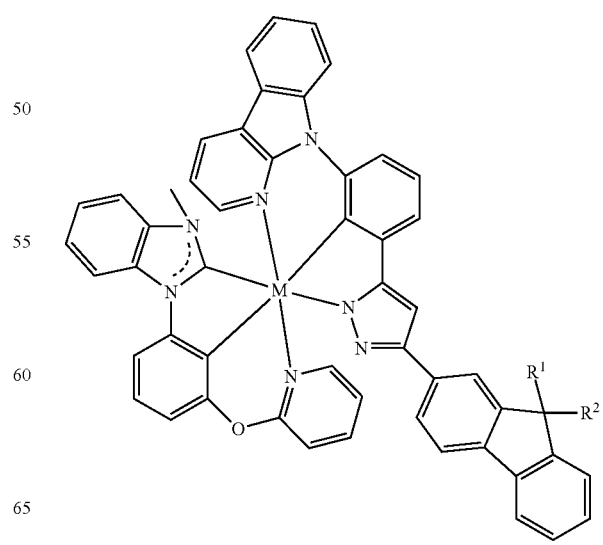

323
-continued
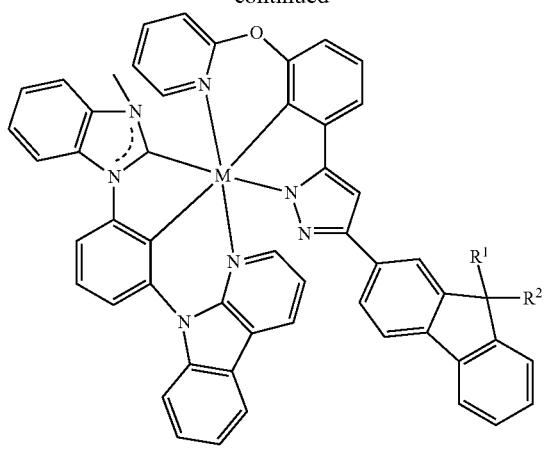
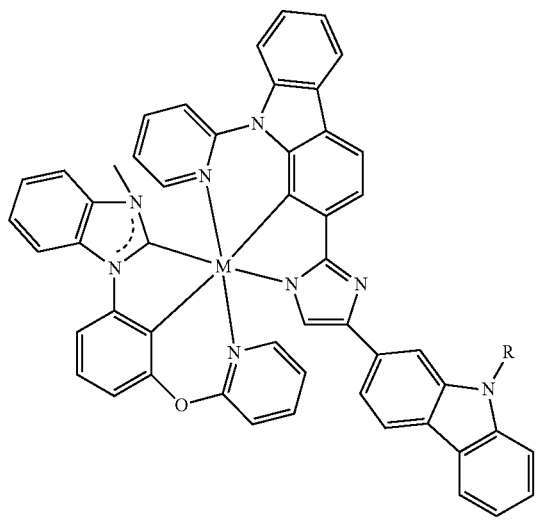
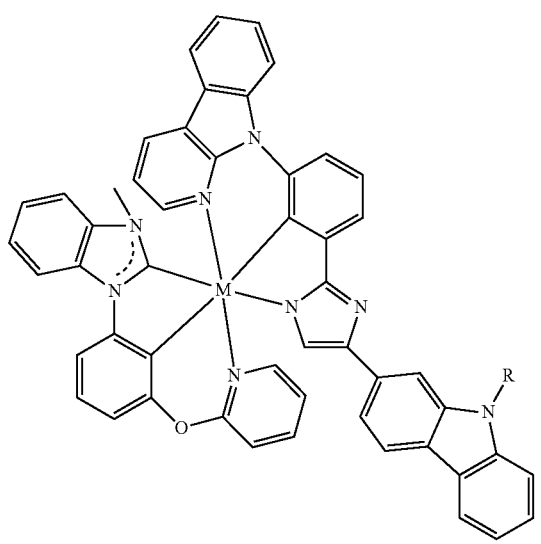
324
-continued
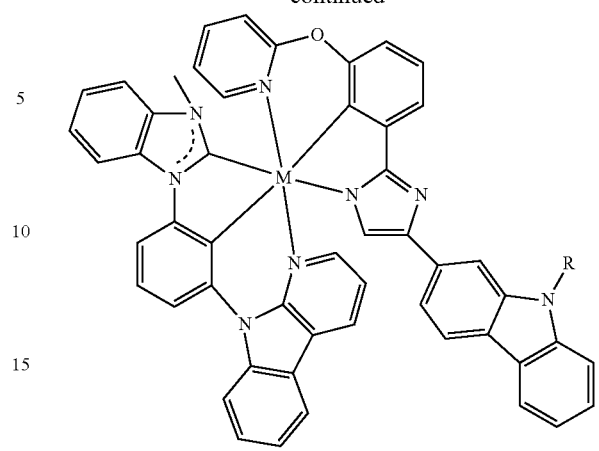
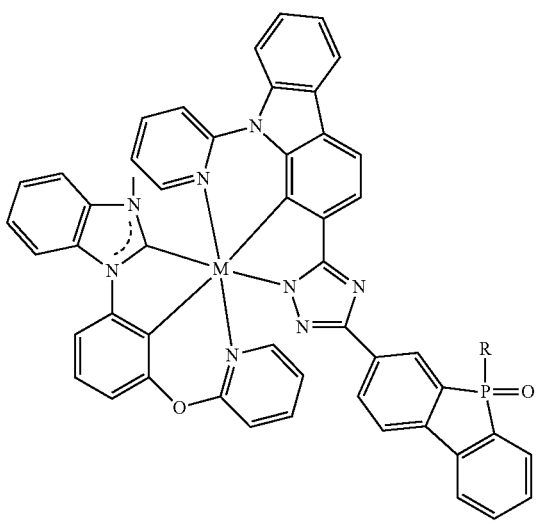

325
-continued
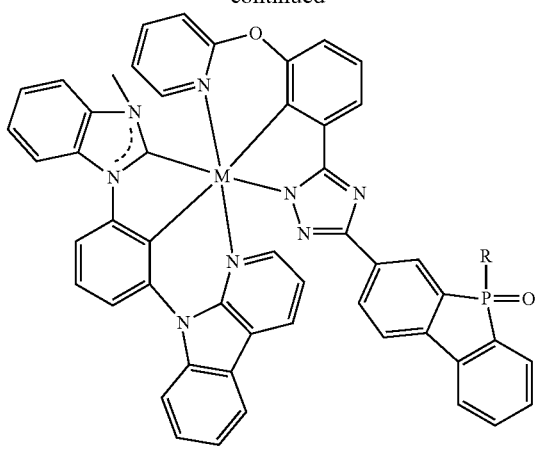
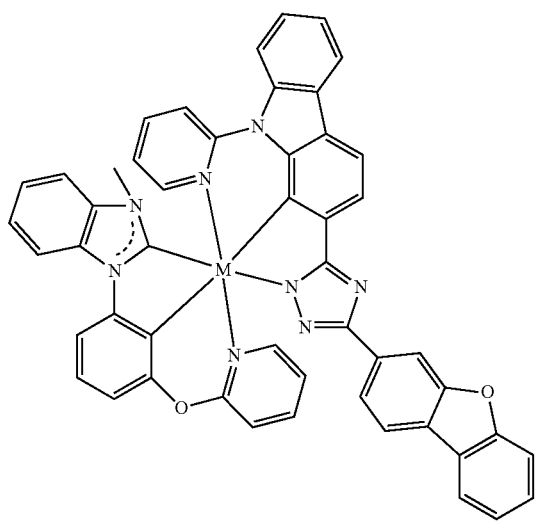
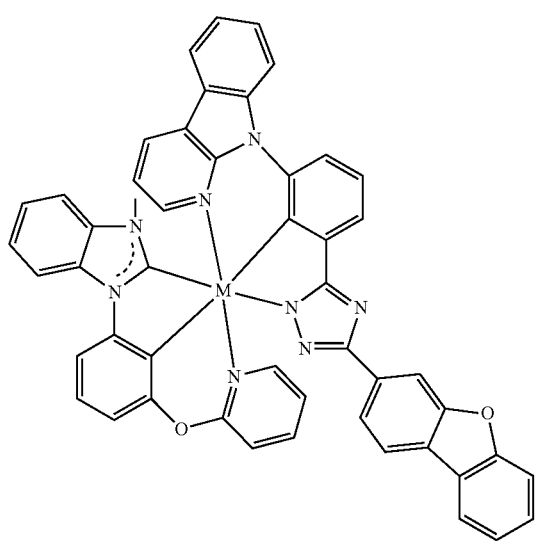
326
-continued
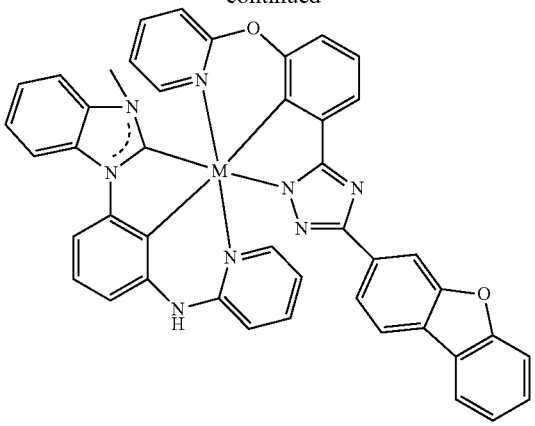
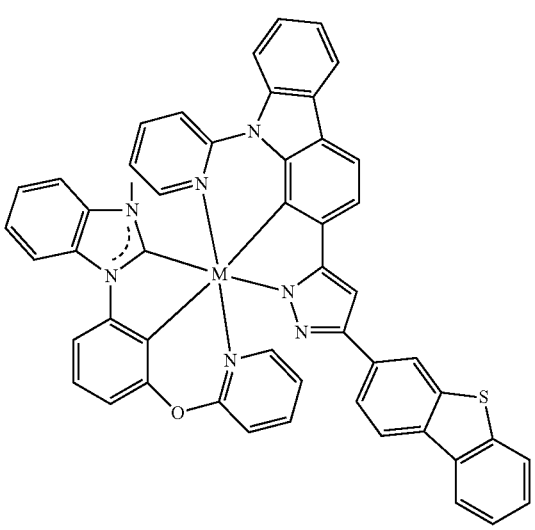

327
-continued
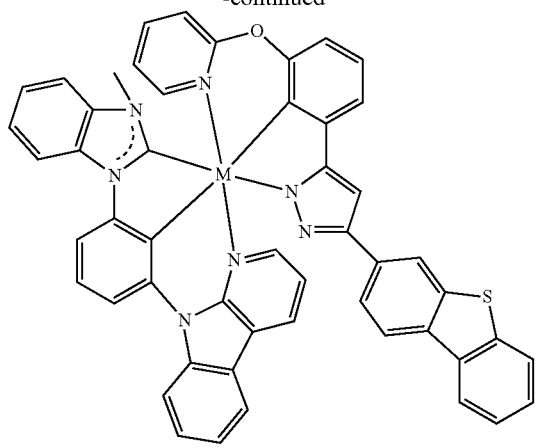
328
-continued
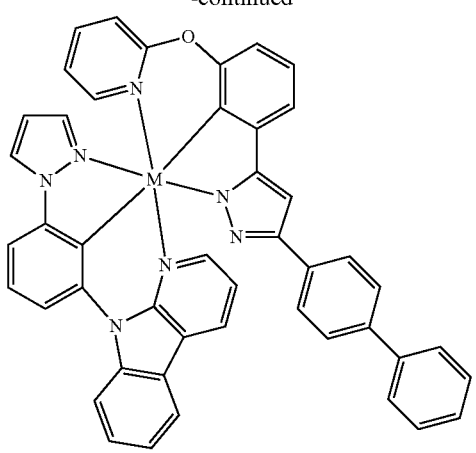
Structures M-23 (M = Ir, Rh)
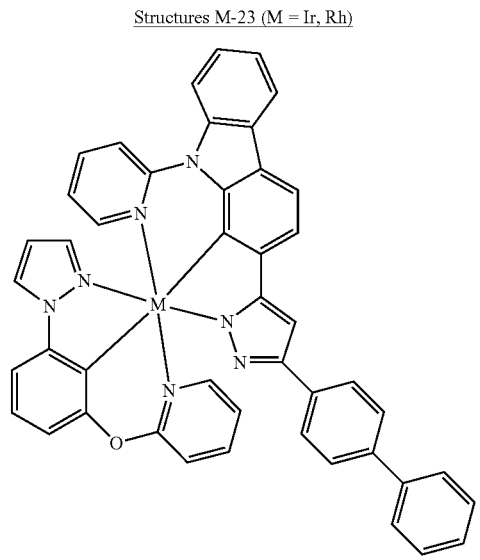
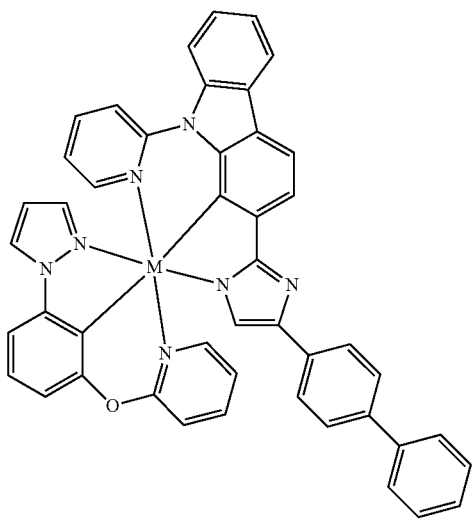
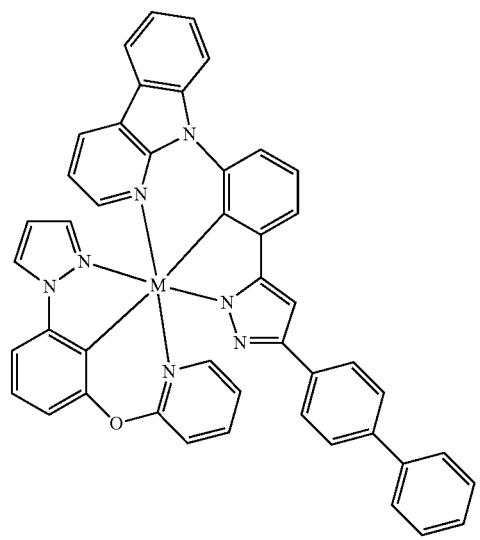
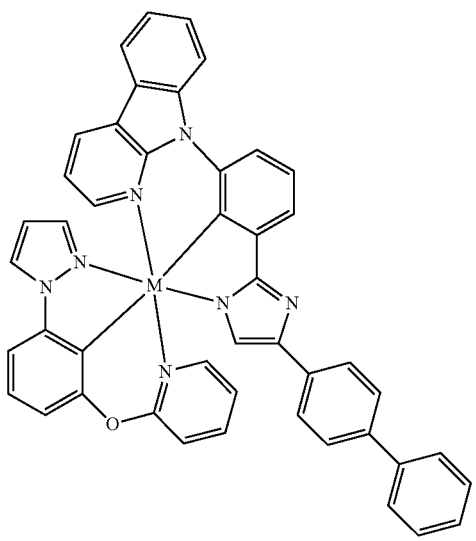

| 329 -continued | 330 -continued |
|---|---|
| 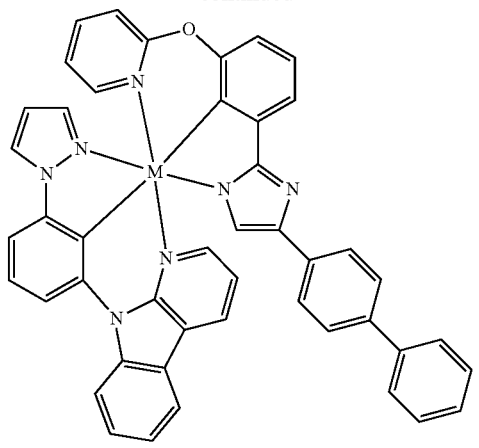 | 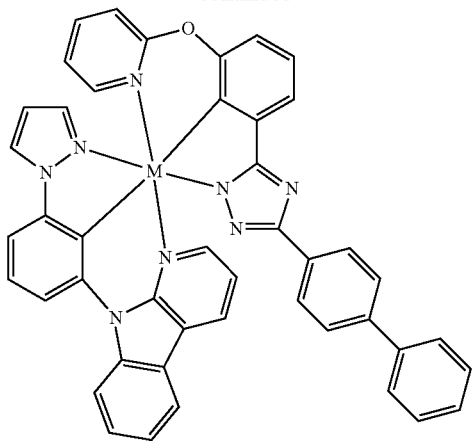 |
| 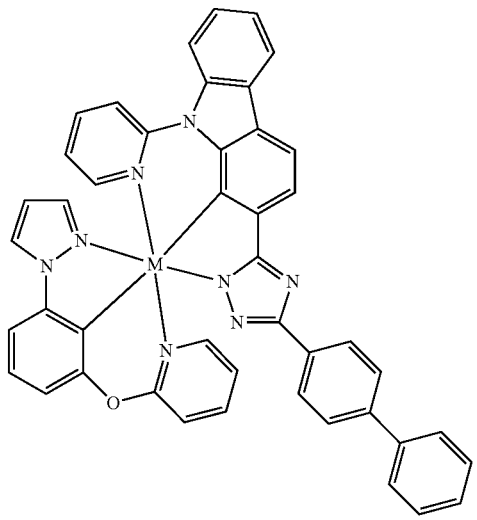 | 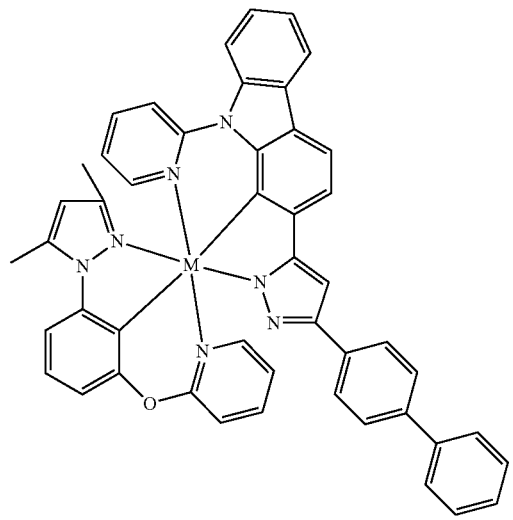 |
| 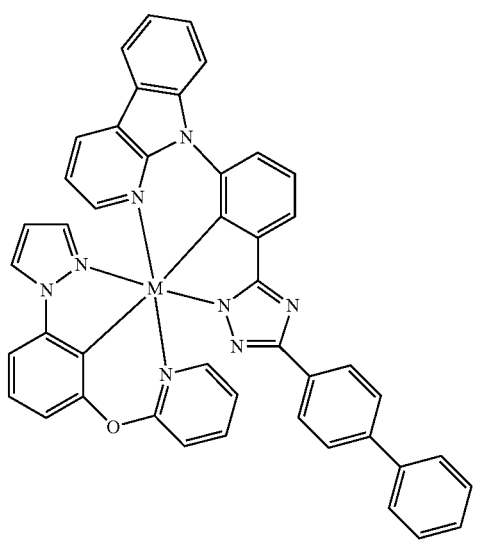 | 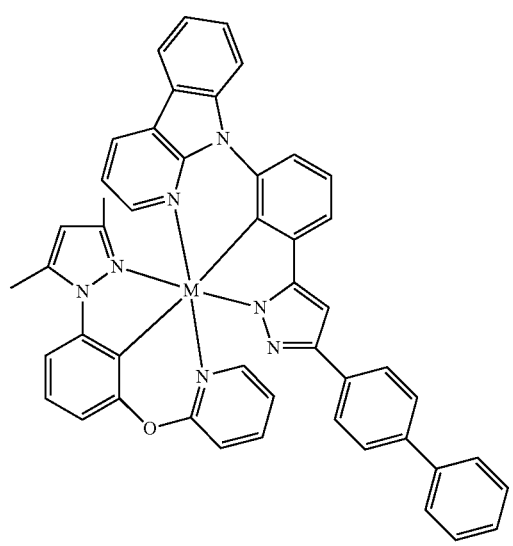 |

331
-continued
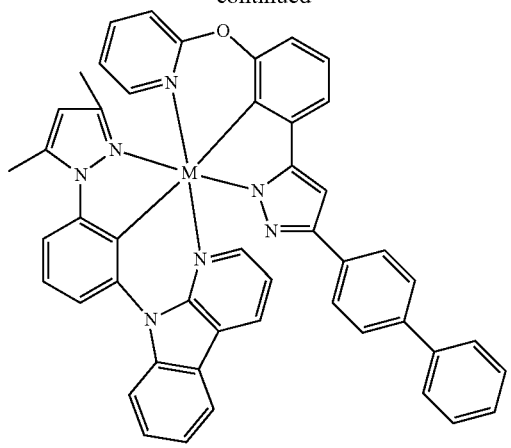
332
-continued
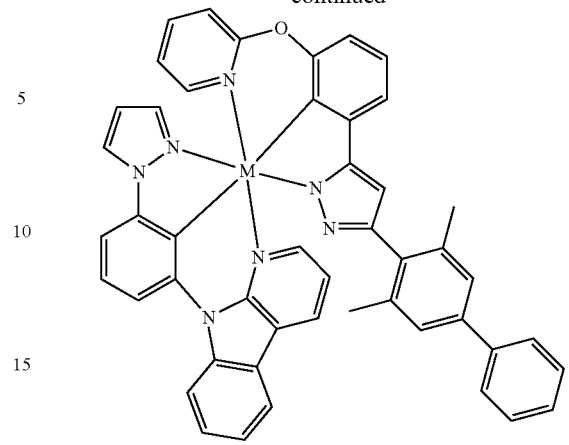
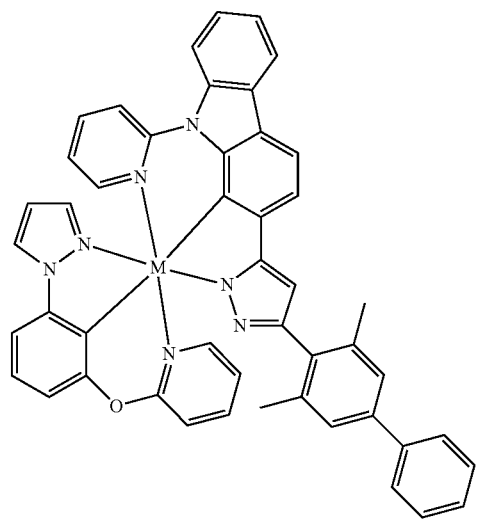
Structures M-24 (M = Ir, Rh)
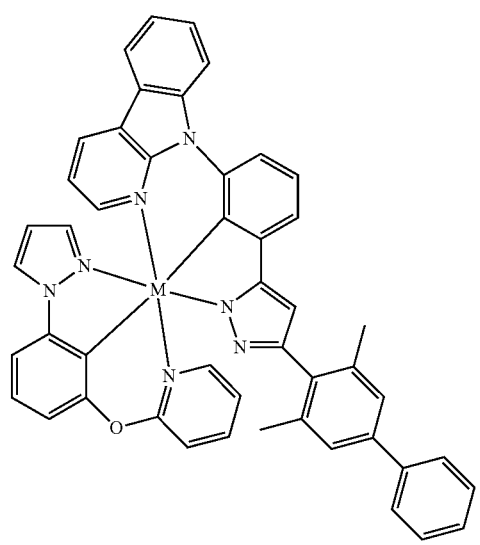

333
-continued
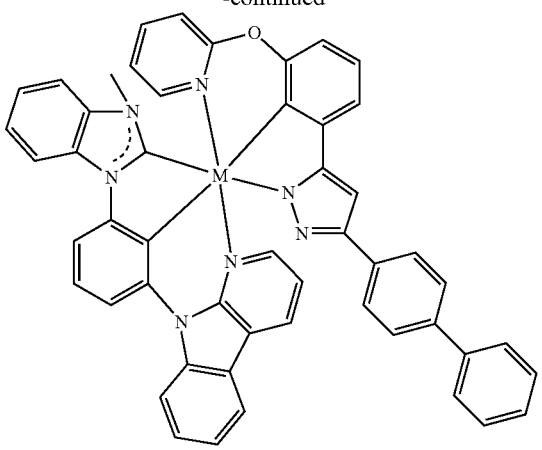
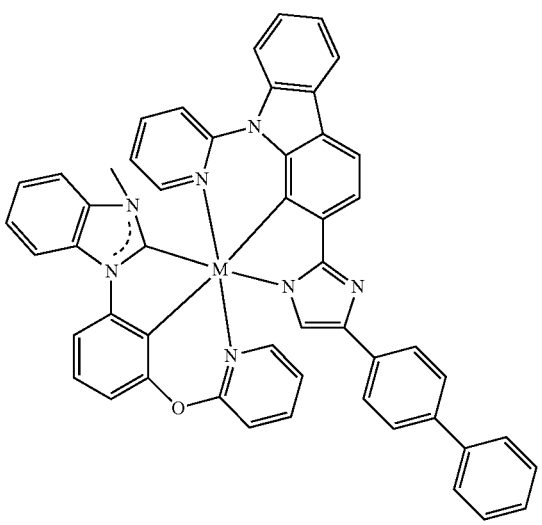
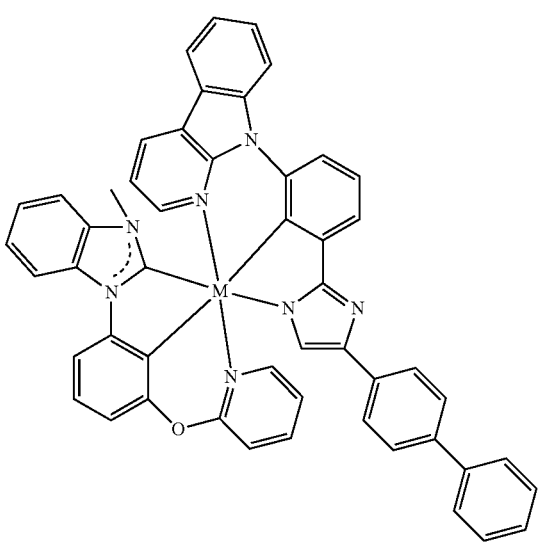
334
-continued
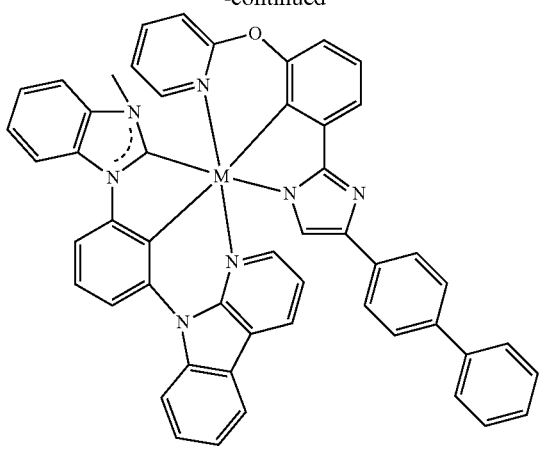
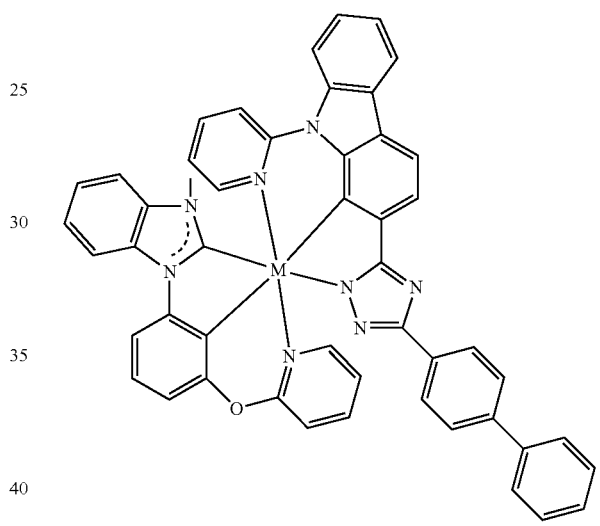
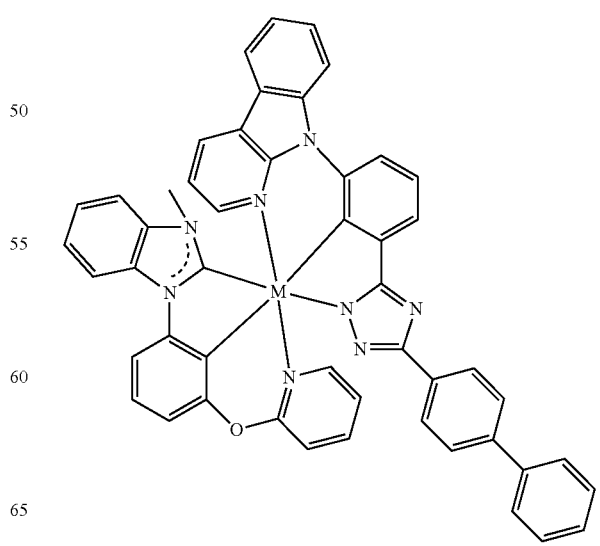

335
-continued
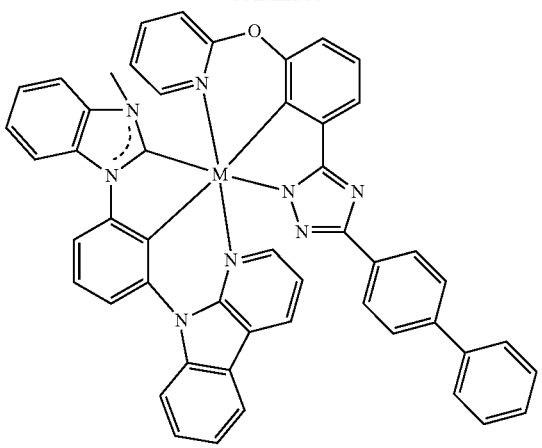
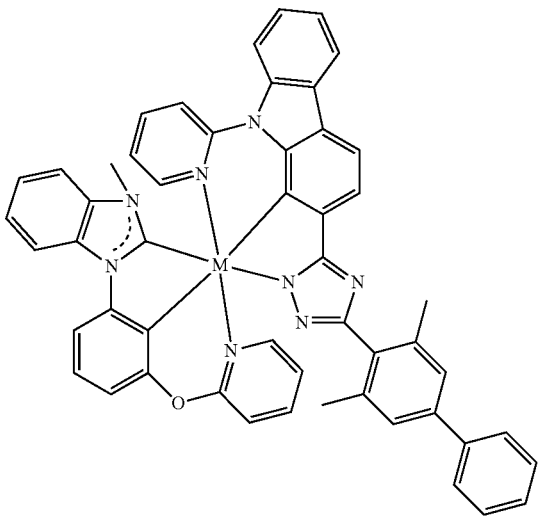
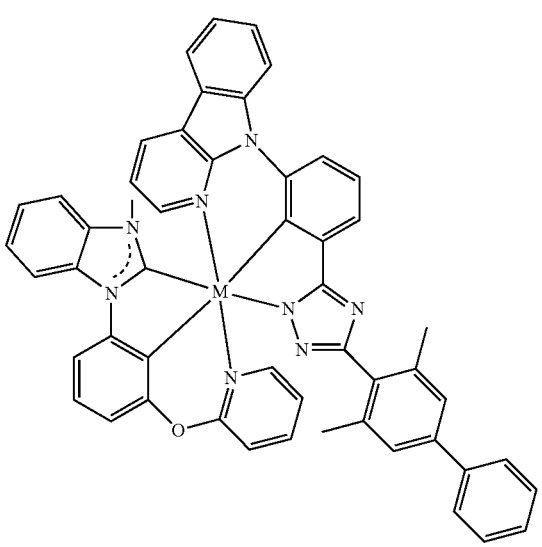
336
-continued
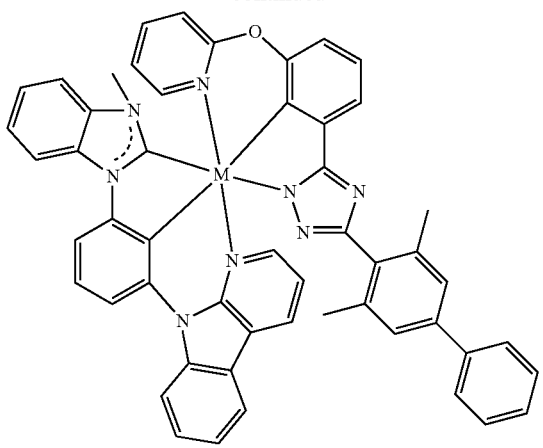
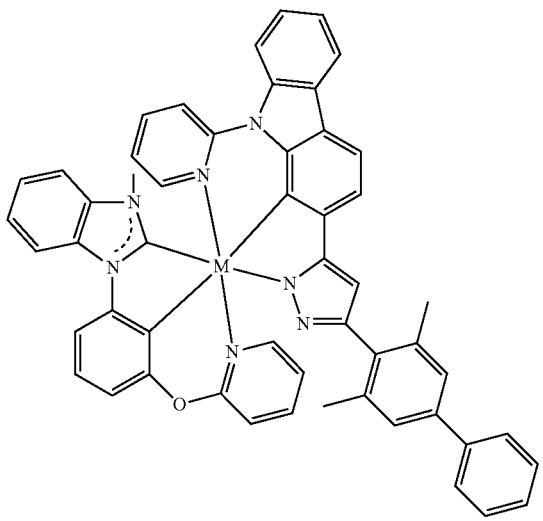
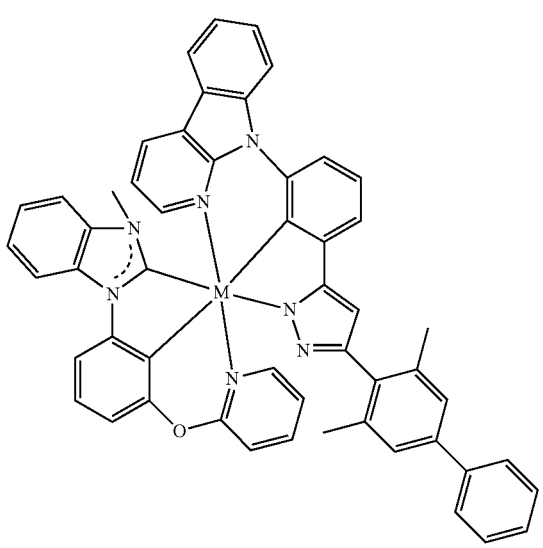

337
-continued
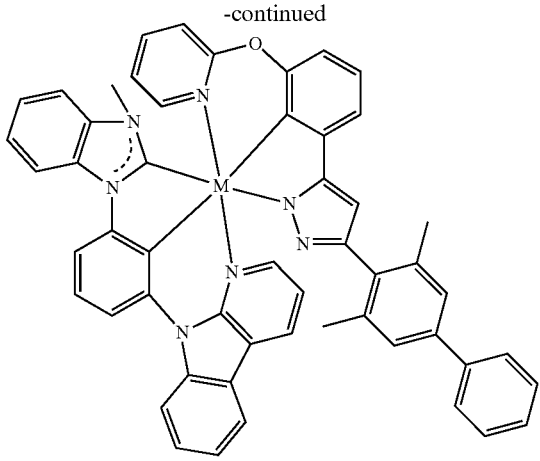
338
-continued
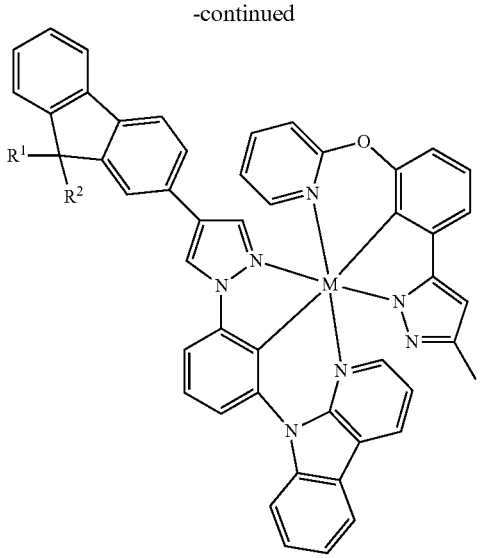
Structures M-25 (M = Ir, Rh)
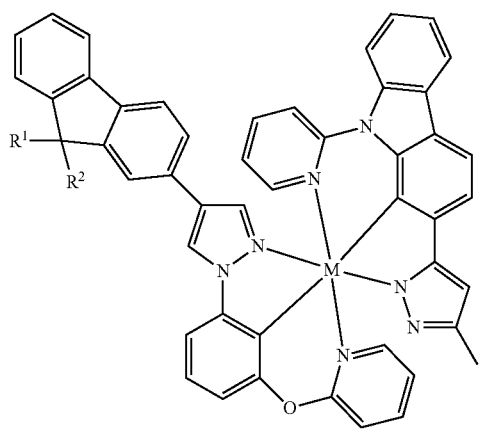
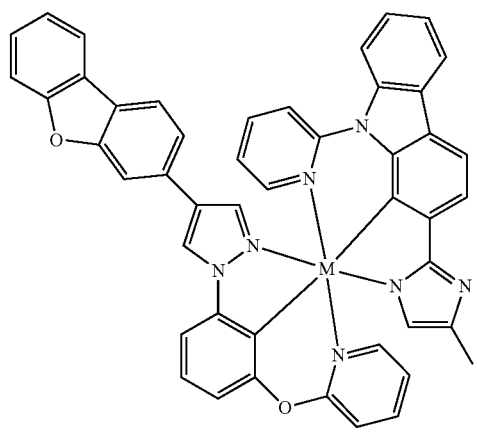
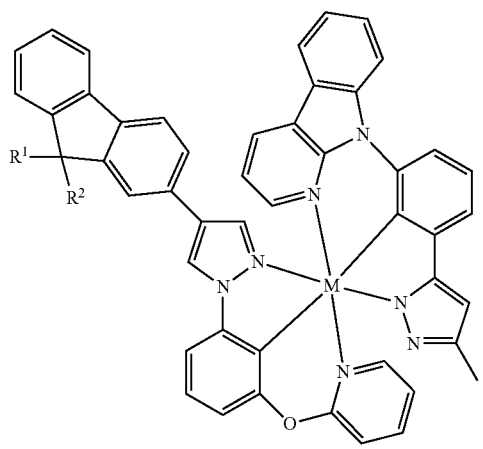
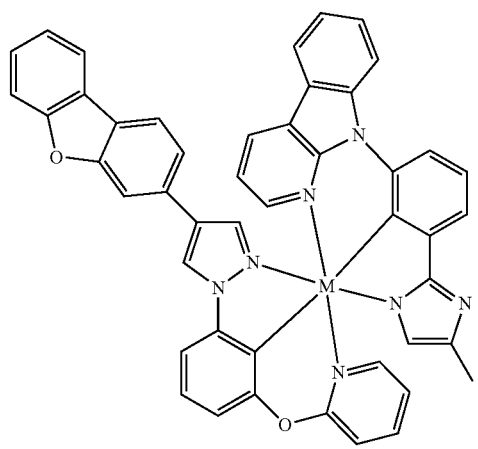

339
-continued
340
-continued
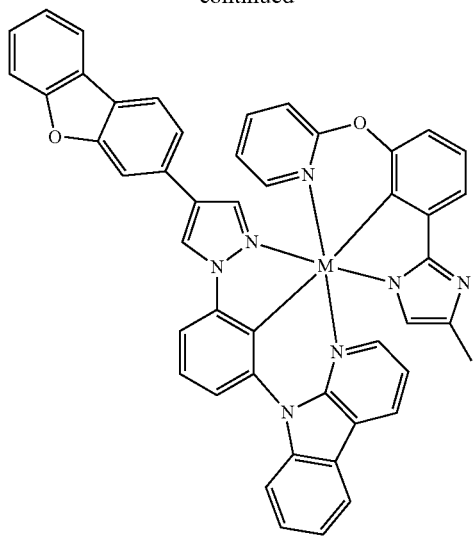
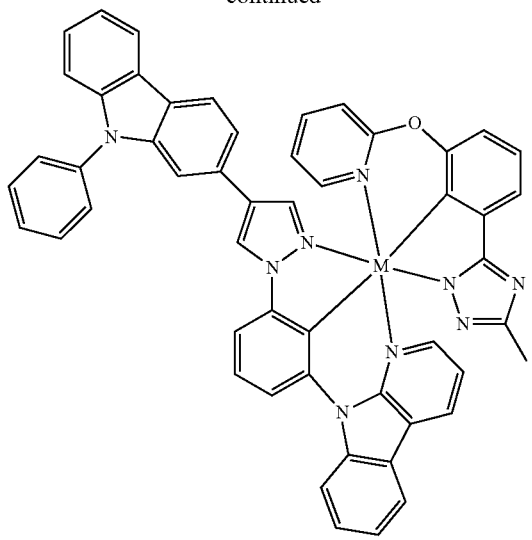
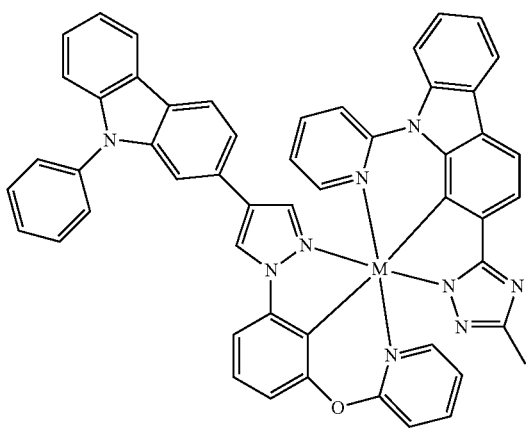
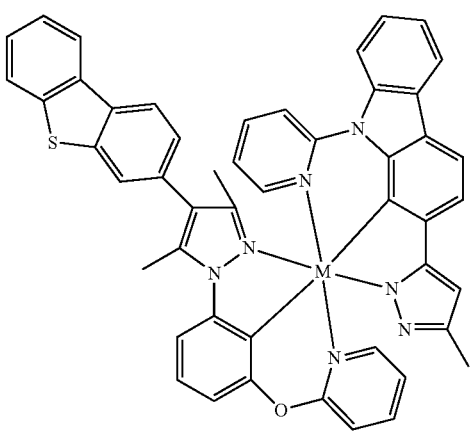
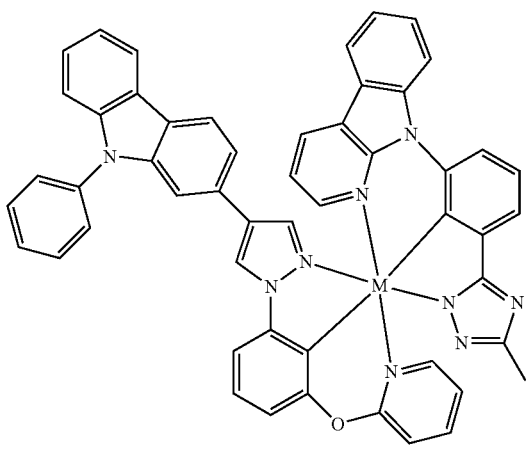

341
-continued
342
-continued
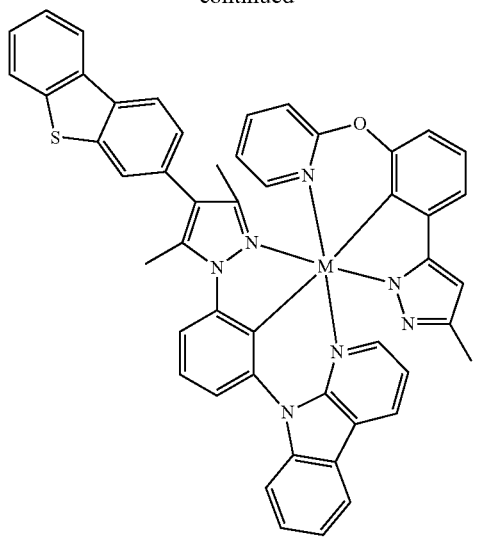
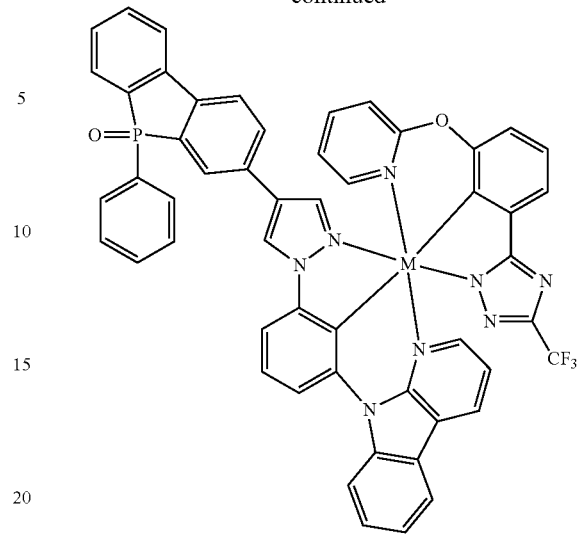
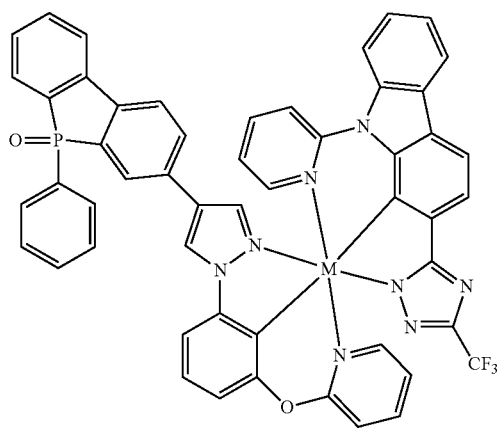
Structures M-26 (M = Ir, Rh)
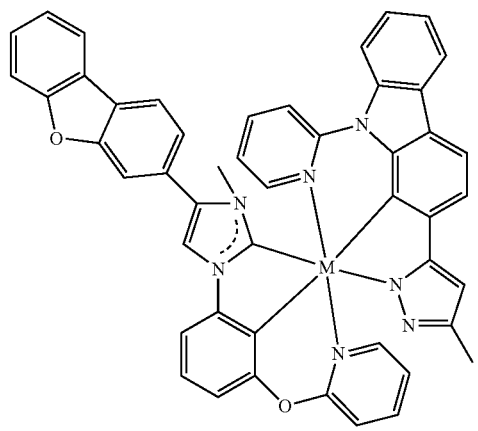
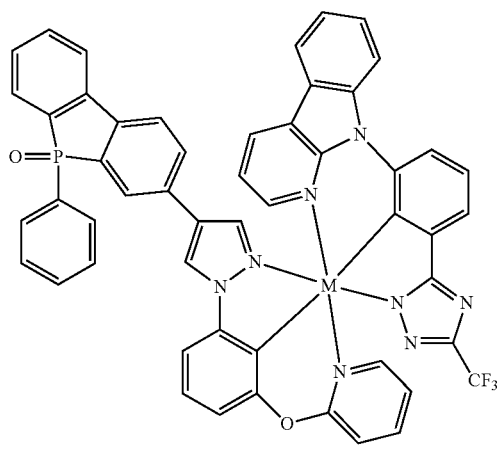
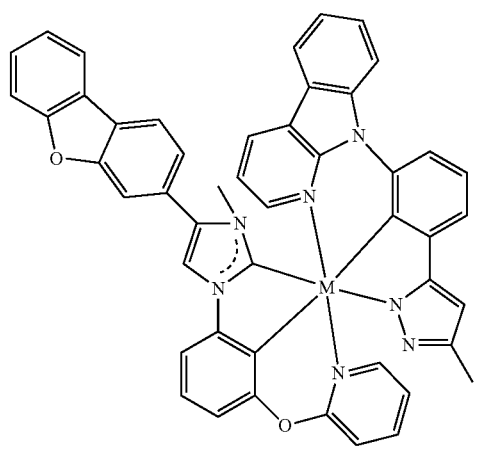

343
-continued
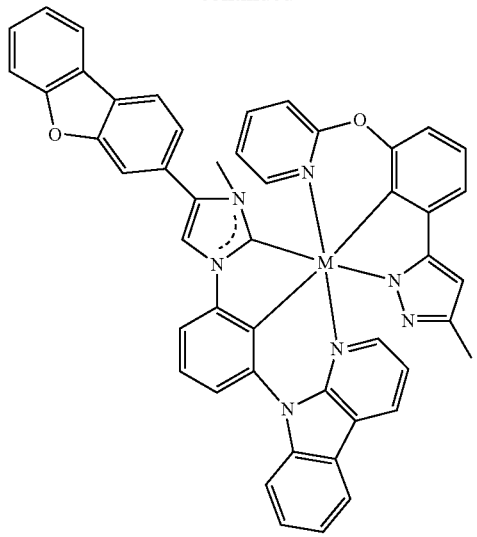
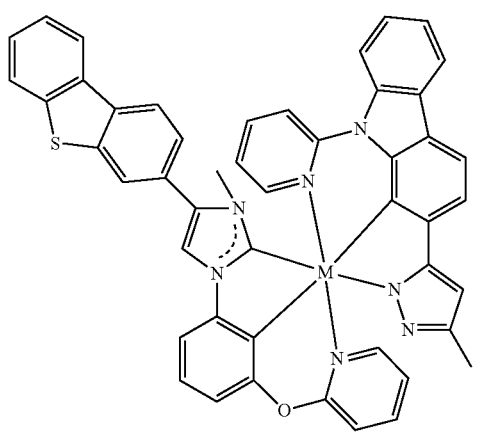
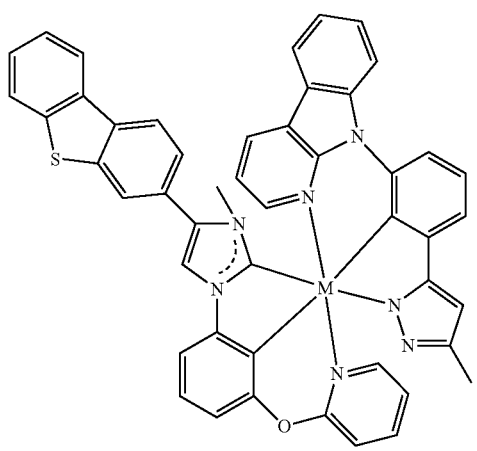
344
-continued
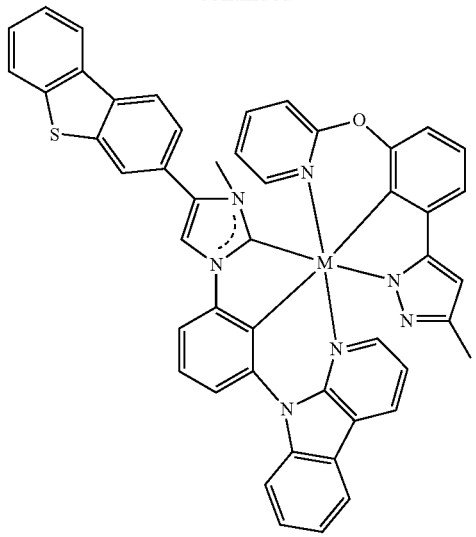
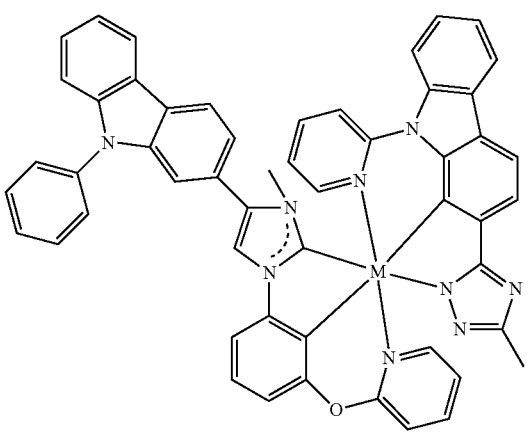
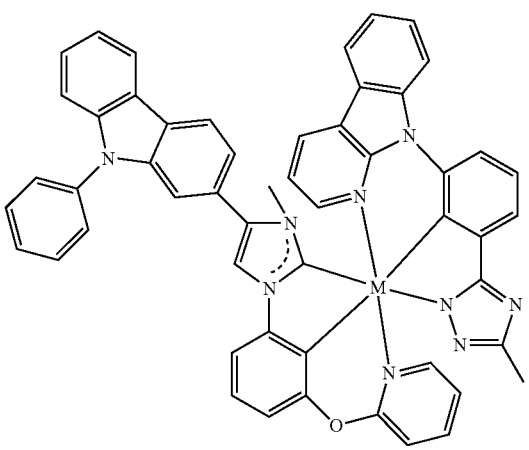

345
-continued
346
-continued
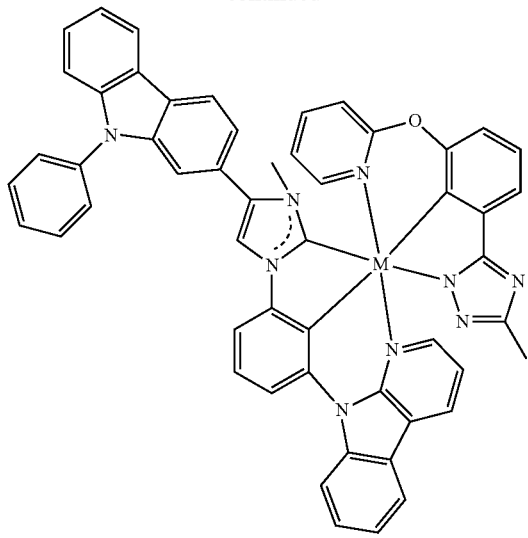
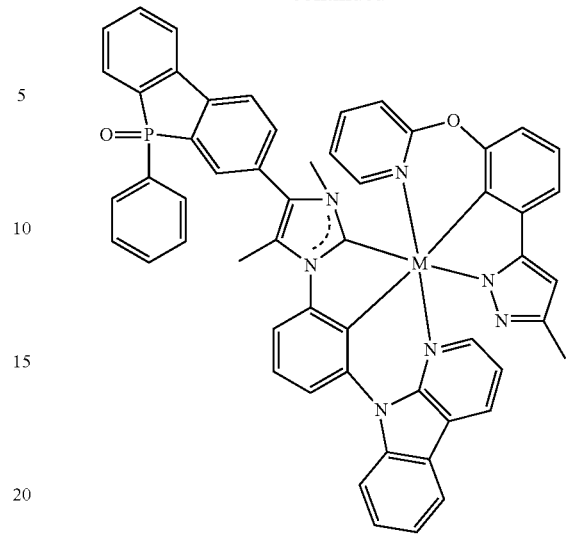
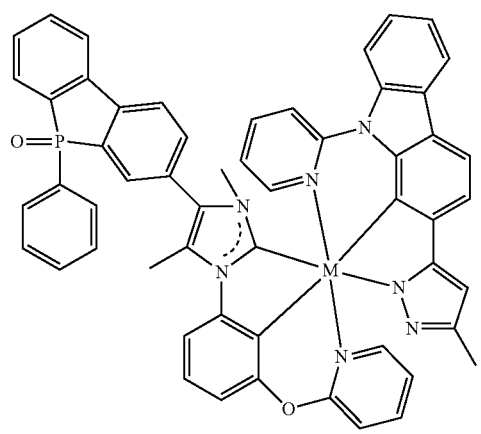
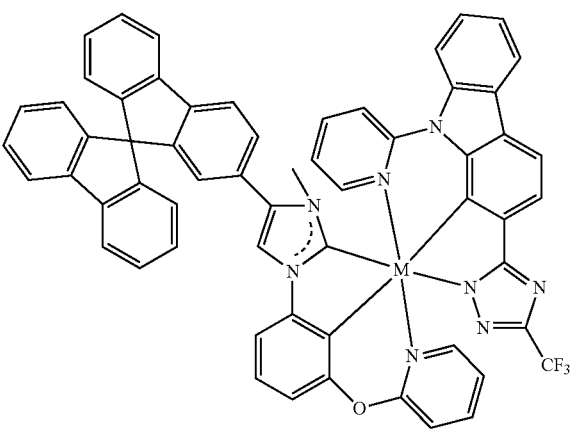
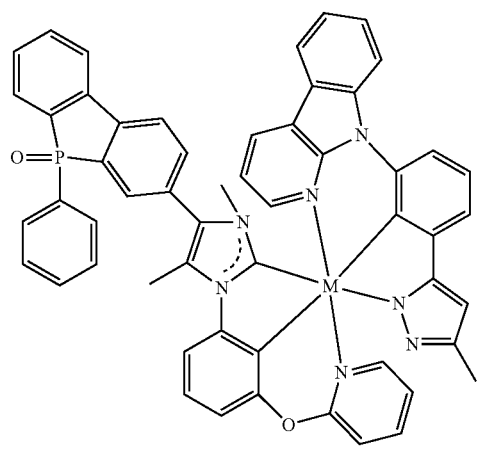
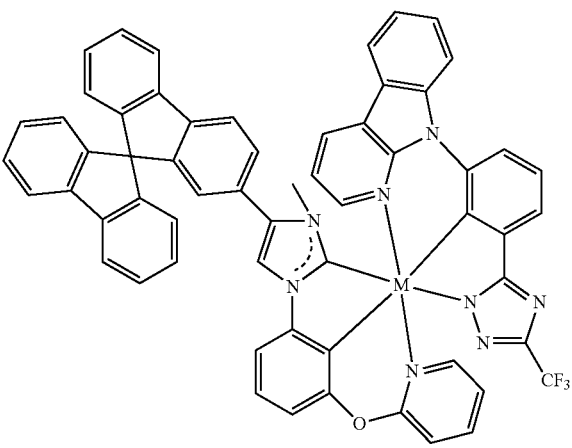

347
-continued
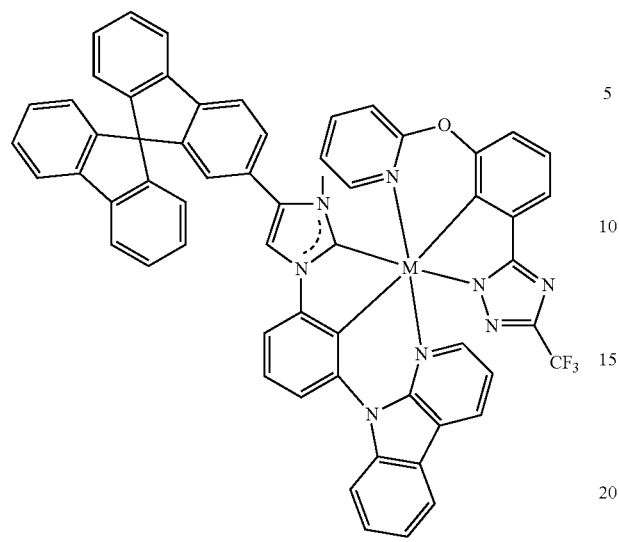
Structures M-27 (M = Ir, Rh)
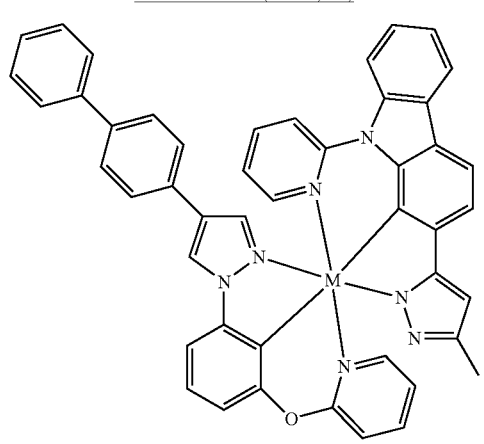
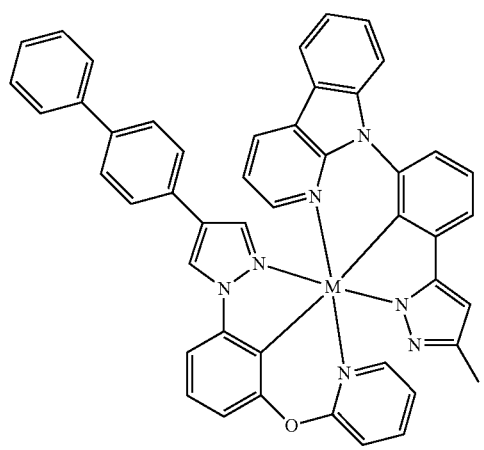
348
-continued
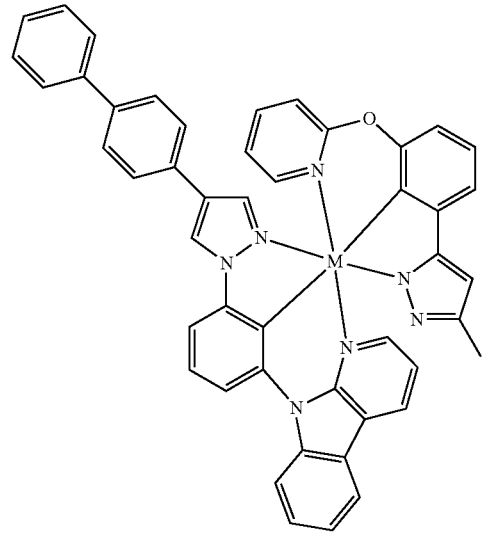
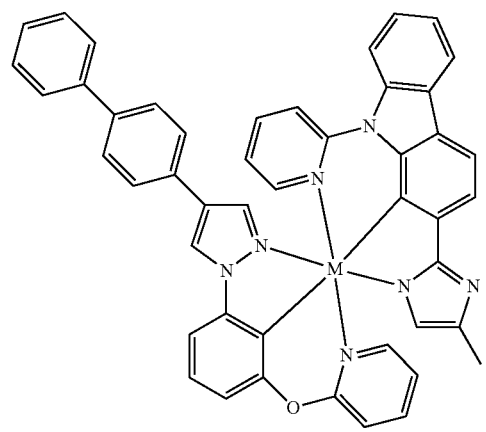
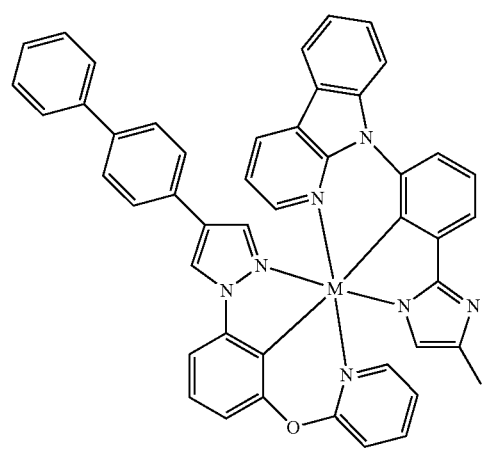

349
-continued
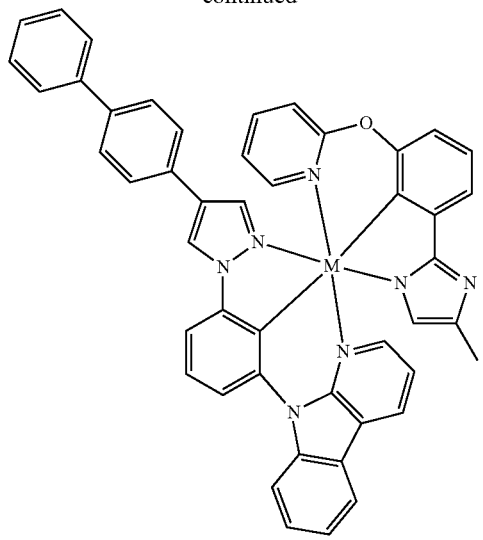
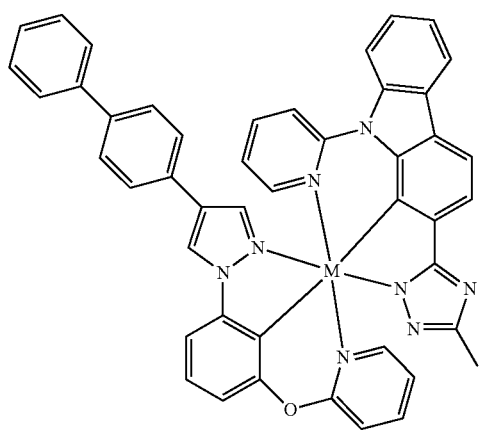
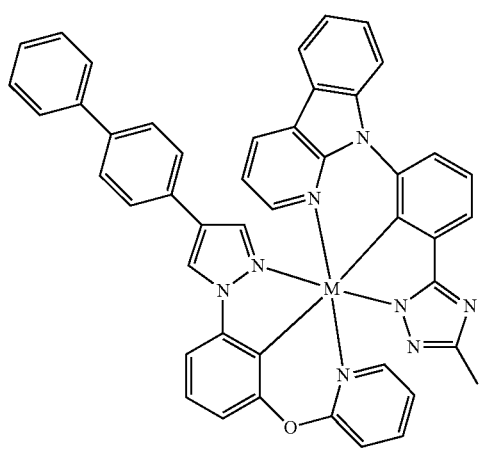
350
-continued
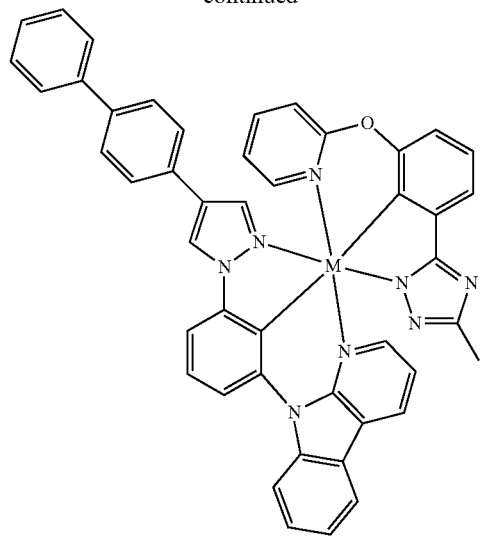
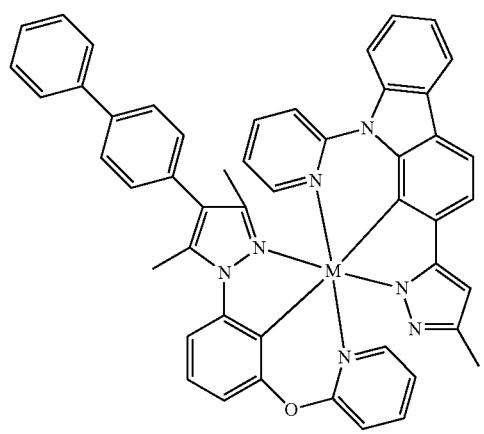
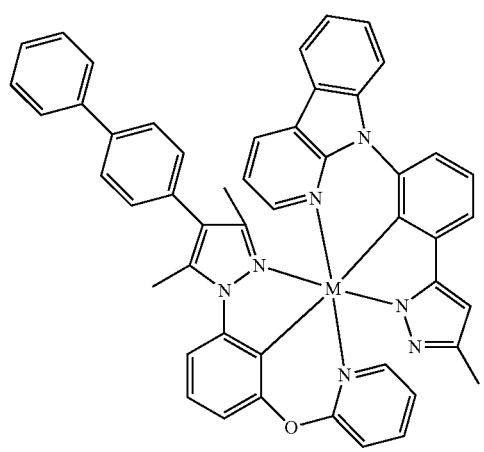

351
-continued
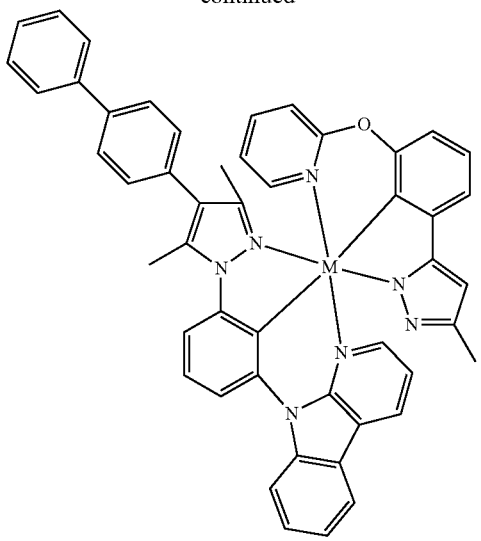
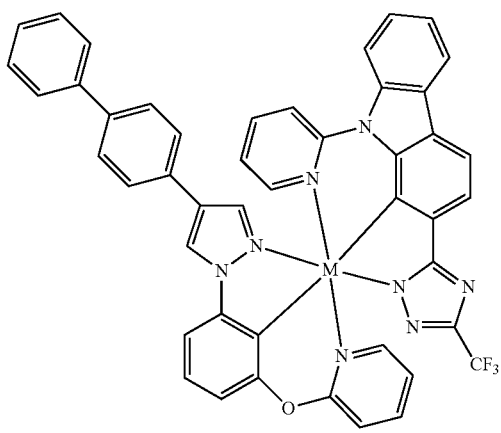
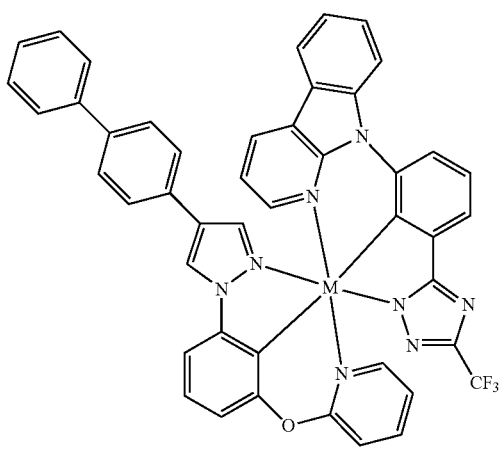
352
-continued
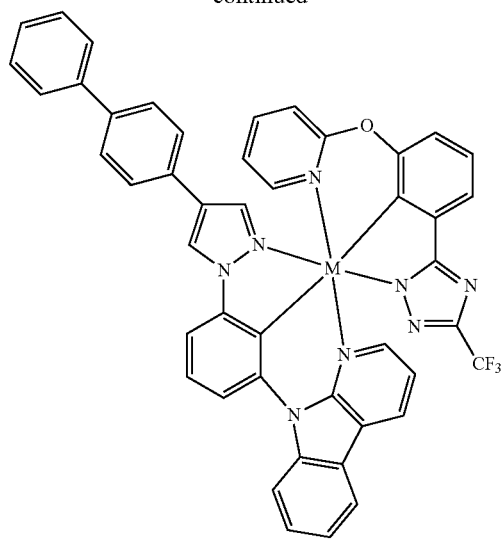
Structures M-28 (M = Ir, Rh)
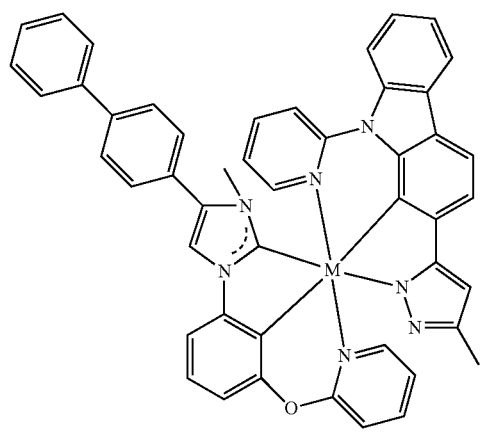
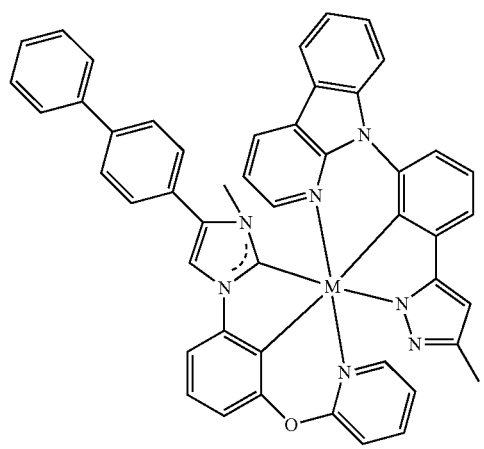

353
-continued
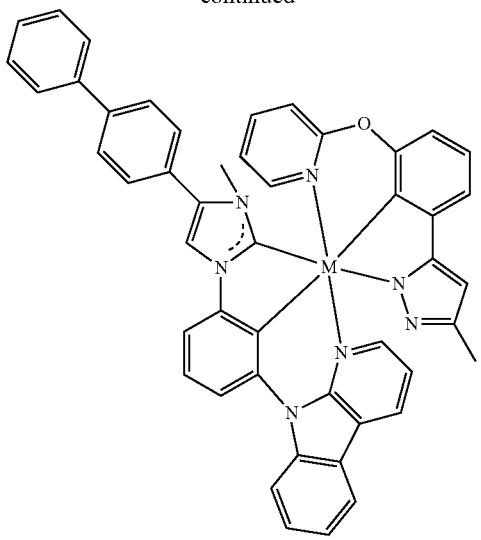
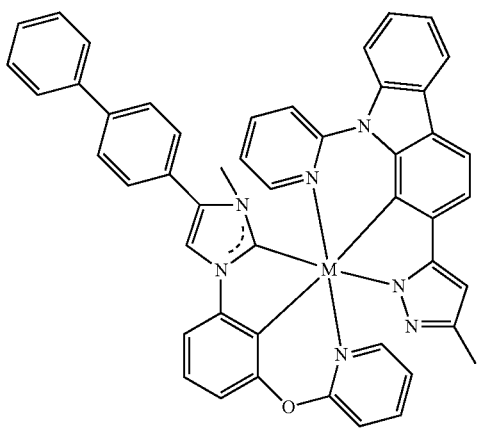
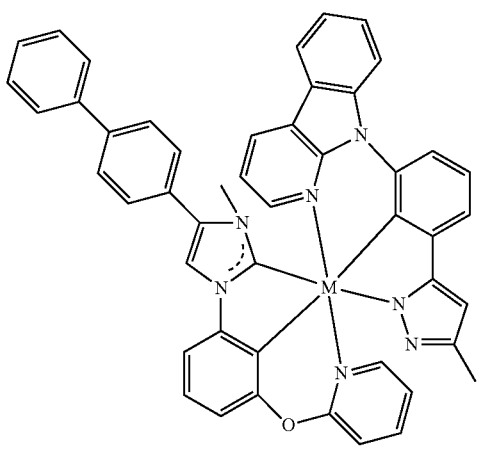
354
-continued
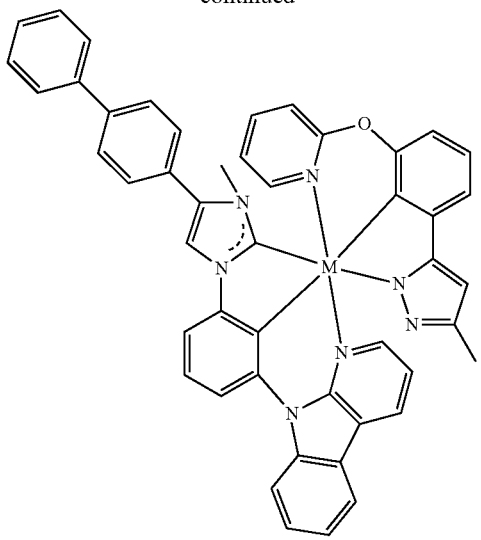
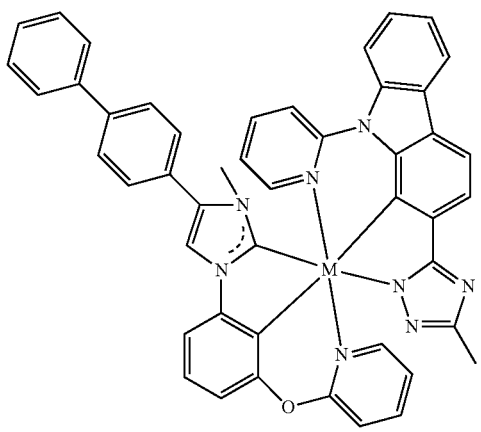
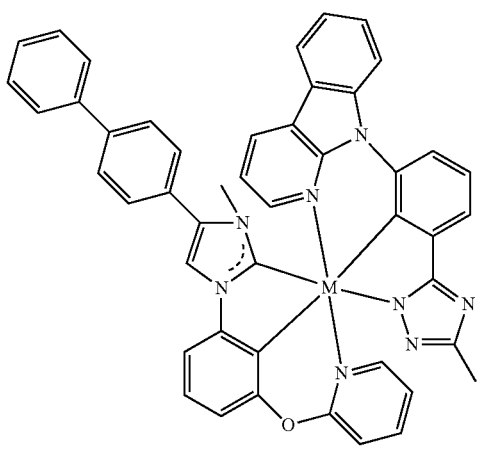

355
-continued
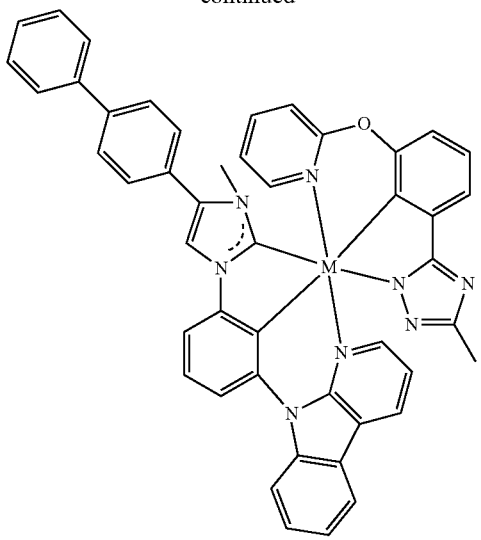
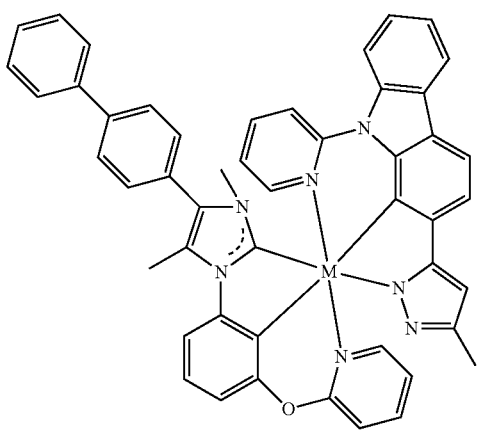
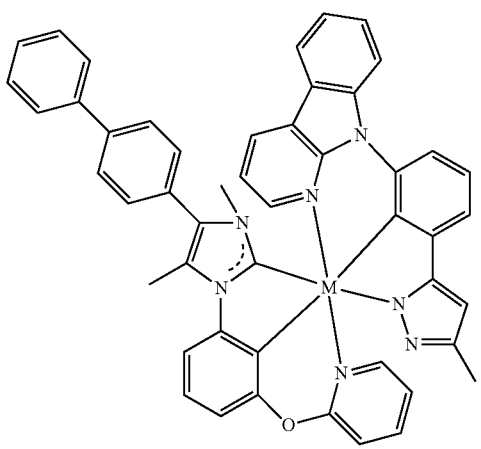
356
-continued
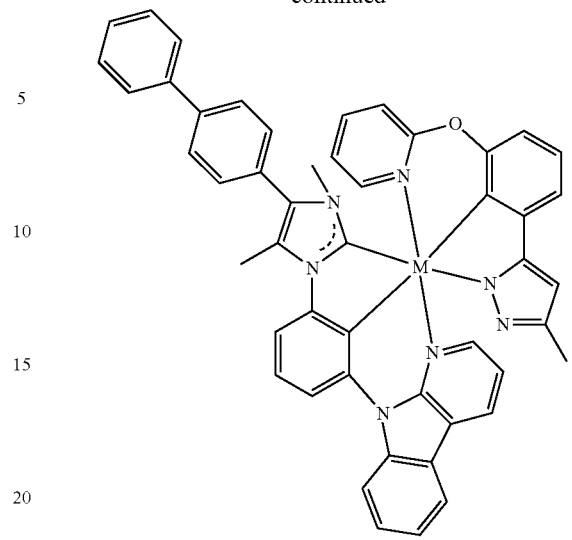
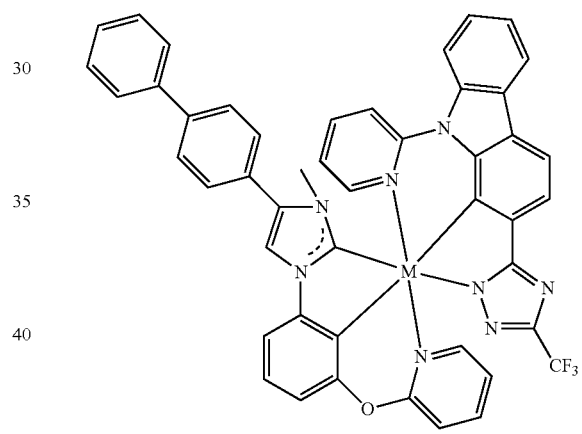
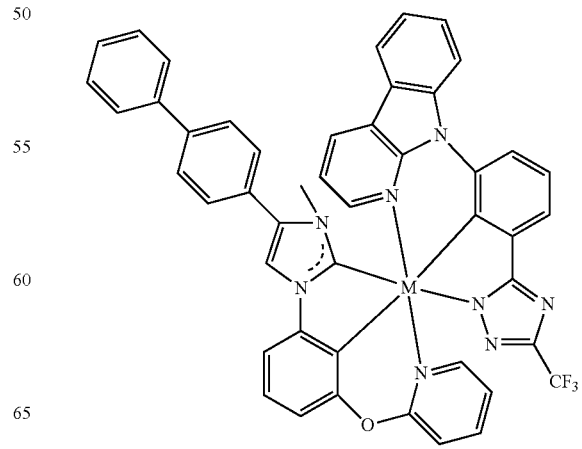

357
-continued
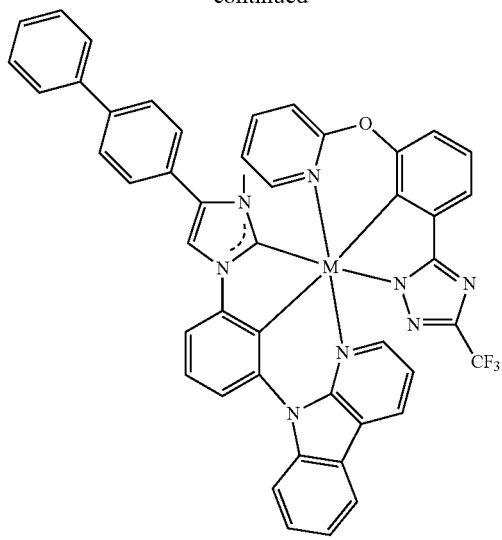
Structures M-29 (M = Ir, Rh)
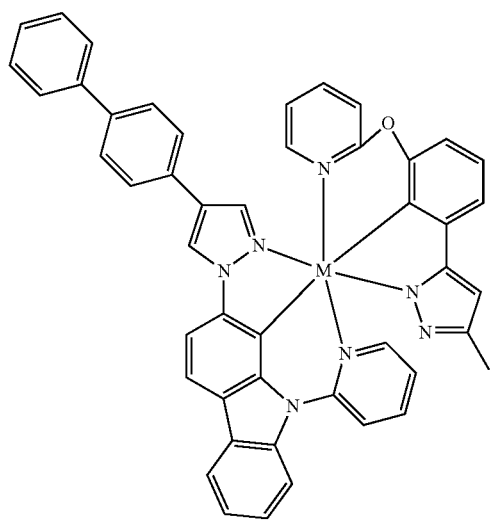
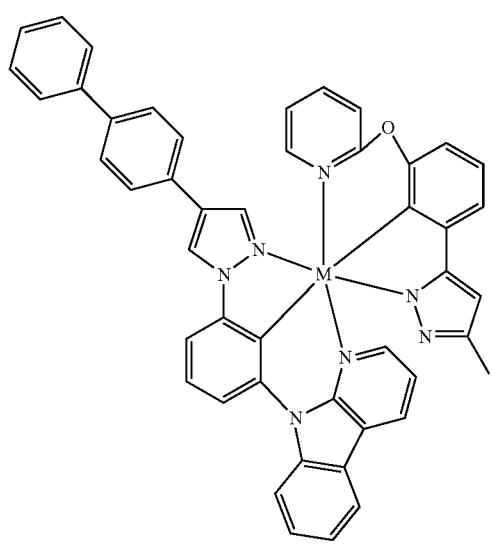
358
-continued
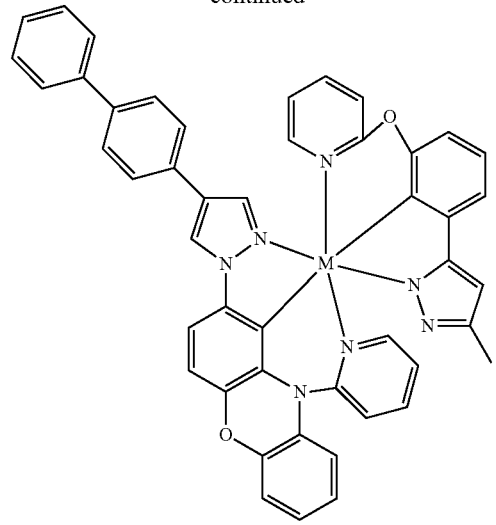
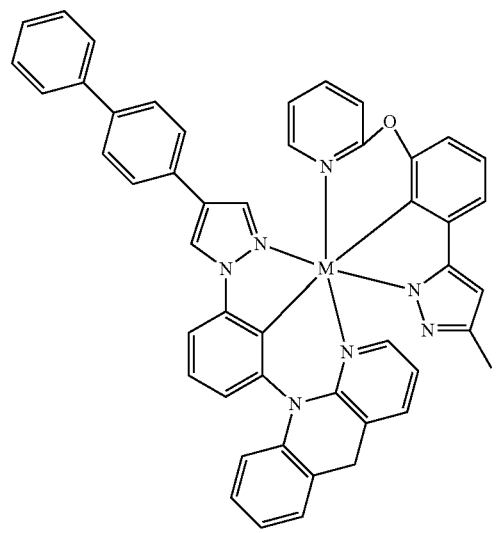
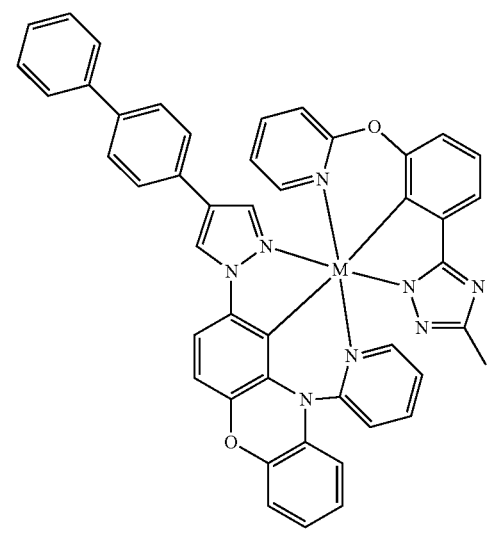

359
-continued
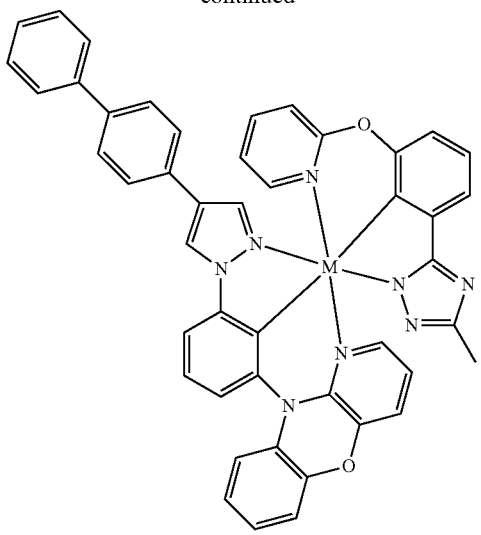
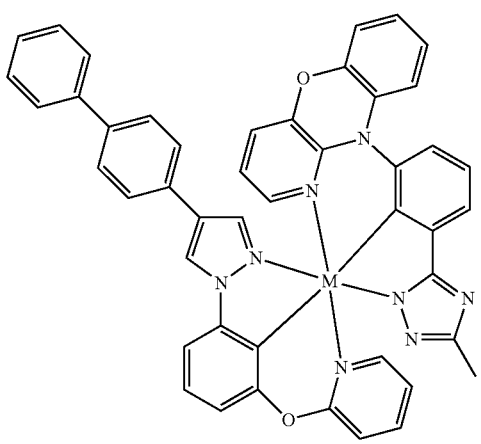
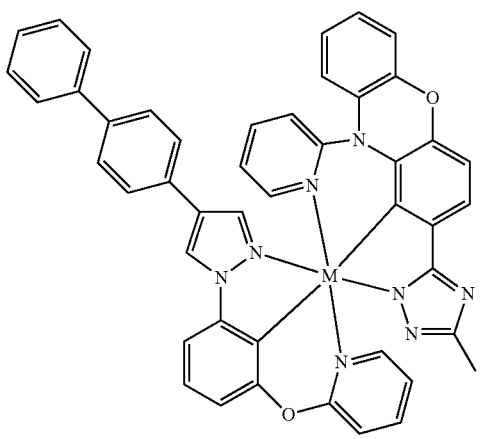
360
-continued
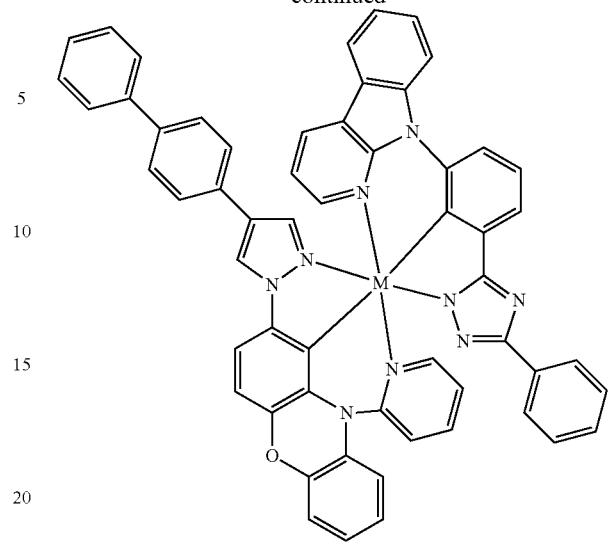
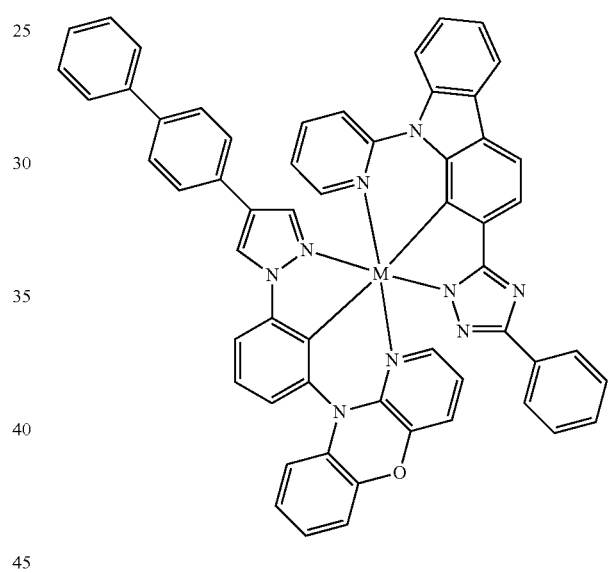
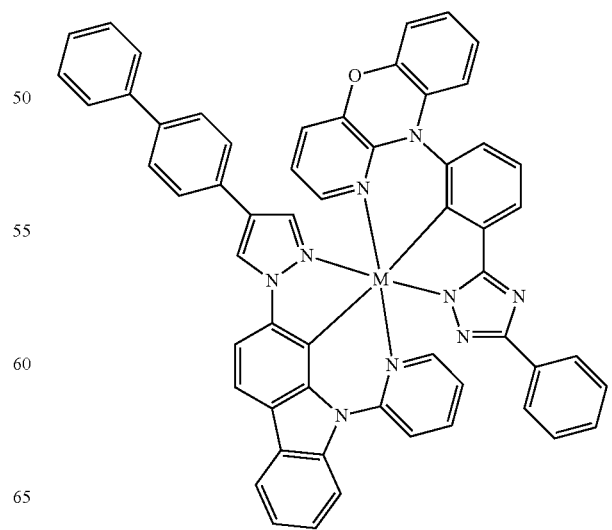

361
-continued
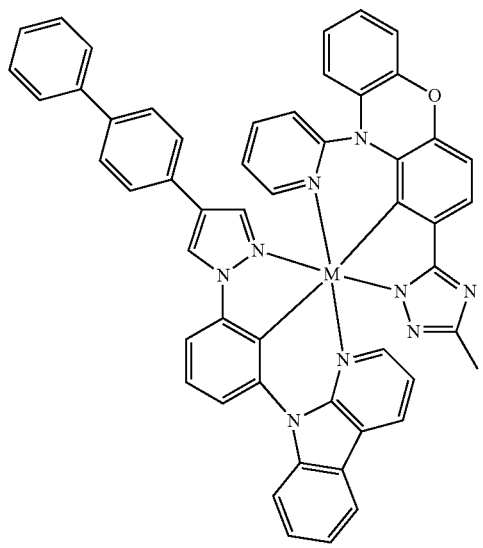
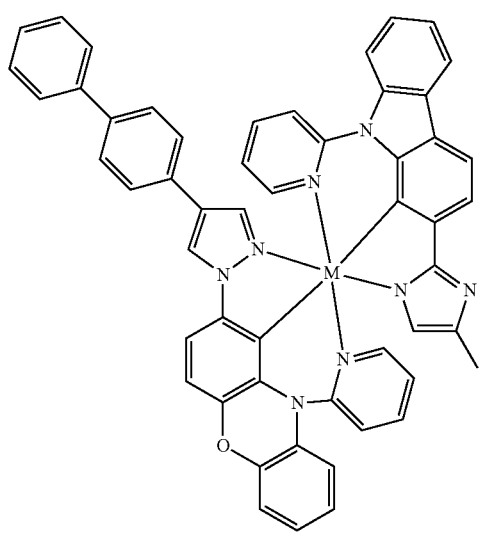
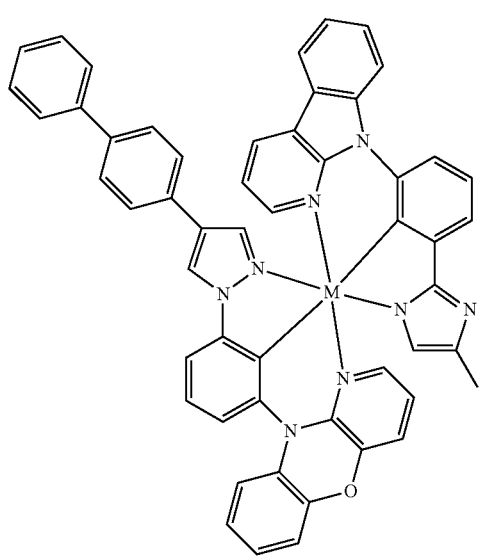
362
-continued
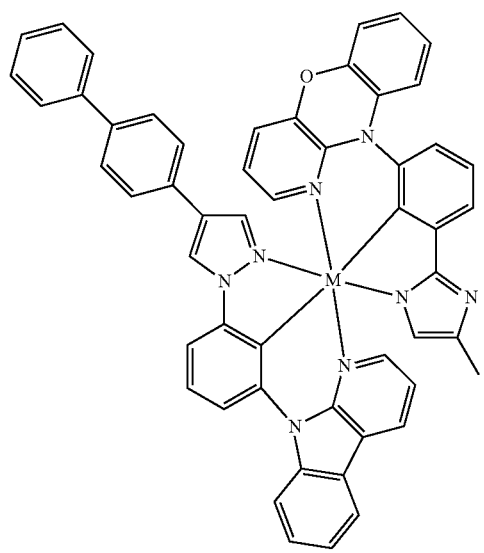
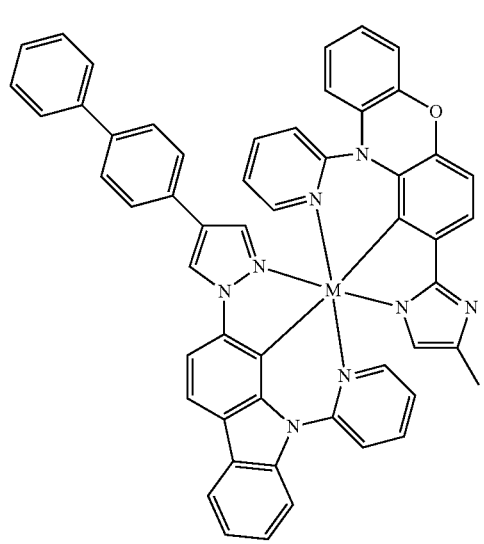
Structures M-30 (M = Ir, Rh)
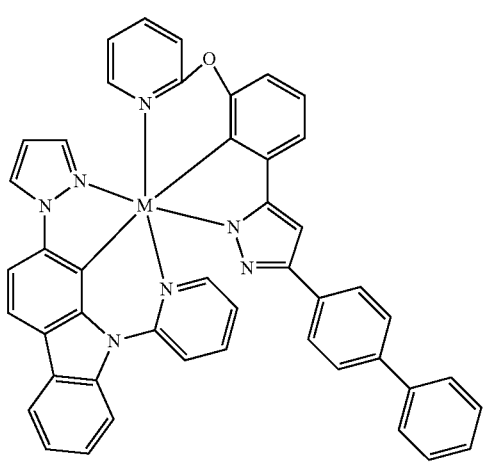

363
-continued
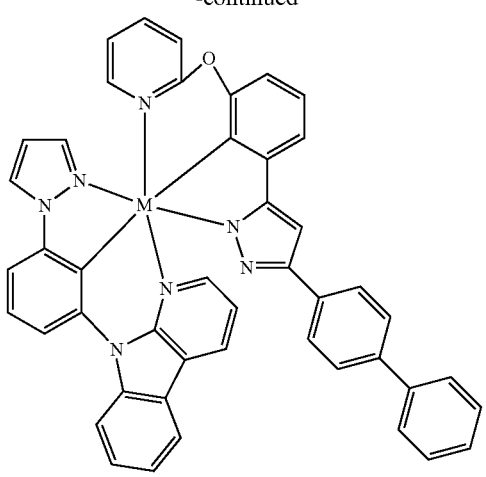
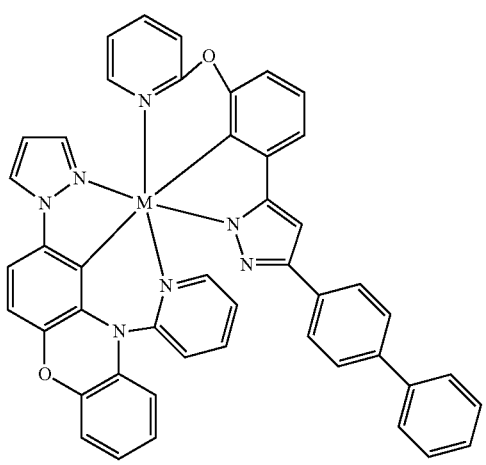
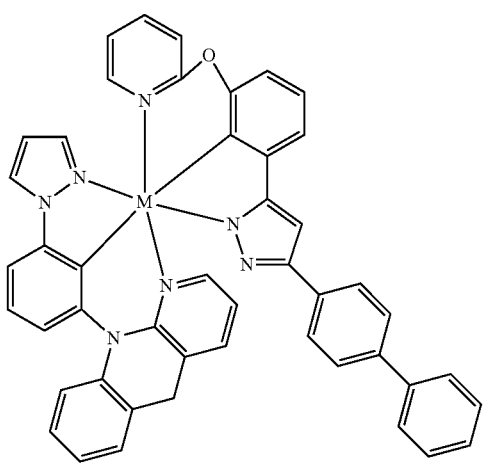
364
-continued
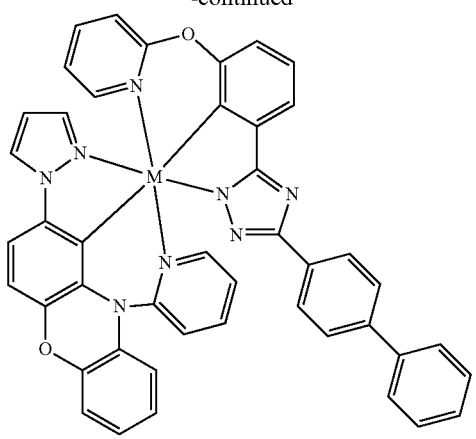
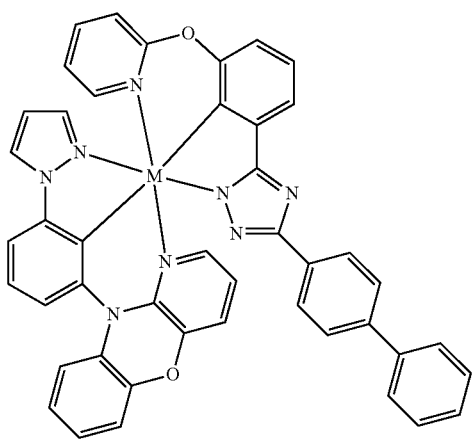
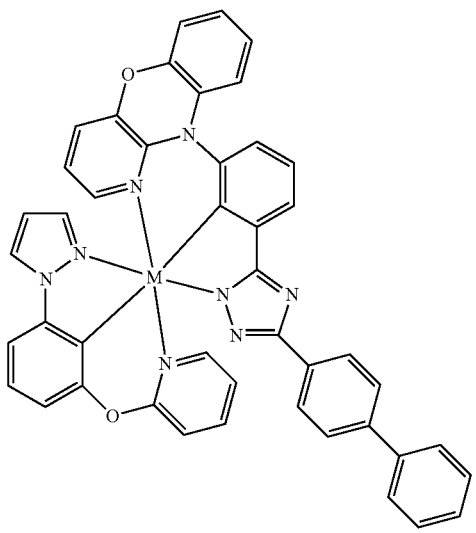

365
-continued
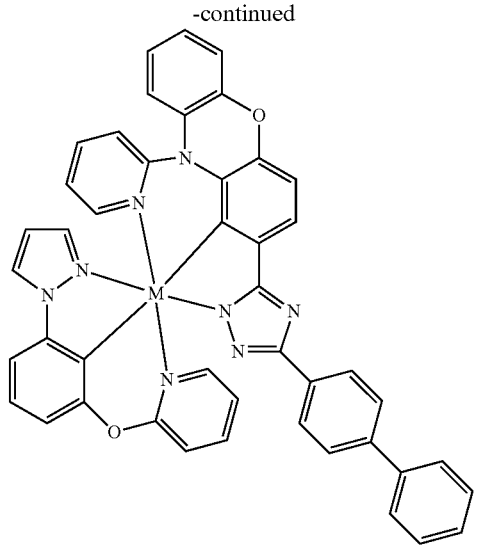
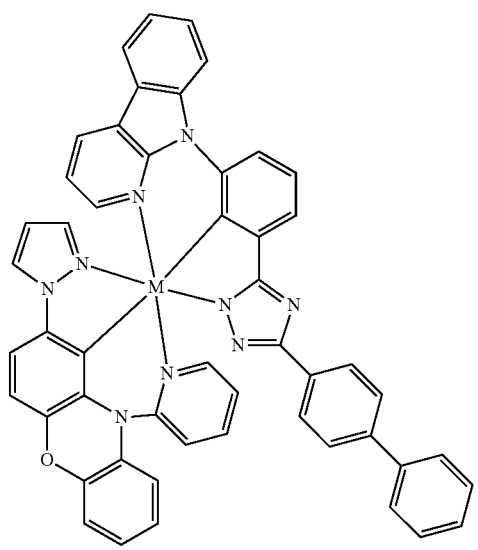
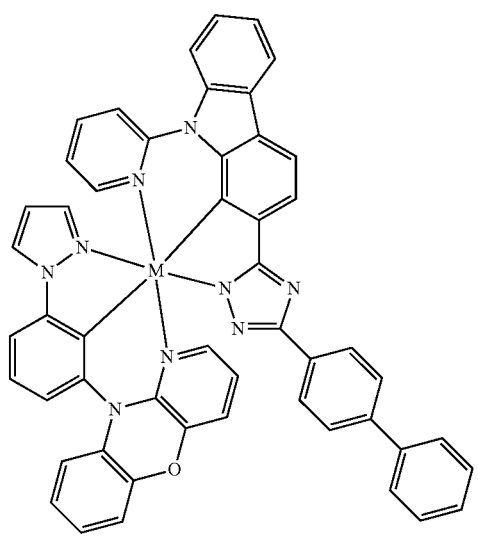
366
-continued
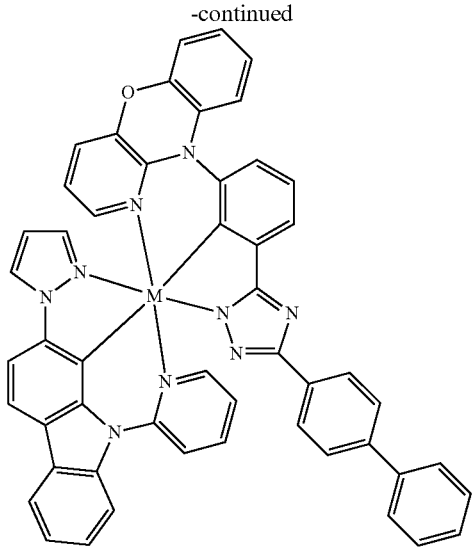
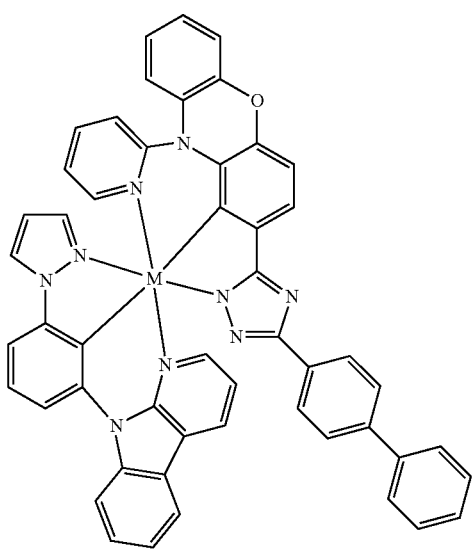
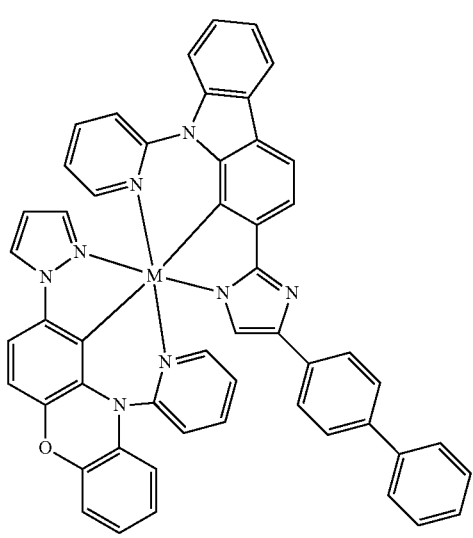

367
-continued
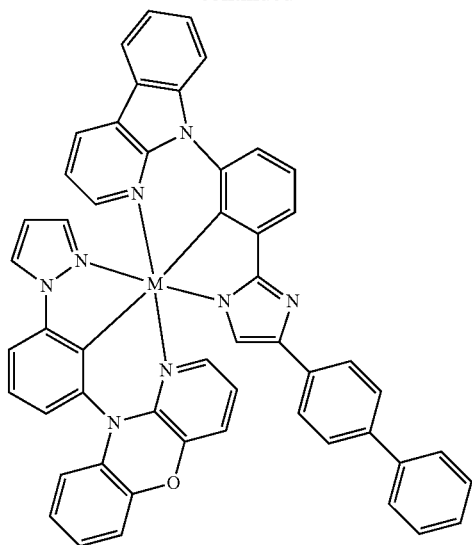
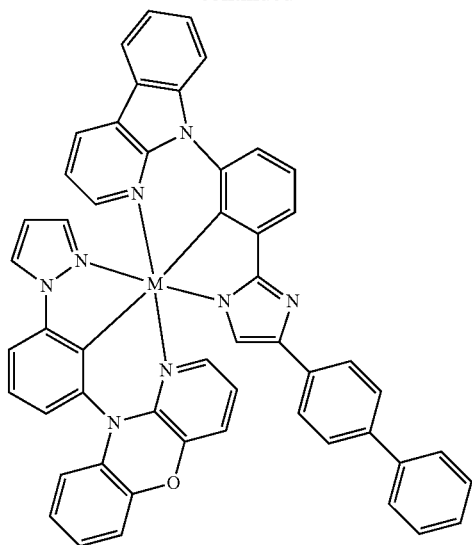
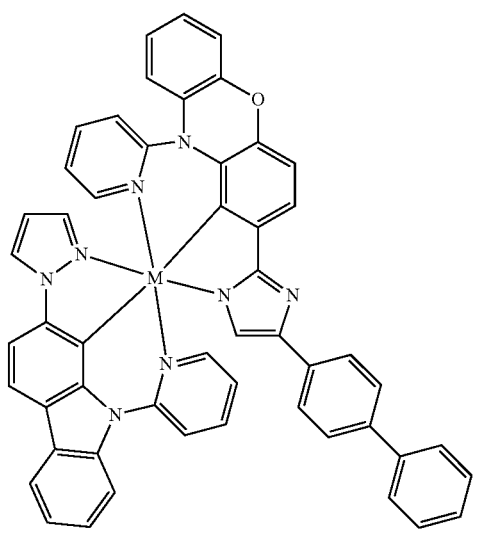
368
-continued
Structures M-31 (M = Ir, Rh)
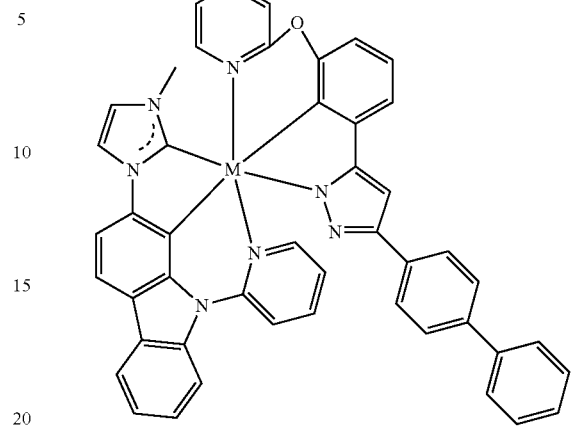
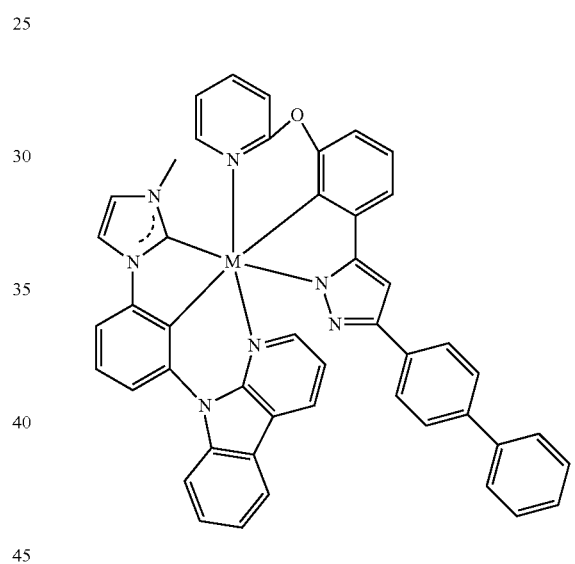
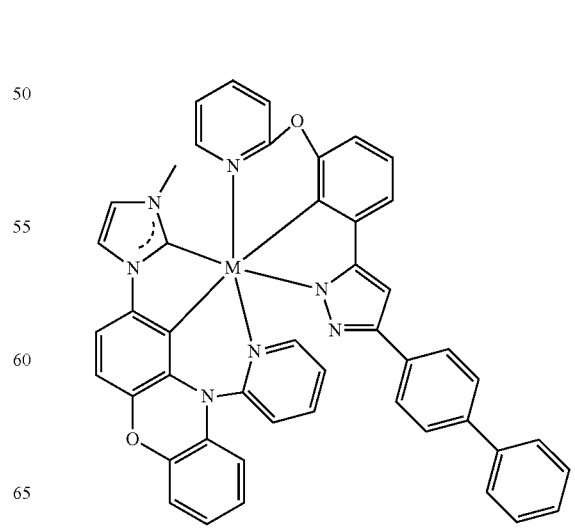

369
-continued
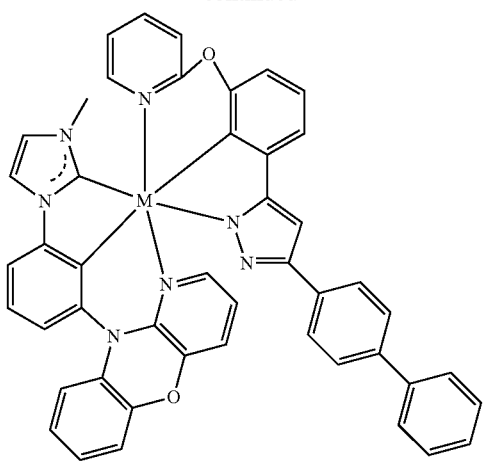
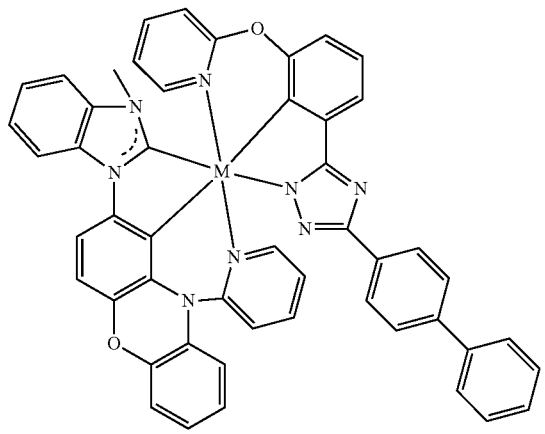
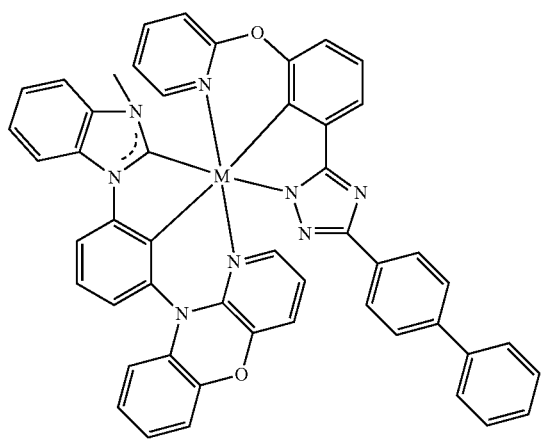
370
-continued
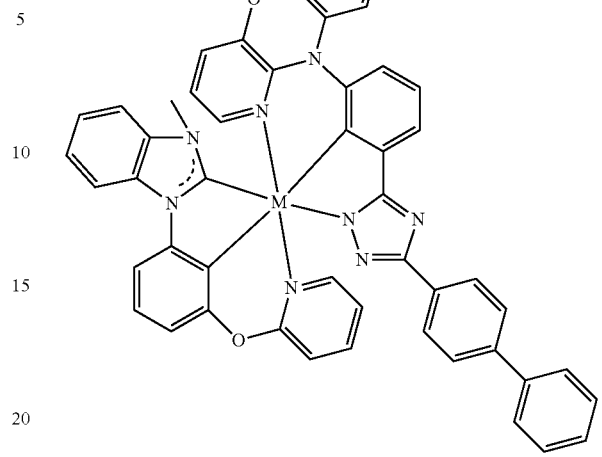
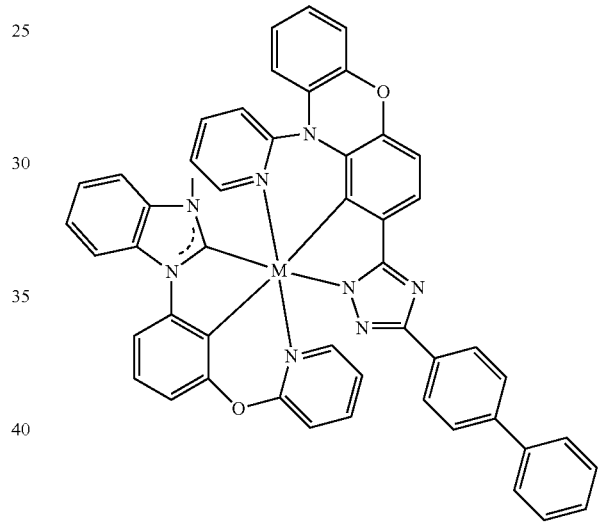
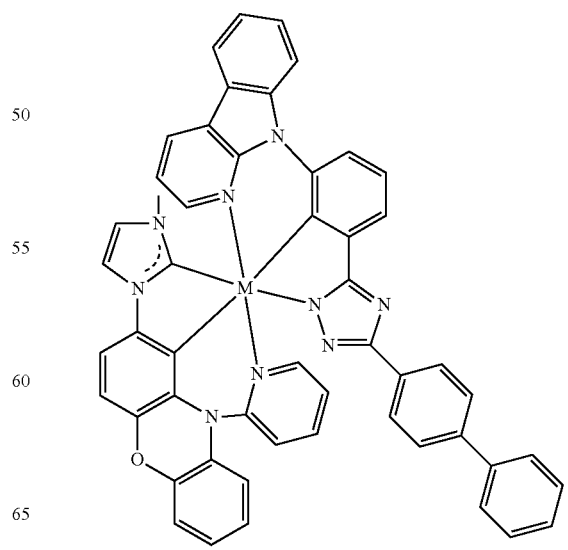

371
-continued
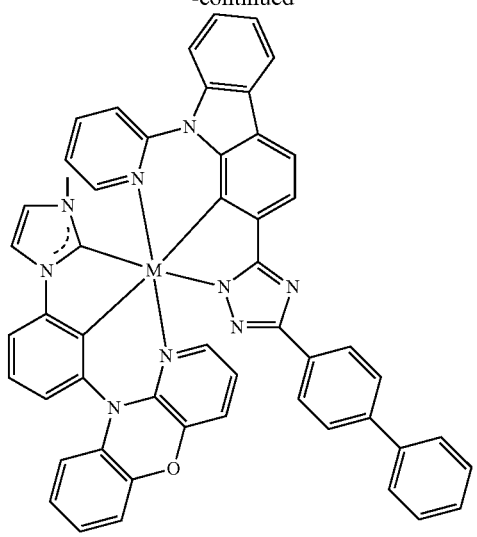
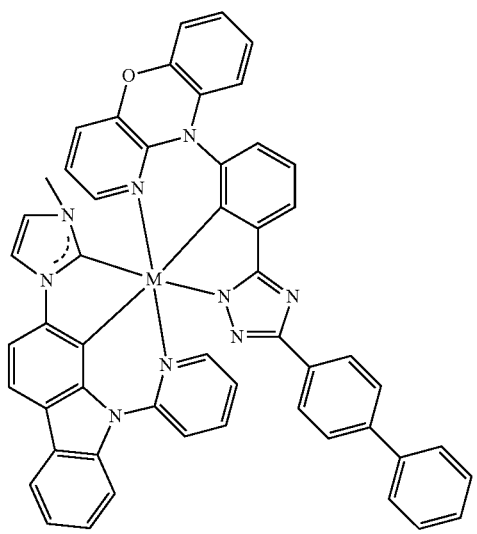
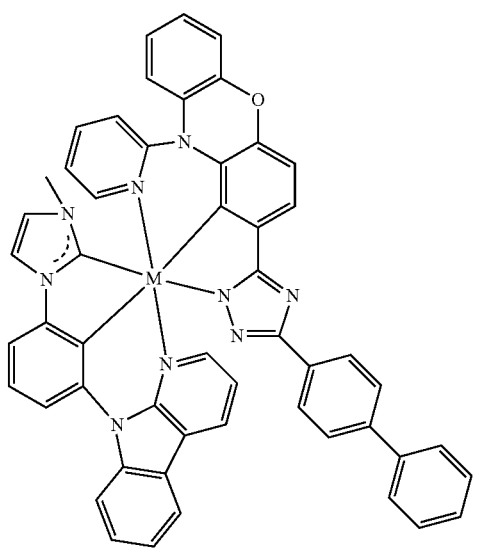
372
-continued
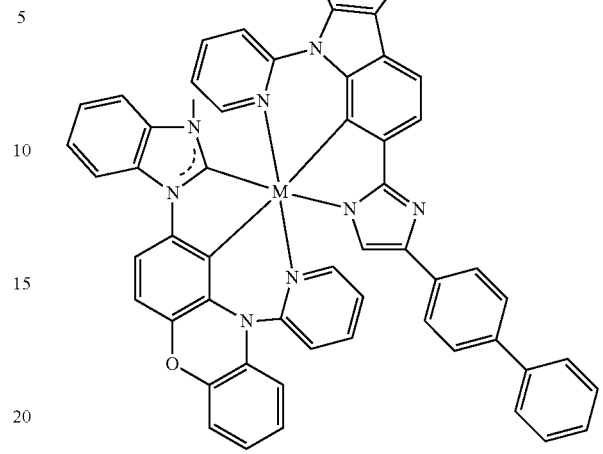
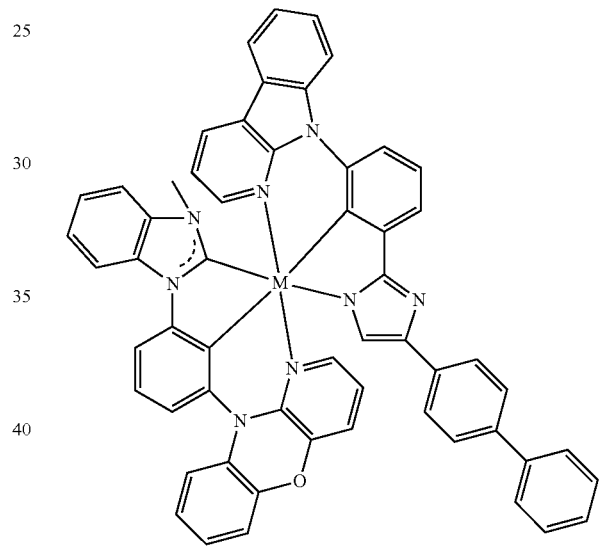
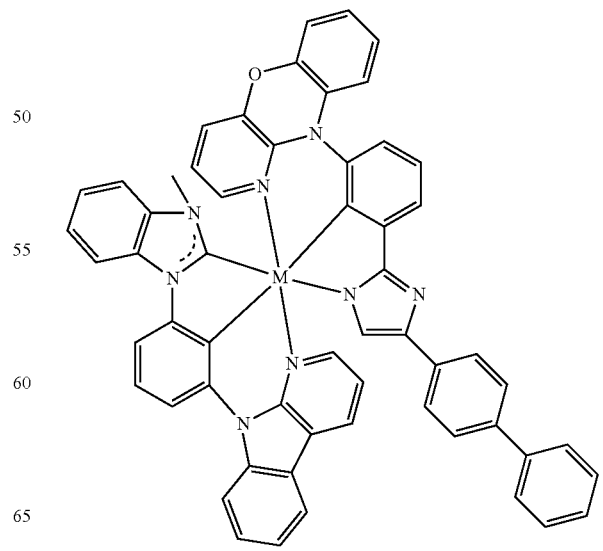

373
-continued
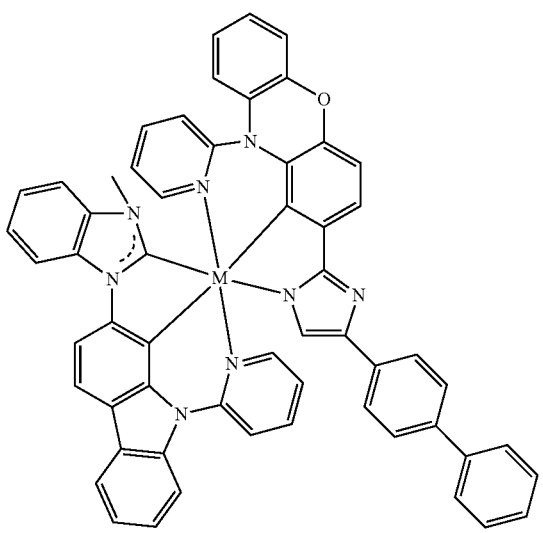
Structures M-32 (M = Ir, Rh)
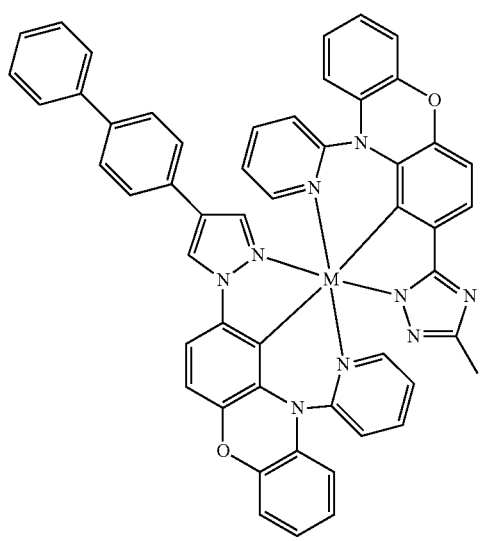
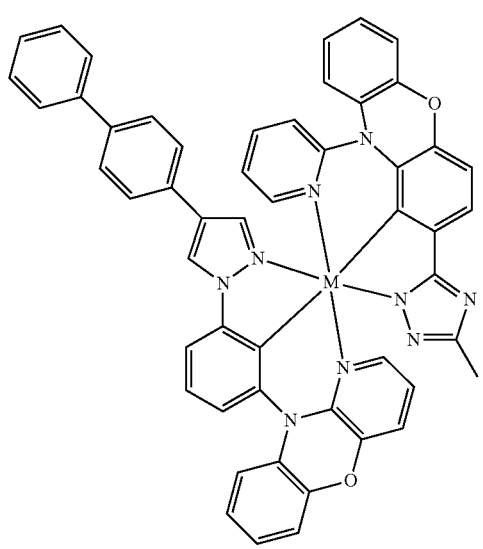
374
-continued
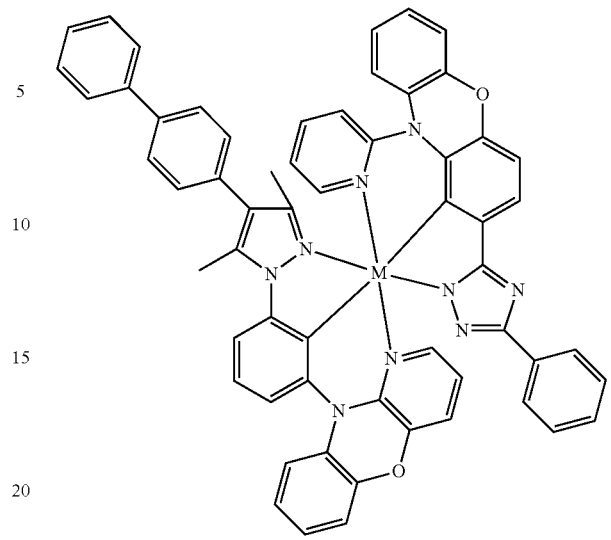
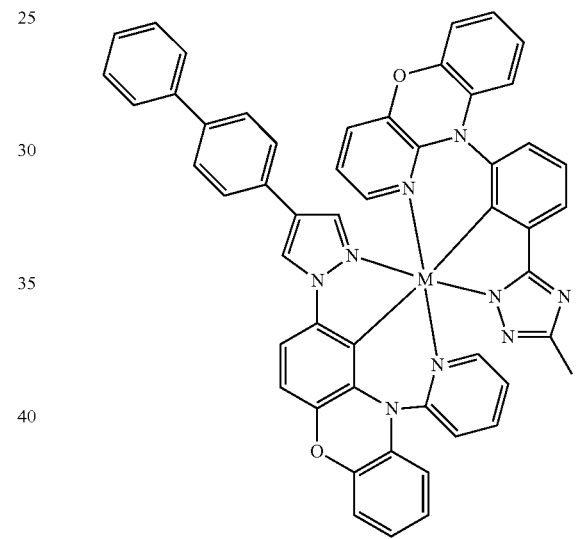
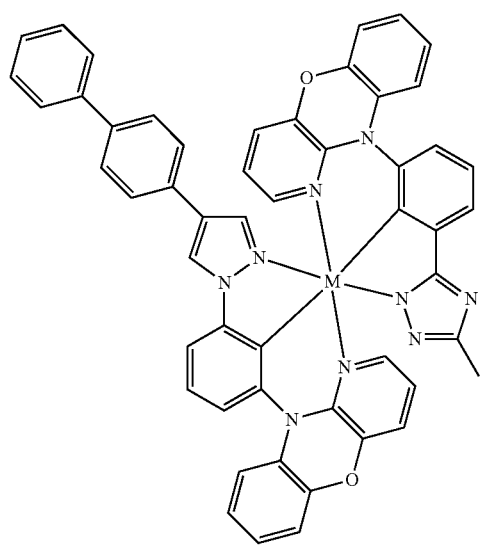

375
-continued
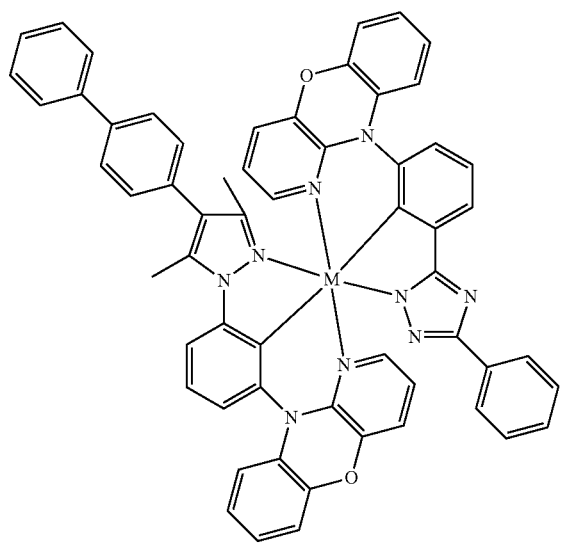
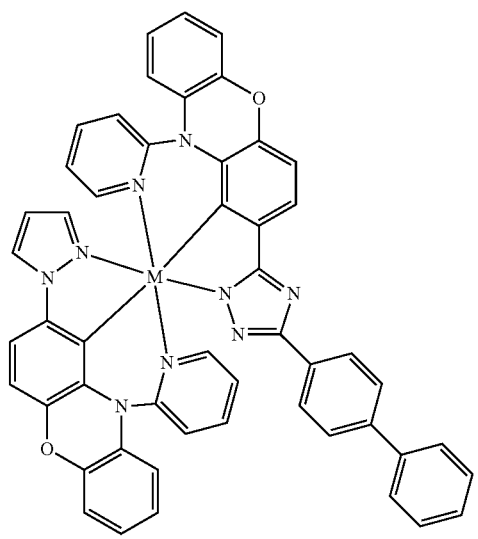
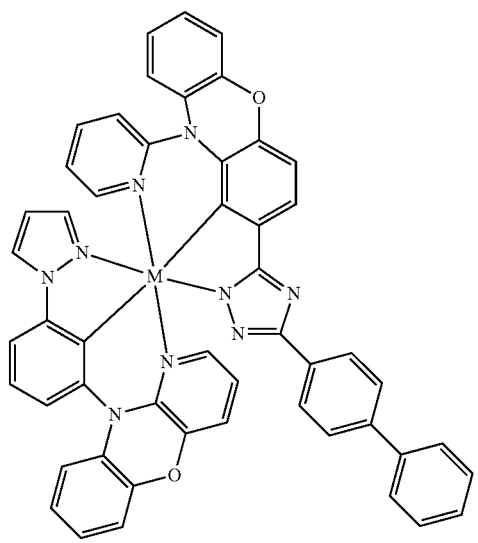
376
-continued
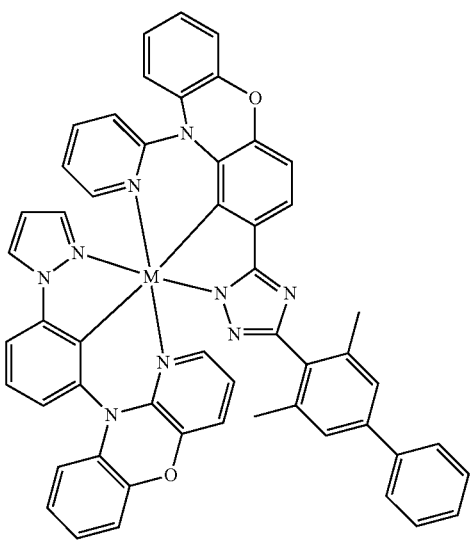
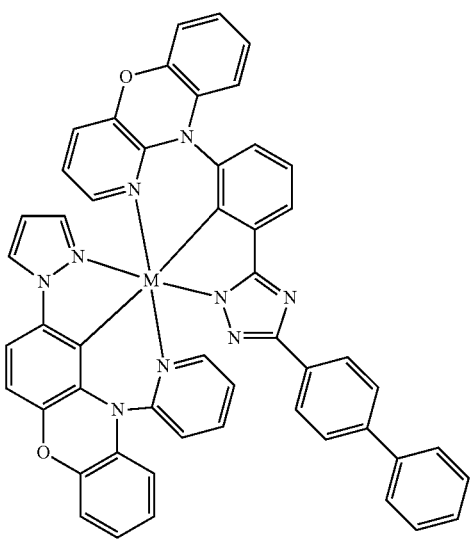
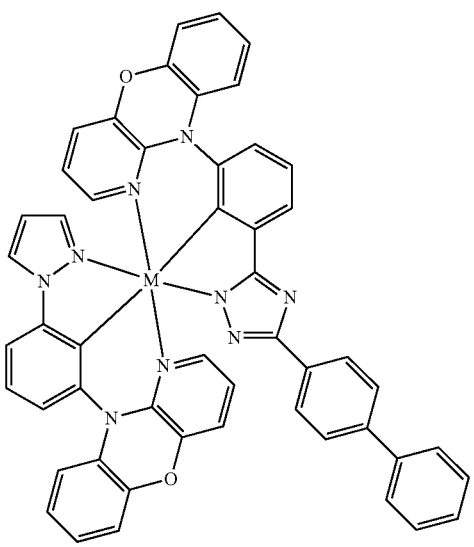

377
-continued
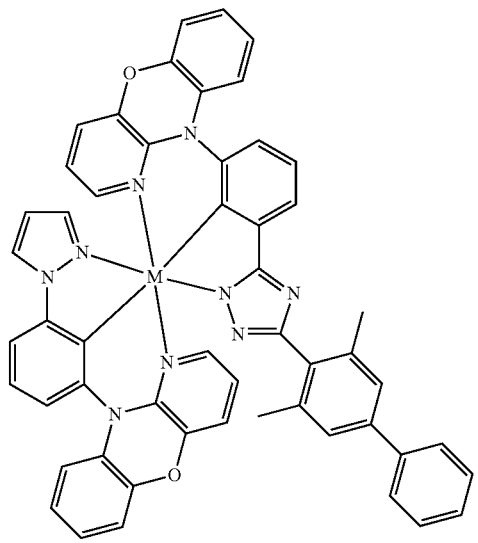
Structures M-33 (M = Ir, Rh)
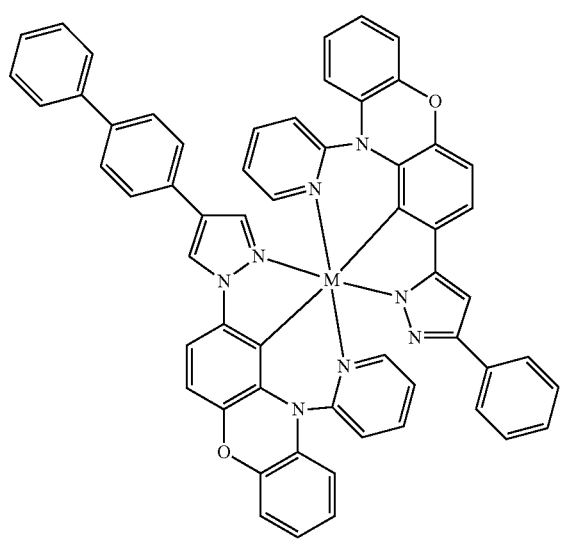
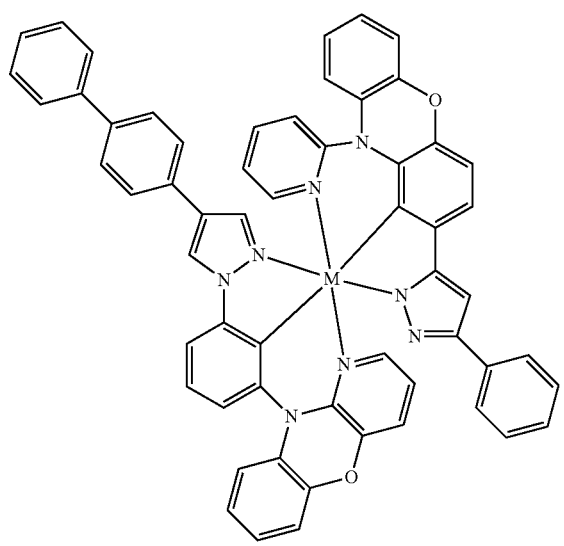
378
-continued
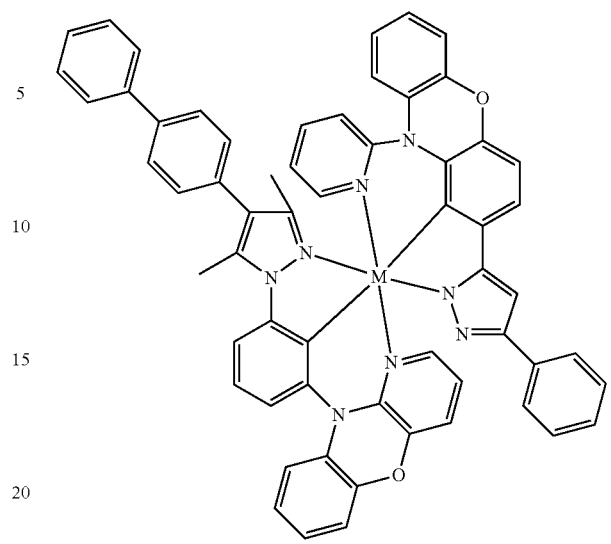
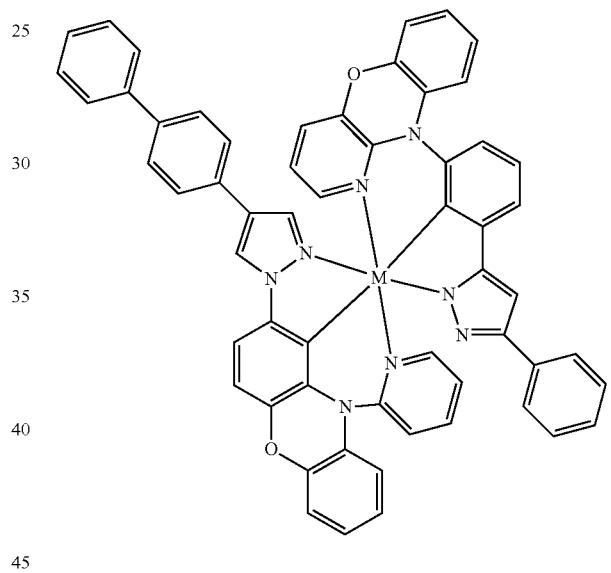
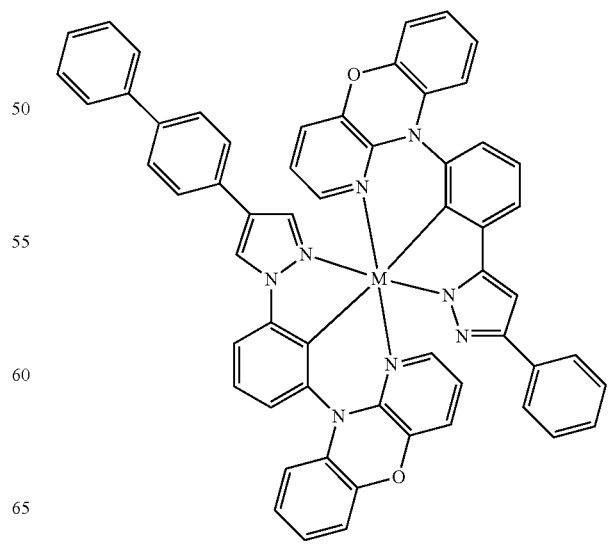

379
-continued
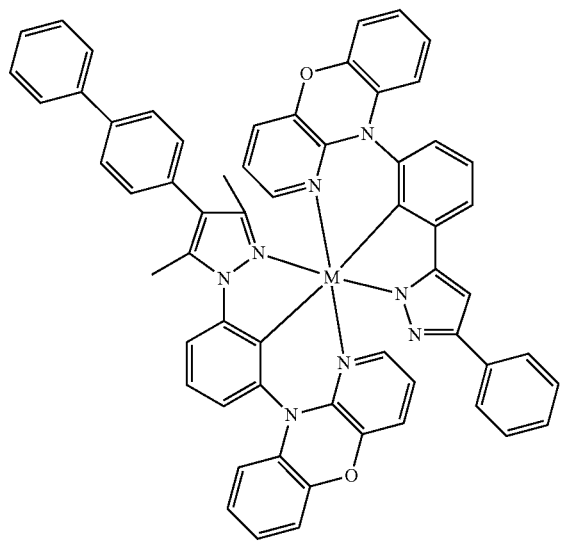
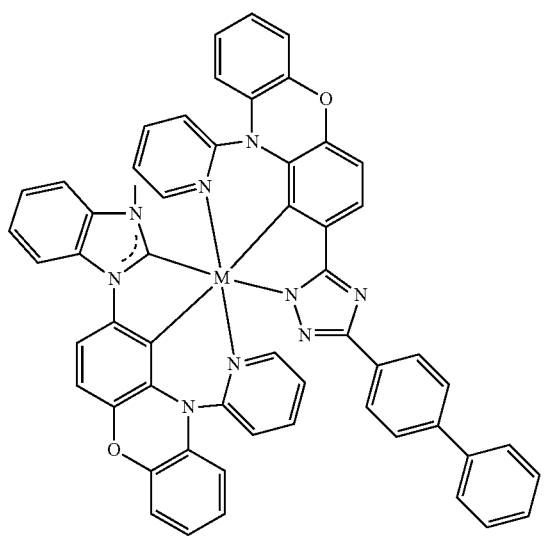
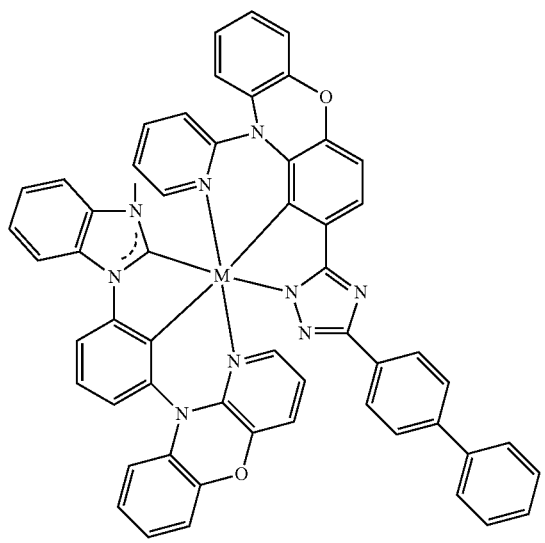
380
-continued
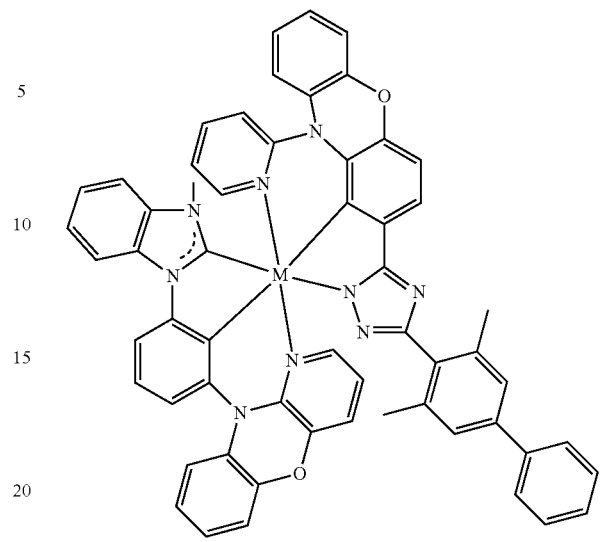
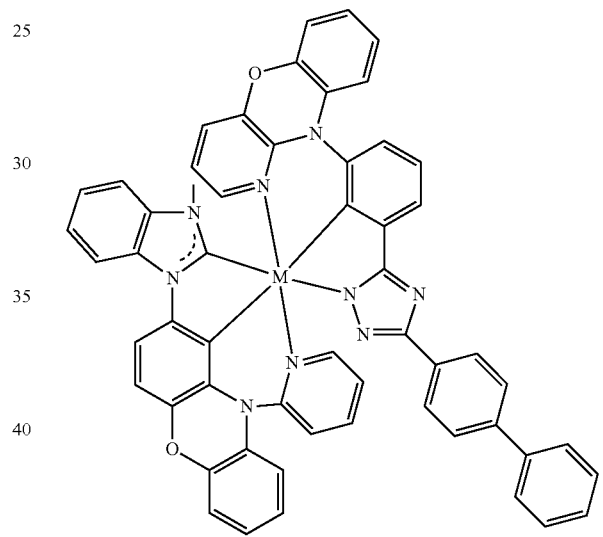
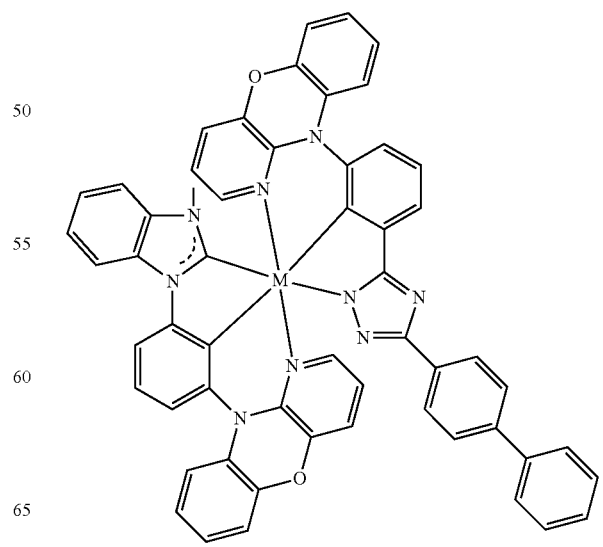

381
-continued
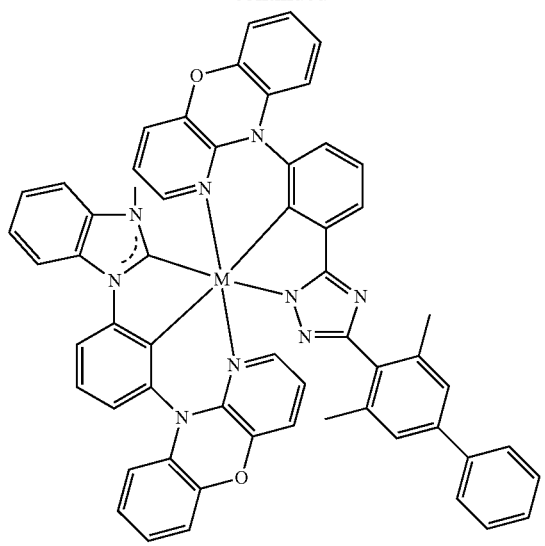
Structures M-34 (M = Ir, Rh)
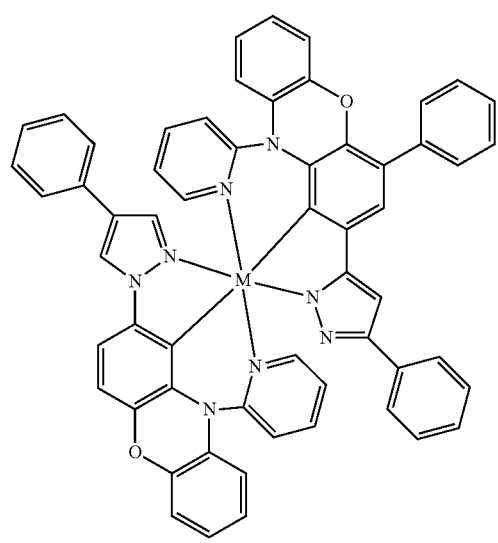
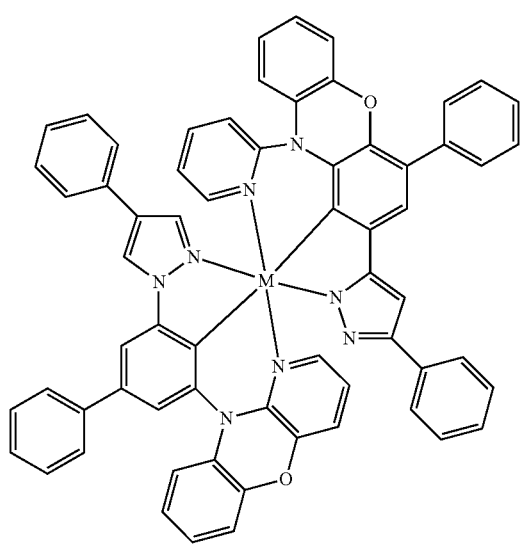
382
-continued
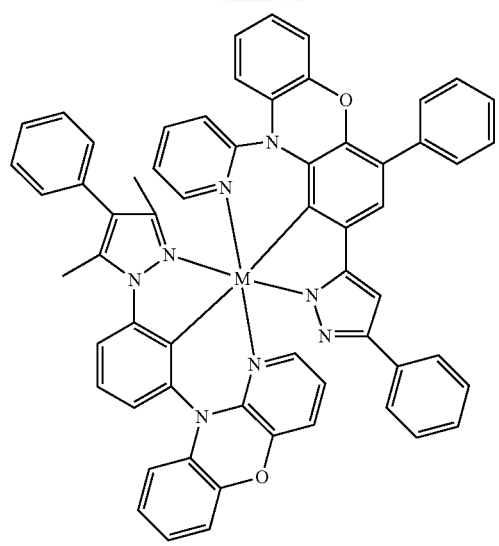
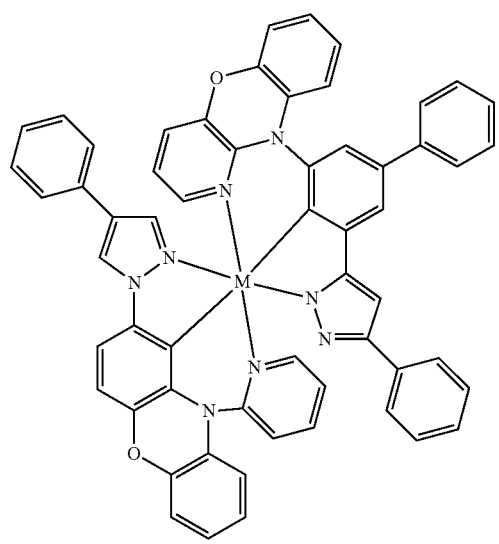
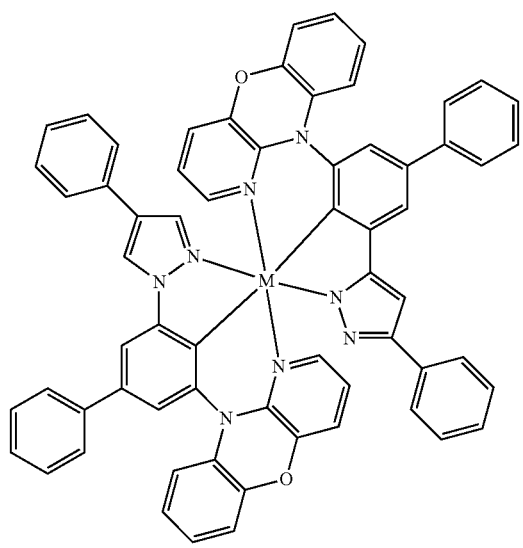

383
-continued
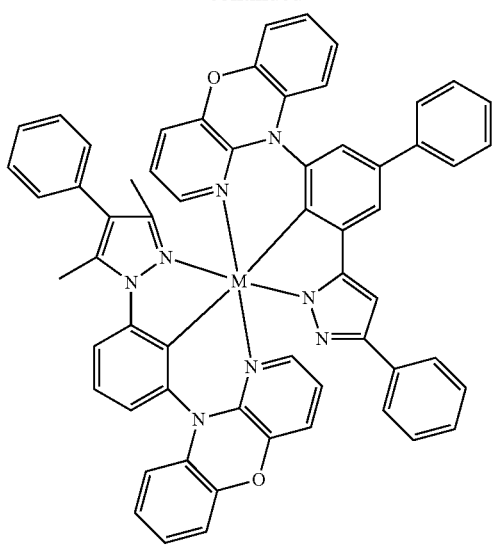
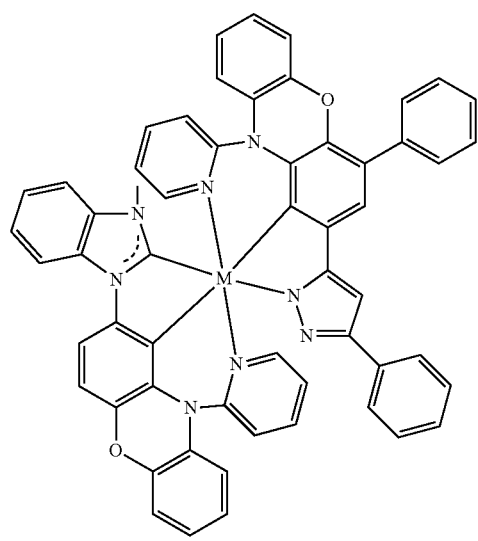
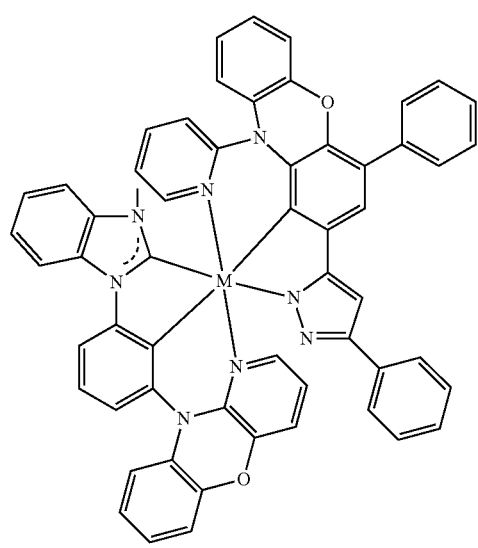
384
-continued
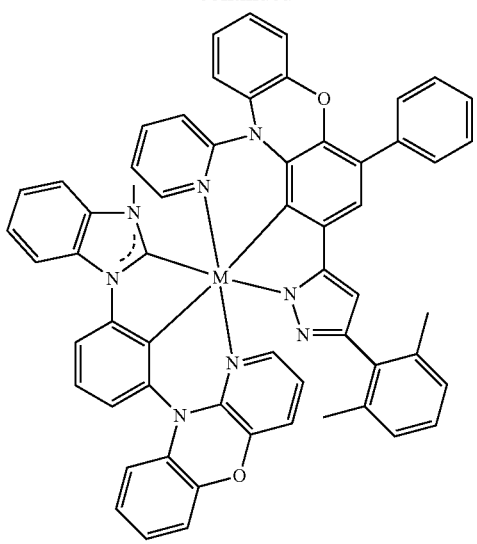
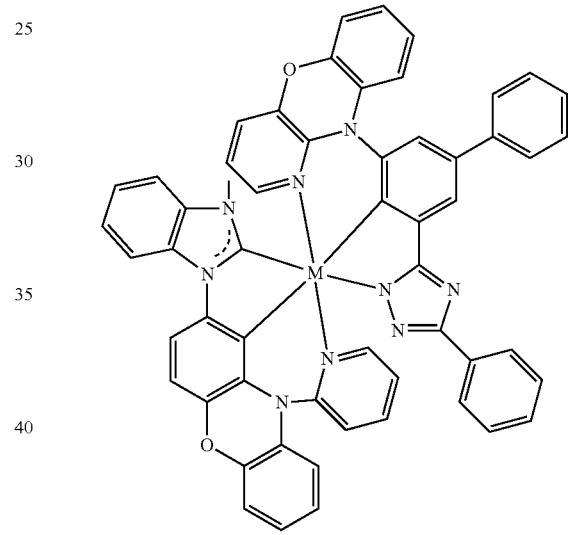
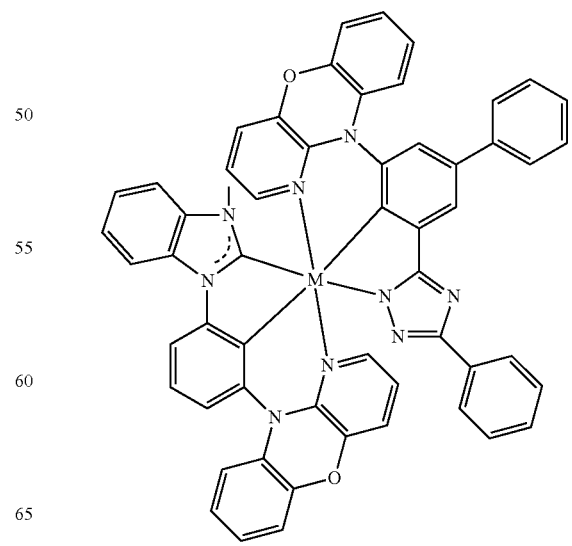

385
-continued
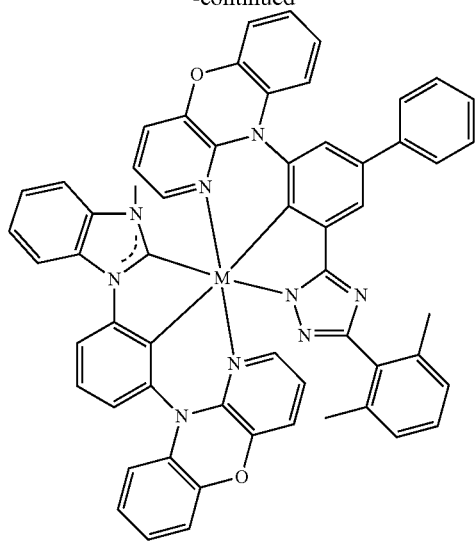
386
-continued
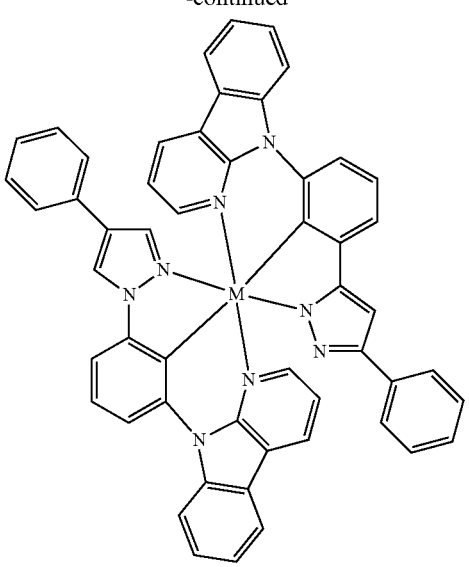
Structures M-35 (M = Ir, Rh)
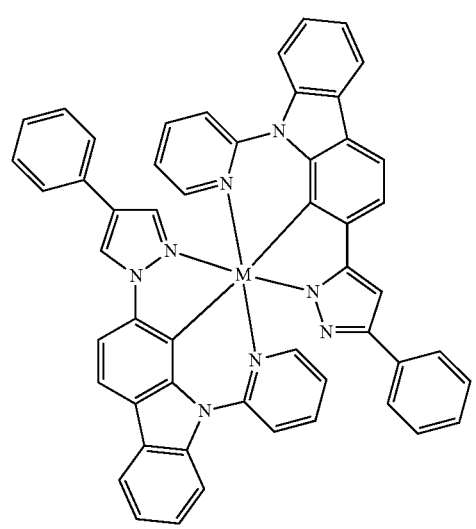
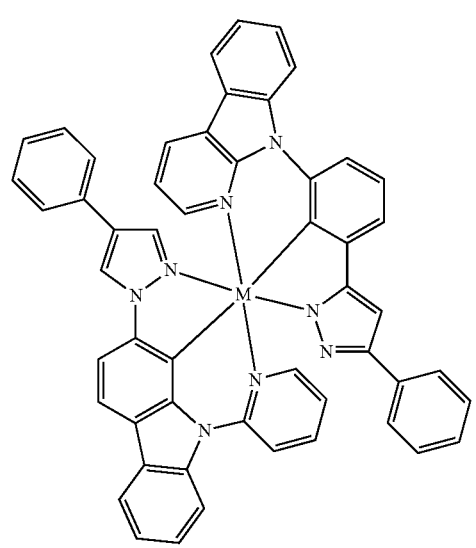

387
-continued
388
-continued
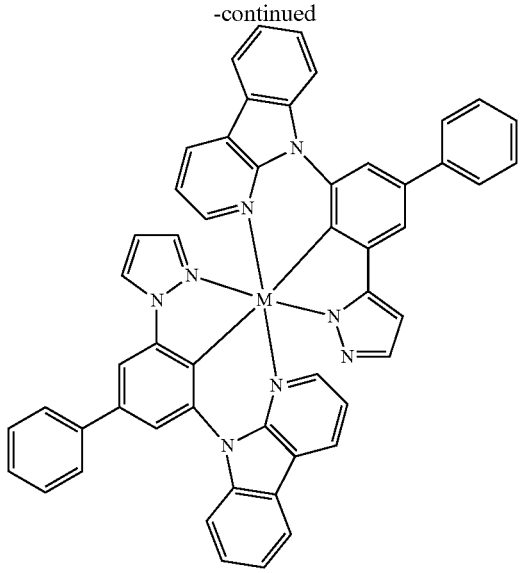
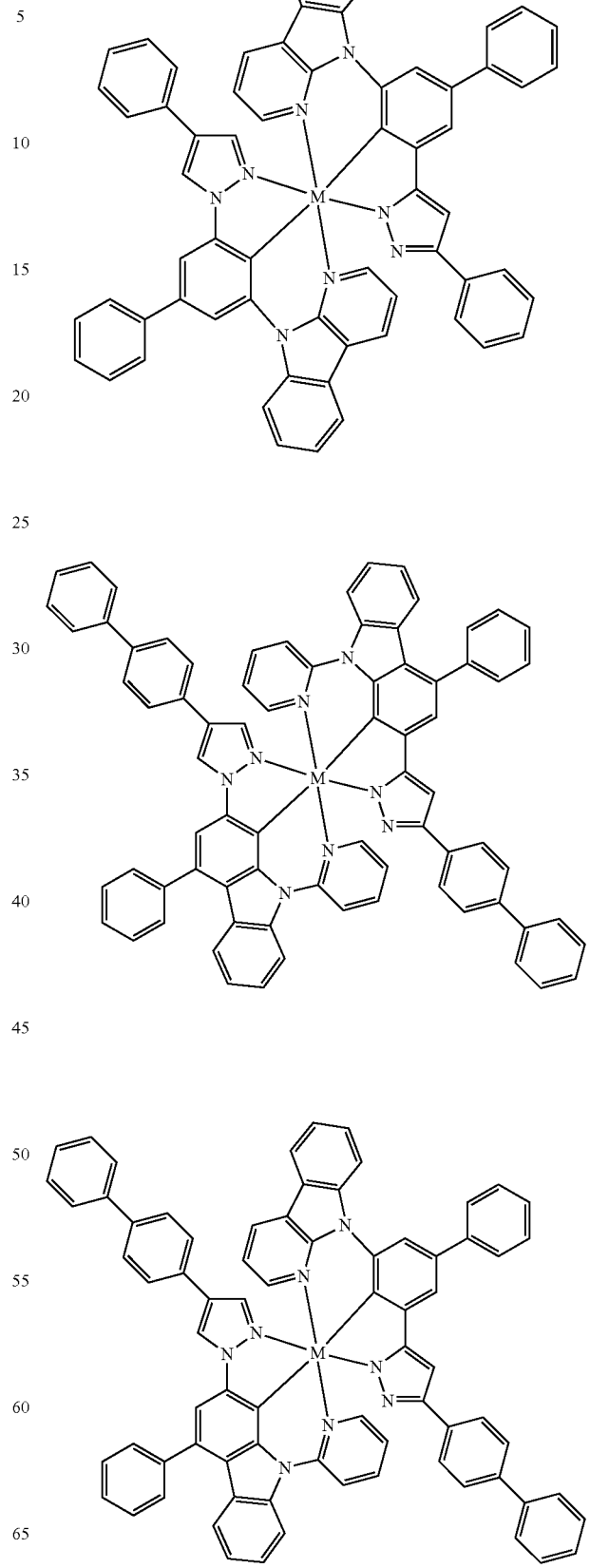

389
-continued
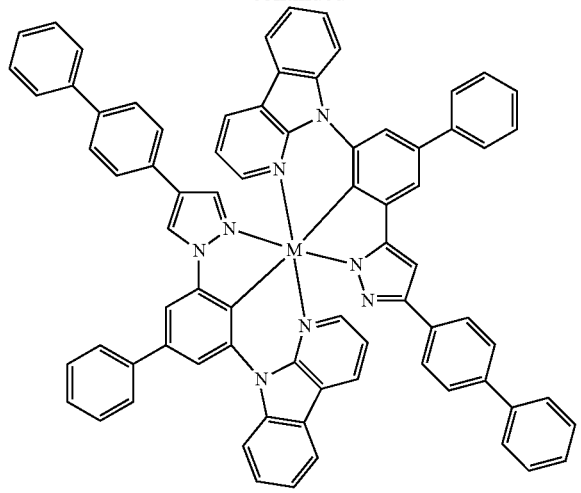
390
-continued
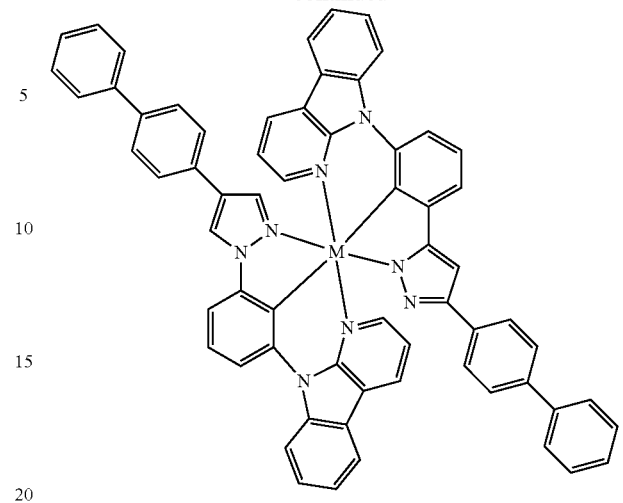
Structures M-36 (M = Ir, Rh)
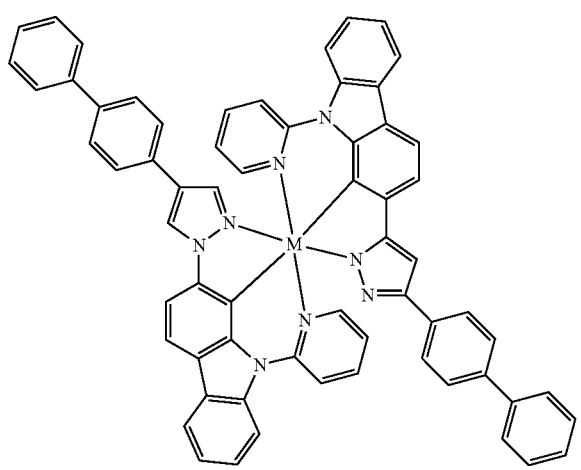
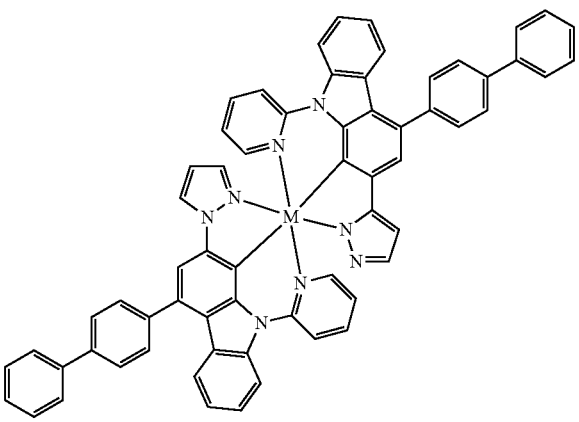
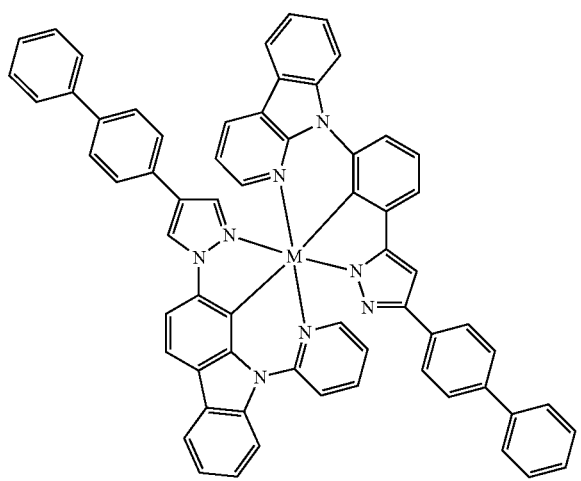
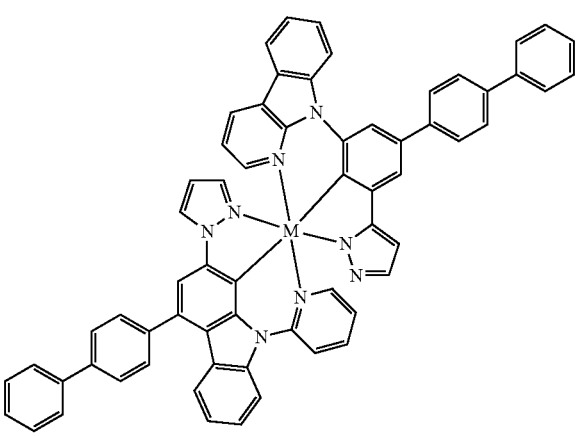

391
-continued
392
-continued
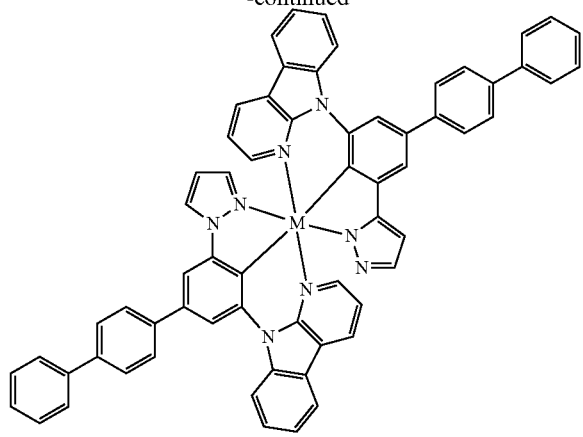
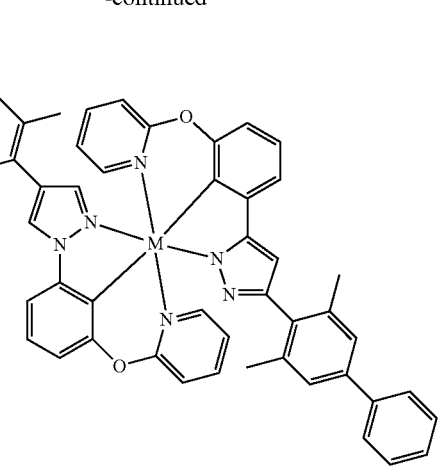
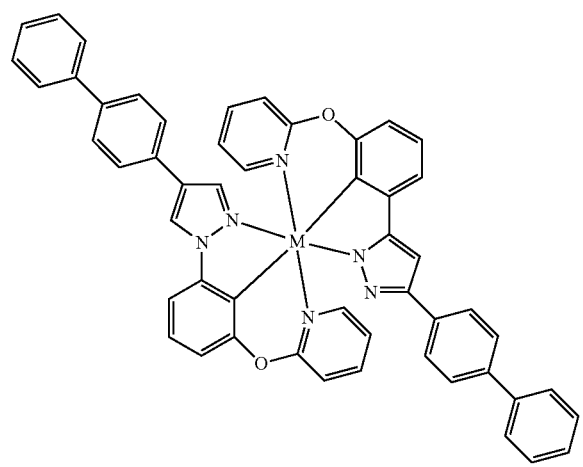
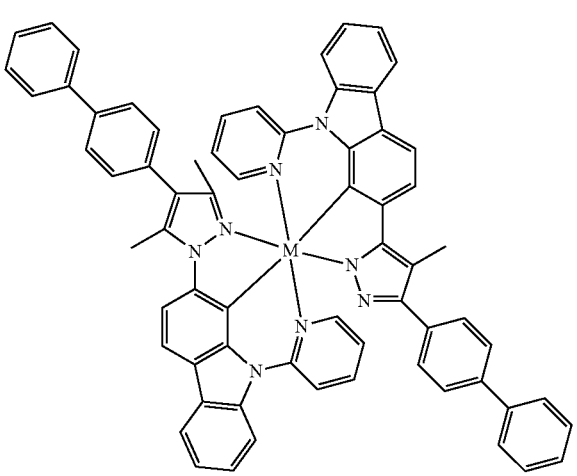
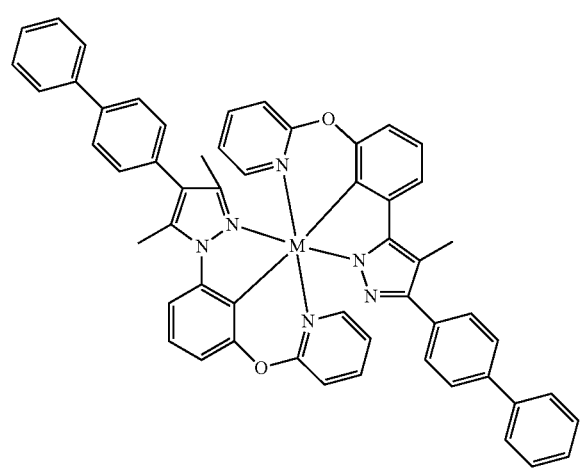
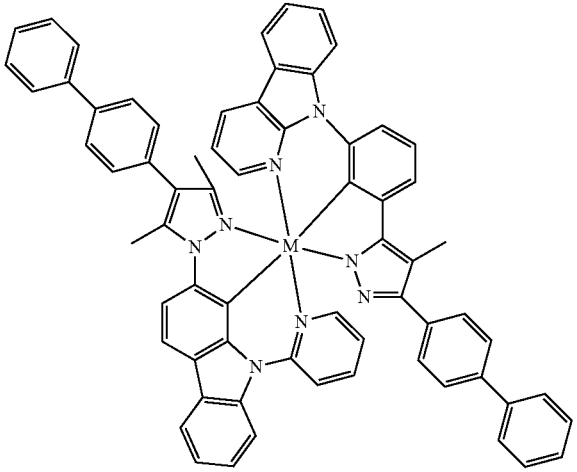

393
-continued
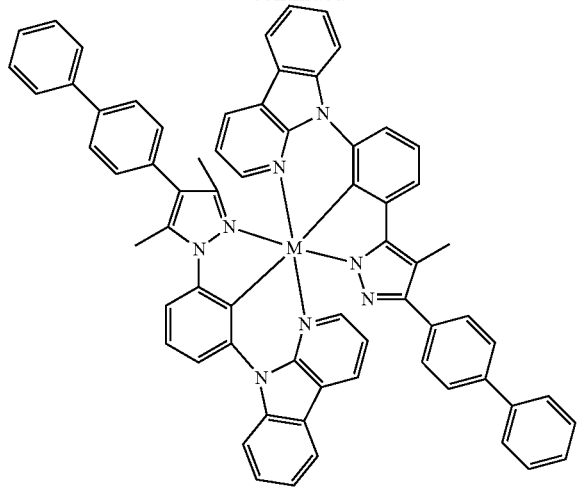
Structures M-37 (M = Ir, Rh)
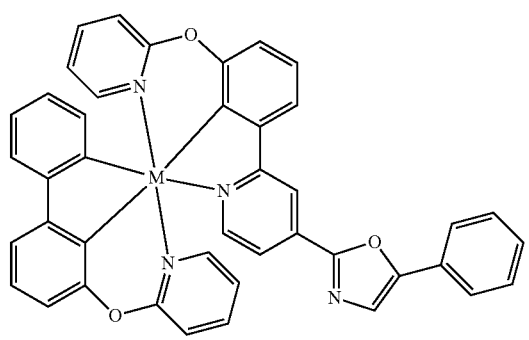
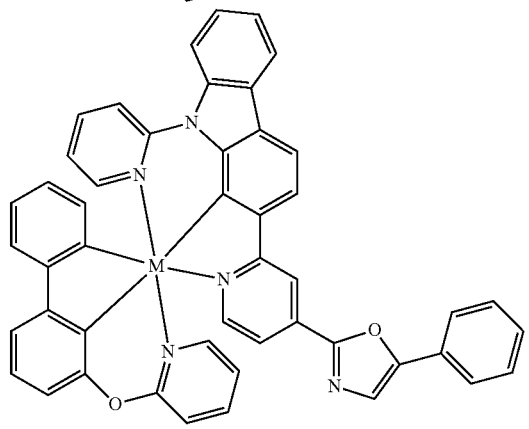
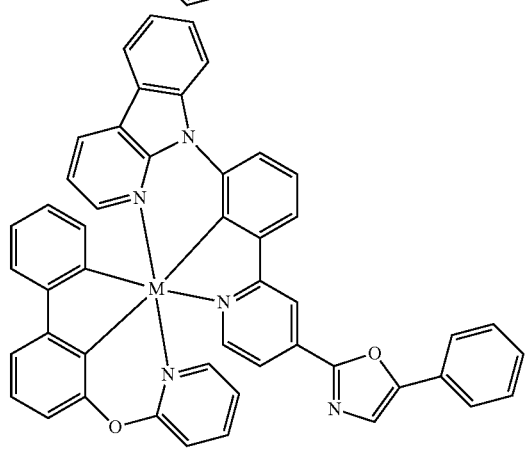
394
-continued
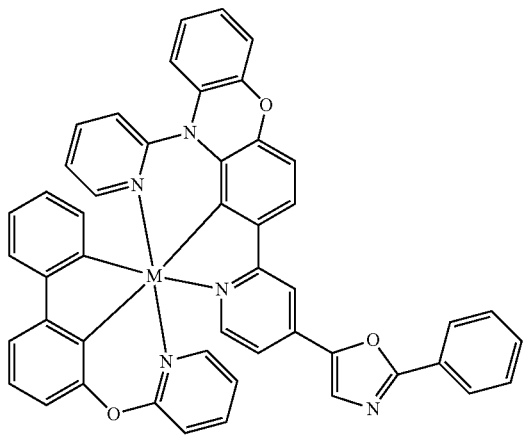
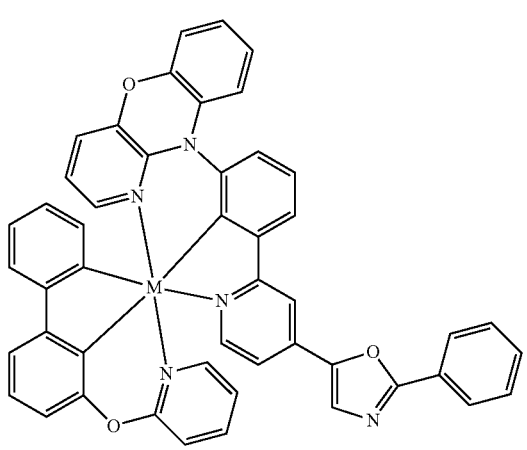
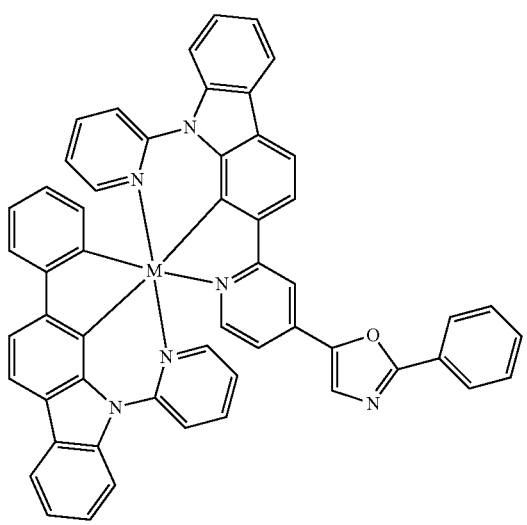

395
-continued
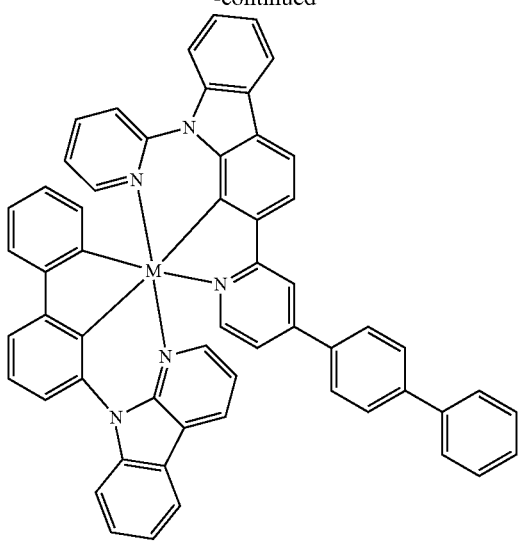
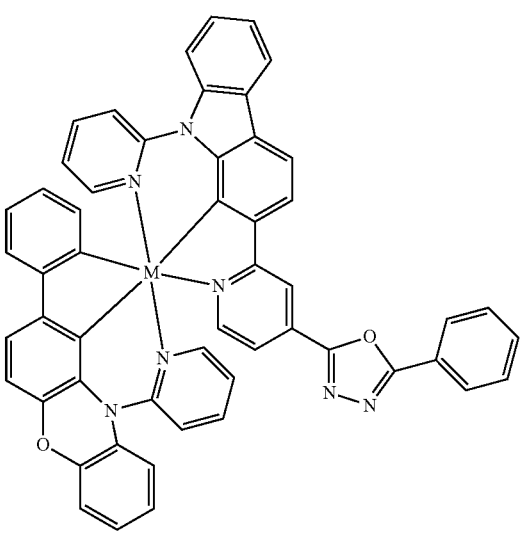
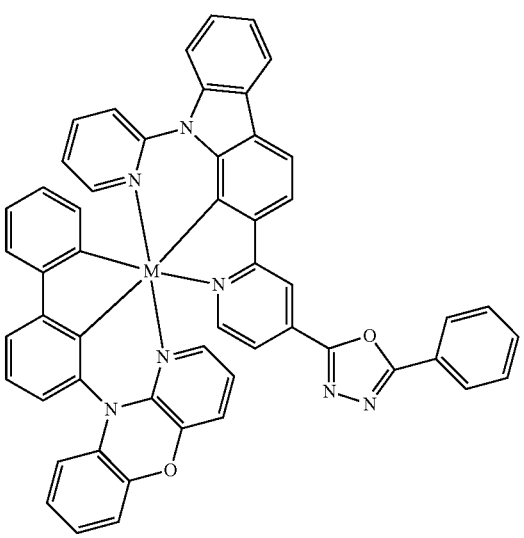
396
-continued
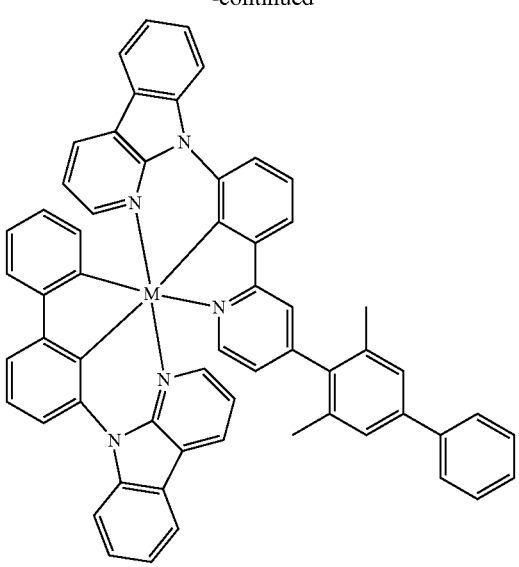
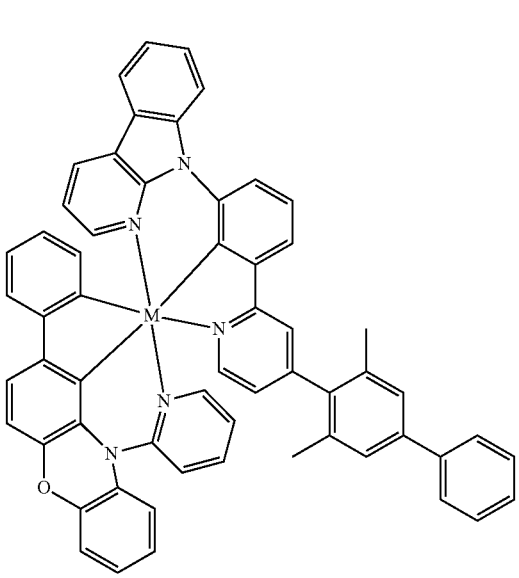
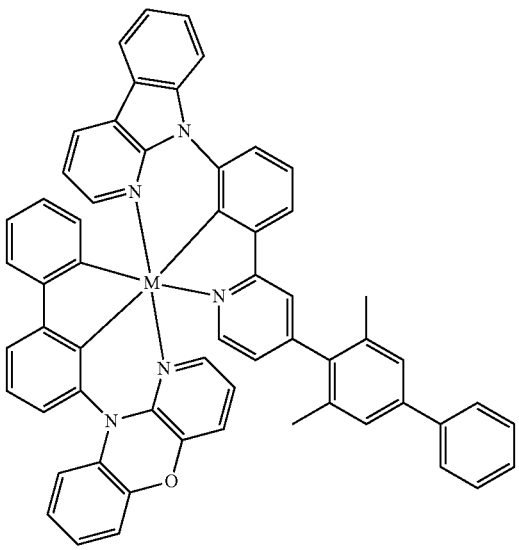

-continued
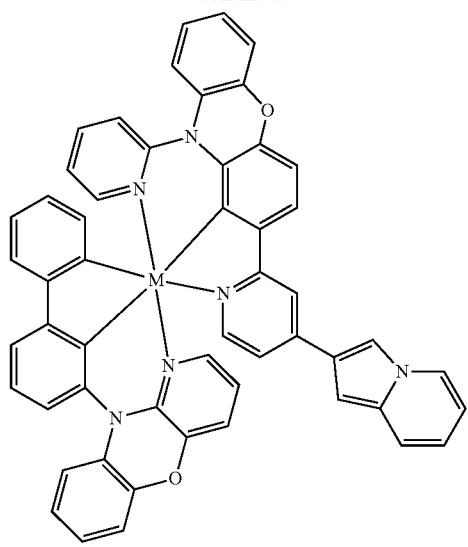
-continued
Structures M-38 (M = Ir, Rh)
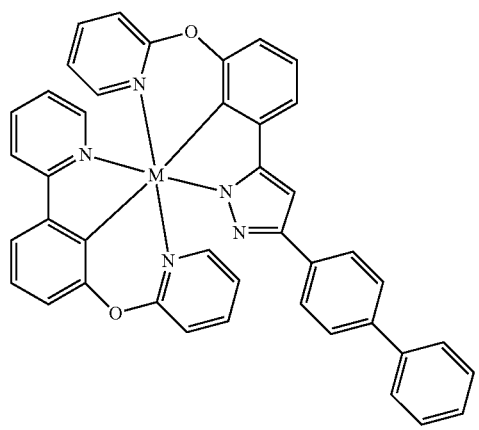
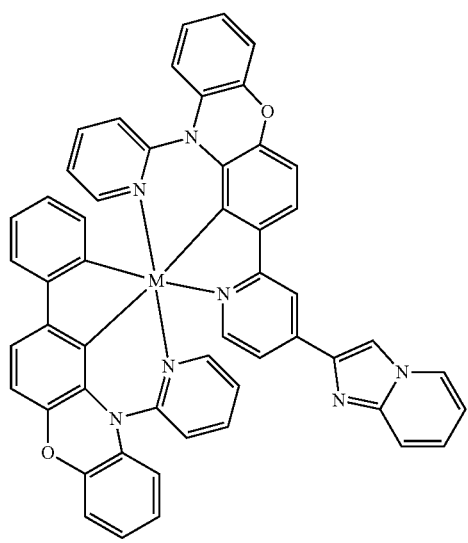
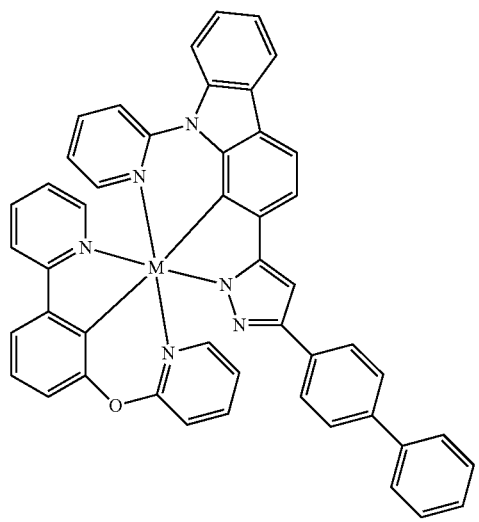
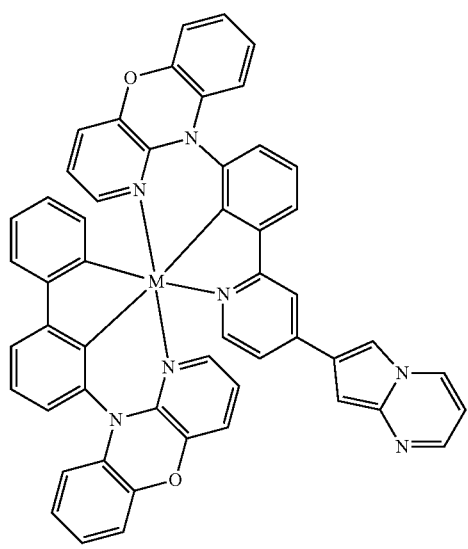
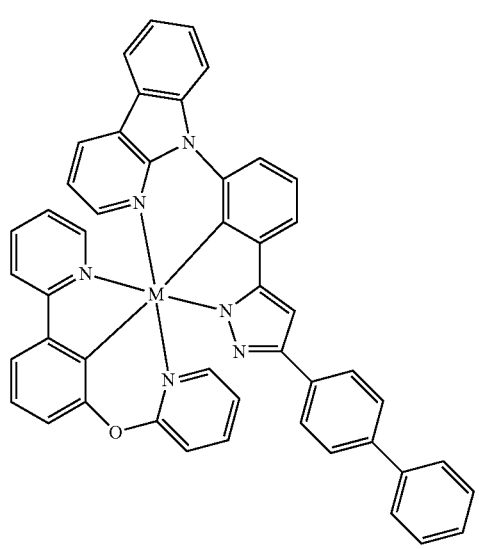

399
-continued
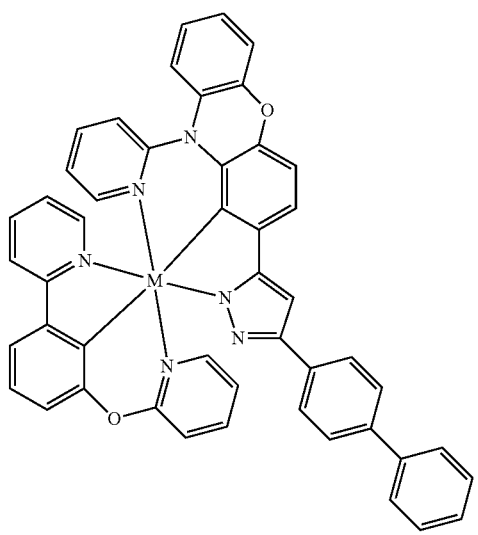
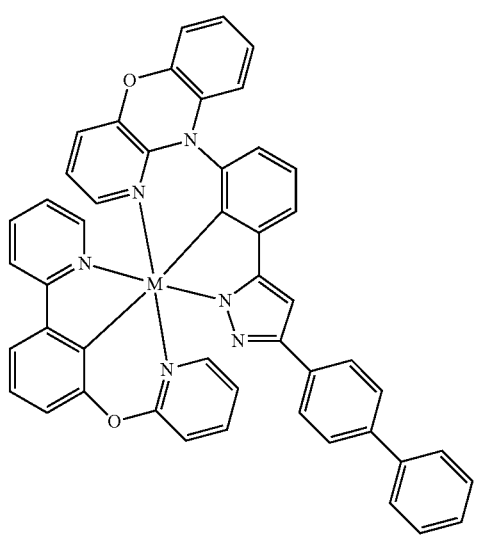
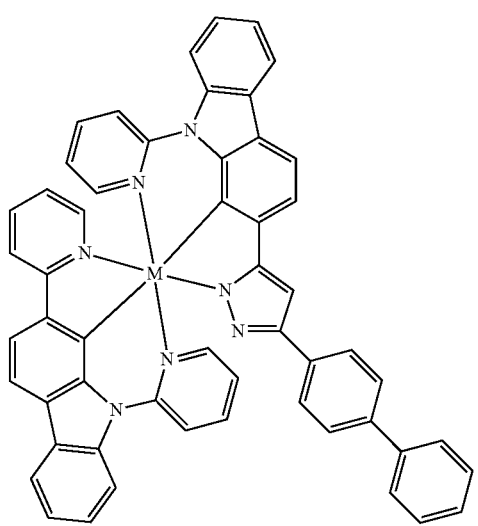
400
-continued
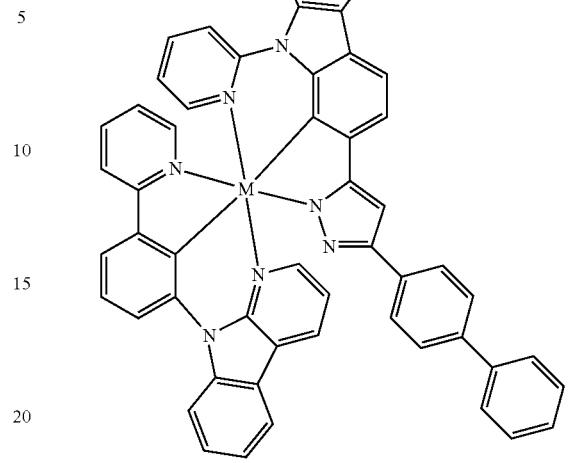
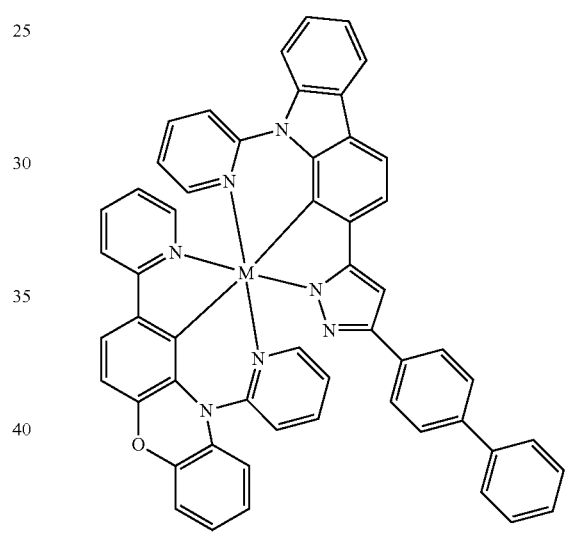
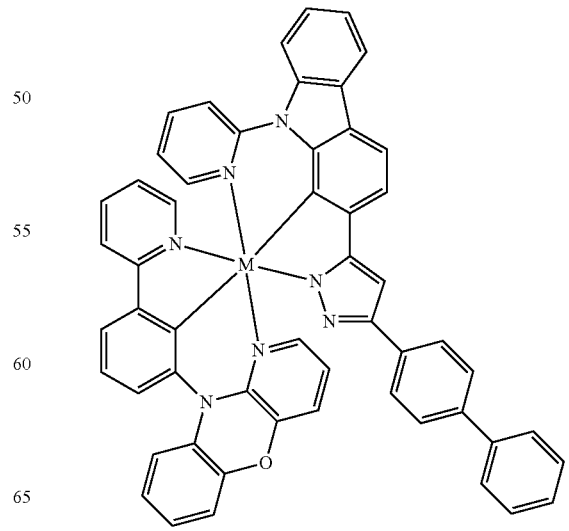

401
-continued
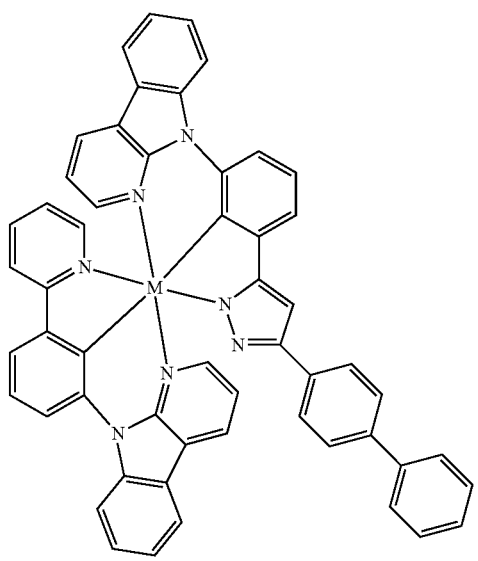
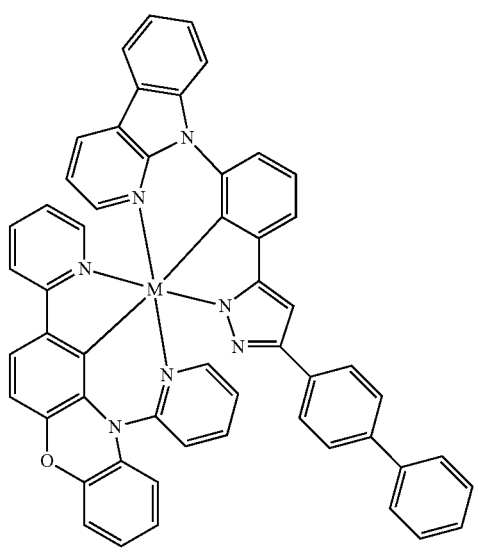
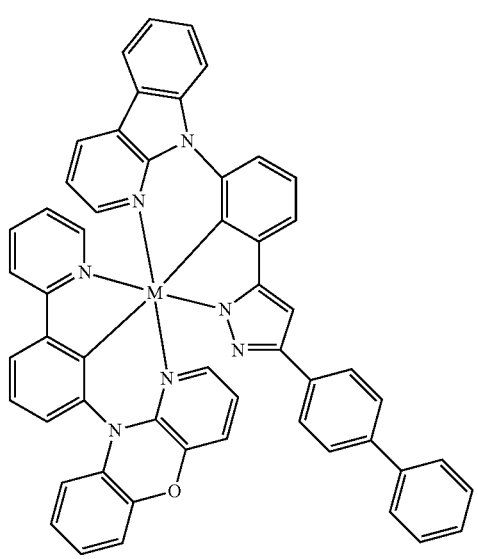
402
-continued
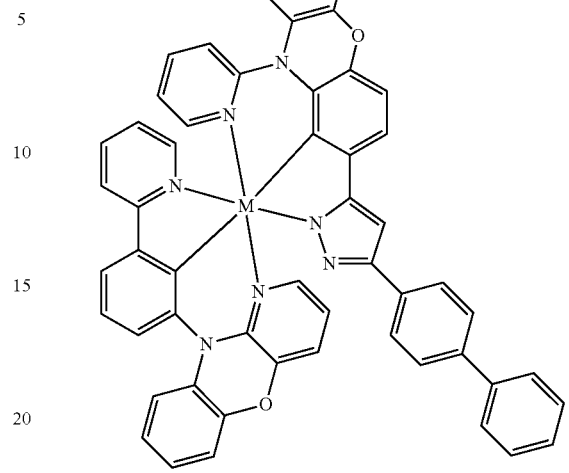
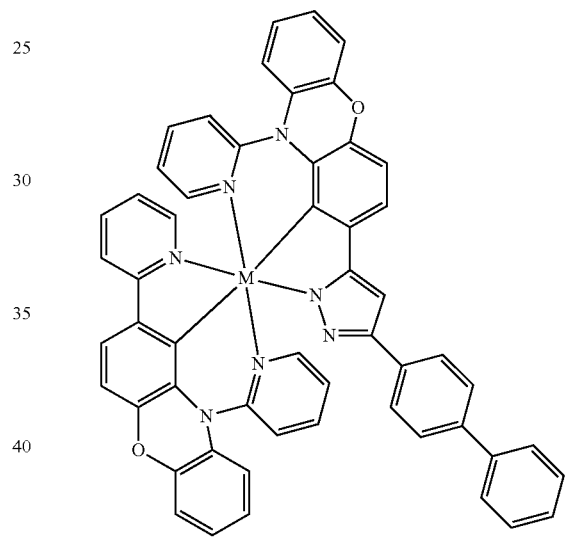
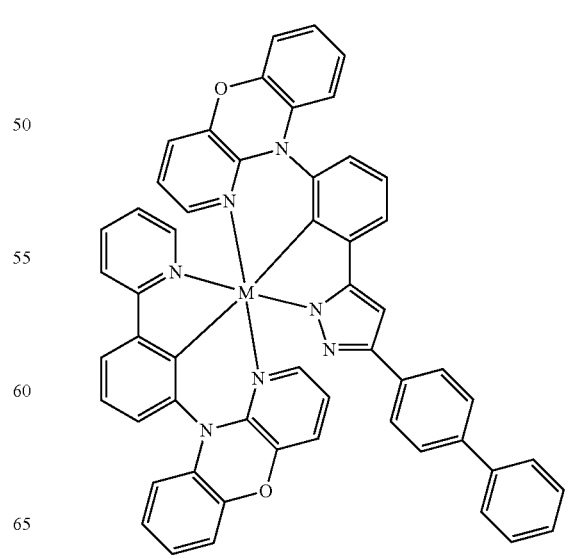

-continued
Structures M-39 (M = Ir, Rh)
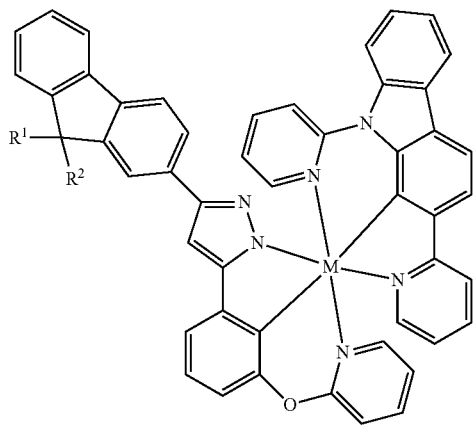
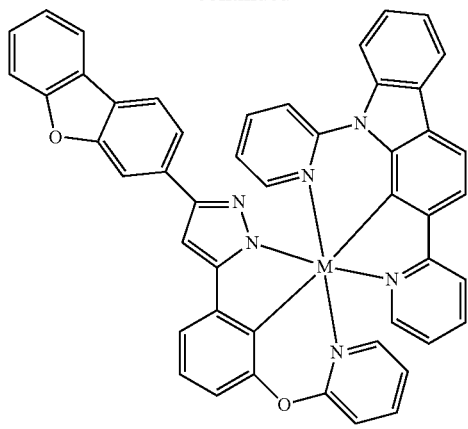
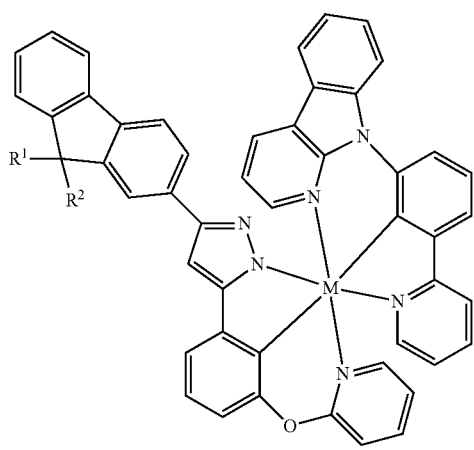
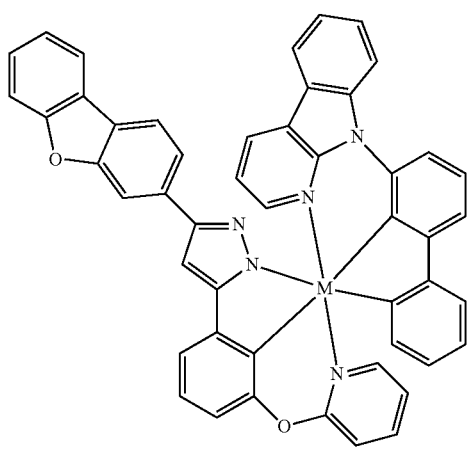
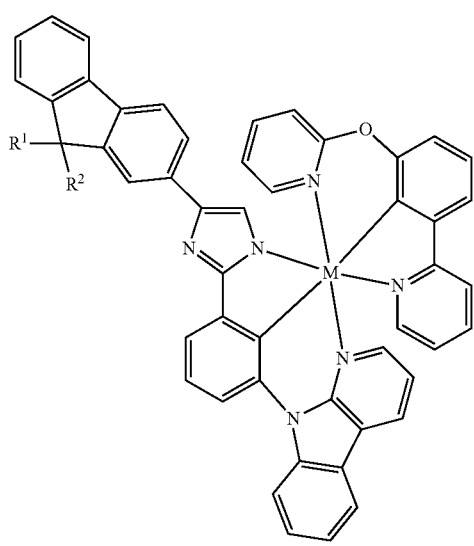
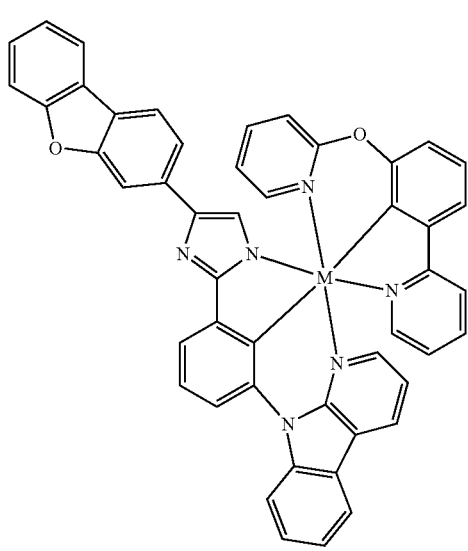

405
-continued
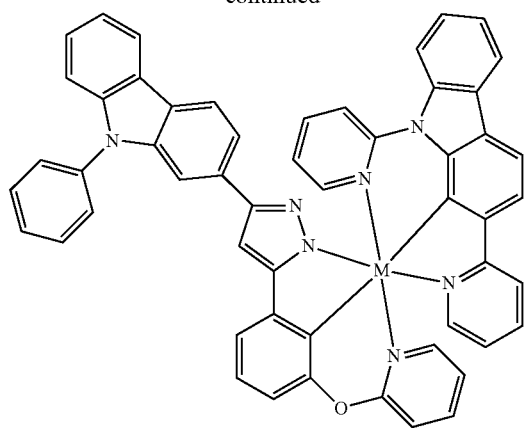
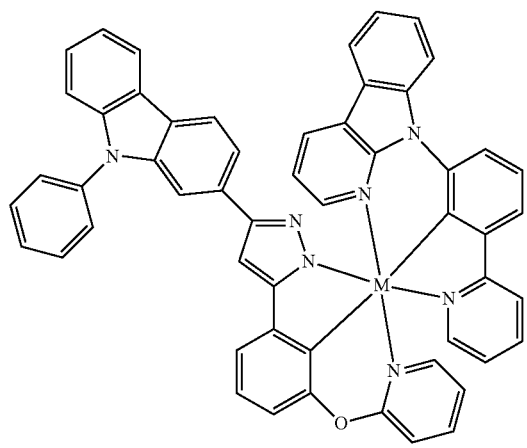
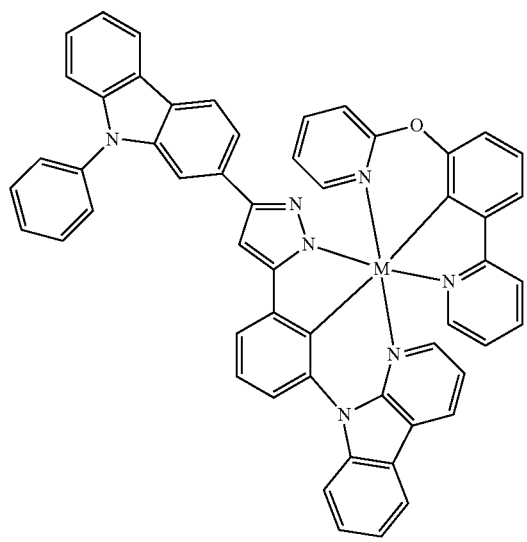
406
-continued
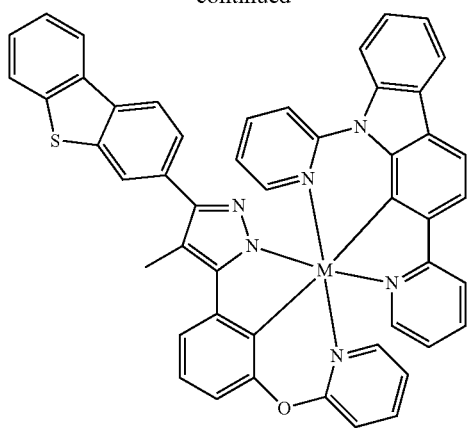
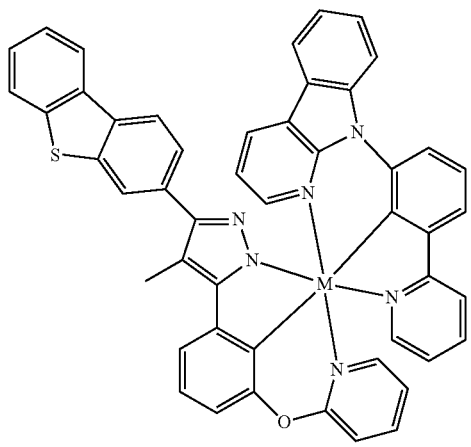
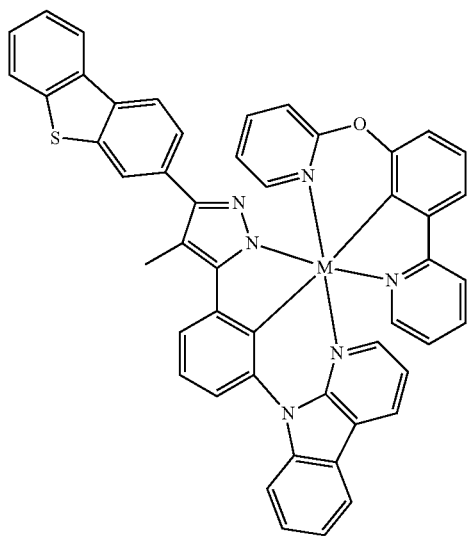

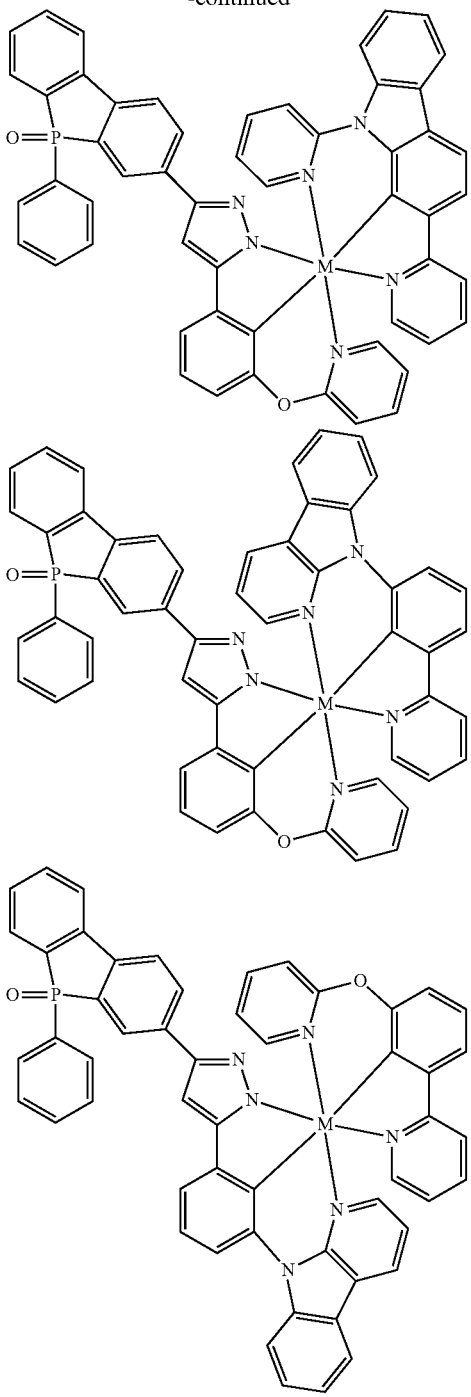

wherein:

each of R, R¹, and R² is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Also disclosed herein are compositions including one or more of the compounds disclosed herein. These compositions are suitable for use in a wide variety of optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications.

Also disclosed herein are devices including one or more of the compounds or compositions disclosed herein, including, for example, optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications.

Figure 2:
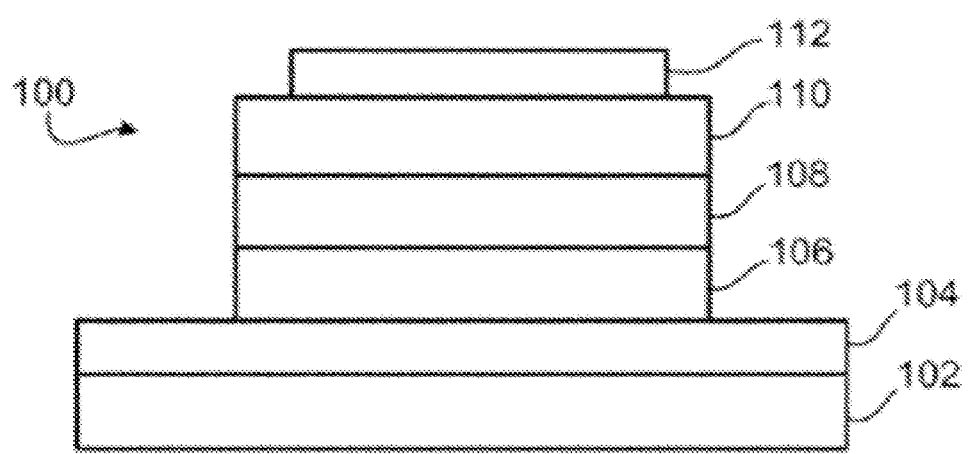
FIG. 2 depicts a cross-sectional view of an exemplary organic light emitting device (OLED).

Compounds described herein can be used in an OLED. FIG. 2 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 2 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds and/or the host material. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of this disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation of compounds described herein are recited in the examples. These methods are provided to illustrate various methods of preparation, but are not intended to be limited to any of the methods recited herein. Accordingly, one of skill in the art in possession of this disclosure could readily modify a recited method or utilize a different method to prepare one or more of the compounds described herein. The following aspects are only exemplary and are not intended to be limiting. Temperatures, catalysts, concentrations, reactant compositions, and other process conditions can vary, and one of skill in the art, in possession of this disclosure, could readily select appropriate reactants and conditions for a desired complex.

$^1$H spectra were recorded at 400 MHz, $^{13}$C NMR spectra were recorded at 100 MHz on Varian Liquid-State NMR instruments in CDCl$_3$ or DMSO-d$_6$ solutions and chemical shifts were referenced to residual protiated solvent. If CDCl$_3$ was used as solvent, $^1$H NMR spectra were recorded with tetramethylsilane ($\delta$=0.00 ppm) as internal reference; $^{13}$C NMR spectra were recorded with CDCl$_3$ ($\delta$=77.00 ppm) as internal reference. If DMSO-d$_6$ was used as solvent, $^1$H NMR spectra were recorded with residual H$_2$O ($\delta$=3.33 ppm) as internal reference; $^{13}$C NMR spectra were recorded with DMSO-d$_6$ ($\delta$=39.52 ppm) as internal reference. The following abbreviations (or combinations thereof) were used to explain $^1$H NMR multiplicities: s=singlet, d=doublet, t=triplet, q=quartet, p=quintet, m=multiplet, br=broad.

1. Example 1

Platinum complex Pt1aOpyCl was prepared according to the following scheme:

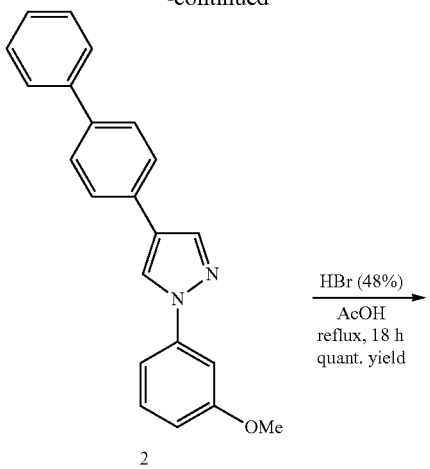

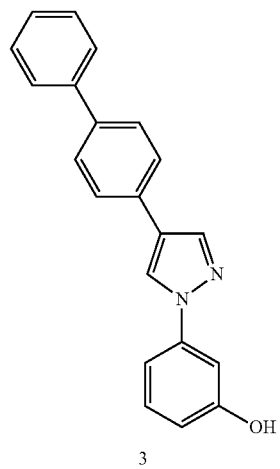

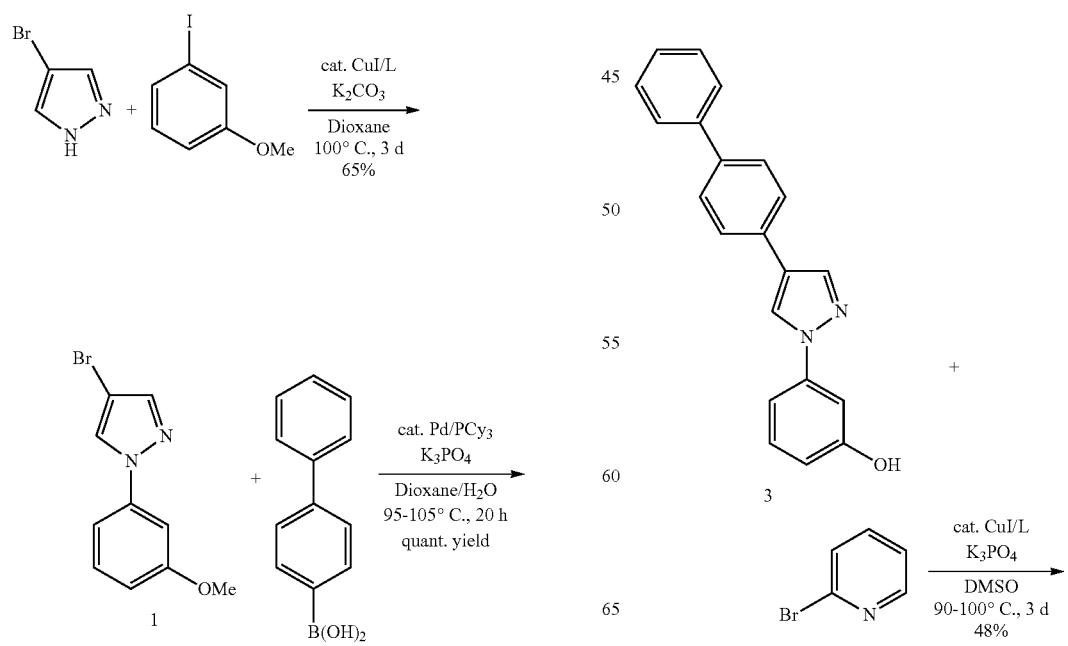

-continued

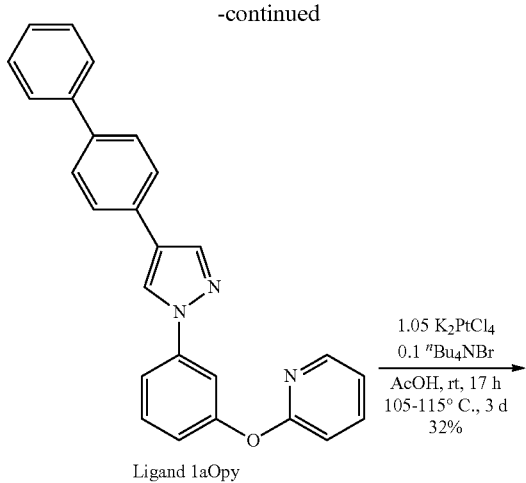

Ligand 1aOpy 1.05 K$_2$PtCl$_4$
0.1 $^n$Bu$_4$NBr
AcOH, rt, 17 h
105-115° C., 3 d
32%

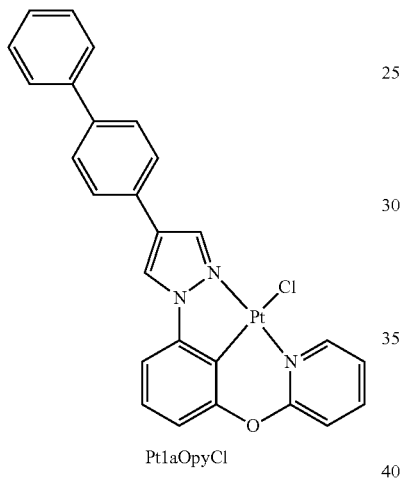

Pt1aOpyCl

Synthesis of 4-bromo-1-(3-methoxyphenyl)-1H-pyrazole 1

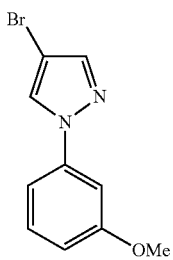 [SMILES: COc1cccc(-n2cc(Br)cn2)c1]

4-Bromo-1H-pyrazole (3.674 g, 25 mmol, 1.0 eq), CuI (95 mg, 0.5 mmol, 0.02 eq) and K$_2$CO$_3$ (7.256 g, 52.5 mmol, 2.1 eq) were added to a dry pressure tube equipped with a magnetic stir bar. Then trans-1,2-cyclohexanediamine (570 mg, 5 mmol, 0.2 eq), 1-iodo-3-methoxybenzene (3.57 mL, 30 mmol, 1.2 eq) and dioxane (50 mL) were added to a nitrogen-filled glove box. The mixture was bubbled with nitrogen for 5 minutes. The tube was sealed before being taken out of the glove box. The mixture was stirred in an oil bath at a temperature of 100° C. for two days. Then the mixture was cooled down to ambient temperature, filtered and washed with ethyl acetate. The filtrate was concentrated under reduced pressure and the residue was purified through column chromatography on silica gel using hexane and ethyl acetate (20:1-15:1) as eluent to obtain the desired product 4-bromo-1-(3-methoxyphenyl)-1H-pyrazole 1 as a colorless sticky liquid 4.09 g in 65% yield. $^1$H NMR (DMSO-d$_6$, 400 MHz): δ 3.82 (s, 3H), 6.89-6.92 (m, 1H), 7.39-7.41 (m, 3H), 7.86 (s, 1H), 8.81 (s, 1H). $^{13}$C NMR (DMSO-d$_6$, 100 MHz): δ 55.45, 94.92, 104.01, 110.35, 112.54, 128.30, 130.51, 140.26, 141.16, 160.15.

Synthesis of 4-(biphenyl-4-yl)-1-(3-methoxyphenyl)-1H-pyrazole 2

To a three-necked flask equipped with a magnetic stir bar and a condenser was added biphenyl-4-ylboronic acid (1012 mg, 5.11 mmol, 1.2 eq), Pd$_2$(dba)$_3$ (156 mg, 0.17 mmol, 0.04 eq) and tricyclohexylphosphine PCy$_3$ (115 mg, 0.41 mmol, 0.096 eq). The tube was evacuated and backfilled with nitrogen. This evacuation and backfill procedure was repeated for another two cycles. Then a solution of 4-bromo-1-(3-methoxyphenyl)-1H-pyrazole 1 (1.078 g, 4.26 mmol, 1.0 eq) in dioxane (25 mL) and a solution of K$_3$PO$_4$ (1.537 g, 7.24 mmol, 1.7 eq) in H$_2$O (10 mL) were added by syringe independently under nitrogen. The mixture was stirred in an oil bath at a temperature of 95-105° C. for 20 hours, cooled down to ambient temperature, filtered, and washed with ethyl acetate. The organic layer of the filtrate was separated, dried over sodium sulfate, filtered, concentrated under reduced pressure, and the residue was purified through column chromatography on silica gel using hexane/ethyl acetate (10:1-5:1-3:1) as eluent to obtain the desired product 4-(biphenyl-4-yl)-1-(3-methoxyphenyl)-1H-pyrazole 2 as a brown solid in quantitative yield. $^1$H NMR (DMSO-d$_6$, 400 MHz): δ 3.85 (s, 3H), 6.90 (dd, J=8.0, 2.4 Hz, 1H), 7.36-7.50 (m, 6H), 7.70-7.73 (m, 4H), 7.82 (d, J=8.4 Hz, 2H), 8.26 (s, 1H), 9.07 (s, 1H).

Synthesis of 3-(4-(biphenyl-4-yl)-1H-pyrazol-1-yl)phenol 3

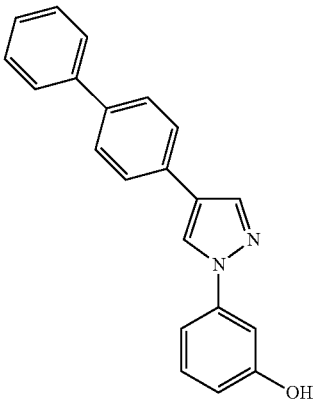 [SMILES: Oc1cccc(-n2cc(-c3ccc(-c4ccccc4)cc3)cn2)c1]

A solution of 4-(biphenyl-4-yl)-1-(3-methoxyphenyl)-1H-pyrazole 2 (4.26 mmol) in a mixture of acetic acid (20 mL) and hydrobromic acid (10 mL, 48%) was refluxed at 120-130° C. for 18 hours at a atmosphere of nitrogen. Then the mixture was cooled to room temperature. After most of the acetic acid was removed under reduced pressure, the residue was neutralized with a solution of $K_2CO_3$ in water until there was no further gas generation. Then the precipitate was filtered and washed with water for several times. The collected solid was dried in air to afford the product 3-(4-(biphenyl-4-yl)-1H-pyrazol-1-yl)phenol 3 as a brown solid in quantitative yield. $^1$H NMR (DMSO-$d_6$, 400 MHz): δ 6.59 (dt, J=6.8, 2.0 Hz, 1H), 7.23-7.28 (m, 3H), 7.32 (t, J=7.6 Hz, 1H), 7.43 (t, J=8.0 Hz, 2H), 7.67 (d, J=8.8 Hz, 4H), 7.77 (d, J=8.4 Hz, 2H), 8.19 (s, 1H), 8.94 (s, 1H), 9.76 (bs, 1H).

Synthesis of 2-(3-(4-(biphenyl-4-yl)-1H-pyrazol-1-yl)phenoxy)pyridine Ligand 1aOpy

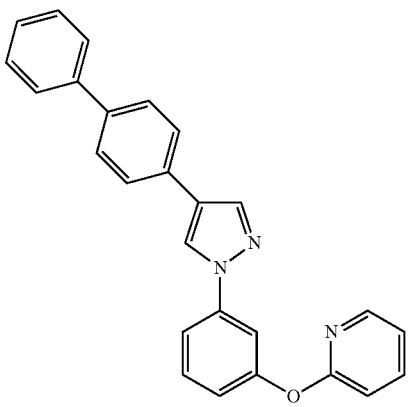

Ligand 1aOpy

To a dry pressure vessel equipped with a magnetic stir bar was added 3-(4-(biphenyl-4-yl)-1H-pyrazol-1-yl)phenol 3 (624 mg, 2.0 mmol, 1.0 eq), 2-bromopyridine (632 mg, 4.0 mmol, 2.0 eq), CuI (38 mg, 0.2 mmol, 0.1 eq), picolinic acid (49 mg, 0.4 mmol, 0.2 eq) and $K_3PO_4$ (849 mg, 4.0 mmol, 2.0 eq). The tube was evacuated and backfilled with nitrogen. This evacuation and backfill procedure was repeated for another two cycles. Then DMSO (12 mL) was added under nitrogen. The mixture was stirred at a temperature of 90-100° C. for 3 days and then cooled down to ambient temperature. Water was added to dissolve the solid. The mixture was extracted with ethyl acetate three times. The combined organic layer was washed with water three times and then dried over sodium sulfate and filtered. The filtrate was concentrated under reduced pressure and the residue was purified through column chromatography on silica gel using hexane/ethyl acetate (10:1) as eluent to obtain the desired product Ligand 1aOpy as a brown solid, 371 mg, 48% yield. $^1$H NMR (DMSO-$d_6$, 400 MHz): δ 7.08 (dd, J=8.0, 2.0 Hz, 1H), 7.11 (d, J=8.0 Hz, 1H), 7.15-7.18 (m, 1H), 7.34 (t, J=7.6 Hz, 1H), 7.45 (t, J=7.6 Hz, 2H), 7.55 (t, J=8.0 Hz, 1H), 7.68-7.71 (m, 5H), 7.77-7.81 (m, 3H), 7.86-7.91 (m, 1H), 8.18-8.19 (m, 1H), 8.27 (s, 1H), 9.10 (s, 1H). $^{13}$C NMR (DMSO-$d_6$, 100 MHz): δ 111.16, 111.72, 114.08, 118.89, 119.36, 123.88, 124.82, 125.84, 126.43, 127.10, 127.36, 128.93, 130.72, 130.86, 138.29, 138.90, 139.70, 140.36, 140.68, 147.52, 154.82, 162.80.

Synthesis of 2-(3-(4-(biphenyl-4-yl)-1H-pyrazol-1-yl)phenoxy)pyridine platinum complex Pt1aOpyCl

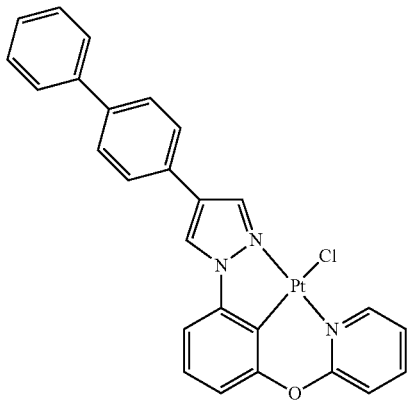

Pt1aOpyCl

Figure 3:
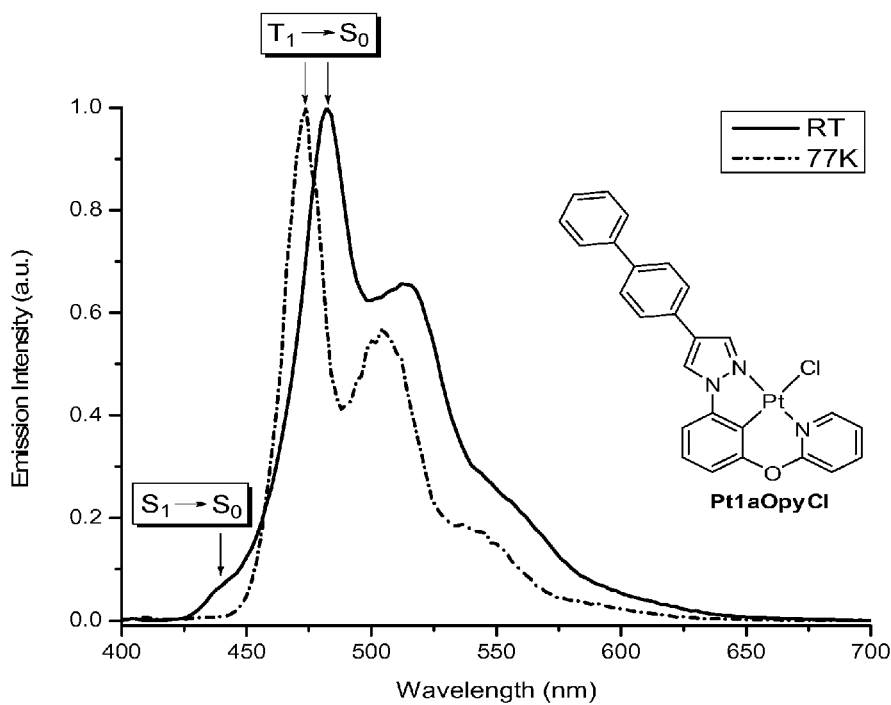
FIG. 3 shows emission spectra of Pt1aOpyCl in $CH_2Cl_2$ at room temperature and in 2-methyltetrahydrofuran at 77K.

To a dry pressure tube equipped with a magnetic stir bar was added 2-(3-(4-(biphenyl-4-yl)-1H-pyrazol-1-yl)phenoxy)pyridine Ligand 1aOpy (335 mg, 0.86 mmol, 1.0 eq), $K_2PtCl_4$ (378 mg, 0.90 mmol, 1.05 eq), $^n$Bu$_4$NBr (28 mg, 0.086 mmol, 0.1 eq) and solvent acetic acid (52 mL) under nitrogen. After bubbling with nitrogen for 20 minutes, the tube was sealed and the mixture was stirred at room temperature for 17 hours, followed by 105-115° C. for 3 days. The resulting mixture was cooled to room temperature and water (104 mL) was added. The precipitate was filtered and washed with water twice, then washed with ethanol twice. Then the solid was dried in air under reduced pressure to yield a gray solid, 475 mg. The collected solid 314 mg was further purified by recrystallization from DMSO to obtain the platinum complex Pt1aOpyCl 112 mg in 32% total yield. FIG. 3 shows emission spectra of Pt1aOpyCl in $CH_2Cl_2$ at room temperature and in 2-methyltetrahydrofuran at 77K $^1$H. NMR (DMSO-$d_6$, 500 MHz): δ 7.05 (d, J=7.5 Hz, 1H), 7.30-7.33 (m, 1H), 7.38-7.42 (m, 2H), 7.48-7.53 (m, 3H), 7.57 (d, J=7.5 Hz, 1H), 7.74-7.76 (m, 2H), 7.79 (d, J=8.5 Hz, 2H), 7.89 (d, J=8.5 Hz, 2H), 8.21-8.25 (m, 1H), 8.57 (s, 1H), 9.48 (s, 1H), 9.92 (dd, J=6.5, 2.0 Hz, 1H). MS (MALDI) for $C_{26}H_{18}N_3OPt$ [M-Cl]$^+$: calcd 583.11, found 583.29.
2. Example 2
Platinum complex Pt1bOpyCl can be prepared according to the following scheme:
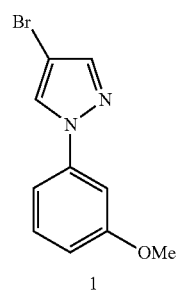
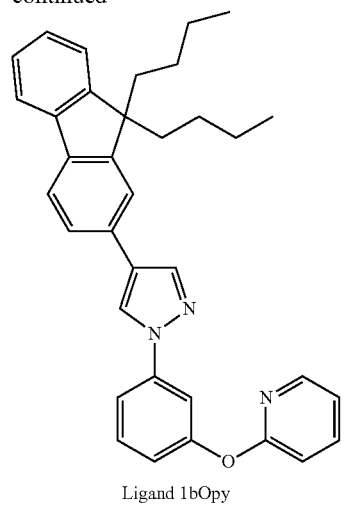
Ligand 1bOpy
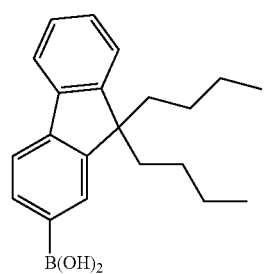
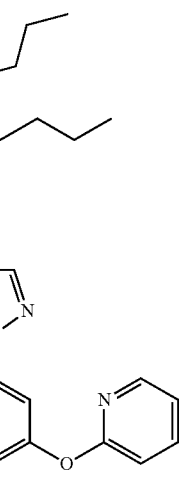
Ligand 1bOpy
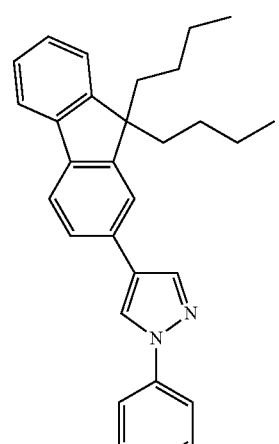
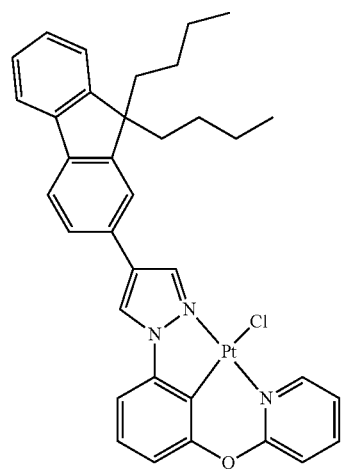
Pt1bOpyCl

Synthesis of 3-(4-(9,9-dibutyl-9H-fluoren-2-yl)-1H-pyrazol-1-yl)phenol 4

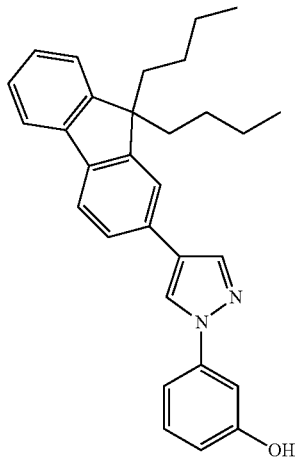 [SMILES: CCCCC1(CCCC)c2ccccc2-c2ccc(-c3cnn(-c4cccc(O)c4)c3)cc21]

To a three-necked flask equipped with a magnetic stir bar and a condenser was added 9,9-dibutyl-9H-fluoren-2-ylboronic acid (1.805 g, 5.60 mmol, 1.4 eq), Pd$_2$(dba)$_3$ (14 mg, 0.16 mmol, 0.04 eq) and tricyclohexylphosphine PCy$_3$ (108 mg, 0.38 mmol, 0.096 eq). Then the flask was evacuated and backfilled with nitrogen. The evacuation and back fill procedure was repeated for another two cycles. Then a solution of 4-bromo-1-(3-methoxyphenyl)-1H-pyrazole 1 (1.012 g, 4.00 mmol, 1.0 eq) in dioxane (25 mL) and a solution of K$_3$PO$_4$ (1.443 g, 6.80 mmol, 1.7 eq) in H$_2$O (10 mL) were added by syringe independently under nitrogen. The mixture was stirred at a temperature of 95-105° C. for 27 hours, cooled down to ambient temperature, filtered, and washed with ethyl acetate. The organic layer of the filtrate was separated, dried over sodium sulfate, filtered, concentrated, and the residue was purified through column chromatography on silica gel using hexane/ethyl acetate (20:1-15) as eluent to obtain a colorless sticky liquid which was used directly for the next step. A solution of the sticky liquid in a mixture of acetic acid (30 mL) and hydrobromic acid (15 mL, 48%) was stirred at a temperature of 125-130° C. for 17 hours under nitrogen. Then the mixture was cooled to room temperature. After most of the acetic acid was removed under reduced pressure, the residue was neutralized with a solution of K$_2$CO$_3$ in water until there was no further gas generation. Then the precipitate was filtered off and washed with water several times. The collected solid was dried in air to afford the product 3-(4-(9,9-dibutyl-9H-fluoren-2-yl)-1H-pyrazol-1-yl)phenol 4 as a brown solid in 83% total yield for the two steps. $^1$H NMR (DMSO-d$_6$, 400 MHz): δ 0.19-0.32 (m, 4H), 0.37 (t, J=7.2 Hz, 6H), 0.74-0.84 (m, 4H), 1.78 (t, J=7.2 Hz, 4H), 6.48 (dt, J=6.8, 2.0 Hz, 1H), 7.03-7.10 (m, 5H), 7.18 (dd, J=6.4, 2.0 Hz, 1H), 7.44 (dd, J=8.0, 1.6 Hz, 1H), 7.53-7.58 (m, 3H), 8.01 (s, 1H), 8.75 (s, 1H), 9.55 (bs, 1H).

Synthesis of 2-(3-(4-(9,9-dibutyl-9H-fluoren-2-yl)-1H-pyrazol-1-yl)phenoxy)pyridine Ligand 1bOpy

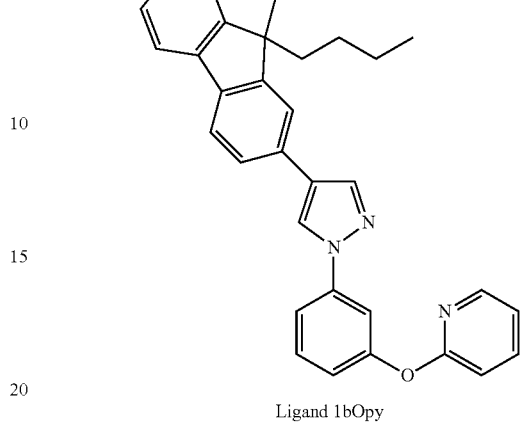

Ligand 1bOpy

To a dry pressure vessel equipped with a magnetic stir bar was added 3-(4-(9,9-dibutyl-9H-fluoren-2-yl)-1H-pyrazol-1-yl)phenol 4 (655 mg, 1.5 mmol, 1.0 eq), 2-bromopyridine (711 mg, 4.5 mmol, 3.0 eq), CuI (29 mg, 0.15 mmol, 0.1 eq), picolinic acid (37 mg, 0.30 mmol, 0.2 eq) and K$_3$PO$_4$ (637 mg, 3.0 mmol, 2.0 eq). The tube was evacuated and backfilled with nitrogen. This evacuation and backfill procedure was repeated for another two cycles. Then DMSO (9 mL) was added under nitrogen. The mixture was stirred at a temperature of 95-105° C. for 3 days and then cooled down to ambient temperature. Water was added to dissolve the salt. The mixture was extracted with ethyl acetate for three times. The combined organic layer was washed with water for three times and then dried over sodium sulfate and filtered. The filtrate was concentrated under reduced pressure and the residue was purified through column chromatography on silica gel using hexane/ethyl acetate (10:1-5:1-3:1) as eluent to obtain the desired product as a brown solid, 581 mg in 75% yield. $^1$H NMR (DMSO-d$_6$, 400 MHz): δ 0.46-0.58 (m, 4H), 0.62 (t, J=7.6 Hz, 6H), 0.99-1.06 (m, 4H), 2.03 (dd, J=8.4 Hz, 4H), 7.09-7.11 (m, 1H), 7.14 (d, J=8.4 Hz, 1H), 7.17-7.20 (m, 1H), 7.29-7.35 (m, 2H), 7.42-7.44 (m, 1H), 7.58 (t, J=8.0 Hz, 1H), 7.71 (dd, J=7.6, 1.6 Hz, 1H), 7.73 (t, J=2.0 Hz, 1H), 7.79-7.83 (m, 4H), 7.91 (td, J=8.4, 2.0 Hz, 1H), 8.21 (dd, J=5.2, 1.2 Hz, 1H), 8.32 (s, 1H), 9.13 (s, 1H).

Synthesis of 2-(3-(4-(9,9-dibutyl-9H-fluoren-2-yl)-1H-pyrazol-1-yl)phenoxy)pyridine platinum complex Pt1bOpyCl

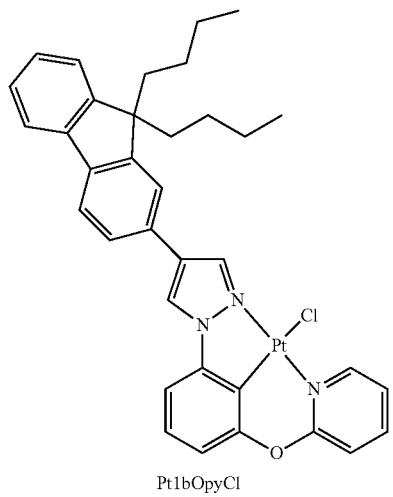

Pt1bOpyCl

419

Figure 4:
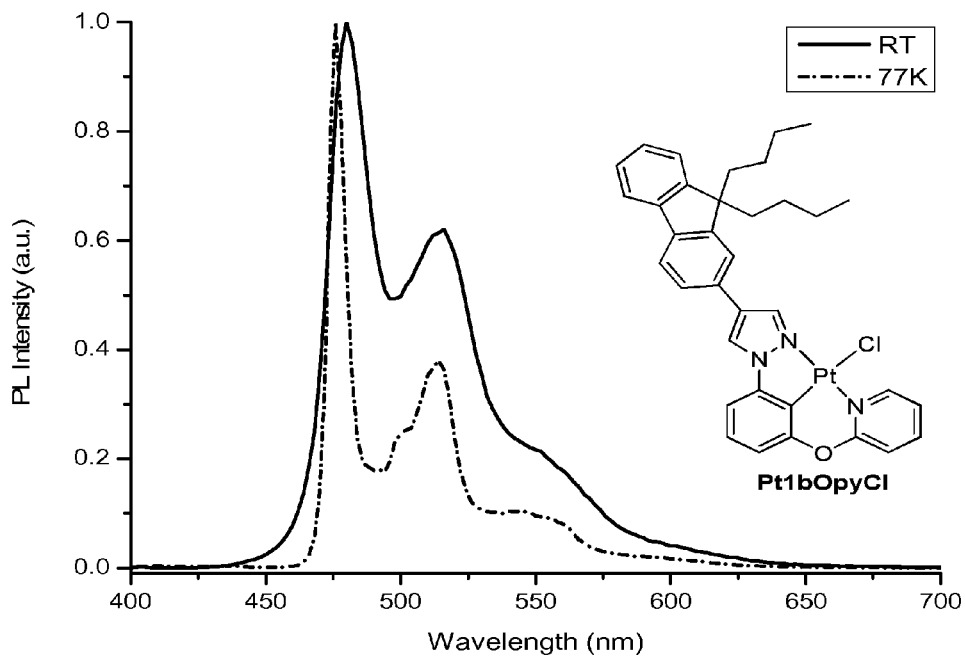
FIG. 4 shows emission spectra of Pt1bOpyCl in $CH_2Cl_2$ at room temperature and in 2-methyltetrahydrofuran at 77K.

To a dry pressure tube equipped with a magnetic stir bar was added 2-(3-(4-(9,9-dibutyl-9H-fluoren-2-yl)-1H-pyrazol-1-yl)phenoxy)pyridine Ligand 1bOpy (280 mg, 0.545 mmol, 1.0 eq), K$_2$PtCl$_4$ (240 mg, 0.572 mmol, 1.05 eq), $^n$Bu$_4$NBr (18 mg, 0.0545 mmol, 0.1 eq) and acetic acid (33 mL) under the protection of nitrogen. After bubbling with nitrogen for 20 minutes, the tube was sealed and the mixture was stirred at room temperature for 12 hours, then stirred at 105-115° C. for 3.5 days. The resulting mixture was cooled to room temperature. The precipitate was filtered and washed with water twice, then washed with ethanol twice. Then the solid was dried in air under reduced pressure and further purified by recrystallization in DMSO to obtain the platinum complex Pt1bOpyCl, 263 mg in 65% yield. FIG. 4 shows emission spectra of Pt1bOpyCl in CH$_2$Cl$_2$ at room temperature and in 2-methyltetrahydrofuran at 77K. $^1$H NMR (DMSO-d$_6$, 400 MHz): δ 0.45-0.57 (m, 4H), 0.64 (t, J=7.6 Hz, 6H), 1.02-1.11 (m, 4H), 2.02-2.16 (m, 4H), 7.04 (d, J=8.0 Hz, 1H), 7.30-7.42 (m, 4H), 7.46-7.48 (m, 1H), 7.52 (d, J=8.8 Hz, 1H), 7.58 (d, J=8.0 Hz, 1H), 7.77 (d, J=7.6 Hz, 1H), 7.84-7.86 (m, 1H), 7.90 (d, J=8.0 Hz, 1H), 7.95 (s, 1H), 8.24 (t, J=7.6 Hz, 1H), 8.63 (s, 1H), 9.47 (s, 1H), 9.94 (dd, J=5.2 Hz, 1H).

3. Example 3

Palladium complex Pd1bOpyAc can be prepared according to the following scheme:

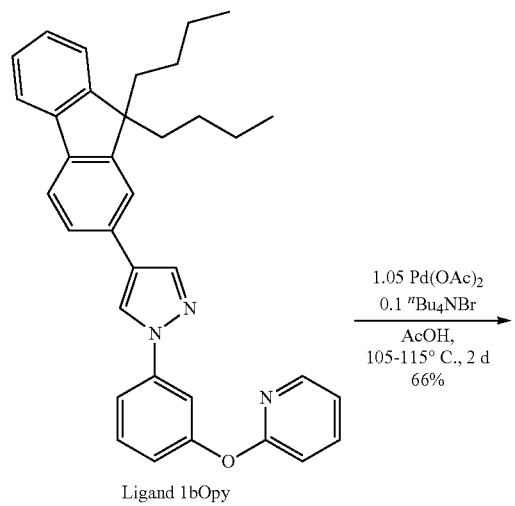

Ligand 1bOpy 1.05 Pd(OAc)$_2$
0.1 $^n$Bu$_4$NBr
AcOH,
105-115° C., 2 d
66%

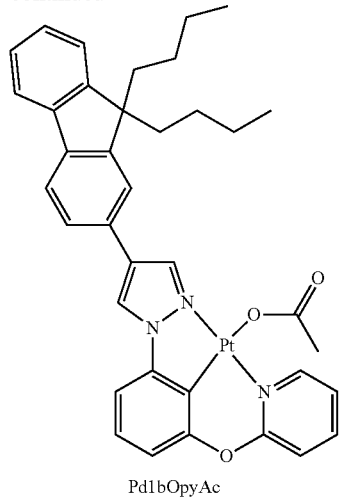

Pd1bOpyAc

Synthesis of 2-(3-(4-(9,9-dibutyl-9H-fluoren-2-yl)-1H-pyrazol-1-yl)phenoxy)pyridine palladium complex Pd1bOpyAc

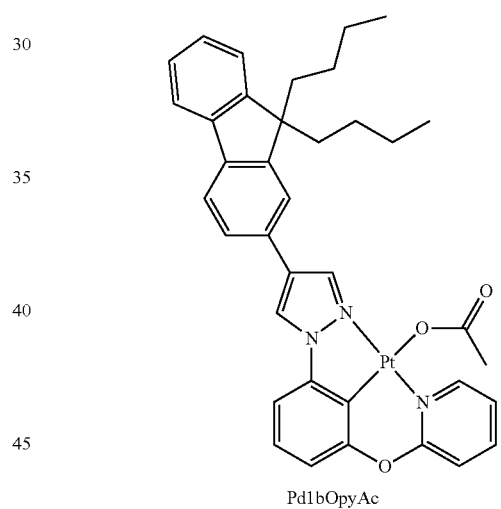

Pd1bOpyAc

Figure 5:
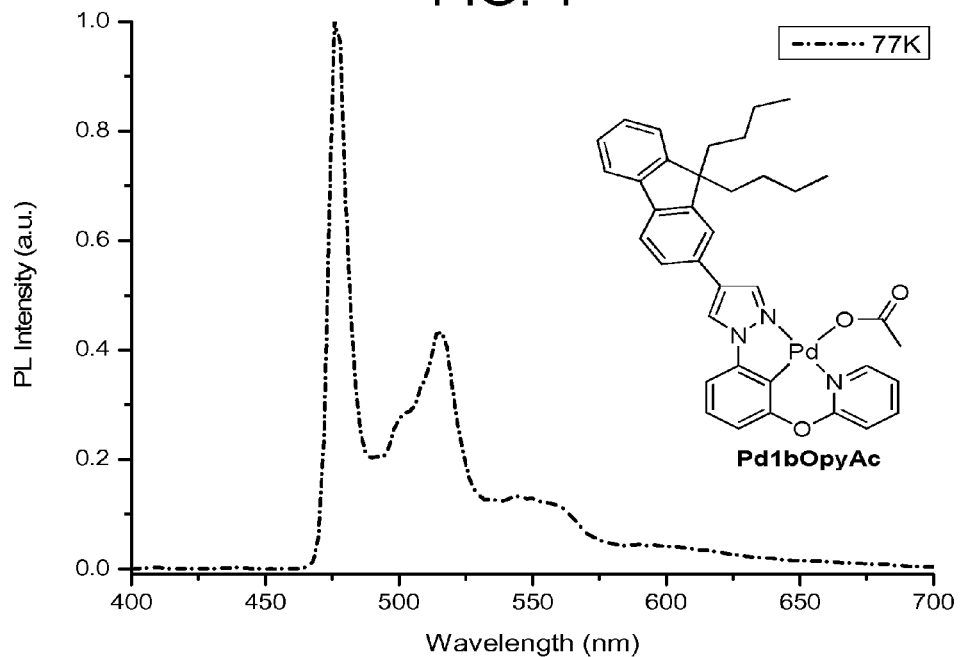
FIG. 5 shows an emission spectrum of Pd1bOpyAc in 2-methyltetrahydrofuran at 77K.

To a dry pressure tube equipped with a magnetic stir bar was added 2-(3-(4-(9,9-dibutyl-9H-fluoren-2-yl)-1H-pyrazol-1-yl)phenoxy)pyridine Ligand 1bOpy (280 mg, 0.545 mmol, 1.0 eq), Pd(OAc)$_2$ (128 mg, 0.572 mmol, 1.05 eq), $^n$Bu$_4$NBr (18 mg, 0.0545 mmol, 0.1 eq) and acetic acid (33 mL) under nitrogen. The mixture was stirred at 105-115° C. for 3.5 days then cooled to room temperature. The precipitate was filtered, the filtrate was concentrated under reduced pressure, and the resulting residue was diluted with water. The precipitate was filtered off and washed with water twice. Then the solid was dried in air under reduced pressure to obtain the palladium complex Pd1bOpyAc, 245 mg in 66% yield. FIG. 5 shows an emission spectrum of Pt1bOpyAc in 2-methyltetrahydrofuran at 77K. $^1$H NMR (DMSO-d$_6$, 400 MHz): δ 0.49-0.61 (m, 4H), 0.65 (t, J=7.2 Hz, 6H), 1.02-1.10 (m, 4H), 2.08 (t, J=8.0 Hz, 4H), 2.11 (s, 3H), 7.00 (d, J=7.6 Hz, 1H), 7.32-7.37 (m, 3H), 7.41 (t, J=8.0 Hz, 1H), 7.47-7.50 (m, 2H), 7.54 (d, J=7.6 Hz, 1H), 7.74 (d, J=7.6 Hz, 1H), 7.84-7.90 (m, 3H), 8.12 (t, J=7.6 Hz, 1H), 8.20 (bs, 1H), 8.76 (bs, 1H), 9.40 (s, 1H).

A number of embodiments have been described. Nevertheless, it will be understood that various modifications may be made without departing from the spirit and scope of the disclosure. Accordingly, other embodiments are within the scope of the following claims.

What is claimed is:
1. A compound represented by Formula A-1:

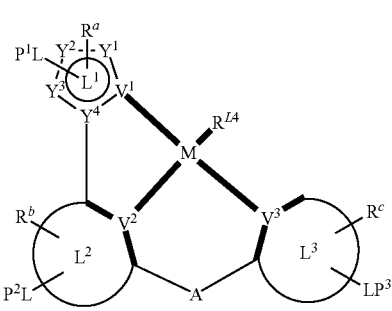

A-1 wherein:
M is Pt, Pd, or Au,
$L^1$ is a five-membered heterocyclyl, five-membered heteroaryl, five-membered carbene, or five-membered N-heterocyclic carbene,
$L^2$ is phenyl,
$L^3$ is pyridyl,
$R^{L4}$ is an inorganic anion or organic anion,
each of $LP^1$, $LP^2$, and $LP^3$ is independently present or absent, wherein at least one of $LP^1$, $LP^2$, or $LP^3$ is present and is independently an aromatic hydrocarbon, an aromatic hydrocarbon derivative, a polyphenyl hydrocarbon, a hydrocarbon with condensed aromatic nuclei, naphthalene, anthracene, phenanthrene, chrysene, pyrene, triphenylene, perylene, acenaphthene, tetracene, pentacene, tetraphene, coronene, fluorene, biphenyl, p-terphenyl, o-diphenylbenzene, m-diphenylbenzene, p-quaterphenyl, benzo[a]tetracene, benzo[k]tetraphene, indeno[1,2,3-cd]fluoranthene, tetrabenzo[de,hi,op,st]pentacene, arylethylene, arylacetylene, an arylacetylene derivative, a diarylethylene, a diarylpolyene, a diaryl-substituted vinylbenzene, a distyrylbenzene, a trivinylbenzene, an arylacetylene, a functional substitution product of stilbene, a five-, six- or seven-membered heterocyclic compound derivative, a furan derivative, a thiophene derivative, a pyrrole derivative, an aryl-substituted oxazole, a 1,3,4-oxadiazole, a 1,3,4-thiadiazole, an aryl-substituted 2-pyrazoline, an aryl-substituted pyrazole, a benzazole, 2H-benzotriazole, a substitution product of 2H-benzotriazole, a heterocycle with one, two or three nitrogen atoms, an oxygen-containing heterocycle, a coumarin, a coumarin derivative, a dye, an acridine dye, a xanthene dye, an oxazine, a thiazine, or a derivative thereof,
A is O,
$V^1$ is N, C, P, B, or Si,
$V^2$ is C,
$V^3$ is N,
each of $Y^1$, $Y^2$, $Y^3$, and $Y^4$ is independently C, N, O, S, S=O, $SO_2$, Se, Se=O, $SeO_2$, $PR^3$, $R^3P$=O, $AsR^3$, $R^3As$=O, or $BR^3$, each of $R^a$, $R^b$, and $R^c$ is independently present or absent, and if present each of $R^a$, $R^b$ and $R^c$ is independently a mono-, di-, tri-, or tetra-substitution, valency permitting, and each $R^a$, $R^b$, and $R^c$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of $R^3$ is independently hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, monoalkylamino, dialkylamino, monoarylamino, diarylamino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, mercapto, sulfo, carboxyl, hydrazino, substituted silyl, or polymeric; or any conjugate or combination thereof.

2. The compound of claim 1, wherein $M-R^{L4}$ is one of:

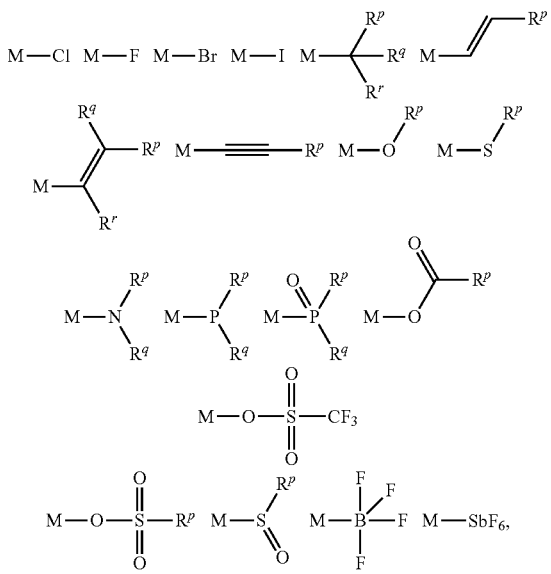

wherein each of $R^p$, $R^q$, and $R^r$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, di alkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, and polymeric; or any conjugate or combination thereof.

3. The compound of claim 1, wherein the five-membered heterocyclyl

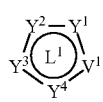
represents one of the following structures:
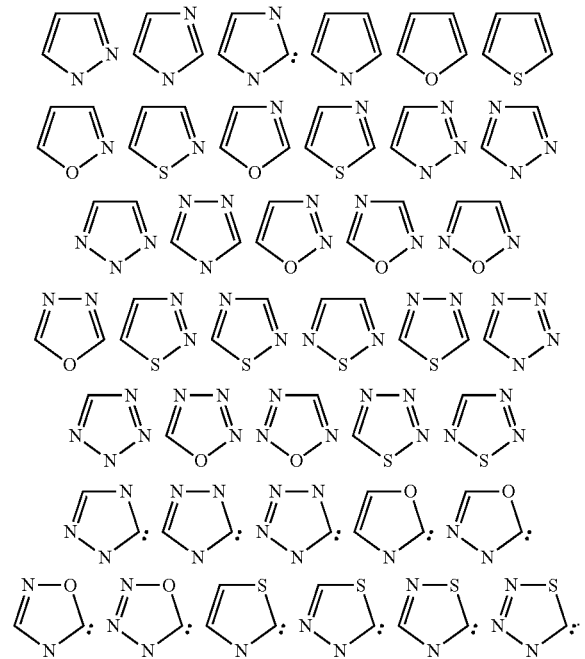
4. The compound of claim 1, wherein:
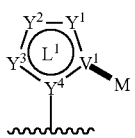
represents one of the following structures:
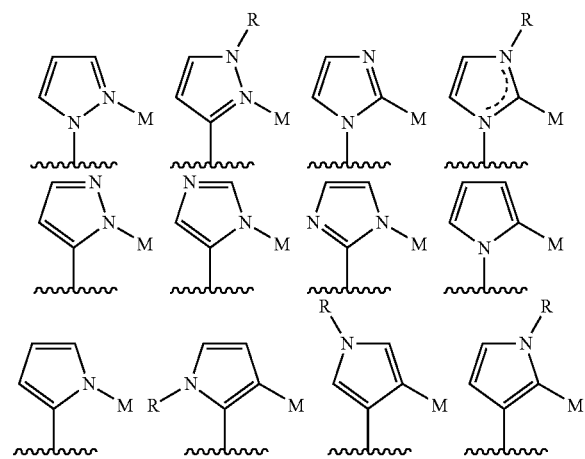
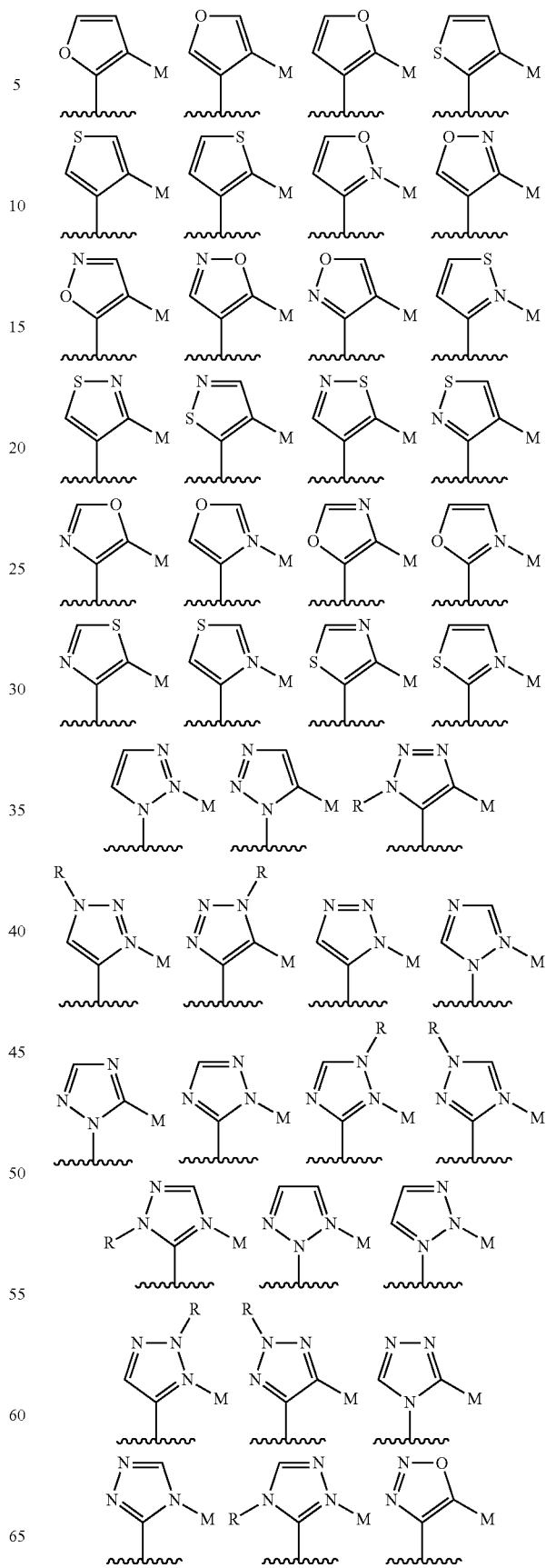

-continued

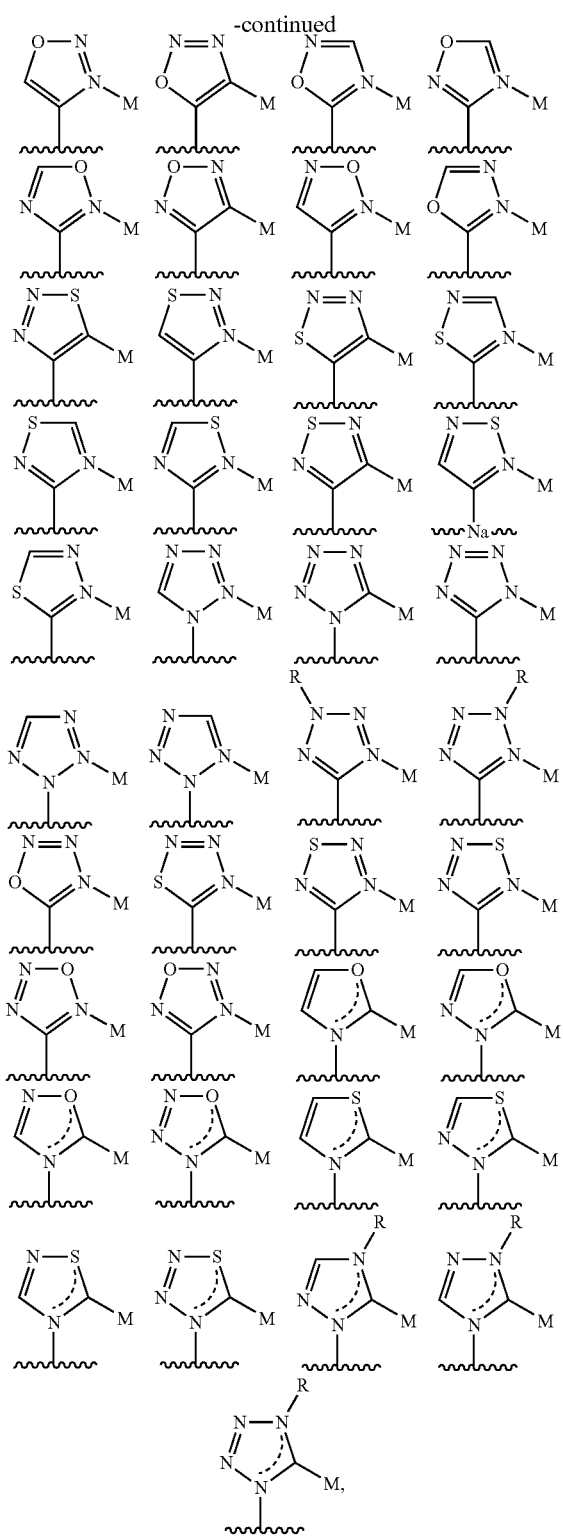

R is hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, monoalkylamino, dialkylamino, monoarylamino, diarylamino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, mercapto, sulfo, carboxyl, hydrazino, substituted silyl, polymeric, or any conjugate or combination thereof.

5. The compound of claim 1, wherein each of $LP^1$, $LP^2$ and $LP^3$, if present, independently represents one of the following structures:

aromatic hydrocarbons selected from the group consisting of:

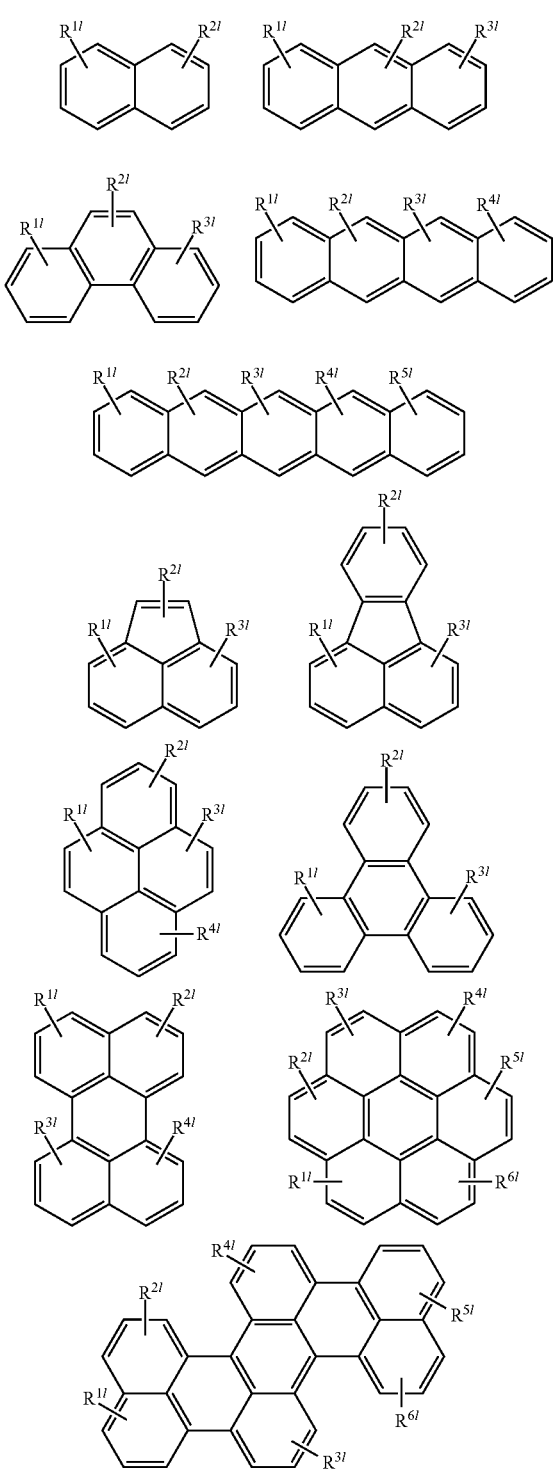

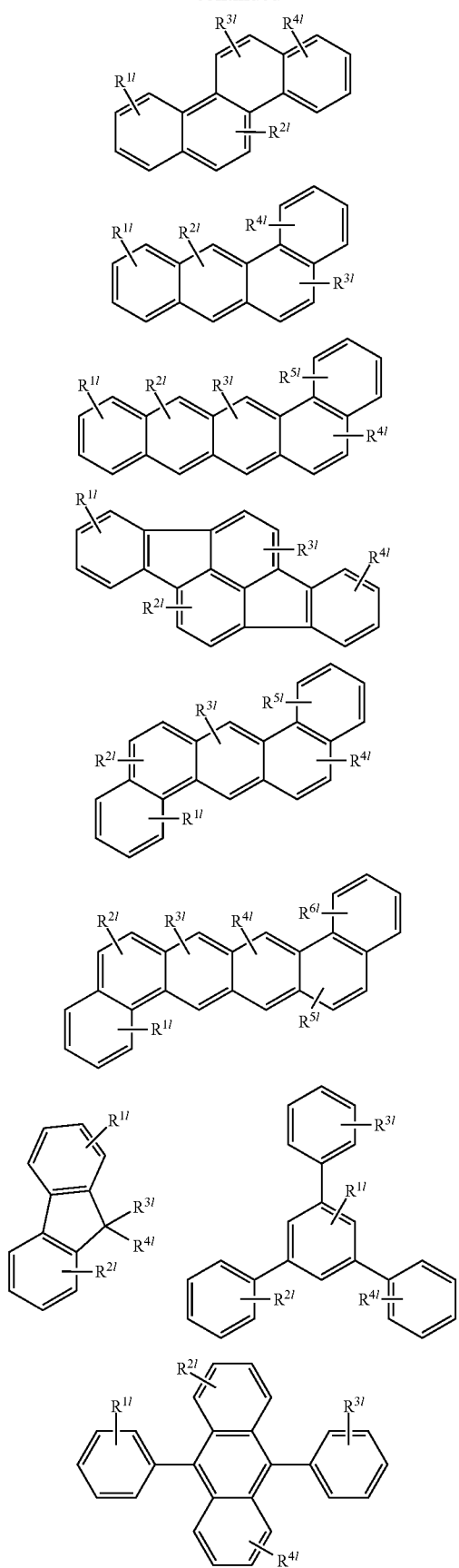
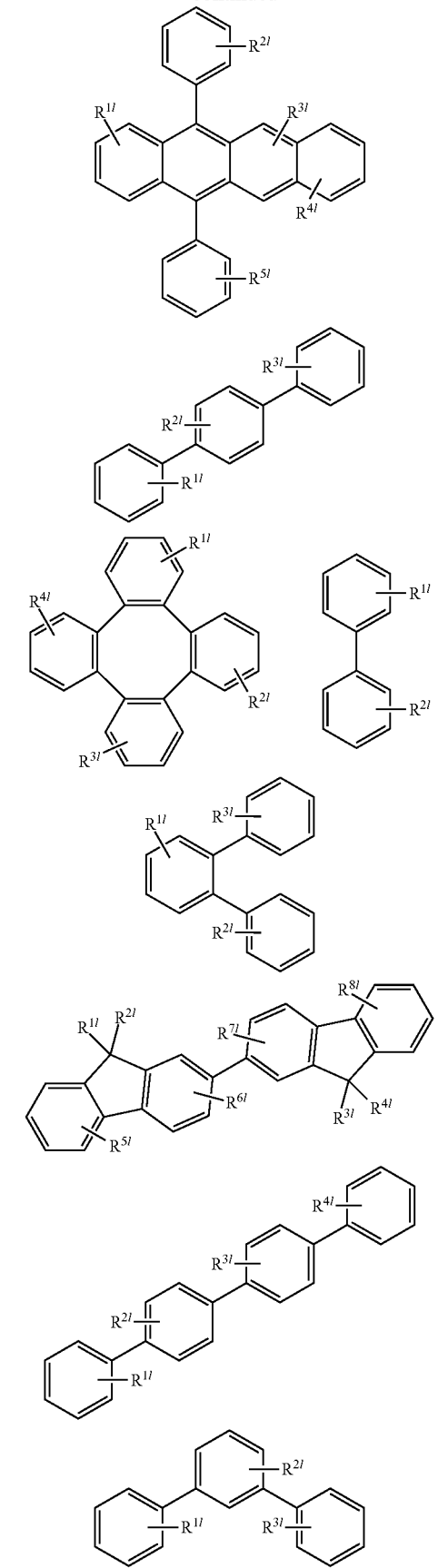

-continued
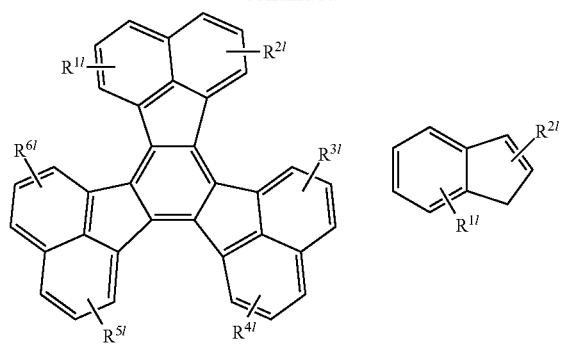
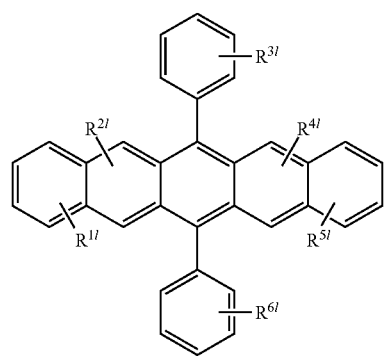
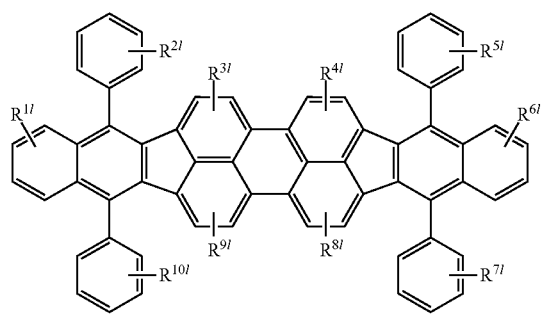
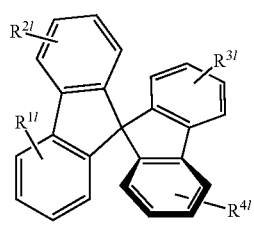
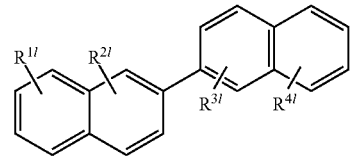
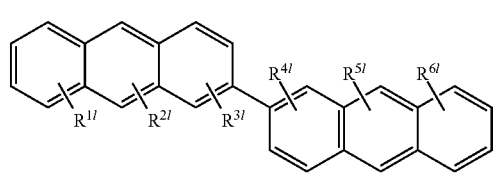
-continued
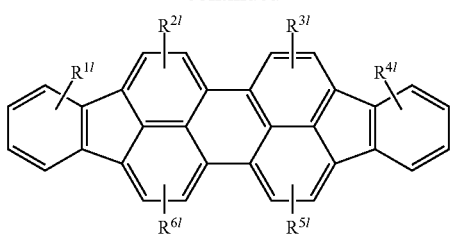
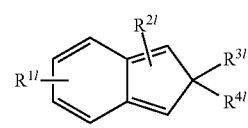
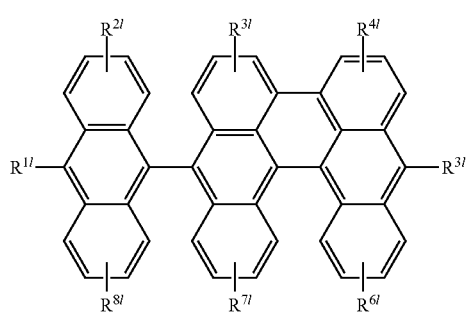
and derivatives thereof,
arylethylenes and arylacetylenes selected from the group consisting of:
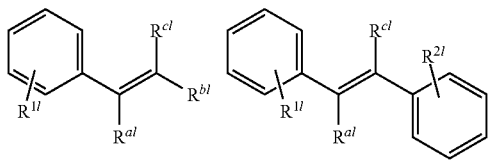
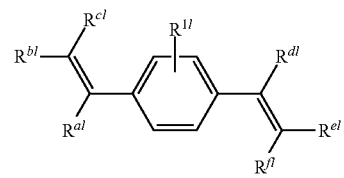
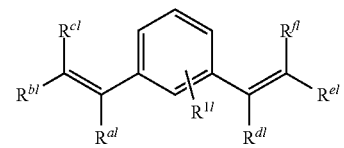
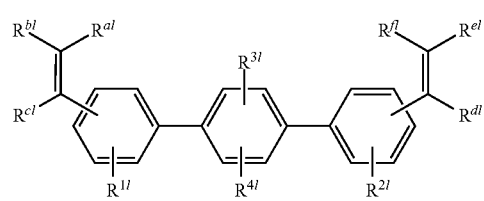

431
-continued
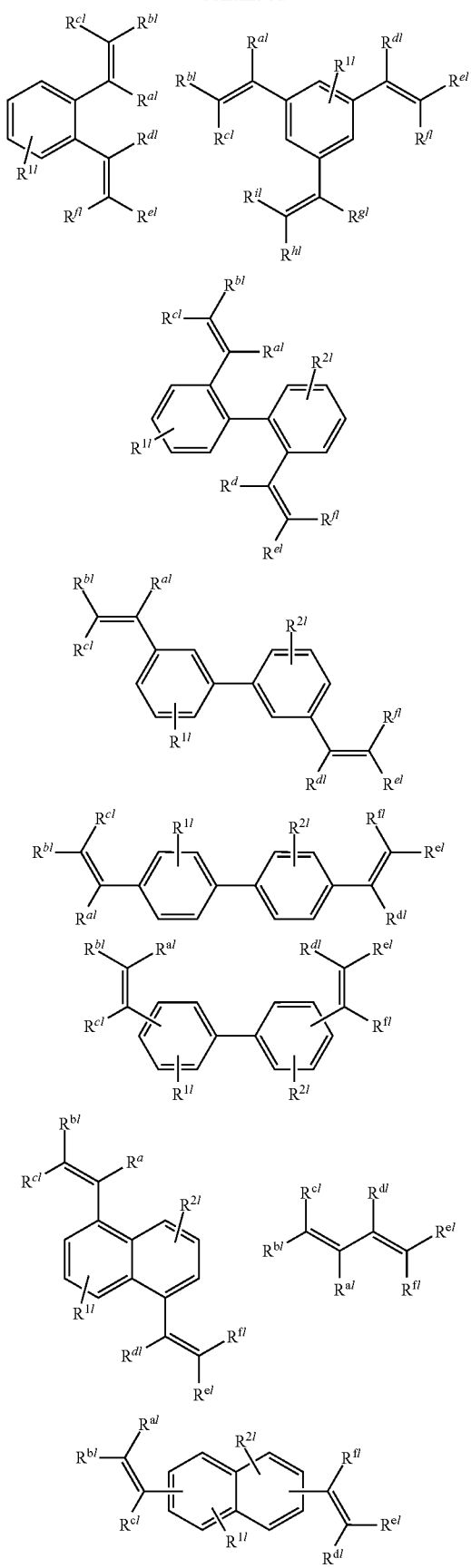
432
-continued
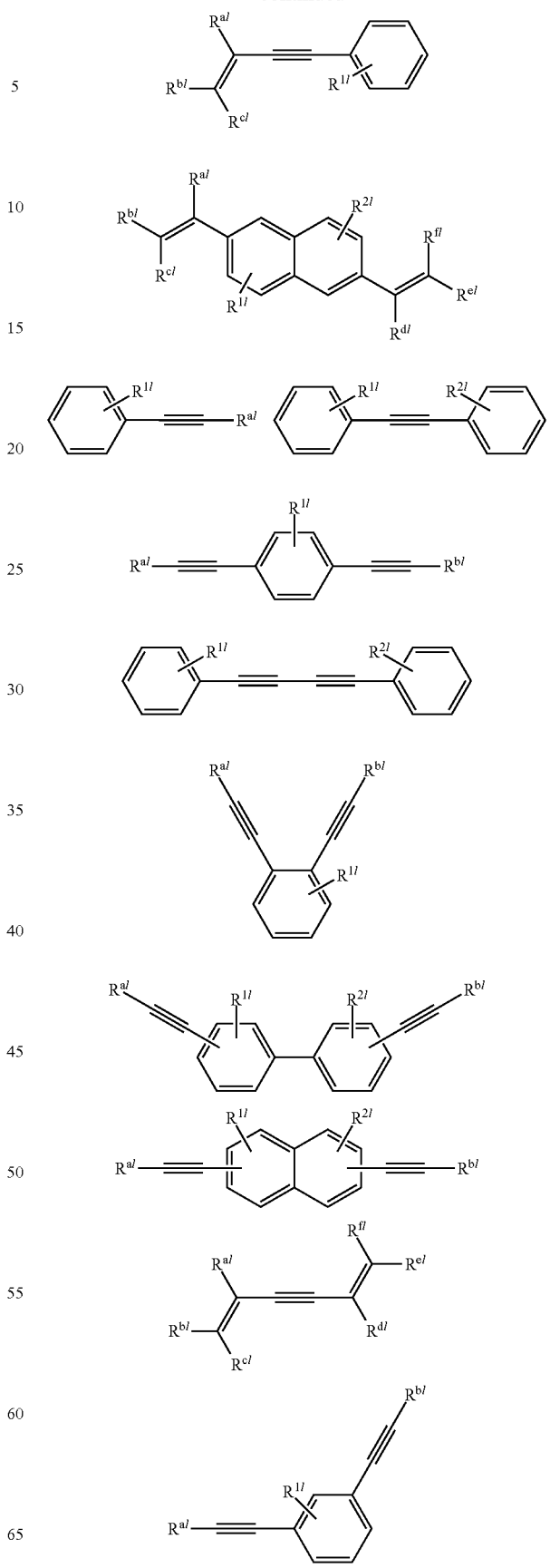

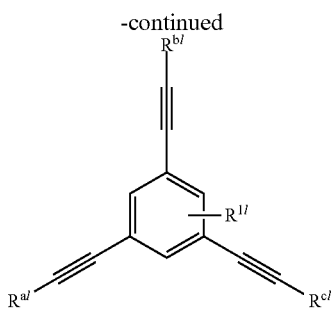
and derivatives thereof,
heterocyclic compounds selected from the group consisting of:
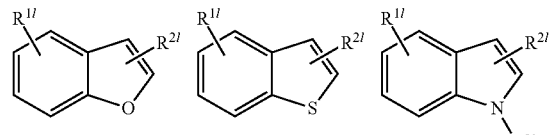
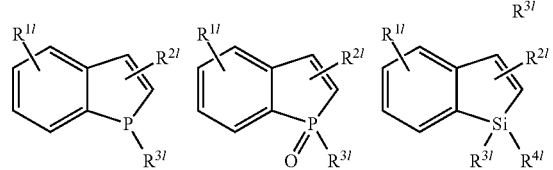
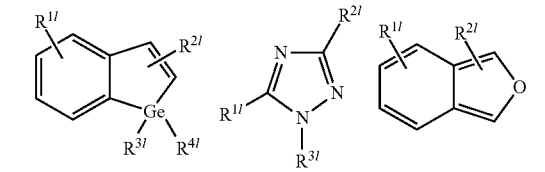
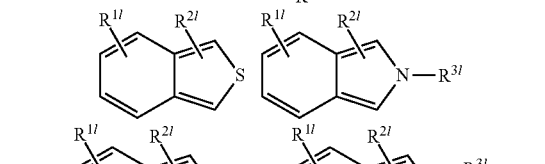
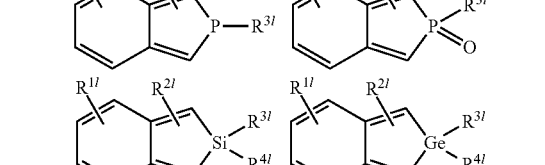
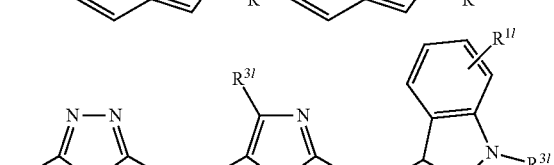
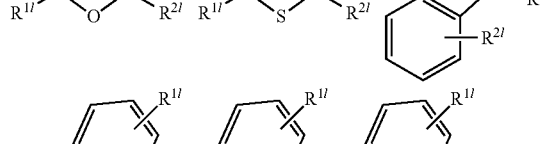
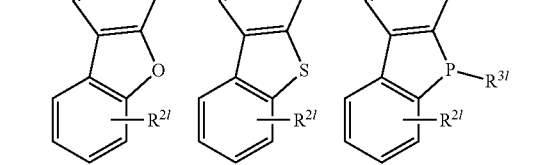
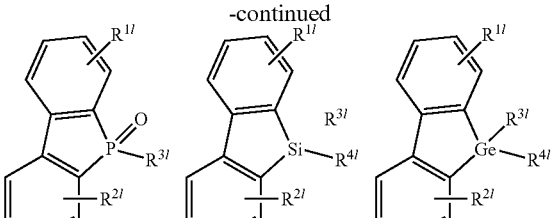
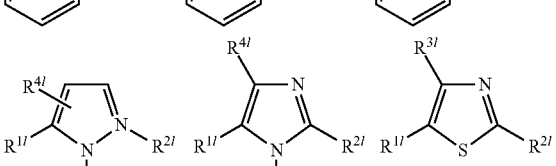
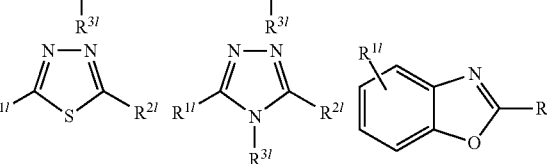
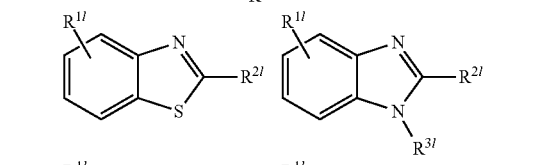
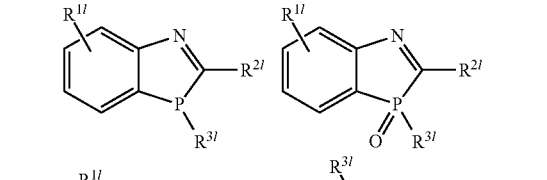
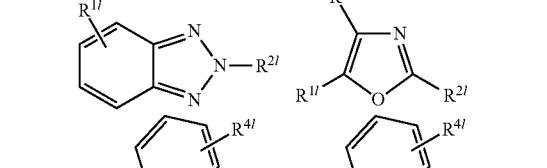
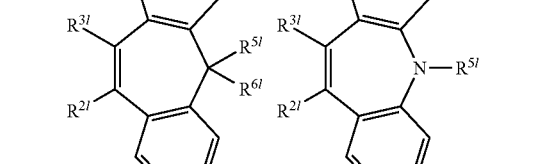
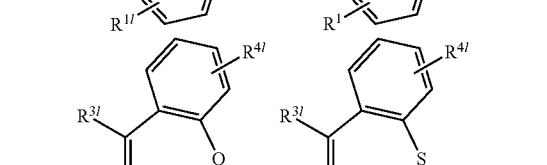
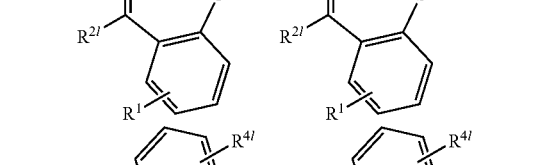
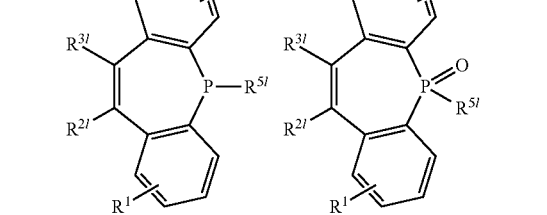

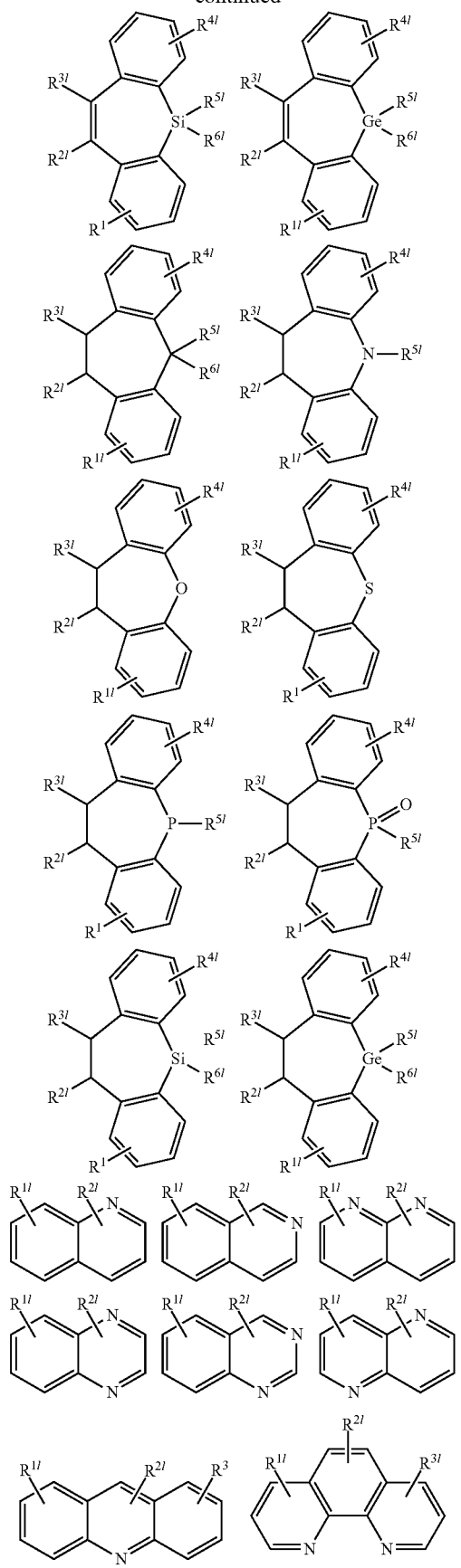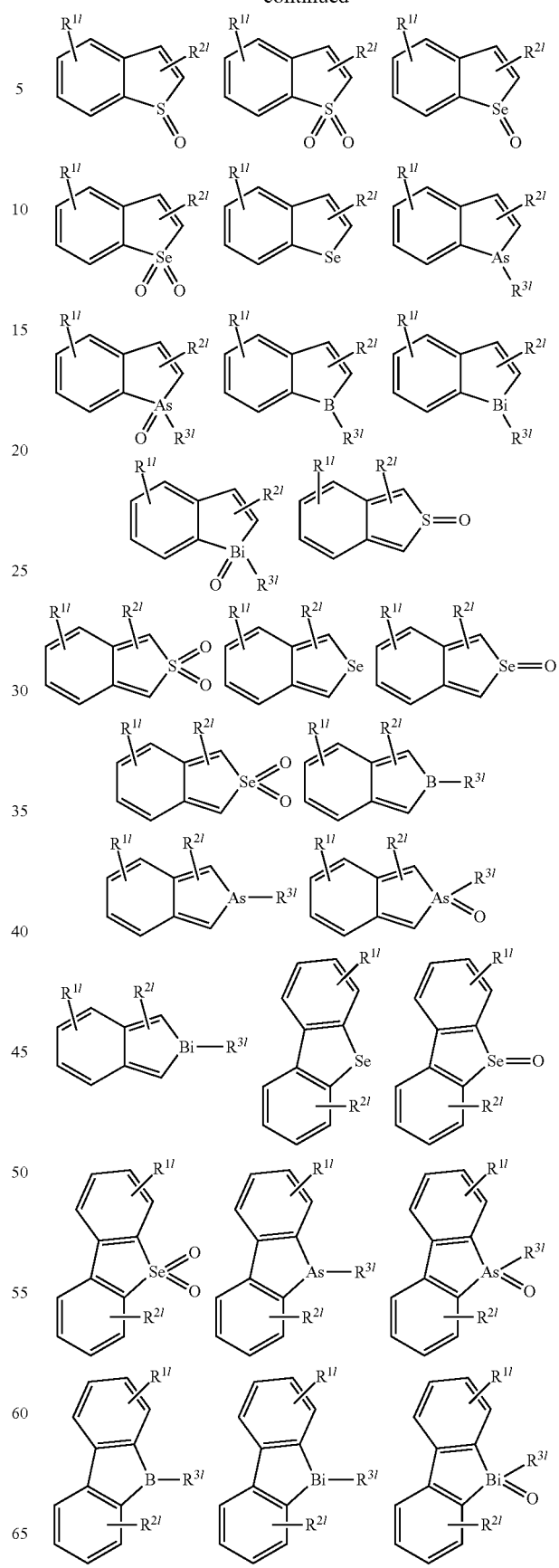

-continued
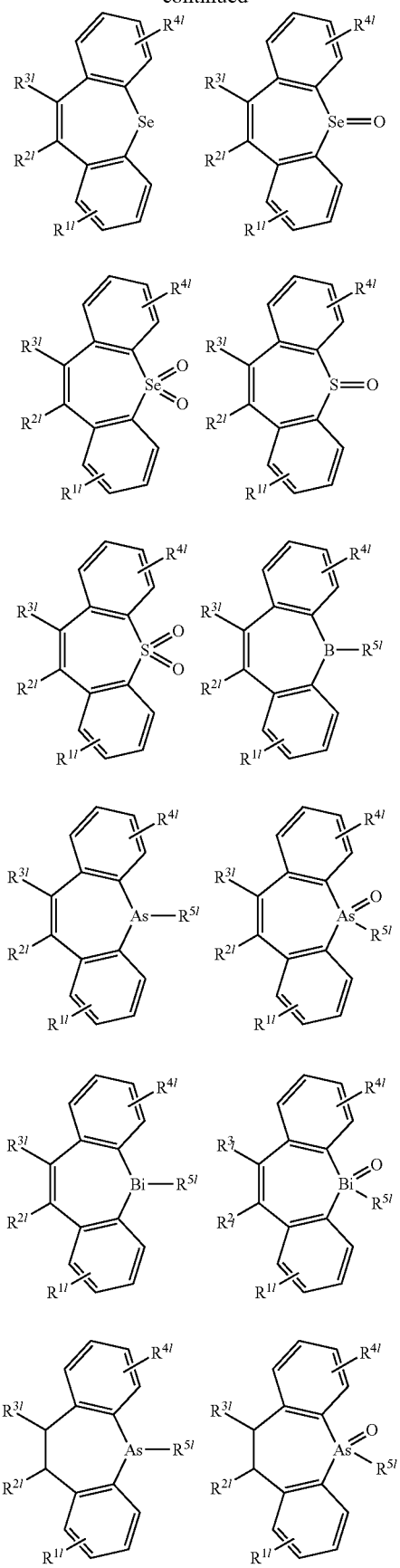
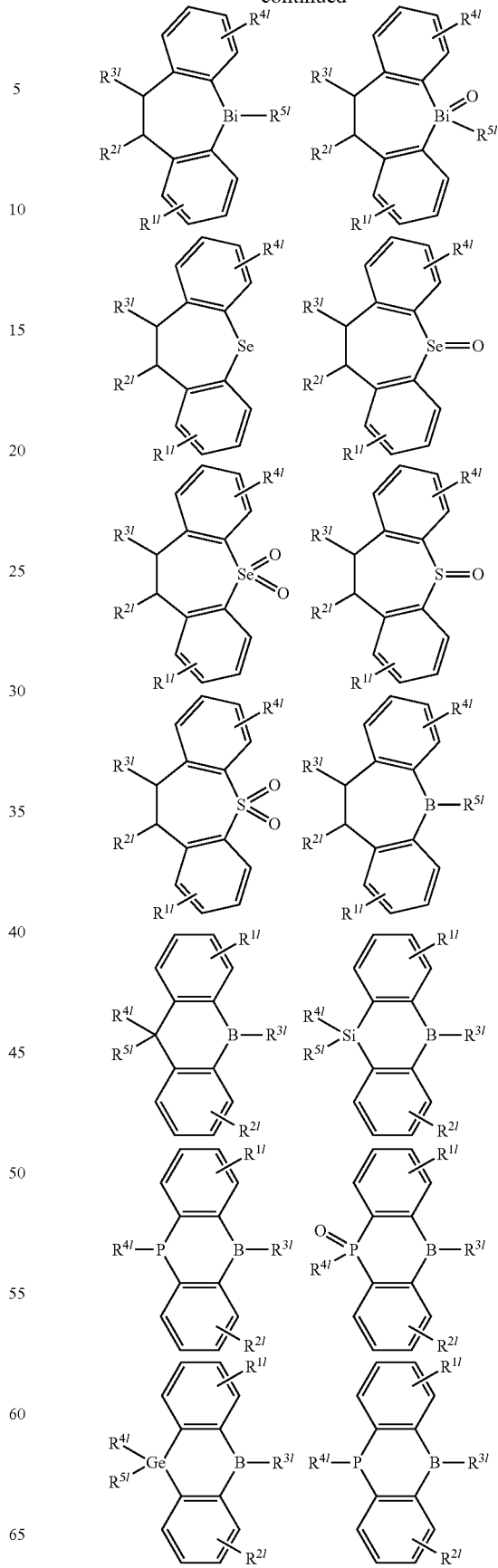

-continued
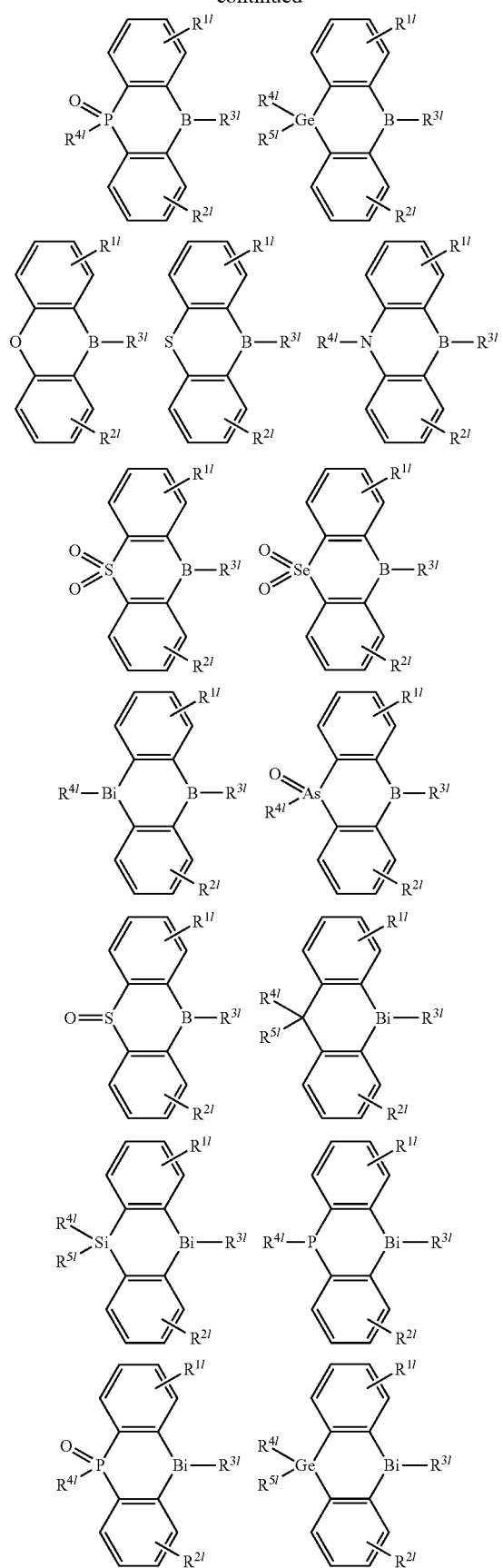
-continued
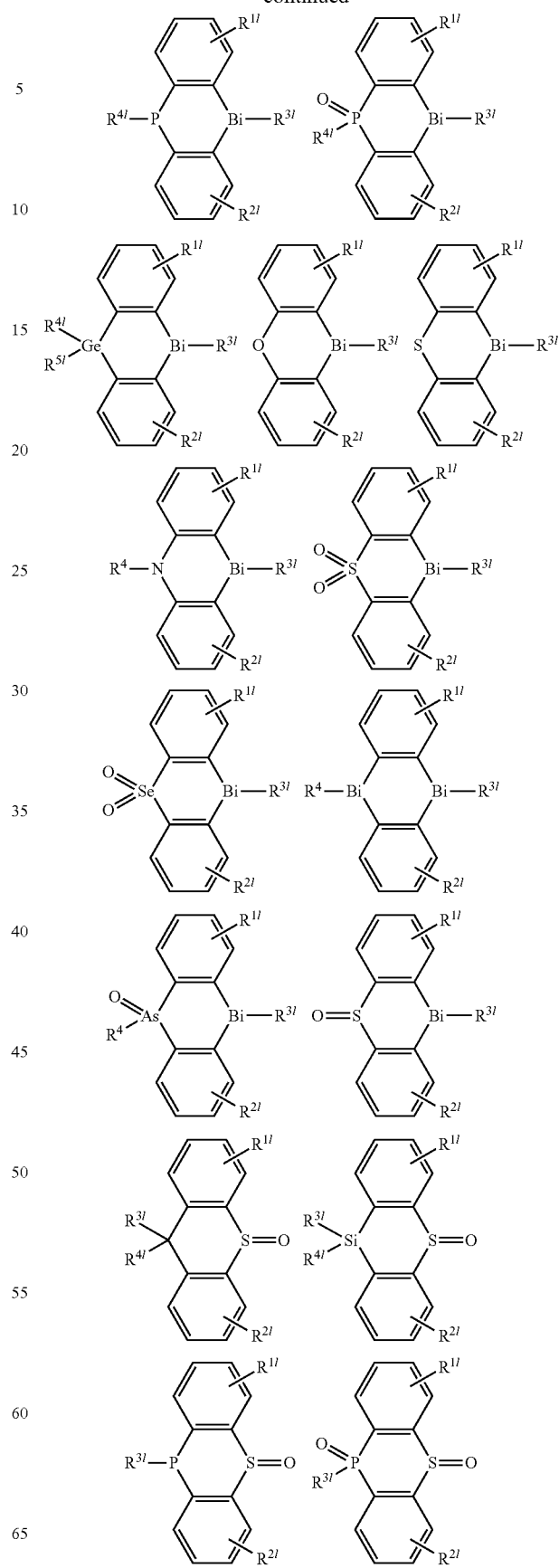

-continued
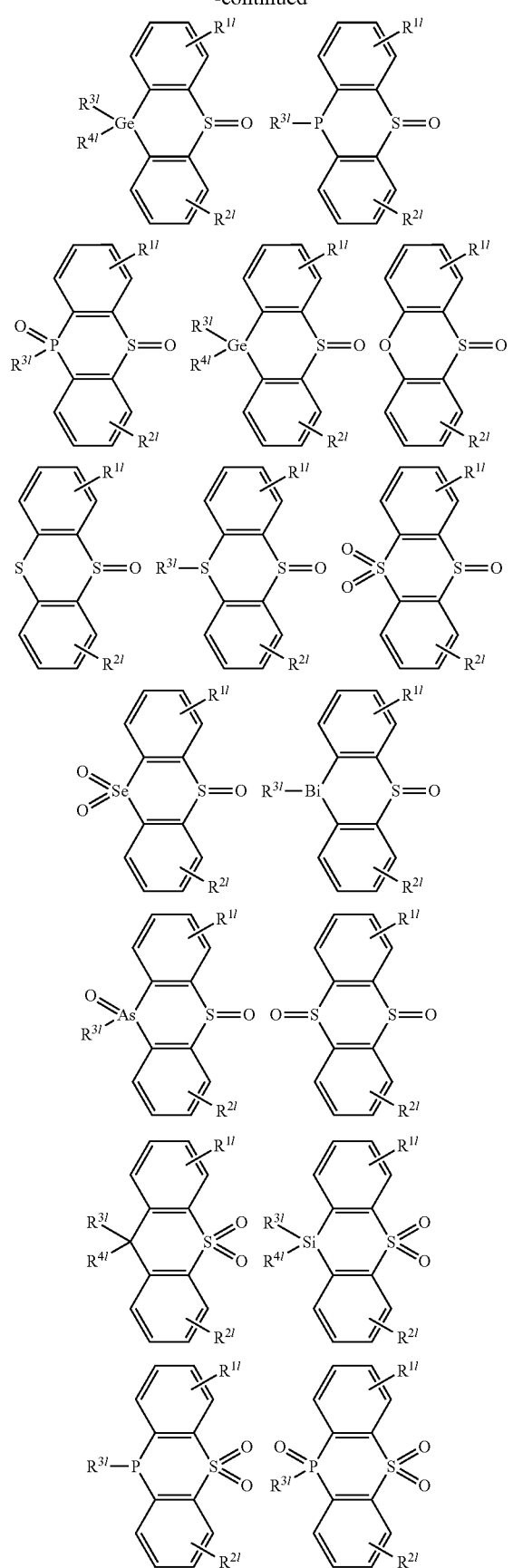
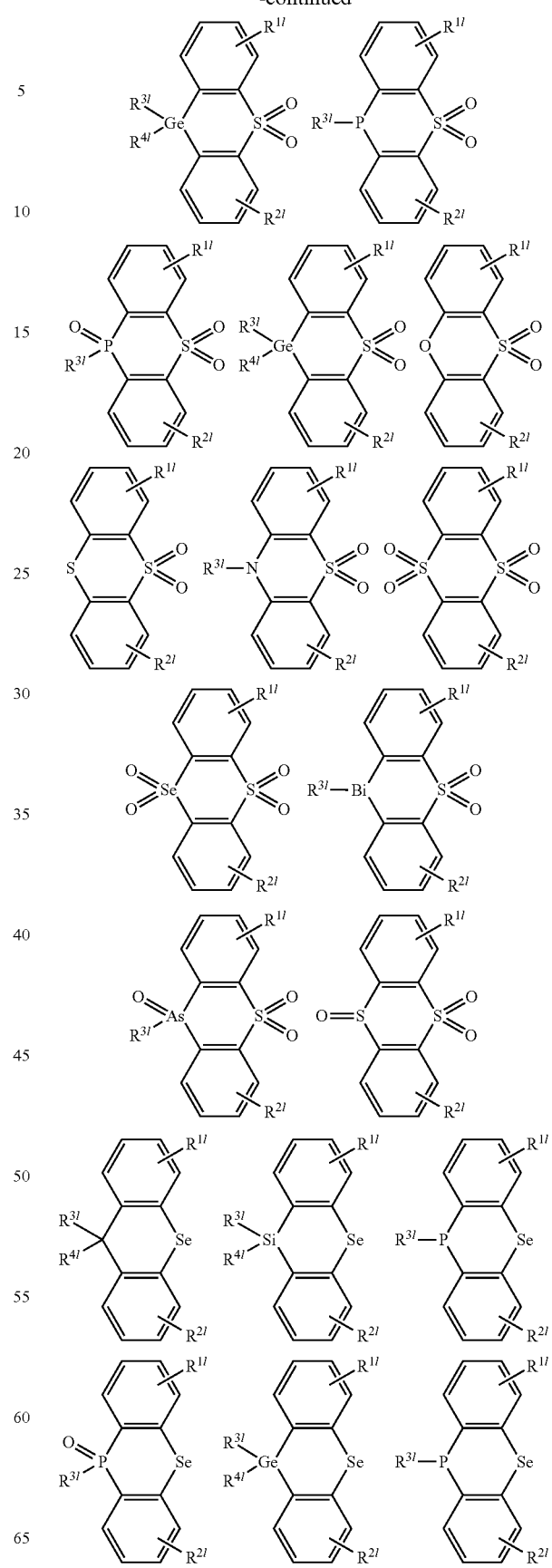

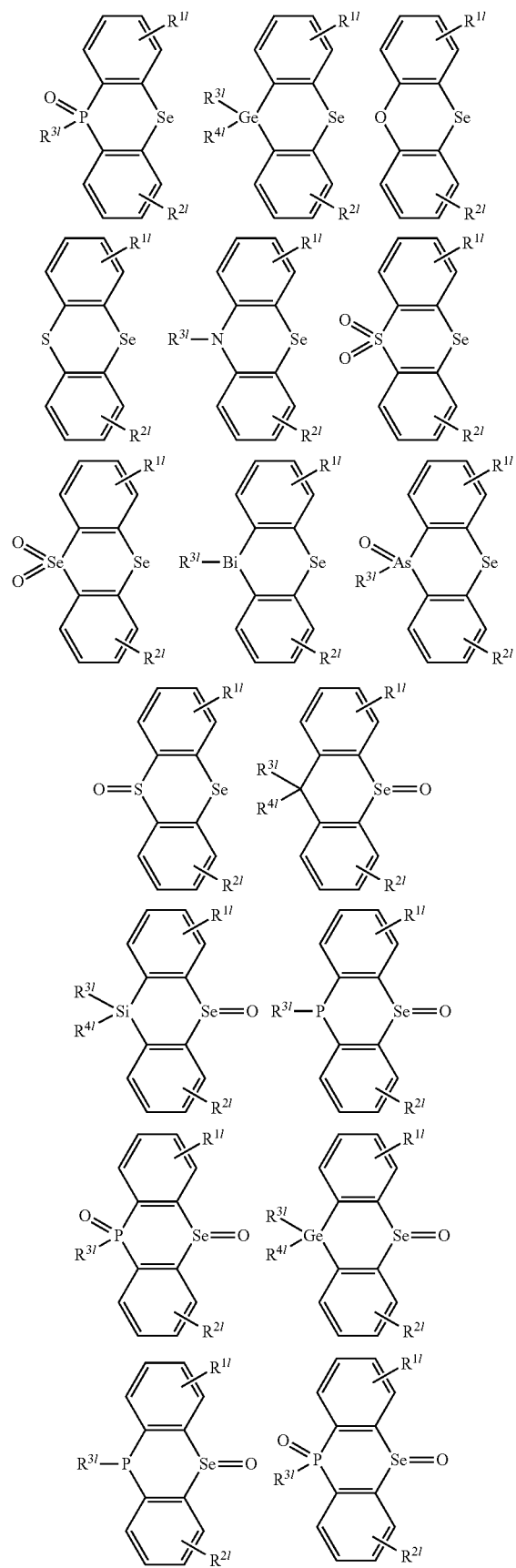
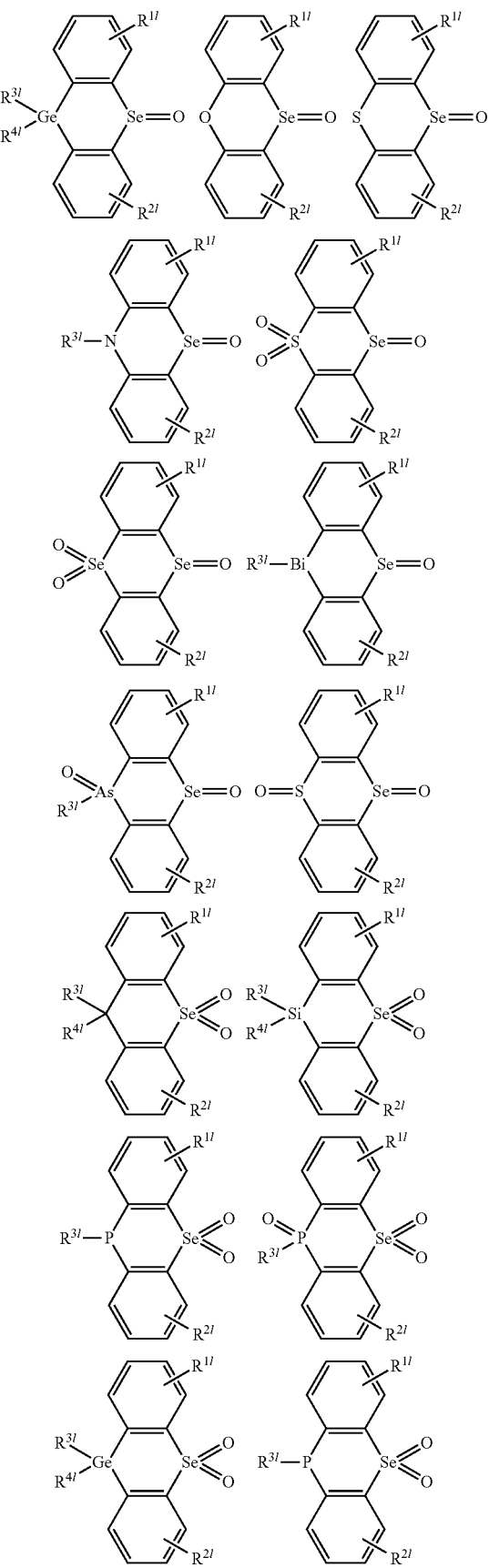

-continued
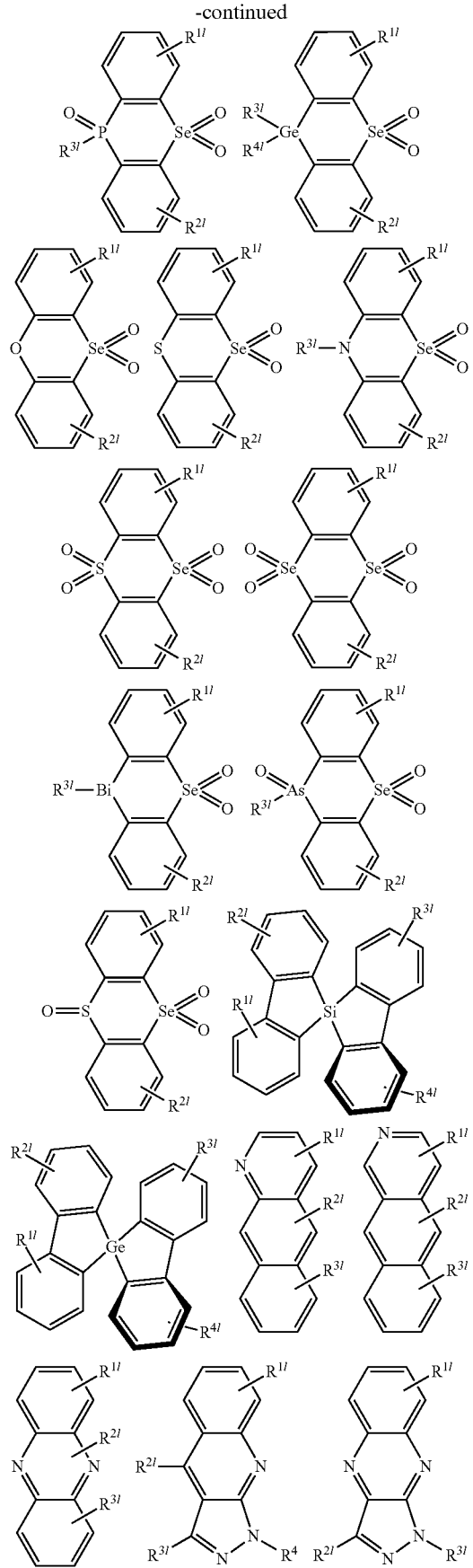
-continued
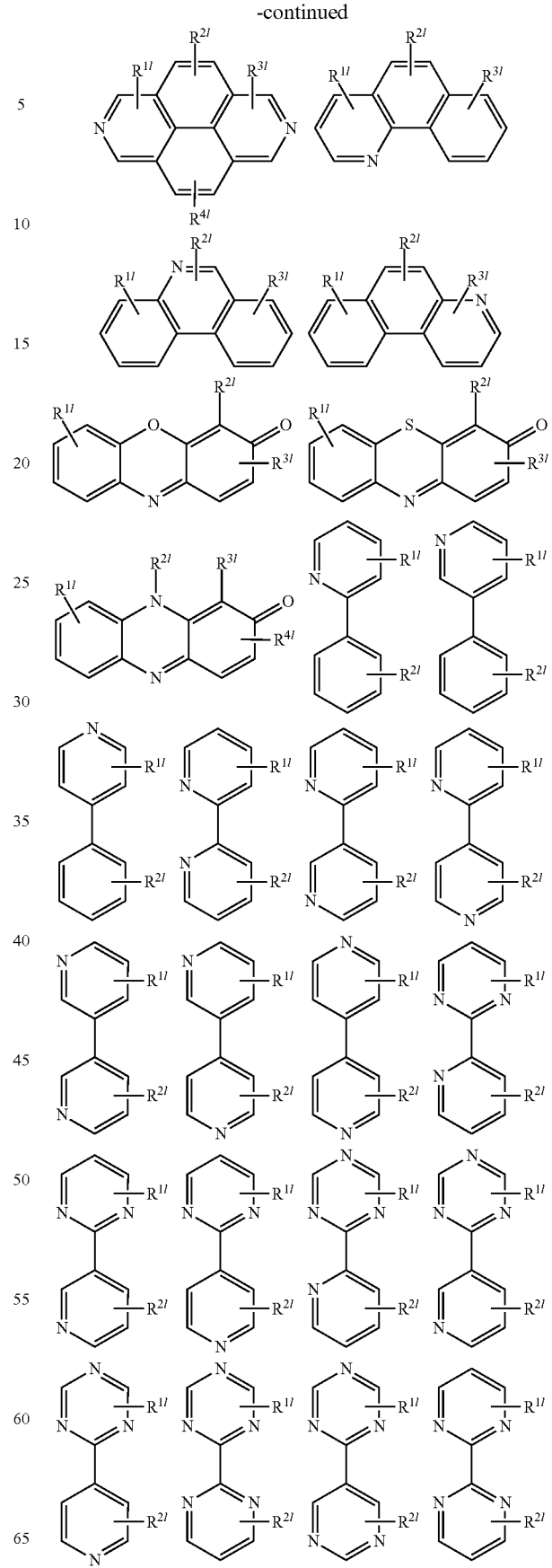

-continued
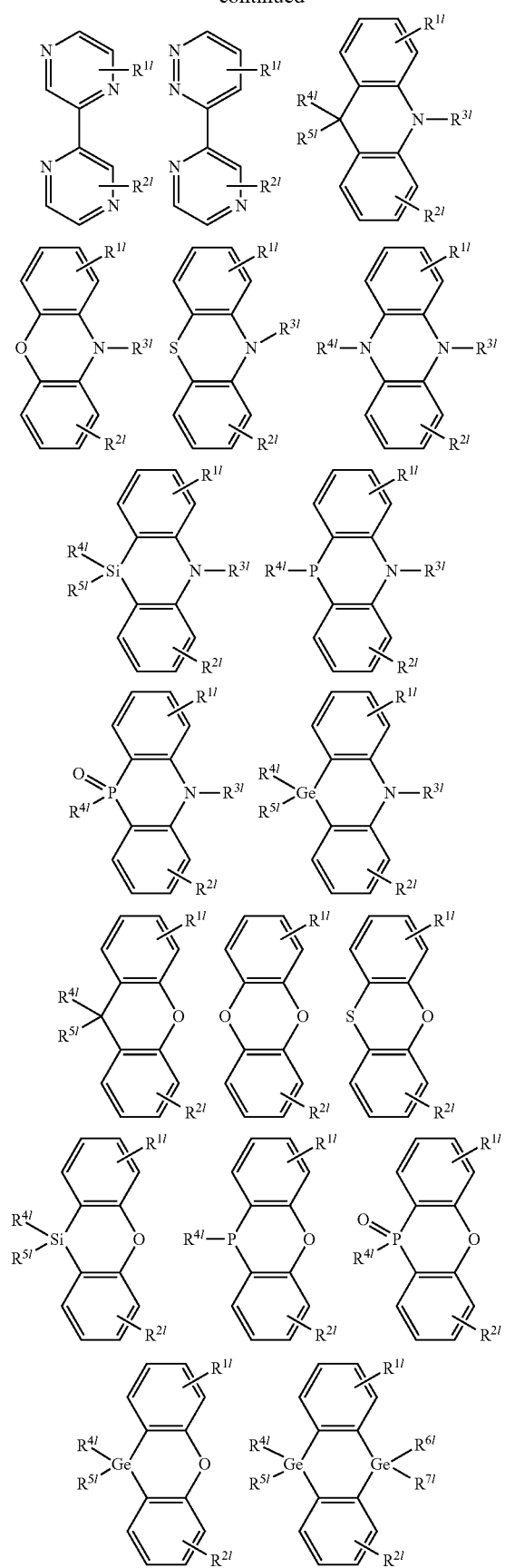
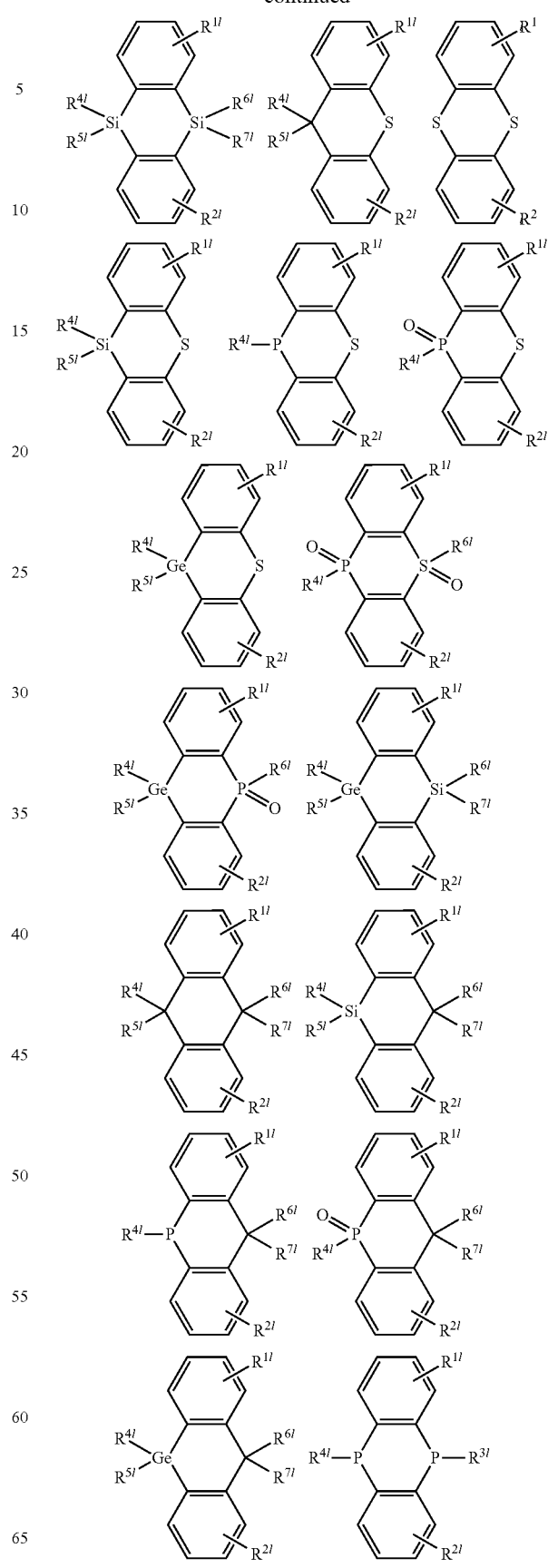

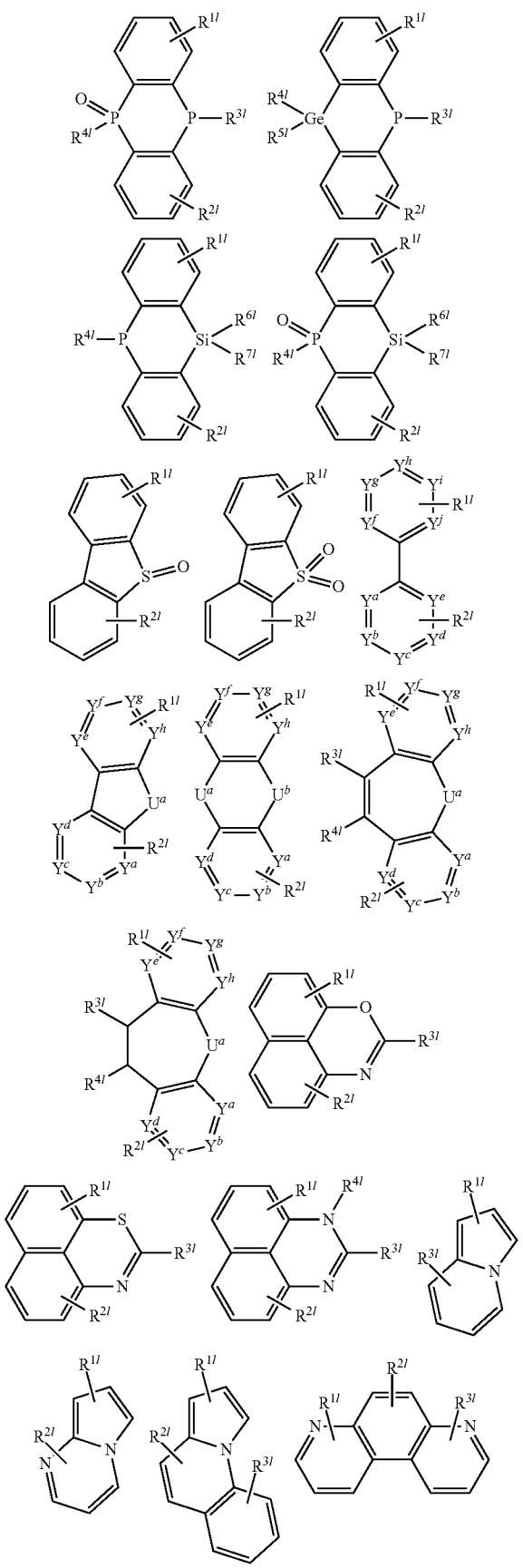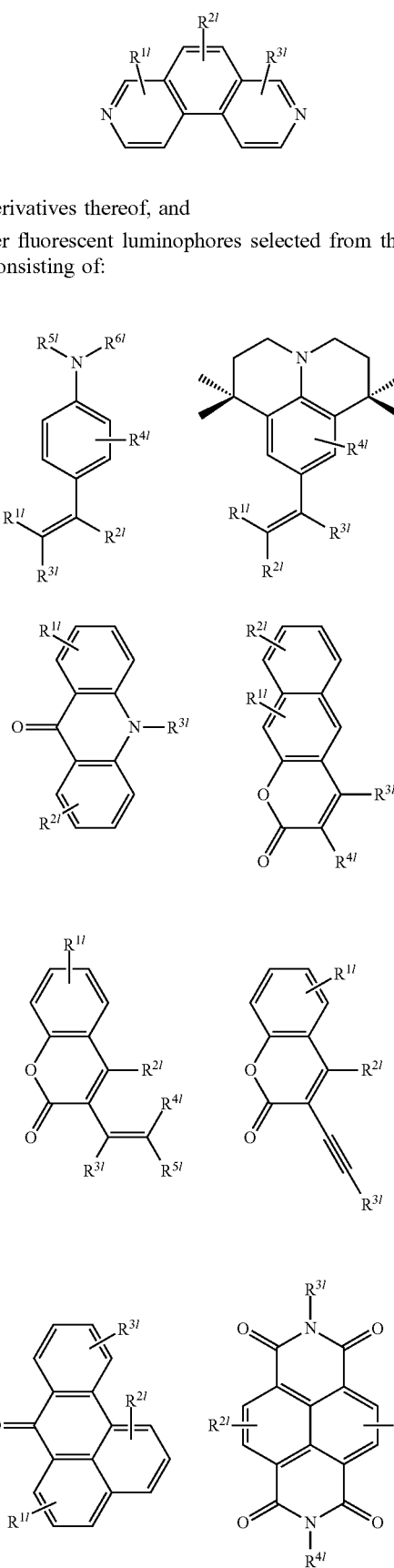
and derivatives thereof, and
other fluorescent luminophores selected from the group consisting of:

451
-continued
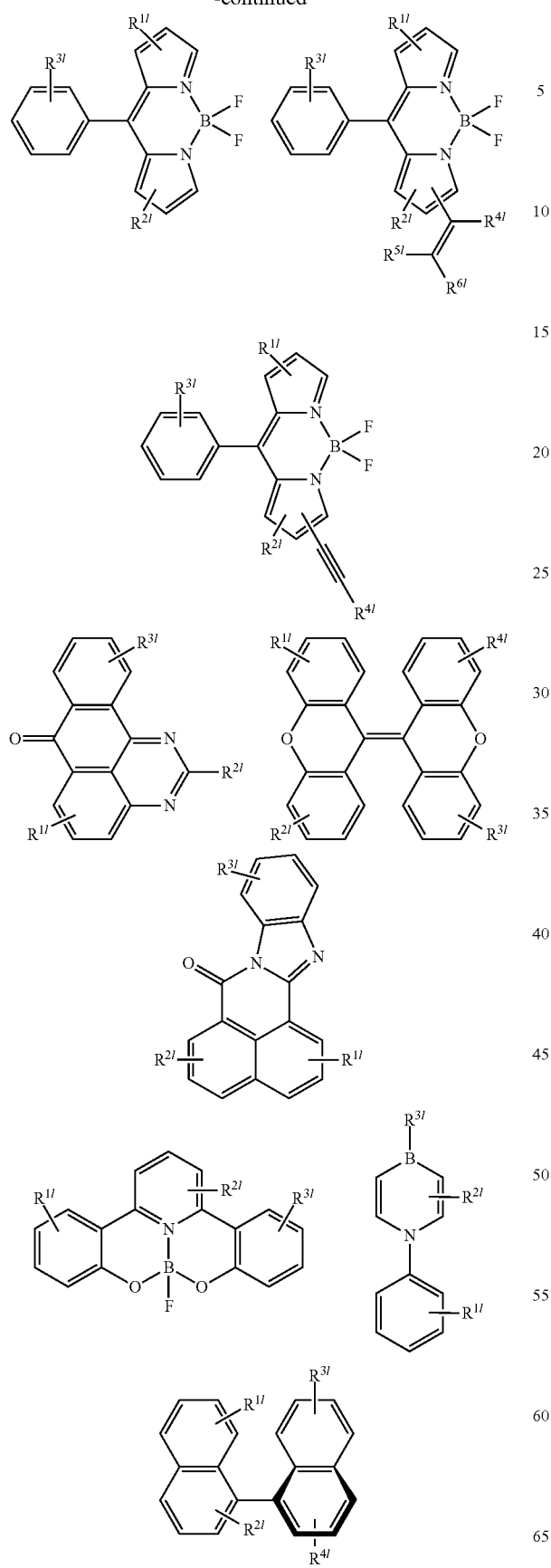
452
-continued
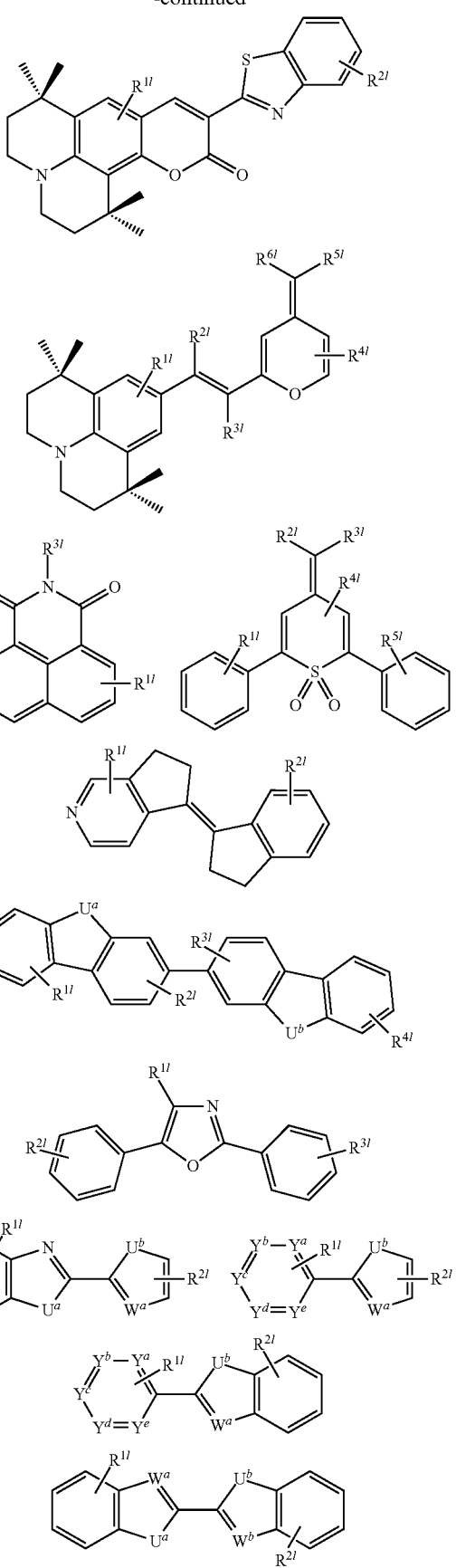

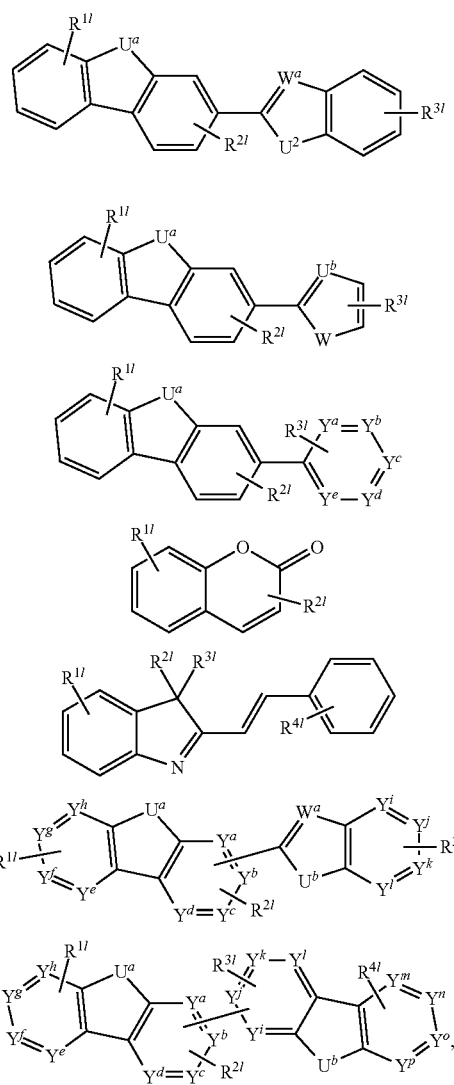
wherein:
each of $R^{al}$, $R^{bl}$, $R^{cl}$, $R^{dl}$, $R^{el}$, $R^{fl}$, $R^{gl}$, $R^{hl}$, and $R^{il}$ independently represents one of the following structures:
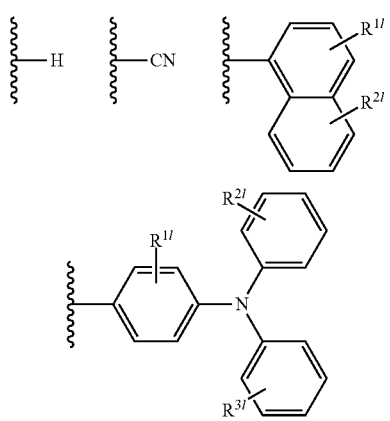
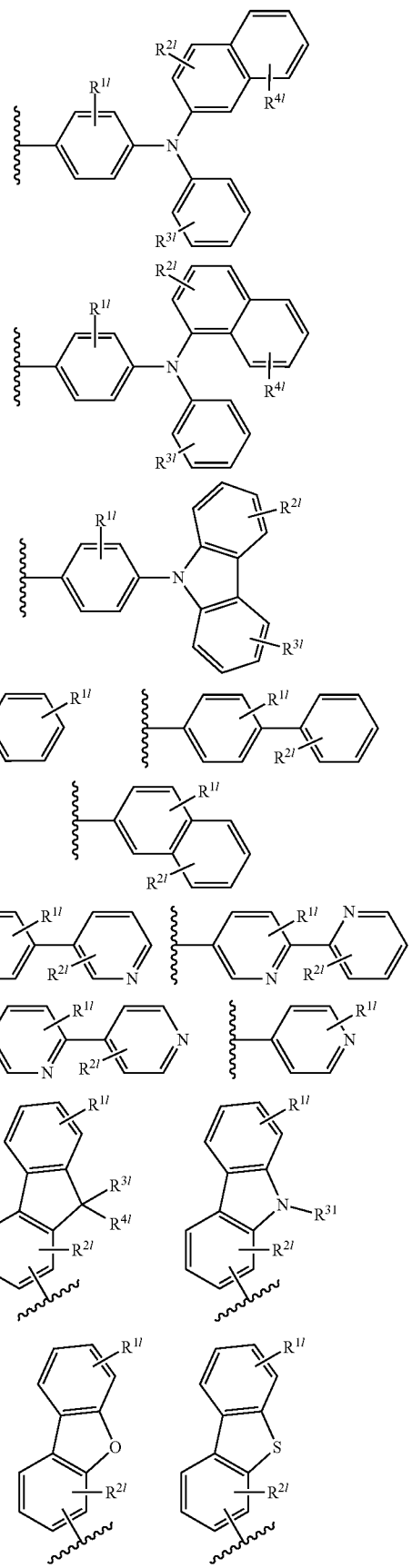

-continued

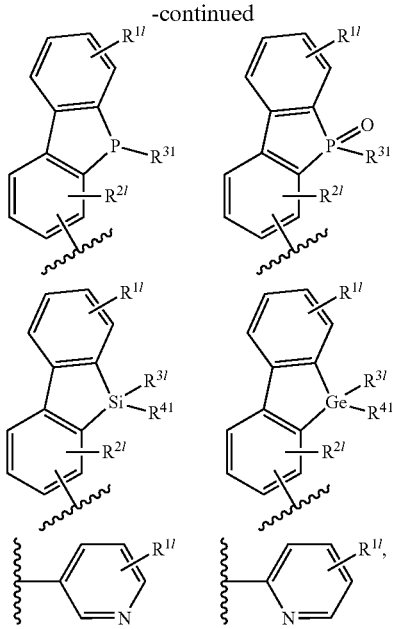

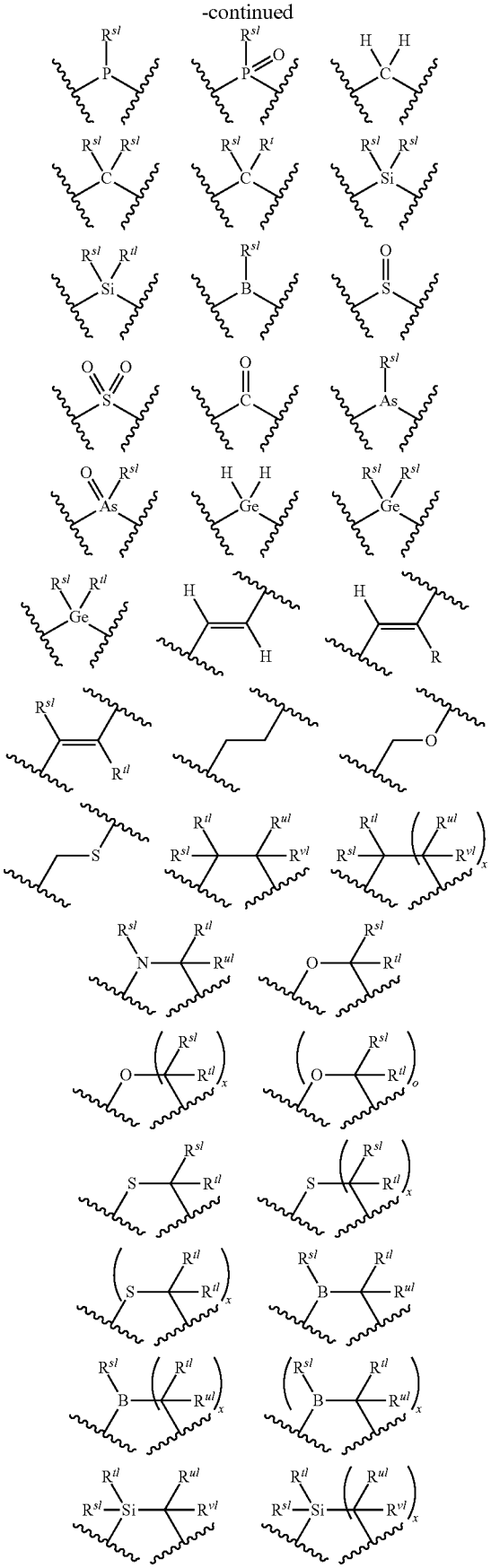

each $R^{1l}$, $R^{2l}$, $R^{3l}$, $R^{4l}$, $R^{5l}$, $R^{6l}$, $R^{7l}$, $R^{8l}$, $R^{9l}$ and $R^{10l}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, each of $Y^a$, $Y^b$, $Y^c$, $Y^d$, $Y^e$, $Y^f$, $Y^g$, $Y^h$, $Y^i$, $Y^j$, $Y^k$, $Y^l$, $Y^m$, $Y^n$, $Y^o$, and $Y^p$ is independently C, N or B, each of $U^a$, $U^b$, and $U^2$ is independently $CH_2$, $CR^1R^2$, C=O, $CH_2$, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$, each of W, $W^a$, and $W^b$ is independently CH, $CR^1$, $SiR^1$, GeH, $GeR^1$, N, P, B, Bi, and Bi=O, and each of $R^1$, $R^2$, $R^3$ and $R^4$ is independently hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, monoalkylamino, dialkylamino, monoarylamino, diarylamino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, mercapto, sulfo, carboxyl, hydrazino, substituted silyl, or polymeric; or any conjugate or combination thereof.

6. The compound of claim 1, wherein each $LP^1$, $LP^2$ and $LP^3$, if present, is independently bonded indirectly to $L^1$, $L^2$, or $L^3$, respectively, through a linking atom or linking group selected from the group consisting of:

457
-continued

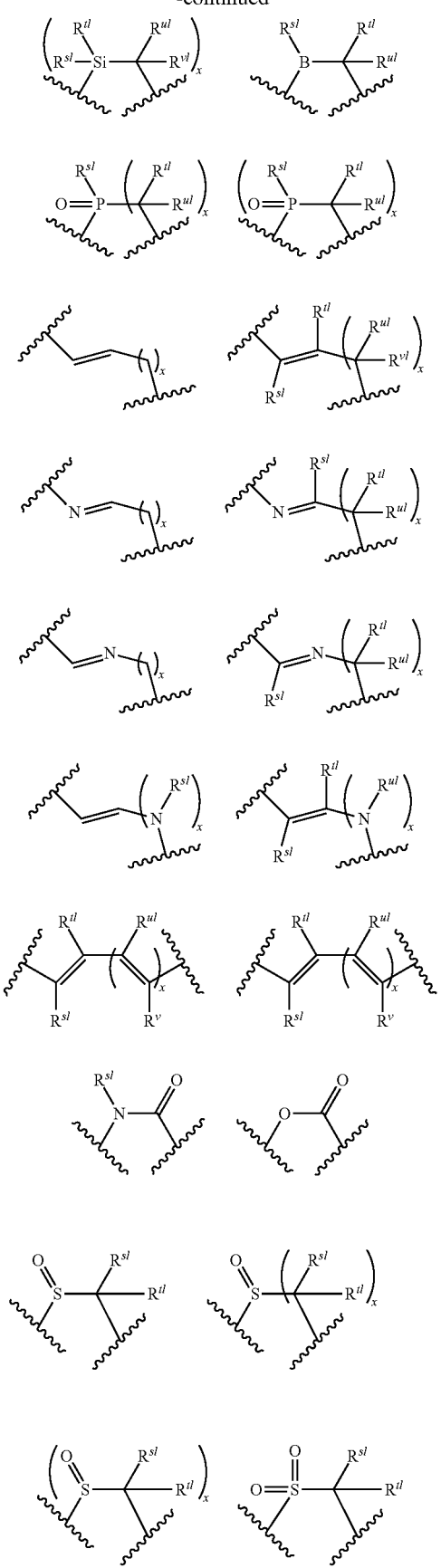

458
-continued

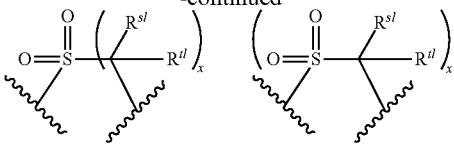

wherein:
x is an integer from 1 to 10,
each of $R^t$, Rv, $R^{sl}$, $R^{tl}$, $R^{ul}$, and $R^{vl}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, di alkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric, and any conjugate or combination thereof, and
wherein the linking atom or linking group is covalently bonded to any atom of $LP^1$, $LP^2$, and $LP^3$ as valency permits.

7. The compound of claim 1, wherein M is Pt.

8. The compound of claim 1, wherein $L^1$ is a five-membered heterocyclyl, five-membered heteroaryl, five-membered carbene, or five-membered N-heterocyclic carbene.

9. The compound of claim 1, wherein $L^1$ is a five-membered heterocyclyl or five-membered heteroaryl.

10. The compound of claim 1, wherein $L^1$ is pyrazolyl or imidazolyl.

11. The compound of claim 1, wherein $LP^1$ is present, and $LP^2$ and $LP^3$ are absent.

12. The compound of claim 1, wherein $LP^1$ is present and is an aromatic hydrocarbon, an aromatic hydrocarbon derivative, a polyphenyl hydrocarbon, a hydrocarbon with condensed aromatic nuclei, naphthalene, anthracene, phenanthrene, chrysene, pyrene, triphenylene, perylene, acenaphthene, tetracene, pentacene, tetraphene, coronene, fluorene, biphenyl, p-terphenyl, o-diphenylbenzene, m-diphenylbenzene, p-quaterphenyl, benzo[a]tetracene, benzo[k]tetraphene, indeno[1,2,3-cd]fluoranthene, or tetrabenzo[de,hi,op,st]pentacene.

13. The compound of claim 1, wherein $LP^1$ is present and is an aromatic hydrocarbon.

14. The compound of claim 5, wherein $LP^1$ is present and is

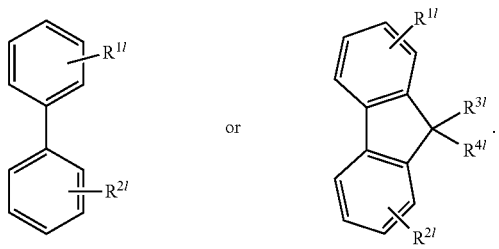

15. The compound of claim 1, wherein $V^1$ is independently N or C.

16. The compound of claim 1, wherein each of $Y^1$, $Y^2$, $Y^3$, and $Y^4$ is independently C or N.

17. The compound of claim 1, wherein the compound is selected from:

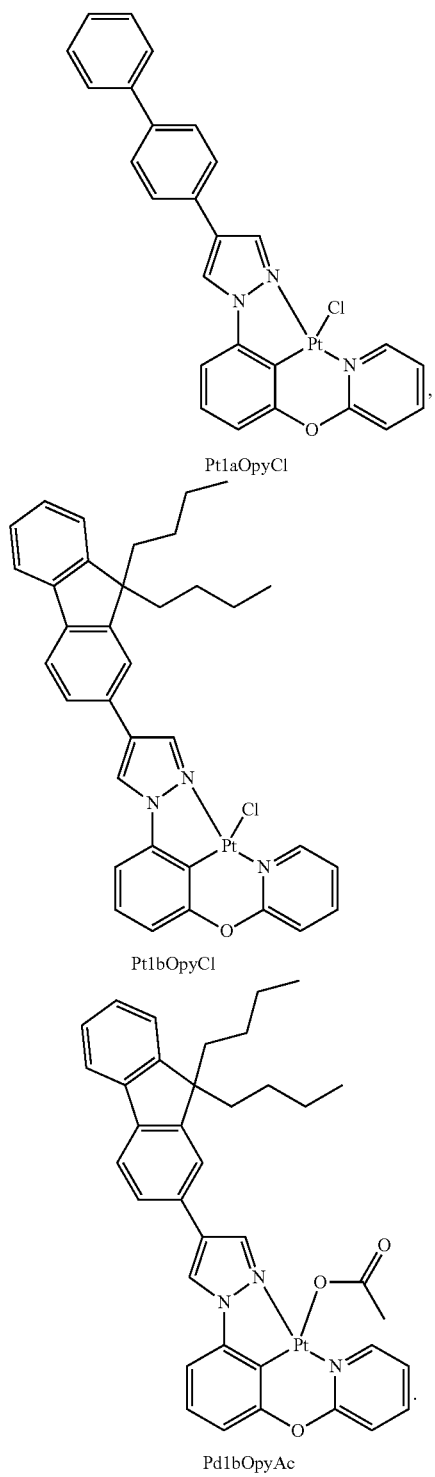
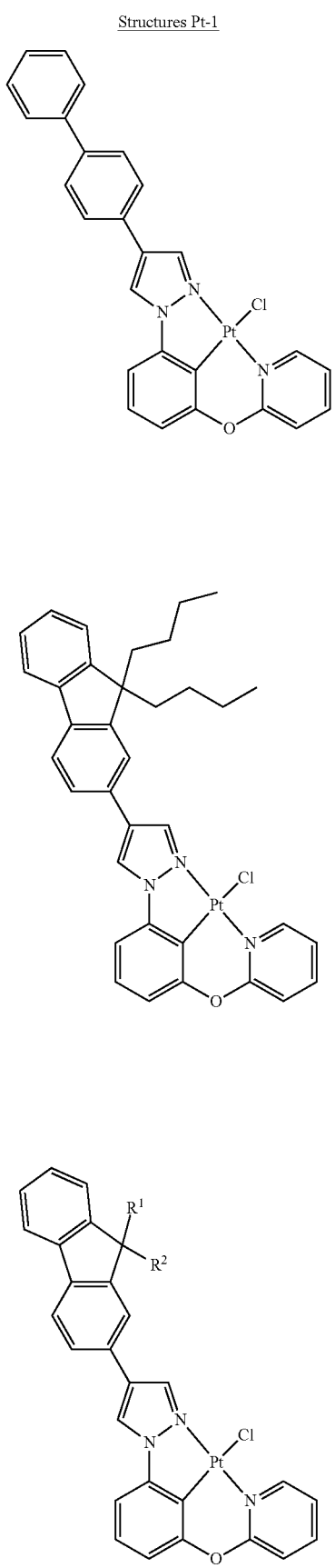
18. The compound of claim 1, wherein the compound is a delayed fluorescent and phosphorescent emitter, a phosphorescent emitter, or a delayed fluorescent emitter.
19. A device comprising the compound of claim 1, wherein the device is an organic light emitting diode or a full color display.
20. The compound of claim 1, wherein the compound is selected from:

461
-continued
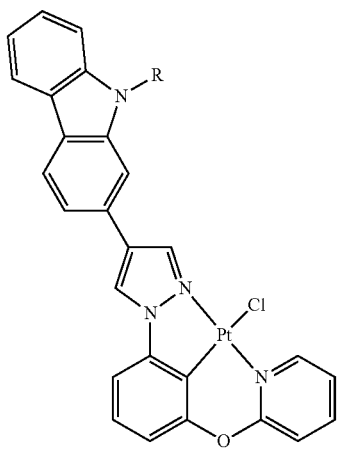
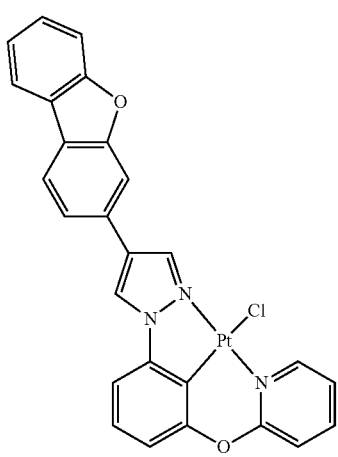
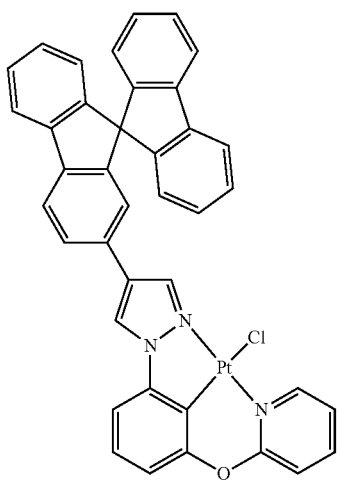
462
-continued
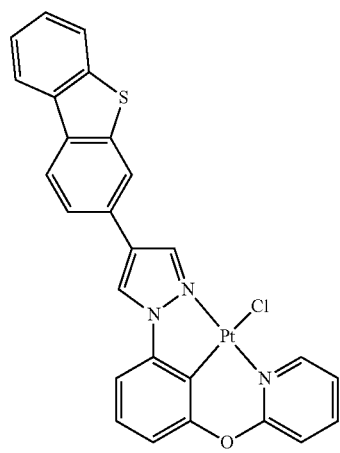
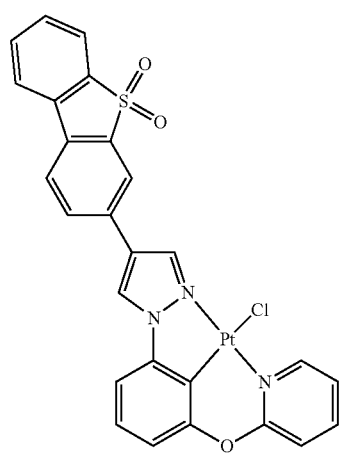
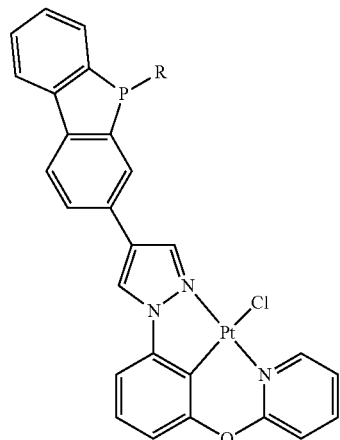

463
-continued
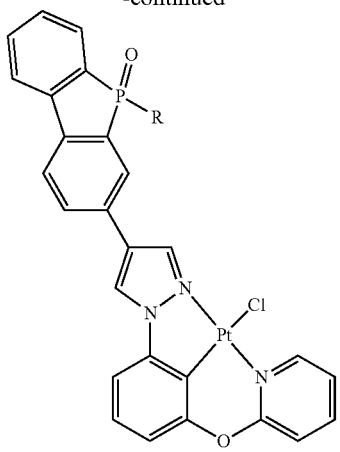
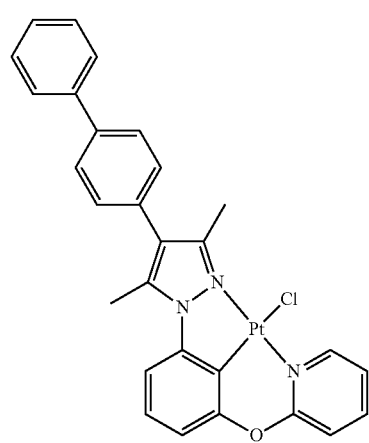
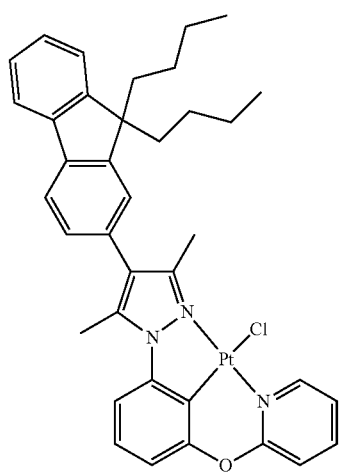
464
-continued
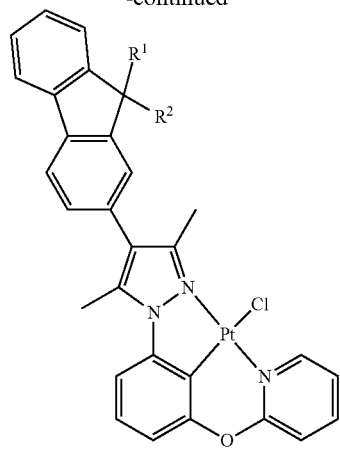
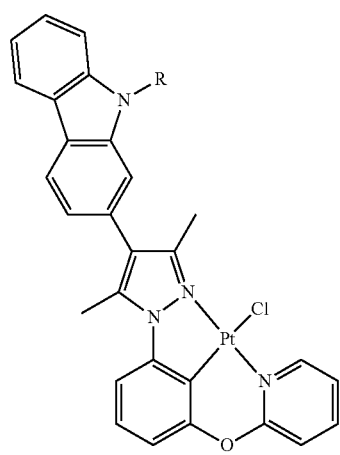
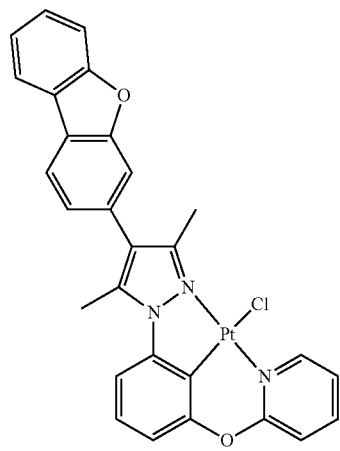

465
-continued
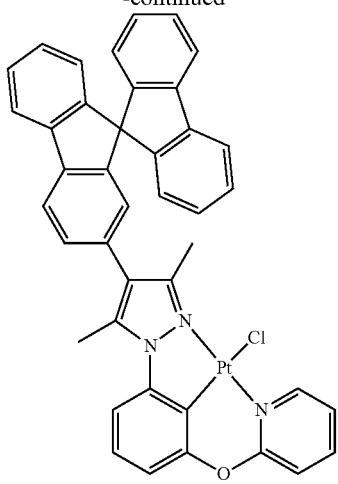
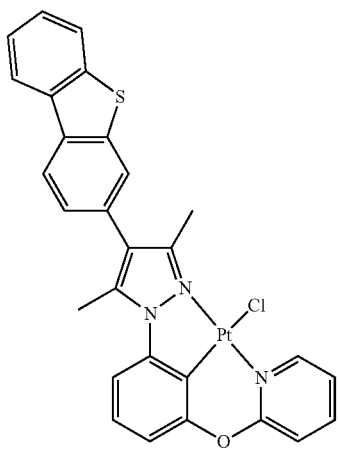
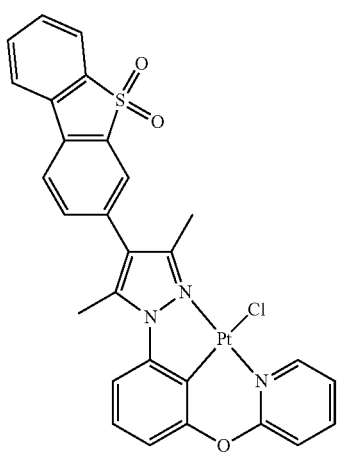
466
-continued
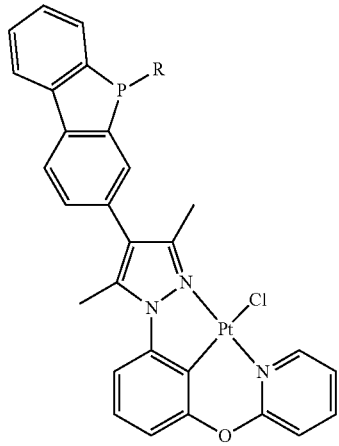
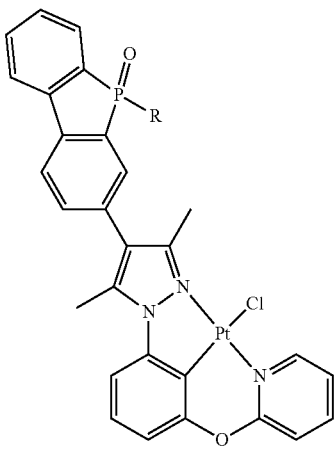
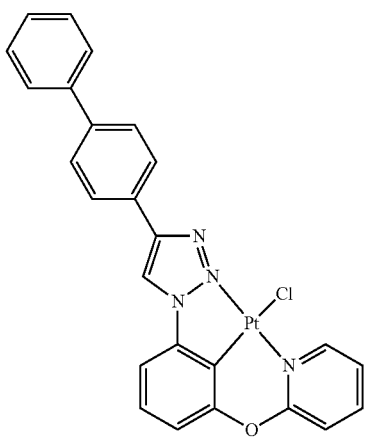

467
-continued
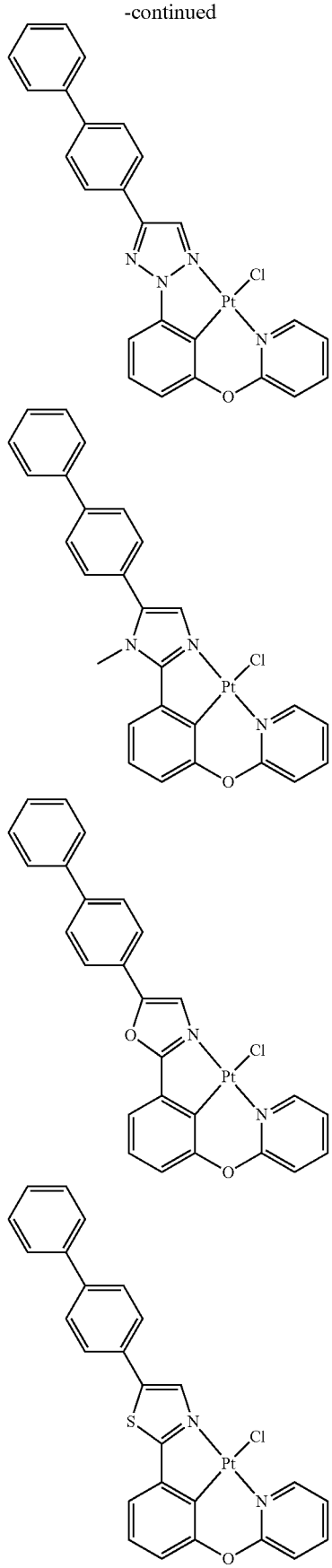
468
-continued
Structures Pt-2
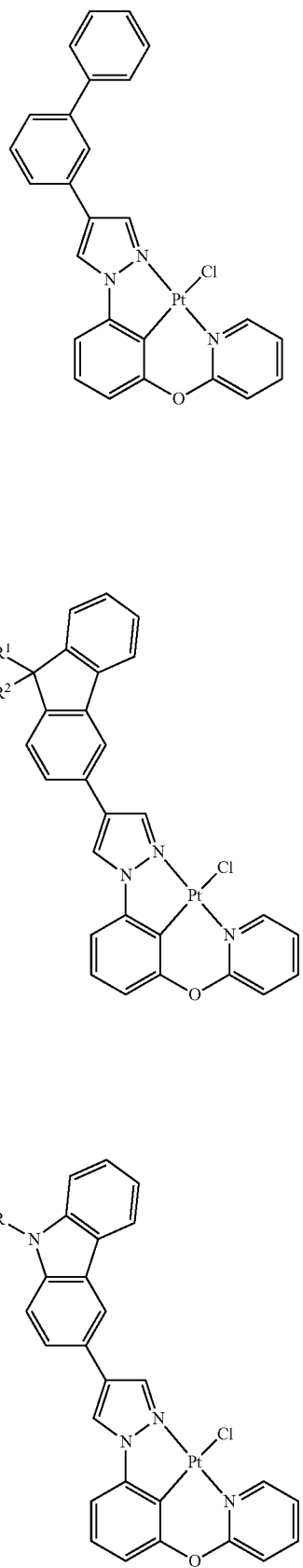

469
-continued
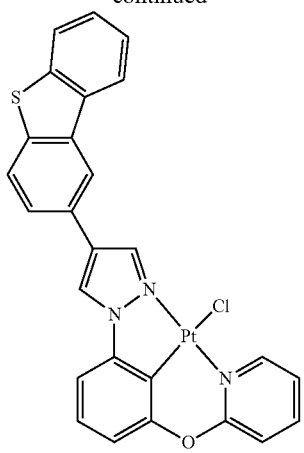
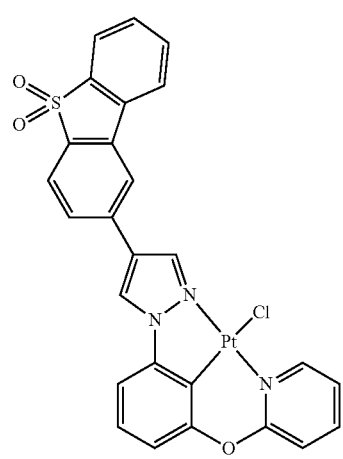
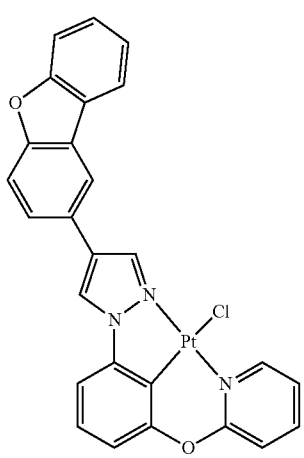
470
-continued
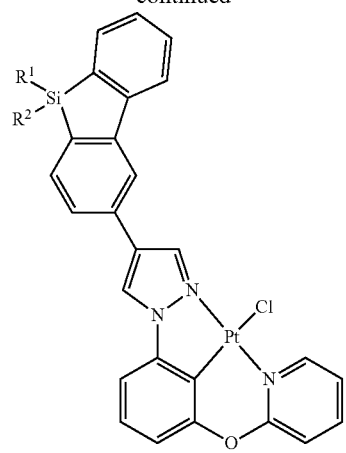
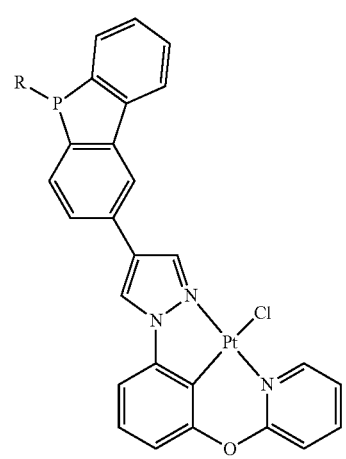
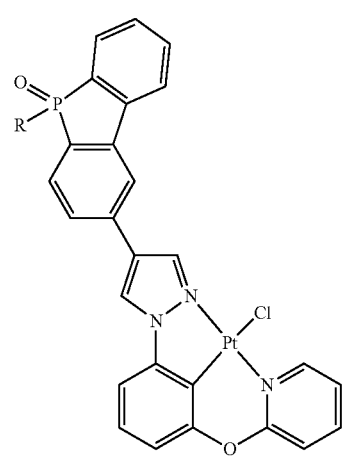

471
-continued
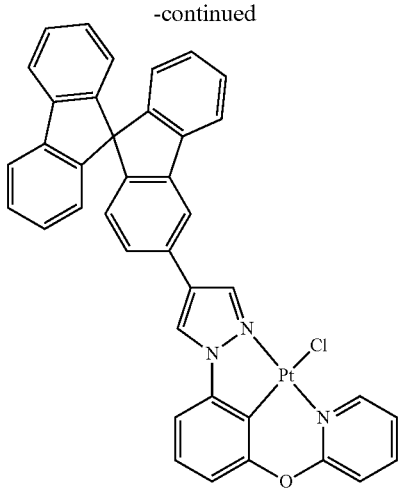
472
-continued
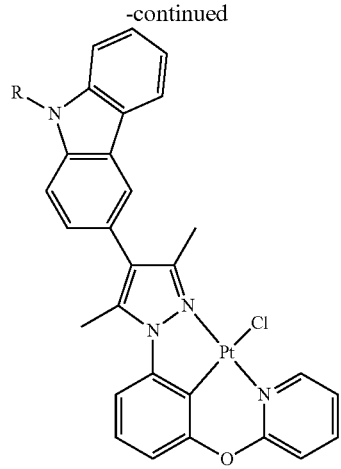
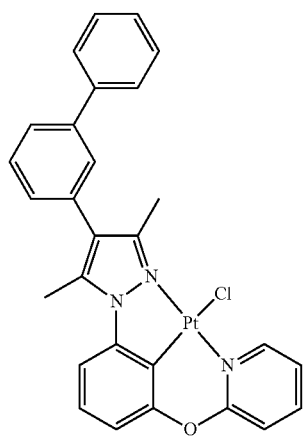
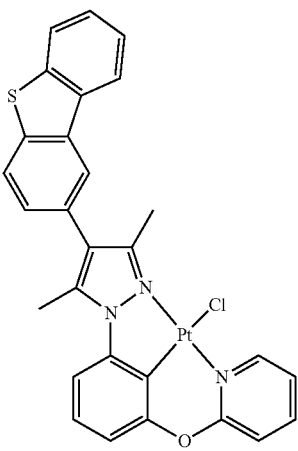
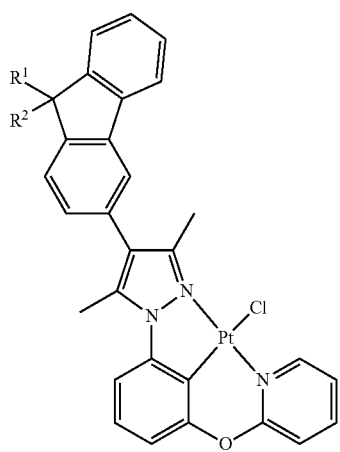
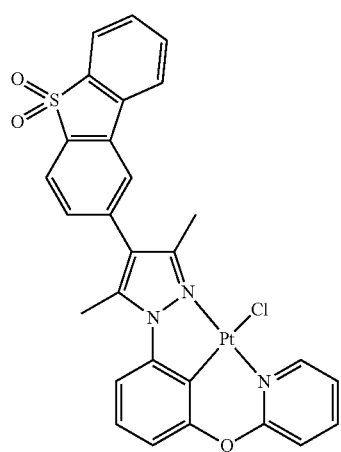

473
-continued
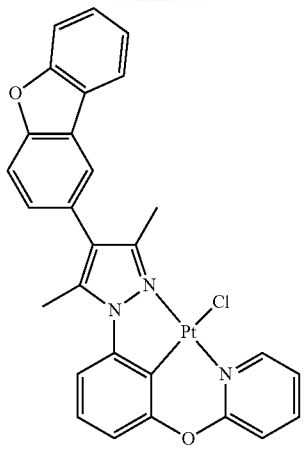
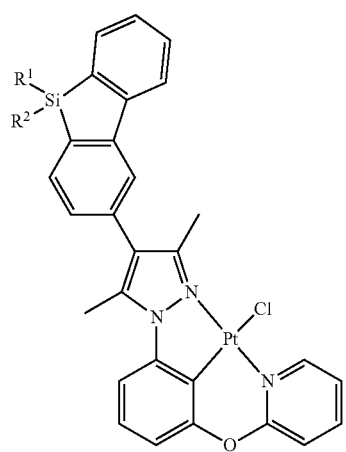
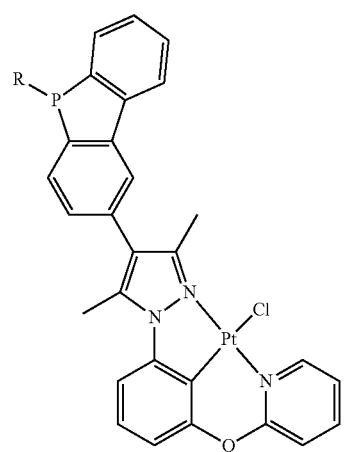
474
-continued
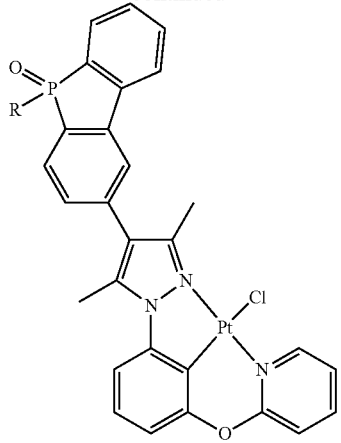
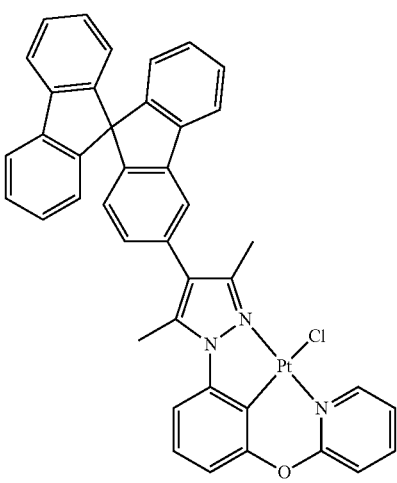
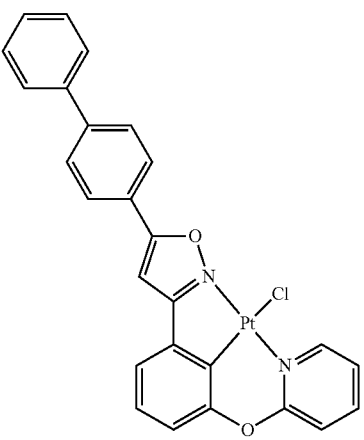

475
-continued
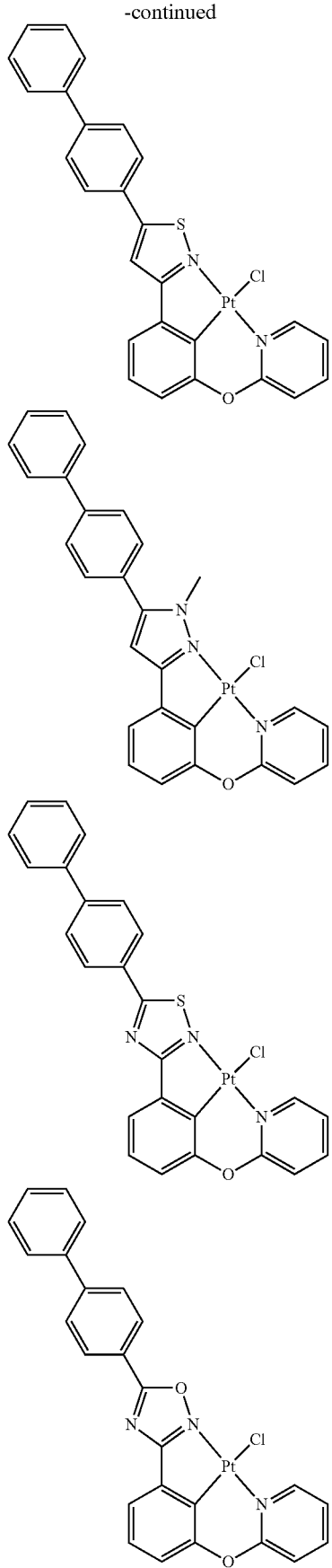
476
-continued
Structures Pt-3
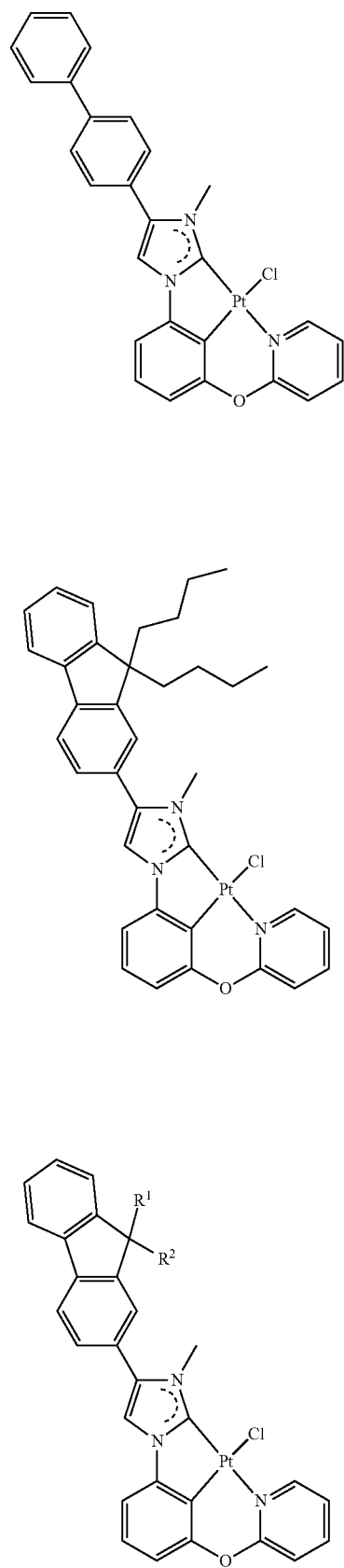

477
-continued
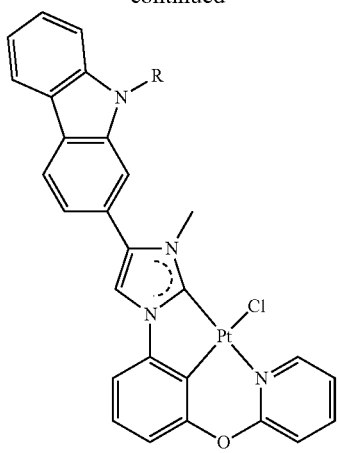
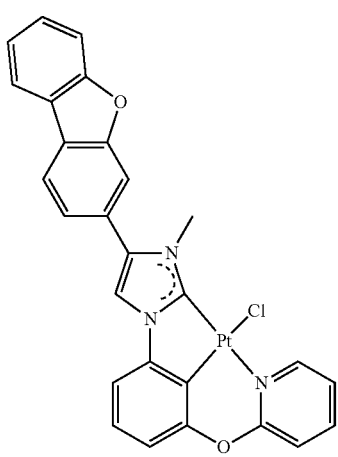
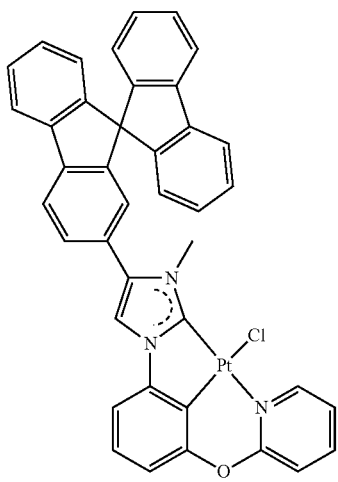
478
-continued
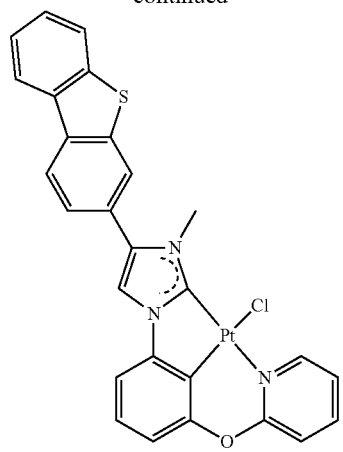
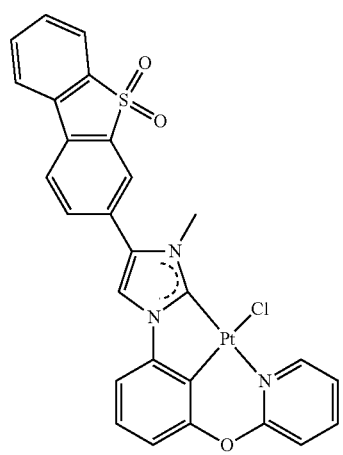
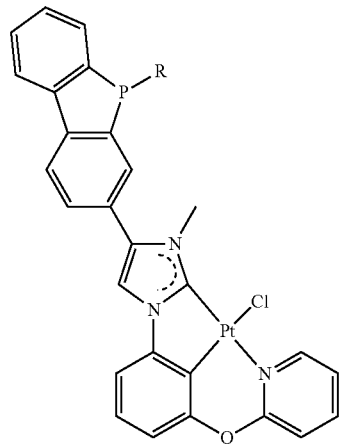

479
-continued
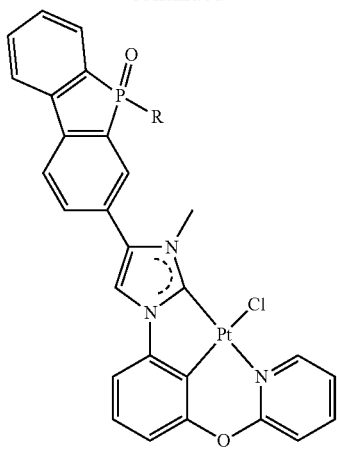
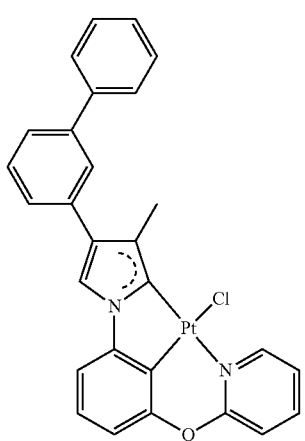
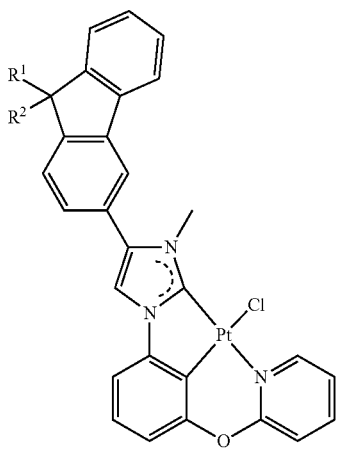
480
-continued
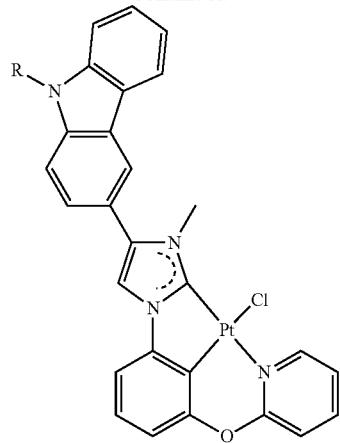
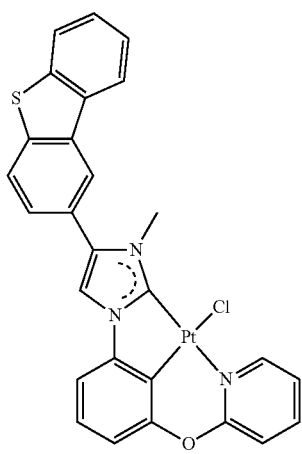
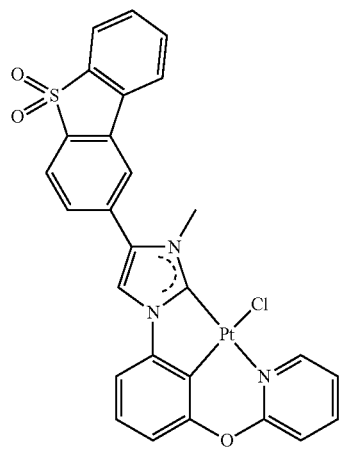

481
-continued
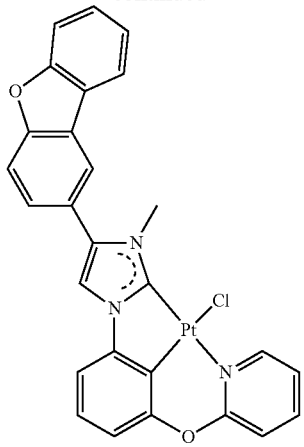
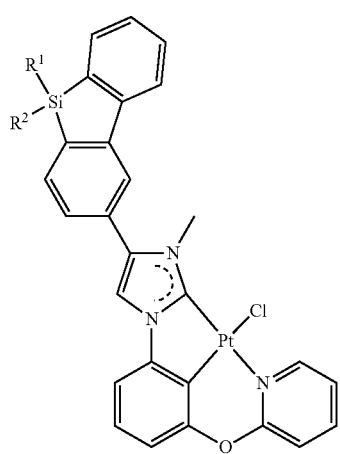
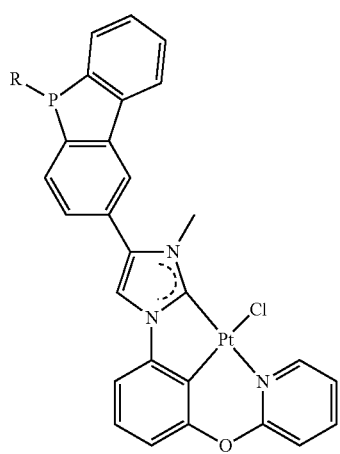
482
-continued
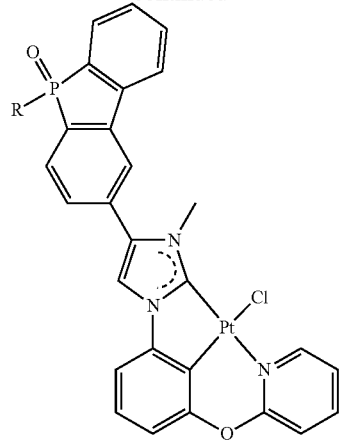
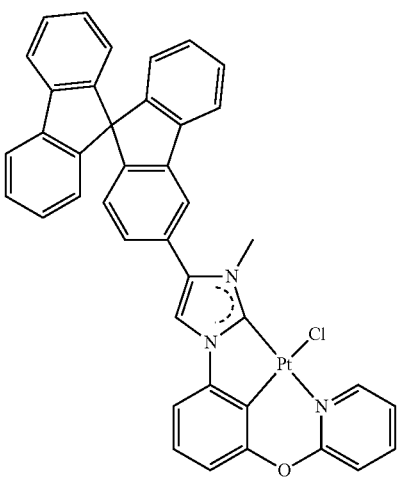
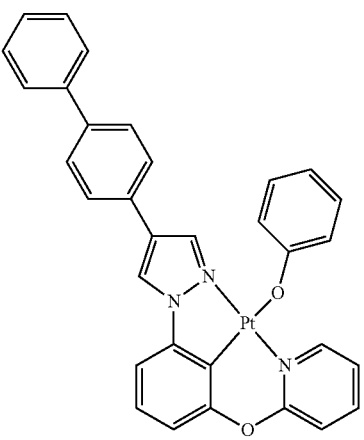

483
-continued
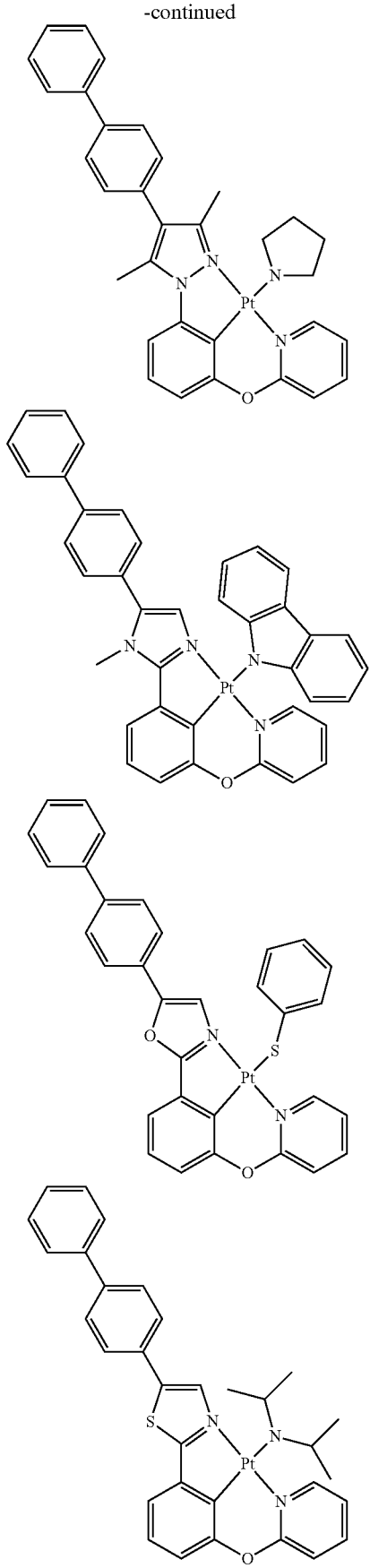
484
-continued
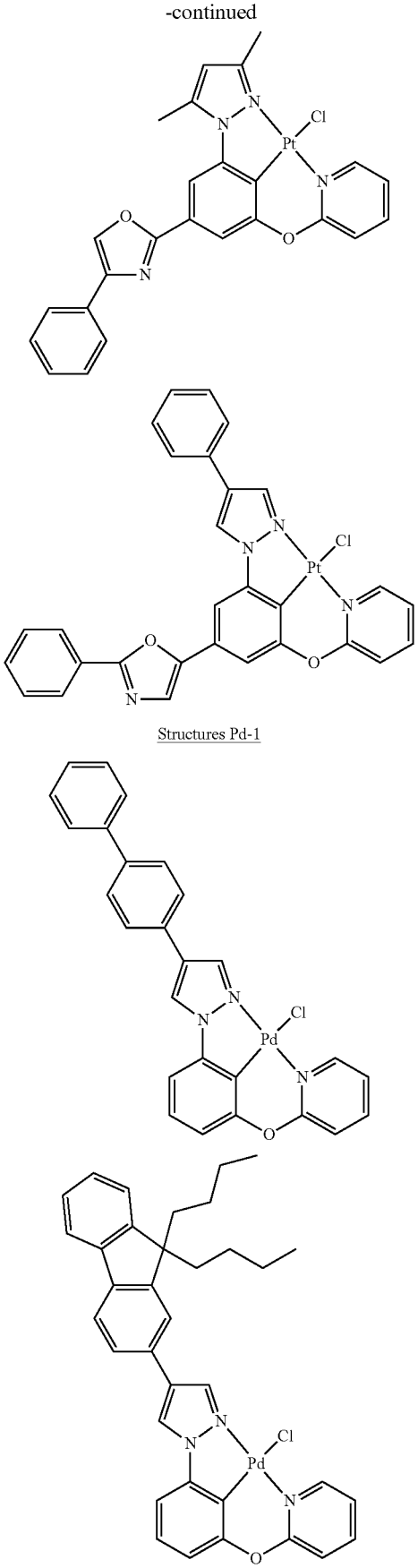
Structures Pd-1

485
-continued
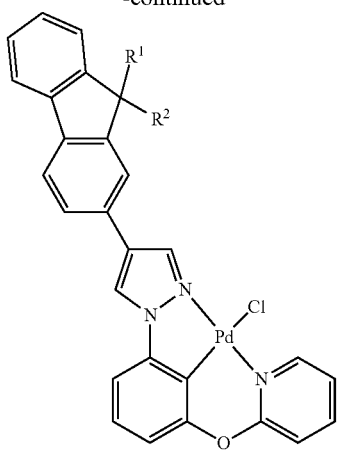
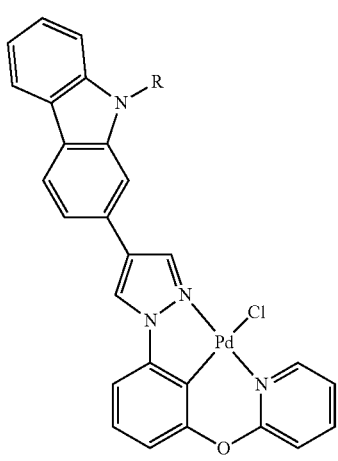
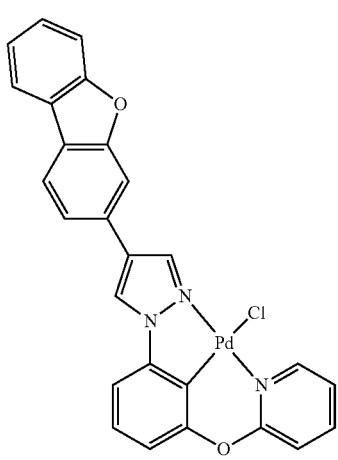
486
-continued
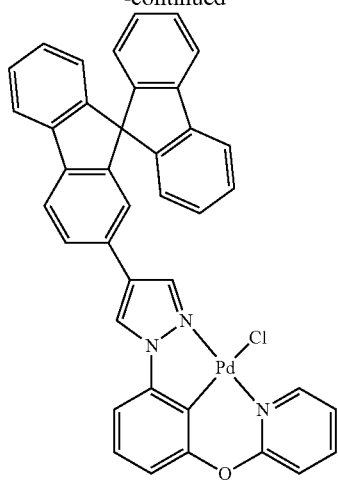
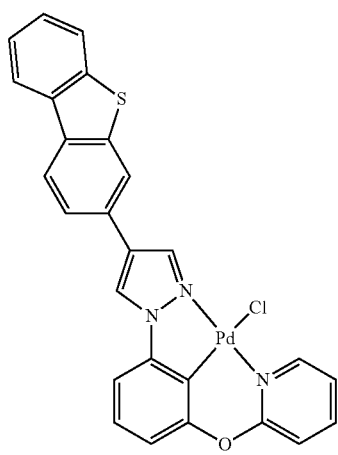
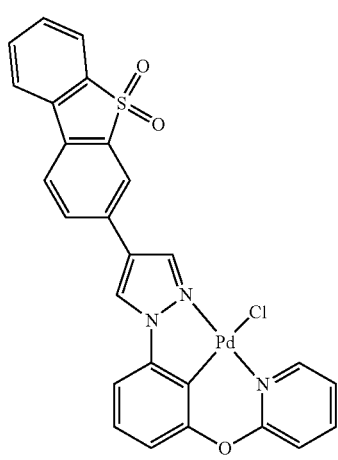

487
-continued
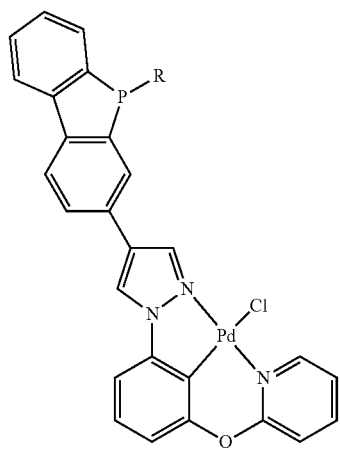
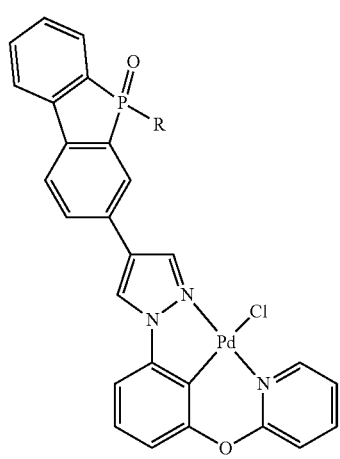
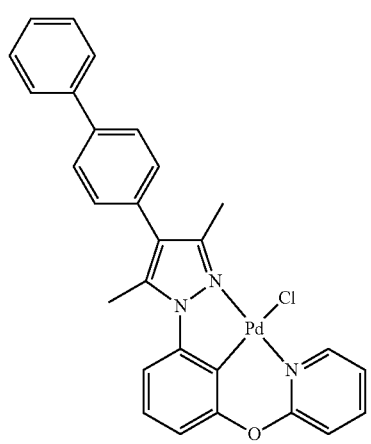
488
-continued
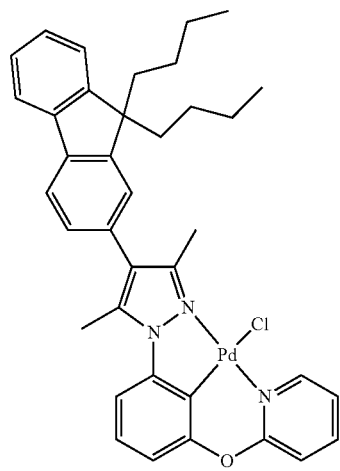
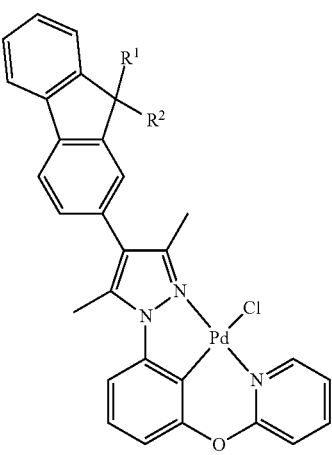
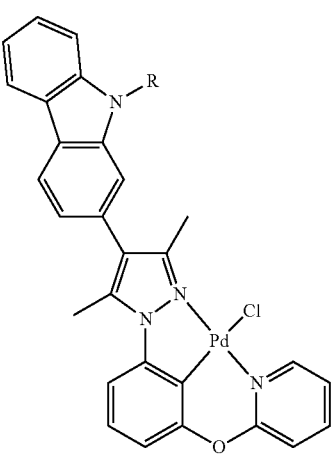

489
-continued
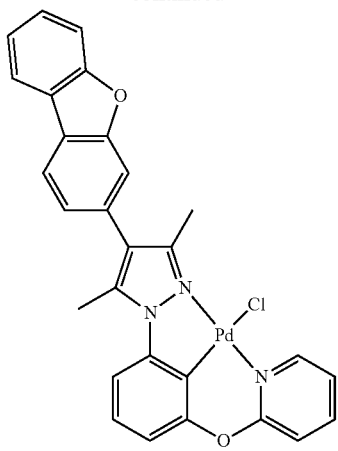
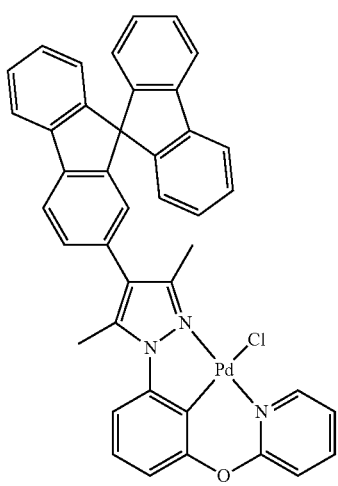
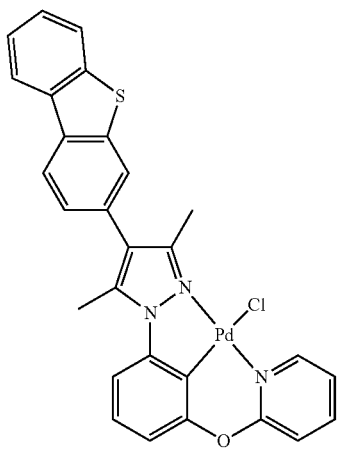
490
-continued
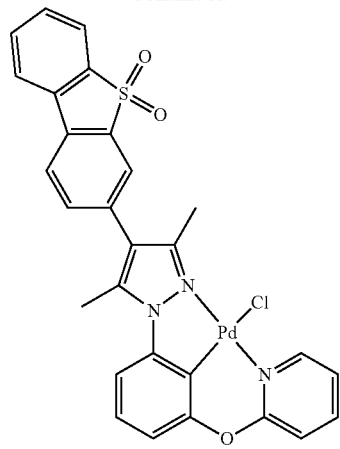
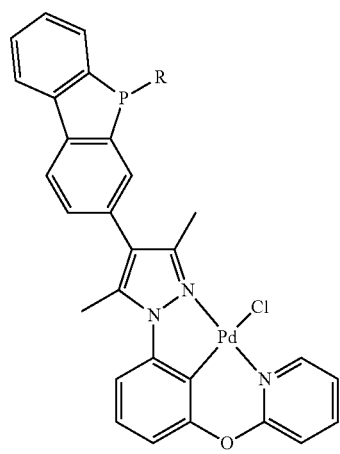
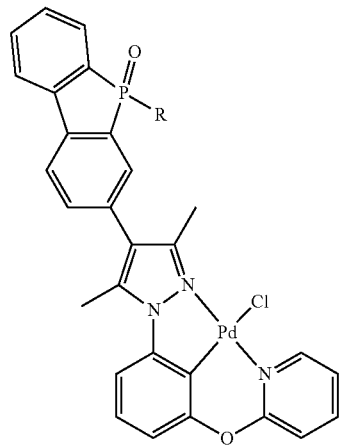

491
-continued
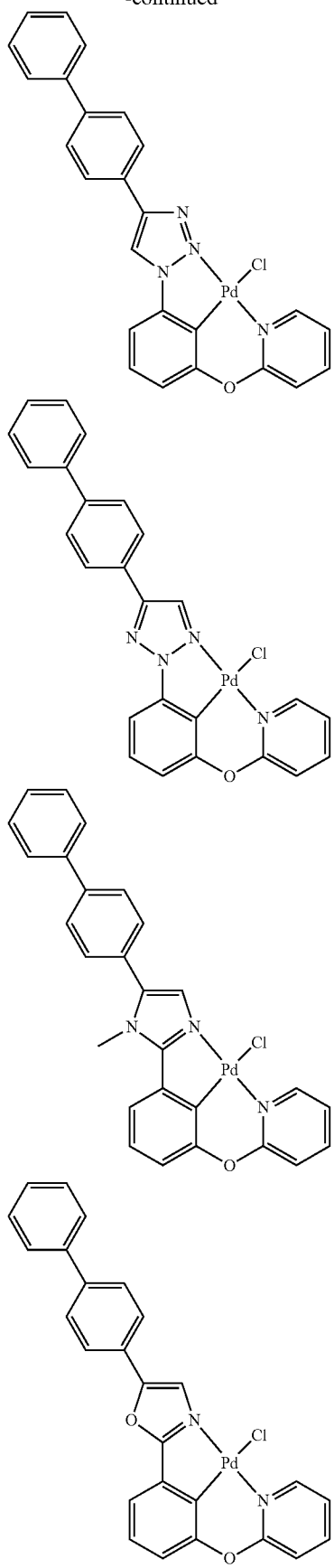
492
-continued
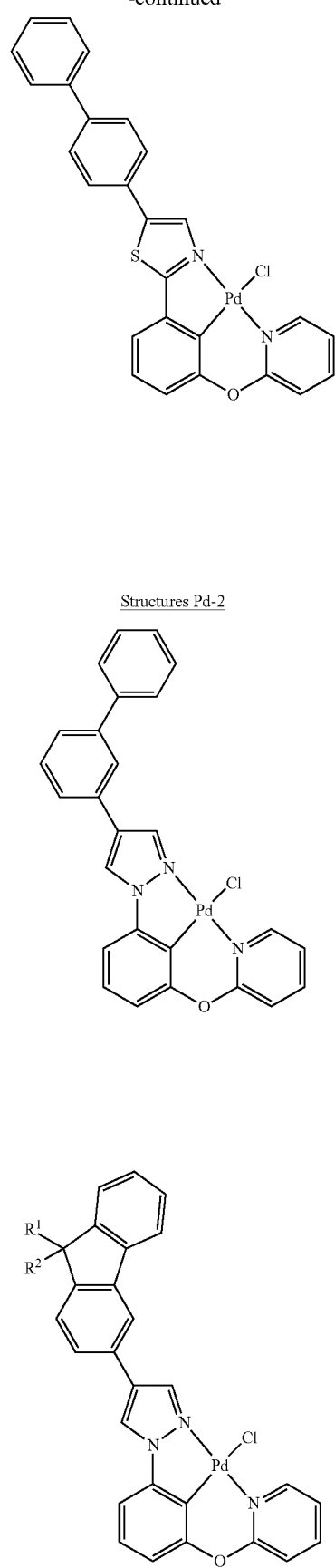
Structures Pd-2

493
-continued
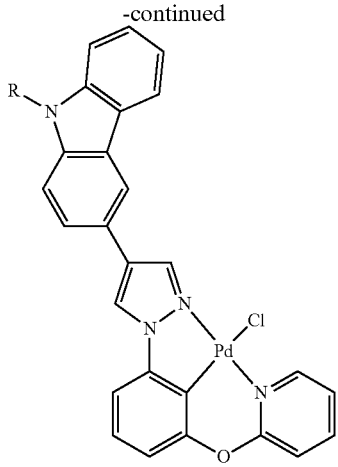
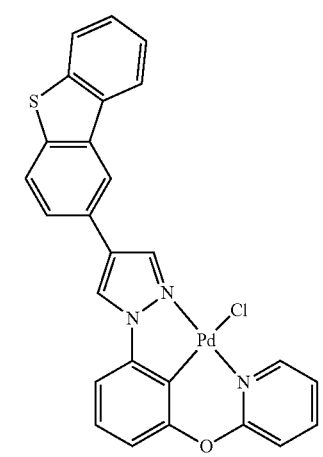
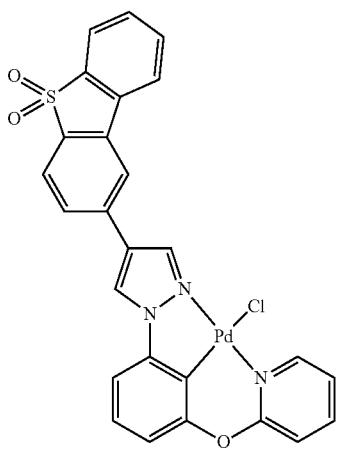
494
-continued
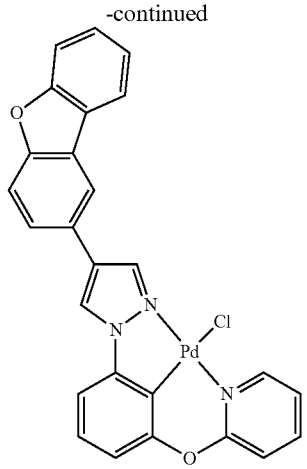
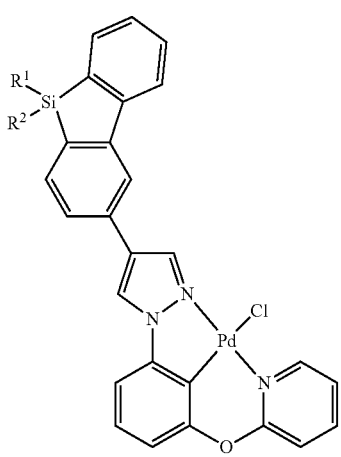
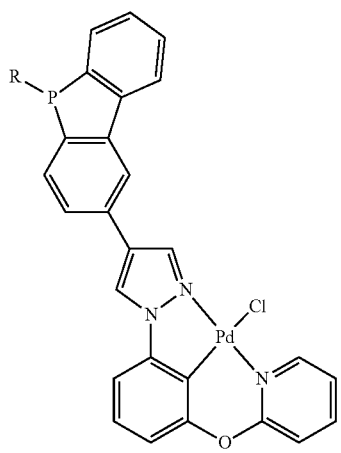

495
-continued
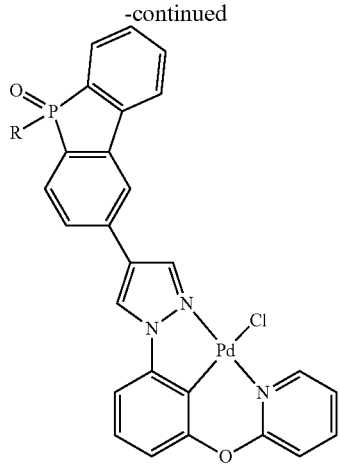
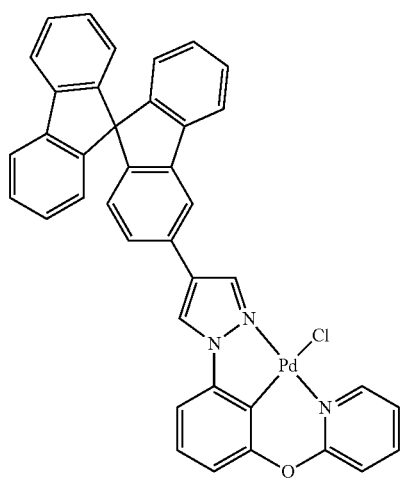
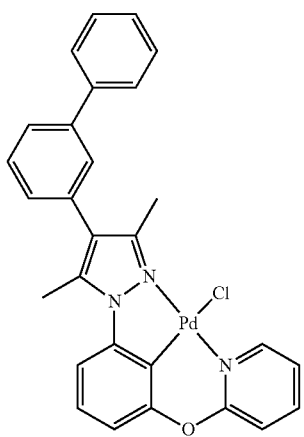
496
-continued
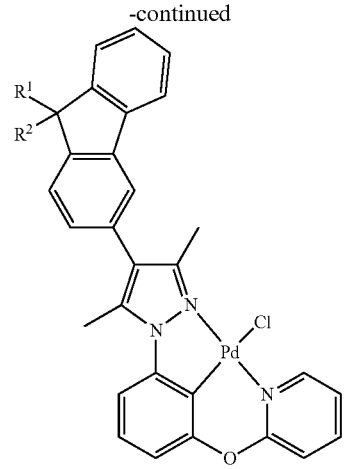
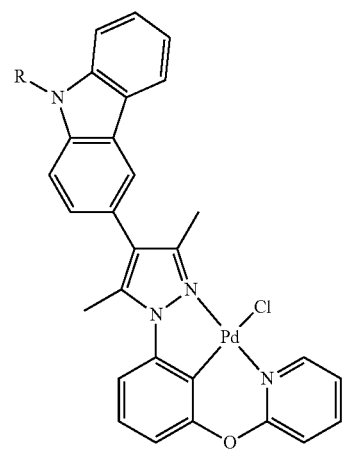
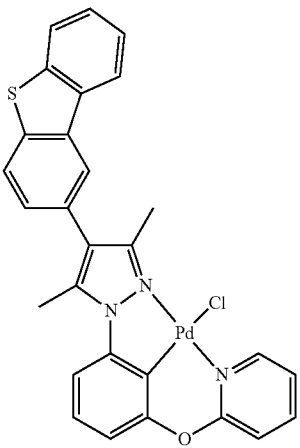

497
-continued
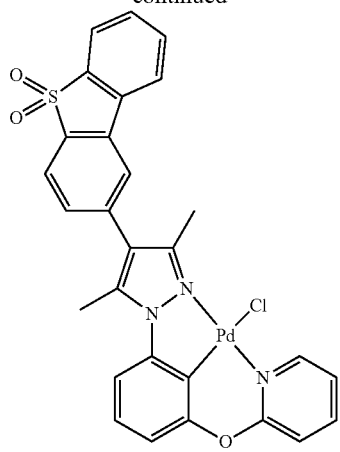
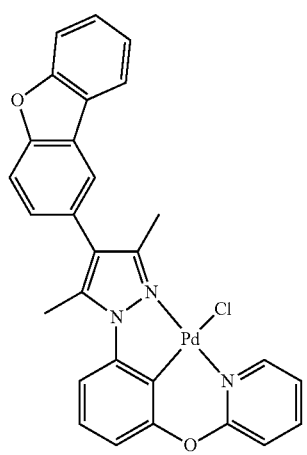
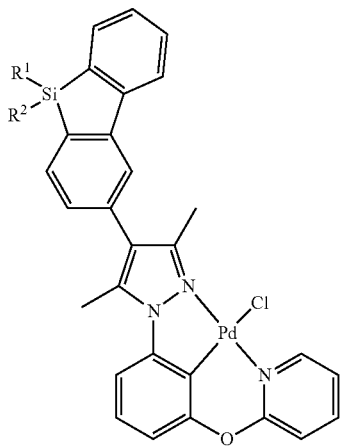
498
-continued
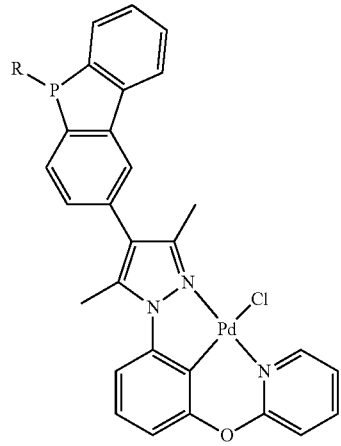
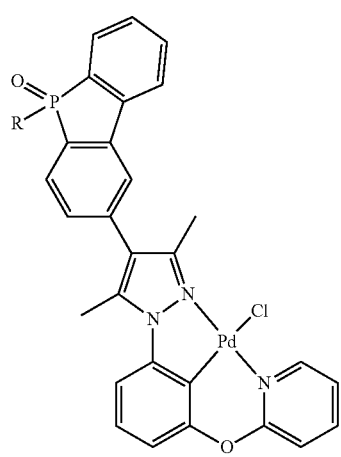

499
-continued
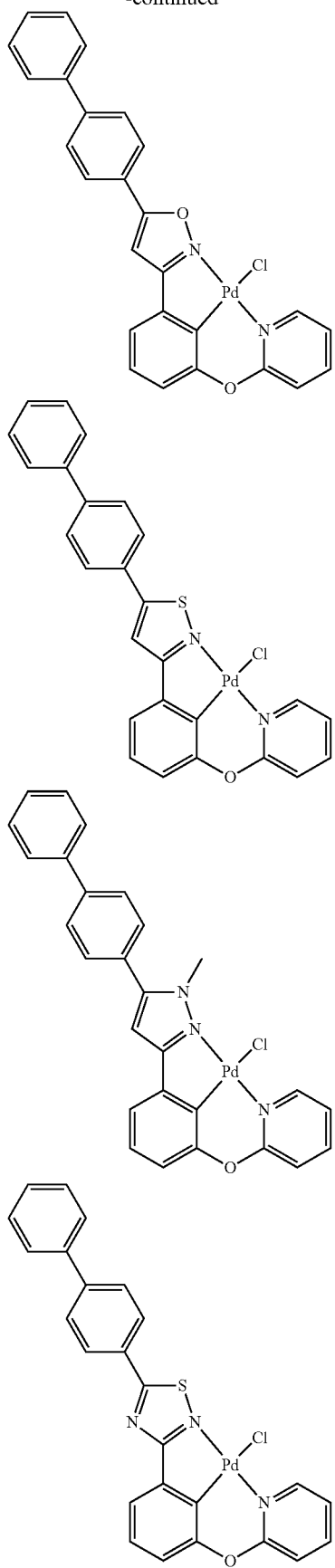
500
-continued
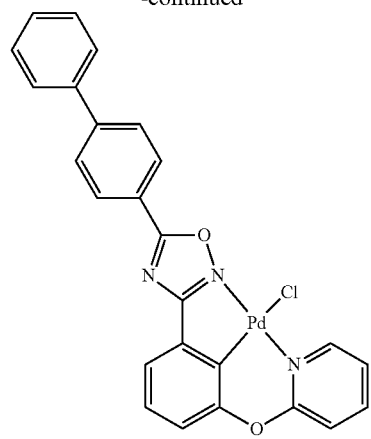
Structures Pd-3
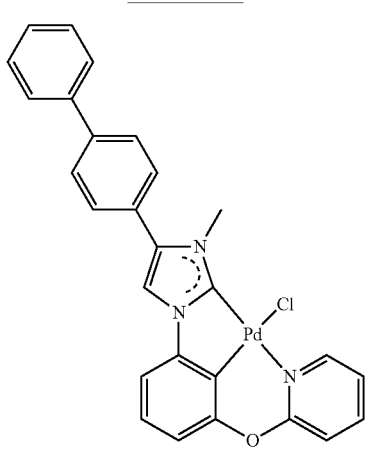
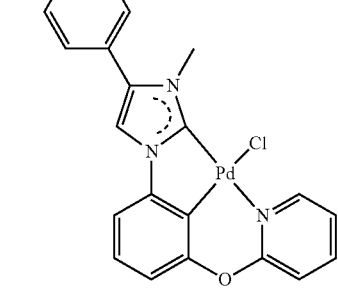

501
-continued
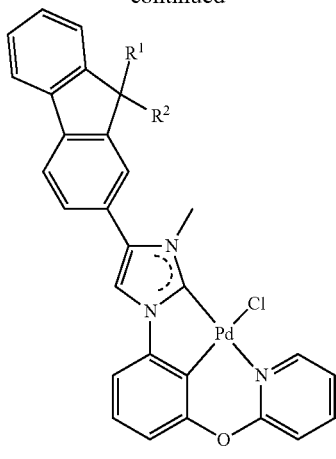
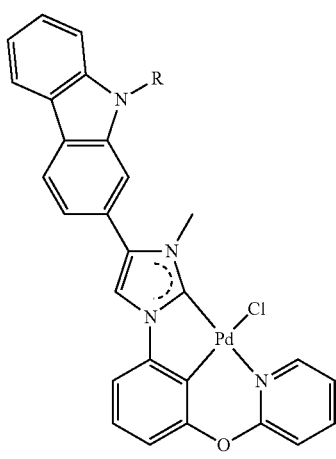
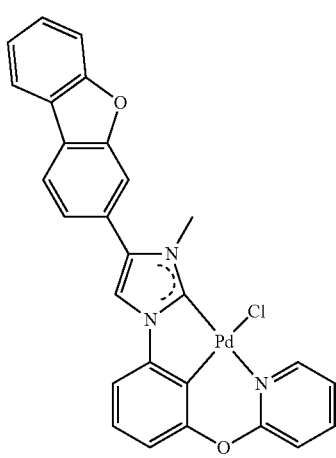
502
-continued
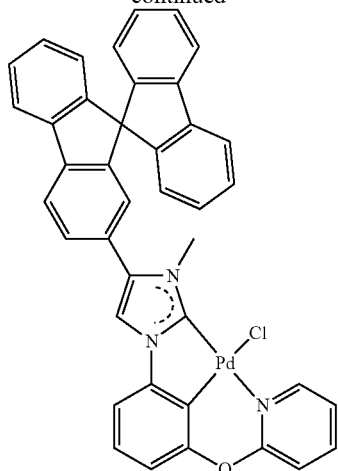
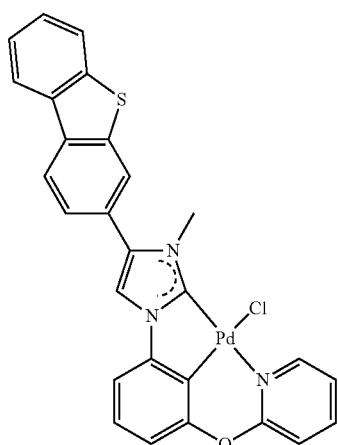
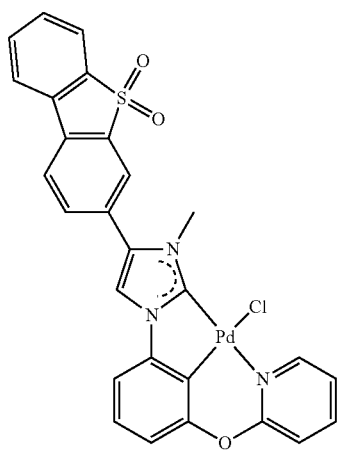

503
-continued
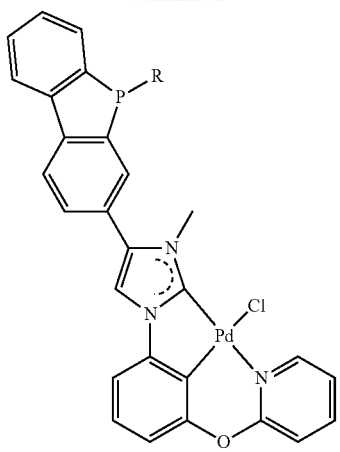
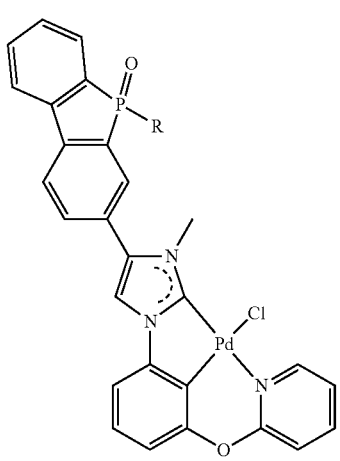
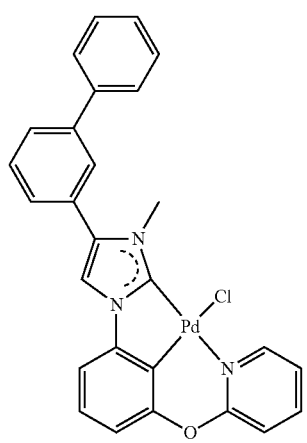
504
-continued
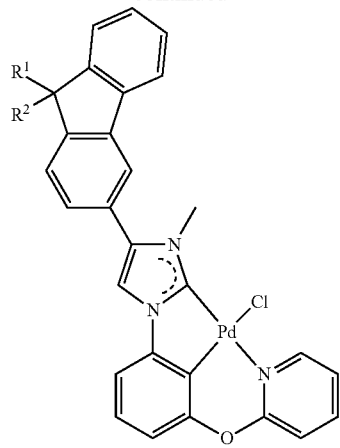
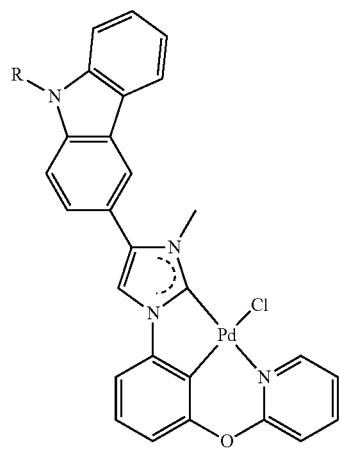
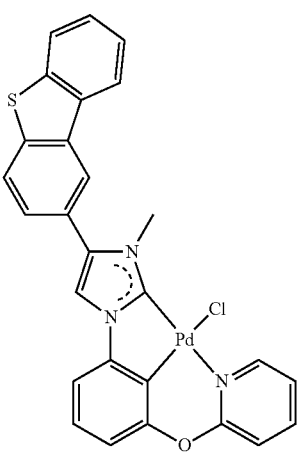

505
-continued
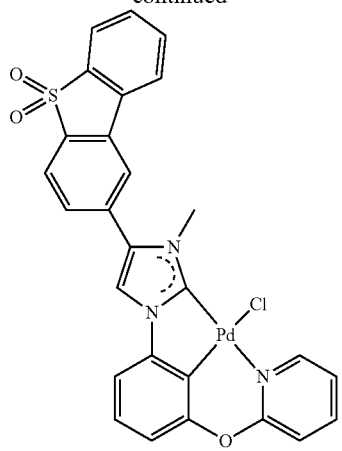
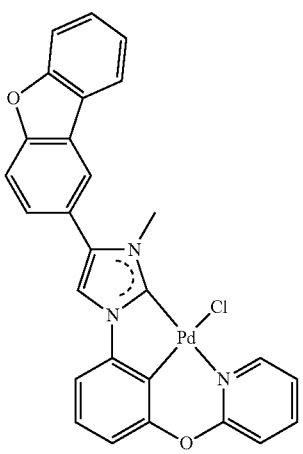
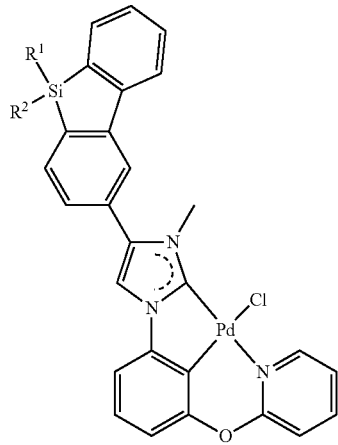
506
-continued
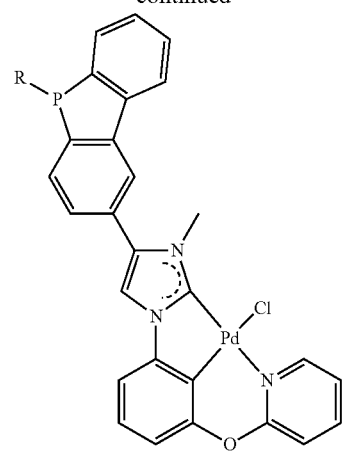
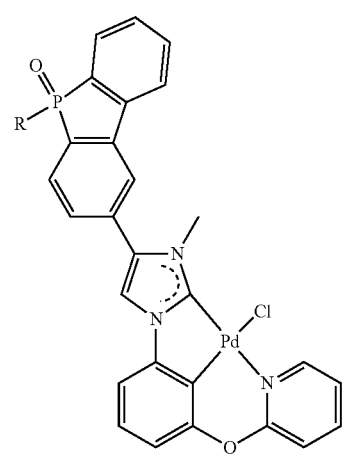
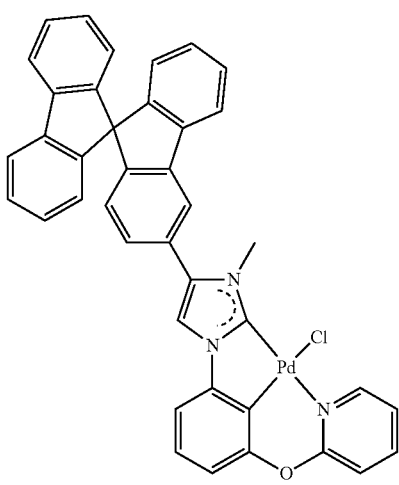

507
-continued
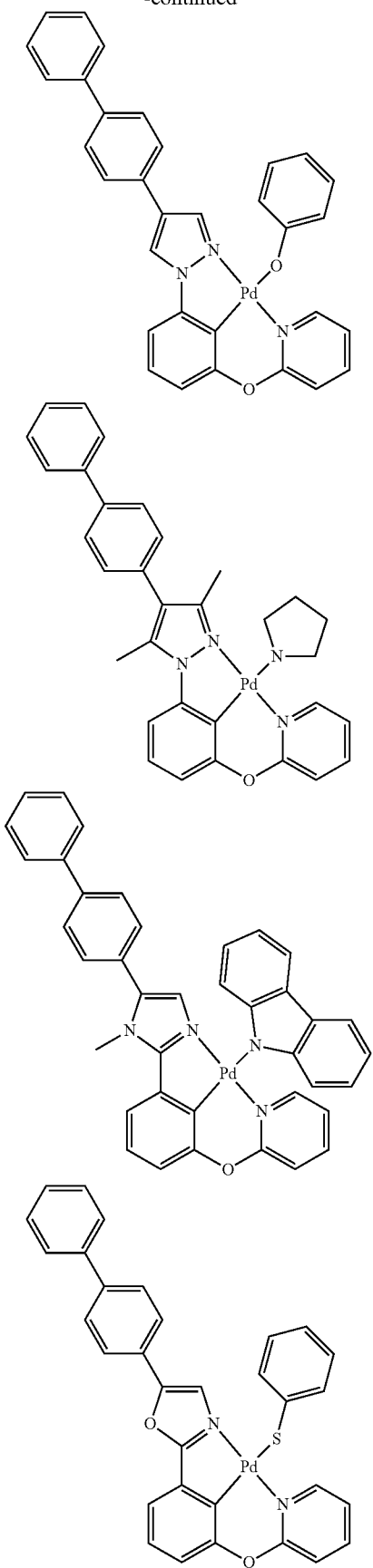
508
-continued
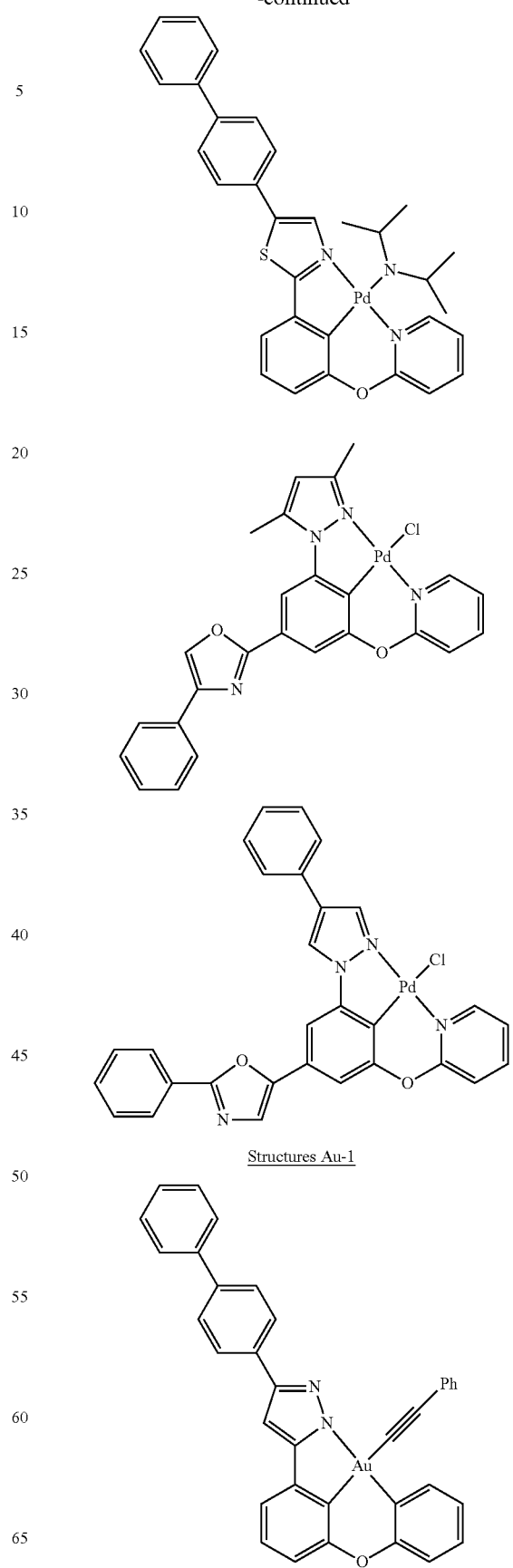
Structures Au-1

509
-continued
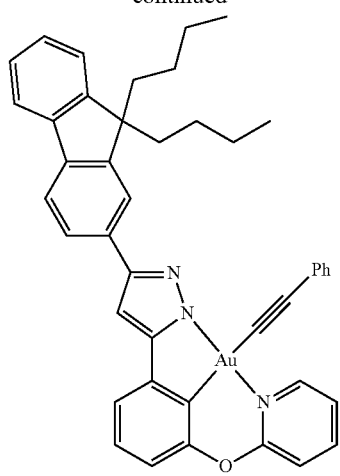
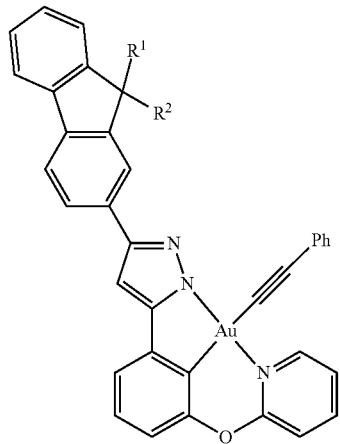
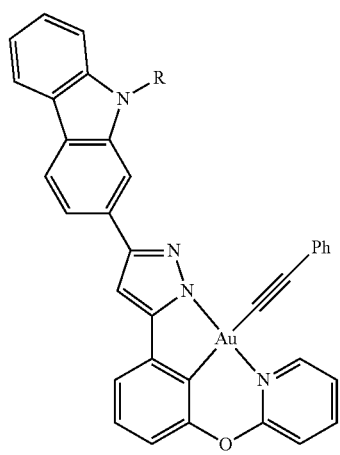
510
-continued
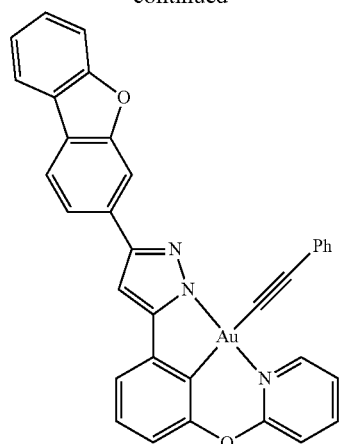
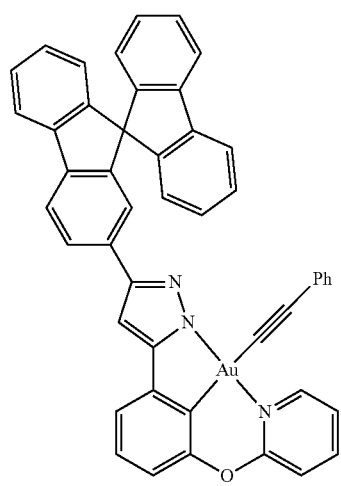
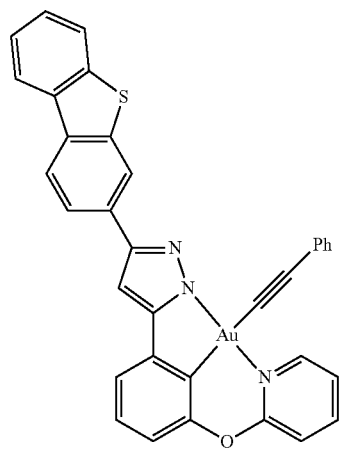

511
-continued
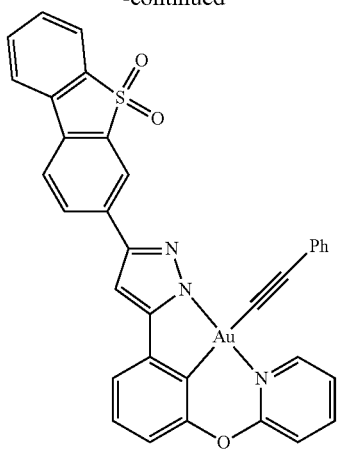
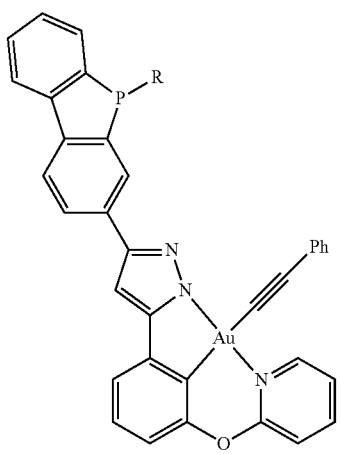
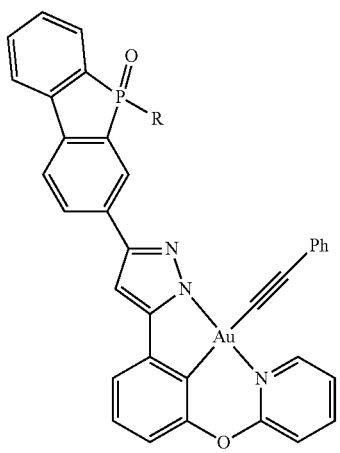
512
-continued
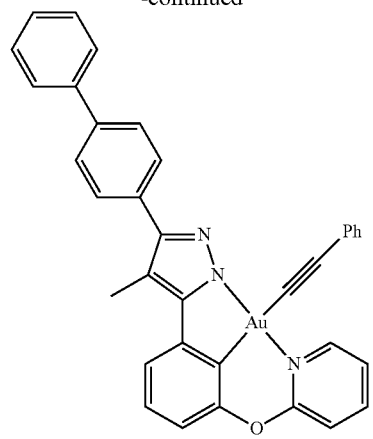
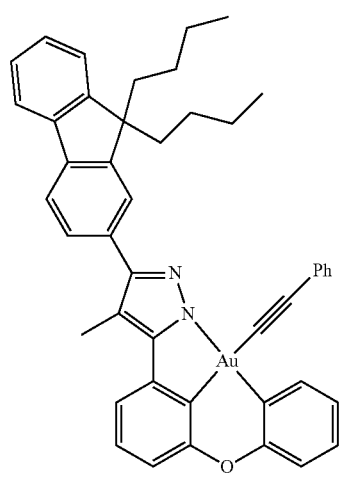
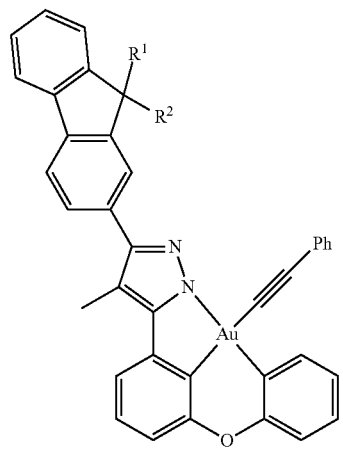

513
-continued
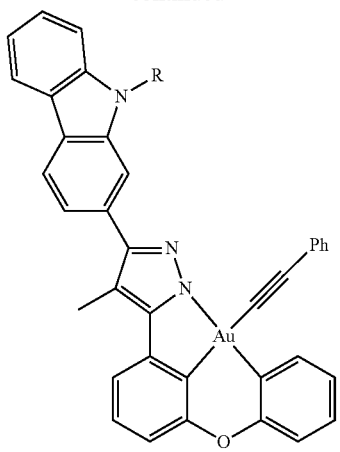
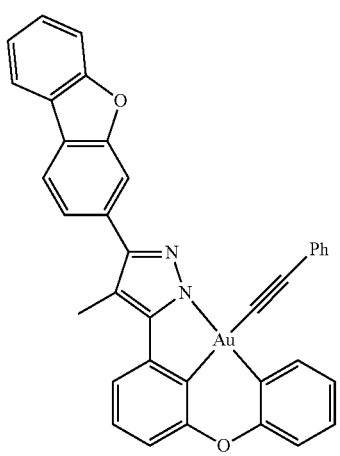
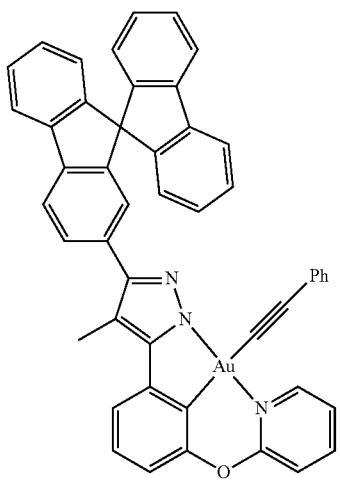
514
-continued
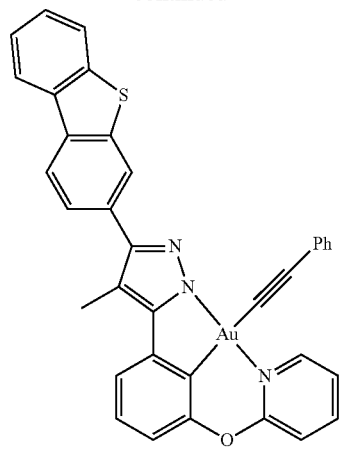
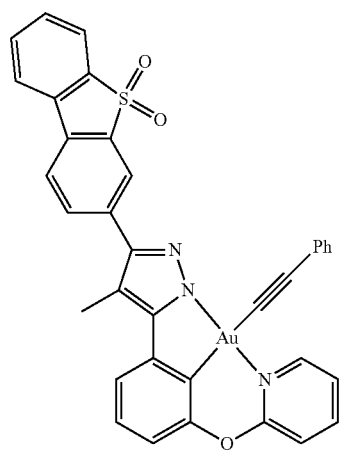
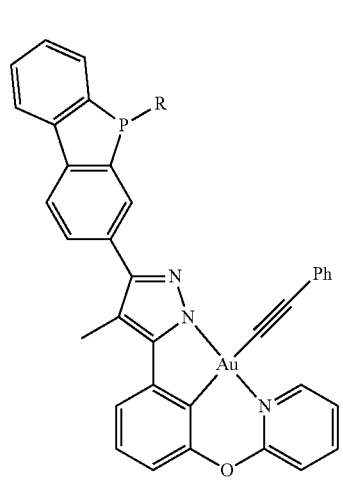

515
-continued
516
-continued
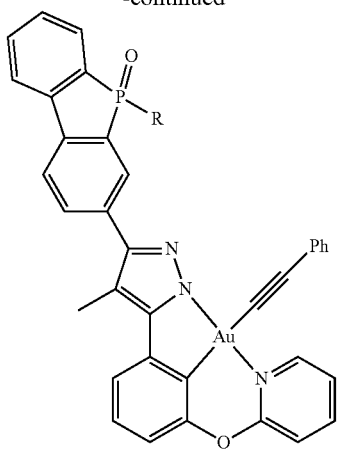
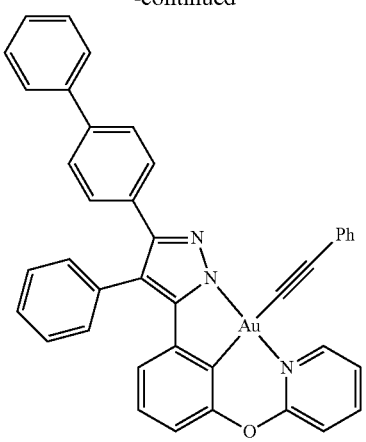
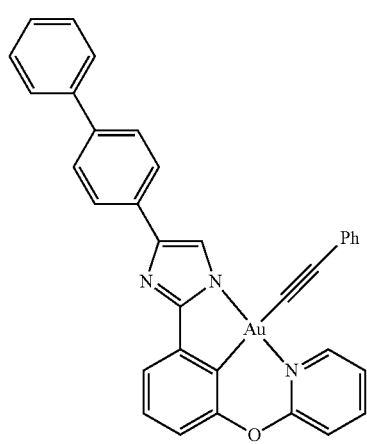
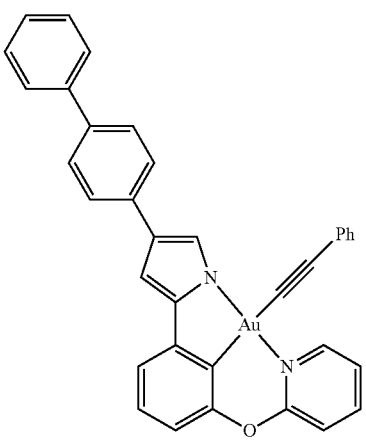
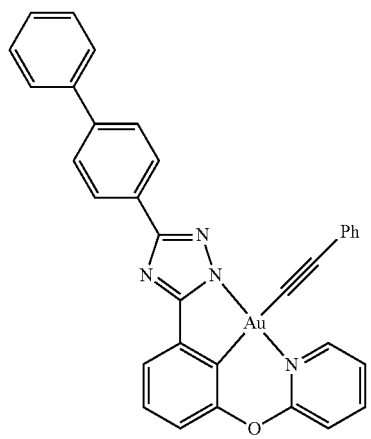
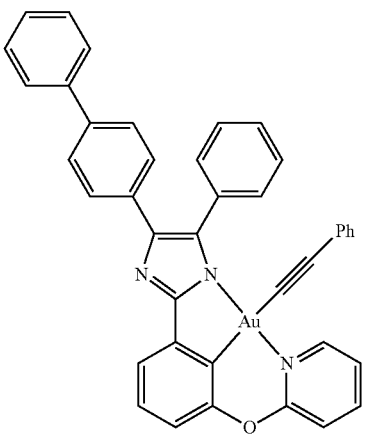

-continued
Structures Au-2
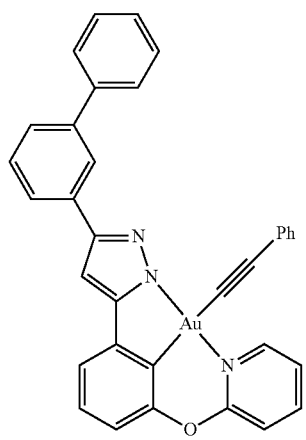
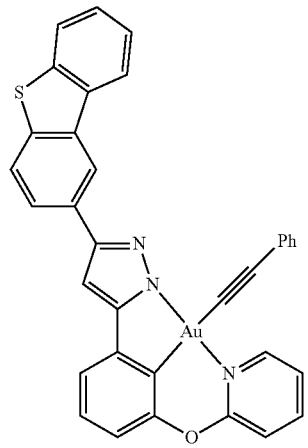
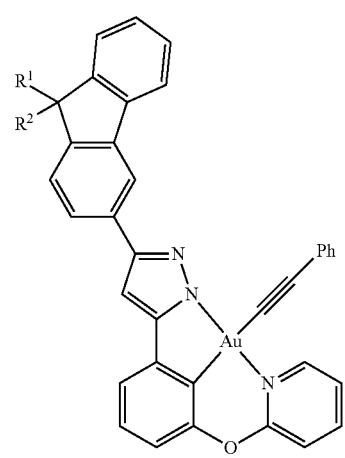
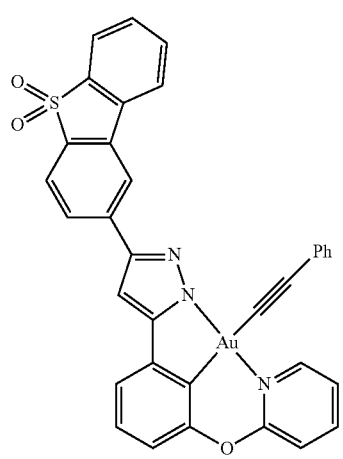
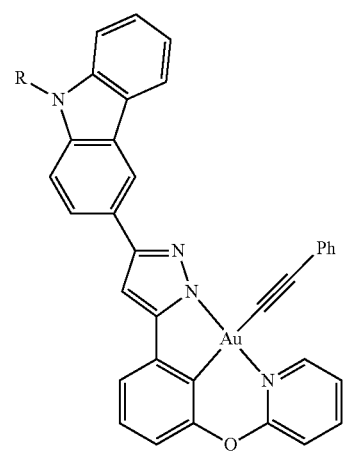
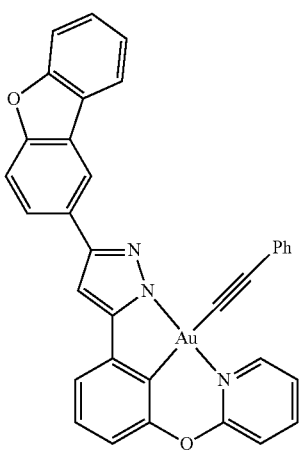

| 519 -continued | 520 -continued |
|---|---|
| 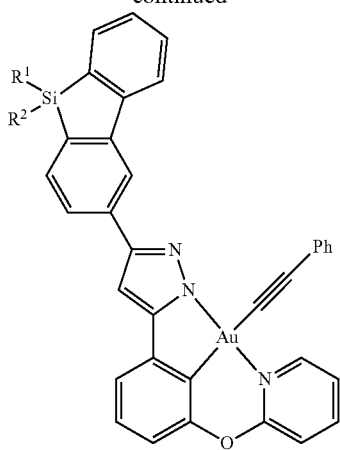 | 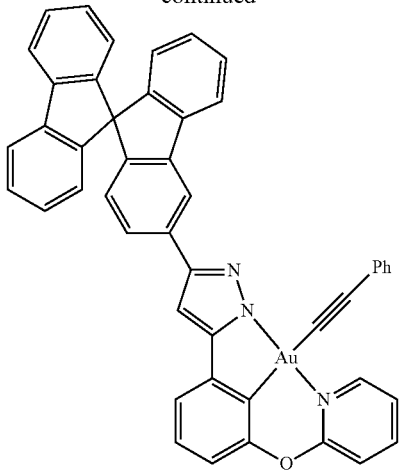 |
| 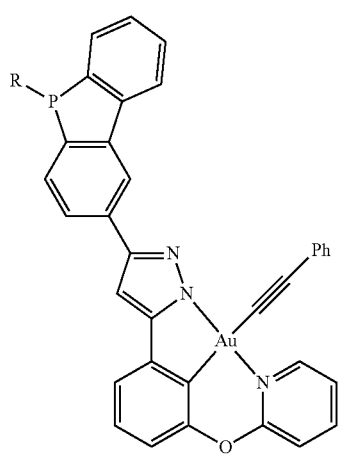 | 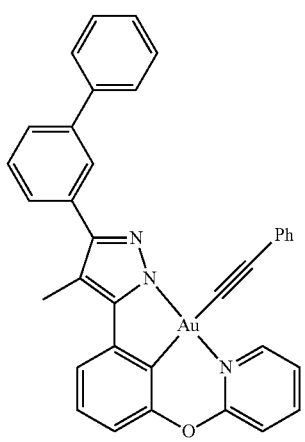 |
| 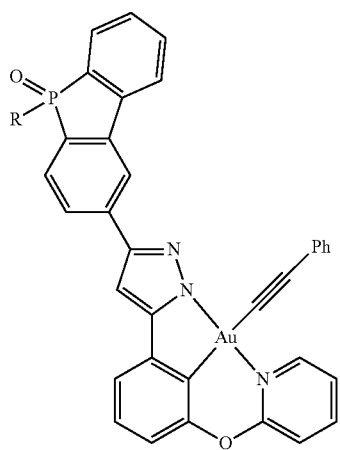 | 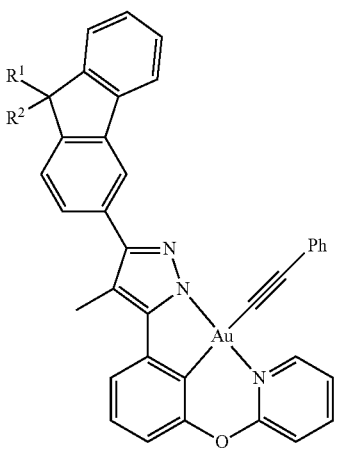 |

521
-continued
522
-continued
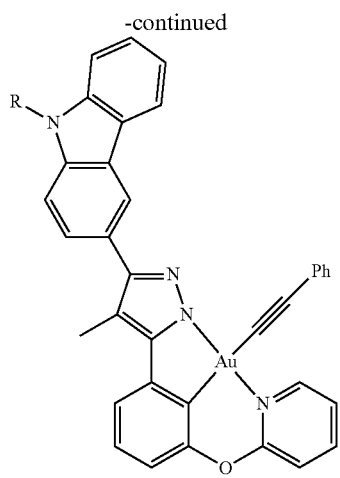
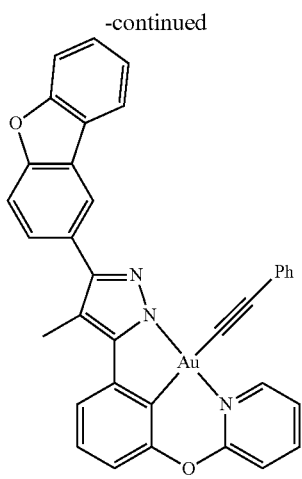
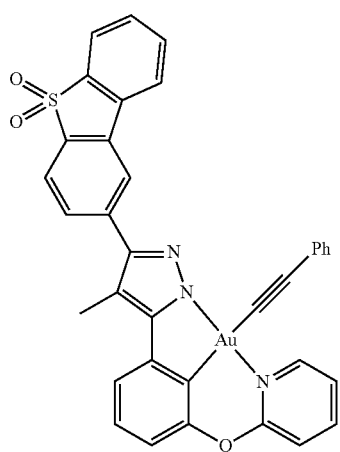

| 523 | 524 |
|---|---|
| -continued | -continued |
| 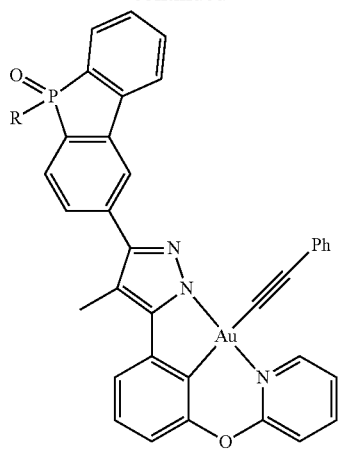 | 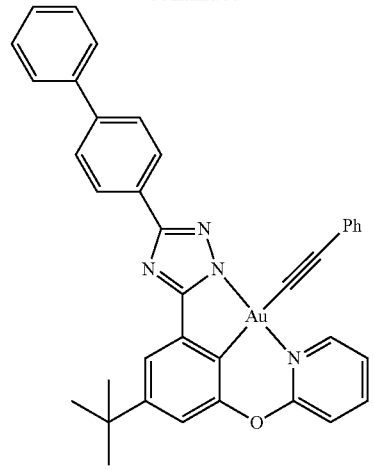 |
| 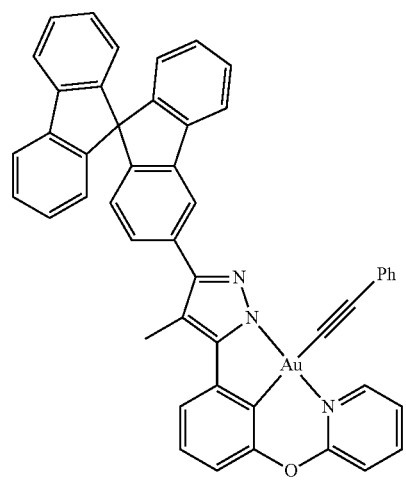 | 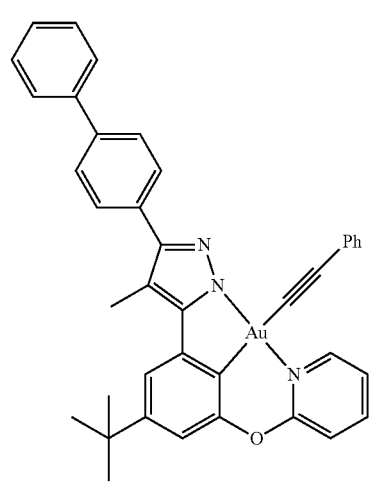 |
| 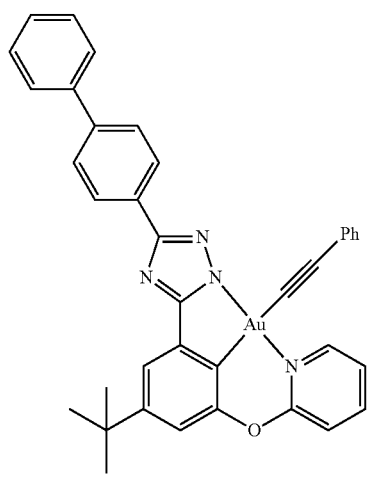 | 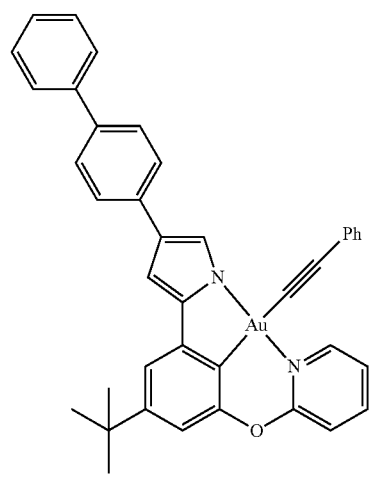 |

-continued

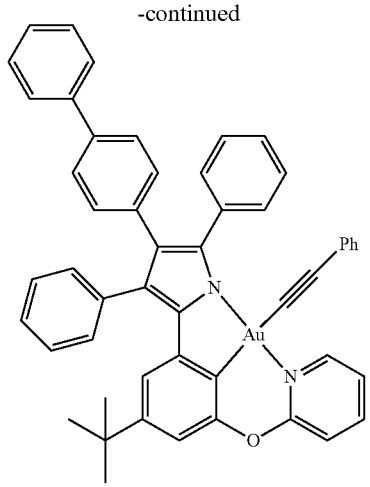

wherein:

each of R, R¹, and R² is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

* * * * *

UNITED STATES PATENT AND TRADEMARK OFFICE
CERTIFICATE OF CORRECTION

PATENT NO.       : 9,818,959 B2
APPLICATION NO.  : 14/809981
DATED            : November 14, 2017
INVENTOR(S)      : Jian Li and Guijie Li It is certified that error appears in the above-identified patent and that said Letters Patent is hereby corrected as shown below:

On the Title Page

Column 1 (Assignee), Line 1, delete "behlaf" and insert -- behalf --, therefor.

In the Claims

In Claim 2, Column 422, Line 60 (Approx.) delete "di alkylamino," and insert -- dialkylamino, --, therefor.

In Claim 5, Column 430, Line 35-44

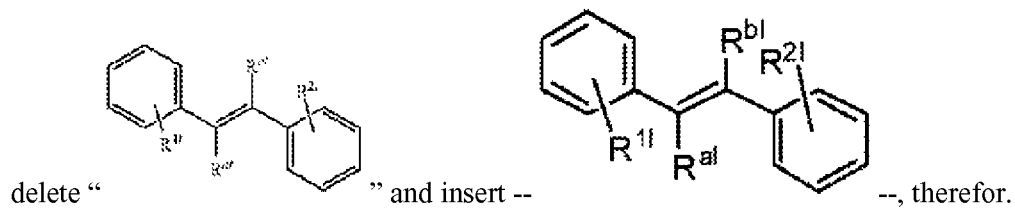

In Claim 5, Column 448, Line 2-11 (Approx.)

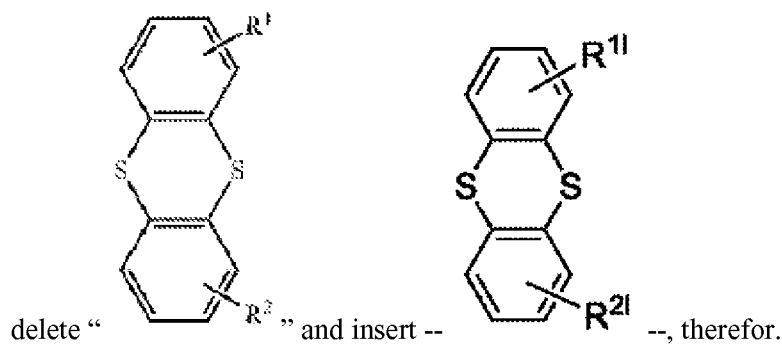

Signed and Sealed this
Tenth Day of April, 2018

Andrei Iancu
*Director of the United States Patent and Trademark Office*

In Claim 5, Column 449, Line 40-49 (Approx.)
delete " 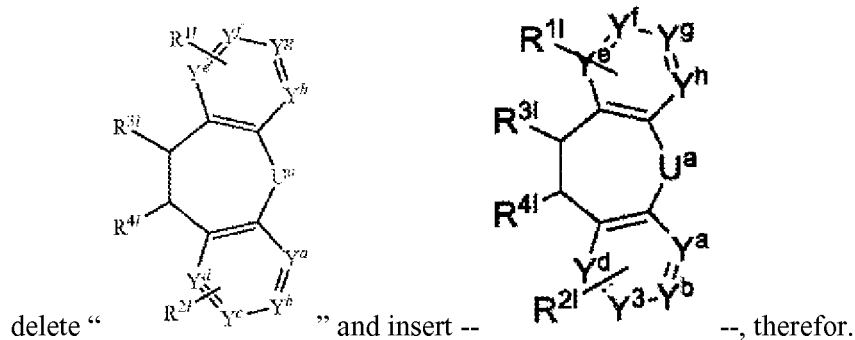 " and insert -- -- , therefor.
In Claim 5, Column 454, Line 2-13 (Approx.)
delete " 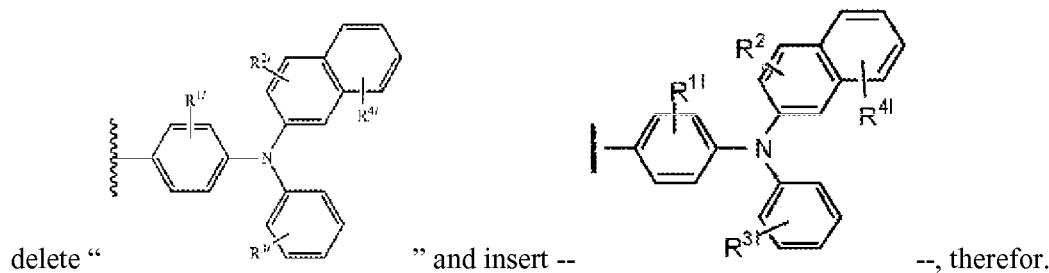 " and insert -- -- , therefor.
In Claim 5, Column 455, Line 26 after "R$^{9l}$" insert -- , --.
In Claim 6, Column 458, Line 15-16 (Approx.) delete "di alkylamino," and insert -- dialkylamino, --, therefor.